(12) United States Patent  
Frincke

(10) Patent No.: US 7,910,571 B2
(45) Date of Patent: Mar. 22, 2011

(54) CYSTIC FIBROSIS TREATMENT METHODS

(75) Inventor: James M. Frincke, Carlsbad, CA (US)

(73) Assignee: Harbor BioSciences, Inc., San Diego, CA (US)

( * ) Notice: Subject to any disclaimer, the term of this patent is extended or adjusted under 35 U.S.C. 154(b) by 709 days.

(21) Appl. No.: 11/549,580

(22) Filed: Oct. 13, 2006

(65) Prior Publication Data

US 2008/0090791 A1 Apr. 17, 2008

Related U.S. Application Data

(63) Continuation of application No. 10/651,515, filed on Aug. 28, 2003, now abandoned.

(60) Provisional application No. 60/479,257, filed on Jun. 17, 2003, provisional application No. 60/408,332, filed on Sep. 4, 2002, provisional application No. 60/407,146, filed on Aug. 28, 2002.

(51) Int. Cl.
*A61K 31/58* (2006.01)
*A61K 31/56* (2006.01)
*A01N 45/00* (2006.01)
*C07J 41/00* (2006.01)

(52) U.S. Cl. ........ 514/173; 514/169; 514/172; 514/176; 514/177; 514/178; 540/106; 552/516; 552/519; 552/522

(58) Field of Classification Search ............. 514/169, 514/172, 173, 176, 177, 178; 540/106; 552/519, 552/522
See application file for complete search history.

(56) References Cited

U.S. PATENT DOCUMENTS

| | | | |
|---|---|---|---|
| 2,566,336 A | 9/1951 | Julian et al. | |
| 3,001,988 A | 9/1961 | Nysted | |
| 3,137,710 A | 6/1964 | de Ruggieri et al. | |
| 3,153,063 A | 10/1964 | de Ruggieri et al. | |
| 3,155,690 A | 11/1964 | Cole | |
| 3,169,093 A * | 2/1965 | Davis | 514/172 |
| 3,189,597 A | 6/1965 | MacPhillamy et al. | |
| 4,330,539 A | 5/1982 | Sleigh et al. | |
| 4,898,694 A | 2/1990 | Schwartz et al. | |
| 4,908,358 A | 3/1990 | Schreiber | |
| 5,206,008 A | 4/1993 | Loria | |
| 5,387,583 A | 2/1995 | Loria | |
| 5,461,042 A | 10/1995 | Loria | |
| 5,506,223 A | 4/1996 | Lardy et al. | |
| 5,585,371 A | 12/1996 | Lardy | |
| 5,635,496 A | 6/1997 | Daynes et al. | |
| 5,686,438 A | 11/1997 | Daynes et al. | |
| 5,811,418 A | 9/1998 | Daynes et al. | |
| 7,396,827 B2 | 7/2008 | Ahlem et al. | |
| 7,462,610 B2 | 12/2008 | Lardy et al. | |
| 7,482,334 B2 | 1/2009 | Frincke et al. | |
| 7,524,835 B2 | 4/2009 | Frincke | |
| 7,547,687 B2 | 6/2009 | Frincke et al. | |
| 2006/0073099 A1 | 4/2006 | Frincke | |
| 2007/0077201 A1 | 4/2007 | Reading et al. | |
| 2007/0129282 A1 | 6/2007 | Ahlem | |
| 2007/0213309 A1 | 9/2007 | Reading et al. | |
| 2007/0265236 A1 | 11/2007 | Reading et al. | |
| 2008/0058301 A1 | 3/2008 | Lardy | |
| 2008/0085873 A1 | 4/2008 | Reading et al. | |
| 2008/0176823 A1 | 7/2008 | Lardy | |

OTHER PUBLICATIONS

Arth, G., et al, Steroidal androgen biosynthesis inhibitors, *J. Med. Chem.*, 14(8):675-679 (1971).
Davis, M., et al, Steroid Amines. Part II. 17α-aminoandrostane derivatives, *J. Chem. Soc.*, 1698-1700 (1966).
Flouret, G., et al, 17-aminocylamido-5-androsten-3β-ols, *J. Med. Chem.*, 11:880-882 (1968).
Hewett, C., et al, Amino-steroids. Part IV. 16β-morpholino-17-oxo- and 17β-morpholino-16-oxo-5α-androstanes, *J. Chem. Soc.*, 1880-1883 (1969).
Hussain, A., et al, Testosterone 17β-N, N-dimenthylglycinate hydrochloride: A prodrug with a potential for nasal delivery of testosterone, *J. Pharmaceutical Sciences*, 91:785-789 (2002).
Irmscher, K., et al, Cholesterol analogues with oxa and oxa-aza side chain a novel class of inhibitors of cholesterol biosynthesis, *Steroids*, 7(6):557-576 (1966).
Johnson, K., et al, Solution kinetics of a water soluble hydrocortisone prodrug: Hydrocortisone-21-lysinate, *J. Pharmaceutical Sciences*, 74(1):87-89 (1985).
Jones, J., et al, Steroids and steroidases. 10. Studies on some potentially antitumor active androstane compounds containing C-17 nitrogen mustard functions, *J. Med. Chem.*, 14:(9) 827-833 (1971).
Kabara, J., et al, Structure-function activity of azasterols and nitrogen-containing steroids, *Lipids*, 11(10):755-762 (1976).
Mokotoff, M., et al, Peptidyl aminosteroids as potential new antiarrhythmic agents, *Steroids*, 55:399-404 (1990).
Pettit, G., et al, Structural biochemistry. IV. 3β-hydroxy-17β-(L-prolyl) amino-androst-5-ene$^{1\text{-}3}$, *Canadian J. Chem.*, 45:502-507 (1967).
Pettit, R., et al, Antimicrobial and cancer cell growth inhibitory activities of 3β-acetoxy-17β-(L-prolyl)amino-5α-androstane *in vitro*, *International J. Antimicrob. Agents*, 15:299-304 (2000).
Robinson, C., et al, the synthesis of 17α-amino-5-androsten-3β-ol; N.M.R. spectra of 17-substituted androstanes, *Steroids*, 6(5):509-518 (1965).
Yagishita, K, Studies on antimicrobial activities of aminosteroids—II, *Bull Coll Agr & Vet Med, Nihon Univ*, 28:8-17 (1971).
Zheng, G, et al, Tricarbocyanine cholesteryl laureates labeled LDL: New near infrared fluorescent probes (NIRFs) for monitoring tumors and gene therapy of familial hypercholesterolemia, *Bioorganic & Med. Chem. Letters*, 12:1485-1488 (2002).
U.S. Appl. No. 11/549,598, filed Oct. 13, 2006, Reading et al.

* cited by examiner

*Primary Examiner* — Sreeni Padmanabhan
*Assistant Examiner* — Sarah Pihonak
(74) *Attorney, Agent, or Firm* — Daryl D. Muenchau

(57) ABSTRACT

The invention relates to the use of compounds to ameliorate or treat an condition such as a cystic fibrosis, neutropenia or other exemplified conditions. Exemplary compounds that can be used include 3β-hydroxy-17β-aminoandrost-5-ene, 3β-hydroxy-16α-fluoro-17β-aminoandrost-5-ene, 3α-hydroxy-16α-fluoro-17β-aminoandrost-5-ene, 3β-hydroxy-16β-fluoro-17β-aminoandrost-5-ene, 1α,3β-dihydroxy-4α-fluoroandrost-5-ene-17-one, 1α,3β,17β-trihydroxy-4α-fluoroandrost-5-ene, 1β,3β-dihydroxy-6α-bromoandrost-5-ene, 1α-fluoro-3β,12α-dihydroxyandrost-5-ene-17-one, 1α-fluoro-3β,4α-dihydroxyandrost-5-ene and 4α-fluoro-3β,6α,17β-trihydroxyandrostane.

13 Claims, No Drawings

CYSTIC FIBROSIS TREATMENT METHODS

CROSS REFERENCE TO RELATED APPLICATIONS

This application is a Continuation of application under 37 C.F.R. 1.53(b) and claims priority of abandoned U.S. application Ser. No. 10/651,515, filed Aug. 28, 2003 which claims priority of U.S. provisional application Ser. No. 60/407,146, filed Aug. 28, 2002, U.S. provisional application Ser. No. 60/408,332, filed Sep. 4, 2002 and U.S. provisional application Ser. No. 60/479,257, filed Jun. 17, 2003 all of which are incorporated herein by reference.

FIELD OF THE INVENTION

The invention relates to methods to use compounds, such as 3β-hydroxy-16α-fluoro-17β-aminoandrost-5-ene, 3β-hydroxy-16β-fluoro-17β-aminoandrost-5-ene, 3β-hydroxy-17β-aminoandrost-5-ene, 1α,3β-dihydroxy-4α-fluoroandrost-5-ene, 1α,3β,17β-trihydroxy-4α-fluoroandrost-5-ene, 1β,3β-dihydroxy-6-bromoandrost-5-ene-17-one, 1α-fluoro-3β,12α-dihydroxyandrost-5-ene-17-one, 1α-fluoro-3β,4α-dihydroxyandrost-5-ene and 4α-fluoro-3β,6α,17β-trihydroxyandrostane to treat, ameliorate or prevent neutropenia, cystic fibrosis conditions or other pathological or disease conditions or their symptoms.

BACKGROUND

Immune dysregulation can be a component of many pathological diseases or conditions. Such dysregulation may be a factor that favors the establishment, maintenance or progression of these diseases or conditions. Deficient immune responses or immune suppression can enhance a mammal's susceptibility to infection or to the development of cancer. Conversely, excessive or inappropriate immune responses can play a role in the establishment or progression of unwanted inflammation or autoimmune conditions. It would thus be advantageous to utilize agents that can modulate immune responses and to at least partially reverse immune dysregulation when such dysregulation is a component of a given pathological condition. Some agents are known that can ameliorate some aspects of immune dysregulation, but typically such agents have their own unwanted effects on either the host's immune system or other organs or tissues. Agents such as glucocorticoid steroids have been used to reduce unwanted inflammation in a number of clinical conditions, but such compounds often have serious limitations, such as inducing immune suppression or causing unwanted mood changes.

Human and mammalian immune responses to infections or other conditions are often characterized by responses mediated by different immune effector cell populations. In some situations, helper T cells designated Th1 in the murine system, facilitate immune effector functions that are typically dominated by cell-mediated responses. In other cases, helper T cells designated Th2 cells facilitate immune effector functions that are typically dominated by humoral responses. A vigorous Th1 response is usually desirable to help clear infections or to slow the progression of an infection. When a subject's immune response is biased to, or dominated by, a Th2-type response, the cytokines associated with the Th2 response tend to suppress the immune system's capacity to mount a vigorous Th1 response at the same time. The converse is also generally true. When mammalian immune responses begin to result in an increasing Th1 response, Th2 responses tend to weaken. Insufficient Th1 responses may be associated with progression of some infections or other conditions, see, e.g., M. Clerici and G. M. Shearer, *Immunol. Today* 14:107-111, 1993; M. Clerici and G. M. Shearer, *Immunol. Today* 15:575-581, 1994.

Methods to make and use 3β-hydroxyandrost-5-ene-17-one (dehydroepiandrosterone) and certain other steroids and their biological properties have been described, see, e.g., U.S. Pat. Nos. 2,833,793, 2,911,418, 3,148,198, 3,471,480, 3,976, 691, 4,268,441, 4,427,649, 4,542,129, 4,666,898, 4,956,355, 5,001,119, 5,043,165, 5,077,284, 5,028,631, 5,110,810, 5,157,031, 5,162,198, 5,175,154, 5,277,907, 5,292,730, 5,296,481, 5,372,996, 5,387,583, 5,407,684, 5,424,463, 5,461,042, 5,478,566, 5,506,223, 5,518,725, 5,527,788, 5,527,789, 5,532,230, 5,559,107, 5,562,910, 5,583,126, 5,585,371, 5,587,369, 5,591,736, 5,593,981, 5,610,150, 5,635,496, 5,641,766, 5,641,768, 5,656,621, 5,660,835, 5,686,438, 5,696,106, 5,700,793, 5,707,983, 5,709,878, 5,710,143, 5,714,481, 5,728,688, 5,736,537, 5,744,462, 5,753,237, 5,756,482, 5,776,921, 5,776,923, 5,780,460, 5,795,880, 5,798,347, 5,798,348, 5,804,576, 5,807,848, 5,807,849, 5,811,418, 5,824,313, 5,824,668, 5,824,671, 5,827,841, 5,837,269, 5,837,700, 5,843,932, 5,846,963, 5,859,000, 5,872,114, 5,872,147, 5,162,198, 5,206,008, 5,292,730, 5,407,684, 5,461,042, 5,461,768, 5,478,566, 5,585,371, 5,635,496, 5,641,766, 5,837,269, 5,885,977, 5,846,963, 5,919,465, 5,869,090, 5,863,910, 5,856,340, 5,804,576, 5,714,481, 4,978,532, 4,898,694, 4,542,129, 3,711,606, 3,710,795, 3,189,597, 3,137,710 and 2,531,441; German patent numbers 2035738 and 2705917; PCT publication numbers WO 95/21617, WO 97/38695, WO 97/48367, WO 98/05338, WO 98/50040, WO 98/50041, WO 98/58650, WO 00/32176, WO 00/32177, WO 00/32201, WO 00/35472, WO 00/56757, WO 01/30802, WO 93/20696, WO 99/25333, WO 01/30802, WO 01/23405, WO 02/28880, WO 02/69977 and WO 03/039554; European publication numbers 0020029, 0090736, 0133995, 0934745 and 0637203; E. R. Glazier, *J. Org. Chem.* 1962 27:2937-2938, Ben-David, et al., *Proc. Soc. Expt. Biol. Med.* 1967 125:1136-1140, Coleman et al., *Diabetes* 1982 31:830, Oertel, et al., *J. Steroid Biochem.* 1972 3:493-496, Pashko, et al., *Carcinogenesis* 1981 2:717-721, Schwartz et al., *Nutr. Cancer* 1981 3:46-53, Dyner et al., *J. Acquired Immune Deficiency Syndromes* 1993 6:459-465, M. H. Whitnall et al., *Int'l. J. Immunopharmacology* 2000 22:1-14, 1. Porsova-Dutoit et al., *Physiological Res.* 2000 49 (Suppl. 1):S43-S56, R. L. Jesse et al., *Ann. N.Y. Acad. Sci.* 1995 774:281-290, C. Chavis et al., *Steroids* 1982 39:129-147, M. Numazawa and Y. Osawa *Steroids* 1981 38:149-159, G. Flouret et al., *J. Med. Chem.* 1972 15:1281-1283 and A. A. Afanasii and Y. A. Titov, *Total Steroid Synthesis*, Plenum Press, New York, 1970, see, e.g., p 1-304.

U.S. Pat. Nos. 4,908,358 and 4,902,681 describe the capacity of compounds such as 5α-pregnan-3,20-dione, cortexolone, 17-hydroxyprogesterone and 16α-methylprogesterone to inhibit the clearance of antibody-coated cells from circulation in disorders such as immune thrombocytopenic purpura or immune hemolytic anemia.

U.S. Pat. Nos. 5,532,230, 5,686,438, 5,753,640 and 5811418 and J. Bratt and M. Heimburger, *Scand. J. Rheumatol.* 1999 28:308-313 describe the capacity of compounds such as prednisolone, and 3β-hydroxyandrost-5-ene-17-one to limit tissue damage in ischemic tissues by inhibiting adhesion of cells such as neutrophils to endothelial cells or to treat pulmonary hypertension.

U.S. Pat. No. 5,859,000 describes the capacity compounds such as 3β-hydroxyandrost-5-ene-17-one to reduce mast cell mediated allergic reactions.

U.S. Pat. Nos. 5,763,433 and 6,372,732 and PCT publication WO 96/35428 describe the capacity of certain androstane and androstene compounds such as 3β-hydroxyandrost-5-ene-17-one to treat certain immune disorder conditions such as systemic lupus erythematosus.

U.S. Pat. Nos. 5,925,630, 5,939,545 and 5962443 describe the capacity of 19-nur-pregnane steroids, 3α-hydroxy-5α-pregnan-20-one and related steroids to modulate certain neurological activities such as hypothalamic function and GABA receptor activity.

Other biological effects and/or metabolic conversions of steroid compounds have been described, e.g., Batta et al., *J. Biol. Chem.* 1986 25:127-133, Belli et al., *Liver* 1991 11:162-169, Bhattacharjee et al., *Anal. Biochem.* 1992 201:233-236, Blake et al., *Int. J. Peptide Protein Res.* 1982 20:97-101, 1986 25:127-133, Bonaventura, *Am. J. Obstet. Gynecol.* 1978 131: 403-409, Bucala et al., *J. Steroid Biochem.* 1986 25:127-133, Carey et al., *Biochem.* 1981 20:3637-3648, Chen et al., *Carcinogenesis* 1999 20:249-254, Chen et al., *Carcinogenesis* 1998 19:2187-2193, Chow et al., *Antisense Res. Dev.* 1994 4:81-86, Citro et al., *Dis. Colon Rectum* 1994 37(2 Suppl): S127-S132, Cleary, *Proc. Soc. Exp. Biol. Med.* 1991 196:8-16, Cleary, *Int. J. Biochem.* 1990 22:205-210, Crawford et al., *Lab. Invest.* 1994 71:42-51, Danenberg et al., *Antimicrob. Agents Chemother.* 1992 36:2275-2279, Dotzlaw et al., *Cancer Res.* 1999 59:529-532, Falany et al., *J. Steroid Biochem. Mol. Biol.* 1994 48:369-375, Faredin et al., *J. Investigative Dermatol.* 1969 52:357-361, Galigniana et al., *Mol. Pharmacol.* 1999 55:317-323, Goto et al., *J. Chromatogr.* 1983 276: 289-300, Grenot *Biochem.* 1992 31:7609-7621, Hofbauer et al., *Life Sci.* 1999 64:671-679, Huijghebaert et al., *J. Lipid Res.* 1986 27:742-752, Hurd et al., *Oncogene* 1999 18:1067-1072, Iida et al., *J. Lipid Res.* 1995 36:628-638, Jellinck et al., *Steroids* 1967 10:329-346, Jonsson et al., *J. Pediatr. Gastroenterol. Nutr.* 1995 20:394-402, Kalimi et al, *Mol. Cell. Biochem.* 1994 131:99-108, Kramer et al., *J. Biol. Chem.* 1994 269:10621-10627, LaRochelle et al., *Steroids* 1984 43: 209-217, Liao et al., *Carcinogenesis* 1998 19:2173-2180, Lillienau et al., *J. Clin. Invest.* 1992 89:420-431, Loria, *Psychoneuroendocrinology* 1997 22:S103-S108, Luscher et al *Mol. Immunol.* 1983 20:1099-1105, Manna et al., *J. Biol. Chem.* 1999 274:5909-5918, Marschall et al., *J. Biol. Chem.* 1989 264:12989-12993, Medh et al., *Cancer Res.* 1998 15:3684-3693, Mohan et al., *Steroids* 1992 57:244-247, Munoz de Toro et al., *J. Steroid Biochem. Mol. Biol.* 1998 67:333-339, Padgett et al., *J. Neuroimmunol.* 1998 84:61, Padgett et al., *Ann. N.Y. Acad. Sci.* 1995 774:323, Padgett et al., *J. Immunol.* 1994 153:1544-1552, Pashko et al., *Carcinogenesis* 1984 5:463-466, Pashko et al., *Carcinogenesis* 1981 2:717, Petrylak et al., *J. Clin. Oncology* 1999 17:958-967, Podesta et al., *Steroids* 1996 61:622-626, Regelson et al., *Ann. N.Y. Acad. Sci.* 1994 719:564, Schmassmann et al., *Gastroenterology* 1993 104:1171-1181, Schmassmann et al., *Hepatology* 1990 11:989-996, Schreiber et al., *Lancet* 353: 459-461, Schreiber, *Neth. J. Med.* 1998 53:S24-31, Schwartz et al., *Cancer Res.* 1988 48:4817, Shahidi et al., *Biochem. Biophys. Res. Commun.* 1999 254:559-565, Steer et al., *Ann. Rheum. Dis.* 1998 57:732-737, Suzuki et al., *Steroids* 1998 63:672-677, Suzuki et al., *Steroids* 1996 61:296-301, Swaan et al., *Bioconjugate Chem.* 1997 8:520-525, Tang et al, *Anti-cancer Drug Res.* 1998 13:815-824, Thomas et al., *J. Steroid Biochem.* 1986 25:103-108, Utsumi et al., *Cancer Res.* 1999 59:377-381, Vanden Heuvel, *J. Nutr.* 1999 129(2S Suppl.): 575S-580S, Wang et al., *Endocrinology* 1998 139:3903-3912, Wong et al., *J. Biol. Chem.* 1999 274:5443-5453, Xie et al., *Endocrinology* 1999 140:219-227, Yen et al., *Lipids* 1977 12:409-413, Zackheim et al., *Arch. Dermatology* 1998 134: 949-954, Zhang et al., *Biochim. Biophys. Acta* 1991 1096: 179-186, Zhu et al., *Carcinogenesis* 1988 19:2101-2106.

Some proteins such as interleukin-6 ("IL-6"), erythropoietin ("EPO") and thrombopoietin ("TPO") have been examined for their capacity to enhance various aspects hematopoiesis, e.g., *Hematology—Basic Principles and Practice*, 3rd edition, R. Hoffman, E. J. Benz Jr. et al., editors, Churchill Livingstone, N.Y., 2000 (see, e.g., Chapter 14 at pages 154-202), O. J. Borge et al., *Blood* 1996 88:2859-2870, M. Cremer et al., *Ann. Hematol.* 1999 78:401-407, Y. Sasaki et al., *Blood* 1999 94:1952-1960, U.S. Pat. No. 5,879,673. Recombinant IL-6 was shown in model systems to affect platelet counts in peripheral circulation, e.g., Stahl et al., *Blood* 1991 78:1467-1475, although significant toxicities are associated with its administration to humans, e.g., Andus et al., *FEBS Lett.* 1987 221:18, J. Gauldie et al., *P.N.A.S. U.S.A.* 1987 84:7251-7255, T. Geiger et al., *Eur. J. Immunol.* 1988 18:717-721. The IL-6 molecule has been described in detail, e.g., publication no. WO 88/00206. Administration of proteins is typically expensive, given factors such as the complexity of producing pharmaceutical grade material.

There is a current need for cost-effective pharmaceutical agents and treatment methods for treating various immune dysregulation conditions. The invention provides compounds that can be used in such treatments to treat or ameliorate one or more aspects of immune dysregulation conditions. Such agents can be used to treat autoimmune or inflammation conditions, immune suppression conditions, infections, blood cell deficiencies and other described conditions. The agents and methods are useful to ameliorate these conditions or one or more symptoms associated with any of these conditions. The use of these agents can be combined with one or more conventional treatments for these disorders.

DESCRIPTION OF THE INVENTION

Summary of Invention Embodiments

In principal embodiments the invention provides therapeutic treatment methods.

The methods include a method to prevent, treat, ameliorate or slow the progression of cystic fibrosis, sickle cell disease, neutropenia or thrombocytpoenia in a subject, or to treat a symptom of the cystic fibrosis, sickle cell disease, neutropenia or thrombocytopenia, comprising administering to a subject, or delivering to the subject's tissues, an effective amount of a formula 1 compound having the structure 5, 6, 7, 8, 9, 10, 11, 12, 13 or 14

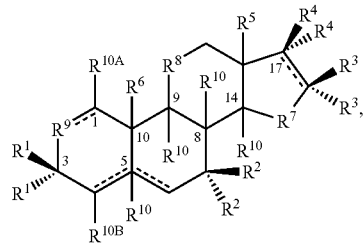

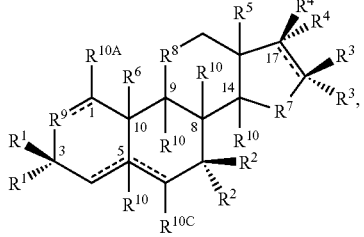

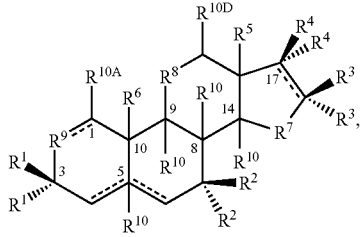

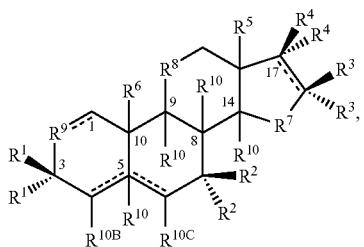

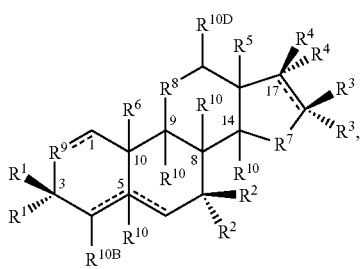

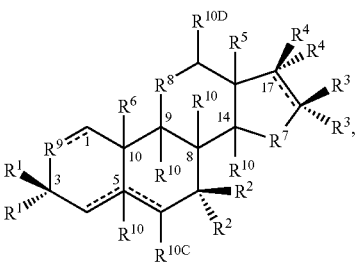

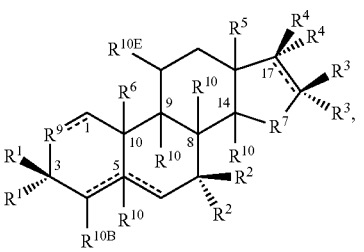

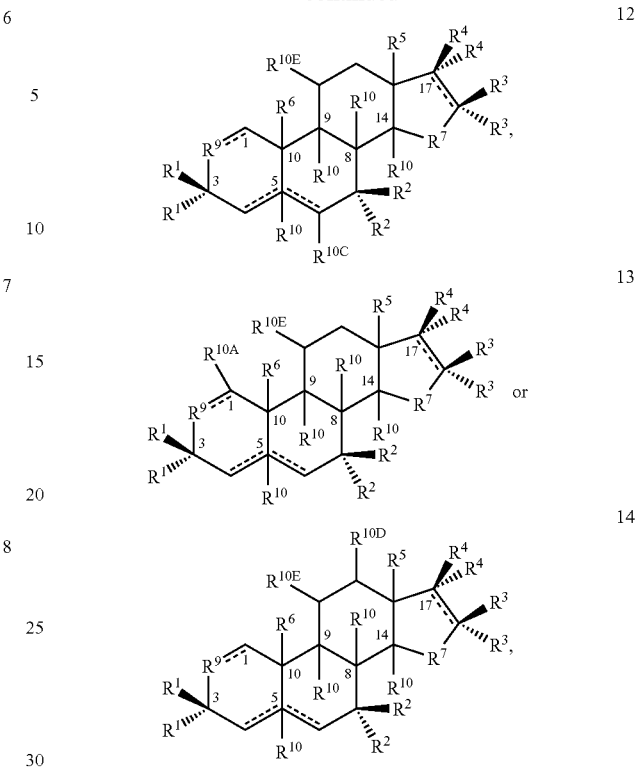

or a metabolic precursor or a metabolite thereof, wherein $R^{10}$ moieties at the 5 (if present), 8, 9 and 14 positions respectively are in the α,α,α,α, α,α,α,β, α,α,β,α, α,β,α,α, β,α,α,α, α,α,β,β, α,β,α,β, β,α,α,β, β,α,β,α, β,β,α,α, α,β,β,α, α,β,β,β, β,α,β,β, β,β,α,β, β,β,β,α or β,β,β,β configurations, wherein $R^{10A}$, $R^{10B}$, $R^{10C}$, $R^{10D}$ and $R^{10E}$ respectively are in the α,α, α,β, β,α or β,β configurations, wherein, each $R^1$, $R^2$, $R^3$, $R^4$, $R^5$, $R^6$, $R^{10}$, $R^{10A}$, $R^{10B}$, $R^{10C}$, $R^{10D}$ and $R^{10E}$ independently are —H, —OH, —OR$^{PR}$, —SR$^{PR}$, —N(R$^{PR}$)$_2$, —O—Si—(R$^{13}$)$_3$, —CHO, —CHS, —CN, —SCN, —NO$_2$, —NH$_2$, —COOH, —OSO$_3$H, —OPO$_3$H, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide, a polymer, or, one more of $R^1$, $R^2$, $R^3$, $R^4$, $R^5$, $R^6$, $R^{10}$, $R^{10A}$, $R^{10B}$, $R^{10C}$, $R^{10D}$ and $R^{10E}$ are =O, =S, =N—OH, =CH$_2$, =CH—CH$_3$, or an independently selected spiro ring and the hydrogen atom or the second variable group that is bonded to the same carbon atom is absent, or, one or more of two adjacent $R^1$-$R^6$, $R^{10}$, $R^{10A}$, $R^{10B}$, $R^{10C}$, $R^{10D}$ and $R^{10E}$ comprise an independently selected epoxide, acetal, a thioacetal, ketal or thioketal;

$R^7$ is —C(R$^{10}$)$_2$—, —C(R$^{10}$)$_2$—C(R$^{10}$)$_2$—, —C(R$^{10}$)$_2$—C(R$^{10}$)$_2$—C(R$^{10}$)$_2$—, —C(R$^{10}$)$_2$—O—C(R$^{10}$)$_2$—, —C(R$^{10}$)$_2$—S—C(R$^{10}$)$_2$—, —C(R$^{10}$)$_2$—NR$^{PR}$—C(R$^{10}$)$_2$—,

—O—, —O—C($R^{10}$)$_2$—, —S—, —S—C($R^{10}$)$_2$—, —$NR^{PR}$— or —$NR^{PR}$—C($R^{10}$)$_2$—;

$R^8$ and $R^9$ independently are —C($R^{10}$)$_2$—, —C($R^{10}$)$_2$—C($R^{10}$)$_2$—, —O—, —O—C($R^{10}$)$_2$—, —S—, —S—C($R^{10}$)$_2$—, —$NR^{PR}$— or —$NR^{PR}$—C($R^{10}$)$_2$—, or one or both of $R^3$ or $R^9$ independently are absent, leaving a 5-membered ring;

$R^{13}$ independently is $C_{1-6}$ alkyl; and $R^{PR}$ independently is —H or a protecting group. In typical embodiments, one or two of $R^{10A}$, $R^{10B}$, $R^{10C}$, $R^{10D}$ and $R^{10E}$ are not hydrogen or one $R^4$ is —NH$_2$, an optionally substituted amine, —N($R^{PR}$)$_2$, =NOH, =NO-optionally substituted alkyl, an amide or an N-linked amino acid.

Other embodiments include (1) certain new formula 1 compounds, which are new chemical entities, (2) compositions that comprise a formula 1 compound and another compound or an excipient, (3) formulations that comprise a formula 1 compound and 1, 2, 3, 4, 5, 6 or more excipients. The formulations can be designed for human pharmaceutical use or they can be suitable for veterinary use. Therapeutic use embodiments include (1) use of a formula 1 compound for the preparation of a medicament and (2) use of a formula 1 compound for the preparation of a medicament for the prophylaxis or treatment of a condition or symptom disclosed herein.

Other embodiments are as described elsewhere in the specification including the claims.

DEFINITIONS

As used herein and unless otherwise stated or implied by context, terms that are used herein have the meanings defined below. Unless otherwise contraindicated or implied, e.g., by including mutually exclusive elements or options, in these definitions and throughout this specification, the terms "a" and "an" mean one or more and the term "or" means and/or.

Reference to an androstane compound, e.g., 3β,16α,17β-trihydroxyandrostane, means that the hydrogen atom at the 5-position is in the α-configuration. For androstanes with hydrogen in the β-configuration, the compound name will specify this configuration, e.g., 3β,16α,17β-trihydroxy-5β-androstane.

An "invention formulation", "formulation", "pharmaceutical formulation" or the like means a composition that one can administer to a subject, e.g., human, mammal or other animal, without further manipulations that change the ingredients or the ingredient proportions that are present. Formulations will typically comprise a single formula 1 compound and one or more excipients. Formulations are suitable for human or veterinary applications and would typically have expected characteristics for the formulation, e.g., parenteral formulations for human use would usually be sterile and stored in a suitable closed container.

When referring to mixtures that contain a formula 1 compound, an "invention composition", "composition" or the like means a composition, that is a formulation or that can be an intermediate one can use, e.g., to make a formulation or a formula 1 compound. Compositions also include other types of mixtures, e.g., (1) reagents for assays or cells that are optionally contacted with a formula 1 compound or mixtures of compounds and (2) compounds used to make a formula 1 compound or by-products of formula 1 compound synthesis or analysis. Invention compositions include compositions where further processing may be required before it is a formulation, e.g., mixing or addition of a desired amount of an excipient.

Phrases such as "administration of a compound of formula 1", "treatment with a formula 1 compound", "use of a formula 1 compound" or similar terms mean that the compound(s) is administered to, contacted with or delivered to, the subject or to the subject's cells or tissues in vitro or in vivo by one or more suitable methods, e.g., in vivo delivery can be by an oral, topical, subcutaneous, parenteral, buccal or sublingual route.

Expressions such as "a formula 1 compound(s)", "a formula 1 compound" and the like mean invention compositions or formulations where one or more than one formula 1 compound is present, e.g., in a composition, or is used in the disclosed method, typically 1, 2, 3 or 4, usually 1. Any reference to a "formula 1 compound", "one or more compounds of formula 1" or the like means that the formula 1 compound can have the formula 2 structure or any other structure disclosed herein that is within the definition of formula 1 compounds. The phrase formula 1 compound or formula 1 compound(s) is sometimes abbreviated as "F1C" or "F1C(s)" and formula 1 compounds may be abbreviated as "F1Cs".

Reference to subject matter "as disclosed herein" such as a "therapeutic treatment or agent as disclosed herein", a "dosing protocol as disclosed herein" or a "clinical condition or symptom as disclosed herein" or the like means a treatment, agent, protocol, condition, symptom or the like that is described herein or in any reference that is cited herein.

An "excipient", "carrier", "pharmaceutically acceptable excipient", "pharmaceutically acceptable carrier" or similar terms mean one or more component(s) or ingredient(s) that is acceptable in the sense of being compatible with the other ingredients of invention compositions or formulations and not overly deleterious to the patient, animal, tissues or cells to which the F1C, composition or formulation is to be administered.

A "subject" means a human or animal. Usually the animal is a mammal or vertebrate such as a primate, rodent, lagomorph, domestic animal or game animal. Primates include chimpanzees, cynomologous monkeys, spider monkeys, and macaques, e.g., *Rhesus* or *Pan*. Rodents and lagomorphs include mice, rats, woodchucks, ferrets, rabbits and hamsters. Domestic and game animals include cows, horses, pigs, sheep, deer, bison, buffalo, mink, felines, e.g., domestic cat, canines, e.g., dog, wolf and fox, avian species, e.g., chicken, turkey, emu and ostrich, and fish, e.g., trout, catfish and salmon. Subject includes any subset of the foregoing, e.g., all of the above, but excluding one or more groups or species such as humans, primates or rodents. Other subsets of subjects include subjects of a given species or group of species of varying ages, e.g., young humans, e.g., about 1 week of age to about 9 years of age, adolescent humans, e.g., about 10-19 years of age, adult humans, e.g., about 20-100 years of age, and mature adult or elderly humans, e.g., at least about 55 years of age, at least about 60 years of age, at least about 65 years of age or a range of ages such as about 60-100 years of age. Thus, as used herein, prevention or treatment of a disease, condition or symptom may include or exclude any subset of subjects that are grouped by age.

The terms "effective amount", "effective dose" or the like with reference to a F1C(s) mean an amount of the F1C(s) that is sufficient to elicit a desired response, e.g., detectable restoration of normal immune responsiveness in an immunodeficient subject to which it is administered, e.g., a human, or to detectable modulation or amelioration of an immune or cellular parameter or a clinical condition or symptom. An effective amount, e.g., for human therapeutic use, may be a single dose or two or more subdoses of a F1C administered in one day, or it may be administered as multiple doses over a period of time, e.g., over 1, 2, 3, 4 or about 7 days to about 1 year.

Terms such as "use", "treat", "treatment", "address" or the like in the context of using the F1Cs in the treatment methods or other methods disclosed herein mean that a F1C is administered to a subject, delivered to the subject's tissues or contacted with tissues, cells or cell free systems in vivo or in vitro, e.g., as described herein or a reference cited herein. Typically such use or treatment results in, e.g., (1) detectable improvement in or amelioration of the condition or symptom being treated, (2) detectable modulation in the activity, level or numbers of a relevant biomolecule, therapeutic immune cell population or a pathological cell population, (3) slowing of the progression of a condition or delaying its onset, or reduction of the severity of a symptom(s) of the condition or (4) another detectable response as described herein. Any such amelioration may be transient, e.g., lasting for at least a few, e.g., about 1 to 24, hours or days, e.g., about 1, 2, 3, 4, 5, 6 or 7 days, or amelioration may be prolonged, e.g., lasting about 8, 9, 10, 11, 12, 13, 14, 15, 16, 17, 18, 19, 20, 21, 22, 24, 26, 28, 35, 42, 49, 56 to about 60 days or more, or amelioration may be permanent. A treatment may slow the progression of a disease or symptom or it may reduce the severity thereof, e.g., onset of a disease or a symptom may be delayed in at least some subjects for about 1-24 hours, about 2-10 days, about 2-30 days or for about 1-5 years compared to subjects who are not treated with sufficient amounts of the F1C. Thus, a F1C use or treatment typically results in detectable modulation in a relevant immune parameter such as modulation of the level, activity or relative amount of a target effector or suppressor immune cell population, interleukin, cytokine, chemokine, immunoglobulin compared to a suitable control, e.g., untreated. A F1C treatment can also cause modulation of the level or activity of a relevant transcription factor, enzyme, cell biological activity or level or activity of the etiological agent of the disease such as a pathogen, tumor cell or autoreactive immune cell subset. A treatment with a F1C may be used to delay or prevent the onset of a disease, symptom or complication or to ameliorate or slow the progression of a preexisting disease, condition, symptom or complication, or to facilitate elimination of a disease, condition, symptom or complication.

"Ameliorate", "amelioration", "improvement" or the like means a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with a F1C, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after a F1C is administered to a subject or is used in an assay or other method described herein or a cited reference, e.g., within about 1 hour of the administration or use of a F1C to about 3, 6, 9 months or more after a subject(s) has received a F1C.

The "modulation" of, e.g., a symptom, level or biological activity of a molecule, replication of a pathogen, cellular response, cellular activity or the like, means that the cell, level or activity, or the like is detectably increased or decreased. Such increase or decrease may be observed in treated subjects as compared to subjects not treated with a F1C, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after a F1C is administered to a subject or is used in an assay or other method described herein or a cited reference, e.g., within about 1 hour of the administration or use of a F1C to about 3, 6, 9 months or more after a subject(s) has received a F1C.

Terms such as "antigen", "immunogen", "antigenic fragment" or the like mean a molecule that comprises one or more epitopes that are capable of stimulating a subject's immune system to make, e.g., a secretory, humoral or cellular antigen-specific response against the antigen, immunogen or fragment. Antigenic fragments are synthetic or natural derivatives of natural or intact antigens or immunogens that retain at least a detectable capacity, e.g., at least about 10%, 20%, 30%, 40%, 50% or more of the native antigen's antigenic capacity, to stimulate a subject's immune system in a desired manner.

"Vaccine composition", "vaccine" or similar terms mean an agent suitable for stimulating a subject's immune system to ameliorate a current condition or to protect against or to reduce present or future harm or infection, e.g., reduced tumor cell proliferation or survival, reduced pathogen replication or spread in a subject or a detectably reduced unwanted symptom(s) associated with a condition. Vaccines may modulate, typically detectably enhance, humoral, cell mediated or innate immune responses.

"Immunization" means the process of inducing a detectable and continuing moderate or high level of antibody or cellular immune response that is directed against an antigen to which the subject has been exposed. Such responses are typically detectably maintained for at least about 3-48 months or more.

At various locations in the present disclosure, e.g., in any disclosed embodiments or in the claims, reference is made to compounds, compositions, formulations, or methods that "comprise" one or more specified components, elements or steps. Invention embodiments also specifically include those compounds, compositions, formulations or methods that are or that consist of or that consist essentially of those specified components, elements or steps. The terms "comprising", "consist of" and "consist essentially of" have their normally accepted meanings under U.S. patent law. For example, disclosed compositions or methods that "comprise" a component or step are open and they include or read on those compositions or methods plus an additional component(s) or step(s). Similarly, disclosed compositions or methods that "consist of" a component or step are closed and they would not include or read on those compositions or methods having appreciable amounts of an additional component(s) or an additional step(s).

"Alkyl" as used here means linked normal, secondary, tertiary or cyclic carbon atoms, i.e., linear, branched, cyclic or any combination thereof. Alkyl moieties, as used herein, may be saturated, or unsaturated, i.e., the moiety may comprise one, two, three or more independently selected double bonds or triple bonds. Unsaturated alkyl moieties include moieties as described for alkenyl and alkynyl moieties described below. The number of carbon atoms in an alkyl group or moiety can vary and typically is 1 to about 50, e.g., about 1-30 or about 1-20, unless otherwise specified, e.g., $C_{1-8}$ alkyl or C1-C8 alkyl means an alkyl moiety containing 1, 2, 3, 4, 5, 6, 7 or 8 carbon atoms. When an alkyl group is specified, species may include methyl, ethyl, 1-propyl (n-propyl), 2-propyl (i-propyl, —CH(CH$_3$)$_2$), 1-butyl (n-butyl), 2-methyl-1-propyl (i-butyl, —CH$_2$CH(CH$_3$)$_2$), 2-butyl (s-butyl, —CH(CH$_3$)CH$_2$CH$_3$), 2-methyl-2-propyl (t-butyl, —C(CH$_3$)$_3$), 1-pentyl (n-pentyl), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl, 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), cyclopropyl (—CH<CH$_2$CH$_2$), cyclobutyl (—CH<CH$_2$CH$_2$CH$_2$), cyclopentyl, cyclohexyl, cycloheptyl, cyclooctyl, —(CH$_2$)$_n$—(CHCH$_3$)$_m$—(CH$_2$)$_o$—CH$_3$, —(CH$_2$)$_n$—(CHC$_2$H$_5$)$_m$—(CH$_2$)$_o$—CH$_3$ and species and groups described below for alkenyl, alkynyl groups aryl groups, arylalkyl groups alkylaryl groups and the like, where n, m and o independently are 0, 1, 2, 3, 4, 5, 6, 7 or 8.

For any group or moiety described by a given range of carbon atoms, the designated range means that any individual number of carbon atoms is described. Thus, reference to, e.g., "C1-C4 optionally substituted alkyl", "$C_{2-6}$ alkenyl", or "C2-C6 optionally substituted alkenyl", specifically means that a 1, 2, 3 or 4 carbon optionally substituted alkyl moiety as defined herein is present, or a 2, 3, 4, 5 or 6 carbon alkenyl or optionally substituted alkenyl moiety as defined herein is present. All such designations are expressly intended to disclose all of the individual carbon atom groups and thus "C1-C4 optionally substituted alkyl" means, e.g., 3 carbon alkyl, 4 carbon substituted alkyl and the like are disclosed and can be expressly referred to or named.

"Alkenyl" as used here means a moiety that comprises linked normal, secondary, tertiary or cyclic carbon atoms, i.e., linear, branched, cyclic or any combination thereof, that comprises one or more double bonds (e.g., —CH═CH—), e.g., 1, 2, 3, 4, 5, 6 or more, typically 1 or 2. The number of carbon atoms in an alkenyl group or moiety can vary and typically is 2 to about 50, e.g., about 2-30 or about 2-20, unless otherwise specified, e.g., $C_{2-8}$ alkenyl or C2-8 alkenyl means an alkenyl moiety containing 2, 3, 4, 5, 6, 7 or 8 carbon atoms. When an alkenyl group is specified, species may include methylene (═CH$_2$), methylmethylene (═CH—CH$_3$), ethylmethylene (═CH—CH$_2$—CH$_3$), ═CH—CH$_2$—CH$_2$—CH$_3$, vinyl (—CH═CH$_2$), allyl, —(CH$_2$)$_n$—(CH═CH)—(CH$_2$)$_m$—CH$_3$, —(CH$_2$)$_n$—(CCH$_3$═CH)—(CH$_2$)$_m$—CH$_3$, —(CH$_2$)$_n$—(CH═CCH$_3$)—(CH$_2$)$_m$—CH$_3$ and —(CH$_2$)$_n$—(CH═CH)$_{0-1}$—(CH$_2$)$_m$—CH$_2$CH═CH$_2$, where n and m independently are 0, 1, 2, 3, 4, 5, 6, 7 or 8.

"Alkynyl" as used here means a moiety that comprises linked normal, secondary, tertiary or cyclic carbon atoms, i.e., linear, branched, cyclic or any combination thereof, that comprises one or more triple bonds (—C≡C—), e.g., 1, 2, 3, 4, 5, 6 or more, typically 1 or 2 triple bonds, optionally comprising 1, 2, 3, 4, 5, 6 or more double bonds, with the remaining bonds being single bonds. The number of carbon atoms in an alkenyl group or moiety can vary and typically is 2 to about 50, e.g., about 2-30 or about 2-20, unless otherwise specified, e.g., $C_{2-8}$ alkynyl or C2-8 alkynyl means an alkynyl moiety containing 2, 3, 4, 5, 6, 7 or 8 carbon atoms. When an alkynyl group is specified, groups and species may include —CCH, —CCCH$_3$, —CCCH$_2$CH$_3$, —CCC$_3$H$_7$, —CCCH$_2$C$_3$H$_7$, —(CH$_2$)$_n$—(C≡C)—(CH$_2$)$_m$—CH$_3$, and —(CH$_2$)$_n$—(C≡C)$_{0-1}$—(CH$_2$)$_m$—CH$_2$C═CH, where n and m independently are 0, 1, 2, 3, 4, 5, 6, 7 or 8.

"Aryl" means an aromatic ring or fused ring system with no ring heteroatoms, e.g., phenyl or naphthyl.

"Arylalkyl" means a moiety where an alkyl group is bonded to an aryl group, i.e., -alkyl-aryl, where alkyl and aryl groups are as described above, e.g., —CH$_2$—C$_6$H$_5$ or —CH$_2$CH(CH$_3$)—C$_6$H$_5$.

"Alkylaryl" means a moiety where an aryl group is bonded to an alkyl group, i.e., -aryl-alkyl, where aryl and alkyl groups are as described above, e.g., —C$_6$H$_4$—CH$_3$ or —C$_6$H$_4$—CH$_2$CH(CH$_3$).

"Substituted alkyl", "substituted alkenyl", "substituted alkynyl", substituted alkylaryl", "substituted arylalkyl", "substituted heterocycle", "substituted aryl", "substituted monosaccharide" and the like mean an alkyl, alkenyl, alkynyl, alkylaryl, arylalkyl heterocycle, aryl, monosaccharide or other group or moiety as defined or disclosed herein that has a substituent(s) that replaces a hydrogen atom(s) or a substituent(s) that interrupts a carbon atom chain. Substituted heterocycles may thus have a substituent bonded to a ring carbon or a ring heteroatom such as a nitrogen. Substituents for any of these moieties include 1, 2, 3, 4, 5, 6, 7, 8, 9, or 10 or more independently selected —O—, —S—, —NH—, —C(O)—, —C(O)OH, —C(O)OR$^{154}$, C(O)OR$^{PR}$, C(O)SR$^{154}$, C(O)S-R$^{PR}$, CHO, —CHS, —CH$_2$SH, —C═N—, —OH, ═O, —OR$^{154}$, —OR$^{PR}$, —C(O)OR$^{PR}$, —O—C(O)H, —C(O)CH$_3$, —C(S)CH$_3$, —C(S)SH, C(S)SR$^{154}$, C(S)SR$^{PR}$, C(O)CH$_2$OH, —C(O)CH$_2$F, —C(O)CH$_2$Cl, —C(O)CH$_2$Br, —C(O)CH$_2$I, —C(O)CF$_2$H, —C(O)CF$_3$, —C(O)NHCH$_3$, —C(O)NHC$_2$H$_5$, —C(O)NHC(CH$_3$)$_3$, —O—CH$_2$—C(O)—C(CH$_3$)$_3$, —C(O)—C(CH$_3$)$_3$, —O—CH(CH$_3$)—O—C(CH$_3$)$_3$, —C(O)O—, C(S)OR$^{PR}$, —C(S)O—, —OC(O)—, —C(O)H, —OCH$_2$—, —CH$_2$—O—CH$_2$—, —(CH$_2$)$_{1-2}$—O—(CH$_2$)$_2$, —OCH$_2$CH$_2$—, —OCH$_2$O—, —OCH$_2$CH$_2$O—, —CH$_2$OH, —CH$_2$F, —CHF$_2$, —CF$_3$, —CH$_2$Cl, —CH$_2$Br, —CH$_2$I, —C$_2$H$_4$Cl, —C$_2$H$_4$Br, —C$_2$H$_4$I, —CH$_2$CH$_2$F, —CH$_2$CHF$_2$, —CH$_2$CF$_3$, —NH$_2$, —NHR$^{154}$, —N(R$^{154}$)$_2$, —N(R$^{PR}$)$_2$, —NHR$^{PR}$, —NHC(O)—, —CH$_2$—NR$^{PR}$, —CH$_2$—NHR$^{PR}$, —CH$_2$—NHC(O)—, —C(O)NH—, —C(O)NHR$^{PR}$, —OC(O)NR$^{PR}$—, —OC(O)NHR$^{PR}$, —C(═NH)—NH$_2$, —C(═NH)OH, —C(═N—NH$_2$)OH, —C(O)NHOH, ═NOH, ═NOCH$_3$, ═NOC$_2$H$_5$, ═NOC$_3$H$_7$, ═NOC$_4$H$_9$, —NHR$^{154}$, ═NR$^{154}$, ═N—, —NR$^{PR}$C(O)NR$^{PR}$—, —NR$^{PR}$C(O)NHR$^{PR}$, —NR$^{PR}$CH$_2$—, —NR$^{PR}$CH$_2$CH$_2$—, —NO$_2$, —ONO$_2$, —S—, —SH, —SR$^{154}$, —SR$^{PR}$, ═S, —S(O)R$^{154}$, —S(O)OR$^{154}$, —S(O)—, —S(O)(O)—, —O—S(O)(O)—NR$^{PR}$—, —O—S(O)(O)—NR$^{PR}$—CH$_2$—, —CH$_2$—S(O)(O)H, —CH$_2$—NH—S(O)(O)H, —CHR$^{154}$, —NH—S(O)(O)H, —O—S(O)(O)—CHR$^{154}$—, —CH, R$^{154}$—O—S(O)(O)—, —CHR$^{154}$—S(O)(O)—CHR$^{154}$—, —S(O)(O)H, —CHR$^{154}$—S(O)(O)H, —NH—S(O)(O)—NH—, —CHR$^{154}$—NH—S(O)(O)—NH—, —CHR$^{154}$—NH—S(O)(O)—NH—CHR$^{154}$, —NH—S(O)(O)—NHR$^{PR}$, —NH—S(O)(O)—NH$_2$, —NH—S(O)(O)—NHCH$_3$, —NH—S(O)—NH—, —CHR$^{154}$—NH—S(O)—NH—, —CHR$^{154}$—NH—S(O)—NH—CHR$^{154}$, —NH—S(O)—

NHR$^{PR}$, —NH—S(O)—NH$_2$, —NH—S(O)—NHCH$_3$, —NH—S(O)—, —CHR$^{15A}$—NH—S(O)—, —NH—S(O)—CHR$^{15A}$, —S(O)—NHR$^{PR}$, —S(O)—NH$_2$, —S(O)—NHCH$_3$, —S(O)(O)—O—, —S(O)OR$^{PR}$, —S(O)(O)OH, —OSO$_3$H$_2$, —S(O)(O)OR$^{15A}$, —S(O)(O)OR$^{PR}$, —S(O)OH, —S(O)OR$^{15A}$, —S(O)OR$^{PR}$, —S(O)R$^{15A}$, —S(O)R$^{PR}$, —CN, —SCN, —C(O)OH, —C(O)OR$^{15A}$, —C(O)OR$^{PR}$, —C(O)SH, —C(O)SR$^{15A}$, —C(O)SR$^{PR}$, —C(S)OH, —C(S)OR$^{15A}$, —C(S)OR$^{PR}$, —O—P(O)(O)OH, —O—P(O)(O)OR$^{15A}$, —O—P(O)(O)OR$^{15A}$, —O—P(S)(O)OH, —O—P(S)(O)OR$^{15A}$, —O—P(S)(O)OR$^{PR}$, —O—P(O)(O)SH, —O—P(O)(O)SR$^{15A}$, —P(O)(O)SR$^{PR}$, —F, —Cl, —Br, —I, —C≡NH, —C≡NCH$_3$, —C≡NC$_2$H$_5$, —C(=S)—, —C$_6$H$_5$, —CH$_2$C$_6$H$_5$, —O-A8, —S-A8, —C(O)-A8, —OC(O)-A8, —C(O)O-A8, —OPO$_3$(R$^{PR}$)$_2$, -amino acid-, —O-monosaccharide, —O-disaccharide, —S-monosaccharide, —S-disaccharide, a polymer, e.g., a PEG, and combinations of these moieties and salts on any of these moieties that can form a salt, where each R$^{PR}$ independently is —H, an independently selected protecting group or both R$^{PR}$ together are a protecting group, A8 is C1-C10 optionally substituted alkyl, and R$^{15A}$ independently are —H, —CH$_3$, —C$_2$H$_5$, —C$_3$H$_7$, —C$_4$H$_9$, —C(CH$_3$)$_3$, —CH$_2$OH, —C$_2$H$_4$OH, —C$_3$H$_6$OH, —C$_4$H$_8$OH —C(CH$_2$OH)(CH$_3$)$_2$, —C$_3$H$_5$, —C$_4$H$_7$, optionally substituted C1-10 alkyl, C1-10 perfluoroalkyl, optionally substituted aryl, optionally substituted C1-12 alkylaryl, optionally substituted C1-12 arylalkyl, optionally substituted allyl, optionally substituted heterocycle, optionally substituted C1-4 alkyl-optionally substituted heterocycle or optionally substituted heterocycle-optionally substituted C1-4 alkyl. Substituents are independently chosen when more than one is present. Alkenyl and alkynyl groups that comprise a substituent(s), are optionally substituted at a carbon that is one or more methylene moiety removed from the double bond, e.g., the substituent is optionally separated by one, two, three or more independently selected —CH$_2$—, —CH(C$_{1-6}$ optionally substituted alkyl)-, —CH(C$_{1-6}$ optionally substituted alkenyl)-, —CH(C$_{1-6}$ optionally substituted alkynyl)-, —CH(optionally substituted heterocycle)-, —CH(optionally substituted aryl-optionally substituted alkyl)- or —CH(optionally substituted alkyl-optionally substituted aryl)-moieties. Other substituted alkenyl and alkynyl moieties include =CHOH, =CH-halogen, =CH—COOR$^{PR}$, =CH—(CH$_2$)$_m$—NH$_2$, =CH—(CH$_2$)$_m$—NH(C1-C6 alkyl), =CH—N(C1-C6 alkyl)$_2$, =CH—CH$_2$OH, =CH—CH$_2$-halogen, =CH—CH$_2$—COOR$^{PR}$, =CH—CH$_2$—NH$_2$, =CH—CH$_2$—NH(C1-C6 alkyl), =CH—CH$_2$—N(C1-C6 alkyl)$_2$, =CH—CH$_2$—CH$_2$OH, =CH—CH$_2$—CH$_2$-halogen, =CH—CHOH—CH$_3$, =CH—CHOH—CH$_2$—CH$_3$, =CH—CH$_2$—CH$_2$—COOR$^{PR}$, =CH—CH$_2$—CH$_2$—NH$_2$, =CH—CH$_2$—CH$_2$—N(C1-C4 alkyl)$_2$, —CH=CH—(CH$_2$)$_m$—OH, —CH=CH-halogen, —CH=CH—CH$_2$OH, —CH=CH—CH$_2$-halogen, —C≡C-halogen, —C≡C—CH$_2$—NH$_2$, —C≡C—CH$_2$—NH(C1-C6 alkyl), —C≡C—CH$_2$—N(C1-C6 alkyl)$_2$, —C≡C—OH, —C≡C—CO-OR$^{PR}$, —C≡C—CH$_2$-halogen, —C≡C—CH$_2$—OH and —C≡C—CH$_2$—COOR$^{PR}$, where each alkyl moiety is the same or different, e.g., both are methyl, ethyl or propyl or one is methyl and the other is ethyl, propyl or butyl and m is 1, 2, 3 or 4. The organic moieties and substitutions described here, and for other any other moieties described herein, usually will exclude obviously unstable moieties, e.g., —O—O—, except where such unstable moieties are transient species that one can use to make a compound such as a F1C with sufficient chemical stability for the one or more of the uses described herein.

"Heterocycle" or "heterocyclic" includes by way of example and not limitation the heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 1960, 82:5566. Heterocycles are typically bonded to the steroid nucleus through a carbon, nitrogen or sulfur atom in the heterocycle ring.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Typically, nitrogen bonded heterocycles include 1-aziridyl, 1-azetedyl, 1-pyrrolyl, 1-imidazolyl, 1-pyrazolyl, and 1-piperidinyl.

"Heteroaryl" means an aromatic ring or two or more fused rings that contain one or more aromatic rings where the ring or fused rings comprise 1, 2, 3 or more heteroatoms, usually oxygen (—O—), nitrogen (—NX—) or sulfur (—S—) where X is —H, a protecting group or C$_{1-6}$ optionally substituted alkyl, usually —H. Examples are as described for heterocycle.

"Alcohol" as used herein means an alcohol that comprises a C$_{1-12}$ alkyl moiety substituted at a hydrogen atom with one hydroxyl group. Alcohols include methanol, ethanol, n-propanol, i-propanol, n-butanol, i-butanol, s-butanol, t-butanol, n-pentanol, i-pentanol, n-hexanol, cyclohexanol, n-heptanol, n-octanol, n-nonanol and n-decanol. The carbon atoms in alcohols can be straight, branched or cyclic. Alcohol includes any subset of the foregoing, e.g., $C_{1-4}$ alcohols (alcohols having 1, 2, 3 or 4 carbon atoms).

"Halogen" means fluorine, chlorine, bromine or iodine.

"Protecting group" means a moiety that prevents or reduces the atom or functional group to which it is linked from participating in unwanted reactions. For example, for —$OR^{PR}$, $R^{PR}$ may be hydrogen or a protecting group for the oxygen atom found in a hydroxyl, while for —$C(O)$—$OR^{PR}$, $R^{PR}$ may be hydrogen or a carboxyl protecting group, for —$SR^{PR}$, $R^{PR}$ may be hydrogen or a protecting group for sulfur in thiols for instance, and for —$NHR^{PR}$ or —$N(R^{PR})_2$—, $R^{PR}$ may be hydrogen or a nitrogen atom protecting group for primary or secondary amines. Hydroxyl, amine, ketones and other reactive groups are found in F1Cs at, e.g., $R^1$ or $R^2$. These groups may require protection against reactions taking place elsewhere in the molecule. The protecting groups for oxygen, sulfur or nitrogen atoms are usually used to prevent unwanted reactions with electrophilic compounds, such as acylating agents used, e.g., in steroid chemistry.

"Ester" means a moiety that contains a —$C(O)$—$O$— structure. Typically, esters as used here comprise an organic moiety containing about 1-50 carbon atoms (e.g., about 2-20 carbon atoms) and 0 to about 10 independently selected heteroatoms (e.g., O, S, N, P, Si), where the organic moiety is bonded to a formula 1 steroid nucleus at, e.g., $R^1$ or $R^2$ through the —$C(O)$—$O$— structure, e.g., organic moiety-C(O)—O-steroid or organic moiety-O—C(O)-steroid. The organic moiety usually comprises one or more of any of the organic groups described herein, e.g., $C_{1-20}$ alkyl moieties, $C_{2-20}$ alkenyl moieties, $C_{2-20}$ alkynyl moieties, aryl moieties, $C_{2-9}$ heterocycles or substituted derivatives of any of these, e.g., comprising 1, 2, 3, 4 or more substituents, where each substituent is independently chosen. Exemplary substitutions for hydrogen or carbon atoms in these organic groups are as described above for substituted alkyl and other substituted moieties. Substitutions are independently chosen. The organic moiety includes compounds defined by the $R_4$ variable. The organic moieties exclude obviously unstable moieties, e.g., —O—O—, except where such unstable moieties are transient species that one can use to make a compound with sufficient chemical stability for one or more of the uses described herein, including for synthesis of the formula 1 or other compounds. The substitutions listed above are typically substituents that one can use to replace one or more carbon atoms, e.g., —O— or —C(O)—, or one or more hydrogen atom, e.g., halogen, —$NH_2$ or —OH. Exemplary esters include one or more independently selected acetate, enanthate, propionate, isopropionate, isobutyrate, butyrate, valerate, caproate, isocaproate, hexanoate, heptanoate, octanoate, nonanoate, decanoate, undecanoate, phenylacetate or benzoate, which are typically hydroxyl esters.

"Thioester" means a moiety that comprises a —$C(O)$—$S$— structure. Typically, thioesters as used here comprise an organic moiety containing about 1-50 carbon atoms (e.g., about 1-20 carbon atoms) and 0 to about 10 independently selected heteroatoms (e.g., O, S, N, P, Si), where the organic moiety is bonded to a formula 1 steroid nucleus at a variable group such as $R^1$, $R^2$, $R^3$, $R^4$ or $R^{10}$ through the —$C(O)$—$S$— structure, e.g., organic moiety-C(O)—S-steroid or organic moiety-S—C(O)-steroid. The organic moiety is as described above for esters.

"Thionoester" means a moiety that comprises a —$C(S)$—$O$— structure. Typically, thionoesters as used here comprise an organic moiety containing about 1-50 carbon atoms (e.g., about 1-20 carbon atoms) and 0 to about 10 independently selected heteroatoms (e.g., O, S, N, P, Si), where the organic moiety is bonded to a formula 1 steroid nucleus at a variable group such as $R^1$, $R^2$, $R^3$, $R^4$ or $R^{10}$ through the —$C(S)$—$O$— structure, e.g., organic moiety-C(S)—O-steroid or organic moiety-O—C(S)-steroid. The organic moiety is as described above for esters.

"Acetal", "thioacetal", "ketal", "thioketal" "spiro ring" and the like mean a cyclic organic moiety that is bonded to a steroid ring atom in the F1Cs, e.g., steroid nucleus atoms at one, two or more of the 1, 2, 3, 4, 6, 7, 11, 12, 15, 16, 17, 18 or 19 positions. Typically, acetals comprise an organic moiety containing about 1-20 carbon atoms (e.g., about 1-10 carbon atoms) and 0 to about 10 independently selected heteroatoms (e.g., O, S, N, P, Si). For acetals (or ketals), the steroid nucleus atoms are usually carbons and the acetal is bonded to a steroid carbon through two oxygen atoms. Thioacetals (or thioketals) are bonded to the steroid nucleus through one oxygen and one sulfur atom or, more often, through two sulfur atoms. One, two or more of e.g., $R^1$, $R^2$, $R^3$, $R^4$, $R^{10}$ at the 2, 11 or 15 positions, $R^{10A}$, $R^{10B}$, $R^{10C}$ and $R^{10D}$, may be an independently selected acetal, thioacetal or spiro ring in any of the F1Cs disclosed herein. The oxygen or sulfur atoms in ketals and thioketals are linked by an optionally substituted alkyl moiety. Typically the alkyl moiety is an optionally substituted C1-C6 alkylene or branched alkyl structure such as —$C(CH_3)_2$—, —$CH(CH_3)$—, —$CH_2$—, —$CH_2$—$CH_2$—, —$C[(C2\text{-}C4\ alkyl)_2]_{1,\ 2,\ 3}$- or —$[CH(C2\text{-}C4\ alkyl)]_{1,\ 2,\ 3}$—. Acetals include moieties having the structure —O—[C$(R^{36})_2]_{1-6}$—O—, —O—$CH_2$—[C$(R^{36})_2]_2$—O—, —O—$CH_2$—$CH_2$—[C$(R^{36})_2]_2$—O—, —O—$CH_2$—[C$(R^{36})_2]_2$—$CH_2$—O—, and —O—$CH_2$—$C(R^{36})_2$—O—, where each $R^{36}$ independently is —H, —OH, =O, =S, —SH, —F, —Cl, —Br, —I or an organic moiety such as C1-C6 alkyl (e.g., methyl, ethyl, hydroxymethyl or halomethyl), C2-C6 alkenyl, C2-C6 alkenyl, aryl or an heterocycle, any of which are optionally substituted, e.g., —$CF_3$ or —$CH_2OH$. In some of these embodiments, one $R^{36}$ is —H and the other is another atom or moiety, e.g., —OH, methyl or a halogen. In other embodiments, neither $R^{36}$ is —H, e.g., both are methyl. Thioacetals include moieties that comprise a —S—[C$(R^{36})_2]_{1-6}$—O— or —S—[C$(R^{36})_2]_{1-6}$—S— structure where the open valences are bonded to the same carbon on the steroid nucleus. Typically, thioacetals as used here comprise an organic moiety containing about 1-50 carbon atoms (e.g., about 2-20 carbon atoms) and 0 to about 10 independently selected heteroatoms (e.g., O, S, N, P, Si), where the organic moiety is bonded to a formula 1 steroid nucleus at variable groups such as $R^1$, $R^2$, $R^3$, $R^4$ or $R^{10}$ through the —S—[C$(R^{36})_2]_m$—O— or —S—[C$(R^{36})_2]_m$—S— structure, e.g., 17-steroid-S—[C$(R^{36})_2]_m$—O-17-steroid, 17-steroid-S—$CH_2$—$CH_2$—O-17-steroid, 17-steroid-O—[C$(R^{36})_2]_m$—S-17-steroid, 17-steroid-S—[C$(R^{36})_2]_m$—S-17-steroid, 17-steroid-S—[C$(R^{36})_2]_m$—O-17-steroid, where m is 1, 2, 3, 4, 5 or 6. The organic moiety is as described above for esters. Other exemplary acetal and thioacetals are —O—$C(CH_3)_2$—O—, —O—$CH_2$—$CH_2$—$CH_2$—O—, —O—$CH_2$—$CH_2$—O—, —O—$CH_2$—O—, —O—$C(CH_3)$(heterocycle)-O—, —O—CH (heterocycle)-O—, —O—$C(CH_3)$(aryl)-O—, —O—CH (aryl)-O—, —S—$C(CH_3)_2$—O—, —S—$C(CH_3)_2$—S—, —S—$CH_2$—$CH_2$—O—, —S—$CH_2$—$CH_2$—S—, —S—$CH_2$—O—, —S—$CH_2$—S—, —O—$C(CH_3)_2$—$CH_2$—O—, —O—$C(CH_3)_2$—$C(CH_3)_2$—O—, —S—$C(CH_3)_2$—$CH_2$—O— and —O—C ($CH_3$)$_2$—$CH_2$—S—. Some of these moieties can serve as protecting groups for a ketone or hydroxyl, e.g., acetals such as —O—$CH_2$—$CH_2$—$CH_2$—O— or —O—$CH_2$—$CH_2$—O— for ketones, which form a spiro ring that can be removed by chemical synthesis methods or by metabolism in cells or biological fluids. For any spiro ring disclosed herein and unless otherwise specified, the $1^{st}$ and $2^{nd}$ open valences can be bonded to the carbon in the steroid nucleus in the α- and β-configurations respectively or in the α- and β-configurations respectively. For example, in a spiro —NH—$CH_2$—$CH_2$—O— structure, the $1^{st}$ open valence, i.e., at the nitrogen atom, can be, e.g., at the 17-position in the β-configuration and the $2^{nd}$ open valence, i.e., at the oxygen, would then be in the α-configuration.

"Phosphoester" or "phosphate ester" means a moiety that comprises a —O—P(OR$^{PR}$)(O)—O— structure where R$^{PR}$ is hydrogen (—H), a protecting group or an organic moiety as described for esters. Typically, phosphoesters as used here comprise a hydrogen atom, a protecting group or an organic moiety containing about 1-50 carbon atoms and 0 to about 10 independently selected heteroatoms (e.g., O, S, N, P, Si) linked to a formula 1 steroid nucleus at a variable group such as $R^1$-$R^6$, $R^{10}$, $R^{15}$, $R^{17}$ or $R^{18}$ through the —O—P(O)(O)—O— structure, e.g., organic moiety-O—P(O)(OH)—O-steroid. The organic moiety is as described above for esters. Exemplary phosphoesters include —O—P(O)(OH)—O—$CH_3$, —O—P(O)(O$CH_3$)—O—$CH_3$, —O—P(O)(OH)—O—$CH_2$—$CH_3$, —O—P(O)(O$C_2H_5$)—O—$CH_2$—$CH_3$, —O—P(O)(OH)—O—$CH_2$—$CH_2$—$CH_3$, —O—P(O)(OH)—O—CH($CH_3$)—$CH_3$, —O—P(O)(OH)—O—$CH_2$—$CH_2$—$CH_2$—$CH_3$, —O—P(O)(O($CH_3$)$_3$)—O—C($CH_3$)$_3$ and —O—P(O)(OH)—O—C($CH_3$)$_3$.

"Phosphothioester" means a moiety that comprises a —O—P(SR$^{PR}$)(O)—O— structure where R$^{PR}$ is —H, a protecting group or an organic moiety as described for esters. Typically, phosphothioesters as used here comprise a hydrogen atom, a protecting group or an organic moiety containing about 1-50 carbon atoms and 0 to about 10 independently selected heteroatoms (e.g., O, S, N, P, Si) linked to a formula 1 steroid nucleus at a variable group such as $R^1$-$R^6$, $R^{10}$, $R^{15}$, $R^{17}$ or $R^{18}$ through the —O—P(O)(O)—O— structure, e.g., organic moiety-O—P(O)(SH)—O-steroid. The organic moiety is as described above for esters. Exemplary phosphothioesters are as described for phosphoesters, except that sulfur replaces the appropriate oxygen atom.

"Phosphonoester" means a moiety that comprises a —P(OR$^{PR}$)(O)— structure where R$^{PR}$ is —H, a protecting group or an organic moiety as described for esters. Typically, phosphonoesters as used here comprise a hydrogen atom, a protecting group or an organic moiety containing about 1-50 carbon atoms and 0 to about 10 independently selected heteroatoms (e.g., O, S, N, P, Si) linked to a formula 1 steroid nucleus at a variable group such as $R^1$-$R^6$, $R^{10}$, $R^{15}$, $R^{17}$ or $R^{18}$ through the —P(OR$^{PR}$)(O)—O— structure, i.e., organic moiety-P(OR$^{PR}$)(O)—O-steroid or steroid-P(OR$^{PR}$)(O)—O-organic moiety. The organic moiety is as described above for esters.

"Phosphiniester" means a moiety that comprises a —P(O)H— structure where R$^{PR}$ is —H, a protecting group or an organic moiety as described for esters. Typically, phosphiniesters as used here comprise a hydrogen atom, a protecting group or an organic moiety containing about 1-50 carbon atoms and 0 to about 10 independently selected heteroatoms (e.g., O, S, N, P, Si) linked to a formula 1 steroid nucleus at a variable group such as $R^1$-$R^6$, $R^{10}$, $R^{15}$, $R^{17}$ or $R^{18}$ through the —P(O)H— structure, i.e., organic moiety-P(O)H-steroid or steroid-P(O)H-organic moiety. The organic moiety is as described above for esters.

"Sulfate ester" means a moiety that comprises a —O—S(O)(O)—O— structure. Typically, sulfate esters as used here comprise a hydrogen atom, a protecting group or an organic moiety containing about 1-50 carbon atoms and 0 to about 10 independently selected heteroatoms (e.g., O, S, N, P, Si) linked to a formula 1 steroid nucleus at a variable group such as $R^1$-$R^6$, $R^{10}$, $R^{15}$, $R^{17}$ or $R^{13}$ through the —O—S(O)(O)—O— structure, e.g., organic moiety-O—S(O)(O)—O-steroid. The organic moiety is as described above for esters.

"Sulfite ester" means a moiety that comprises a —O—S(O)—O— structure. Typically, sulfite esters as used here comprise an organic moiety containing about 1-50 carbon atoms and 0 to about 10 independently selected heteroatoms (e.g., O, S, N, P, Si) linked to a formula 1 steroid nucleus at a variable group such as $R^1$-$R^6$, $R^{10}$, $R^{15}$, $R^{17}$ or $R^{18}$ through the —O—S(O)—O— structure, e.g., organic moiety-O—S(O)—O-steroid. The organic moiety is as described above for esters.

"Sulfamate ester", "sulfamate derivative", "sulfamate" and the like mean a moiety that comprises a —O—S(O)(O)—NH— or —O—S(O)(O)—$NH_2$ structure. Typically, sulfamate derivatives as used here comprise an organic moiety containing about 1-50 carbon atoms and 0 to about 10 independently selected heteroatoms (e.g., O, S, N, P, Si) linked to a formula 1 steroid nucleus at a variable group such as $R^1$-$R^6$, $R^{10}$, $R^{15}$, $R^{17}$ or $R^{18}$ through a suitable structure such as —O—S(O)(O)—NH—, e.g., organic moiety-O—S(O)(O)—NH-steroid, steroid-O—S(O)(O)—NH-organic moiety or steroid-O—S(O)(O)—$NH_2$. The organic moiety is as described above for esters.

"Sulfamide" and the like mean a moiety that comprises a —NH—S(O)(O)—NH— or —NH—S(O)(O)—$NH_2$ structure. Typically, sulfamide moieties comprise an organic moiety containing about 1-50 carbon atoms and 0 to about 10 independently selected heteroatoms (e.g., O, S, N, P, Si) linked to a formula 1 steroid nucleus at a variable group such as $R^1$-$R^6$, $R^{10}$, $R^{15}$, $R^{17}$ or $R^{18}$ through a suitable structure such as —NH—S(O)(O)—NH—, e.g., steroid-NH—S(O)(O)—NH-organic moiety, steroid-NH—S(O)(O)—$NH_2$, steroid-NH—S(O)(O)—NHR$^{PR}$ or steroid-NH—S(O)(O)—N(R$^{PR}$)$_2$, where R$^{PR}$ independently or together are a protecting group such as C1-C8 optionally substituted alkyl. The organic moiety is as described above for esters.

"Sulfinamide" and the like mean a moiety that comprises a —C—S(O)—NH— structure. Typically, sulfinamide moieties comprise an organic moiety containing about 1-50 carbon atoms and 0 to about 10 independently selected heteroatoms (e.g., O, S, N, P, Si) linked to a formula 1 steroid nucleus at a variable group such as $R^1$-$R^6$, $R^{10}$, $R^{15}$, $R^{17}$ or $R^{18}$ through a suitable structure such as steroid-S(O)—NH-organic moiety, steroid-NH—S(O)-organic moiety, steroid-S(O)—$NH_2$, steroid-S(O)—NHR$^{PR}$ moiety or steroid-S(O)—N(R$^{PR}$)$_2$, where R$^{PR}$ independently or together are a protecting group such as C1-C8 optionally substituted alkyl. The organic moiety is as described above for esters.

"Sulfurous diamide" and the like mean a moiety that comprises a —NH—S(O)—NH— or —NH—S(O)—$NH_2$ structure. Typically, sulfurous diamide moieties comprise an organic moiety containing about 1-50 carbon atoms and 0 to about 10 independently selected heteroatoms (e.g., O, S, N, P, Si) linked to a formula 1 steroid nucleus at a variable group such as $R^1$-$R^6$, $R^{10}$, $R^{15}$, $R^{17}$ or $R^{18}$ through a suitable structure such as —C—NH—S(O)—NH—C— or —$CH_2$—NH—S(O)—NH—$CH_2$—, e.g., steroid-NH—S(O)—NH-organic moiety, steroid-NH—S(O)—NH$_2$, steroid-NH—S(O)—NHR$^{PR}$ or steroid-NH—S(O)—N(R$^{PR}$)$_2$, where R$^{PR}$ independently or together are a protecting group such as C1-C8 optionally substituted alkyl. The organic moiety is as described above for esters.

"Sulfonate ester", "sulfonate derivative", "sulfonate" and the like mean a moiety that comprises a —O—S(O)(O)— or —S(O)(O)—O— structure. Typically, sulfonate derivatives comprise an organic moiety containing about 1-50 carbon atoms and 0 to about 10 independently selected heteroatoms (e.g., O, S, N, P, Si) linked to a formula 1 steroid nucleus at a variable group such as R$^1$-R$^6$, R$^{10}$, R$^{15}$, R$^{17}$ or R$^{18}$ through a suitable structure such as —S(O)(O)—O—, e.g., organic moiety-O—S(O)(O)-steroid, HO—S(O)(O)-steroid or organic moiety-S(O)(O)—O-steroid. The organic moiety is as described above for esters.

"Amide", "amide derivative" and the like mean an organic moiety as described for ester that comprises a —C(O)—NR$^{PR}$— or —C(O)—NH— moiety, where R$^{PR}$ is —H or a protecting group. In some embodiments, the —C(O)NR$^{PR}$— group is linked to the steroid nucleus at a variable group such as R$^1$-R$^6$, R$^{10}$, R$^{15}$, R$^{17}$ or R$^{18}$, i.e., organic moiety-C(O)NR$^{PR}$-steroid, organic moiety-C(O)—NH-steroid or steroid-C(O)NR$^{PR}$-organic moiety. The organic moiety is as described above for esters.

"Ether" means an organic moiety as described for ester that comprises 1, 2, 3, 4 or more —O— moieties, usually 1 or 2. In some embodiments, the —O— group is linked to the steroid nucleus at a variable group such as R$^1$-R$^6$, R$^{10}$, R$^{15}$, R$^{17}$ or R$^{18}$, e.g., organic moiety-O-steroid. The organic moiety is as described above for esters.

"Thioether" means an organic moiety as described for ester that comprises 1, 2, 3, 4 or more —S— moieties, usually 1 or 2. In some embodiments, the —S— group is linked to the steroid nucleus at a variable group such as R$^1$-R$^6$, R$^{10}$, R$^{15}$, R$^{17}$ or R$^{18}$, e.g., organic moiety-S-steroid, organic moiety-S—CH$_2$—S-steroid or organic moiety-S—S-steroid. The organic moiety is as described above for esters.

"Acyl group" or "acyl" means an organic moiety as described for ester that comprises 1, 2, 3, 4 or more —C(O)— groups. In some embodiments, the —C(O)— group is linked to the steroid nucleus at a variable group such as R$^1$-R$^6$, R$^{10}$, R$^{15}$, R$^{17}$ or R$^{18}$, e.g., organic moiety-C(O)-steroid. The organic moiety is as described above for esters. Exemplary acyl moieties include moieties such as —C(O)—N(C1-C6 alkyl)$_2$, —C(O)—NH(C1-C6 alkyl), —C(O)—NH—C(CH$_3$)$_3$, —C(O)—NH—CH(CH$_3$)$_2$, —C(O)—NH—C(CH$_3$)$_2$—CH$_3$, —C(O)—NH—CH(CH$_3$)—CH$_3$, —C(O)—NH—C(CH$_3$)—CH$_2$—CH$_3$, —C(O)NH$_2$, —C(O)NHR$^{PR}$, —C(O)—CH$_3$, —C(O)—CH$_2$—CH$_3$, —C(O)—CH$_2$—CH$_2$—CH$_3$, —C(O)—CH$_2$OH, —C(O)—CH$_2$OR$^{PR}$, —C(O)—CH$_2$—CH$_2$H, —C(O)—CH$_2$—CH$_2$OR$^{PR}$, —C(O)—CH$_2$-halogen, —C(O)—CH$_2$—CH$_2$-halogen, —C(O)—CH$_2$—COOR$^{PR}$, —C(O)—CH$_2$—CH$_2$—COOR$^{PR}$, —C(O)—CH$_2$—CH$_2$—CHOH, —C(O)—CH$_2$—NH$_2$, —C(O)—CH$_2$—NHR$^{PR}$, —C(O)—CH$_2$—N(R$^{PR}$)$_2$, —C(O)—CH$_2$—NH—(C1-C6 alkyl), —C(O)—CH$_2$—N(C1-C6 alkyl)$_2$, —C(O)—NH—CH=CH$_2$, —C(O)—NH—C≡CH, —C(O)—NH—CH$_3$, —C(O)—NH—CN, —C(O)—NH—CH$_2$—CN, where each alkyl is the same or different and is optionally independently substituted and each R$^{PR}$ is —H or an independently selected protecting group for the atom or functional group to which it is attached, or two R$^{PR}$ together are a protecting group for the atom or functional group to which they are attached.

"Thioacyl" means an organic moiety as described for ester that comprises 1, 2, 3, 4 or more —C(S)— groups. In some embodiments, the —C(S)— group is linked to the steroid nucleus at a variable group such as R$^1$-R$^6$, R$^{10}$, R$^{15}$, R$^{17}$ or R$^{18}$, e.g., organic moiety-C(S)-steroid. The organic moiety is as described above for esters. Exemplary thioacyl moieties include moieties as described above for the acyl group, except that sulfur replaces the appropriate oxygen atom.

"Carbonate" means an organic moiety as described for ester that comprises 1, 2, 3, 4 or more —O—C(O)—O— structures. Typically, carbonate groups as used here comprise an organic moiety containing about 1-50 carbon atoms and 0 to about 10 independently selected heteroatoms (e.g., O, S, N, P, Si) linked to a formula 1 steroid nucleus at a variable group such as R$^1$-R$^6$, R$^{10}$, R$^{15}$, R$^{17}$ or R$^{13}$ through the —O—C(O)—O— structure, e.g., organic moiety-O—C(O)—O-steroid. The organic moiety is as described above for esters.

"Carbamate" means an organic moiety as described for ester that comprises 1, 2, 3, 4 or more —O—C(O)NR$^{PR}$— structures where R$^{PR}$ is —H, a protecting group or an organic moiety as described for ester. Typically, carbamate groups as used here comprise an organic moiety containing about 1-50 carbon atoms and 0 to about 10 independently selected heteroatoms (e.g., O, S, N, P, Si) linked to a formula 1 steroid nucleus at a variable group such as R$^1$-R$^6$, R$^{10}$, R$^{15}$, R$^{17}$ or R$^{13}$ through the —O—C(O)—NR$^{PR}$— structure, e.g., organic moiety-O—C(O)—NR$^{PR}$-steroid or steroid-O—C(O)—NR$^{PR}$-organic moiety. The organic moiety is as described above for esters.

As used herein, "monosaccharide" means a polyhydroxy aldehyde or ketone having the empirical formula $(CH_2O)_n$ where n is 3, 4, 5, 6 or 7. Monosaccharide includes open chain and closed chain forms, but will usually be closed chain forms. Monosaccharide includes hexofuranose and pentofuranose sugars such as 2'-deoxyribose, ribose, arabinose, xylose, their 2'-deoxy and 3'-deoxy derivatives and their 2',3'-dideoxy derivatives. Monosaccharide also includes the 2',3' dideoxydidehydro derivative of ribose. Monosaccharides include the D-, L- and DL-isomers of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, dihydroxyacetone and their monodeoxy or other derivatives such as rhamnose and glucuronic acid or a salt of glucuronic acid. Monosaccharides are optionally protected or partially protected. Exemplary monosaccharides include

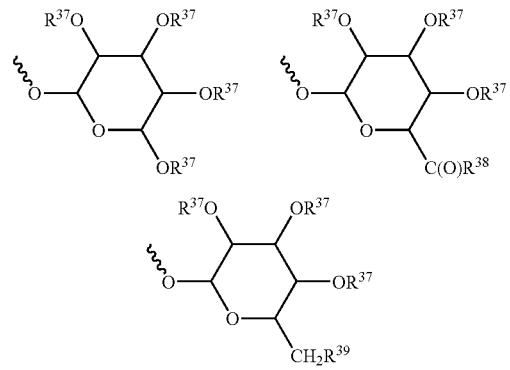

where R$^{37}$ independently is hydrogen, a protecting group, acetamido (—NH—Ac), optionally substituted alkyl such as methyl or ethyl, or an ester such as acetate or proprionate, $R^{33}$ is hydrogen, hydroxyl, —$NH_2$, —$NHR^{PR}$, optionally substituted alkyl such as methyl or ethyl, or a cation such as $NH_4^+$, $Na^+$ or $K^+$ and $R^{39}$ is hydrogen, hydroxyl, acetate, proprionate, optionally substituted alkyl such as methyl, ethyl, methoxy or ethoxy.

Optionally substituted alkyl group, optionally substituted alkenyl group, optionally substituted alkynyl group, optionally substituted aryl moiety and optionally substituted heterocycle mean an alkyl, alkenyl, alkynyl, aryl or heterocycle moiety that contains an optional substitution(s). Such moieties include $C_{1-20}$ alkyl moieties, $C_{2-20}$ alkenyl moieties, $C_{2-20}$ alkynyl moieties, aryl moieties, $C_{2-9}$ heterocycles or substituted derivatives of any of these.

Optionally substituted "monosaccharide" comprise any C3-C7 sugar, D-, L- or DL-configurations, e.g., erythrose, glycerol, ribose, deoxyribose, arabinose, glucose, mannose, galactose, fucose, mannose, glucosamine, N-acetylneuraminic acid, N-acetylglucosamine, N-acetylgalactosamine that is optionally substituted at one or more hydroxyl groups or hydrogen or carbon atoms. Suitable substitutions are as described above for substituted alkyl moieties and include independently selected hydrogen, hydroxyl, protected hydroxyl, carboxyl, azido, cyano, —O—$C_{1-6}$ alkyl, —S—$C_{1-6}$ alkyl, —O—$C_{2-6}$ alkenyl, —S—$C_{2-6}$ alkenyl, ester, e.g., acetate or proprionate, optionally protected amine, optionally protected carboxyl, halogen, thiol or protected thiol. The linkage between the monosaccharide and the steroid is α or β.

Optionally substituted "oligosaccharide" comprises two, three, four or more of any C3-C7 sugars that are covalently linked to each other. The linked sugars may have D-, L- or DL-configurations. Suitable sugars and substitutions are as described for monosaccharides. The linkage between the oligosaccharide and the steroid is α or β, as are the linkages between the monosaccharides that comprise the oligosaccharide. Adjacent monosaccharides may be linked by, e.g., 1→2, 1→3, 1→4, and/or 1→6 glycosidic bonds.

Nucleoside includes 3TC, AZT, D4T, ddI, ddC, G, A, U, C, T, dG, dA, dT and dC.

Polymer includes biocompatible organic polymers, e.g., polyethyleneglycols ("PEGs") and polyhydroxyalkyl polymers. PEG means an ethylene glycol polymer that contains about 2, 3, 4, 5, 6, 7, 8, 9, 10, 11, 12 or more linked monomers, e.g., about 50-1000 linked monomers. Average molecular weights typically are about 80, 100, 200, 300, 400 or 500, and mixtures thereof may are included, e.g., PEG100 and PEG200, PEG200 and PEG300, PEG100 and PEG300 or PEG200 and PEG400.

As used herein, position numbers that are given for the F1Cs use the numbering convention for cholesterol.

Spiro ring substituents are cyclic structures that are usually 3, 4, 5, 6, 7 or 8 membered rings, e.g., they include 3, 4-, 5-, 6-, 7- or 8-sided rings. In some embodiments, spiro structures share a carbon atom that is present in the steroid ring system, e.g., at the 2, 3, 7, 11, 15, 16 or 17 positions of the F1Cs. Spiro structures include, acetals, thioacetals and lactone rings or cyclic esters. Spirolactones, spiro ring compounds and dihydroxy F1Cs containing cyclic diol groups include F1Cs having the structures

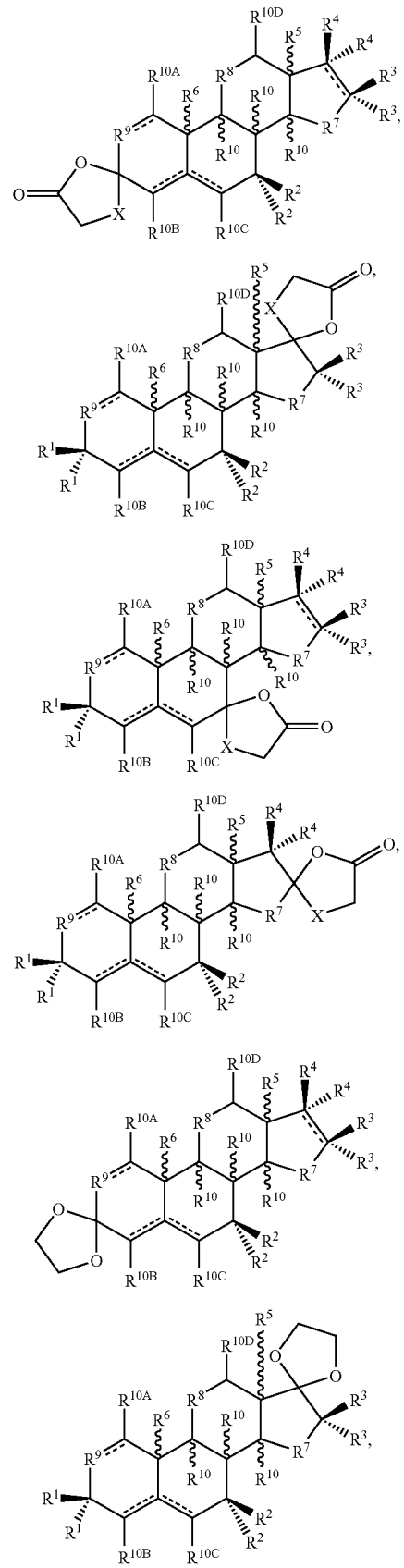

-continued

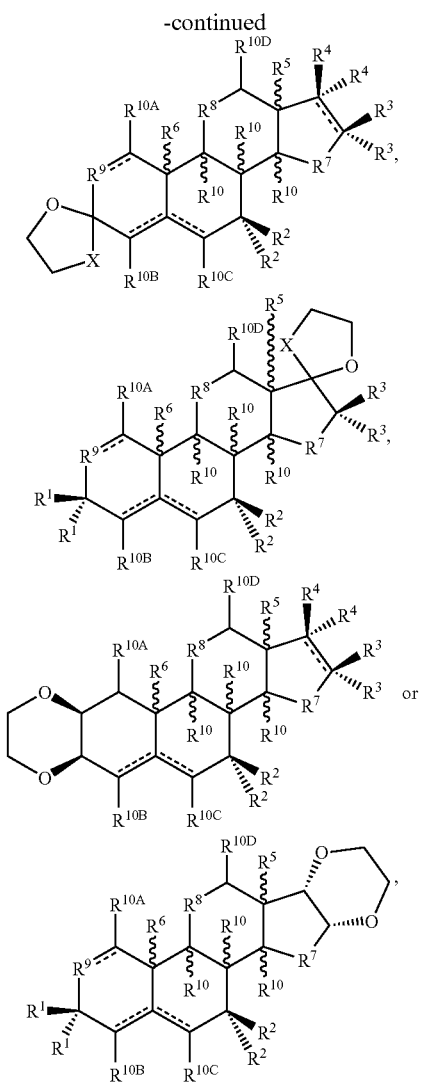

where X is —C(R$^{10}$)$_2$— or —CHR$^{10}$—, and R$^{10}$ are independently selected. In some of these embodiments, the R$^{10}$, R$^{10A}$, R$^{10B}$, R$^{10C}$ and R$^{10D}$ variable groups are in the α- or β-configuration and are independently selected from —H, —F, —Cl, —Br, —OH, —OCH$_3$, —OC$_2$H$_5$, an optionally substituted ester such as acetate or propionate, an optionally substituted alkyl such as methyl or ethyl or an amino acid.

As used herein, "innate immunity" refers to one or more components typically associated with nonspecific immune defense mechanisms in a subject. These components include the alternate complement pathway, e.g., Factor B, Factor D and properdin; NK cells, phagocytes (monocytes, macrophages), neutrophils, eosinophils, dendritic cells, fibrocytes; anti-microbial chemicals, e.g., one or more of defensins; physical barriers—skin, mucosal epithelium; or certain interleukins, chemokines, cytokines, lung or alveolar macrophage respiratory burst activity or a lung surfactant protein such as surfactant protein A or surfactant protein D. Innate immunity plays a role in resistance to intracellular parasite infections, e.g., white blood cell infection, a liver infection, and other infections, e.g., lymph node infections. Detectable enhancement of innate immunity mechanism by F1Cs or method described herein can also enhance phagolysosome fusion or movement, which some pathogens, e.g., intracellular bacteria such as mycobacteria, or *Listeria* inhibit.

Terms such as "immune dysregulation", "immune dysregulation condition", "unwanted immune response" and the like mean that a subject has or is subject to developing an immune response that is not desirable or is suboptimal for the subject's condition. Such dysregulation or unwanted responses can arise from various clinical conditions or diseases or as a result of treatment of such conditions or diseases, e.g., inflammation, autoimmunity, organ or tissue transplant rejection (e.g., allograft, xenograft), infections, cancers, chemotherapy treatments, trauma, allergy conditions or in conditions where a subject mounts a Th1, Tc1, Th2 or Tc2 immune response that is considered to be pathogenic, ineffective, insufficient or suboptimal. Immune dysregulation conditions are as described herein or in the cited references.

Terms such as "cellular response", "cellular activity", "biological response", "biological activity" and the like mean a response or activity that is detectably modulated in response to the presence of a F1C. Such responses or activities can be direct effects or indirect effects on one or more cellular activities or on the expression or level of one or more molecules that the affected cell(s) bind, sequester, synthesize or respond to. Such responses or activities include a detectable change in the synthesis or level of one or more cytokines, growth factors, transcription factors (including receptors and their cofactors), enzymes, Th1- or Th2-associated antibody subtype responses or the like. Typically, the cytokines, growth factors, transcription factors, enzymes or antibodies that are modulated are involved in the amelioration of a pathological condition or in the establishment, maintenance, severity or progression of a pathological condition.

As used herein, references to CD molecules, specific immune cell subsets, immune responses and the like, generally use nomenclature that applies to molecules, cells or the like that are found in humans. Analogs or counterparts of such molecules, cells or the like in other species may have a differing nomenclature, but are included in this invention. A description of the nomenclature and function of various CD molecules and immune cell subsets are as found in the scientific literature. References to Th0, Th1 or Th2 cells and references to Th1 or Th2 immune responses in the context of human patients refers to the human counterparts of the murine Th0, Th1 or Th2 immune cells or responses. For reviews see, e.g., A. K. Abbas et al., editors, *Cellular and Molecular Immunology*, W.B. Saunders Company, third edition, 1997, ISBN 0-7216-4024-9, pages 4-469, and 1. Kimber and M. K. Selgrade, editors, *T Lymphocyte Subpopulations in Immunotoxicology*, John Wiley & Sons Ltd., 1998, ISBN 0-471-97194-4, pages 1-53.

"Immunosuppressive molecule" means molecules such as cyclosporin, cyclohexamide, mitomycin C, adriamycin, taxol and amphotericin B. These molecules tend to have toxicities toward the immune system and are directly or indirectly immunosuppressive, e.g., they are toxic to dividing cells, they inhibit proliferation of immune cell precursors or they can downregulate an otherwise desired or improved immune response or condition.

"Nuclear hormone receptor" means a gene product, typically as a protein monomer or dimer that can bind to a ligand and affect transcription of one or more genes. Ligands include, e.g., certain natural steroids, steroid analogs, F1Cs or another ligand such as a lipid, e.g., a prostaglandin, or the like. Nuclear hormone receptors include orphan steroid receptors, which typically function as heterodimers and the classical steroid receptors, e.g., androgen receptor ("AR"), estrogen receptor α ("ERα"), estrogen receptor β ("ERβ"), that function as homodimers. Nuclear hormone receptors include species that form heterodimers, e.g., VDR-RXR or TR-RXR.

Nuclear hormone receptors also include isoforms, e.g., PXR.1 and PXR.2 for the PXR receptor, The natural ligand and/or biological function for some orphan steroid receptors is at least partially unknown. Nuclear hormone receptors include the homologs of the receptors, e.g., the homolog of CARβ known as MB67. Isoforms are typically generated by different splicing pathways for a nuclear RNA from one gene, while homologs are typically a distinct copy of a nuclear hormone receptor gene, where the gene copy encodes only relatively small differences compared to the reference nuclear hormone receptor gene product. Such differences are most often found in areas other than the dimerization region and the steroid binding region of the nuclear hormone receptor's structure. Typically isoforms and homologs bind the same or similar ligands as the reference gene product or nuclear hormone receptor. Nuclear hormone receptors may be of human or animal origin, e.g., obtained from cells, tissues or cDNA expression libraries derived from cells or tissues of any primate, rodent (including murine), avian, ovine, bovine, equine, canine, feline, insect species, e.g., *Drosophila*, nematode, e.g., *Caenorhabditis elegans*, or any of the species within any group (e.g., Family or Genus) of species mentioned herein or in any reference cited herein. Modulation of nuclear hormone receptors by F1Cs can arise from (1) their direct interaction with the receptor or a cofactor thereof or (2) indirect effects such as (A) detectably increased or decreased synthesis or level of the receptor or (B) generation of a signal or stimulus that leads to detectable modulation of one or more biological activities of the receptor, e.g., detectable inhibition of receptor mediated gene transcription or detectable enhancement of receptor mediated gene transcription.

An "agonist" or an "antagonist" is a compound or composition, usually containing a F1C, that respectively, either detectably increases or decreases the activity of a receptor, an enzyme or another biological molecule, which can lead to increased or decreased transcription or mRNA levels of a regulated gene or to another measurable effect such as altered level of activity of the gene product or protein. The increase or decrease in a receptor's or enzyme's activity will be an increase or a decrease of at least about 5%, 10%, 20%, 30%, 40%, 50%, 60%, 70%, 80%, 90%, 95% or a range about between any two of these values, for one or more measurable activities. Receptors, their accessory factors and associated transcription factors can modulate transcription of their target gene(s) by detectably increasing or decreasing transcription or mRNA levels. Biological activities of receptors may also include modulating biological responses such as signal transduction within a cell or ion flux, e.g., sodium, potassium or calcium, across cell or organelle membranes, e.g., across mitochondria.

Terms such as "biologically active metabolite" and the like mean derivatives of the F1Cs that retain a detectable level, e.g., at least about 10%, at least about 20%, at least about 30% or at least about 50%, of at least one desired activity of the parent compound, e.g., antiinflammatory activity or stimulation of a desired immune response. Determination of a desired activity is accomplished essentially as described herein. Such metabolites can be generated in the gastrointestinal tract, in blood or in one or more subject tissues. Such metabolites are detected using standard analytical methods, e.g., GC-MS analysis of an optionally radiolabeled F1C and its metabolites, in blood, urine or other biological samples after it is administered to a subject by one or more routes as disclosed herein. Terms such as "metabolic precursor" of F1Cs and the like can include compounds that generate a detectable level of the F1C or a detectable level, e.g., at least about 10%, at least about 20%, at least about 30% or at least about 50%, of at least one desired activity of the F1C. Determination of a desired activity is accomplished essentially as described herein. Conversion of metabolic precursors can occur in the gastrointestinal tract, in blood or in one or more subject tissues.

"Amino acid" means an amino acid moiety that comprises any naturally-occurring or synthetic amino acid residue, i.e., any moiety comprising at least one carboxyl and at least one amino residue directly linked by one, two three or more carbon atoms, typically one (α) carbon atom. The nature and identity of the intervening structure located between the carboxyl and amino groups can have a variety of structures including those described herein. Typically, amino acids linked to the steroid through the amine group ("N-linked amino acid") have sufficient conformation and length to be capable of autocatalytic hydrolysis of the amino acid-steroid bond and release of the steroid. This can occur when the free carboxyl is generated in vivo by deesterification, deamidation or peptidolytic cleavage of the precursor containing a linkage between the amino acid's amine group and the steroid. Hydrolysis of the bond between an amino acid's carboxyl or amino group and the steroid can also occur by chemical or enzymatic activity, e.g., esterase cleavage or non-enzymatic hydrolysis.

In general, the amino acids corresponding to the residues employed in the F1Cs are naturally occurring and have no significant pharmacological activity per se. However, optimal pharmacokinetic activity, (substantially complete hydrolysis upon hydrolysis of the distal amide or ester bond) may be achieved by using non-naturally occurring amino acid residues. The intervening structure may be as simple as methylene when the amino acid residue is glycyl, or substituted methylene for other a amino acids. The structure ordinarily contains up to about 5 carbon or heteroatoms in the direct linkage between the amino acid's carboxyl carbon and the amine nitrogen. Thus, amino acids can comprise intervening ethylene, propylene, butylene, or pentylene groups or their substituted analogs, such as for example, oxyesters or ethers in which oxygen replaces carbon and, as appropriate, hydrogen. An example of such an intervening structure would be —CH—O—C($R^{22}$)($R^{23}$)—, where $R^{22}$ and $R^{23}$ are independently selected hydrogen or organic moieties as described above for esters. In some embodiments one of $R^{22}$ and $R^{23}$ is hydrogen and the other is a C2-20 organic moiety. Typically the organic moieties contain about 1-20 carbon atoms and 0, 1, 2, 3, 4 or 5 independently selected heteroatoms, which are typically selected from oxygen, nitrogen, sulfur and phosphorus. In general, fewer intervening atoms are used when more rapid hydrolysis is desired, although larger structures are suitable if, e.g., they possess sufficient flexibility or have conformations to allow positioning of the carboxyl group in proximity to the amino acid-steroid bond.

Ordinarily, $R^{22}$ is —H, methyl or hydroxymethyl, usually —H, and $R^{23}$ is a side chain or group of a naturally occurring amino acid. Amino acid side chains include analogs where the side chain is a $C_{1-15}$ homolog of the corresponding natural compound, e.g., methylene, ethylene, propylene, butylene or a substituted derivative thereof, e.g., an alkyl, ether or alkoxy (e.g., methoxy, ethoxy, propoxy) substituted derivative. In general, for carboxyl-containing side chains, if the C atom of the side chain carboxyl is linked by 5 or less atoms to the N then the carboxyl optionally will be blocked, e.g. by esterification or amidation wherein the ester or amide bonds are hydrolyzable in vivo. $R^{22}$ also is taken together with $R^{30}$ to form a proline residue (—$CH_2$—)$_3$. Thus, $R^{23}$ is generally a side group such as —H, —$CH_3$, —$CH(CH_3)_2$, —$CH_2$—CH$(CH_3)_2$, —CHCH$_3$—CH$_2$—CH$_3$, —$CH_2$—$C_6H_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. R$^{23}$ also includes 1-guanidinoprop-3-yl, benzyl, 4-hydroxybenzyl, imidazol-4-yl, indol-3-yl, methoxyphenyl and ethoxyphenyl. The optimal R$^{30}$ group is readily selected using routine assays.

In general, the amino acid residue has the structure shown in the formulas below. Ordinarily, n is 1 or 2, R$^{22}$ is —H and R$^{23}$ is a moiety containing one or more of the following groups: amino, carboxyl, amide, carboxyl ester, hydroxyl, C$_6$-C$_7$ aryl, ether (—O—), thioether (—S—), n-, s- or t-alkyl (C$_1$-C$_6$), guanidinyl, imidazolyl, indolyl, sulfhydryl, sulfoxide, and phosphoryl. The R$^{22}$ and R$^{23}$ substituents can have a wide variety of structures including those disclosed herein, e.g., esters, ethers or carbonates.

When the amino acid residues contain one or more chiral centers, any of the D, L, meso, threo or erythro (as appropriate) racemates or mixtures thereof, fall within the scope of this invention. In general, if it is desired to rely on non-enzymatic means of hydrolysis, D isomers should be used. On the other hand, L isomers may be more versatile since they can be susceptible to both non-enzymatic as well as potential targeted enzymatic hydrolysis, and are more efficiently transported by amino acid or dipeptidyl transport systems in the gastrointestinal tract.

Examples of suitable amino acid residues include the following: Glycyl; aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid residues; amino acid amides such as glutaminyl and asparaginyl; polyamino- or polybasic-monocarboxylic acids such as arginine, lysine, β-aminoalanine, γ-aminobutyrine, ornithine, citruline, homoarginine, homocitrulline, 5-hydroxy-2,6-diaminohexanoic acid (commonly, hydroxylysine, including allohydroxylysine) and diaminobutyric acid residues; other basic amino acid residues such as histidinyl; diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid residues; imino acids such as proline, 4- or 3-hydroxy-2-pyrrolidinecarboxylic acid (commonly, hydroxyproline, including allohydroxyproline), γ-methylproline, pipecolic acid, 5-hydroxypipecolic acid, —N([CH$_2$]$_n$COOR$^{PR}$)$_2$, wherein n is 1, 2, 3, 4, 5 or 6 and R$^{PR}$ is —H or a protecting group, and azetidine-2-carboxylic acid residues; a mono- or di-alkyl (typically C$_1$-C$_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid; isoleucine, alloisoleucine, tert-leucine, β-methyltryptophan and α-amino-β-ethyl-β-phenylpropionic acid residues; β-phenylserinyl; aliphatic α-amino-β-hydroxy acids such as serine, β-hydroxyleucine, β-hydroxynorleucine, β-hydroxynorvaline, and α-amino-β-hydroxystearic acid residues; α-Amino, α-, γ-, δ- or ε-hydroxy acids such as homoserine, γ-hydroxynorvaline, δ-hydroxynorvaline and epsilon-hydroxynorleucine residues; canavinyl and canalinyl; γ-hydroxyornithinyl; 2-Hexosaminic acids such as D-glucosaminic acid or D-galactosaminic acid residues; α-amino-β-thiols such as penicillamine, β-thiolnorvaline or β-thiolbutyrine residues; other sulfur containing amino acid residues including cysteine; homocystine; β-phenylmethionine; methionine; S-allyl-L-cysteine sulfoxide; 2-thiolhistidine; cystathionine; and thiol ethers of cysteine or homocysteine; phenylalanine, tryptophan and ring-substituted α amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro, 2-hydroxy-5-nitro and p-nitro-phenylalanine); furyl-, thienyl-, pyridyl-, pyrimidinyl-, purine or naphthylalanines; and tryptophan analogues and derivatives including kynurenine, 3-hydroxykynurenine, 2-hydroxytryptophan and 4-carboxytryptophan residues; α-amino substituted amino acid residues including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acid residues including serine, threonine, allothreonine, phosphoserine and phosphothreonine residues.

Any one of the foregoing or other known amino acids are suitably employed in this invention. Typically, amino acids are capable of autocatalytically hydrolyzing the amino acid-steroid bond. Thus, they typically contain, or upon being hydrolyzed in vivo, contain a free carboxyl group or amine group.

Also of interest are hydrophobic amino acids such as mono- or di-alkyl or aryl amino acids, cycloalkylamino acids and the like. These residues, together with R$^{29}$-R$^{34}$ (R$^{31}$-R$^{34}$ are defined below) can contribute to cell permeability by modulating the lipophilicity of a F1C. Typically, the residue does not contain a sulfhydryl or guanidino substituent.

Peptide means 2, 3 or more of the two or more amino acids as defined above are bonded together, usually by an amide bond or normal peptide bond. Variable groups in the F1Cs such as R$^1$-R$^{10}$ can comprise a peptide. Typically the amino acids are linked through normal peptide bonds, e.g., —CO—NH—, between adjacent amino acid residues. Peptides comprise dipeptides (dimers), tripeptides (trimers), short peptides of 4, 5, 6, 8, 10 or 15 residues, and longer peptides or proteins having about 100 or more residues. F1Cs that comprise a peptide can be used as immunogens, prodrugs or as synthetic precursors for other steroid derivatives. In one embodiment, the peptide will contain a peptidolytic enzyme cleavage site at the peptide bond linking the first residue and the next residue distal to the steroid residue. Such cleavage sites are optionally flanked by enzymatic recognition structures, e.g. particular residues recognized by a hydrolytic enzyme, e.g., a peptidase located in the serum or in cells.

Peptidolytic enzymes are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide having a given pair of residues and a free carboxyl terminus is covalently bonded through its α-amino group to the steroid nucleus. It is expected that the peptide will be cleaved by the appropriate dipeptidase, protease or by chemical hydrolysis, leaving the carboxyl of the proximal amino acid residue to autocatalytically cleave the amidate bond.

Examples of suitable dipeptidyl groups (designated by their single letter symbols) are shown in the table below. The single letter designations are: Y tyrosine, G glycine, F phenylalanine, M methionine, A alanine, S serine, I isoleucine, L leucine, T threonine, V valine, P praline, L lysine, H histidine, Q glutamine, E glutamic acid, W tryptophan, R arginine, D aspartic acid, N asparagine and C cysteine.

of $R^1$ through $R^4$, where each $R^{29}$-$R^{31}$ is independently selected; $R^{29}$ independently are —H or a C1-C20 organic moiety (e.g., $C_{1-6}$ alkyl, e.g. —$CH_3$ or —$C_2H_5$); $R^{30}$ independently are the side chain of an amino acid, including the side chain of naturally occurring amino acids as described above, e.g., —H, —$CH_3$, —$CH_2C_6H_5$; $R^{31}$ is —H or a protecting group; $R^{32}$ and $R^{33}$ independently comprise —H, a protecting group, an ester or an amide where each atom or group is independently chosen; a, b, c and d independently are 1, 2, 3, 4 or 5, usually 1; e, f and g independently are an integer from 0 to about 1000, typically they independently are 0, 1, 2, 3, 4, 5, 6, 7 or 8; a, b, c and d independently are 1 or 2; e, f and g independently are 0, 1, 2, 3, 4 or 5.

| Dipeptides |
|---|
| AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY, VV |

Such dipeptides include species where both amino acids are in the L configuration, the D configuration or mixtures of configurations.

Tripeptides, i.e., 3 linked amino acid residues, are also useful embodiments. Each amino acid in a tripeptide may be in an L, D or mixed configuration. Tripeptides include those where A, C, D, E, F, G, H, I, K, L, M, N, P, Q, R, S, T, V, W or Y is linked by a standard peptide bond to the amino or the carboxyl terminus of any of the dipeptides listed above. The sequence —X1-pro-X2- (where X1 is any amino acid and X2 is hydrogen, any amino acid residue or a carboxyl ester of proline) will be cleaved by luminal carboxypeptidase to yield X1 with a free carboxyl, which in turn autocatalytically cleaves the amidate bond. X2 usually will be a benzyl ester of the carboxy group of X2. Other embodiments include tetrapeptides such as ones where any two of the dipeptides listed above, which may be the same or different dipeptides (e.g., AA and AA linked together or, e.g., AA and GI linked together), are linked to each other by a peptide bond through the amino terminus or carboxyl terminus. One, 2 or more tetrapeptides may bonded to the formula 1 or formula 2 compound through the tetrapeptide's amino or carboxyl terminus.

In some embodiments, the formula 1 or formula 2 compound comprises one or more amino acids or peptides having the structure (A), (B) or (C): (A) $R^{32}$—NH—$\{[C(R^{29})(R^{30})]_b$—C(O)—N($R^{31}$)$\}_f$—[C($R^{29}$)($R^{30}$)]$_a$—C(O)—O-steroid; (B) $R^{33}$—O—$\{C(O)$—[C($R^{29}$)($R^{30}$)]$_d$—N($R^{31}$)$\}_g$—C(O)—[C($R^{29}$)($R^{30}$)]$_c$—N($R^{31}$)—O-steroid; or (C)$R^{33}$—O—$\{C(O)$—[C($R^{29}$)($R^{30}$)]$_d$—N($R^{31}$)$\}_e$—C(O)—[C($R^{29}$)($R^{30}$)]$_c$—N($R^{31}$)—C(O)—O-steroid, wherein (A), (B) or (C) are independently selected and they are bonded to 1, 2, 3 or more If the amino acid(s) or residue(s) has 2 or more amine groups, e.g., a lysinyl or arginyl, or ornithinyl residue, then $R^{29}$ is usually —H and $R^{30}$ may comprise —[C($R^{34}$)$_2$]$_{n2}$N ($R^{PR}$)— where n2 is 0, 1, 2, 3, 4, 5 or 6, $R^{PR}$ is —H or a protecting group and each $R^{34}$ independently is —H, $C_1$-$C_{20}$ optionally substituted alkyl, $C_6$-$C_{20}$ optionally substituted aryl, $C_7$-$C_{20}$ optionally substituted alkylaryl, $C_7$-$C_{20}$ optionally substituted arylalkyl, $C_1$-$C_{20}$ optionally substituted alkoxy, $C_6$-$C_{20}$ optionally substituted aryloxy or hydroxyl. Such compounds will contain a plurality of steroid moieties. For example when both the epsilon (ε) or delta (δ) and alpha (α) amino groups of lysine or ornithine are substituted with steroid moieties the amidate is believed to be capable of releasing two molecules of active drug, each expected to emerge under different pharmacokinetics and therefore further sustaining the drug release.

Salts of F1Cs. Invention embodiments include salts and complexes of F1Cs, including pharmaceutically acceptable or salts that are relatively non-toxic. Some of the F1Cs have one or more moieties that carry at least a partial positive or negative charge in aqueous solutions, typically at a pH of about 4-10, that can participate in forming a salt, a complex, a composition with partial salt and partial complex properties or other noncovalent interactions, all of which we refer to as a "salt(s)". Salts are usually biologically compatible or pharmaceutically acceptable or non-toxic, particularly for mammalian cells. Salts that are biologically toxic are optionally used with synthetic intermediates of F1Cs. When a water-soluble composition is desired, monovalent salts are usually used.

Metal salts typically are prepared by reacting the metal hydroxide with a compound of this invention. Examples of metal salts that are optionally prepared in this way are salts containing $Li^+$, $Na^+$, and $K^+$. A less soluble metal salt can be precipitated from the solution of a more soluble salt by adding a suitable metal compound. Invention salts may be formed from acid addition of certain organic acids, such as organic carboxylic acids, and inorganic acids, such as alkylsulfonic acids or hydrogen halide acids, to acidic or basic centers on F1Cs, such as basic centers on the invention pyrimidine base analogs. Metal salts include ones containing $Na^+$, $Li^+$, $K^+$, $Ca^{++}$ or $Mg^{++}$. Other metal salts may contain aluminum, barium, strontium, cadmium, bismuth, arsenic or zinc ion.

Salt(s) of F1Cs may comprise a combination of appropriate cations such as alkali and alkaline earth metal ions or ammonium and quaternary ammonium ions with the acid anion moiety of the phosphoric acid or phosphonic acid group, which may be present in polymers or monomers.

Salts are produced by standard methods, including dissolving free base in an aqueous, aqueous-alcohol or aqueous-organic solution containing the selected acid, optionally followed by evaporating the solution. The free base is reacted in an organic solution containing the acid, in which case the salt usually separates directly or one can concentrate the solution.

Suitable amine salts include amines having sufficient basicity to form a stable salt, usually amines of low toxicity including trialkyl amines (tripropylamine, triethylamine, trimethylamine), procaine, dibenzylamine, N-benzyl-betaphenethylamine, ephenamine, N,N'-dibenzylethylenediamine, N-ethylpiperidine, benzylamine and dicyclohexylamine.

Salts include organic sulfonic acid or organic carboxylic acid salts, made for example by addition of the acids to basic centers, typically amines. Exemplary sulfonic acids include $C_{6-16}$ aryl sulfonic acids, $C_{6-16}$ heteroaryl sulfonic acids and $C_{1-16}$ alkyl sulfonic acids such as phenyl sulfonic acid, a-naphthalene sulfonic acid, β-naphthalene sulfonic acid, (S)-camphorsulfonic acid, methyl ($CH_3SO_3H$), ethyl ($C_2H_5SO_3H$), n-propyl, i-propyl, n-butyl, s-butyl, i-butyl, t-butyl, pentyl and hexyl sulfonic acids. Exemplary organic carboxylic and other acids include $C_{1-16}$ alkyl, $C_{6-16}$ aryl carboxylic acids and $C_{4-16}$ heteroaryl carboxylic acids such as acetic, glycolic, lactic, pyruvic, malonic, glutaric, tartaric, citric, fumaric, succinic, malic, maleic, oxalic, hydroxymaleic, benzoic, hydroxybenzoic, phenylacetic, cinnamic, salicylic, nicotinic, 2-phenoxybenzoic, methanesulfonic, pamoic, propionic, toluenesulfonic and trifluoroacetic acids.

Invention salts include those made from inorganic acids, e.g., HF, HCl, HBr, $H_1$, $H_2SO_4$, $H_3PO_4$, $Na_2CO_3$, $K_2CO_3$, $CaCO_3$, $MgCO_3$ and $NaClO_3$. Suitable anions, which are optionally present with a cation such a $Ca^{++}$, $Mg^{++}$, $Li^{++}$, $Na^+$ or $K^+$, include arsenate, arsenite formate, sorbate, chlorate, perchlorate, periodate, dichromate, glycodeoxycholate, cholate, deoxycholate, desoxycholate, taurocholate, taurodeoxycholate, taurolithocholate, tetraborate, nitrate, nitrite, sulfite, sulfamate, hyposulfite, bisulfite, metabisulfite, thiosulfate, thiocyanate, silicate, metasilicate, $CN^-$, gluconate, gulcuronate, hippurate, picrate, hydrosulfite, hexafluorophosphate, hypochlorite, hypochlorate, borate, metaborate, tungstate and urate.

Salts also include the F1C salts with one or more amino acids. Many amino acids are suitable, especially the naturally-occurring amino acids found as protein components, although the amino acid typically is one bearing a side chain with a basic or acidic group, e.g., lysine, arginine, histidine or glutamic acid, or a neutral group such as glycine, serine, threonine, alanine, isoleucine, or leucine.

The invention compositions include F1Cs, their hydrates and the compounds in their ionized, un-ionized, as well as zwitterionic form. Thus, for any F1Cs or compounds described herein with any substituent that contains a moiety that is partially or completely ionizable, e.g., a carboxyl group, the ionizable atom, usually hydrogen, may be replaced with one or more suitable counter ions such as a monovalent metal, a multivalent metal, an alkaline metal, or an ionizable organic moiety, e.g., $Li^+$, $Na^+$, $K^+$, $Ca^{+2}$, $Mg^{+2}$, $SO_4^{-2}$, $PO_4^{-2}$, $CH_3C(O)O^-$, $CF_3C(O)O^-$, $F^-$, $Cl^-$, $Br^-$, $I^-$, $NH_4^+$, $N^+(CH_3)_4$, $N^+(C_2H_5)_4$, $HN^+(C_2H_5)_3$, $H_2N^+(C_2H_5)_2$, β-hydroxyethyltrimethylammonium, piperazinium, pyridinium, N-methylpyridinium, morpholinium, N,N-dimethylmorpholinium, p-toluidinium or another ionizable moiety described herein. When a F1C is under conditions, e.g., in a solution, where such moieties can partially or completely ionize, the ionizable moiety may be partially or completely charged, e.g., $—C(O)—O^-$, $—NH_3^+$, $—C(O)—NH_3^+$ or $—O—S(O)(O)—O^-$ may be partially for fully ionized.

Stereoisomers. The F1Cs include enriched or resolved optical isomers at any or all asymmetric atoms as are apparent from the depictions or are included in the compound structures. Both racemic and diasteromeric mixtures, as well as the individual optical isomers can be isolated or synthesized so as to be substantially free of their enantiomeric or diastereomeric partners, and these are all within the scope of the invention. Chiral centers may be found in F1Cs at, for example, one or more of $R^1$, $R^2$, $R^3$, $R^4$ or $R^{10}$.

One or more of the following methods are used to prepare the enantiomerically enriched or pure isomers herein. The methods are listed in approximately their order of preference, i.e., one ordinarily should employ stereospecific synthesis from chiral precursors before chromatographic resolution before spontaneous crystallization.

Stereospecific synthesis is described in the examples. Methods of this type conveniently are used when the appropriate chiral starting material is available and reaction steps are chosen do not result in undesired racemization at chiral sites. One advantage of stereospecific synthesis is that it does not produce undesired enantiomers that must be removed from the final product, thereby lowering overall synthetic yield. In general, those skilled in the art would understand what starting materials and reaction conditions should be used to obtain the desired enantiomerically enriched or pure isomers by stereospecific synthesis.

If a suitable stereospecific synthesis cannot be empirically designed or determined with routine experimentation then those skilled in the art would turn to other methods. One method of general utility is chromatographic resolution of enantiomers on chiral chromatography resins. These resins are packed in columns, commonly called Pirkle columns, and are commercially available. The columns contain a chiral stationary phase. The racemate is placed in solution and loaded onto the column, and thereafter separated by HPLC. See for example, Proceedings Chromatographic Society—International Symposium on Chiral Separations, Sep. 3-4, 1987. Examples of chiral columns that could be used to screen for the optimal separation technique would include Diacel Chriacel OD, Regis Pirkle Covalent D-phenylglycine, Regis Pirkle Type 1A, Astec Cyclobond II, Astec Cyclobond III, Serva Chiral D-DL=Daltosil 100, Bakerbond DNBLeu, Sumipax OA-1000, Merck Cellulose Triacetate column, Astec Cyclobond I-Beta, or Regis Pirkle Covalent D-Naphthylalanine. Not all of these columns are likely to be effective with every racemic mixture. However, those skilled in the art understand that a certain amount of routine screening may be required to identify the most effective stationary phase. When using such columns it is desirable to employ embodiments of the compounds of this invention in which the charges are not neutralized, e.g., where acidic functionalities such as carboxyl are not esterified or amidated.

Another method entails converting the enantiomers in the mixture to diasteriomers with chiral auxiliaries and then separating the conjugates by ordinary column chromatography. This is a very suitable method, particularly when the embodiment contains free carboxyl, amino or hydroxyl that will form a salt or covalent bond to a chiral auxiliary. Chirally pure amino acids, organic acids or organosulfonic acids are all worthwhile exploring as chiral auxiliaries, all of which are well known in the art. Salts with such auxiliaries can be formed, or they can be covalently (but reversibly) bonded to the functional group. For example, pure D or L amino acids can be used to amidate the carboxyl group of invention embodiments that comprise a carboxyl group and then separated by chromatography.

Enzymatic resolution is another method of potential value. In such methods one prepares covalent derivatives of the enantiomers in the racemic mixture, generally lower alkyl esters (for example of carboxyl), and then exposes the derivative to enzymatic cleavage, generally hydrolysis. For this method to be successful an enzyme must be chosen that is capable of stereospecific cleavage, so it is frequently necessary to routinely screen several enzymes. If esters are to be cleaved, then one selects a group of esterases, phosphatases, and lipases and determines their activity on the derivative. Typical esterases are from liver, pancreas or other animal organs, and include porcine liver esterase.

If the enantiomeric mixture separates from solution or a melt as a conglomerate, i.e., a mixture of enantiomerically pure crystals, then the crystals can be mechanically separated, thereby producing the enantiomerically enriched preparation. This method, however, is not practical for large-scale preparations and is of limited value for true racemic compounds. Asymmetric synthesis is another technique for achieving enantiomeric enrichment. For example, a chiral protecting group is reacted with the group to be protected and the reaction mixture allowed to equilibrate. If the reaction is enantiomerically specific then the product will be enriched in that enantiomer.

Embodiments of formula 1 compounds. For formula 1 compounds ("F1Cs"), 2, 3 or more of $R^1$, $R^2$, $R^3$ and $R^4$ are usually not —H, and typically one or both $R^1$ and $R^4$, $R^3$ and $R^4$, $R^2$, $R^3$ and $R^4$ or $R^2$ and $R^4$ are not —H, and/or 1 or 2 of $R^{10A}$, $R^{10B}$, $R^{10C}$ and $R^{10D}$ are optionally not —H. For any F1C disclosed herein, steroid nucleus carbon atoms that contain two variable groups (e.g., two $R^{10}$ at $R^8$ or $R^9$ or two $R^3$ or $R^4$ at the 16- or 17-position), each variable group is independently selected and each can thus be the same or different, e.g., both can be methyl, ethyl, methoxy, ethoxy, —F, —Cl, —Br, —I, or they can be different. As is apparent from the F1C structures, a double bond can be present at either the 4-5 position or at the 5-6 position, but not at both positions at the same time. Steroid nucleus carbon atoms refers generally to the carbons that make up the rings in F1Cs and carbons, if present, that are bonded to the 10, 13 and 17 positions. Additional carbons that may be at the 17-position are typically numbered using the cholesterol numbering system, although any other suitable nomenclature can be used to describe species or genera of F1C. Exemplary F1C embodiments are described below.

F1Cs include 16α-bromoepiandrosterone ("BrEA") hemihydrate

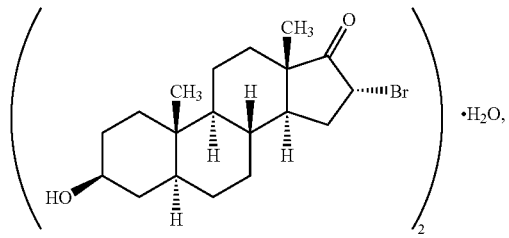

which has previously been described, e.g., WO 00/56757. BrEA hemihydrate is used as a F1C either as a pure compound or substantially free of other forms of BrEA, such as amorphous BrEA or anhydrous BrEA.

F1Cs include compounds having the structure 5, 6, 7, 8, 9 and 10,

5

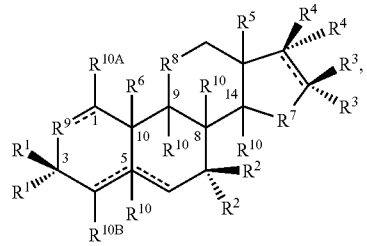

6

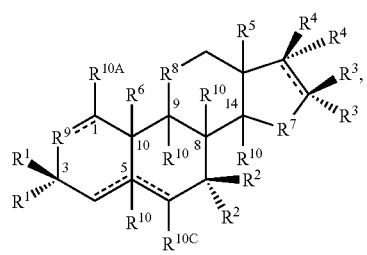

7

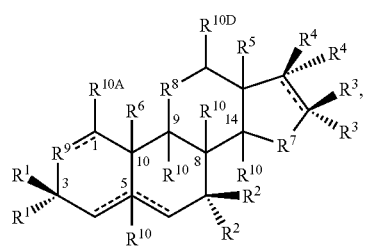

8

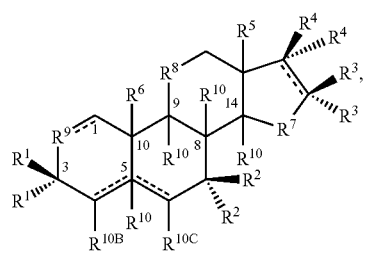

-continued

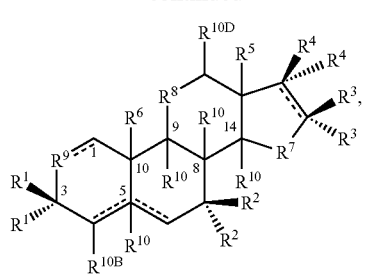

9

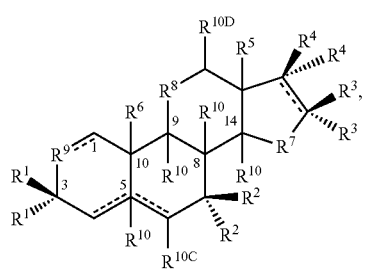

10 or a metabolic precursor, a metabolite or salt thereof, wherein each $R^1$, $R^2$, $R^3$, $R^4$, $R^{10}$ at the 2, 11 and 15 positions, $R^{10A}$, $R^{10B}$, $R^{10C}$ and $R^{10D}$ independently are —H, —OH, —OR$^{PR}$, —SR$^{PR}$, —N(R$^{PR}$)$_2$, —O—Si—(R$^{13}$)$_3$, —CHO, —CHS, —CN, —SCN, —NO$_2$, —ONO$_2$, —N$_3$, —NH$_2$, —COOH, —OSO$_3$H, —OPO$_3$H, =O, =S, =NOH, =CH$_2$, =CH$_2$CH$_3$, =N—NH—C(=NH)—N(R$^{PR}$)$_2$, =N—NH—C(=NH)—NH$_2$, an ester, a thioester, a thionoester, a phosphoester, a phosphothioester, a phosphonoester, a phosphiniester, a sulfite ester, a sulfate ester, a sulfoxide, a sulfamate, a sulfonate, a sulfamide, a sulfinamide, a sulfurous diamide, an amide, an amino acid, a peptide, an ether, a thioether, an acyl group, a thioacyl group, a carbonate, a carbamate, a halogen, an acetal, a thioacetal a spiro ring, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide, a polymer, or, one or more of two adjacent $R^1$-$R^4$, $R^{10}$, $R^{10A}$, $R^{10B}$, $R^{10C}$ and $R^{10D}$ are an independently selected epoxide or cyclopropyl ring;

$R^5$, $R^6$ and $R^{10}$ at the 5 (if present), 8, 9 and 14 positions independently are —H, —CH$_3$, —C$_2$H$_5$, —OH, —OR$^{PR}$, —SR$^{PR}$, —N(R$^{PR}$)$_2$, —O—Si—(R$^{13}$)$_3$, —CHO, —CHS, —CN, —SCN, —N$_3$, —COOH, —OS(O)(O)OH, an ester, a thioester, a thionoester, a sulfite ester, a sulfate ester, a sulfoxide, a sulfamate, a sulfonate, a sulfamide, a sulfinamide, a sulfurous diamide, an amide, an amino acid, a peptide, an ether, a thioether, an acyl group, a thioacyl group, a carbonate, a carbamate, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, or, one, two or more of $R^5$, $R^6$ and $R^{10}$ at the 5, 8, 9 and 14 positions, together with a carbon atom that is adjacent to the carbon to which the $R^5$, $R^6$ or $R^{10}$ at the 5, 8, 9 or 14 position is bonded are an independently selected epoxide or cyclopropyl ring;

$R^7$ is —C(R$^{10}$)$_2$—, —C(R$^{10}$)$_2$—C(R$^{10}$)$_2$—, —C(R$^{10}$)$_2$—C(R$^{10}$)$_2$—C(R$^{10}$)$_2$—, —C(R$^{10}$)$_2$—O—C(R$^{10}$)$_2$—, —C(R$^{10}$)$_2$—S—C(R$^{10}$)$_2$—, —C(R$^{10}$)$_2$—NR$^{PR}$—C(R$^{10}$)$_2$—, —O—, —O—C(R$^{10}$)$_2$—, —S—, —S—C(R$^{10}$)$_2$—, —NR$^{PR}$—, —NH— or —NR$^{PR}$—C(R$^{10}$)$_2$—;

$R^8$ and $R^9$ independently are —C(R$^{10}$)$_2$—, —C(R$^{10}$)$_2$—C(R$^{10}$)$_2$—, —O—, —O—C(R$^{10}$)$_2$—, —S—, —S—C(R$^{10}$)$_2$—, —NR$^{PR}$—, —NR$^{PR}$— or —NR$^{PR}$—C(R$^{10}$)$_2$—, or one or both of $R^8$ or $R^9$ independently are absent, leaving a 5-membered ring;

$R^{13}$ independently is $C_{1-6}$ alkyl; and $R^{PR}$ independently are —H, a protecting group or together are a protecting group, wherein 0, 1, 2, 3 or 4 of $R^{10A}$, $R^{10B}$, $R^{10C}$ and $R^{10D}$ are —H, $R^5$ and $R^6$ respectively are in the β,β, α,β, β,α or α,α configurations, and wherein, $R^{10}$ moieties at the 5 (if present), 8, 9 and 14 positions respectively are in the α,α,α,α, α,α,α,β, α,α,β,α, α,β,α,α, β,α,α,α, α,α,β,β, α,β, α,β, β,α,α,β, β,α,β,α, β,β,α,α, α,β,β,α, α,β,β,β, β,α,β,β, β,β,α,β, β,β,β,α or β,β,β,β configurations. For any of the F1Cs of structure 5, 6, 7, 8, 9 or 10 where two variable groups are bonded to the same carbon, e.g., $R^1$, $R^2$, $R^3$, $R^4$ or $R^{10}$ at the 11 position, the each variable group at that position is independently selected.

In the F1Cs, each $R^1$, $R^2$, $R^3$, $R^4$, $R^{10}$ at the 2, 11 and 15 positions, is independently selected. In some embodiments one of the $R^1$, $R^2$, $R^3$, $R^4$, $R^{10}$ at the 2, 11 and 15 positions is hydrogen and the other is —H another moiety, but usually 2, 3, 4, 5 or 6 of the remaining variable groups are not —H, i.e., they are another moiety as defined for those groups. In other embodiments, both $R^1$, $R^2$, $R^3$, $R^4$, $R^{10}$ at the 2, 11 and 15 positions, are independently selected moieties other than hydrogen, i.e., they are another moiety as defined for those groups such as a C1-C20 organic moiety or C1-C20 optionally substituted alkyl group. In many embodiments $R^1$ at the 1-position in the β-configuration or $R^1$ at the 1-position in the α-configuration is not —H and $R^4$ at the 1-position in the β-configuration or $R^1$ at the 1-position in the α-configuration is not —H.

F1Cs include compounds having structure 2

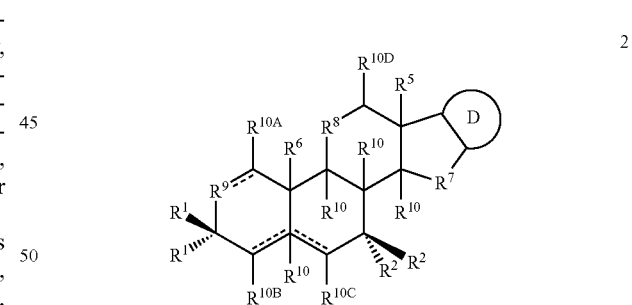

2 wherein, each $R^1$, $R^2$, $R^3$, $R^4$, $R^5$, $R^6$, $R^7$, $R^8$, $R^9$, $R^{10}$ at the 2, 5, 8, 9, 11, 14 and 15 positions, $R^{10A}$, $R^{10B}$, $R^{10C}$ and $R^{10D}$ are each independently chosen and have the meanings given above for compounds of structure 5, 6, 7, 8, 9 or 10;

$R^3$ and $R^4$ are, if present, both in the α-configuration or the β-configuration or one of $R^3$ and $R^4$ is in the α-configuration and the other is in the β-configuration;

D is a heterocycle, a 4-, 5-, 6- or 7-membered carbon ring, or two fused rings, each being 4-, 5-, 6- or 7-membered carbon ring, wherein 1, 2 or 3 ring carbon atoms of the 4-, 5-, 6- or 7-membered carbon ring(s) are optionally independently substituted with substituents described for substituted alkyl groups, e.g., —O—, —S— or —NR$^{PR}$— or where 1, 2 or 3 hydrogen atoms of the heterocycle or where 1, 2 or 3 hydrogen atoms of the 4-, 5-, 6- or 7-membered ring are substituted with —OR$^{PR}$, —SR$^{PR}$, —N(R$^{PR}$)$_2$, —O—Si—(R$^{13}$)$_3$, —CHO, —CHS, —CN, —NO$_2$, —OSO$_3$H, —OPO$_3$H, =O, =S, =N—OH, =CH$_2$ or a spiro ring an ester, a thioester, a thionoester, a phosphoester, a phosphothioester, a phosphonoester, a phosphiniester, a sulfite ester, a sulfate ester, a sulfoxide, a sulfamate, a sulfonate, a sulfamide, a sulfinamide, a sulfurous diamide, an amide, an amino acid, a peptide, an ether, a thioether, an acyl group, a thioacyl group, a carbonate, a carbamate, an acetal, a thioacetal, a halogen, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide or a polymer.

In some embodiments, D comprises two 5- or 6-membered rings, wherein the rings are fused or are linked by 1 or 2 bonds, wherein 0, 1, 2 or 3 of R$^7$, R$^8$ and R$^9$ are not —CHR$^{10}$— or —C(R$^{10}$)$_2$—

Exemplary F1C of structure 2 include the following structures,

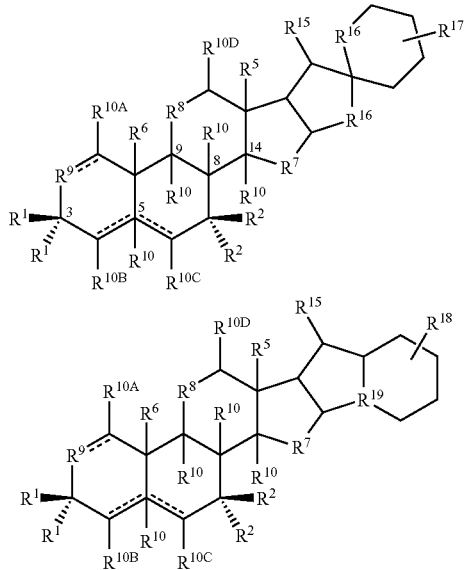

wherein, R$^{16}$ independently are —CH$_2$—, —O—, —S— or —NH—; R$^{15}$, R$^{17}$ and R$^{18}$ are independently selected R$^1$ moieties, e.g., —H, —OH, —OR$^{PR}$, =O, —SR$^{PR}$, =S, —O—Si—(R$^{13}$)$_3$, ester, ether, acyl, halogen or an optionally substituted alkyl group; and R$^{19}$ is nitrogen or CH; R$^1$-R$^{10}$, R$^{10A}$, R$^{10B}$, R$^{10C}$ and R$^{10D}$ are each independently chosen and have the meanings given above for compounds of structure 5, 6, 7, 8, 9 or 10; R$^{10}$ moieties at the 5 (if present), 8, 9 and 14 positions respectively are in the α,α,α,α, α,α,α,β, α,α,β,α, α,β,α,α, β,α,α,α, α,α,β,β, α,β,α,β, β,α,α,β, β,α,β,α, β,β,α,α, α, α,β,β,α, α,β,β,β, β,α,β,β, β,β,α,β, β,β,β,α or β,β,β,β configurations; and R$^5$ and R$^6$ are in the β,β, β,α, α,β or α,α configurations. For F1Cs of structure 2 where two variable groups are bonded to the same carbon, e.g., R$^1$, R$^2$ or R$^{10}$ at the 11 position, the each variable group at that position is independently selected. As shown in the structure, the R$^{17}$ moiety can be bonded to the ring carbon adjacent to R$^{16}$, or it can be bonded to the adjacent 1, 2 or 3 ring carbons. Similarly, the R$^{13}$ moiety can be bonded to the ring carbon adjacent to R$^{19}$, or it can be bonded to the adjacent 1, 2 or 3 ring carbons.

Structure 2 F1Cs can have 1, 2, 3 or 4 of R$^{10A}$, R$^{10B}$, R$^{10C}$ and R$^{10D}$ as —H, but usually 2 or 3 of R$^{10A}$, R$^{10B}$, R$^{10C}$ and R$^{10D}$ are —H, Structure 2 compounds include structures wherein one, two or three of R$^7$, R$^8$ and R$^9$ are independently —O—, —S—, or —NH— or wherein one or both of R$^5$ and R$^6$ independently are —H, —CH$_3$, —CH$_2$OR$^{PR}$, —CH$_2$OH, —CH$_2$SH, —CH$_2$SR$^{PR}$, —CH$_2$O—C(O)—C$_{1-10}$ alkyl, —CH$_2$S—C(O)—C$_{1-10}$ alkyl, —CH$_2$O—C(O)—C$_{1-10}$ alkenyl, —CH$_2$S—C(O)—C$_{1-10}$ alkenyl, —CH$_2$O—C(O)—C$_{0-4}$ alkyl-heterocycle, —CH$_2$S—C(O)—C$_{0-4}$ alkyl-heterocycle, —CH$_2$O—C(O)—C$_{0-4}$ alkyl-phenyl, —CH$_2$S—C(O)—C$_{0-4}$ alkyl-phenyl, wherein any C alkyl, heterocycle or phenyl moiety is optionally substituted with one or more substituents, wherein the one or more substituents are one, two, three or more independently selected —O—, =O, or R$^{PR}$, —S—, =S, —SR$^{PR}$, —NH—, —N(R$^{PR}$)$_2$ or —C(O)—NH—, wherein each R$^{PR}$ independently is —H or a protecting group.

The structure 2 compounds described above include

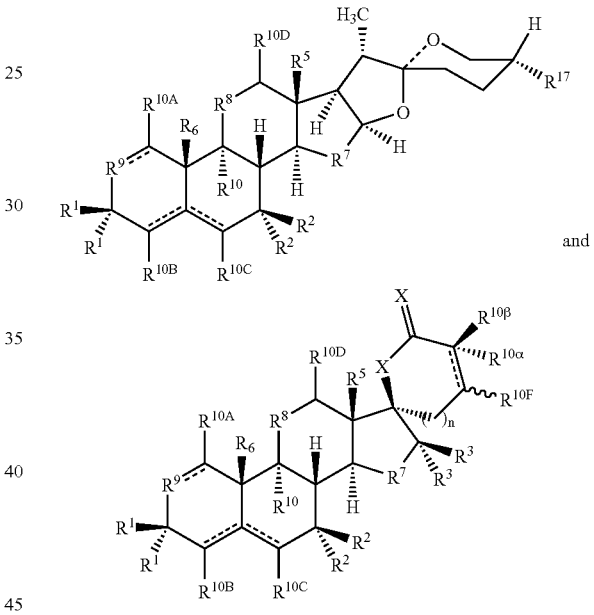

and where X independently are O or S, typically both X are O. R$^{10E}$ is an independently selected R$^{10}$ moiety in the α-configuration, or if a double bond is present, R$^{10α}$ is absent, R$^{10β}$ is an independently selected R$^{10}$ moiety in the β-configuration, R$^{10F}$ is an independently selected R$^{10}$ moiety in the α- or β-configuration, n is 0, 1 or 2, and remaining variable groups are as defined above. These compounds include ones where R$^1$ in the α- and β-configurations independently are an R$^1$ moiety such as H, OH, halogen, an optionally substituted monosaccharide, an optionally substituted disaccharide or a dicarboxylic acid ester such as —OC(O)—(CH$_2$)$_2$—COOH, —OC(O)—(CH$_2$)$_3$—COOH or —OC(O)—(CH$_2$)$_4$—COOH, R$^2$ in the α- and β-configurations independently are an R$^2$ moiety such as —H, —OH, =O, —SH, =S, halogen, optionally substituted alkyl, a monosaccharide or a disaccharide, R$^5$ is C1-C4 alkyl, R$^6$ is —H, halogen or C1-C4 alkyl or R$^7$ and R$^3$ independently are moieties as previously defined such as independently selected —CH$_2$—, —CH(α-OR$^{PR}$)—, —CH(β-R$^{PR}$)—, —C(O)— or —O—, R$^9$ is a moiety as previously defined such as —CH$_2$—, —CH(α-halogen)-, —CH(α-OH)—, —CH(α-optionally substituted alkyl)-, —C(halogen)$_2$-, —C(β-optionally substituted alkyl)(α-OH)—, —CH (α-optionally substituted alkyl)-, $R^{10}$ at the 9-position is a $R^{10}$ moiety such as —H, —F, —Cl, or optionally substituted alkyl, $R^{PR}$ is —H or a protecting group such as an ester or optionally substituted alkyl and other variable groups are as previously defined. For any of these compounds, 1, 2, 3 or 4 of $R^{10A}$, $R^{10B}$, $R^{10C}$ and $R^{10D}$ may be substituted, or they all be —H, while $R^{17}$ may be a moiety defined previously such as C1-C6 optionally substituted alkyl, e.g., —CH$_3$ or —C$_2$H$_5$.

Monosaccharides and disaccharides are described above and are optionally bonded at one or more of $R^1$ or other variable groups in these structure 2 or other formula 1 compounds include

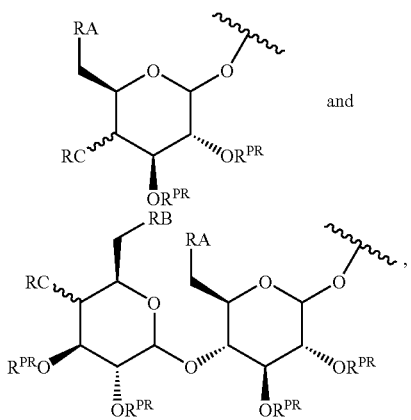

where RA and RB independently are —H, —OH, halogen, —NH$_2$, —NHR$^{PR}$, —N$_3$, C1-C6 alkoxy or —RD-RE, RC is —H, —OH, halogen, —NH$_2$, —NHR$^{PR}$, —N$_3$, C1-C6 alkoxy or a monosaccharide or disaccharide linked through a glycosidic bond, RD is —NH—C(O)—, —O—C(O)—, —O—C(O)—N(R$^{PR}$)—, —NH—C(O)—N(R$^{PR}$)—, —O—C(S)—N(R$^{PR}$)— or —C(O)—N—(R$^{PR}$)—, RE is aryl, arylalkyl, alkenyl, alkyl, cycloalkyl or cycloalkyl-alkyl, where each RE is optionally independently substituted with 1, 2 or 3 independently selected halogens, —OH, =O, —SH, =S, —NO$_2$, —CF$_3$, C1-C6 alkyl, phenoxy, C1-C6 alkoxy, methylenedioxy, C1-C6 alkylsulfanyl, C1-C6 alkylsulfinyl, C1-C6 alkylsulfonyl, dimethylamino, mono- or di-C1-C6 alkylaminocarbonyl, C1-C6 alkylcarbonyl, C1-C6 alkoxycarbonyl or pyrrolidinylcarbonyl, R$^{PR}$ independently is —H or a protecting group such as C1-C6 optionally substituted alkyl, ester such as acetate or, if bonded to nitrogen, R$^{PR}$ together with the nitrogen to which it is attached is pyrrolidinyl, piperidinyl, N-methylpiperazinyl, indolinyl or morpholinyl, where the cyclic group may be monosubstituted on a carbon atom with C1-C6 alkoxycarbonyl or C1-C6 optionally substituted alkyl. In some of these embodiments, RA, RB and RC are —OH.

For any F1C of structure 2, 5, 6, 7, 8, 9 or 10, one, two or more of $R^1$-$R^{10}$, $R^{10A}$, $R^{10B}$, $R^{10C}$, $R^{10D}$, $R^{15}$, $R^{17}$ and $R^{13}$ may be moieties that are chemically and/or enzymatically hydrolysable or removable, typically under physiological conditions, e.g., esters, thioesters, thionoesters, carbonates, amino acids, peptides and/or carbamates. Such moieties are independently chosen. These moieties will typically give rise to moieties such as to —OH, =O, —SH or =S at the steroid nucleus. Embodiments of F1Cs include compounds where (1) one of $R^1$, $R^2$ and $R^4$ is a hydrolyzable moiety (e.g., ester, thioester, thionoester, carbonate, amino acid, peptide or carbamate), the other two of $R^1$, $R^2$ and $R^4$ are —H, $R^3$ is not hydrogen and $R^5$ and $R^6$ are both —CH$_3$, (2) two of $R^1$, $R^2$ and $R^4$ are hydrolyzable moieties (e.g., independently chosen esters, thioesters, thionoesters, carbonates, amino acids, peptides and/or carbamates), the other of $R^1$, $R^2$ and $R^4$ is —H, $R^3$ is not hydrogen and $R^5$ and $R^6$ are both —CH$_3$, (3) $R^1$, $R^2$ and $R^4$ are hydrolyzable moieties, $R^3$ is not hydrogen and $R^5$ and $R^6$ are both —CH$_3$. In these embodiments, the $R^3$ group is typically in the β-configuration and the $R^1$, $R^2$ and $R^4$-$R^6$ groups are typically in the α-configuration.

In other embodiments, one or more of $R^1$-$R^6$, $R^{10}$, $R^{15}$, $R^{17}$ and $R^{13}$, usually one, comprises an amino acid or a peptide, while the remaining groups are independently selected from the moieties defined herein. In these embodiments, the peptides are typically dimers (dipeptides) or trimers (tripeptides). For example one of $R^1$, $R^2$ or $R^4$ comprises an amino acid, the remaining of $R^1$, $R^2$ or $R^4$ independently comprise —OH, =O, an ester, a carbonate or a carbamate, while $R^3$ is a halogen, hydroxyl or an ester and $R^5$ and $R^6$ independently are —H, —(CH$_2$)$_n$—CH$_3$, —(CH$_2$)$_n$—CH$_2$OH, or —(CH$_2$)$_n$—CH$_2$F, —(CH$_2$)$_{2-4}$—O—(CH$_2$)$_{2-4}$—CH$_3$, where n is 0, 1, 2, 3, 4, 5, 6, 7 or 8 often 0, 1, or 2, usually 0. Typically the ester, carbonate or carbamate are hydrolyzable under physiological conditions.

Hydrolyzable or removable moieties typically comprise acyl groups, esters, ethers, thioethers, amides, amino acids, peptides, carbonates and/or carbamates. In general, the structure of hydrolyzable moieties is not critical and can vary. In some embodiments, these moieties contain a total of about 4 to about 10 carbon atoms. These hydrolyzable moieties in other embodiments comprise an organic moiety, as described above for ester, that contains 2, 3, 4, 5, 6, 7, 8, 9, 10, 11, 12 13, 14, 15 or 16 carbon atoms and 1, 2, 3, 4, 5, 6, 7 or 8 heteroatoms, e.g., oxygen, nitrogen or sulfur. These hydrolyzable moieties can comprise no groups that are charged in plasma, blood, intracellular cytoplasm or in the gut, or they can comprise 1, 2, 3 or more positive, negative or positive and negative charges under one or more of these conditions. The charges may be fractional depending on the group and the conditions it is under. These hydrolyzable moieties may comprise 1, 2, 3, 4 or more substitutions at a hydrogen atom(s) and/or a carbon atom(s), e.g., —OH, protected hydroxyl, —SH, protected thiol, carboxyl, protected carboxyl, amine, protected amine, —O—, —S—, —CO—, —CS—, alkoxy, alkylthio, alkenyloxy, aryl, —OP(O)(O)—O—, —OS(O)(O)—O— and/or heterocycle. Such substitutions are independently selected. Embodiments of F1Cs include ones wherein one, two, three, four or more of the variable groups that are bonded to the steroid rings, e.g., $R^1$-$R^6$ or $R^{10}$, comprise a moiety that can hydrolyze or metabolize to, e.g., a —H, —OH, =O, —SH, =S, —COOH, —NH$_2$, —CH$_2$OH, —CH$_2$SH, —C(O)—C1-C6 alkyl-OH, —C(O)—C1-C6 alkyl-SH, —C(S)—C1-C6 alkyl-OH, —C(O)—C1-C6 alkyl or —C(O)—NH$_2$ atom or group.

F1Cs that comprise a hydrolyzable or removable moiety(ies) may include one or more independently chosen —O—CHR$^{24}$C(O)OR$^{25}$, —S—CHR$^{24}$C(O)OR$^{25}$, —NH—CHR$^{24}$C(O)OR$^{25}$, —O—CHR$^{24}$C(S)OR$^{25}$, —S—CHR$^{24}$C(S)OR$^{25}$, —NH—CHR$^{24}$C(S)OR$^{25}$, —O—CHR$^{24}$OC(O)R$^{25}$, —S—CHR$^{24}$OC(O)R$^{25}$, —NH—CHR$^{24}$OC(O)R$^{25}$, —O—CHR$^{24}$C(O)N(R$^{25}$)$_2$, —S—CHR$^{24}$C(O)N(R$^{25}$)$_2$, —NH—CHR$^{24}$C(O)N(R$^{25}$)$_2$, —O—CHR$^{24}$OR$^{25}$, —S—CHR$^{24}$OR$^{25}$, —NH—CHR$^{24}$OR$^{25}$, —O—CHR$^{24}$C(R$^{25}$)$_2$CH$_2$OX, —S—CHR$^{24}$C(R$^{25}$)$_2$CH$_2$OX, —NH—CHR$^{24}$C(R$^{25}$)$_2$CH$_2$OX, —O—CHR$^{24}$C(R$^{25}$)$_2$OX, —S—CHR$^{24}$C(R$^{25}$)$_2$OX or —NH—CHR$^{24}$C(R$^{25}$)$_2$OX, groups that one or more of $R^1$-$R^6$, $R^{10}$, $R^{15}$, $R^{17}$ and $R^{13}$ comprise. For these hydrolyzable moieties, $R^{24}$ independently is —H, —CH$_2$—C$_6$H$_5$, —CH$_2$CH$_2$—C$_6$H$_5$, C$_{1-8}$ alkyl, C$_{2-8}$ alkenyl, aryl or heterocycle where each alkyl, alkenyl, aryl and heterocycle moiety is independently optionally substituted with 1, 2, or 3, usually 1, —O—, —S—, —NH—, halogen, aryl, —OX, —SX, —NHX, ketone (=O) or —CN moieties or the C$_{1-8}$ alkyl is optionally substituted with 3, 4, 5 or 6 halogens, and X is —H or a protecting group. Exemplary R$^{24}$ are —H, —CH$_3$, —C$_2$H$_5$, —C(CH$_3$)$_3$, —CH$_2$—C$_{1-5}$ optionally substituted alkyl, —CH$_2$CH$_2$—C$_{1-4}$ optionally substituted alkyl and —CH$_2$CH$_2$—O—C$_{1-4}$ optionally substituted alkyl. R$^{25}$ independently is —H or a C$_{1-30}$ organic moiety such as —CH$_2$—C$_6$H$_5$, —CH$_2$CH$_2$—C$_6$H$_5$, C$_{1-12}$ alkyl, C$_{2-12}$ alkenyl, C$_{2-12}$ alkynyl, aryl, a heterocycle, —CH$_2$-heterocycle or —CH$_2$-aryl, where each alkyl, alkenyl, alkynyl, aryl, heterocycle, —CH$_2$-heterocycle or —CH$_2$-aryl moiety is independently optionally substituted with 1 or 2, usually 1, —O—, —S—, —NH—, halogen, aryl, —OX, —SX, —NHX, ketone (=O), —C(O)OX or —CN moieties or the C$_{1-12}$ alkyl, C$_{2-12}$ alkenyl or aryl, are optionally independently substituted with 3, 4, 5 or 6 halogens, where X is —H or a protecting group, or the aryl, heterocycle, —CH$_2$-heterocycle or —CH$_2$-aryl moieties are optionally independently substituted with 1, 2 or 3 C$_{1-4}$ alkyl moieties or with 1, 2 or 3 C$_{1-4}$ alkoxy moieties at the aryl moiety or at the heterocycle, usually at a ring carbon. Exemplary R$^{25}$ are —H, —CH$_3$, —C$_2$H$_5$, —C$_3$H$_7$, —C$_4$H$_9$, —C$_6$H$_{13}$, —C$_6$H$_5$, —C$_6$H$_4$OH, —C$_6$H$_4$OCH$_3$, —C$_6$H$_4$F, —CH$_2$—C$_{1-5}$ optionally substituted alkyl, —CH$_2$CH$_2$—(S)$_{0-1}$—C$_{1-4}$ optionally substituted alkyl and —CH$_2$CH$_2$—O—C$_{1-4}$ optionally substituted alkyl.

For any formula 1, 2, 5, 6, 7, 8, 9 or 10 compounds, whenever a variable moiety such as R$^7$, R$^8$ or R$^9$ or a substitution at a variable group includes moieties such as —O—CHR$^{10}$—, —NR$^{PR}$—CHR$^{10}$—, or =N— it is intended that such moieties can be present in either orientation relative to the other ring atoms that may be present, i.e., —O—CHR$^{10}$—, —NR$^{PR}$—CHR$^{10}$—, —CHR$^{10}$—O—, —CHR$^{10}$—NR$^{PR}$—, =N— and —N= are all included, unless defined or implied otherwise by the structure.

Invention embodiments include a composition comprising a F1C and 1, 2, 3, 4 or more nonaqueous liquid excipients. These compositions can contain less than about 3% w/v water, less than about 2% w/v water, less than about 1.5% w/v water, less than about 1% w/v water, less than about 0.8% w/v water, less than about 0.5% w/v water, less than about 0.3% w/v water or less than about 0.1% w/v water. Typically, the nonaqueous liquid excipients include propylene glycol and a PEG or a PEG mixture and can optionally include one or both of benzyl alcohol and benzyl benzoate.

Embodiments of F1Cs include or exclude any subset of compounds within the definition of formula 1, provided that at least one F1C remains. For example, a subset of F1Cs that are may be included, for example in the invention nonaqueous formulations and in the invention intermittent dosing protocols and immune modulation methods, are (1) F1Cs where R$^2$ is hydroxyl, or a group that can hydrolyze or metabolize to hydroxyl or thiol, in either configuration and R$^5$ and R$^6$ are methyl in the α-configuration or (2) any 1, 2, 3, 4, 5, 6 or more of the F1Cs or genera of compounds that are disclosed herein. Another group of compounds that are optionally excluded from F1Cs comprises one or all compounds that are disclosed in one or more prior art references or publications, e.g., one or more compounds that are disclosed in one or more of the references cited herein, especially for those compounds that can render any claim or embodiment unpatentable for novelty, obviousness and/or inventive step reasons.

Other embodiments of species and genera of F1Cs include compounds of structures B, C, D, E, F and G

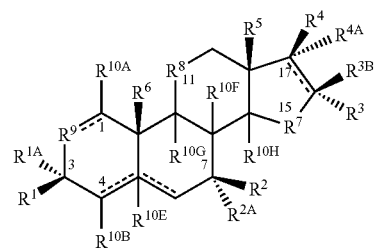

B

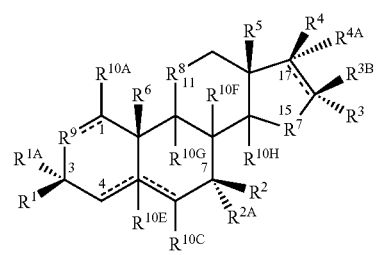

C

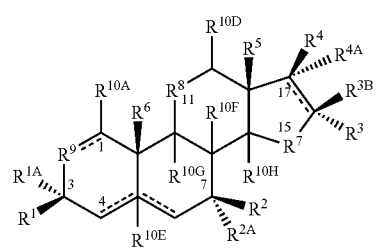

D

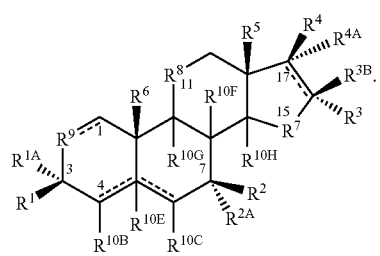

E

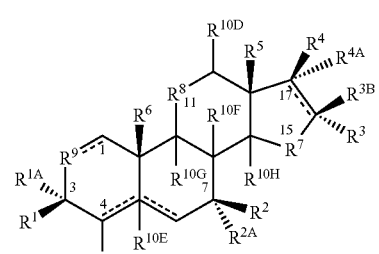

F

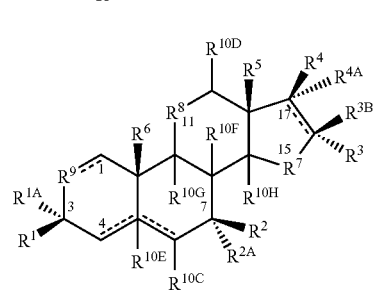

G where the dotted lines represent double or single bonds, each $R^{10A}$, $R^{10B}$, $R^{10C}$, $R^{10D}$, $R^{10E}$ (when present), $R^{10F}$, $R^{10G}$ and $R^{10H}$ is an independently selected single bonded $R^{10}$ moiety in the α-configuration or the β-configuration, or each $R^{10A}$, $R^{10B}$, $R^{10C}$ and $R^{10D}$ is an independently selected double bonded $R^{10}$ moiety (e.g., =O or =CH$_2$), $R^{1A}$ is a single bonded $R^1$ moiety in the α-configuration, or $R^{1A}$ together with $R^1$ is a double bonded moiety (e.g., =O, =NOH, =CH$_2$ or =CH—CH$_3$), $R^{2A}$ is a single bonded $R^2$ moiety in the α-configuration, or $R^{2A}$ together with $R^2$ is a double bonded moiety, $R^{3B}$ is a single bonded $R^3$ moiety in the β-configuration, or $R^{3B}$ together with $R^3$ is a double bonded moiety, or $R^{3B}$ is absent if a double bond is present at the 16-17 position, $R^{4A}$ is a single bonded $R^4$ moiety in the α-configuration, or $R^{4A}$ together with $R^4$ is a double bonded moiety, or $R^{4A}$ is absent if a double bond is present at the 16-17 position, and $R^5$, $R^6$, $R^7$, $R^8$ and $R^9$ are as previously defined. When a double bond is present at the 4-5 or the 5-6 positions, $R^{10E}$ is absent. For these structures, $R^{10A}$, $R^{10B}$, $R^{10C}$ and $R^{10D}$ may be in the α,β, α,β, β,α, or β,β°configurations respectively, while $R^{10E}$, $R^{10F}$, $R^{10G}$ and $R^{10H}$ may be in the α,α,α,α, α,α,α,β, α,α,β,α, α,β,α,α, β,α,α,α, α,α,β,β, α,β,α,β, β,α,α,β, β,α,β,α, β,β,α,α, α,β,β,α, α,β,β,β, β,α,β,β, β,β,α,β, β,β,β,α or β,β,β,β configurations respectively, typically the α,β,α,α or β,β,α,α configurations.

Thus, when $R^{10E}$, $R^{10F}$, $R^{10G}$ and $R^{10H}$ respectively are in the α,β,α,α configurations and $R^{10A}$ and $R^{10B}$ or $R^{10A}$ and $R^{10C}$ or $R^{10A}$ and $R^{10D}$ or $R^{10B}$ and $R^{10C}$ or $R^{10B}$ and $R^{10D}$ or $R^{10C}$ and $R^{10D}$ are both in α-configurations exemplary B, C, D, E, F and G structures include

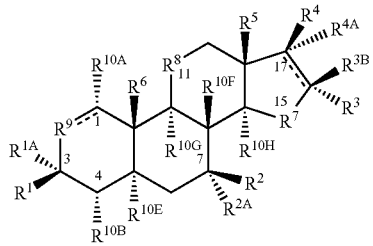

B

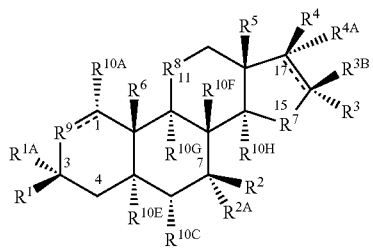

C

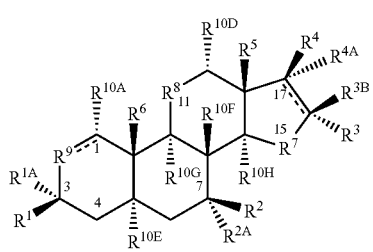

D

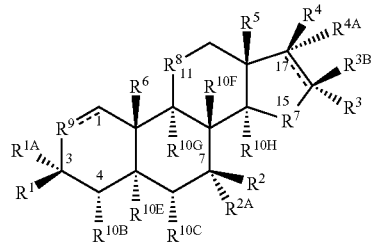

E

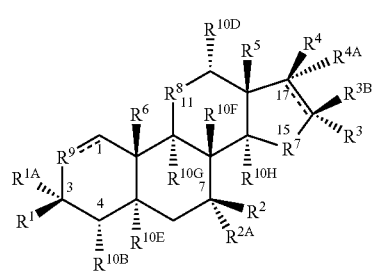

F

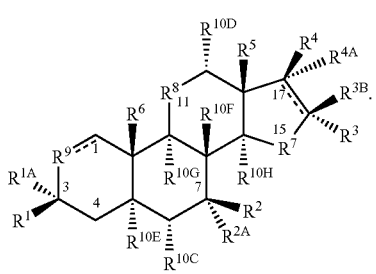

G

Similarly, when $R^{10E}$, $R^{10F}$, $R^{10G}$ and $R^{10H}$ respectively are in the α,β,α,α configurations and $R^{10A}$ and $R^{10B}$ or $R^{10A}$ and $R^{10C}$ or $R^{10A}$ and $R^{10D}$ or $R^{10B}$ and $R^{10C}$ or $R^{10B}$ and $R^{10D}$ or $R^{10C}$ and $R^{10D}$ respectively are in the β,α configurations exemplary B, C, D, E, F and G structures include

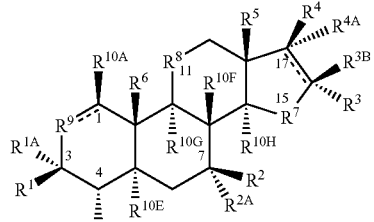

B

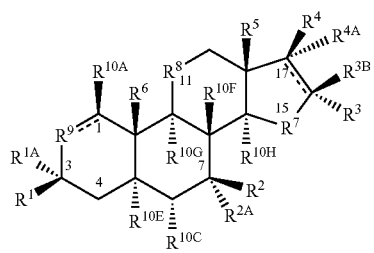

C

D

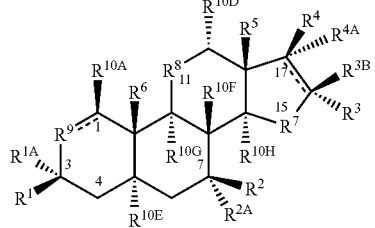

E

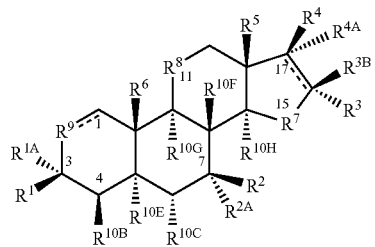

F

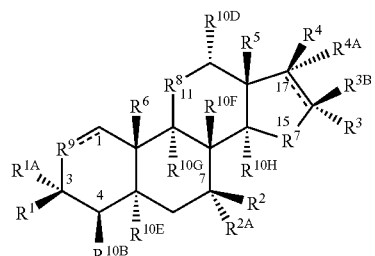

G

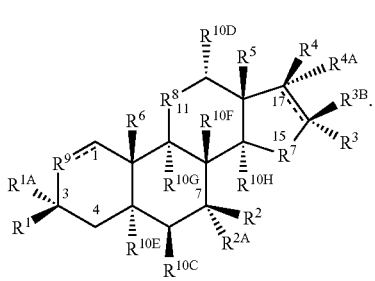

When $R^{10E}$, $R^{10F}$, $R^{10G}$ and $R^{10H}$ respectively are in the configurations and $R^{10A}$ and $R^{10B}$ or $R^{10A}$ and $R^{10C}$ or $R^{10A}$ and $R^{10D}$ or $R^{10B}$ and $R^{10C}$ or $R^{10B}$ and $R^{10D}$ or $R^{10C}$ and $R^{10D}$ respectively are in the α,β configurations exemplary B, C, D, E, F and G structures include

B

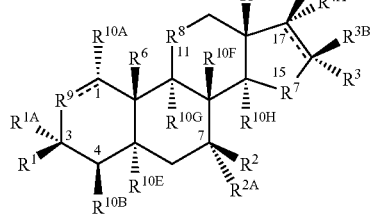

C

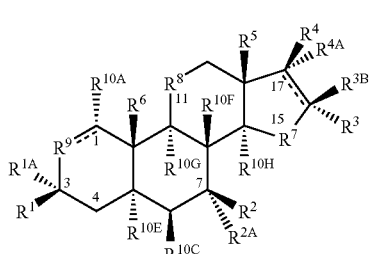

D

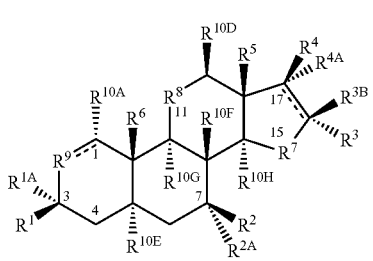

E

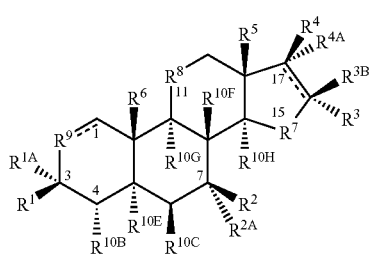

F

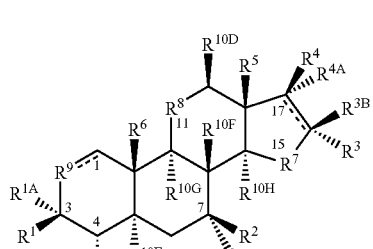

G

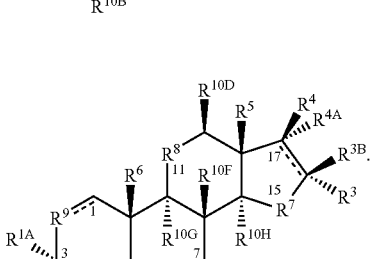

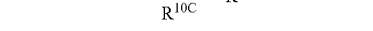

When $R^{10E}$, $R^{10F}$, $R^{10G}$ and $R^{10H}$ respectively are in the α,β,α,α configurations and $R^{10A}$ and $R^{10B}$ or $R^{10A}$ and $R^{10C}$ or $R^{10A}$ and $R^{10D}$ or $R^{10B}$ and $R^{10C}$ or $R^{10B}$ and $R^{10D}$ or $R^{10C}$ and $R^{10D}$ respectively are in the β,β configurations exemplary B, C, D, E, F and G structures include

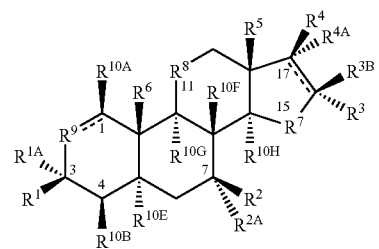
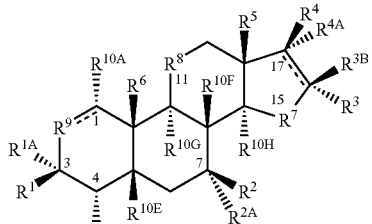
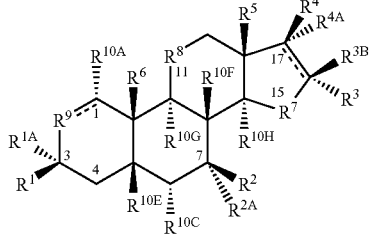
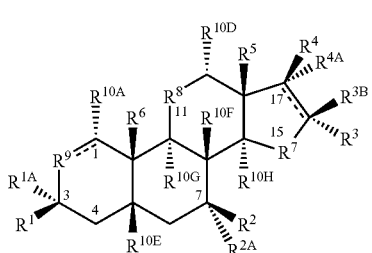
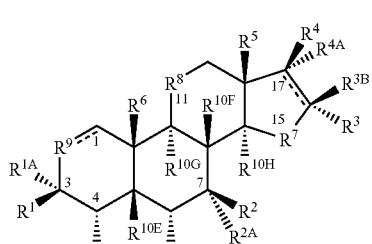
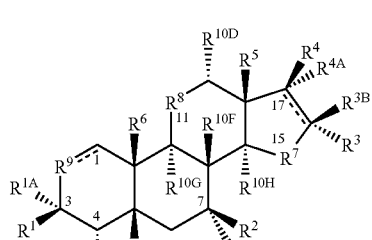
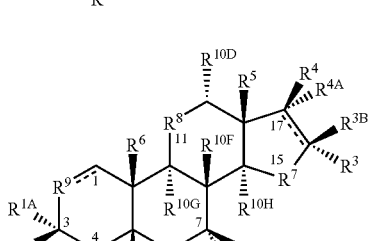
When $R^{10E}$, $R^{10F}$, $R^{10G}$ and $R^{10H}$ respectively are in the β,β,α,α configurations exemplary B, C, D, E, F and G structures include B
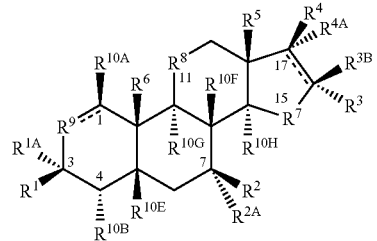
C
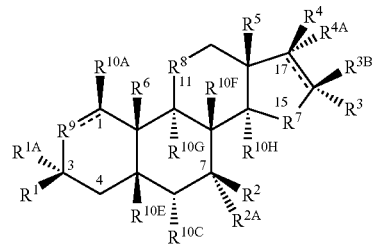
D
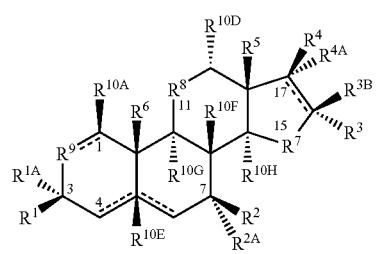
E
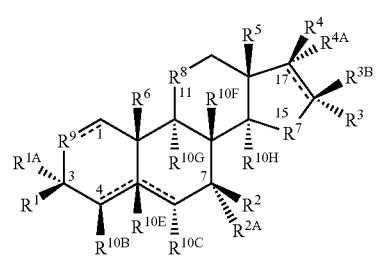
F
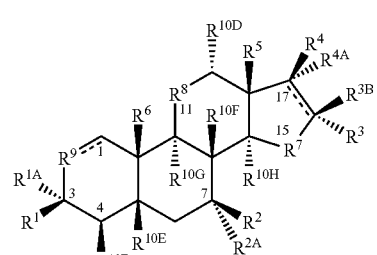
G
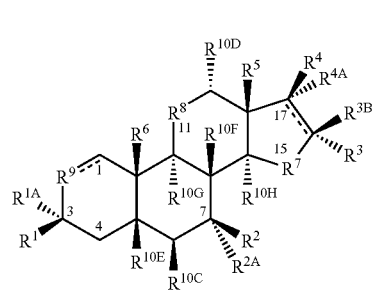
B
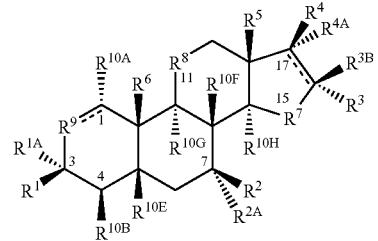
C
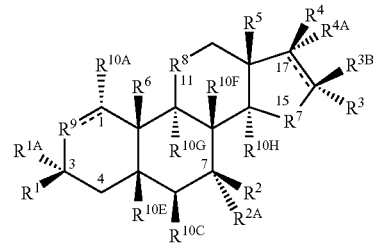
D
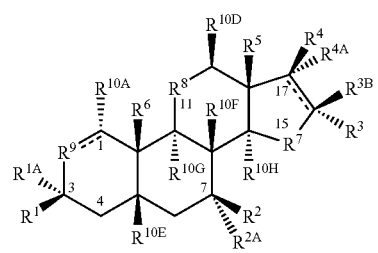
E
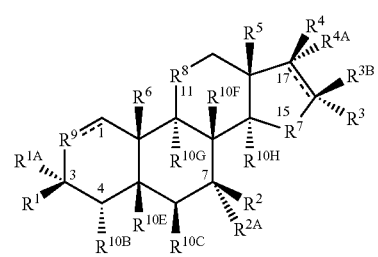
F
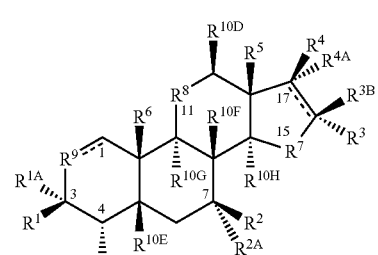
G
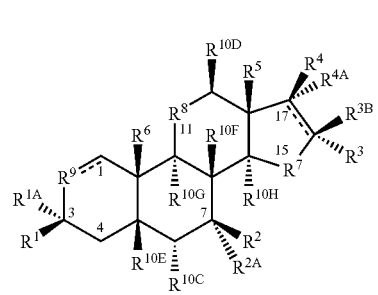

B
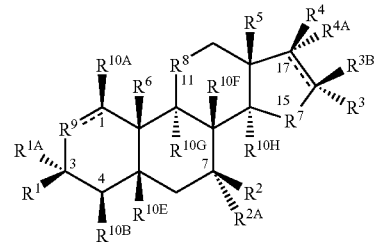
C
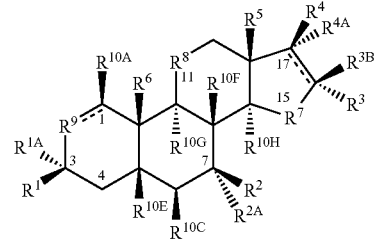
D
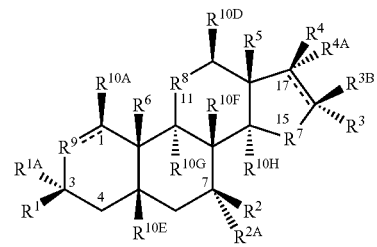
E
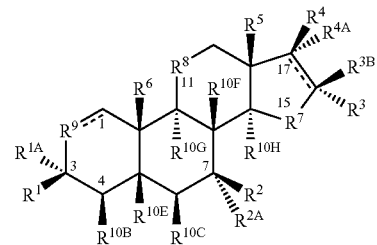
F
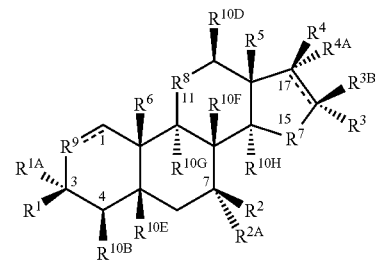
G
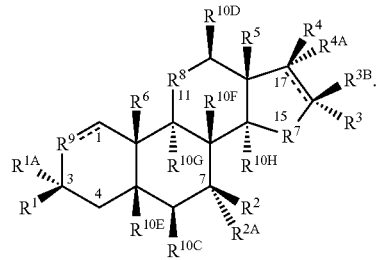
B
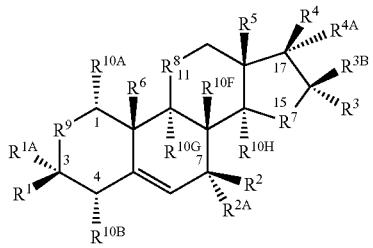
C
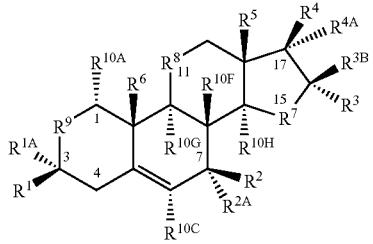
D
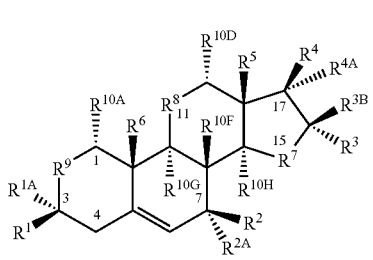
E
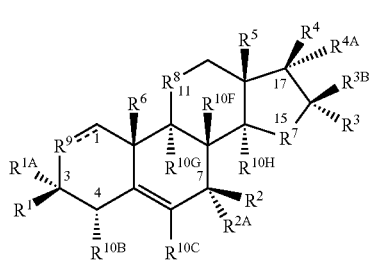
F
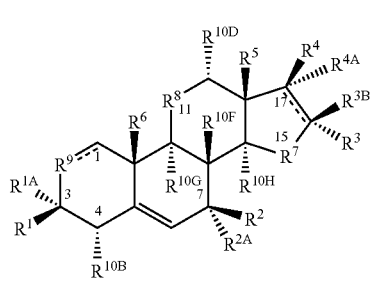
G
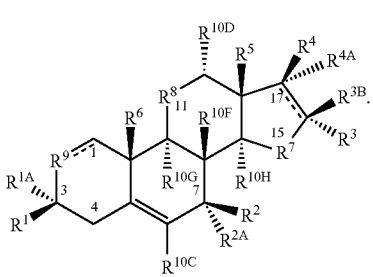
When a double bond is present at the 5-6 position, and $R^{10F}$, $R^{10G}$ and $R^{10H}$ respectively are in the β,α,α configurations exemplary B, C, D, E, F and G structures include
When a double bond is present at the 1-2 and 5-6 positions, and $R^{10F}$, $R^{10G}$ and $R^{10H}$ respectively are in the β,α,α configurations exemplary B, C, D, E, F and G structures include B
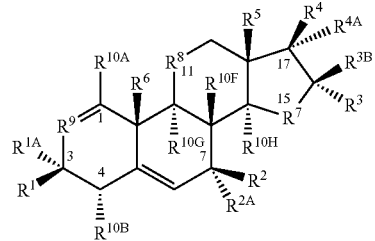
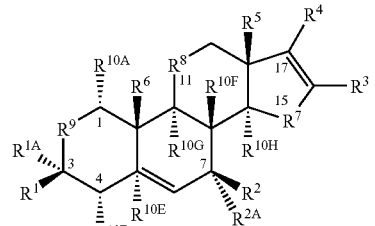
B
C
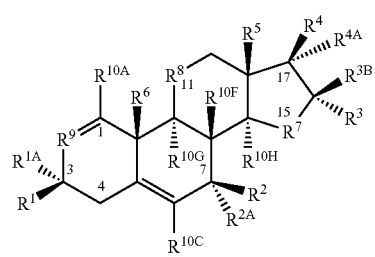
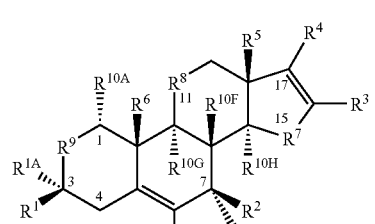
C
D
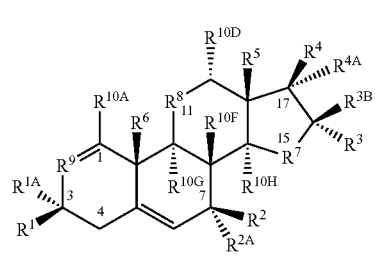
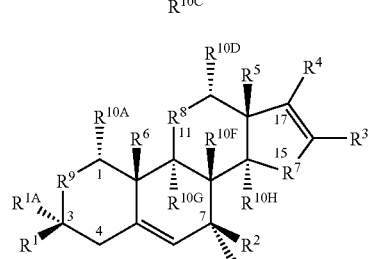
D
E
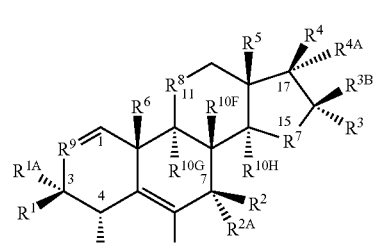
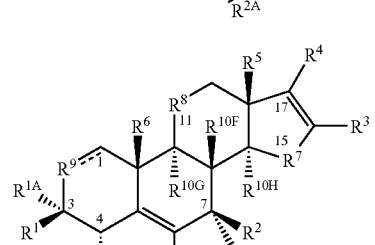
E
F
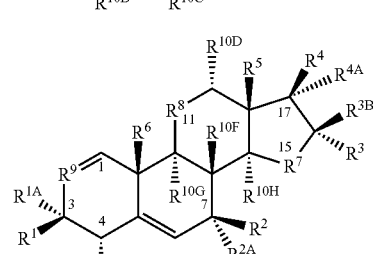
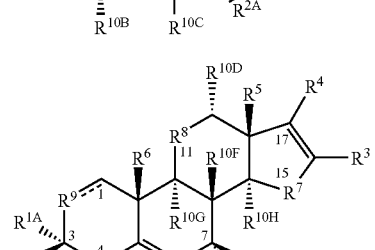
F
G
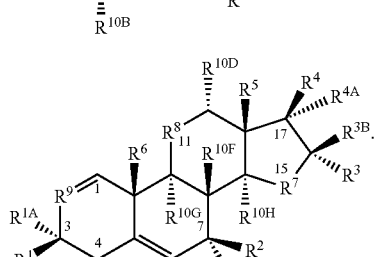
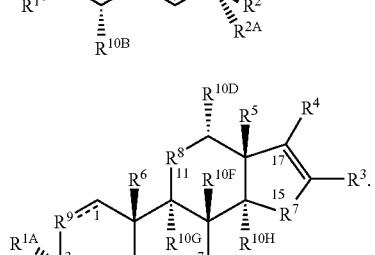
G
When a double bond is present at the 5-6 and 16-17 positions, and $R^{10F}$, $R^{10G}$ and $R^{10H}$ respectively are in the β,α,α configurations exemplary B, C, D, E, F and G structures include
When $R^6$ and $R^{10C}$ are linked through a —CH$_2$—O— moiety there is no double bond at the 5-6 position and exemplary F1C structures include

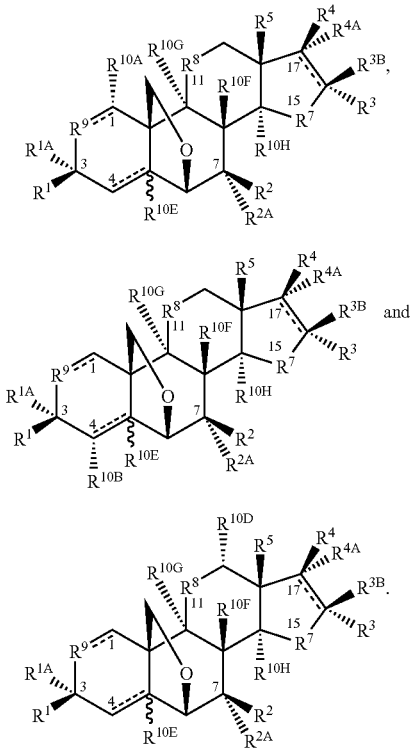

When adjacent variable groups are an epoxide or an optionally substituted cyclopropyl ring, exemplary F1C structures include

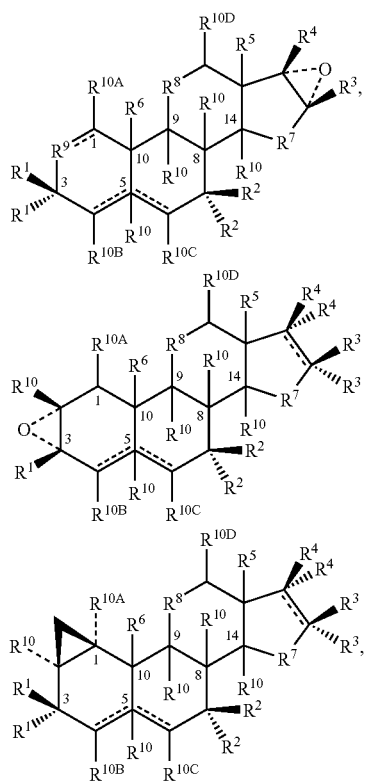

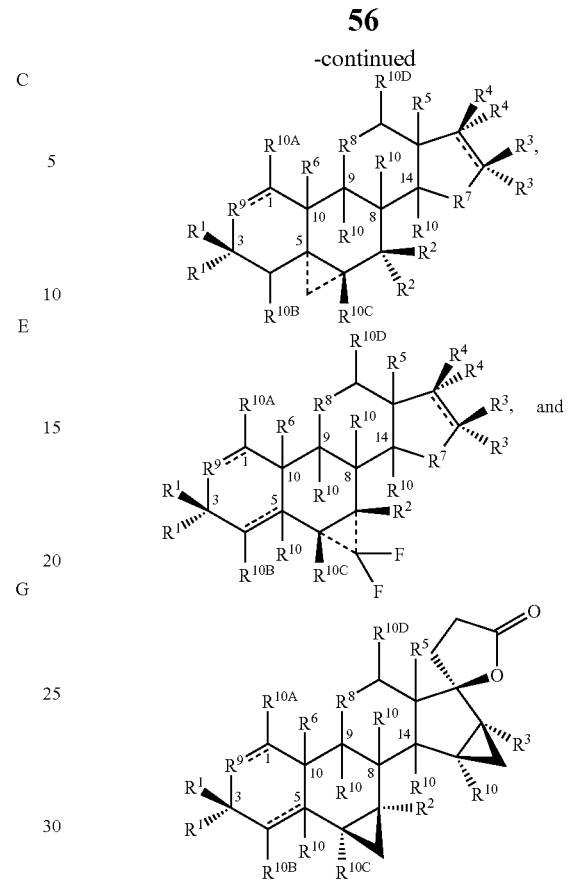

wherein variable groups are independently selected and, when not specified otherwise, are in the α- or β-configuration. Substituents at the cyclopropyl ring include one or two halogen atoms, e.g., dichloro, dibromo or difluoro. Typically these F1C contain one or two epoxide or cyclopropyl moieties.

Other F1Cs and structures having B, C, D, E, F and G structures are apparent from the foregoing descriptions and variable group definitions.

Thus, exemplary F1C, e.g., 2, 5, 6, 7, 8, 9, 10, B, C, D, E, F and G structures are characterized as having the following:

(1) a double bond at the 5-6 position, no double bonds with $R^{10E}$ at the 5 position in the α-configuration, no double bonds with $R^{10E}$ in the β-configuration, a double bond at the 4-5 position, a double bond at the 1-2 position with $R^{10E}$ in the (α-configuration, a double bond at the 1-2 position with $R^{10E}$ in the β-configuration, double bonds at the 1-2 and 4-5 positions, double bonds at the 1-2 and 5-6 positions, a double bond at the 16-17 position with $R^{10E}$ in the α-configuration, a double bond at the 16-17 position with $R^{10E}$ in the β-configuration, double bonds at the 4-5 and 16-17 positions, double bonds at the 5-6 and 16-17 positions, double bonds at the 1-2 and 16-17 positions with $R^{10E}$ in the α-configuration, double bonds at the 1-2 and 16-17 positions with $R^{10E}$ in the β-configuration, double bonds at the 1-2, 5-6 and 16-17 positions or double bonds at the 1-2, 4-5 and 16-17 positions, and (2) $R^{10A}$, $R^{10B}$, $R^{10C}$ and $R^{10D}$ are independently selected $R^{10}$ groups in the α,α, α,β, β,α or β,β configurations respectively, and (3) $R^{10E}$, $R^{10F}$, $R^{10G}$ and $R^{10H}$ are independently selected $R^{10}$ groups in the α,α,α,α, α,α,α,β, α,α,β,α, α,β,α,α, β,α, α,α, α,α,β,β, α,β,α,β, β,α,α,β, β,α,β,α, β,β,α,α, α,β,β,α, α,β,β,β, β,α,β,β, β,β,α,β, β,β,β,α or β,β,β,β configurations respectively, and (4) $R^{1A}$, $R^{2A}$, $R^{3B}$ and $R^{4A}$ are —H, $R^{1A}$ is not —H and $R^{2A}$, $R^{3B}$ and $R^{4A}$ are —H, $R^{2A}$ is not —H and $R^{1A}$, $R^{3B}$ and $R^{4A}$ are —H, $R^{3B}$ is not —H and $R^{1A}$, $R^{2A}$ and $R^{4A}$ are —H, $R^{4A}$ is not —H and $R^{1A}$, $R^{2A}$ and $R^{3B}$ are —H, $R^{1A}$ and $R^{2A}$ are not —H and $R^{3B}$ and $R^{4A}$ are —H, $R^{1A}$ and $R^{3B}$ are not —H and $R^{2A}$ and $R^{4A}$ are —H, $R^{1A}$ and $R^{4A}$ are not —H and $R^{2A}$ and $R^{3B}$ are —H, $R^{2A}$ and $R^{3B}$ are not —H and $R^{1A}$ and $R^{4A}$ are —H, $R^{2A}$ and $R^{4A}$ are not —H and $R^{1A}$ and $R^{3B}$ are —H, $R^{3B}$ and $R^{4A}$ are not —H and $R^{1A}$ and $R^{2A}$ are —H, $R^{1A}$, $R^{2A}$ and $R^{3B}$ are not —H and $R^{4A}$ is —H, $R^{1A}$, $R^{2A}$ and $R^{4A}$ are not —H and $R^{3B}$ is —H, $R^{1A}$, $R^{3B}$ and $R^{4A}$ are not —H and $R^{2A}$ is —H, $R^{2A}$, $R^{3B}$ and $R^{4A}$ are not —H and $R^{1A}$ is —H, $R^{1A}$, $R^{2A}$, $R^{3B}$ and $R^{4A}$ are not —H, $R^{1A}$ and $R^{2A}$ are —H and $R^{3B}$ and $R^{4A}$ are absent (i.e., a 16-17 double bond is present), $R^{1A}$ is —H and $R^{2A}$ is not —H and $R^{3B}$ and $R^{4A}$ are absent, $R^{2A}$ is —H and $R^{1A}$ is not —H and $R^{3B}$ and $R^{4A}$ are absent, or, $R^{1A}$ and $R^{2A}$ are not —H and $R^{3B}$ and $R^{4A}$ are absent, where each $R^{1A}$, $R^{2A}$, $R^{3B}$ and $R^{4A}$ are independently selected, and (5) each $R^1$, $R^2$, $R^3$ and $R^4$ are independently selected.

For these exemplary formula B, C, D, E, F and G structures and any other F1C structures disclosed herein, each $R^1$, $R^{1A}$, $R^2$, $R^{2A}$, $R^3$, $R^{3B}$, $R^4$, $R^{4A}$, $R^{10}$, $R^{10A}$, $R^{10B}$, $R^{10C}$, $R^{10D}$, $R^{10E}$, $R^{10F}$ and $R^{10G}$ are an independently selected atom or moiety as described herein, e.g., —H, —OH, =O, —SH, =S, —F, —Cl, —Br, —I, —CN, —SCN, —N$_3$, —NH—C1-C8 optionally substituted alkyl, —N(C1-C8 optionally substituted alkyl)$_2$ where each optionally substituted alkyl moiety is the same or different, protected ketone, e.g., ethylene ketal (—O—CH$_2$—CH$_2$—O—), —NO$_2$, —ONO$_2$, —(CH$_2$)$_n$—CH(O), —(CH$_2$)$_n$—COOH, —(CH$_2$)$_n$—COOR$^{PR}$, —(CH$_2$)$_n$—NHCH$_3$, —(CH$_2$)$_n$—NHR$^{PR}$, —(CH$_2$)$_n$—CH(S), —O—S(O)(O)—OH, —O—P(O)(O)—OH, where n is 0, 1, 2, 3, 4, 5 or 6, —O-β-D-glucopyranosiduronate, —OP(O)(OH)—NH—C(=NH)—N(CH$_3$)—CH$_2$—C(O)OH, or a group such as:

optionally substituted alkyl, e.g., —CH$_3$, —C$_2$H$_5$, —CH$_2$CH$_2$CH$_3$, —CH$_2$CH$_2$CH$_2$CH$_3$, —CH$_2$CH$_2$OCH$_2$CH$_3$, —CH$_2$OH, —CH$_2$CH$_2$OH, —CHOHCH$_3$, —CH(OC(O)CH$_3$)—CH$_3$, —CH(OR$^{PR}$)—CH$_3$, —CHOH—(CH$_2$)$_n$—OH, —CH(OR$^{PR}$)—(CH$_2$)$_n$—OR$^{PR}$, —CHOH—(CH$_2$)$_n$—CH$_2$OH, —CH(OR$^{PR}$)—(CH$_2$)$_n$—CH$_2$OR$^{PR}$, —CHOH—(CH$_2$)$_n$—CH$_2$SH, —CH(OR$^{PR}$)—(CH$_2$)$_n$—CH$_2$SR$^{PR}$, —CH$_2$—(CH$_2$)$_n$—OCH$_3$, —CF$_3$, —(CH$_2$)$_t$—CF$_3$, —(CH$_2$)$_t$—NH$_2$, —(CH$_2$)$_2$—NH$_2$, —(CH$_2$)$_3$—NH$_2$, —CH$_2$—NH(CH$_3$), —(CH$_2$)$_2$—NHCH$_3$, —(CH$_2$)$_3$—NHCH$_3$, —(CH$_2$)$_t$—N(CH$_3$)$_2$, —(CH$_2$)$_n$—CH$_2$OH, —(CH$_2$)$_n$—CH$_2$F, —(CH$_2$)$_n$—CH$_2$Cl, —(CH$_2$)$_n$—CH$_2$Br, —CH(CH$_3$)—(CH$_2$)$_3$—CH(CH$_3$)$_2$, —CH(CH$_3$)—(CH$_2$)$_n$—CH(CH$_3$)$_2$, —CH(CH$_3$)—(CH$_2$)$_3$—CH(CH$_3$)—CH$_2$OH, —CH(CH$_3$)—(CH$_2$)$_n$—CH(CH$_3$)—CH$_2$OH, —CH(CH$_3$)—(CH$_2$)$_3$—CH(CH$_3$)—CH$_2$F, —CH(CH$_3$)—(CH$_2$)$_n$—CH(CH$_3$)—CH$_2$F, —CH(CH$_3$)—(CH$_2$)$_3$—CH(CH$_3$)—CH$_2$Cl, —CH(CH$_3$)—(CH$_2$)$_n$—CH(CH$_3$)—CH$_2$Cl, —CH(CH$_3$)—(CH$_2$)$_3$—CH(CH$_3$)—CH$_2$Br, —CH(CH$_3$)—(CH$_2$)$_n$—CH(CH$_3$)—CH$_2$Br, —CH(CH$_3$)—(CH$_2$)$_3$—CH(CH$_2$F)$_2$, —CH(CH$_3$)—(CH$_2$)$_n$—CH(CH$_2$F)$_2$, —(CH$_2$)$_3$—CH(CH$_3$)$_2$, —(CH$_2$)$_n$—CH(CH$_3$)$_2$, —(CH$_2$)$_3$—CH(CH$_3$)—CH$_2$OH, —(CH$_2$)$_n$—CH(CH$_3$)—CH$_2$OH, —(CH$_2$)$_3$—CH(CH$_3$)—CH$_2$F, —(CH$_2$)$_n$—CH(CH$_3$)—CH$_2$F, —(CH$_2$)$_3$—CH(CH$_3$)—CH$_2$Cl, —(CH$_2$)$_n$—CH(CH$_3$)—CH$_2$Cl, —(CH$_2$)$_3$—CH(CH$_3$)—CH$_2$Br, —(CH$_2$)$_n$—CH(CH$_3$)—CH$_2$Br, —(CH$_2$)$_3$—CH(CH$_2$F)$_2$, —CH$_3$, —CH$_2$CH$_3$, —CH$_2$CH$_2$CH$_3$, —CH$_2$OH, —CH$_2$CH$_2$OH, —CH$_2$CH$_2$CH$_2$OH, —CH$_2$CH(OH)CH$_3$, —(CH$_2$)$_n$—CH(CH$_2$F)$_2$, —CH(CH$_3$)—(CH$_2$)$_n$—CH(CH$_2$CH$_3$)—CH(CH$_3$)$_{m(CH_2)}$R$^{51}$)P, —C≡CH, —C≡CCH$_3$, —C≡CCF$_3$, —C≡CCl, —CH=CH$_2$, —CF=CF$_2$, —CF=CFCH$_3$, —CH=CHCH$_3$, —C(O)—NH—C$_6$H$_5$, —C(O)—NH—CH$_3$, —C(O)—NH—C$_2$H$_5$, —C(CH$_3$)=N—OH, —C(CH$_3$)=N—NH—C(O)—OC$_2$H$_5$, —C(CH$_3$)=N—NH—C(O)—OC$_4$H$_9$, —C(CH$_3$)=N—NH—C(O)—OC$_6$H$_5$, —CH$_2$—C$_6$H$_5$, —CH$_2$—C$_6$H$_5$(CH$_2$)$_n$—F, —C$_6$H$_5$, —C$_6$H$_4$(CH$_2$)$_n$—F, —C$_6$H$_4$(CH$_2$)$_n$—OH, —C$_6$H$_4$(CH$_2$)$_n$—C(O)OH, —C$_6$H$_4$(CH$_2$)$_n$—C(O)OCH$_3$, —CH=CH—(CH$_2$)$_n$—CH$_3$, —CH(CH$_3$)—(CH$_2$)$_n$—CH$_2$—C(H)$_q$(CH$_3$)$_m$(CH$_2$R$^{51}$)$_p$, —CH(CH$_3$)—(CH$_2$)$_n$—CH=C(CH$_3$)(CH$_2$OH), —CH(CH$_2$OH)—(CH$_2$)$_n$—CH=C(CH$_3$)$_2$, =CH—(CH$_2$)$_n$—R$^{45}$, =CH—(CH$_2$)$_t$—(CH=CH)—R$^{45}$, =C(CH$_3$)—CH$_2$—C(O)—N(C1-C6 alkyl)$_2$, =C(CH$_3$)—(CH$_2$)$_2$—C(O)—N(C1-C6 alkyl)$_2$, =C(CH$_3$)—CH$_2$—C(O)—NH—C1-C6 alkyl, =C(CH$_3$)—(CH$_2$)$_2$—C(O)—NH—C1-C6 alkyl, =C(CH$_3$)—CH$_2$—N(C1-C6 alkyl)$_2$, =C(CH$_3$)—(CH$_2$)$_2$—N(C1-C6 alkyl)$_2$, =C(CH$_3$)—CH$_2$—NH—C1-C6 alkyl, =C(CH$_3$)—(CH$_2$)$_2$—NH—C1-C6 alkyl, =CH—CH$_2$—C(O)—N(C1-C6 alkyl)$_2$, =CH—(CH$_2$)$_2$—C(O)—N(C1-C6 alkyl)$_2$, =CH—CH$_2$—C(O)—NH—C1-C6 alkyl, =CH—(CH$_2$)$_2$—C(O)—NH—C1-C6 alkyl, =CH—CH$_2$—N(C1-C6 alkyl)$_2$, =CH—(CH$_2$)$_2$—N(C1-C6 alkyl)$_2$, =CH—CH$_2$—NH—C1-C6 alkyl, =CH—(CH$_2$)$_2$—NH—C1-C6 alkyl, =C(CH$_3$)—CH$_2$—C(O)—NH$_2$, =C(CH$_3$)—(CH$_2$)$_2$—C(O)—NH$_2$, =C(CH$_3$)—(CH$_2$)$_2$—NH$_2$, =C(CH$_3$)—CH$_2$—NH$_2$, =CH—CH$_2$—C(O)—NH$_2$, =CH—(CH$_2$)$_2$—C(O)—NH$_2$, =CH—CH$_2$—NH$_2$ or =CH—(CH$_2$)$_2$—NH$_2$, where R$^{45}$ is an R$^1$ substituent disclosed herein, e.g., —H, —OH, —F, —Cl, —Br, —I, —OCH$_3$, —C(O)OH, —C(O)OCH$_3$, —OR$^{PR}$, —SH, —SR$^{PR}$, —NH$_2$—NH—C1-C8 optionally substituted alkyl, —N(C1-C8 optionally substituted alkyl)$_2$ where each optionally substituted alkyl moiety is the same or different, or —NHR$^{PR}$, R$^{51}$ independently are an R$^1$ substituent disclosed herein, e.g., an ester, —F, —Cl, —Br, —I, alkyl (e.g., —CH$_3$), an ether (e.g., (—OCH$_3$), a thioether (e.g., (—SCH$_3$), an optionally substituted heterocycle, —C(O)OH, —NH$_2$ or —CN, m is 0, 1, 2 or 3, n is 0, 1, 2, 3, 4, 5 or 6, p is 0, 1, 2 or 3, q is 0, 1, 2 or 3, t is 1, 2, 3, 4, 5 or 6 and R$^{PR}$ are —H or independently selected protecting groups, or optionally substituted alkenyl, e.g., =CH$_2$, =CH$_2$CH$_3$, =CH—CH$_2$OH, =CH—(CH$_2$)$_n$—OR$^{PR}$, —CH=CH$_2$, —CH=CHF, —CH=CHCl, —CH=CHBr, —CH=CHI, —CH=CH—(CH$_2$)$_n$—OH, —CH=CH—(CH$_2$)$_n$—F, —CH=CH—(CH$_2$)$_n$—Cl, —CH=CH—(CH$_2$)$_n$—Br, —CH=CH—(CH$_2$)$_n$-1, —CH=NCH$_3$, —CH=NR$^{PR}$, —CH=N—CH$_3$, —CH=CH—CH$_3$, —CH=CH—(CH$_2$)$_n$—COOR$^{PR}$, —CH=CH—(CH$_2$)$_n$—NHR$^{PR}$, —CH=CH—CH$_2$—OR$^{PR}$, —CH=CH—CH$_2$—CF$_3$, —CH=CH$_2$—CH$_2$-halogen, —CH=CH—(CH$_2$)$_n$—OCH$_3$, —CH=CH—(CH$_2$)$_n$—C(O)—O-optionally substituted alkyl, —CH=CH—(CH$_2$)$_n$—C(O)—S-optionally substituted alkyl, =CH—CH$_2$—(CH$_2$)$_n$—SR$^{PR}$, =CH—(CH$_2$)$_n$—C(O)NHR$^{PR}$, =CH—(CH$_2$)$_n$—C(O)NHCH$_3$, =CH—(CH$_2$)$_n$—C(O)NHC$_2$H$_5$, =CH—CH$_2$CH$_3$, =CH—(CH$_2$)$_n$—CH(CH$_3$)$_2$, =CH—(CH$_2$)$_n$—CH(CH$_3$)(CH$_2$OR$^{PR}$), =CH—(CH$_2$)$_n$—CH(CH$_3$)(CH$_2$C(O)OR$^{PR}$), =CH—(CH$_2$)$_n$—OH, =CCH$_3$—(CH$_2$)$_n$—OR$^{PR}$, =CCH$_3$—(CH$_2$)$_n$—C(O)OR$^{PR}$, =CCH$_3$—(CH$_2$)$_n$—C(O)NHR$^{PR}$, =CCH$_3$—(CH$_2$)$_n$-halogen, =CH—CHOH—CH$_2$—OH or =CH—CH$_2$CH$_2$-halogen, where R$^{PR}$ is —H or a protecting group and n is 0, 1, 2, 3, 4, 5 or 6, or optionally substituted alkynyl, e.g., —C≡CH, —C≡C—(CH$_2$)$_m$—OH, —C≡C—halogen, —C≡C—CH$_3$, —C≡CCF$_3$, —C≡CCH$_2$F, —C≡CCH$_2$Cl, —C≡CCH$_2$Br, —C≡CCH$_2$I, —C≡CCH$_2$OH, —C≡C—CH$_2$-halogen, —C≡C—CH$_2$—C(O)OR$^{PR}$, —C≡C—CH$_2$—CH$_3$, —C≡CCH$_2$CF$_3$, —C≡C—CH$_2$—

$CH_2OH$, —C≡C—$CH_2$—$CH_2$-halogen, —C≡C—$(CH_2)_n$—$C_6H_5$, —C≡C—$(CH_2)_n$—$C_6H_4OH$, —C≡C—$(CH_2)_n$—$C_6H_4COOR^{PR}$, —C≡C—$(CH_2)_n$—$C_6H_3(OH)_2$, —C≡C—$(CH_2)_n$—$C_6H_4F$, —C≡C—$(CH_2)_n$—$C_6H_4Br$, —C≡C—$CH_2$—$CH_2$—$C(O)OR^{PR}$, —C≡C—$(CH_2)_n$—$CH_3$, —C≡C—$CH(CH_3)$—$(CH_2)_n$—$CH_3$, —C≡C—$(CH_2)_n$—$CHOR^{PR}$, —C≡C—$CH(CH_3)$—$(CH_2)_n$—$CHOR^{PR}$, —C≡C—$(CH_2)_n$—$CHCOOR^{PR}$, —C≡C—$CH(CH_3)$—$(CH_2)_n$—$NHR^{PR}$, —C≡C—$(CH_2)_n$—$NHR^{PR}$, —C≡C—$(CH_2)_n$—$C(O)NH$—$(CH_2)_n$—$CH_3$, —C≡C—C≡C—$(CH_2)_n$—$CH_3$, —C≡C—C≡C—$(CH_2)_n$-halogen, —C≡C—$(CH_2)_n$—$OS(O)(O)$—O—$R^{PR}$, —C≡C—$(CH_2)_n$—$OS(O)(O)$—O-optionally substituted alkyl, —C≡C—C≡C—$(CH_2)_n$—$OR^{PR}$ or —C≡C—CH$(CH_3)$—$(CH_2)_n$—$CHOR^{PR}$, where n is 0, 1, 2, 3, 4, 5 or 6, m is 1, 2, 3 or 4 and $R^{PR}$ is —H or a protecting group, or optionally substituted aryl, optionally substituted alkylaryl, optionally substituted alkenylaryl or optionally substituted alkynylaryl, e.g., optionally substituted phenyl, optionally substituted benzyl, —$(CH_2)_n$—$C_6H_4OH$, —$(CH_2)_n$—$C_6H_4OR^{PR}$, —$(CH_2)_n$—$C_6H_3(OH)_2$, —$(CH_2)_n$—$C_6H_4F$, —$(CH_2)_n$—$C_6H_4Br$, —$(CH_2)_n$—$C_6H_4C(O)OR^{PR}$, —$(CH_2)_n$—$C_6H_4C(O)SR^{PR}$, or analogs where the aromatic ring contains 1, 2, 3 or 4 independently chosen substituents such as independently chosen halogen, —OH, —SH, —$NO_2$, —CN, —SCN, —$N_3$, C1-C6 ester, C1-C6 alkyl, C1-C6 ether, C1-C6 thioether, —$OR^{PR}$, —$(CH_2)_n$—$C(O)OR^{PR}$, —$(CH_2)_n$—$NHR^{PR}$, —$(CH_2)_n$—$OR^{PR}$ or —$(CH_2)_m$—O—$(CH_2)_m$—$OR^{PR}$ where n is 0, 1, 2, 3, 4, 5 or 6, m independently are 1, 2 or 3 and $R^{PR}$ independently are —H or a protecting group, or ether, e.g., optionally substituted alkoxy, optionally substituted alkenyloxy, optionally substituted alkynyloxy, optionally substituted aryloxy, —$OCH_3$, —$OC_2H_5$, —$OC_3H_7$, —$OC_4H_9$, —$OC_2H_3$, —$OC_3H_5$, —$OC_4H_7$, —O—$C(CH_3)_3$, —$OCH_2CH_2OH$, —$O(CH_2)_2$—O—$CH_3$, —$O(CH_2)_3$—O—$CH_3$, —O—$CH(CH_3)CH_3$, —O—$CH_2CH_2CH_3$, —$OCH_2CH_2F$, —$OCH_2CHF_2$, —$OCH_2CF_3$, —$OCH_2CH_2Cl$, —$OCH_2CH_2Br$, —$OCH_2CH_2I$, —$OCH_2CH_2CH_2F$, —O—$CH_2$—$CH(C(O)$—NH—$CH_2C(O)OH)$—NH—$C(O)$—$(CH_2)_2$—$CH(NH_2)$—$C(O)$—OH, —O—$(CH_2)_2$—$N^+(CH_3)_3$,), —O—$(CH_2)_{0-3}$—(CH═CH)$_{0-1}$—$(CH_2)_{0-3}$—$CH_3$, —O—$(CH_2)_{0-3}$—(CH═CH)—$(CH_2)_{0-3}$—$CH_2F$, —O—$(CH_2)_{1-3}$—(C≡C)—$(CH_2)_{0-3}$—$CH_3$, —O—$(CH_2)_{1-3}$—(C≡C)—$(CH_2)_{0-3}$—$CH_2F$, —O—$C_6H_5$, —O—$CH_2$—$C_6H_5$, —O—C1-C20 organic moiety where the organic moiety is, e.g., —$CH_3$, —$C_2H_5$, i-propyl, n-propyl, t-butyl, n-butyl, l-butyl, n-hexyl, n-octyl, n-decyl, —$(CH_2)_{1-8}$—OH, —CHO, —$(CH_2)_{1-8}$—$NH_2$, —$(CH_2)_{1-8}$—C(O)—OH, —$(CH_2)_{0-3}$—(CH═CH)$_{0-1}$—$(CH_2)_{0-3}$—$CH_3$, —$(CH_2)_{0-3}$—(CH═CH)$_{0-1}$—$(CH_2)_{0-3}$—$CH_2F$, —$(CH_2)_{0-3}$—(CH═CH)$_{0-1}$—$(CH_2)_{0-3}$—$CH_2Br$, —$(CH_2)_{0-3}$—(CH═CH)$_{0-1}$—$(CH_2)_{0-3}$—C(O)—$OR^{PR}$, —$(CH_2)_{0-3}$—(CH═CH)$_{0-1}$—$(CH_2)_{0-3}$—$NHR^{PR}$, —C(O)—$CH_3$, —C(O)—$C_2H_5$, —C(O)—$C_6H_5$, —$CF_3$, —$CH_2CF_3$ or —$C_2F_5$, wherein $R^{PR}$ is —H or a protecting group, —O—$C_{1-10}$ optionally substituted alkyl such as i-propyl, n-propyl, t-butyl, n-butyl, n-hexyl, n-octyl, n-decyl, —$(CH_2)_{1-8}$—OH, —$(CH_2)_{1-8}$—$NH_2$, —$(CH_2)_{1-8}$—C(O)—OH, —$(CH_2)_{0-3}$—(CH═CH)$_{0-1}$—$(CH_2)_{0-3}$—$CH_3$, —$(CH_2)_{0-3}$—(CH═CH)$_{0-1}$—$(CH_2)_{0-3}$—$CH_2F$, —$(CH_2)_{0-3}$—(CH═CH)$_{0-1}$—$(CH_2)_{0-3}$—$CH_2Br$, —$(CH_2)_{0-3}$—(CH═CH)$_{0-1}$—$(CH_2)_{0-3}$—C(O)—$OR^{PR}$, —$(CH_2)_{0-3}$—(CH═CH)$_{0-1}$—$(CH_2)_{0-3}$—$NHR^{PR}$, —$CF_3$ and —$C_2F_5$, wherein $R^{PR}$ is —H or a protecting group, or ester, e.g., —OC(O)$CH_3$, —OC(O)$C_2H_5$, —OC(O)$C_2H_3$, —OC(O)$CH_2CH_2CH_3$, —OC(O)$CH(CH_3)_2$, —O—C(O)—$(CH_2)_2$—C(O)OH, —O—C(O)—$(CH_2)_2$—$C(O)OR^{PR}$, —O—C(O)—$(CH_2)_3$—C(O)OH, o—C(O)—$(CH_2)_3$—$C(O)OR^{PR}$, —O—C(O)—$(CH_2)_4$—C(O)OH, —O—C(O)—$(CH_2)_5$—C(O)OH, —O—C(O)—$(CH_2)_5$—$C(O)OR^{PR}$, —O—C(O)—$(CH_2)_4$—$C(O)OR^{PR}$, —O—C(O)—$(CH_2)_2$—C(O)$ONH_2$, —C(O)—$(CH_2)_2$—C(O)$ONHCH_3$, —O—C(O)—$(CH_2)_2$—C(O)$ONHC_2H_5$, —O—C(O)—$(CH_2)_2$—C(O)$ONHC_3H_7$, —O—C(O)—$(CH_2)_2$—C(O)$ONHC_3H_5$, —O—C(O)—$(CH_2)_2$—$C(O)ONHR^{PR}$, —O—C(O)—$(CH_2)_2$—$C(O)ON(R^{PR})_2$, —OC(O)—$C(CH_3)_2$—$(CH_2)_m$—$CH_3$, —OC(O)—$(CH_2)_m$—$CH_3$, —OC(O)—$CH(CH_3)$—$(CH_2)_m$—$CH_3$, —OC(O)—$C(CF_3)_2$—$(CH_2)_m$—$CH_3$, —OC(O)—$CH(CF_3)$—$(CH_2)_m$—$CH_3$, —OC(O)$C_3H_7$, —OC(O)$C_3H_5$, —OC(O)$C_4H_9$, —OC(O)$C_4H_7$, —OC(O)$C(CH_3)_3$, —OC(O)$CH_2CH_2CH_2CH_3$, —OC(O)$C_6H_5$, —OC(O)$CH_2C_6H_5$, —OC(O)—$(CH_2)_2$—C(O)OH, —OC(O)—$(CH_2)_2$—C(O)$OCH_3$, —OC(O)—$(CH_2)_3$—C(O)OH, —OC(O)—$(CH_2)_3$—C(O)$OCH_3$, —OC(O)—$(CH_2)_4$—C(O)OH, —OC(O)—$(CH_2)_4$—C(O)$OCH_3$, —OC(O)—$CH(CH_3)$—$CH_2$—C(O)OH, —OC(O)—$CH(CH_3)$—$CH_2$—C(O)$OCH_3$, —OC(O)—$CH(CH_3)$—$(CH_2)_2$—C(O)OH, —OC(O)—$CH(CH_3)$—$(CH_2)_2$—C(O)$OCH_3$, —OC(O)—$C(CH_3)_2$—$CH_2$—C(O)OH, —OC(O)—$C(CH_3)_2$—$CH_2$—C(O)$OCH_3$, —OC(O)—$C(CH_3)_2$—$(CH_2)_2$—C(O)OH, —OC(O)—$C(CH_3)_2$—$(CH_2)_2$—C(O)$OCH_3$, —OC(O)—$(CH_2)_2$—C(O)OH, —O—C(O)—C(O)—O—$(CH_2)_m$—$CH_3$, —C(O)—O—$(CH_2)$, —$CH_2OH$, —O—C(O)—$(CH_2)_n$—C(O)—O—$(CH_2)_m$—$CH_3$, —O—C(O)—$(CH_2)_n$—C(O)—O—$(CH_2)$—$CH_2OH$, —C(O)—$CH(NH_2)$—$CH_2OH$, —O—C(O)—$CH_2$—$N(CH_3)$—C(═NH)—$NH_2$, —O—C(O)—$CH_2$—NH—C(O)—$CH(CH_2SH)$—NH—C(O)—$(CH_2)_2$—$CH(NH_2)$—C(O)—OH, a C2-C20 ester such as —O—C(O)—$CH_3$, —O—C(O)—$CF_3$, —O—C(O)—$CCl_3$, —O—C(O)—$C_2H_5$, —O—C(O)—$C_4H_7$, —O—C(O)—$C_6H_5$, —O—C(O)—$(CH_2)_2$—$CH_3$, —O—C(O)—$(CH_2)_3$—$CH_3$, —O—C(O)—$(CH_2)_4$—$CH_3$, —O—C(O)—$(CH_2)_5$—$CH_3$, —O—C(O)—$(CH_2)_6$—$CH_3$, —O—$C(O)_2$ furanyl, —O—$C(O)_2$ thiophenyl, —O—$C(O)_2$ pyrrolyl, —O—$C(O)_2$ pyrimidinyl, —O—$C(O)_3$ pyrimidinyl, —O—$C(O)_2$ pyridyl, —O—C(O)-3 pyridyl, —O—C(O)-heterocycle, —O—C(O)—$(CH_2)_m$—C(O)O—C1-C10 optionally substituted alkyl, —O—C(O)—$(CH_2)_m$—C(O)O—C2-C10 optionally substituted alkenyl, —O—C(O)—$(CH_2)_m$—O—$(CH_2)_m$—C(O)O—C1-C10 optionally substituted alkyl, —C(O)—$(CH_2)_m$—$(CH_2)_m$—$C(O)OR^{PR}$, —O—C(O)—$(CH_2)_m$—S—$(CH_2)_m$—C(O)O—C1-C10 optionally substituted alkyl, —O—C(O)—$(CH_2)_m$—S—$(CH_2)_m$—$C(O)OR^{PR}$, —O—C(O)—$(CH_2)_m$—$NR^{PR}$—$(CH_2)_m$—C(O)O—C1-C10 optionally substituted alkyl, —O—C(O)—$(CH_2)_m$—$NR^{PR}$—$(CH_2)_m$—$C(O)OR^{PR}$, —O—C(O)—$C_{1-12}$ optionally substituted alkyl, —OC(O)—$(CH_2)_q$—C(O)OH, —OC(O)—$(CH_2)_q$—C(O)O—$C_{1-8}$ optionally substituted alkyl, —OC(O)—$CH(CH_3)$—$(CH_2)_q$—C(O)OH, —OC(O)—$CH(CH_3)$—$(CH_2)_q$—C(O)O—$C_{1-8}$ optionally substituted alkyl, —OC(O)—$C(CH_3)_2$—$(CH_2)_q$—C(O)OH, —OC(O)—$C(CH_3)_2$—$(CH_2)_q$—C(O)O—$C_{l_8}$ optionally substituted alkyl, —OC(O)—$C(C_2H_5)(CH_3)$—$(CH_2)_q$—C(O)OH, —OC(O)—$C(C_2H_5)(CH_3)$—$(CH_2)_q$—C(O)O—$C_{l_8}$ optionally substituted alkyl, —OC(O)—$C(C_2H_5)_2$—$(CH_2)_q$—C(O)OH, —OC(O)—$C(C2H_5)_2$—$(CH_2)_q$—C(O)O—$C_{1-8}$ optionally substituted alkyl, —OC(O)—$C(C_2H_5)(C_3H_7)$—$(CH_2)_q$—C(O)OH, —OC(O)—$C(C_2H_5)(C_3H_7)$—$(CH_2)_q$—C(O)O—$C_{1-8}$ optionally substituted alkyl, where the optionally substituted alkyl optionally is methyl, ethyl, i-propyl, n-propyl, t-butyl, n-butyl, n-hexyl, n-octyl, n-decyl, vinyl, allyl, phenyl, monosubstituted phenyl, disubstituted phenyl, trisubstituted phenyl, —$CH_2OH$, —$CH_2OR^{PR}$, —$CH_2F$, —$CF_2H$, —$(CH_2)_n$—$CH_3$, —$(CH_2)_n$—OH, —$(CH_2)_n$—F, —(CH$_2$)$_n$—Br, —(CH$_2$)$_n$—NH$_2$, —(CH$_2$)$_n$—C(O)—OR$^{PR}$, —(CH$_2$)$_n$—O—CH$_3$, —(CH$_2$)$_n$—S—CH$_3$, —(CH$_2$)$_m$—(CH=CH)$_p$—(CH$_2$)$_q$—CH$_3$, —(CH$_2$)$_m$—(CH=CH)$_p$—(CH$_2$)$_q$—CH$_2$F, —(CH$_2$)$_m$—(CH=CH)$_p$—(CH$_2$)$_q$—CH$_2$Br, —(CH$_2$)$_m$—(CH=CH)$_p$—(CH$_2$)$_q$—C(O)—OR$^{PR}$, —(CH$_2$)$_m$—(CH=CH)$_p$—(CH$_2$)$_q$—NHR$^{PR}$, —CF$_3$, —CH$_2$CF$_3$ or —C$_2$F$_5$, wherein R$^{PR}$ independently are —H, a protecting group such as C1-C10 optionally substituted alkyl (e.g., —CH$_3$, —C$_2$H$_5$, —C$_3$H$_6$OH) or together are a protecting group, n is 1, 2, 3, 4, 5, 6, 7 or 8, m is 0, 1, 2, 3, 4, 5 or 6, p is 0 or 1 and q is 0, 1, 2, 3, 4, 5 or 6, or acyl, e.g., —C(O)OH, —C(O)—CH$_2$OH, —C(O)—CH$_2$F, —C(O)—CH$_2$Cl, —C(O)—CH$_2$Br, —C(O)—CH$_2$I, —C(O)—CH$_2$COOH, —C(O)—CH$_2$COOR$^{PR}$, —C(O)—CH$_3$, —C(O)—CF$_3$, —C(O)—CH$_2$CF$_3$, —C(O)—CH(NH$_2$)—CH$_2$OH, —C(O)—CH$_2$—N(CH$_3$)—C(=NH)—NH$_2$, —C(O)—(CH$_2$)$_n$—CH$_2$OH, —C(O)—O—C(O)—C(CH$_3$)$_3$, —C(O)—O—C(O)—CH(CH$_3$)$_2$, —C(O)—O—C(O)—CH$_3$, —C(O)—O—C(O)—C$_2$H$_5$, —C(O)—(CH$_2$)$_n$—CH$_2$F, —C(O)—N(CH$_3$)$_2$, —C(O)—N(C$_2$H$_5$)$_2$, —C(O)—N(CH$_3$)(C$_2$H$_5$), —C(O)—NH[C(CH$_3$)$_3$], —C(O)—NH(CH$_3$), —C(O)NH$_2$, —C(O)—N(R$^{PR}$)$_2$, —C(O)—(CH$_2$)$_n$—CH$_2$Cl, —C(O)—(CH$_2$)$_n$—CH$_2$Br, —C(O)—(CH$_2$)$_n$—CH$_2$—C(O)OH, —C(O)—(CH$_2$)$_n$—CH$_2$—NH$_2$, —C(O)—CH(CH$_3$)—(CH$_2$)$_3$—CH(CH$_3$)$_2$, —C(O)—CH(CH$_3$)—(CH$_2$)$_n$—CH(CH$_3$)$_2$, —C(O)—CH(CH$_3$)—(CH$_2$)$_3$—CH(CH$_3$)—CH$_2$OH, —C(O)—CH(CH$_3$)—(CH$_2$)$_n$—CH(CH$_3$)—CH$_2$OH, —C(O)—CH(CH$_3$)—(CH$_2$)$_3$—CH(CH$_3$)—CH$_2$F, —C(O)—CH(CH$_3$)—(CH$_2$)$_n$—CH(CH$_3$)—CH$_2$F, —C(O)—CH(CH$_3$)—(CH$_2$)$_3$—CH(CH$_3$)—CH$_2$Cl, —C(O)—CH(CH$_3$)—(CH$_2$)$_n$—CH(CH$_3$)—CH$_2$Cl, —C(O)CH$_3$, —C(O)CHO, —C(O)CH$_2$OH, —C(O)CH$_2$F, —C(O)CH$_2$Cl, —C(O)CH$_2$Br, —C(O)—CH$_2$OH, —C(O)—CH$_2$OR$^{PR}$, —C(O)—(CH$_2$)$_n$—CH$_2$OH, —C(O)—(CH$_2$)$_n$—CH$_2$OR$^{PR}$, —C(O)—S—(CH$_2$)$_n$—CH$_2$F, —C(O)—S—(CH$_2$)$_n$—CHF$_2$, —C(O)—S—(CH$_2$)$_n$—CF$_3$, —C(O)$_2$ furanyl, —C(O)-2 thiophenyl, —C(O)-2 pyrrolyl, —C(O)-2 pyrimidinyl, —C(O)-3 pyrimidinyl, —C(O)-2 pyridyl, —C(O)$_3$ pyridyl, —C(O)-heterocycle, —C(O)—C1-C10-optionally substituted alkyl, —C(O)—NH-optionally substituted phenyl, —C(O)—NH-optionally substituted heterocycle, —C(O)—(CH$_2$)$_n$-optionally substituted heterocycle, —C(O)—(CH$_2$)$_n$-optionally substituted phenyl, or —C(O)NR$^{50}$R$^{51}$ where R$^{PR}$ independently are —H or a protecting group such as C1-C10 optionally substituted alkyl, m is 0 or 1, n is 0, 1, 2, 3, 4, 5 or 6, and R$^{50}$ and R$^{51}$ independently are —H, optionally substituted phenyl, optionally substituted phenylalkyl, optionally substituted alkyl optionally substituted alkenyl, or an optionally substituted heterocycle, e.g., pyridyl, pyrrolyl, pyrimidyl, benzimidazolyl, benzoxazolyl, benzofuranyl, —CH$_3$, —C$_2$H$_5$, 2-, 3- or 4-fluorophenyl, 2-, 3- or 4-chlorophenyl, 2-, 3- or 4-methoxyphenyl 2-, 3- or 4-methylphenyl or 2-, 3- or 4-trifluoromethylphenyl, or thioester, e.g., —SC(O)CH$_3$, —SC(O)C$_2$H$_5$, —SC(O)C$_3$H$_7$, —SC(O)C$_4$H$_9$, —SC(O)C$_6$H$_5$, —SC(O)CH$_2$C$_6$H$_5$, —C(O)SCH$_3$, —CS(O)C$_2$H$_5$, —CS(O)C$_3$H$_7$, —CS(O)C$_4$H$_9$, —CS(O)C$_6$H$_5$, —CS(O)CH$_2$C$_6$H$_5$, —S—C(O)—(CH$_2$)$_2$—C(O)OH, —S—C(O)—(CH$_2$)$_2$—C(O)OR$^{PR}$, —S—C(O)—(CH$_2$)$_3$—C(O)OH, S—C(O)—(CH$_2$)$_3$—C(O)OR$^{PR}$, —S—C(O)—(CH$_2$)$_4$—C(O)OH, —S—C(O)—(CH$_2$)$_5$—C(O)OH, —S—C(O)—(CH$_2$)$_5$—C(O)OR$^{PR}$, —S—C(O)—(CH$_2$)$_4$—C(O)OR$^{PR}$, —S—C(O)—CH(NH$_2$)—CH$_2$OH, —S—C(O)—CH$_2$—N(CH$_3$)—C(=NH)—NH$_2$, —S—C(O)—CH$_2$—NH—C(O)—CH(CH$_2$SH)—NH—C(O)—(CH$_2$)$_2$—CH(NH$_2$)—C(O)—OH), a C2-C20 such as —S—C(O)—CH$_3$, —S—C(O)—CF$_3$, —S—C(O)—CCl$_3$, —S—C(O)—C$_2$H$_5$, —S—C(O)—C$_6$H$_5$, —S—C(O)—C$_6$H$_4$—OCH$_3$, —S—C(O)—C$_6$H$_4$—F, —S—C(O)—C$_6$H$_4$—Cl, —S—C(O)—C$_6$H$_4$—CH$_3$, —S—C(O)—C$_{1-12}$ optionally substituted alkyl, —S—C(O)—CH$_2$—NHR$^{PR}$, —S—C(O)—CHOH—NHR$^{PR}$, —S—C(O)—CH[(CH(OH)(CH$_3$)]—NHR$^{PR}$, —S—C(O)—CH(CH$_3$)—NHR$^{PR}$, —S—C(O)—CH[(CH$_2$)$_2$C(O)OR$^{PR}$]—NHR$^{PR}$, —S—C(O)—CH(CH$_2$C(O)OR$^{PR}$—NHR$^{PR}$, —S—C(O)—CH[(CH$_2$)$_4$NHR$^{PR}$]—NHR$^{PR}$, —S—C(O)—CH[(CH$_2$)$_2$C(O)NHR$^{PR}$]—NHR$^{PR}$, —S—C(O)—CH(CH$_2$C(O)NHR$^{PR}$)—NHR$^{PR}$, —S—C(O)—(CH$_2$)$_m$—C(O)ON(R$^{PR}$)$_2$, —S—C(O)—(CH$_2$)$_m$—O—(CH$_2$)$_m$—C(O)OR$^{PR}$, —S—C(O)—(CH$_2$)$_m$—S—(CH$_2$)$_m$—C(O)OR$^{PR}$, —S—C(O)—(CH$_2$)$_m$—NR$^{PR}$—(CH$_2$)$_m$—C(O)OR$^{PR}$, —S—C(O)—(CH$_2$)$_m$—O—(CH$_2$)—C(O)ON(R$^{PR}$)$_2$, —S—C(O)—(CH$_2$)—O—(CH$_2$)$_m$—C(O)O—C1-C10 optionally substituted alkyl, —S—C(O)—(CH$_2$)$_m$—O—(CH$_2$)$_m$—C(O)OR$^{PR}$, —S—C(O)—(CH$_2$)$_m$—S—(CH$_2$)$_m$—C(O)O—C1-C10 optionally substituted alkyl, —S—C(O)—(CH$_2$)—S—(CH$_2$), —C(O)OR$^{PR}$, —S—C(O)—(CH$_2$)$_m$—NR$^{PR}$—(CH$_2$), —C(O)O—C1-C10 optionally substituted alkyl, —S—C(O)—(CH$_2$)$_m$—NR$^{PR}$—(CH$_2$)$_m$—C(O)OR$^{PR}$, where the optionally substituted alkyl optionally is methyl, ethyl, i-propyl, n-propyl, t-butyl, n-butyl, n-hexyl, n-octyl, n-decyl, vinyl, allyl, phenyl, —CH$_2$OH, —CH$_2$F, —CF$_2$H, —(CH$_2$)$_n$—CH$_3$, —(CH$_2$)$_n$—OH, —(CH$_2$)$_n$—F, —(CH$_2$)$_n$—Br, —(CH$_2$)$_n$—NH$_2$, —(CH$_2$)$_n$—C(O)—OR$^{PR}$, —(CH$_2$)$_n$—O—CH$_3$, —(CH$_2$)$_n$—S—CH$_3$, —(CH$_2$)$_m$—(CH=CH)$_p$—(CH$_2$)$_q$—CH$_3$, —(CH$_2$)$_m$—(CH=CH)$_p$—(CH$_2$)$_q$—CH$_2$F, —(CH$_2$)$_m$—(CH=CH)$_p$—(CH$_2$)$_q$—CH$_2$Br, —(CH$_2$)$_m$—(CH=CH)$_p$(CH$_2$)$_q$—C(O)—OR$^{PR}$, —(CH$_2$)$_m$—(CH=CH)$_p$—(CH$_2$)$_q$—NHR$^{PR}$, —CF$_3$, —CH$_2$CF$_3$, —C$_2$F$_5$, or a thio analog of any ester moiety described herein, wherein R$^{PR}$ independently are —H, a protecting group such as C1-C10 optionally substituted alkyl (e.g., —CH$_3$, —C$_2$H$_5$, —C$_3$H$_6$OH) or together are a protecting group, n is 1, 2, 3, 4, 5, 6, 7 or 8, m is 0, 1, 2, 3, 4, 5 or 6, p is 0 or 1 and q is 0, 1, 2, 3, 4, 5 or 6, or thioether, e.g., —SCH$_3$, —SC$_2$H$_5$, —SC$_3$H$_7$, —SC$_4$H$_9$, —SC$_2$H$_3$, —SC$_3$H$_5$, —SC$_4$H$_7$, —SCH$_2$CH$_2$OH, —S—CH$_2$—CH(C(O)—NH—CH$_2$C(O)OH)—NH—C(O)—(CH$_2$)$_2$—CH(NH$_2$)—C(O)—OH, —S—(CH$_2$)$_2$—N$^+$(CH$_3$)$_3$,), —SCH$_2$CH$_2$F, —SCH$_2$CHF$_2$, —SCH$_2$CF$_3$, —SCH$_2$CH$_2$Cl, —SCH$_2$CH$_2$Br, —SCH$_2$CH$_2$I, —SCH$_2$CH$_2$CH$_2$F, —S—SCH$_3$, —S—SC$_2$H$_5$, —S—SC$_3$H$_7$, —S—SC$_4$H$_9$, —S—C$_{1-20}$ organic moiety, —S—S—C$_{1-20}$ organic moiety, —S—CH$_2$—S—C$_{1-20}$ organic moiety, —S—(CH$_2$)$_2$—S—C$_{1-20}$ organic moiety, —S—(CH$_2$)$_2$—O—C$_{1-20}$ organic moiety, —S—S—CH$_3$, —S—S—C$_2$H$_5$, where the organic moiety is any moiety described herein such as —CH$_3$, —C$_2$H$_5$, i-propyl, n-propyl, t-butyl, n-butyl, n-hexyl, n-octyl, n-decyl, —(CH$_2$)$_{1-8}$—OH, —(CH$_2$)$_{1-8}$—NH$_2$, —(CH$_2$)$_{1-8}$—C(O)—OH, —(CH$_2$)$_{0-3}$—(CH=CH)$_{0-1}$—(CH$_2$)$_{0-3}$—CH$_3$, —(CH$_2$)$_{0-3}$—(CH=CH)$_{0-1}$—(CH$_2$)$_{0-3}$—CH$_2$F, —(CH$_2$)$_{0-3}$—(CH=CH)$_{0-1}$—(CH$_2$)$_{0-3}$—CH$_2$Br, —(CH$_2$)$_{0-3}$—(CH=CH)$_{0-1}$—(CH$_2$)$_{0-3}$—C(O)—OR$^{PR}$, —(CH$_2$)$_{0-3}$—(CH=CH)$_{0-1}$—(CH$_2$)$_{0-3}$—NHR$^{PR}$, —C(O)—CH$_3$—C(O)—C$_2$H$_5$, —C(O)—C$_6$H$_5$, —S—C$_{3-8}$ alkyl, —S—C$_{3-8}$ substituted alkyl, —CF$_3$, —CH$_2$CF$_3$ or —C$_2$F$_5$, wherein R$^{PR}$ is —H or a protecting group, —S—C$_{1-10}$ optionally substituted alkyl such as i-propyl, n-propyl, t-butyl, n-butyl, n-hexyl, n-octyl, n-decyl, —(CH$_2$)$_{1-8}$—OH, —(CH$_2$)$_{1-8}$—NH$_2$, —(CH$_2$)$_{1-8}$—C(O)—OH, —(CH$_2$)$_{0-3}$—(CH=CH)$_{0-1}$—(CH$_2$)$_{0-3}$—CH$_3$, —(CH$_2$)$_{0-3}$—(CH=CH)$_{0-1}$—(CH$_2$)$_{0-3}$—CH$_2$F, —(CH$_2$)$_{0-3}$—(CH=CH)$_{0-1}$—(CH$_2$)$_{0-3}$—CH$_2$Br, —(CH$_2$)$_{0-3}$—

$(CH=CH)_{0-3}$—$(CH_2)$—$(CH_2)_{0-3}$—$(CH=CH)_{0-1}$—$(CH_2)_{0-3}$—$NHR^{PR}$, —$CF_3$, —$C_2F_5$, wherein $R^{PR}$ is —H or a protecting group, or thioacyl, e.g., —C(S)—$(CH_2)_n$—$CH_2OH$, —C(S)—$(CH_2)_n$—$CH_2F$, —C(S)—$(CH_2)_n$—$CH_2Cl$, —C(S)—$(CH_2)_n$—$CH_2Br$, —C(S)—$CH(CH_3)$—$(CH_2)_3$—$CH(CH_3)_2$, —C(S)—$CH(CH_3)$—$(CH_2)_n$—$CH(CH_3)_2$, —C(S)—$CH(CH_3)$—$(CH_2)_3$—$CH(CH_3)$—$CH_2OH$, —C(S)—$CH(CH_3)$—$(CH_2)_n$—$CH(CH_3)$—$CH_2OH$, —C(S)—$CH(CH_3)$—$(CH_2)_3$—$CH(CH_3)$—$CH_2F$, —C(S)—$CH(CH_3)$—$(CH_2)_n$—$CH(CH_3)$—$CH_2F$, —C(S)—$CH(CH_3)$—$(CH_2)_3$—$CH(CH_3)$—$CH_2Cl$, —C(S)—$CH(CH_3)$—$(CH_2)_n$—$CH(CH_3)$—$CH_2Cl$, —$C(S)CH_3$, —$C(S)CH_2OH$, —$C(S)CH_2F$, —$C(S)CH_2Cl$, —$C(S)CH_2Br$, —C(S)-2 furanyl, —C(S)-2 thiophenyl, —C(S)-2 pyrrolyl, —C(S)-2 pyrimidinyl, —C(S)-3 pyrimidinyl, —C(S)-2 pyridyl, —C(S)-3 pyridyl, —C(S)-heterocycle, —C(S)—C1-C20-optionally substituted alkyl or a thio analog of any acyl moiety described herein, where n is 0, 1, 2, 3, 4, 5 or 6, or optionally substituted amine, e.g., —$NH_2$, —$NH_3^+Cl^-$, —$NH_3^+Br^-$, —$NH_3^+I^-$, alkylamine, dialkylamine, —NH—$CH_3$, —$N(CH_3)_2$, —$N^+(CH_3)_3$, —$N^+(C_2H_5)_3$, —NHOH, —$NHR^{PR}$, —$N(R^{PR})_2$, —NH—$C(O)CH_3$, —NH—C(O)$CF_3$, —$N(C(O)CF_3)_2$, —NH—$C(O)CCl_3$, —$N(C(O)CCl_3)_2$, —NH—$C(O)C_6H_5$, —$N(C(O)C_6H_5)_2$, —NH—$C_2H_5$, —$N(C_2H_5)_2$, —NH—$CH_2OH$, —NH—$CH_2$—$CH_2OH$, —NH—$C_3H_7$, —$N(C_3H_7)_2$, —NH—C(=NH)—$N(CH_3)$—$CH_2$—$C(O)OR^{PR}$, —$N(CH_3)_2$, —$N(C_2H_5)_2$, —$N(CH_3)(C_2H_5)$—$N(CH_2OH)(CH_3)$, —$N=C[(CH_2)_n$—H]-OH, —NH—NH—C(O)-optionally substituted alkyl, —NH—C(NH-optionally substituted alkyl)=N-optionally substituted alkyl, —$N=C[(CH_2)_n$—H]-O-optionally substituted alkyl, —NH-organic moiety, —NH—C(O)-organic moiety, e.g., —NH—C(O)—$CH_3$, —NH—$(CH_2)_n$-optionally substituted phenyl, —NH-optionally substituted alkyl, —N(optionally substituted alkyl)$_2$, —N(C(O)-optionally substituted alkyl)$_2$, —NH—C(O)-optionally substituted alkyl or —NH—$(CH_2)_n$-optionally substituted alkyl, wherein any of the phenyl or alkyl moieties are the same or different and are optionally substituted with 1, 2, 3 or more independently selected with substituents described herein, e.g., —O—, —NH—, —S—, —F, —Cl, —Br, —I, —OH, —$OR^{PR}$, —SH, —$SR^{PR}$, —$CH_3$, —$C_2H_5$, —O—$CH_3$, —O—$C_2H_5$, —$NO_2$, —CN, —SCN, —$NH_2$, —$C(O)OR^{PR}$ or —$(CH_2)_n$—C(O)—$OR^{PR}$, wherein n is 0, 1, 2, 3 or 4, $R^{PR}$ independently or together are —H or a protecting group and the organic moiety is as described herein, e.g., optionally substituted alkyl or an ester, or optionally substituted amide, e.g., —C(O)—$NH_2$, —C(O)—NH—$C(CH_3)_3$, —C(O)—$NH_2$, —C(O)—NH—$CH_3$, —C(O)—NH—$(CH_2)_m$—$CH_3$, —C(O)—NH—$(CH_2)_m$—$NH_2$, —C(O)—NH—$(CH_2)_m$—$NHR^{PR}$, —C(O)—NH—$(CH_2)_m$—NH—$(CH_2)_n$—$CH_3$, —NH—C(O)H, —NH—C(O)—$CH_2$—$CH_2$—C(O)OH, —NH—C(O)—$CH_2$—$CH_2$—$C(O)OR^{PR}$, —NH—C(O)—$(CH_2)_m$—C(O)OH, —NH—C(O)—$(CH_2)_m$—$C(O)OR^{PR}$, —NH—C(O)—$CH_3$, —NH—C(O)—$(CH_2)_m$—$CH_3$, —NH—C(O)—$(CH_2)_m$—$NH_2$, —NH—C(O)—$(CH_2)_m$—$NHR^{PR}$, —NH—C(O)—O—$C(CH_3)_3$, —NH—C(O)—O—$CH_3$, —NH—C(O)—$(CH_2)_m$—NH—$(CH_2)_n$—$CH_3$, —C(O)—NH-organic moiety, —C(O)—NH-optionally substituted alkyl, —C(O)—$NR^{49}$—$(O)_p$-organic moiety, —C(O)—NH—$(O)_p$—$(CH_2)_n$-optionally substituted phenyl, —C(O)—NH—$(CH_2)_n$—$(O)_p$-optionally substituted alkyl, —NH—C(O)—$(O)_p$-optionally substituted alkyl, —NH—C(S)—$(O)_p$-optionally substituted alkyl, —NH—C(O)—$(S)_p$-optionally substituted alkyl, wherein 1, 2 or more of any organic, phenyl, alkyl, alkylene, e.g., —$(CH_2)$—, —$(CH_2)_m$— or —$(CH_2)_n$—, methyl, ethyl, n-butyl or t-butyl, moieties are optionally substituted with 1, 2, 3, 4, 5 or more independently selected substituents described herein, e.g., —F, —Cl, —Br, —I, —OH, —$CH_3$, —$C_2H_5$, —O—$CH_3$, —O—$C_2H_5$, —$NO_2$, —CN, —SCN, —$NH_2$, —$C(O)OR^{PR}$ or —$(CH_2)_{1-4}$—C(O)—$OR^{PR}$, where $R^{49}$ is a protecting group, an organic moiety comprising about 1-10 carbon atoms or $R^{49}$ together with the organic moiety is a protecting group and the organic group optionally is optionally substituted alkyl such as i-propyl, n-propyl, t-butyl, n-butyl, n-hexyl, n-octyl, n-decyl, —$(CH_2)_m$—OH, —$(CH_2)_m$—F, —$(CH_2)_m$—Cl, —$(CH_2)_m$—Br, —$(CH_2)_m$—$NH_2$, —$(CH_2)_m$—C(O)—OH, —$(CH_2)_m$—C(O)—H, —$(CH_2)_m$—C(O)—$CH_3$, —$(CH_2)_n$—(CH=CH)$_p$—$(CH_2)_n$—$CH_3$, —$(CH_2)_n$—(CH=CH)$_p$—$(CH_2)_n$—$CH_2F$, —$(CH_2)_n$—(CH=CH)$_p$—$(CH_2)_n$—$CH_2Br$, —$(CH_2)_n$—(CH=CH)$_p$—$(CH_2)_n$—C(O)—$OR^{PR}$, —$(CH_2)_n$—(CH=CH)$_p$—$(CH_2)_n$—$NHR^{PR}$, —$CF_3$ or —$C_2F_5$, and $R^{PR}$ is —H or a protecting group, optionally substituted alkyl moieties contain 1, 2, 3, 4, 5, 6, 7, 8, 9, 10 or more carbon atoms and wherein m independently are 1, 2, 3, 4, 5 or 6, n independently are 0, 1, 2, 3 or 4 and p is 0 or 1, or epoxide or optionally substituted cyclopropyl, when taken together with a hydrogen at an adjacent position on the steroid nucleus, usually where the epoxide or optionally substituted cyclopropyl bonds are both in the α-configuration or the β-configuration, e.g., one or more independently selected epoxide or optionally substituted cyclopropyl ring is present at the 1-2 positions, the 2-3 positions, the 4-5 positions, the 5-6 positions, the 10-11 positions, the 11-12 positions, the 15-16 positions, the 16-17 positions, or at the 2-3 and 16-17 positions of the steroid nucleus, or —O—Si(C1-C6 alkyl)$_3$ where each alkyl is independently chosen, e.g., —O—Si$(CH_3)_3$, —O—Si$[C(CH_3)_3](CH_3)_2$, —O—Si$[C(CH_3)_3](C_2H_5)_2$, or phosphate ester, phosphoester, or an ether or thioether derivative thereof, e.g., —O—P(O)(OH)—$OCH_3$, —O—P(O)(OH)—$OC_2H_5$, —O—P(O)(OH)—$OC_3H_7$, —O—P(O)(OH)—$OCH_2CH=CH_2$, —O—P(O)($OCH_3$)—$OCH_3$, —O—P(O)($OC_2H_5$)—$OC_2H_5$, —O—P(O)(OH)—O—$(CH_2)_2$—$N^+(CH_3)_3$, —O—P(O)(OH)—O—$(CH_2)_2$—$NH_2$), —O—P(O)(OH)—OH, —O—P(O)(OH)—SH, —O—P(O)($OR^{PR}$)—OH, —O—P(O)($OR^{PR}$)—SH, —S—P(O)(OH)—OH, —O—P(O)(OH)—S—$(CH_2)_2$—NH—$(CH_2)_3$—$NH_2$, —O—P(O)(OH)—S—$CH_3$, —O—P(O)($OCH_3$)$_2$, —O—P(O)(OH)—O—$C_2H_5$, —O—P(O)($OC_2H_5$)$_2$, —O—P(O)(OH)—O—$C_3H_7$, —O—P(O)($OC_3H_7$)$_2$, —O—P—(O)(OH)—O—$CH_2$—CH(O—C(O)—$(CH_2)_y$(CH=CH)$_q$—$(CH_2)_y$—$CH_3$)—$CH_2$—O—C(O)—$(CH_2)_y$(CH=CH)$_q$—$(CH_2)_y$—$CH_3$, —O—P—(O)(OH)—O—$CH_2$—CH(O—C(O)—$(CH_2)_x CH_3$)—$CH_2$—O—C(O)—$(CH_2)_x CH_3$), —O—P—(O)(OH)—O—$CH_2$—CH(O—C(O)—$(CH_2)_{14} CH_3$)—$CH_2$—O—C(O)—$(CH_2)_{14} CH_3$), —O—P—(O)(OH)—O—$CH_2$—CH(O—C(O)—$(CH_2)_{12} CH_3$)—$CH_2$—O—C(O)—$(CH_2)_{12} CH_3$), —O—P(O)(OH)—O-optionally substituted alkyl, —S—P(O)(OH)—O-optionally substituted alkyl, —O—P(O)(OH)—S-optionally substituted alkyl, —O—P(O)(O-optionally substituted alkyl)-O-optionally substituted alkyl, —S—P(O)(O-optionally substituted alkyl)-O-optionally substituted alkyl, —O—P(O)(O-optionally substituted alkyl)-S-optionally substituted alkyl, where the optionally substituted alkyl moieties are as described herein and are independently selected, e.g., i-propyl, n-propyl, t-butyl, n-butyl, n-hexyl, n-octyl, n-decyl, —$(CH_2)_m$—OH, —$(CH_2)_m$—F, —$(CH_2)_m$—Cl, —$(CH_2)_m$—Br, —$(CH_2)_m$—$NH_2$, —$(CH_2)_m$—C(O)—OH, —$(CH_2)_m$—C(O)—H, —$(CH_2)_m$—C(O)—$CH_3$, —$(CH_2)_n$—$(O)_p$—

$(CH_2)_n$—$CH_3$, —$(CH_2)_n$—$(O)_p$—$(CH_2)_n$—$CH_2OH$, —$(CH_2)_n$—$(CH=CH)_p$—$(CH_2)_n$—$CH_3$, —$(CH_2)_n$—$(CH=CH)_p$—$(CH_2)_n$—$CH_2OH$, —$(CH_2)_n$—$(CH=CH)_p$—$(CH_2)_n$—$CH_2F$, —$(CH_2)_n$—$(CH=CH)_p$—$(CH_2)_n$—$CH_2Br$, —$(CH_2)_n$—$(CH=CH)_p$—$(CH_2)_n$—$C(O)$—$OR^{PR}$, —$(CH_2)_n$—$(CH=CH)_p$—$(CH_2)_n$—$NHR^{PR}$, —$(CH_2)_n$—$(C\equiv C)_p$—$(CH_2)_n$—$CH_3$, —$(CH_2)_n$—$(C\equiv C)_p$—$(CH_2)_n$—$CH_2OH$, —$(CH_2)_n$—$(C\equiv C)_p$—$(CH_2)_n$—$CH_2F$, —$(CH_2)_n$—$(C\equiv C)_p$—$(CH_2)_n$—$CH_2Br$, —$(CH_2)_n$—$(C\equiv C)_p(C(CH_2)_n$—$(C\equiv C)_p$—$(CH_2)_n$—$NHR^{PR}$, —$CF_3$ or —$C_2F_5$, wherein $R^{PR}$ is —H or a protecting group, m is 1, 2, 3, 4, 5 or 6, n independently are 0, 1, 2, 3, 4, 5 or 6 and p is 0 or 1, q is 0 or 1, x independently are 0, 1, 2, 3, 4, 5, 6, 7, 8, 9, 10, 11, 12, 13, 14, 15, 16 or 17, y independently are 0, 1, 2, 3, 4, 5, 6, 7, 8 or 9 and substituents bonded at double bonds are in the cis, trans or mixed cis and trans configuration, wherein In some embodiments, both n and p are 1 or p is 1 and both n are 2 or one n is 1, the other n is 2 and p is 1, or thionoester, e.g., a C2-C20 thionoester such as —O—C(S)—$CH_3$, —O—C(S)—$CF_3$, —O—C(S)—$C_2H_5$ or —O—C(S)—$C_{1-12}$ optionally substituted alkyl where the optionally substituted alkyl optionally is i-propyl, n-propyl, t-butyl, n-butyl, n-hexyl, n-octyl, n-decyl, vinyl, allyl, phenyl, —$CH_2OH$, —$CH_2F$, —$CF_2H$, —$(CH_2)_n$—$CH_3$, —$(CH_2)_n$—OH, —$(CH_2)_n$—F, —$(CH_2)_n$—Br, —$(CH_2)_n$—$NH_2$, —$(CH_2)_n$—C(O)—$OR^{PR}$, —$(CH_2)_n$—O—$CH_3$, —$(CH_2)_n$—S—$CH_3$, —$(CH_2)_m$—$(CH=CH)_p$—$(CH_2)_q$—$CH_3$, —$(CH_2)_m$—$(CH=CH)_p$—$(CH_2)_q$—$CH_2F$, —$(CH_2)_m$—$(CH=CH)_p$—$(CH_2)_q$—$CH_2Br$, —$(CH_2)_m$—$(CH=CH)_p$—$(CH_2)_q$—C(O)—$OR^{PR}$, —$(CH_2)_m$—$(CH=CH)_p$—$(CH_2)_q$—$NHR^{PR}$, —$CF_3$, —$CH_2CF_3$ or —$C_2F_5$, wherein $R^{PR}$ is —H or a protecting group, n is 1, 2, 3, 4, 5, 6, 7 or 8, m is 0, 1, 2, 3, 4, 5 or 6, p is 0 or 1 and q is 0, 1, 2, 3, 4, 5 or 6, or amino acid or peptide, e.g., a dipeptide, —O—C(O)—$CH_2$—$NHR^{PR}$, —O—C(O)—CHOH—$NHR^{PR}$, —O—C(O)—CH[(CH(OH)($CH_3$)]—$NHR^{PR}$, —O—C(O)—CH($CH_3$)—$NHR^{PR}$, —O—C(O)—CH[($CH_2$)$_2$C(O)$OR^{PR}$]—$NHR^{PR}$, —O—C(O)—CH($CH_2$C(O)$OR^{PR}$—$NHR^{PR}$, —O—C(O)—CH[($CH_2$)$_4$$NHR^{PR}$]—$NHR^{PR}$, —O—C(O)—CH[($CH_2$)$_2$C(O)$NHR^{PR}$]—$NHR^{PR}$, —O—C(O)—CH($CH_2$C(O)$NHR^{PR}$)—$NHR^{PR}$, —O—C(O)—$CHR^{42}$—$NHR^{PR}$, —NH—$(CH_2)_{14}$—C(O)$OR^{46}$ or —O—C(O)—$(CH_2)_{1-4}$—$NHR^{47}$ where $R^{42}$ is —H, —$CH_3$, —$C_2H_5$, —$(CH_2)_n$—C(O)—$OR^{PR}$, —$CH_2$—C(O)—OH, —$CH_2$—C(O)—$NHR^{PR}$, —$CH_2F$, —$CH_2Cl$, —$CH_2Br$, —CHOH—$CH_3$ or —$CH_2OH$, $R^{46}$ is —H, optionally substituted alkyl (e.g., —$CH_3$, —$C_2H_5$, —$C_2H_3$, —$C_3H_7$, —$C_3H_5$, —$(CH_2)_{1-8}$—OH, —$(CH_2)_{1-8}$—$NH_2$, —$(CH_2)_{1-8}$—C(O)—OH, —$(CH_2)_{0-3}$—(CH=CH)$_{0-1}$—$(CH_2)_{0-3}$—$CH_3$, —$(CH_2)_{0-3}$—(CH=CH)$_{0-1}$—$(CH_2)_{0-3}$—$CH_2F$, —$(CH_2)_{0-3}$—(CH=CH)$_{0-1}$—$(CH_2)_{0-3}$—$CH_2Br$, —$(CH_2)_{0-3}$—(CH=CH)$_{0-1}$—$(CH_2)_{0-3}$—C(O)—OH, —$(CH_2)_{0-3}$—(CH=CH)$_{0-1}$—$(CH_2)_{0-3}$—$NH_2$, —$CF_3$ or —$C_2F_5$) or a protecting group (e.g., t-butyl, phenyl, benzyl or substituted phenyl), $R^{47}$ is —H, optionally substituted alkyl (e.g., —$CH_3$, —$C_2H_5$, —$C_2H_3$, —$C_3H_7$, —$C_3H_5$, —$(CH_2)_{1-8}$—OH, —$(CH_2)_{1-8}$—$NH_2$, —$(CH_2)_{1-8}$—C(O)—OH, —$(CH_2)_{0-3}$—(CH=CH)$_{0-1}$—$(CH_2)_{0-3}$—$CH_3$, —$(CH_2)_{0-3}$—(CH=CH)$_{0-1}$—$(CH_2)_{0-3}$—$CH_2F$, —$(CH_2)_{0-3}$—(CH=CH)$_{0-1}$—$(CH_2)_{0-3}$—$CH_2Br$, —$(CH_2)_{0-3}$—(CH=CH)$_{0-1}$—$(CH_2)_{0-3}$—C(O)—OH, —$(CH_2)_{0-3}$—(CH=CH)$_{0-1}$—$(CH_2)_{0-3}$—$NH_2$, —$CF_3$ or —$C_2F_5$) or a protecting group (e.g., t-butyl, phenyl, benzyl or substituted phenyl) and $R^{PR}$ is —H or an independently selected protecting group such as C1-C8 optionally substituted alkyl and n is 0, 1, 2, or 3, or optionally substituted heterocycle or —O—[C(O)]$_m$—$(CH_2)_n$-optionally substituted heterocycle, —$(CH_2)_n$-optionally substituted heterocycle, e.g., 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, 1-aziridyl, 1-azetedyl, 1-pyrrolyl, 1-imidazolyl, 1-pyrazolyl or 1-piperidinyl, wherein m is 0 or 1 and n is 0, 1, 2 or 3, e.g., m and n are both 0, m is 1 and n is 0, m is 0 and n is 1, m and n are both 1, or carboxyl which is optionally substituted, e.g., —C(O)OH, —C(O)$OR^{PR}$, —C(O)OM, —C(O)O—$CH_3$, —C(O)—O—$(CH_2)_n$—$CH_3$, —C(O)—O—CH($CH_3$)—$(CH_2)_n$—$CH_3$, —C(O)—O—C($CH_3$)$_2$—$(CH_2)_n$—$CH_3$, —C(O)—O—$(CH_2)_n$—C(O)$OR^{PR}$, —C(O)—O—CH($CH_3$)—$(CH_2)_n$—C(O)$OR^{PR}$, —C(O)—O—C($CH_3$)$_2$—$(CH_2)_n$—C(O)—O—$(CH_2)_n$—$CH_2OR^{PR}$, —C(O)—O—CH($CH_3$)—$(CH_2)_n$—$CH_2OR^{PR}$, —C(O)—O—C($CH_3$)$_2$—$(CH_2)_n$—$CH_2OR^{PR}$, —C(O)—O—$(CH_2)_n$—$CH_2NHR^{PR}$, —C(O)—O—CH($CH_3$)—$(CH_2)_n$—$CH_2NHR^{PR}$, —C(O)—O—C($CH_3$)$_2$—$(CH_2)_n$—$(CH_2)_n$—$CH_2NHR^{PR}$, —C(O)—O—$(CH_2)_n$—$CH_2SR^{PR}$, —C(O)—O—CH($CH_3$)—$(CH_2)_n$—$CH_2SR^{PR}$, —C(O)—O—C($CH_3$)$_2$—$(CH_2)_n$—$CH_2SR^{PR}$, —C(O)O-organic moiety, —C(O)O—$(CH_2)_n$-optionally substituted phenyl or —C(O)O—$(CH_2)_n$-optionally substituted alkyl, wherein the phenyl and alkyl moieties are optionally substituted with 1, 2 or 3 independently selected with substituents described herein, e.g., —F, —Cl, —Br, —I, —OH, —$CH_3$, —$C_2H_5$, —O—$CH_3$, —O—$C_2H_5$, —$NO_2$, —CN, —SCN, —$NH_2$, —C(O)$OR^{PR}$ or —$(CH_2)_{1-4}$—C(O)—$OR^{PR}$, where n is 0, 1, 2, 3, 4, 5 or 6, $R^{PR}$ is —H or a protecting group such as methyl, ethyl, propyl or butyl, and M is a metal such as an alkali metal, e.g., Li$^+$, Na$^+$ or K$^+$ or M is another counter ion such as an ammonium ion, or carbonate, e.g., —O—C(O)—O—$CH_3$, —O—C(O)—O—$(CH_2)_n$—$CH_3$, —O—C(O)—O—CH($CH_3$)—$(CH_2)_n$—$CH_3$, —O—C(O)—O—$CH_2$-halogen, —O—C(O)—O—$(CH_2)_n$—$CH_2$-halogen, —O—C(O)—O—CH($CH_3$)—$(CH_2)_n$—$CH_2$-halogen, —O—C(O)—O—C($CH_3$)$_2$—$(CH_2)_n$—$CH_3$, —O—C(O)—O—$(CH_2)_n$—C(O)$OR^{PR}$, —O—C(O)—O—CH($CH_3$)($CH_2$)$_n$C(O)$OR^{PR}$, —O—C(O)—O—C($CH_3$)$_2$—$(CH_2)_n$—C(O)$OR^{PR}$, —C(O)—$OR^{PR}$, —O—C(O)—O—CH($CH_3$)—$(CH_2)_n$—$CH_2OR^{PR}$, —O—C(O)—O—C($CH_3$)$_2$—O—C(O)—O—C($CH_3$)$_2$—$(CH_2)_n$—$CH_2NHR^{PR}$, —O—C(O)—O—CH($CH_3$)—$(CH_2)_n$—$CH_2SR^{PR}$, —O—C(O)—O—C($CH_3$)$_2$—$(CH_2)_n$—$CH_2SR^{PR}$, —O—C(O)—O-organic moiety, —O—C(O)—O($CH_2$)$_n$-optionally substituted phenyl or —C(O)—O—$(CH_2)_n$-optionally substituted alkyl, wherein the phenyl or alkyl moieties are optionally substituted with 1, 2 or 3, 4 or more independently selected with substituents described herein, e.g., —F, —Cl, —Br, —I, —OH, —$CH_3$, —$C_2H_5$, —O—$CH_3$, —O—$C_2H_5$, —$NO_2$, —CN, —SCN, —$NH_2$, —C(O)$OR^{PR}$ or —$(CH_2)_{1-4}$—C(O)—$OR^{PR}$, and wherein n is 0, 1, 2, 3, 4, 5 or 6 and $R^{PR}$ is —H or a protecting group, or carbamate, e.g., —O—C(O)—$NH_2$, —O—C(O)—NH—$CH_3$, —O—C(O)—NH—$C_2H_5$, —O—C(O)—NH—$C_3H_7$, —O—C(O)—NH—$C_4H_9$, —O—C(O)—NH—$C_2H_3$, —O—C(O)—NH—$C_3H_5$, —O—C(O)—NH—$C_4H_7$, —O—C(O)—$NHR^{PR}$, —O—C(O)—N[($CH_2$)$_n$$CH_3$]—$CH_3$, —O—C(O)—N[($CH_2$)$_n$$CH_3$]—$C_2H_5$, —O—C(O)—N[($CH_2$)$_n$$CH_3$]—$C_3H_7$, —O—C(O)—N[($CH_2$)$_n$$CH_3$]—$C_4H_9$, —O—C(O)—N[($CH_2$)$_n$$CH_3$]—$C_2H_3$, —O—C(O)—N[($CH_2$)$_n$$CH_3$]—$C_3H_5$, —O—C(O)—N[($CH_2$)$_n$$CH_3$]—$C_4H_7$, —O—C(O)—NH-organic moiety, —O—C(O)—$NR^{48}$-organic moiety, —NH—C(O)—O-organic moiety, —$NR^{48}$—C(O)—O-organic moiety, wherein the organic moiety is as described herein, e.g., it optionally comprises about 1-20 carbon atoms, and wherein $R^{48}$ is —H, a protecting group, an organic moiety or $R^{48}$ together with the organic moiety is a protecting group and the organic moiety optionally is optionally substituted alkyl such as i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, or phosphothioester or thiophosphate or an ether or thioether derivative thereof, e.g., —O—P(S)(OH)—OH, —O—P(S)(OH)—SH, —O—P(S)(OR$^{PR}$)—OH, —O—P(S)(OR$^{PR}$)—SH, —S—P(S)(OH)—OH, —O—P(S)(OH)—O—CH$_3$, —O—P(S)(OH)—O—C$_2$H$_5$, —O—P(S)(OH)—O—C$_3$H$_7$, —O—P(S)(OH)—O-optionally substituted alkyl, —S—P(S)(OH)—O-optionally substituted alkyl, —O—P(S)(OH)—S-optionally substituted alkyl, —O—P(S)(O-optionally substituted alkyl)-O-optionally substituted alkyl, —S—P(S)(O-optionally substituted alkyl)-O-optionally substituted alkyl, —O—P(S)(O-optionally substituted alkyl)-S-optionally substituted alkyl, where the optionally substituted alkyl moieties are as described herein and are independently selected, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, or phosphonoester, phosphonate or an ether or thioether derivative thereof, e.g., —P(O)(OH)—OH, —P(O)(OH)—SH, —P(O)(OR$^{PR}$)—OH, —P(O)(OR$^{PR}$)—SH, —P(O)(OH)—OH, —P(O)(OH)—O—CH$_3$, —P(O)(OH)—O—C$_2$H$_5$, —P(O)(OH)—O—C$_3$H$_7$, —O—P(O)(OH)—H, —S—P(O)(OH)—H, —O—P(O)(OR$^{PR}$)—H, —S—P(O)(OR$^{PR}$)—H, —O—P(O)(OH)—CH$_3$, —O—P(O)(OH)—C$_2$H$_5$, —O—P(O)(OH)—C$_3$H$_7$, —O—P(O)(OH)-optionally substituted alkyl, —S—P(O)(OH)-optionally substituted alkyl, —P(O)(OH)—O-optionally substituted alkyl, —P(O)(OH)—S-optionally substituted alkyl, —P(O)(O-optionally substituted alkyl)-O-optionally substituted alkyl, —P(O)(O-optionally substituted alkyl)-S-optionally substituted alkyl, where the optionally substituted alkyl moieties are as described herein and are independently selected, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6, p is 0 or 1, q is 0 or 1, x independently are 0, 1, 2, 3, 4, 5, 6, 7, 8, 9, 10, 11, 12, 13, 14, 15, 16 or 17, y independently are 0, 1, 2, 3, 4, 5, 6, 7, 8 or 9 and substituents bonded at double bonds are in the cis, trans or mixed cis and trans configuration, wherein In some embodiments, both n and p are 1 or p is 1 and both n are 2 or one n is 1, the other n is 2 and p is 1, or sulfate ester or an ether or thioether derivative thereof, e.g., —O—S(O)(O)—OH, —O—S(O)(O)—SH, —O—S(O)(O)—OR$^{PR}$, —O—S(O)(O)—O—CH$_3$, —O—S(O)(O)—O—C$_2$H$_5$, —O—S(O)(O)—O—C$_3$H$_7$, —O—S(O)(O)—S—CH$_3$, —O—S—(O)(O)—O—CH$_2$—CH(O—C(O)—(CH$_2$)$_y$(CH=CH)$_q$(CH$_2$)$_y$—CH$_3$)—CH$_2$—O—C(O)—(CH$_2$)$_y$(CH=CH)$_q$(CH$_2$)$_y$—CH$_3$, —O—S—(O)(O)—O—CH$_2$—CH(O—C(O)—(CH$_2$)$_x$CH$_3$)—CH$_2$—O—C(O)—(CH$_2$)$_x$CH$_3$), —O—S—(O)(O)—O—CH$_2$—CH(O—C(O)—(CH$_2$)$_{14}$CH$_3$)—CH$_2$—O—C(O)—(CH$_2$)$_{14}$CH$_3$), —O—S—(O)(O)—O—CH$_2$—CH(O—C(O)—(CH$_2$)$_{12}$CH$_3$)—CH$_2$—O—C(O)—(CH$_2$)$_{12}$CH$_3$), —O—S(O)(O)—O-optionally substituted alkyl, —O—S(O)(OH)—S-optionally substituted alkyl, where the optionally substituted alkyl moiety is as described herein, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6, p is 0 or 1, q is 0 or 1, x independently are 0, 1, 2, 3, 4, 5, 6, 7, 8, 9, 10, 11, 12, 13, 14, 15, 16 or 17, y independently are 0, 1, 2, 3, 4, 5, 6, 7, 8 or 9 and substituents bonded at double bonds are in the cis, trans or mixed cis and trans configuration, wherein In some embodiments, both n and p are 1 or p is 1 and both n are 2 or one n is 1, the other n is 2 and p is 1, or optionally substituted oxime, e.g., =NOH, =NOCH$_3$, =NOC$_2$H$_5$, =NOC$_3$H$_7$, =N—(CH$_2$)$_n$—(X)$_q$—(CH$_2$)$_n$-optionally substituted alkyl, where X is —O—, —C(O)—, —S— or —NH— and the optionally substituted alkyl moiety is as described herein, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_m$-heterocycle, —(CH$_2$)$_n$—(O)$_p$—

—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6, p is 0 or 1, and q is 0 or 1, e.g., both n and p are 1 or p is 1 and both n are 2 or one n is 1, the other n is 2 and p is 1, or sulfite ester, sulfite ether, sulfite or sulfoxide, e.g., —O—S(O)—OH, —O—S(O)—OR$^{PR}$, —O—S(O)—O—CH$_3$, —O—S(O)—O—C$_2$H$_5$, —O—S(O)—O—C$_3$H$_7$, —O—S(O)—O-organic moiety, —O—S(O)—O-optionally substituted alkyl, —S(O)—O—CH$_3$, —S(O)—O—C$_2$H$_5$, —S(O)—O—C$_3$H$_7$, —S(O)-organic moiety, —S(O)-optionally substituted alkyl, where the optionally substituted alkyl moiety is as described herein, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_2$)$_n$—C(O)—OR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, and the organic moiety is as described herein, or sulfonamide or a sulfonamide derivative, e.g., —S(O)(O)—NH$_2$, —S(O)(O)—NHR$^{PR}$, —S(O)(O)—NH-optionally substituted alkyl, —NH—S(O)(O)-optionally substituted alkyl, —S(O)(O)—NH—CH$_3$, —S(O)(O)—NH—C$_2$H$_5$, —S(O)(O)—NH—C$_3$H$_7$, —NH—S(O)(O)—CH$_3$, —NH—S(O)(O)—C$_2$H$_5$, —NH—S(O)(O)—C$_3$H$_7$, where the optionally substituted alkyl moiety is as described herein, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, or sulfamate or a sulfamate derivative, e.g., —O—S(O)(O)—NH$_2$, —O—S(O)(O)—NHR$^{PR}$, —O—S(O)(O)—N(RD)$_2$, —O—S(O)(O)—NH-optionally substituted alkyl, —NH—S(O)(O)—O-optionally substituted alkyl, —O—S(O)(O)—NH—C(O)—CH$_3$, —O—S(O)(O)—NH—C(O)-optionally substituted alkyl, —O—S(O)(O)—NH—CH$_3$, —O—S(O)(O)—NH—C$_2$H$_5$, —O—S(O)(O)—NH—C$_3$H$_7$, —O—S(O)(O)—N(C(O)-optionally substituted alkyl)-R$^{52}$, —O—S(O)(O)—N(C(O)—N-optionally substituted alkyl)-R$^{52}$, —NH—S(O)(O)—O—CH$_3$, —NH—S(O)(O)—O—C$_2$H$_5$, —NH—S(O)(O)—O—C$_3$H$_7$, —NH—S(O)(O)—O-optionally substituted alkyl, where any optionally substituted alkyl moiety is as described herein, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, RD independently are —H, optionally substituted alkyl (e.g., —CH$_3$, —C$_2$H$_5$, —C$_3$H$_7$, —CHO, —CH$_2$OH), acyl, benzoyl or benzyl, R$^{52}$ is —H, optionally substituted alkyl, —COOH, —COOR$^{PR}$, —COO-optionally substituted alkyl or —C(O)—N(R$^{53}$)$_2$, R$^{53}$ independently are —H, optionally substituted alkyl, optionally substituted aryl, optionally substituted alkylaryl or optionally substituted arylalkyl, or both R$^{53}$ together with the nitrogen atom to which they are bonded are an N-containing ring such as morpholino or a C2-C6 polyemthyleneimino residue, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, or a sulfonate, a sulfamide, a sulfinamide or a sulfurous diamide, e.g., —O—S(O)(O)—CH$_2$-optionally substituted alkyl, —O—S(O)(O)-optionally substituted alkyl, —NH—S(O)(O)—NHR$^{PR}$, —NH—S(O)(O)—NH-optionally substituted alkyl, —NH—S(O)—NHR$^{PR}$, —NH—S(O)—NH-optionally substituted alkyl, —S(O)—NHR$^{PR}$, —S(O)—NHCH$_3$, —S(O)—N(CH$_3$)$_2$, —S(O)—NHC$_2$H$_5$, —S(O)—NH-optionally substituted alkyl, —NH—S(O)—NHR$^{PR}$, —NH—S(O)—NHCH$_3$, —NH—S(O)—NHC$_2$H$_5$ or —NH—S(O)—NH-optionally substituted alkyl, or a monosaccharide, e.g., a D-, L- or DL-mixture of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, dihydroxyacetone, a monodeoxy derivative of these monosaccharides such as rhamnose, glucuronic acid or a salt of glucuronic acid, any of which are unprotected, partially protected (e.g., less than all hydroxyl groups are protected) or fully protected with independently selected protecting groups (e.g., acetoxy or propionoxy), or an oligosaccharide, e.g., 2, 3, 4 or more linked and independently selected monosaccharides that comprise a D-, L- or DL-mixture of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, N-acetylglucosamine, dihydroxyacetone or a monodeoxy or dideoxy derivative of any of these, with adjacent monosaccharides having the glycosidic linkage at the anomeric carbon of each monosaccharide unit independently alpha or beta linked, e.g., 1→2, 1→3, 1→4, and/or 1→6 glycosidic bonds in the α- and/or β-configuration, e.g., -glucose-mannose, -glucose-mannose-mannose, -mannose-mannose, -mannose-mannose-mannose, -glucose-galactose, -galactose-glucose, -fructose-galactose, -galactose-fructose, -galactose-galactose, -galactose-mannose, -glucuronic acid-glucose, -glucose-glucose, —(O-1β)-D-glucopyranosyl-(1α-O-4)-D-glucopyranoside, —(O-1β)-tetra-O-acetyl-D-glucopyranosyl-(1β-O-4)-tri-O-acetyl-D-glucopyranoside, —(O-1β)-D-galactopyranosyl-(1β-O-4)-D-glucopyranoside, wherein one or more of the monosaccharides are optionally partially or fully protected, e.g., with —C(O)—CH$_3$ or —C(O)—C$_2$H$_5$ to protect 1, 2, 3, 4 or more hydroxyl groups, or a glycol or polyethyleneglycol or a derivative, e.g., propylene glycol, ethylene glycol, 1,4-butylene glycol, 1,3-butylene glycol, 1,2-butylene glycol, —O—C(O)—O—(CH$_2$CH$_2$O)$_n$—H, —C(O)—CH$_2$—O—C(O)—O—(CH$_2$CH$_2$O)$_n$—H or —O—(CH$_2$CH$_2$O)$_n$—H, where n is 1, 2, 3, 4, 5, 6, 7, 8, 9 or 10, or an acetal or spiro ring, e.g., —O—CH$_2$—O—, —O—(CH$_2$)$_2$—O—, —O—(CH$_2$)$_3$—O— or —[C(R$^{36}$)$_2$]$_{1-4}$—O—, —O—C(O)—CH$_2$—, —O—C(O)—CH$_2$—CH$_2$—, —O—C(O)—CH$_2$—CH$_2$—CH$_2$—, —O—C(O)—CHR$^{10}$—, —O—C(O)—CHR$^{10}$—CHR$^{10}$—, —O—C(O)—(CHR$^{10}$)$_3$—, —NH—(CH$_2$)$_2$—O—, —NH—(CH$_2$)$_2$—NH—, —NH—(CH$_2$)$_2$—S—, —CH$_2$—N=CH—NH—, —NH—(CH$_2$)$_3$—O—, —NH—(CH$_2$)$_3$—S—, —NH—(CH$_2$)$_3$—O—, where R$^{10}$ are independently selected and optionally independently are —H, —F, —Cl, —Br, —I, —CH$_3$, —C$_2$H$_5$, —CF$_3$, —C$_2$F$_5$, —CH$_2$CF$_3$, —OH, —CN, —SCN, —OCH$_3$ or —OC$_2$H$_5$, and where each R$^{36}$ independently is —H, —F, —Cl, —Br, —I or an organic moiety such as C1-C10 optionally substituted alkyl (e.g., methyl or ethyl), C2-10 alkenyl, aryl or a heterocycle, any of which are optionally substituted as described herein, e.g., —CF$_3$ or —CH$_2$OH, or thioacetal, e.g., —S—CH$_2$—O—, —S—(CH$_2$)$_2$—O—, —S—(CH$_2$)$_3$—O—, —S—CH$_2$—S—, —S—(CH$_2$)$_2$—S—, —S—(CH$_2$)$_3$—S— or —S—[C(R$^{36}$)$_2$]$_{1-4}$—S— where each R$^{36}$ independently is —H, —F, —Cl, —Br, —I or an organic moiety such as C1-C10 optionally substituted alkyl (e.g., methyl or ethyl), C2-10 alkenyl, aryl or a heterocycle, any of which are optionally substituted as described herein, e.g., —CF$_3$ or —CH$_2$OH. The salts, ionized forms and solvates of any of these moieties are also included, e.g., where a group such as —NH$_2$ or —COOH is ionized to generate a moiety such as —NH$_3^+$Cl$^-$, —NH$_3^+$Br$^-$, —COO$^-$Na$^+$ or —COO$^-$K$^+$.

For any of these exemplary F1C, e.g., the B, C, D, E, F and G structures, some embodiments are characterized by the presence of one or two independently selected substitutions at R$^{10A}$, R$^{10B}$, R$^{10C}$ and R$^{10D}$ and optionally:

(a) R$^{10E}$ (when present at the 5-position), R$^{10F}$, R$^{10G}$ and R$^{10H}$ are independently selected R$^{10}$ groups in the α,β,α,α or β,β,α,α configurations respectively, R$^1$ is an oxygen-bonded, nitrogen-bonded or a sulfur-bonded moiety such as —OH, =O, —SH, =NOH, —NH(C1-C8 optionally substituted alkyl), an ester, an ether, a thioester, or a thioether, R$^{1A}$ is —H, absent, a carbon-bonded moiety such as an acyl moiety, optionally substituted alkyl or optionally substituted alkylaryl, R$^2$ is a halogen or an oxygen-bonded or a sulfur-bonded moiety, R$^{2A}$ is —H, absent, a carbon-bonded moiety, R$^3$ is a halogen or an oxygen-bonded or a sulfur-bonded moiety, R$^{3B}$ is —H, absent, a carbon-bonded moiety, R$^4$ is a halogen, an oxygen-bonded or a sulfur-bonded moiety, R$^{4A}$ is —H, absent, a carbon-bonded moiety such as an acyl moiety, optionally substituted alkyl or optionally substituted alkylaryl/

(b) R$^{10E}$ (if present), R$^{10F}$, R$^{10G}$ and R$^{10H}$ are independently selected R$^{10}$ groups in the α,β,α,α or β,β,α,α configurations respectively, R$^{1A}$ is —H, an oxygen-bonded, nitrogen-bonded or a sulfur-bonded moiety, R$^1$ is —H, a carbon-bonded moiety, R$^2$ is a halogen or an oxygen-bonded or a sulfur-bonded moiety, R$^{2A}$ is —H, absent, a carbon-bonded moiety, R$^3$ is a halogen or an oxygen-bonded or a sulfur-bonded moiety, R$^{3B}$ is —H, absent, a carbon-bonded moiety, R$^4$ is a halogen, an oxygen-bonded or a sulfur-bonded moiety, R$^{4A}$ is —H, absent or a carbon-bonded moiety, (c) R$^{10E}$ (if present), R$^{10F}$, R$^{10G}$ and R$^{10H}$ are independently selected R$^{10}$ groups in the α,β,α,α or β,β,α,α configurations respectively, R$^1$ is an oxygen-bonded, nitrogen-bonded or a sulfur-bonded moiety, R$^{1A}$ is —H, absent or a carbon-bonded moiety, R$^2$ is a halogen or an oxygen-bonded or a sulfur-bonded moiety, R$^{2A}$ is —H, absent or a carbon-bonded moiety, R$^3$ is a halogen or an oxygen-bonded or a sulfur-bonded moiety, R$^{3B}$ is —H, absent or a carbon-bonded moiety, R$^{4A}$ is a halogen, an oxygen-bonded or a sulfur-bonded moiety, R$^4$ is —H, a halogen or a carbon-bonded moiety, (d) R$^{10E}$ (if present), R$^{10F}$, R$^{10G}$ and R$^{10H}$ are independently selected R$^{10}$ groups in the α,β,α,α or β,β,α,α configurations respectively, R$^1$ is an oxygen-bonded, nitrogen-bonded or a sulfur-bonded moiety, R$^{1A}$ is —H, absent, a carbon-bonded moiety, R$^2$ is a halogen or an oxygen-bonded or a sulfur-bonded moiety, R$^{2A}$ is —H, absent or a carbon-bonded moiety, R$^3$ is a halogen or an oxygen-bonded or a sulfur-bonded moiety, R$^{3B}$ is —H, absent or a carbon-bonded moiety, R$^4$ is a halogen, an oxygen-bonded or a sulfur-bonded moiety, R$^{4A}$ is —H, absent or a carbon-bonded moiety, (e) R$^{10E}$ (if present), R$^{10F}$, R$^{10G}$ and R$^{10H}$ are independently selected R$^{10}$ groups in the α,β,α,α or β,β,α,α configurations respectively, R$^1$ is an oxygen-bonded, nitrogen-bonded or a sulfur-bonded moiety, R$^{1A}$ is —H, absent or a carbon-bonded moiety, R$^2$ is a halogen or an oxygen-bonded or a sulfur-bonded moiety, R$^{2A}$ is —H, absent or a carbon-bonded moiety, R$^{3B}$ is a halogen or an oxygen-bonded or a sulfur-bonded moiety, R$^3$ is —H, a carbon-bonded moiety, R$^4$ is a halogen, an oxygen-bonded or a sulfur-bonded moiety, R$^{4A}$ is —H, absent or a carbon-bonded moiety, (f) R$^{10E}$ (if present), R$^{10F}$, R$^{10G}$ and R$^{10H}$ are independently selected R$^{10}$ groups in the α,β,α,α or β,β,α,α configurations respectively, R$^{1A}$ is —H, an oxygen-bonded, nitrogen-bonded or a sulfur-bonded moiety, R$^1$ is —H, a carbon-bonded moiety, R$^2$ is a halogen or an oxygen-bonded or a sulfur-bonded moiety, R$^{2A}$ is —H, absent or a carbon-bonded moiety, R$^3$ is a halogen or an oxygen-bonded or a sulfur-bonded moiety, R$^{3B}$ is —H, absent or a carbon-bonded moiety, R$^{4A}$ is a halogen, an oxygen-bonded or a sulfur-bonded moiety, R$^4$ is —H, a carbon-bonded moiety, or (g) R$^{10E}$ (if present), R$^{10F}$, R$^{10G}$ and R$^{10H}$ are independently selected R$^{10}$ groups in the α,β,α,α or β,β,α,α configurations respectively, R$^1$ is a halogen or an oxygen-bonded, nitrogen-bonded, carbon bonded or a sulfur-bonded moiety, R$^{1A}$ is —H, a carbon-bonded or nitrogen-bonded moiety and R$^2$, R$^{2A}$, R$^3$ R$^{3B}$, R$^4$ and R$^{4A}$ are as described any of in the foregoing embodiments or elsewhere herein. In any of these embodiments, R$^5$-R$^9$ are independently selected moieties as described herein and the oxygen-bonded, nitrogen-bonded, carbon bonded or sulfur-bonded moieties at R$^1$, R$^{1A}$, R$^2$, R$^{2A}$, R$^3$, R$^{3B}$, R$^4$, and R$^{4A}$ include atoms or groups described herein. These embodiments contain formula B, C, D, E, F and G compounds wherein one or two of $R^1$, $R^{1A}$, $R^2$, $R^{2A}$, $R^3$, $R^{3B}$, $R^4$, and $R^{4A}$ are independently selected nitrogen-bonded moieties, one, two or three of $R^1$, $R^{1A}$, $R^2$, $R^{2A}$, $R^3$, $R^{3B}$, $R^4$, and $R^{4A}$ are independently selected carbon-bonded moieties and one, two, three, four or five of $R^2$, $R^{2A}$, $R^3$, $R^{3B}$, $R^4$, and $R^{4A}$ are independently selected or halogen atoms or oxygen-bonded or sulfur-bonded moieties.

These embodiments contain F1C, such as the B, C, D, E, F and G structures wherein $R^4$ and $R^{4A}$ are present, i.e., no 16-17 double bond is present, and both are the same, such as optionally substituted alkyl, halogen, ether, ester, thioether, thioester, e.g., —$OR^{PR}$, —$SR^{PR}$, —F, —Cl, —Br, —I, methyl, ethyl, methoxy, ethoxy acetate or propionate. However, in many embodiments, when they are both present, $R^4$ and $R^{4A}$ are two independently selected dissimilar moieties defined herein, e.g., independently selected —H, —OH, —$OR^{PR}$, an ester (e.g., —OC(O)—$CH_3$, —OC(O)—$C_2H_5$, —OC(O)—C3 alkyl, —OC(O)—C4 alkyl,), ether (e.g., —$OCH_3$, —$OC_2H_5$, —$OCH_2CH_2CH_3$, or —$OCH(CH_3)CH_3$, —O—C4 alkyl, —O—C5 alkyl or —O—C6 alkyl), a thioester, a thioether, an acyl moiety, a carbonate, a carbamate an amide, a monosaccharide, a disaccharide, or an amino acid, optionally substituted alkyl, optionally substituted alkenyl, optionally substituted alkynyl or another moiety described herein.

For any F1C, examples of dissimilar $R^4$ and $R^{4A}$ moieties at the 17-position include (α-ester, β-optionally substituted alkynyl), (β-ester, α-optionally substituted alkynyl), (α-thioester, β-optionally substituted alkynyl), (β-thioester, α-optionally substituted alkynyl), (α-ester, β-optionally substituted alkenyl), (β-ester, α-optionally substituted alkenyl), (α-thioester, β-optionally substituted alkenyl), (β-thioester, α-optionally substituted alkenyl), (α-optionally substituted alkyl, β-ester), (β-optionally substituted alkyl, α-ester), (α-optionally substituted alkyl, β-optionally substituted amine), (β-optionally substituted alkyl, α-optionally substituted amine), (α-optionally substituted alkyl, β-halogen)-, (β-optionally substituted alkyl, α-halogen), (α-halogen, β-ether), (β-halogen, α-ether), (α-halogen, β-optionally substituted alkyl), (β-halogen, α-optionally substituted alkyl), (β-ester, α-acyl), (α-ester, β-acyl), (β-ester, α-C(O)—C1-C10 optionally substituted alkyl), (α-ester, β-C(O)—C1-C10 optionally substituted alkyl), (H-thioester, α-C(O)—C1-C10 optionally substituted alkyl), (α-thioester, β-C(O)—C1-C10 optionally substituted alkyl), (β-OH, α-ester), (α-OH, β-ester), (β-OH, α-ether), (α-OH, β-ether), (β-OH, α-acyl), (α-OH, β-acyl), (α-halogen, β-$OR^{PR}$), (β-halogen, α-$OR^{PR}$), (α-F, β-ester), (β-F, α-ester), (α-F, β-ether), (β-F, α-ether), (α-Br, β-ether), (β-Br, α-ether), (α-F, β-optionally substituted alkyl), (β-F, α-optionally substituted alkyl), (α-OH, β-optionally substituted alkynyl), (β-OH, α-optionally substituted alkynyl), (α-OH, β-C≡$CCH_2$-halogen), (β-OH, α-C≡$CCH_2$-halogen), (α-OH, β-C≡C-halogen), (β-OH, α-C≡C-halogen), (β-epoxy, α-halogen, where the epoxy is formed with an adjacent steroid nucleus atom), (α-epoxy, β-halogen), (α-cyclopropyl, β-halogen), (β-cyclopropyl, α-halogen), (α-cyclopropyl, β-optionally substituted alkyl), (β-cyclopropyl, α-optionally substituted alkyl), (α-optionally substituted alkyl, β-NH—C1-C8 optionally substituted alkyl), (β-optionally substituted alkyl, α-NH—C1-C8 optionally substituted alkyl), (α-ether, β-NH—C1-C8 optionally substituted alkyl), (β-ether, α-NH—C1-C8 optionally substituted alkyl), (α-thioester, β-NH—C1-C8 optionally substituted alkyl), (β-thioester, α-NH—C1-C8 optionally substituted alkyl), (α-ester, β-NH—C1-C8 optionally substituted alkyl), (β-ester, α-NH—C1-C8 optionally substituted alkyl), (α-C(O)$CH_3$, β-NH—C1-C8 optionally substituted alkyl), (β-C(O)$CH_3$, α—NH—C1-C8 optionally substituted alkyl), (α-OH, β-NH—C1-C8 optionally substituted alkyl), (β-OH, α-NH—C1-C8 optionally substituted alkyl) and other combinations of groups that are within the scope of $R^4$ and $R^{4A}$. Such moieties, which are the same or different can also be at 1, 2, 3 or more $R^1$ and $R^{1A}$, $R^2$ and $R^{2A}$, $R^3$ and $R^{3B}$ variable groups, and/or the $R^{10}$ variable groups at $R^7$, $R^3$ and $R^9$.

Specific dissimilar $R^4$ and $R^{4A}$ moieties include, e.g., (α-F, β-$CH_3$), (β-F, α-$CH_3$), (α-F, β-$C_2H_5$), (β-F, α-$C_2H_5$), (α-Br, β-$OCH_3$), (β-Br, α-$OCH_3$), (α-F, β-$OCH_3$), (β-F, α-$OCH_3$), (α-F, β-OH), (β-F, α-OH), (α-Br, β-$OCH_3$), (β-Br, α-$OCH_3$), (α-F, β-$CH_3$), (β-F, α-$CH_3$), (α-Br, β-$CH_3$), (β-Br, α-$CH_3$), (α-OH, β-CC$CH_3$), (β-OH, α-CC$CH_3$), (α-OH, β-CC$CH_2OH$), (β-OH, α-CC$CH_2OH$), (α-OH, β-CCH), (β-OH, α-CCH), (α-$CH_3$, β-OC(O)$CH_3$), (β-$CH_3$, α-OC(O)$CH_3$), (α-$C_2H_5$, β-OC(O)$CH_3$), (β-$C_2H_5$, α-OC(O)$CH_3$), (α-$C_3H_7$, β-OC(O)$CH_3$), (β-$C_3H_7$, α-OC(O)$CH_3$), (α-$C_4H_9$, β-OC(O)$CH_3$), (β-$C_4H_9$, α-OC(O)$CH_3$), (α-$C_2H_3$, β-OC(O)$CH_3$), (β-$C_2H_3$, α-OC(O)$CH_3$), (α-$C_2H_4OH$, β-OC(O)$CH_3$), (β-$C_2H_4OH$, α-OC(O)$CH_3$), (α-$C_3H_5$, β-OC(O)$CH_3$), (β-$C_3H_5$, α-OC(O)$CH_3$), (α-$C_4H_7$, β-OC(O)$CH_3$), (β-$C_4H_7$, α-OC(O)$CH_3$), (α-$C_3H_3$, β-OC(O)$CH_3$), (β-$C_3H_3$, α-OC(O)$CH_3$), (α-$C_4H_5$, β-OC(O)$CH_3$), (β-$C_4H_5$, β-OC(O)$CH_3$), (α-$CH_3$, β-OC(O)$C_2H_5$), (β-$CH_3$, α-OC(O)$C_2H_5$), (α-$C_2H_5$, β-OC(O)$C_2H_5$), (β-$C_2H_5$, α-OC(O)$C_2H_5$), (α-$C_3H_7$, β-OC(O)$C_2H_5$), (β-$C_3H_7$, α-OC(O)$C_2H_5$), (α-$C_4H_9$, β-OC(O)$C_2H_5$), (β-$C_4H_9$, α-OC(O)$C_2H_5$), (β-$C_2H_3$, β-OC(O)$C_2H_5$), (β-$C_2H_3$, α-OC(O)$C_2H_5$), (α-$C_2H_4OH$, β-OC(O)$C_2H_5$), (β-$C_2H_4OH$, α-OC(O)$C_2H_5$), (α-$C_3H_5$, β-OC(O)$C_2H_5$), (β-$C_3H_5$, α-OC(O)$C_2H_5$), (α-$C_4H_7$, β-OC(O)$C_2H_5$), (β-$C_4H_7$, α-OC(O)$C_2H_5$), (α-$C_3H_3$, β-OC(O)$C_2H_5$), (β-$C_3H_3$, α-OC(O)$C_2H_5$), (α-$C_4H_5$, β-OC(O)$C_2H_5$), (β-$C_4H_5$, α-OC(O)$C_2H_5$), (α-C(O)$CH_3$, β-OC(O)$CH_3$), (β-C(O)$CH_3$, α-OC(O)$CH_3$), (α-C(O)$C_2H_5$, β-OC(O)$CH_3$), (β-C(O)$C_2H_5$, α-OC(O)$CH_3$), (α-$CH_3$, β-SC(O)$CH_3$), (β-$CH_3$, α-SC(O)$CH_3$), (α-$C_2H_5$, β-SC(O)$CH_3$), (β-$C_2H_5$, α-SC(O)$CH_3$), (α-$C_3H_7$, P—SC(O)$CH_3$), (β-$C_3H_7$, α-SC(O)$CH_3$), (α-$C_4H_9$, β-SC(O)$CH_3$), (β-$C_4H_9$, α-SC(O)$CH_3$), (α-$C_2H_3$, β-SC(O)$CH_3$), (β-$C_2H_3$, α-SC(O)$CH_3$), (α-$C_2H_4OH$, β-SC(O)$CH_3$), (β-$C_2H_4OH$, α-SC(O)$CH_3$), (α-$C_3H_5$, β-SC(O)$CH_3$), (β-$C_3H_5$, α-SC(O)$CH_3$), (α-$C_4H_7$, β-SC(O)$CH_3$), (β-$C_4H_7$, α-SC(O)$CH_3$), (α-$C_3H_3$, β-SC(O)$CH_3$), (β-$C_3H_3$, α-SC(O)$CH_3$), (α-$C_4H_5$, β-SC(O)$CH_3$), (β-$C_4H_5$, α-SC(O)$CH_3$), (α-$CH_3$, β-SC(O)$C_2H_5$), (β-$CH_3$, α-SC(O)$C_2H_5$), (α-$C_2H_5$, β-SC(O)$C_2H_5$), (β-$C_2H_5$, α-SC(O)$C_2H_5$), (α-$C_3H_7$, β-SC(O)$C_2H_5$), (β-$C_3H_7$, α-SC(O)$C_2H_5$), (α-$C_4H_9$, β-SC(O)$C_2H_5$), (β-$C_4H_9$, α-SC(O)$C_2H_5$), (α-$C_2H_3$, β-SC(O)$C_2H_5$), (β-$C_2H_3$, α-SC(O)$C_2H_5$), (α-$C_2H_4OH$, β-SC(O)$C_2H_5$), (β-$C_2H_4OH$, α-SC(O)$C_2H_5$), (α-$C_3H_5$, β-SC(O)$C_2H_5$), (β-$C_3H_5$, α-SC(O)$C_2H_5$), (α-$C_4H_7$, β-SC(O)$C_2H_5$), (β-$C_4H_7$, α-SC(O)$C_2H_5$), (α-$C_3H_3$, β-SC(O)$C_2H_5$), (β-$C_3H_3$, α-SC(O)$C_2H_5$), (α-$C_4H_5$, β-SC(O)$C_2H_5$), (β-$C_4H_5$, α-SC(O)$C_2H_5$), (α-C(O)$CH_3$, β-SC(O)$CH_3$), (β-C(O)$CH_3$, α-SC(O)$CH_3$), (α-C(O)$C_2H_5$, β-SC(O)$CH_3$), (β-C(O)$C_2H_5$, α-SC(O)$CH_3$), (α-C(O)$CH_3$, β-NH—$CH_3$), (β-C(O)$CH_3$, α-NH—$CH_3$), (α-OH, β-NH—$CH_3$), (β-OH, α-NH—$CH_3$), (α-C(O)$CH_3$, β-N($CH_3)_2$), (β-C(O)$CH_3$, α-N($CH_3)_2$), (α-OH, β-N($CH_3)_2$), (β-OH, α-N($CH_3)_2$), (α-C(O)$CH_3$, β-N($C_2H_5)_2$), (β-C(O)$CH_3$, α-N($C_2H_5)_2$), (α-OH, β-N($C_2H_5)_2$), (β-OH, α-N($C_2H_5)_2$), (β-epoxy, α-H), (α-epoxy, β-H), (β-epoxy, α-Br), (α-epoxy, β-Br), (β-epoxy, α-F), (α-epoxy, β-F), (β-cyclopropyl, α-H), (α-cyclopropyl, β-H), (β-cyclopropyl, α-F) and (α-cyclopropyl, β-F). For moieties that contain an epoxy, cyclopropyl or other cyclic moiety, the cyclic moiety can be formed with an adjacent variable group, e.g., $R^3$ or $R^{3B}$. As is apparent from the foregoing disclosure, these or other dissimilar moieties can also be present at one or more of, e.g., the 2-, 3-, 7-, 11-, 15- or 16-positions.

Additional embodiments of the F1Cs include any F1Cs or any 2, 5, 6, 7, 8, 9, 10, B, C, D, E, F or G structures, e.g., any of the F1Cs or F1C genera disclosed herein, wherein one or both of $R^5$ or $R^6$ independently are —H, —CH$_2$SH, —CHO, —CH$_2$NR$^{PR}$, —CH$_2$NH$_2$, —C$_4$H$_9$, —C$_3$H$_7$, —C$_2$H$_5$, —CH$_3$, —C$_2$H$_4$OH, —C$_2$H$_4$SH, —C$_2$H$_4$NH$_2$, —CH$_2$CHO, —CH$_2$CH$_2$NR$^{PR}$, —CH$_2$CH$_2$OH, —CH$_2$CH$_2$SH, —CH$_2$CH$_2$C$_6$H$_5$, —CH$_2$C$_6$H$_5$, —C$_6$H$_5$ or optionally substituted alkyl wherein any phenyl (C$_6$H$_5$) moiety in the foregoing groups is optionally substituted at the phenyl ring with 1, 2, 3, 4 or 5 moieties independently selected from those described for esters herein and including C1-C6 alkyl (optionally substituted with 1 or 2 independently selected —OH, —SH, —O—, —S— or —NH—) C1-C6 alkoxy, —F, —Cl, —Br, —I, —CN, —NO$_2$, —OH, —SH, —COOR$^{PR}$, —NHR$^{PR}$ and —C(O)—C1-C6 alkyl. Typically $R^5$ or $R^6$ are both in the β-configuration, but they may be in, e.g., the α,β or β,α configurations respectively.

In some embodiments, one or more of the variable groups that are bonded to the F1C, e.g., $R^1$-$R^5$, $R^{10}$, $R^{10A}$, $R^{10B}$, $R^{10C}$, $R^{10D}$, $R^{15}$, $R^{17}$ and $R^{13}$, independently are —H, —OH, =O, —SH, =S, —SCN, —CN, —NO$_2$, —NH$_2$, —N$_3$, —F, —Cl, —Br, —I, epoxide, —CHO, —CHS, =CH$_2$, =CH—CH$_3$, =CH—CH$_2$OH, =CH—CH$_2$—CH$_3$, =CH—CH(OH)—CH$_3$, =CH—C(O)—CH$_3$, =CH—CH(halogen)-CH$_3$, —CH$_2$(halogen), —CH(halogen)-CH$_3$, —CH$_2$—CH(halogen)-CH$_3$, —CH$_2$—(CH$_2$)$_n$—NH$_2$, —CH$_2$—(CH$_2$)$_n$—N—H[(CH$_2$)$_n$—CH$_3$], —CH(CH$_3$)—NH—(CH$_2$)$_m$—NH$_2$, —CH(CH$_3$)—NH—(CH$_2$)$_m$—N—H[(CH$_2$)$_n$—CH$_3$], —CH(CH$_3$)—NH—(CH$_2$)$_m$—NH(optionally substituted alkyl), —CH(CH$_3$)—NH—(CH$_2$)$_m$—N(optionally substituted alkyl)$_2$, —CH(CH$_3$)—NH—(CH$_2$)$_{2-3}$—N(CH$_3$)$_2$, =NOH, =NOC(O)CH$_3$, =NOCH$_3$, =NO—CH$_2$CH$_3$, —C(O)—CH$_3$, —C(O)—(CH$_2$)$_{1-4}$—CH$_3$, —CCH, —CCCH$_3$, —CH=CH$_2$, —CH=CH$_2$CH$_3$, —O—C(O)—(CH$_2$)$_m$—(CF$_2$)$_n$—CH$_3$, —O—C(O)—(CH$_2$)$_m$—(CF$_2$)$_n$—CF$_3$, —O—C(O)—(CH$_2$)$_m$—(CF$_2$)$_n$—CH$_2$F, —O—C(O)—O—(CH$_2$)$_m$—(CF$_2$)$_n$—CH$_3$, —O—C(O)—O—(CH$_2$)$_m$—(CF$_2$)$_n$—CF$_3$, —O—C(O)—O—(CH$_2$)$_m$—(CF$_2$)$_n$—CH$_2$F, —O—C(O)—NH—(CH$_2$)$_m$—(CF$_2$)$_n$—CH$_3$, —O—C(O)—NH—(CH$_2$)$_m$—(CF$_2$)$_n$—CF$_3$, —O—C(O)—NH—(CH$_2$)$_m$—(CF$_2$)$_n$—CH$_2$F (where m is 1, 2, 3, 4, 5, 6, 7, 8, 9 or 10, n is 0, 1, 2, 3, 4, 5, 6, 7, 8, 9 or 10, and p is 0, 1 or 2), —CH(CH$_3$)—(CH$_2$)$_2$—C(O)NH—CH$_2$COOH, —CH(CH$_3$)—(CH$_2$)$_2$—C(O)NH—CH$_2$SO$_3$H, —OSi(CH$_3$)$_2$C(CH$_3$)$_3$, —C(OH)=CHCH$_3$, =CH(CH$_2$)$_{0-15}$CH$_3$, —(CH$_2$)$_{0-14}$—CH$_2$F, —(CH$_2$)$_{0-14}$—CH$_2$Cl, —(CH$_2$)$_{0-14}$—CH$_2$Br, —(CH$_2$)$_{0-14}$—CH$_2$I, —(CH$_2$)$_{2-10}$—O—(CH$_2$)$_{0-4}$—CH$_3$, —(CH$_2$)$_{2-10}$—S—(CH$_2$)$_{0-4}$—CH$_3$, —(CH$_2$)$_{2-10}$—NH—(CH$_2$)$_{0-4}$—CH$_3$, —O—(CH$_2$)$_{0-14}$—CH$_2$F, —O—(CH$_2$)$_{0-14}$—CH$_2$Cl, —O—(CH$_2$)$_{0-14}$—CH$_2$Br, —O—(CH$_2$)$_{0-14}$—CH$_2$I, —O—(CH$_2$)$_{2-10}$—O—(CH$_2$)$_{0-4}$—CH$_3$, —O—(CH$_2$)$_{2-10}$—S—(CH$_2$)$_{0-4}$—CH$_3$, —O—(CH$_2$)$_{2-10}$—NH—(CH$_2$)$_{0-4}$—CH$_3$, —O—C(O)—(CH$_2$)$_{0-14}$—CH$_2$F, —O—C(O)—(CH$_2$)$_{0-14}$—CH$_2$Cl, —O—C(O)—(CH$_2$)$_{0-14}$—CH$_2$Br, —O—C(O)—(CH$_2$)$_{0-14}$—CH$_2$I, —O—C(O)—(CH$_2$)$_{2-10}$—O—(CH$_2$)$_{0-4}$—CH$_3$, —O—C(O)—(CH$_2$)$_{2-10}$—S—(CH$_2$)$_{0-4}$—CH$_3$, —O—C(O)—(CH$_2$)$_{2-10}$—NH—(CH$_2$)$_{0-4}$—CH$_3$, —O—C(S)—(CH$_2$)$_{0-14}$—CH$_2$F, —O—C(S)—(CH$_2$)$_{0-14}$—CH$_2$Cl, —O—C(S)—(CH$_2$)$_{0-14}$—CH$_2$Br, —O—C(S)—(CH$_2$)$_{0-14}$—CH$_2$I, —O—C(S)—(CH$_2$)$_{2-10}$—O—(CH$_2$)$_{0-4}$—CH$_3$, —O—C(S)—(CH$_2$)$_{2-10}$—S—(CH$_2$)$_{0-4}$—CH$_3$, —O—C(S)—(CH$_2$)$_{2-10}$—NH—(CH$_2$)$_{0-4}$—CH$_3$, —(CH$_2$)$_{0-16}$NH$_2$, —(CH$_2$)$_{0-15}$CH$_3$, —(CH$_2$)$_{0-15}$CN, —(CH$_2$)$_{0-15}$CH=CH$_2$, —(CH$_2$)$_{0-15}$NHCH(O), —(CH$_2$)$_{0-16}$NH—(CH$_2$)$_{0-15}$CH$_3$, —(CH$_2$)$_{0-15}$CCH, —(CH$_2$)$_{0-15}$OC(O)CH$_3$, —(CH$_2$)$_{0-15}$OCH(OH)CH$_3$, —(CH$_2$)$_{0-15}$C(O)OCH$_3$, —(CH$_2$)$_{0-15}$C(O)OCH$_2$CH$_3$, —(CH$_2$)$_{0-15}$C(O)(CH$_2$)$_{0-15}$CH$_3$, —(CH$_2$)$_{0-15}$C(O)(CH$_2$)$_{0-15}$CH$_2$OH, —O(CH$_2$)$_{1-16}$NH$_2$, —O(CH$_2$)$_{1-15}$CH$_3$, —O(CH$_2$)$_{1-15}$CN, —O(CH$_2$)$_{1-15}$CH=CH$_2$, —O(CH$_2$)$_{1-15}$NHCH(O), —O(CH$_2$)$_{1-16}$NH—(CH$_2$)$_{1-15}$CH$_3$, —O(CH$_2$)$_{1-15}$CCH, —O(CH$_2$)$_{1-15}$OC(O)CH$_3$, —O(CH$_2$)$_{1-15}$OCH(OH)CH$_3$, —O(CH$_2$)$_{1-15}$C(O)OCH$_3$, —O(CH$_2$)$_{1-15}$C(O)OCH$_2$CH$_3$, —O(CH$_2$)$_{1-15}$C(O)(CH$_2$)$_{0-15}$CH$_3$, —O(CH$_2$)$_{1-15}$C(O)(CH$_2$)$_{0-15}$CH$_2$OH, —OC(O)(CH$_2$)$_{1-16}$NH$_2$, —OC(O)(CH$_2$)$_{1-15}$CH$_3$, —C(O)O(CH$_2$)$_{1-15}$CN, —C(O)O(CH$_2$)$_{1-15}$CH=CH$_2$, —OC(O)(CH$_2$)$_{1-15}$NHCH(O), —OC(O)(CH$_2$)$_{1-16}$NH—(CH$_2$)$_{1-15}$CH$_3$, —OC(O)(CH$_2$)$_{1-15}$CCH, —OC(O)(CH$_2$)$_{1-15}$OC(O)CH$_3$, —OC(O)(CH$_2$)$_{1-15}$OCH(OH)CH$_3$, —OC(O)(CH$_2$)$_{1-15}$C(O)OCH$_3$, —OC(O)(CH$_2$)$_{1-15}$C(O)OCH$_2$CH$_3$, —OC(O)(CH$_2$)$_{1-15}$C(O)(CH$_2$)$_{0-15}$CH$_3$, —OC(O)(CH$_2$)$_{1-15}$C(O)(CH$_2$)$_{0-15}$CH$_2$OH, —C(O)—(CH$_2$)$_{0,1,2,3,4,5,6}$—OPO$_3$HR$^{PR}$, —C(O)—(CH$_2$)$_{0,1,2,3,4,5,6}$—C(O)—C1-C4 optionally substituted alkyl, —O-cyclopentyl, —O—(CH$_2$)$_{0,1,2,3,4}$—C(O)—CH=CH—CH—(CH$_2$)$_{0,1,2,3,4}$—CH$_3$, —C(O)-optionally substituted phenyl, —C(O)-disubstituted phenyl, —C(O)-p-substituted phenyl, —C(O)-o-substituted phenyl, —CH(CH$_3$)—(CH$_2$)$_{1,2,3,4}$—C(=CH$_2$)—CH(CH$_3$)$_2$, —CH(CH$_3$)—(CH$_2$)$_{1,2,3,4}$—CH(CH$_3$)$_2$, —C(CH$_3$)=N—(CH$_2$)$_{1,2,3,4}$—CH$_2$OH, —C(O)—(CH$_2$)$_{0,1,2,3,4,5,6}$—O—C(O)—(CH$_2$)$_{1,2,3,4,5,6}$—C(O)—O—C1-C4 optionally substituted alkyl, —C(O)—(CH$_2$)$_{0,1,2,3,4,5,6}$—O—C(O)—(CH$_2$)$_{1,2,3,4,5,6}$—C(O)—OR$^{PR}$, —C≡C-cyclopropyl, —CH=CH-cyclopropyl, —C≡C—C(=CH$_2$)—CH$_3$, —C≡C—C(=CH$_2$)—F, —C≡C—C(=CH$_2$)—Cl, —C≡C—C(=CH$_2$)—Br, —C≡C—C(=CH$_2$)—F, —C≡C—C(=CH$_2$)—Cl, —C≡C—C(=CH$_2$)—Br, —O—C(O)—CF$_3$, —O—C(O)-cyclopropyl, —O—C(O)-cyclobutyl, —O—C(O)—CH$_2$—O—C(O)—CH=CH—COOR$^{PR}$, —O—C(O)—CH(C$_2$H$_5$)(C$_4$H$_9$), —O—C(O)—CH(C$_2$H$_5$)$_2$, —O—C(O)—CH(C$_4$H$_9$)$_2$, —O—C(O)—(CH$_2$)$_{1,2,3,4,5,6}$—CH$_3$, =CH—O—(CH$_2$)$_{1,2,3,4,5,6}$—CH$_3$, —CH=CH$_2$, —CH(OH)—(CH$_2$)$_{0,1,2,3,4}$—H, —C(CH$_3$)(OH)—(CH$_2$)$_{0,1,2,3,4}$—H, —O—(C(O)—(CH$_2$)$_{0,1,2,3,4}$—CH$_3$, —O—(C(O)—(CH$_2$)$_{0,1,2,3,4}$—CF$_3$, —C(O)—CH$_2$—O—C(O)—CH$_2$CH$_2$—C(O)OR$^{PR}$

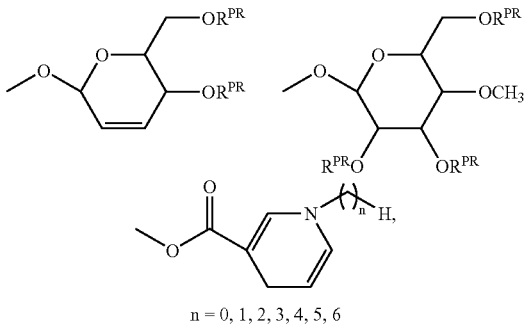

n = 0, 1, 2, 3, 4, 5, 6

C1-C10 optionally substituted alkyl, heterocycle, aryl, phosphoenolpyruvate, D-glucosamine, glucholic acid, glucuronic acid, pantothenic acid, pyruvic acid, glucose, fructose, mannose, sucrose, lactose, fucose, rhamnose, galactose, ribose, (O-1)-D-galactopyranosyl-(1-O-4)-D-glucopyranoside, (O-1)-tetra-O-acetyl-D-glucopyranosyl-(1-O-4)-tri-O- acetyl-D-glucopyranoside, 2'-deoxyribose, 3'-deoxyribose, glycerol, 3-phosphoglycerate, a PEG (PEG 20, PEG 100, PEG 200, PEG 10000), a polyoxyalkylene polymer, glycine, alanine, phenylalanine, threonine, proline, 4-hydroxyproline or an oligonucleotide or analog that comprises about 4 to about 21 monomers, where $R^{PR}$ independently are —H or a protecting group. In some embodiments, one, two or three of $R^1$, $R^2$ and $R^4$ independently are one of these moieties and other variable groups in the F1C are as otherwise defined herein. In other embodiments, one or two of $R^{10A}$, $R^{10B}$, $R^{10C}$, $R^{10D}$, are not —H, and 1, 2, 3 or 4 of (1) $R^1$, $R^3$ and $R^4$, (2) $R^1$, $R^2$ and $R^4$, (3) $R^1$, $R^3$, $R^4$ and $R^9$, (4) $R^1$, $R^3$, $R^4$ and $R^8$, (5) $R^1$, $R^3$, $R^4$ and $R^9$, (6) $R^1$, $R^2$, $R^3$ and $R^4$, (7) $R^1$, $R^2$, $R^3$, $R^4$ and $R^7$ (8) $R^1$, $R^2$, $R^3$, $R^4$ and $R^8$ or (9) $R^1$, $R^2$, $R^3$, $R^4$ and $R^9$, independently are one of these moieties, e.g., any substituent except —H, —CH$_2$— or =CH—, while other variable groups, e.g., $R^5$ and $R^6$, are as otherwise defined herein.

F1C embodiments also include compounds where 1, 2 or more of, e.g., $R^1$, $R^2$, $R^3$, $R^4$ and $R^{10}$ are a lipid moiety such as a fatty acid, a monoacylglyceride, a diacylglyceride, a phospholipid, a glycolipid, a sphingolipid or a glycerophospholipid that is esterified, linked through an ether (—O—) or acyl moiety or otherwise bonded to the F1C. Exemplary fatty acid esters include —C(O)—(CH$_2$)$_m$—H where m is 4, 5, 6, 7, 8, 9, 10, 11, 12, 13, 15, 17, 19 or 21 and —C(O)—(CH$_2$)$_n$—CH=CH—(CH$_2$)$_n$—H where each n independently is 1, 2, 3, 4, 5, 6, 7 or 8. Other lipid moieties that can be bonded to the steroid include phosphatidic acid, phosphatidylethanolamine, phosphatidylcholine, phosphatidylserine and phosphatidylglycerol. The lipid moiety may be bonded to the steroid through a hydroxyl or oxygen, phosphate, sulfate or amine at a variable group. Such lipid moieties may be bonded to any of the F1Cs or genera of F1Cs disclosed herein.

Specific F1Cs that can be used in the clinical treatments and other methods described herein include the following groups of compounds.

Group 1. Exemplary embodiments include the formula 1 compounds named according to the compound structure designations given in Tables A and B below. Each compound named in Table B is depicted as a compound having formula B

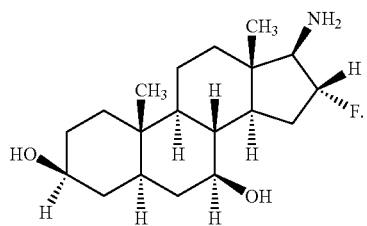

B where $R^5$ and $R^6$ are both —CH$_3$, there is no double bond at the 1-2-, 4-5-, 5-6 or 16-17 positions, $R^7$, $R^8$ and $R^9$ are all —CH$_2$—, $R^{10A}$, $R^{10B}$, $R^{10C}$, $R^{10D}$, $R^{10E}$, $R^{10F}$, $R^{10G}$ and $R^{10H}$ are all —H and $R^1$, $R^2$, $R^3$ and $R^4$ are the substituents designated in Table A. The compounds named according to Tables A and B are referred to as "group 1" compounds.

Compounds named in Table B are named by numbers assigned to $R^1$, $R^2$, $R^3$ and $R^4$ according to the following compound naming convention, $R^1.R^2.R^3.R^4$, using the numbered chemical substituents in Table A. Each Table A number specifies a different structure for each of $R^1$, $R^2$, $R^3$ and $R^4$. When $R^1$, $R^2$, $R^3$ or $R^4$ is a divalent moiety, e.g., =O, the hydrogen at the corresponding position is absent. Thus, the group 1 compound named 1.2.1.1 is a formula B structure with a β-hydroxyl bonded to carbons at the 3- and 7-positions (the variable groups $R^1$ and $R^2$ respectively), an α-bromine bonded to carbon 16 (the variable group $R^3$) and double bonded oxygen (=O) at carbon 17 (the variable group $R^4$), i.e., 1.2.4.1 is 3β,7β-dihydroxy-16α-fluoro-17β-aminoandrostane and has the structure

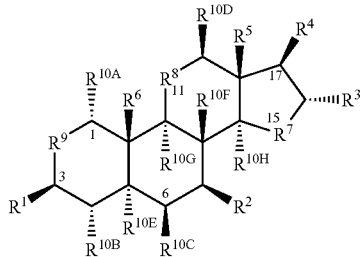

1.2.4.1

Similarly, group 1 compound 1.2.7.1 is 3β,7β-dihydroxy-16-oxo-17β-aminoandrostane and compound 1.1.4.1 is 3-hydroxy-16α-fluoro-17β-aminoandrostane.

TABLE A

| $R^1$ | | $R^2$ | |
|---|---|---|---|
| 1 | —OH | 1 | —H |
| 2 | =O | 2 | —OH |
| 3 | —SH | 3 | =O |
| 4 | =S | 4 | —CH$_3$ |
| 5 | —NH$_2$ | 5 | —OCH$_3$ |
| 6 | —NH—C(O)CH$_3$ | 6 | —F |
| 7 | —H | 7 | —Cl |
| 8 | —CH$_3$ | 8 | —Br |
| 9 | —O—S(O)(O)—OC$_2$H$_5$ | 9 | —I |
| 10 | —O—S(O)(O)—O$^-$Na$^+$ | 10 | =CH$_2$ |

| $R^3$ | | $R^4$ | |
|---|---|---|---|
| 1 | —Br | 1 | —NH$_2$ |
| 2 | —Cl | 2 | —NH—C(O)CH$_3$ |
| 3 | —I | 3 | =NOH |
| 4 | —F | 4 | —NH—CH$_3$ |
| 5 | —H | 5 | —N(CH$_3$)$_2$ |
| 6 | —OH | 6 | —N$^+$(CH$_3$)$_3$ |
| 7 | =O | 7 | —NH—C$_2$H$_5$ |
| 8 | —O—C(O)—CH$_3$ | 8 | —NHOH |
| 9 | —O—C(O)—CH$_2$CH$_3$ | 9 | —OH |
| 10 | =CH$_2$ | 10 | =O |

TABLE B 1.1.1.1, 1.1.1.2, 1.1.1.3, 1.1.1.4, 1.1.1.5, 1.1.1.6, 1.1.1.7, 1.1.1.8, 1.1.1.9, 1.1.1.10, 1.1.2.1, 1.1.2.2, 1.1.2.3, 1.1.2.4, 1.1.2.5, 1.1.2.6, 1.1.2.7, 1.1.2.8, 1.1.2.9, 1.1.2.10, 1.1.3.1, 1.1.3.2, 1.1.3.3, 1.1.3.4, 1.1.3.5, 1.1.3.6, 1.1.3.7, 1.1.3.8, 1.1.3.9, 1.1.3.10, 1.1.4.1, 1.1.4.2, 1.1.4.3, 1.1.4.4, 1.1.4.5, 1.1.4.6, 1.1.4.7, 1.1.4.8, 1.1.4.9, 1.1.4.10, 1.1.5.1, 1.1.5.2, 1.1.5.3, 1.1.5.4, 1.1.5.5, 1.1.5.6, 1.1.5.7, 1.1.5.8, 1.1.5.9, 1.1.5.10, 1.1.6.1, 1.1.6.2, 1.1.6.3, 1.1.6.4, 1.1.6.5, 1.1.6.6, 1.1.6.7, 1.1.6.8, 1.1.6.9, 1.1.6.10, 1.1.7.1, 1.1.7.2, 1.1.7.3, 1.1.7.4, 1.1.7.5, 1.1.7.6, 1.1.7.7, 1.1.7.8, 1.1.7.9, 1.1.7.10, 1.1.8.1, 1.1.8.2, 1.1.8.3, 1.1.8.4, 1.1.8.5, 1.1.8.6, 1.1.8.7, 1.1.8.8, 1.1.8.9, 1.1.8.10, 1.1.9.1, 1.1.9.2, 1.1.9.3, 1.1.9.4,

TABLE B-continued 1.1.9.5, 1.1.9.6, 1.1.9.7, 1.1.9.8, 1.1.9.9, 1.1.9.10, 1.1.10.1, 1.1.10.2, 1.1.10.3, 1.1.10.4, 1.1.10.5,
1.1.10.6, 1.1.10.7, 1.1.10.8, 1.1.10.9, 1.1.10.10, 1.2.1.1, 1.2.1.2, 1.2.1.3, 1.2.1.4, 1.2.1.5, 1.2.1.6,
1.2.1.7, 1.2.1.8, 1.2.1.9, 1.2.1.10, 1.2.2.1, 1.2.2.2, 1.2.2.3, 1.2.2.4, 1.2.2.5, 1.2.2.6, 1.2.2.7, 1.2.2.8,
1.2.2.9, 1.2.2.10, 1.2.3.1, 1.2.3.2, 1.2.3.3, 1.2.3.4, 1.2.3.5, 1.2.3.6, 1.2.3.7, 1.2.3.8, 1.2.3.9, 1.2.3.10,
1.2.4.1, 1.2.4.2, 1.2.4.3, 1.2.4.4, 1.2.4.5, 1.2.4.6, 1.2.4.7, 1.2.4.8, 1.2.4.9, 1.2.4.10, 1.2.5.1, 1.2.5.2,
1.2.5.3, 1.2.5.4, 1.2.5.5, 1.2.5.6, 1.2.5.7, 1.2.5.8, 1.2.5.9, 1.2.5.10, 1.2.6.1, 1.2.6.2, 1.2.6.3, 1.2.6.4,
1.2.6.5, 1.2.6.6, 1.2.6.7, 1.2.6.8, 1.2.6.9, 1.2.6.10, 1.2.7.1, 1.2.7.2, 1.2.7.3, 1.2.7.4, 1.2.7.5, 1.2.7.6,
1.2.7.7, 1.2.7.8, 1.2.7.9, 1.2.7.10, 1.2.8.1, 1.2.8.2, 1.2.8.3, 1.2.8.4, 1.2.8.5, 1.2.8.6, 1.2.8.7, 1.2.8.8,
1.2.8.9, 1.2.8.10, 1.2.9.1, 1.2.9.2, 1.2.9.3, 1.2.9.4, 1.2.9.5, 1.2.9.6, 1.2.9.7, 1.2.9.8, 1.2.9.9, 1.2.9.10,
1.2.10.1, 1.2.10.2, 1.2.10.3, 1.2.10.4, 1.2.10.5, 1.2.10.6, 1.2.10.7, 1.2.10.8, 1.2.10.9, 1.2.10.10,
1.3.1.1, 1.3.1.2, 1.3.1.3, 1.3.1.4, 1.3.1.5, 1.3.1.6, 1.3.1.7, 1.3.1.8, 1.3.1.9, 1.3.1.10, 1.3.2.1, 1.3.2.2,
1.3.2.3, 1.3.2.4, 1.3.2.5, 1.3.2.6, 1.3.2.7, 1.3.2.8, 1.3.2.9, 1.3.2.10, 1.3.3.1, 1.3.3.2, 1.3.3.3, 1.3.3.4,
1.3.3.5, 1.3.3.6, 1.3.3.7, 1.3.3.8, 1.3.3.9, 1.3.3.10, 1.3.4.1, 1.3.4.2, 1.3.4.3, 1.3.4.4, 1.3.4.5, 1.3.4.6,
1.3.4.7, 1.3.4.8, 1.3.4.9, 1.3.4.10, 1.3.5.1, 1.3.5.2, 1.3.5.3, 1.3.5.4, 1.3.5.5, 1.3.5.6, 1.3.5.7, 1.3.5.8,
1.3.5.9, 1.3.5.10, 1.3.6.1, 1.3.6.2, 1.3.6.3, 1.3.6.4, 1.3.6.5, 1.3.6.6, 1.3.6.7, 1.3.6.8, 1.3.6.9, 1.3.6.10,
1.3.7.1, 1.3.7.2, 1.3.7.3, 1.3.7.4, 1.3.7.5, 1.3.7.6, 1.3.7.7, 1.3.7.8, 1.3.7.9, 1.3.7.10, 1.3.8.1, 1.3.8.2,
1.3.8.3, 1.3.8.4, 1.3.8.5, 1.3.8.6, 1.3.8.7, 1.3.8.8, 1.3.8.9, 1.3.8.10, 1.3.9.1, 1.3.9.2, 1.3.9.3, 1.3.9.4,
1.3.9.5, 1.3.9.6, 1.3.9.7, 1.3.9.8, 1.3.9.9, 1.3.9.10, 1.3.10.1, 1.3.10.2, 1.3.10.3, 1.3.10.4, 1.3.10.5,
1.3.10.6, 1.3.10.7, 1.3.10.8, 1.3.10.9, 1.3.10.10, 1.4.1.1, 1.4.1.2, 1.4.1.3, 1.4.1.4, 1.4.1.5, 1.4.1.6,
1.4.1.7, 1.4.1.8, 1.4.1.9, 1.4.1.10, 1.4.2.1, 1.4.2.2, 1.4.2.3, 1.4.2.4, 1.4.2.5, 1.4.2.6, 1.4.2.7, 1.4.2.8,
1.4.2.9, 1.4.2.10, 1.4.3.1, 1.4.3.2, 1.4.3.3, 1.4.3.4, 1.4.3.5, 1.4.3.6, 1.4.3.7, 1.4.3.8, 1.4.3.9, 1.4.3.10,
1.4.4.1, 1.4.4.2, 1.4.4.3, 1.4.4.4, 1.4.4.5, 1.4.4.6, 1.4.4.7, 1.4.4.8, 1.4.4.9, 1.4.4.10, 1.4.5.1, 1.4.5.2,
1.4.5.3, 1.4.5.4, 1.4.5.5, 1.4.5.6, 1.4.5.7, 1.4.5.8, 1.4.5.9, 1.4.5.10, 1.4.6.1, 1.4.6.2, 1.4.6.3, 1.4.6.4,
1.4.6.5, 1.4.6.6, 1.4.6.7, 1.4.6.8, 1.4.6.9, 1.4.6.10, 1.4.7.1, 1.4.7.2, 1.4.7.3, 1.4.7.4, 1.4.7.5, 1.4.7.6,
1.4.7.7, 1.4.7.8, 1.4.7.9, 1.4.7.10, 1.4.8.1, 1.4.8.2, 1.4.8.3, 1.4.8.4, 1.4.8.5, 1.4.8.6, 1.4.8.7, 1.4.8.8,
1.4.8.9, 1.4.8.10, 1.4.9.1, 1.4.9.2, 1.4.9.3, 1.4.9.4, 1.4.9.5, 1.4.9.6, 1.4.9.7, 1.4.9.8, 1.4.9.9, 1.4.9.10,
1.4.10.1, 1.4.10.2, 1.4.10.3, 1.4.10.4, 1.4.10.5, 1.4.10.6, 1.4.10.7, 1.4.10.8, 1.4.10.9, 1.4.10.10,
1.5.1.1, 1.5.1.2, 1.5.1.3, 1.5.1.4, 1.5.1.5, 1.5.1.6, 1.5.1.7, 1.5.1.8, 1.5.1.9, 1.5.1.10, 1.5.2.1, 1.5.2.2,
1.5.2.3, 1.5.2.4, 1.5.2.5, 1.5.2.6, 1.5.2.7, 1.5.2.8, 1.5.2.9, 1.5.2.10, 1.5.3.1, 1.5.3.2, 1.5.3.3, 1.5.3.4,
1.5.3.5, 1.5.3.6, 1.5.3.7, 1.5.3.8, 1.5.3.9, 1.5.3.10, 1.5.4.1, 1.5.4.2, 1.5.4.3, 1.5.4.4, 1.5.4.5, 1.5.4.6,
1.5.4.7, 1.5.4.8, 1.5.4.9, 1.5.4.10, 1.5.5.1, 1.5.5.2, 1.5.5.3, 1.5.5.4, 1.5.5.5, 1.5.5.6, 1.5.5.7, 1.5.5.8,
1.5.5.9, 1.5.5.10, 1.5.6.1, 1.5.6.2, 1.5.6.3, 1.5.6.4, 1.5.6.5, 1.5.6.6, 1.5.6.7, 1.5.6.8, 1.5.6.9, 1.5.6.10,
1.5.7.1, 1.5.7.2, 1.5.7.3, 1.5.7.4, 1.5.7.5, 1.5.7.6, 1.5.7.7, 1.5.7.8, 1.5.7.9, 1.5.7.10, 1.5.8.1, 1.5.8.2,
1.5.8.3, 1.5.8.4, 1.5.8.5, 1.5.8.6, 1.5.8.7, 1.5.8.8, 1.5.8.9, 1.5.8.10, 1.5.9.1, 1.5.9.2, 1.5.9.3, 1.5.9.4,
1.5.9.5, 1.5.9.6, 1.5.9.7, 1.5.9.8, 1.5.9.9, 1.5.9.10, 1.5.10.1, 1.5.10.2, 1.5.10.3, 1.5.10.4, 1.5.10.5,
1.5.10.6, 1.5.10.7, 1.5.10.8, 1.5.10.9, 1.5.10.10, 1.6.1.1, 1.6.1.2, 1.6.1.3, 1.6.1.4, 1.6.1.5, 1.6.1.6,
1.6.1.7, 1.6.1.8, 1.6.1.9, 1.6.1.10, 1.6.2.1, 1.6.2.2, 1.6.2.3, 1.6.2.4, 1.6.2.5, 1.6.2.6, 1.6.2.7, 1.6.2.8,
1.6.2.9, 1.6.2.10, 1.6.3.1, 1.6.3.2, 1.6.3.3, 1.6.3.4, 1.6.3.5, 1.6.3.6, 1.6.3.7, 1.6.3.8, 1.6.3.9, 1.6.3.10,
1.6.4.1, 1.6.4.2, 1.6.4.3, 1.6.4.4, 1.6.4.5, 1.6.4.6, 1.6.4.7, 1.6.4.8, 1.6.4.9, 1.6.4.10, 1.6.5.1, 1.6.5.2,
1.6.5.3, 1.6.5.4, 1.6.5.5, 1.6.5.6, 1.6.5.7, 1.6.5.8, 1.6.5.9, 1.6.5.10, 1.6.6.1, 1.6.6.2, 1.6.6.3, 1.6.6.4,
1.6.6.5, 1.6.6.6, 1.6.6.7, 1.6.6.8, 1.6.6.9, 1.6.6.10, 1.6.7.1, 1.6.7.2, 1.6.7.3, 1.6.7.4, 1.6.7.5, 1.6.7.6,
1.6.7.7, 1.6.7.8, 1.6.7.9, 1.6.7.10, 1.6.8.1, 1.6.8.2, 1.6.8.3, 1.6.8.4, 1.6.8.5, 1.6.8.6, 1.6.8.7, 1.6.8.8,
1.6.8.9, 1.6.8.10, 1.6.9.1, 1.6.9.2, 1.6.9.3, 1.6.9.4, 1.6.9.5, 1.6.9.6, 1.6.9.7, 1.6.9.8, 1.6.9.9, 1.6.9.10,
1.6.10.1, 1.6.10.2, 1.6.10.3, 1.6.10.4, 1.6.10.5, 1.6.10.6, 1.6.10.7, 1.6.10.8, 1.6.10.9, 1.6.10.10,
1.7.1.1, 1.7.1.2, 1.7.1.3, 1.7.1.4, 1.7.1.5, 1.7.1.6, 1.7.1.7, 1.7.1.8, 1.7.1.9, 1.7.1.10, 1.7.2.1, 1.7.2.2,
1.7.2.3, 1.7.2.4, 1.7.2.5, 1.7.2.6, 1.7.2.7, 1.7.2.8, 1.7.2.9, 1.7.2.10, 1.7.3.1, 1.7.3.2, 1.7.3.3, 1.7.3.4,
1.7.3.5, 1.7.3.6, 1.7.3.7, 1.7.3.8, 1.7.3.9, 1.7.3.10, 1.7.4.1, 1.7.4.2, 1.7.4.3, 1.7.4.4, 1.7.4.5, 1.7.4.6,
1.7.4.7, 1.7.4.8, 1.7.4.9, 1.7.4.10, 1.7.5.1, 1.7.5.2, 1.7.5.3, 1.7.5.4, 1.7.5.5, 1.7.5.6, 1.7.5.7, 1.7.5.8,
1.7.5.9, 1.7.5.10, 1.7.6.1, 1.7.6.2, 1.7.6.3, 1.7.6.4, 1.7.6.5, 1.7.6.6, 1.7.6.7, 1.7.6.8, 1.7.6.9, 1.7.6.10,
1.7.7.1, 1.7.7.2, 1.7.7.3, 1.7.7.4, 1.7.7.5, 1.7.7.6, 1.7.7.7, 1.7.7.8, 1.7.7.9, 1.7.7.10, 1.7.8.1, 1.7.8.2,
1.7.8.3, 1.7.8.4, 1.7.8.5, 1.7.8.6, 1.7.8.7, 1.7.8.8, 1.7.8.9, 1.7.8.10, 1.7.9.1, 1.7.9.2, 1.7.9.3, 1.7.9.4,
1.7.9.5, 1.7.9.6, 1.7.9.7, 1.7.9.8, 1.7.9.9, 1.7.9.10, 1.7.10.1, 1.7.10.2, 1.7.10.3, 1.7.10.4, 1.7.10.5,
1.7.10.6, 1.7.10.7, 1.7.10.8, 1.7.10.9, 1.7.10.10, 1.8.1.1, 1.8.1.2, 1.8.1.3, 1.8.1.4, 1.8.1.5, 1.8.1.6,
1.8.1.7, 1.8.1.8, 1.8.1.9, 1.8.1.10, 1.8.2.1, 1.8.2.2, 1.8.2.3, 1.8.2.4, 1.8.2.5, 1.8.2.6, 1.8.2.7, 1.8.2.8,
1.8.2.9, 1.8.2.10, 1.8.3.1, 1.8.3.2, 1.8.3.3, 1.8.3.4, 1.8.3.5, 1.8.3.6, 1.8.3.7, 1.8.3.8, 1.8.3.9, 1.8.3.10,
1.8.4.1, 1.8.4.2, 1.8.4.3, 1.8.4.4, 1.8.4.5, 1.8.4.6, 1.8.4.7, 1.8.4.8, 1.8.4.9, 1.8.4.10, 1.8.5.1, 1.8.5.2,
1.8.5.3, 1.8.5.4, 1.8.5.5, 1.8.5.6, 1.8.5.7, 1.8.5.8, 1.8.5.9, 1.8.5.10, 1.8.6.1, 1.8.6.2, 1.8.6.3, 1.8.6.4,
1.8.6.5, 1.8.6.6, 1.8.6.7, 1.8.6.8, 1.8.6.9, 1.8.6.10, 1.8.7.1, 1.8.7.2, 1.8.7.3, 1.8.7.4, 1.8.7.5, 1.8.7.6,
1.8.7.7, 1.8.7.8, 1.8.7.9, 1.8.7.10, 1.8.8.1, 1.8.8.2, 1.8.8.3, 1.8.8.4, 1.8.8.5, 1.8.8.6, 1.8.8.7, 1.8.8.8,
1.8.8.9, 1.8.8.10, 1.8.9.1, 1.8.9.2, 1.8.9.3, 1.8.9.4, 1.8.9.5, 1.8.9.6, 1.8.9.7, 1.8.9.8, 1.8.9.9, 1.8.9.10,
1.8.10.1, 1.8.10.2, 1.8.10.3, 1.8.10.4, 1.8.10.5, 1.8.10.6, 1.8.10.7, 1.8.10.8, 1.8.10.9, 1.8.10.10,
1.9.1.1, 1.9.1.2, 1.9.1.3, 1.9.1.4, 1.9.1.5, 1.9.1.6, 1.9.1.7, 1.9.1.8, 1.9.1.9, 1.9.1.10, 1.9.2.1, 1.9.2.2,
1.9.2.3, 1.9.2.4, 1.9.2.5, 1.9.2.6, 1.9.2.7, 1.9.2.8, 1.9.2.9, 1.9.2.10, 1.9.3.1, 1.9.3.2, 1.9.3.3, 1.9.3.4,
1.9.3.5, 1.9.3.6, 1.9.3.7, 1.9.3.8, 1.9.3.9, 1.9.3.10, 1.9.4.1, 1.9.4.2, 1.9.4.3, 1.9.4.4, 1.9.4.5, 1.9.4.6,
1.9.4.7, 1.9.4.8, 1.9.4.9, 1.9.4.10, 1.9.5.1, 1.9.5.2, 1.9.5.3, 1.9.5.4, 1.9.5.5, 1.9.5.6, 1.9.5.7, 1.9.5.8,
1.9.5.9, 1.9.5.10, 1.9.6.1, 1.9.6.2, 1.9.6.3, 1.9.6.4, 1.9.6.5, 1.9.6.6, 1.9.6.7, 1.9.6.8, 1.9.6.9, 1.9.6.10,
1.9.7.1, 1.9.7.2, 1.9.7.3, 1.9.7.4, 1.9.7.5, 1.9.7.6, 1.9.7.7, 1.9.7.8, 1.9.7.9, 1.9.7.10, 1.9.8.1, 1.9.8.2,
1.9.8.3, 1.9.8.4, 1.9.8.5, 1.9.8.6, 1.9.8.7, 1.9.8.8, 1.9.8.9, 1.9.8.10, 1.9.9.1, 1.9.9.2, 1.9.9.3, 1.9.9.4,
1.9.9.5, 1.9.9.6, 1.9.9.7, 1.9.9.8, 1.9.9.9, 1.9.9.10, 1.9.10.1, 1.9.10.2, 1.9.10.3, 1.9.10.4, 1.9.10.5,
1.9.10.6, 1.9.10.7, 1.9.10.8, 1.9.10.9, 1.9.10.10, 1.10.1.1, 1.10.1.2, 1.10.1.3, 1.10.1.4, 1.10.1.5,
1.10.1.6, 1.10.1.7, 1.10.1.8, 1.10.1.9, 1.10.1.10, 1.10.2.1, 1.10.2.2, 1.10.2.3, 1.10.2.4, 1.10.2.5,
1.10.2.6, 1.10.2.7, 1.10.2.8, 1.10.2.9, 1.10.2.10, 1.10.3.1, 1.10.3.2, 1.10.3.3, 1.10.3.4, 1.10.3.5,
1.10.3.6, 1.10.3.7, 1.10.3.8, 1.10.3.9, 1.10.3.10, 1.10.4.1, 1.10.4.2, 1.10.4.3, 1.10.4.4, 1.10.4.5,
1.10.4.6, 1.10.4.7, 1.10.4.8, 1.10.4.9, 1.10.4.10, 1.10.5.1, 1.10.5.2, 1.10.5.3, 1.10.5.4, 1.10.5.5,
1.10.5.6, 1.10.5.7, 1.10.5.8, 1.10.5.9, 1.10.5.10, 1.10.6.1, 1.10.6.2, 1.10.6.3, 1.10.6.4, 1.10.6.5,
1.10.6.6, 1.10.6.7, 1.10.6.8, 1.10.6.9, 1.10.6.10, 1.10.7.1, 1.10.7.2, 1.10.7.3, 1.10.7.4, 1.10.7.5,
1.10.7.6, 1.10.7.7, 1.10.7.8, 1.10.7.9, 1.10.7.10, 1.10.8.1, 1.10.8.2, 1.10.8.3, 1.10.8.4, 1.10.8.5,
1.10.8.6, 1.10.8.7, 1.10.8.8, 1.10.8.9, 1.10.8.10, 1.10.9.1, 1.10.9.2, 1.10.9.3, 1.10.9.4, 1.10.9.5,
1.10.9.6, 1.10.9.7, 1.10.9.8, 1.10.9.9, 1.10.9.10, 1.10.10.1, 1.10.10.2, 1.10.10.3, 1.10.10.4, 1.10.10.5,
1.10.10.6, 1.10.10.7, 1.10.10.8, 1.10.10.9, 1.10.10.10, 2.1.1.1, 2.1.1.2, 2.1.1.3, 2.1.1.4, 2.1.1.5, TABLE B-continued 2.1.1.6, 2.1.1.7, 2.1.1.8, 2.1.1.9, 2.1.1.10, 2.1.2.1, 2.1.2.2, 2.1.2.3, 2.1.2.4, 2.1.2.5, 2.1.2.6, 2.1.2.7, 2.1.2.8, 2.1.2.9, 2.1.2.10, 2.1.3.1, 2.1.3.2, 2.1.3.3, 2.1.3.4, 2.1.3.5, 2.1.3.6, 2.1.3.7, 2.1.3.8, 2.1.3.9, 2.1.3.10, 2.1.4.1, 2.1.4.2, 2.1.4.3, 2.1.4.4, 2.1.4.5, 2.1.4.6, 2.1.4.7, 2.1.4.8, 2.1.4.9, 2.1.4.10, 2.1.5.1, 2.1.5.2, 2.1.5.3, 2.1.5.4, 2.1.5.5, 2.1.5.6, 2.1.5.7, 2.1.5.8, 2.1.5.9, 2.1.5.10, 2.1.6.1, 2.1.6.2, 2.1.6.3, 2.1.6.4, 2.1.6.5, 2.1.6.6, 2.1.6.7, 2.1.6.8, 2.1.6.9, 2.1.6.10, 2.1.7.1, 2.1.7.2, 2.1.7.3, 2.1.7.4, 2.1.7.5, 2.1.7.6, 2.1.7.7, 2.1.7.8, 2.1.7.9, 2.1.7.10, 2.1.8.1, 2.1.8.2, 2.1.8.3, 2.1.8.4, 2.1.8.5, 2.1.8.6, 2.1.8.7, 2.1.8.8, 2.1.8.9, 2.1.8.10, 2.1.9.1, 2.1.9.2, 2.1.9.3, 2.1.9.4, 2.1.9.5, 2.1.9.6, 2.1.9.7, 2.1.9.8, 2.1.9.9, 2.1.9.10, 2.1.10.1, 2.1.10.2, 2.1.10.3, 2.1.10.4, 2.1.10.5, 2.1.10.6, 2.1.10.7, 2.1.10.8, 2.1.10.9, 2.1.10.10, 2.2.1.1, 2.2.1.2, 2.2.1.3, 2.2.1.4, 2.2.1.5, 2.2.1.6, 2.2.1.7, 2.2.1.8, 2.2.1.9, 2.2.1.10, 2.2.2.1, 2.2.2.2, 2.2.2.3, 2.2.2.4, 2.2.2.5, 2.2.2.6, 2.2.2.7, 2.2.2.8, 2.2.2.9, 2.2.2.10, 2.2.3.1, 2.2.3.2, 2.2.3.3, 2.2.3.4, 2.2.3.5, 2.2.3.6, 2.2.3.7, 2.2.3.8, 2.2.3.9, 2.2.3.10, 2.2.4.1, 2.2.4.2, 2.2.4.3, 2.2.4.4, 2.2.4.5, 2.2.4.6, 2.2.4.7, 2.2.4.8, 2.2.4.9, 2.2.4.10, 2.2.5.1, 2.2.5.2, 2.2.5.3, 2.2.5.4, 2.2.5.5, 2.2.5.6, 2.2.5.7, 2.2.5.8, 2.2.5.9, 2.2.5.10, 2.2.6.1, 2.2.6.2, 2.2.6.3, 2.2.6.4, 2.2.6.5, 2.2.6.6, 2.2.6.7, 2.2.6.8, 2.2.6.9, 2.2.6.10, 2.2.7.1, 2.2.7.2, 2.2.7.3, 2.2.7.4, 2.2.7.5, 2.2.7.6, 2.2.7.7, 2.2.7.8, 2.2.7.9, 2.2.7.10, 2.2.8.1, 2.2.8.2, 2.2.8.3, 2.2.8.4, 2.2.8.5, 2.2.8.6, 2.2.8.7, 2.2.8.8, 2.2.8.9, 2.2.8.10, 2.2.9.1, 2.2.9.2, 2.2.9.3, 2.2.9.4, 2.2.9.5, 2.2.9.6, 2.2.9.7, 2.2.9.8, 2.2.9.9, 2.2.9.10, 2.2.10.1, 2.2.10.2, 2.2.10.3, 2.2.10.4, 2.2.10.5, 2.2.10.6, 2.2.10.7, 2.2.10.8, 2.2.10.9, 2.2.10.10, 2.3.1.1, 2.3.1.2, 2.3.1.3, 2.3.1.4, 2.3.1.5, 2.3.1.6, 2.3.1.7, 2.3.1.8, 2.3.1.9, 2.3.1.10, 2.3.2.1, 2.3.2.2, 2.3.2.3, 2.3.2.4, 2.3.2.5, 2.3.2.6, 2.3.2.7, 2.3.2.8, 2.3.2.9, 2.3.2.10, 2.3.3.1, 2.3.3.2, 2.3.3.3, 2.3.3.4, 2.3.3.5, 2.3.3.6, 2.3.3.7, 2.3.3.8, 2.3.3.9, 2.3.3.10, 2.3.4.1, 2.3.4.2, 2.3.4.3, 2.3.4.4, 2.3.4.5, 2.3.4.6, 2.3.4.7, 2.3.4.8, 2.3.4.9, 2.3.4.10, 2.3.5.1, 2.3.5.2, 2.3.5.3, 2.3.5.4, 2.3.5.5, 2.3.5.6, 2.3.5.7, 2.3.5.8, 2.3.5.9, 2.3.5.10, 2.3.6.1, 2.3.6.2, 2.3.6.3, 2.3.6.4, 2.3.6.5, 2.3.6.6, 2.3.6.7, 2.3.6.8, 2.3.6.9, 2.3.6.10, 2.3.7.1, 2.3.7.2, 2.3.7.3, 2.3.7.4, 2.3.7.5, 2.3.7.6, 2.3.7.7, 2.3.7.8, 2.3.7.9, 2.3.7.10, 2.3.8.1, 2.3.8.2, 2.3.8.3, 2.3.8.4, 2.3.8.5, 2.3.8.6, 2.3.8.7, 2.3.8.8, 2.3.8.9, 2.3.8.10, 2.3.9.1, 2.3.9.2, 2.3.9.3, 2.3.9.4, 2.3.9.5, 2.3.9.6, 2.3.9.7, 2.3.9.8, 2.3.9.9, 2.3.9.10, 2.3.10.1, 2.3.10.2, 2.3.10.3, 2.3.10.4, 2.3.10.5, 2.3.10.6, 2.3.10.7, 2.3.10.8, 2.3.10.9, 2.3.10.10, 2.4.1.1, 2.4.1.2, 2.4.1.3, 2.4.1.4, 2.4.1.5, 2.4.1.6, 2.4.1.7, 2.4.1.8, 2.4.1.9, 2.4.1.10, 2.4.2.1, 2.4.2.2, 2.4.2.3, 2.4.2.4, 2.4.2.5, 2.4.2.6, 2.4.2.7, 2.4.2.8, 2.4.2.9, 2.4.2.10, 2.4.3.1, 2.4.3.2, 2.4.3.3, 2.4.3.4, 2.4.3.5, 2.4.3.6, 2.4.3.7, 2.4.3.8, 2.4.3.9, 2.4.3.10, 2.4.4.1, 2.4.4.2, 2.4.4.3, 2.4.4.4, 2.4.4.5, 2.4.4.6, 2.4.4.7, 2.4.4.8, 2.4.4.9, 2.4.4.10, 2.4.5.1, 2.4.5.2, 2.4.5.3, 2.4.5.4, 2.4.5.5, 2.4.5.6, 2.4.5.7, 2.4.5.8, 2.4.5.9, 2.4.5.10, 2.4.6.1, 2.4.6.2, 2.4.6.3, 2.4.6.4, 2.4.6.5, 2.4.6.6, 2.4.6.7, 2.4.6.8, 2.4.6.9, 2.4.6.10, 2.4.7.1, 2.4.7.2, 2.4.7.3, 2.4.7.4, 2.4.7.5, 2.4.7.6, 2.4.7.7, 2.4.7.8, 2.4.7.9, 2.4.7.10, 2.4.8.1, 2.4.8.2, 2.4.8.3, 2.4.8.4, 2.4.8.5, 2.4.8.6, 2.4.8.7, 2.4.8.8, 2.4.8.9, 2.4.8.10, 2.4.9.1, 2.4.9.2, 2.4.9.3, 2.4.9.4, 2.4.9.5, 2.4.9.6, 2.4.9.7, 2.4.9.8, 2.4.9.9, 2.4.9.10, 2.4.10.1, 2.4.10.2, 2.4.10.3, 2.4.10.4, 2.4.10.5, 2.4.10.6, 2.4.10.7, 2.4.10.8, 2.4.10.9, 2.4.10.10, 2.5.1.1, 2.5.1.2, 2.5.1.3, 2.5.1.4, 2.5.1.5, 2.5.1.6, 2.5.1.7, 2.5.1.8, 2.5.1.9, 2.5.1.10, 2.5.2.1, 2.5.2.2, 2.5.2.3, 2.5.2.4, 2.5.2.5, 2.5.2.6, 2.5.2.7, 2.5.2.8, 2.5.2.9, 2.5.2.10, 2.5.3.1, 2.5.3.2, 2.5.3.3, 2.5.3.4, 2.5.3.5, 2.5.3.6, 2.5.3.7, 2.5.3.8, 2.5.3.9, 2.5.3.10, 2.5.4.1, 2.5.4.2, 2.5.4.3, 2.5.4.4, 2.5.4.5, 2.5.4.6, 2.5.4.7, 2.5.4.8, 2.5.4.9, 2.5.4.10, 2.5.5.1, 2.5.5.2, 2.5.5.3, 2.5.5.4, 2.5.5.5, 2.5.5.6, 2.5.5.7, 2.5.5.8, 2.5.5.9, 2.5.5.10, 2.5.6.1, 2.5.6.2, 2.5.6.3, 2.5.6.4, 2.5.6.5, 2.5.6.6, 2.5.6.7, 2.5.6.8, 2.5.6.9, 2.5.6.10, 2.5.7.1, 2.5.7.2, 2.5.7.3, 2.5.7.4, 2.5.7.5, 2.5.7.6, 2.5.7.7, 2.5.7.8, 2.5.7.9, 2.5.7.10, 2.5.8.1, 2.5.8.2, 2.5.8.3, 2.5.8.4, 2.5.8.5, 2.5.8.6, 2.5.8.7, 2.5.8.8, 2.5.8.9, 2.5.8.10, 2.5.9.1, 2.5.9.2, 2.5.9.3, 2.5.9.4, 2.5.9.5, 2.5.9.6, 2.5.9.7, 2.5.9.8, 2.5.9.9, 2.5.9.10, 2.5.10.1, 2.5.10.2, 2.5.10.3, 2.5.10.4, 2.5.10.5, 2.5.10.6, 2.5.10.7, 2.5.10.8, 2.5.10.9, 2.5.10.10, 2.6.1.1, 2.6.1.2, 2.6.1.3, 2.6.1.4, 2.6.1.5, 2.6.1.6, 2.6.1.7, 2.6.1.8, 2.6.1.9, 2.6.1.10, 2.6.2.1, 2.6.2.2, 2.6.2.3, 2.6.2.4, 2.6.2.5, 2.6.2.6, 2.6.2.7, 2.6.2.8, 2.6.2.9, 2.6.2.10, 2.6.3.1, 2.6.3.2, 2.6.3.3, 2.6.3.4, 2.6.3.5, 2.6.3.6, 2.6.3.7, 2.6.3.8, 2.6.3.9, 2.6.3.10, 2.6.4.1, 2.6.4.2, 2.6.4.3, 2.6.4.4, 2.6.4.5, 2.6.4.6, 2.6.4.7, 2.6.4.8, 2.6.4.9, 2.6.4.10, 2.6.5.1, 2.6.5.2, 2.6.5.3, 2.6.5.4, 2.6.5.5, 2.6.5.6, 2.6.5.7, 2.6.5.8, 2.6.5.9, 2.6.5.10, 2.6.6.1, 2.6.6.2, 2.6.6.3, 2.6.6.4, 2.6.6.5, 2.6.6.6, 2.6.6.7, 2.6.6.8, 2.6.6.9, 2.6.6.10, 2.6.7.1, 2.6.7.2, 2.6.7.3, 2.6.7.4, 2.6.7.5, 2.6.7.6, 2.6.7.7, 2.6.7.8, 2.6.7.9, 2.6.7.10, 2.6.8.1, 2.6.8.2, 2.6.8.3, 2.6.8.4, 2.6.8.5, 2.6.8.6, 2.6.8.7, 2.6.8.8, 2.6.8.9, 2.6.8.10, 2.6.9.1, 2.6.9.2, 2.6.9.3, 2.6.9.4, 2.6.9.5, 2.6.9.6, 2.6.9.7, 2.6.9.8, 2.6.9.9, 2.6.9.10, 2.6.10.1, 2.6.10.2, 2.6.10.3, 2.6.10.4, 2.6.10.5, 2.6.10.6, 2.6.10.7, 2.6.10.8, 2.6.10.9, 2.6.10.10, 2.7.1.1, 2.7.1.2, 2.7.1.3, 2.7.1.4, 2.7.1.5, 2.7.1.6, 2.7.1.7, 2.7.1.8, 2.7.1.9, 2.7.1.10, 2.7.2.1, 2.7.2.2, 2.7.2.3, 2.7.2.4, 2.7.2.5, 2.7.2.6, 2.7.2.7, 2.7.2.8, 2.7.2.9, 2.7.2.10, 2.7.3.1, 2.7.3.2, 2.7.3.3, 2.7.3.4, 2.7.3.5, 2.7.3.6, 2.7.3.7, 2.7.3.8, 2.7.3.9, 2.7.3.10, 2.7.4.1, 2.7.4.2, 2.7.4.3, 2.7.4.4, 2.7.4.5, 2.7.4.6, 2.7.4.7, 2.7.4.8, 2.7.4.9, 2.7.4.10, 2.7.5.1, 2.7.5.2, 2.7.5.3, 2.7.5.4, 2.7.5.5, 2.7.5.6, 2.7.5.7, 2.7.5.8, 2.7.5.9, 2.7.5.10, 2.7.6.1, 2.7.6.2, 2.7.6.3, 2.7.6.4, 2.7.6.5, 2.7.6.6, 2.7.6.7, 2.7.6.8, 2.7.6.9, 2.7.6.10, 2.7.7.1, 2.7.7.2, 2.7.7.3, 2.7.7.4, 2.7.7.5, 2.7.7.6, 2.7.7.7, 2.7.7.8, 2.7.7.9, 2.7.7.10, 2.7.8.1, 2.7.8.2, 2.7.8.3, 2.7.8.4, 2.7.8.5, 2.7.8.6, 2.7.8.7, 2.7.8.8, 2.7.8.9, 2.7.8.10, 2.7.9.1, 2.7.9.2, 2.7.9.3, 2.7.9.4, 2.7.9.5, 2.7.9.6, 2.7.9.7, 2.7.9.8, 2.7.9.9, 2.7.9.10, 2.7.10.1, 2.7.10.2, 2.7.10.3, 2.7.10.4, 2.7.10.5, 2.7.10.6, 2.7.10.7, 2.7.10.8, 2.7.10.9, 2.7.10.10, 2.8.1.1, 2.8.1.2, 2.8.1.3, 2.8.1.4, 2.8.1.5, 2.8.1.6, 2.8.1.7, 2.8.1.8, 2.8.1.9, 2.8.1.10, 2.8.2.1, 2.8.2.2, 2.8.2.3, 2.8.2.4, 2.8.2.5, 2.8.2.6, 2.8.2.7, 2.8.2.8, 2.8.2.9, 2.8.2.10, 2.8.3.1, 2.8.3.2, 2.8.3.3, 2.8.3.4, 2.8.3.5, 2.8.3.6, 2.8.3.7, 2.8.3.8, 2.8.3.9, 2.8.3.10, 2.8.4.1, 2.8.4.2, 2.8.4.3, 2.8.4.4, 2.8.4.5, 2.8.4.6, 2.8.4.7, 2.8.4.8, 2.8.4.9, 2.8.4.10, 2.8.5.1, 2.8.5.2, 2.8.5.3, 2.8.5.4, 2.8.5.5, 2.8.5.6, 2.8.5.7, 2.8.5.8, 2.8.5.9, 2.8.5.10, 2.8.6.1, 2.8.6.2, 2.8.6.3, 2.8.6.4, 2.8.6.5, 2.8.6.6, 2.8.6.7, 2.8.6.8, 2.8.6.9, 2.8.6.10, 2.8.7.1, 2.8.7.2, 2.8.7.3, 2.8.7.4, 2.8.7.5, 2.8.7.6, 2.8.7.7, 2.8.7.8, 2.8.7.9, 2.8.7.10, 2.8.8.1, 2.8.8.2, 2.8.8.3, 2.8.8.4, 2.8.8.5, 2.8.8.6, 2.8.8.7, 2.8.8.8, 2.8.8.9, 2.8.8.10, 2.8.9.1, 2.8.9.2, 2.8.9.3, 2.8.9.4, 2.8.9.5, 2.8.9.6, 2.8.9.7, 2.8.9.8, 2.8.9.9, 2.8.9.10, 2.8.10.1, 2.8.10.2, 2.8.10.3, 2.8.10.4, 2.8.10.5, 2.8.10.6, 2.8.10.7, 2.8.10.8, 2.8.10.9, 2.8.10.10, 2.9.1.1, 2.9.1.2, 2.9.1.3, 2.9.1.4, 2.9.1.5, 2.9.1.6, 2.9.1.7, 2.9.1.8, 2.9.1.9, 2.9.1.10, 2.9.2.1, 2.9.2.2, 2.9.2.3, 2.9.2.4, 2.9.2.5, 2.9.2.6, 2.9.2.7, 2.9.2.8, 2.9.2.9, 2.9.2.10, 2.9.3.1, 2.9.3.2, 2.9.3.3, 2.9.3.4, 2.9.3.5, 2.9.3.6, 2.9.3.7, 2.9.3.8, 2.9.3.9, 2.9.3.10, 2.9.4.1, 2.9.4.2, 2.9.4.3, 2.9.4.4, 2.9.4.5, 2.9.4.6, 2.9.4.7, 2.9.4.8, 2.9.4.9, 2.9.4.10, 2.9.5.1, 2.9.5.2, 2.9.5.3, 2.9.5.4, 2.9.5.5, 2.9.5.6, 2.9.5.7, 2.9.5.8, 2.9.5.9, 2.9.5.10, 2.9.6.1, 2.9.6.2, 2.9.6.3, 2.9.6.4, 2.9.6.5, 2.9.6.6, 2.9.6.7, 2.9.6.8, 2.9.6.9, 2.9.6.10, 2.9.7.1, 2.9.7.2, 2.9.7.3, 2.9.7.4, 2.9.7.5, 2.9.7.6, 2.9.7.7, 2.9.7.8, 2.9.7.9, 2.9.7.10, 2.9.8.1, 2.9.8.2, 2.9.8.3, 2.9.8.4, 2.9.8.5, 2.9.8.6, 2.9.8.7, 2.9.8.8, 2.9.8.9, 2.9.8.10, 2.9.9.1, 2.9.9.2, 2.9.9.3, 2.9.9.4, 2.9.9.5, 2.9.9.6, 2.9.9.7, 2.9.9.8, 2.9.9.9, 2.9.9.10, 2.9.10.1, 2.9.10.2, 2.9.10.3, 2.9.10.4, 2.9.10.5, 2.9.10.6, 2.9.10.7, 2.9.10.8, 2.9.10.9, 2.9.10.10, 2.10.1.1, 2.10.1.2, 2.10.1.3, 2.10.1.4, 2.10.1.5, 2.10.1.6, 2.10.1.7, 2.10.1.8, 2.10.1.9, 2.10.1.10, 2.10.2.1, 2.10.2.2, 2.10.2.3, 2.10.2.4, 2.10.2.5, 2.10.2.6, 2.10.2.7, 2.10.2.8, 2.10.2.9, 2.10.2.10, 2.10.3.1, 2.10.3.2, 2.10.3.3, 2.10.3.4, 2.10.3.5, 2.10.3.6, 2.10.3.7, 2.10.3.8, 2.10.3.9, 2.10.3.10, 2.10.4.1, 2.10.4.2, 2.10.4.3, 2.10.4.4, 2.10.4.5, 2.10.4.6, 2.10.4.7, 2.10.4.8, 2.10.4.9, TABLE B-continued 2.10.4.10, 2.10.5.1, 2.10.5.2, 2.10.5.3, 2.10.5.4, 2.10.5.5, 2.10.5.6, 2.10.5.7, 2.10.5.8, 2.10.5.9, 2.10.5.10, 2.10.6.1, 2.10.6.2, 2.10.6.3, 2.10.6.4, 2.10.6.5, 2.10.6.6, 2.10.6.7, 2.10.6.8, 2.10.6.9, 2.10.6.10, 2.10.7.1, 2.10.7.2, 2.10.7.3, 2.10.7.4, 2.10.7.5, 2.10.7.6, 2.10.7.7, 2.10.7.8, 2.10.7.9, 2.10.7.10, 2.10.8.1, 2.10.8.2, 2.10.8.3, 2.10.8.4, 2.10.8.5, 2.10.8.6, 2.10.8.7, 2.10.8.8, 2.10.8.9, 2.10.8.10, 2.10.9.1, 2.10.9.2, 2.10.9.3, 2.10.9.4, 2.10.9.5, 2.10.9.6, 2.10.9.7, 2.10.9.8, 2.10.9.9, 2.10.9.10, 2.10.10.1, 2.10.10.2, 2.10.10.3, 2.10.10.4, 2.10.10.5, 2.10.10.6, 2.10.10.7, 2.10.10.8, 2.10.10.9, 2.10.10.10, 3.1.1.1, 3.1.1.2, 3.1.1.3, 3.1.1.4, 3.1.1.5, 3.1.1.6, 3.1.1.7, 3.1.1.8, 3.1.1.9, 3.1.1.10, 3.1.2.1, 3.1.2.2, 3.1.2.3, 3.1.2.4, 3.1.2.5, 3.1.2.6, 3.1.2.7, 3.1.2.8, 3.1.2.9, 3.1.2.10, 3.1.3.1, 3.1.3.2, 3.1.3.3, 3.1.3.4, 3.1.3.5, 3.1.3.6, 3.1.3.7, 3.1.3.8, 3.1.3.9, 3.1.3.10, 3.1.4.1, 3.1.4.2, 3.1.4.3, 3.1.4.4, 3.1.4.5, 3.1.4.6, 3.1.4.7, 3.1.4.8, 3.1.4.9, 3.1.4.10, 3.1.5.1, 3.1.5.2, 3.1.5.3, 3.1.5.4, 3.1.5.5, 3.1.5.6, 3.1.5.7, 3.1.5.8, 3.1.5.9, 3.1.5.10, 3.1.6.1, 3.1.6.2, 3.1.6.3, 3.1.6.4, 3.1.6.5, 3.1.6.6, 3.1.6.7, 3.1.6.8, 3.1.6.9, 3.1.6.10, 3.1.7.1, 3.1.7.2, 3.1.7.3, 3.1.7.4, 3.1.7.5, 3.1.7.6, 3.1.7.7, 3.1.7.8, 3.1.7.9, 3.1.7.10, 3.1.8.1, 3.1.8.2, 3.1.8.3, 3.1.8.4, 3.1.8.5, 3.1.8.6, 3.1.8.7, 3.1.8.8, 3.1.8.9, 3.1.8.10, 3.1.9.1, 3.1.9.2, 3.1.9.3, 3.1.9.4, 3.1.9.5, 3.1.9.6, 3.1.9.7, 3.1.9.8, 3.1.9.9, 3.1.9.10, 3.1.10.1, 3.1.10.2, 3.1.10.3, 3.1.10.4, 3.1.10.5, 3.1.10.6, 3.1.10.7, 3.1.10.8, 3.1.10.9, 3.1.10.10, 3.2.1.1, 3.2.1.2, 3.2.1.3, 3.2.1.4, 3.2.1.5, 3.2.1.6, 3.2.1.7, 3.2.1.8, 3.2.1.9, 3.2.1.10, 3.2.2.1, 3.2.2.2, 3.2.2.3, 3.2.2.4, 3.2.2.5, 3.2.2.6, 3.2.2.7, 3.2.2.8, 3.2.2.9, 3.2.2.10, 3.2.3.1, 3.2.3.2, 3.2.3.3, 3.2.3.4, 3.2.3.5, 3.2.3.6, 3.2.3.7, 3.2.3.8, 3.2.3.9, 3.2.3.10, 3.2.4.1, 3.2.4.2, 3.2.4.3, 3.2.4.4, 3.2.4.5, 3.2.4.6, 3.2.4.7, 3.2.4.8, 3.2.4.9, 3.2.4.10, 3.2.5.1, 3.2.5.2, 3.2.5.3, 3.2.5.4, 3.2.5.5, 3.2.5.6, 3.2.5.7, 3.2.5.8, 3.2.5.9, 3.2.5.10, 3.2.6.1, 3.2.6.2, 3.2.6.3, 3.2.6.4, 3.2.6.5, 3.2.6.6, 3.2.6.7, 3.2.6.8, 3.2.6.9, 3.2.6.10, 3.2.7.1, 3.2.7.2, 3.2.7.3, 3.2.7.4, 3.2.7.5, 3.2.7.6, 3.2.7.7, 3.2.7.8, 3.2.7.9, 3.2.7.10, 3.2.8.1, 3.2.8.2, 3.2.8.3, 3.2.8.4, 3.2.8.5, 3.2.8.6, 3.2.8.7, 3.2.8.8, 3.2.8.9, 3.2.8.10, 3.2.9.1, 3.2.9.2, 3.2.9.3, 3.2.9.4, 3.2.9.5, 3.2.9.6, 3.2.9.7, 3.2.9.8, 3.2.9.9, 3.2.9.10, 3.2.10.1, 3.2.10.2, 3.2.10.3, 3.2.10.4, 3.2.10.5, 3.2.10.6, 3.2.10.7, 3.2.10.8, 3.2.10.9, 3.2.10.10, 3.3.1.1, 3.3.1.2, 3.3.1.3, 3.3.1.4, 3.3.1.5, 3.3.1.6, 3.3.1.7, 3.3.1.8, 3.3.1.9, 3.3.1.10, 3.3.2.1, 3.3.2.2, 3.3.2.3, 3.3.2.4, 3.3.2.5, 3.3.2.6, 3.3.2.7, 3.3.2.8, 3.3.2.9, 3.3.2.10, 3.3.3.1, 3.3.3.2, 3.3.3.3, 3.3.3.4, 3.3.3.5, 3.3.3.6, 3.3.3.7, 3.3.3.8, 3.3.3.9, 3.3.3.10, 3.3.4.1, 3.3.4.2, 3.3.4.3, 3.3.4.4, 3.3.4.5, 3.3.4.6, 3.3.4.7, 3.3.4.8, 3.3.4.9, 3.3.4.10, 3.3.5.1, 3.3.5.2, 3.3.5.3, 3.3.5.4, 3.3.5.5, 3.3.5.6, 3.3.5.7, 3.3.5.8, 3.3.5.9, 3.3.5.10, 3.3.6.1, 3.3.6.2, 3.3.6.3, 3.3.6.4, 3.3.6.5, 3.3.6.6, 3.3.6.7, 3.3.6.8, 3.3.6.9, 3.3.6.10, 3.3.7.1, 3.3.7.2, 3.3.7.3, 3.3.7.4, 3.3.7.5, 3.3.7.6, 3.3.7.7, 3.3.7.8, 3.3.7.9, 3.3.7.10, 3.3.8.1, 3.3.8.2, 3.3.8.3, 3.3.8.4, 3.3.8.5, 3.3.8.6, 3.3.8.7, 3.3.8.8, 3.3.8.9, 3.3.8.10, 3.3.9.1, 3.3.9.2, 3.3.9.3, 3.3.9.4, 3.3.9.5, 3.3.9.6, 3.3.9.7, 3.3.9.8, 3.3.9.9, 3.3.9.10, 3.3.10.1, 3.3.10.2, 3.3.10.3, 3.3.10.4, 3.3.10.5, 3.3.10.6, 3.3.10.7, 3.3.10.8, 3.3.10.9, 3.3.10.10, 3.4.1.1, 3.4.1.2, 3.4.1.3, 3.4.1.4, 3.4.1.5, 3.4.1.6, 3.4.1.7, 3.4.1.8, 3.4.1.9, 3.4.1.10, 3.4.2.1, 3.4.2.2, 3.4.2.3, 3.4.2.4, 3.4.2.5, 3.4.2.6, 3.4.2.7, 3.4.2.8, 3.4.2.9, 3.4.2.10, 3.4.3.1, 3.4.3.2, 3.4.3.3, 3.4.3.4, 3.4.3.5, 3.4.3.6, 3.4.3.7, 3.4.3.8, 3.4.3.9, 3.4.3.10, 3.4.4.1, 3.4.4.2, 3.4.4.3, 3.4.4.4, 3.4.4.5, 3.4.4.6, 3.4.4.7, 3.4.4.8, 3.4.4.9, 3.4.4.10, 3.4.5.1, 3.4.5.2, 3.4.5.3, 3.4.5.4, 3.4.5.5, 3.4.5.6, 3.4.5.7, 3.4.5.8, 3.4.5.9, 3.4.5.10, 3.4.6.1, 3.4.6.2, 3.4.6.3, 3.4.6.4, 3.4.6.5, 3.4.6.6, 3.4.6.7, 3.4.6.8, 3.4.6.9, 3.4.6.10, 3.4.7.1, 3.4.7.2, 3.4.7.3, 3.4.7.4, 3.4.7.5, 3.4.7.6, 3.4.7.7, 3.4.7.8, 3.4.7.9, 3.4.7.10, 3.4.8.1, 3.4.8.2, 3.4.8.3, 3.4.8.4, 3.4.8.5, 3.4.8.6, 3.4.8.7, 3.4.8.8, 3.4.8.9, 3.4.8.10, 3.4.9.1, 3.4.9.2, 3.4.9.3, 3.4.9.4, 3.4.9.5, 3.4.9.6, 3.4.9.7, 3.4.9.8, 3.4.9.9, 3.4.9.10, 3.4.10.1, 3.4.10.2, 3.4.10.3, 3.4.10.4, 3.4.10.5, 3.4.10.6, 3.4.10.7, 3.4.10.8, 3.4.10.9, 3.4.10.10, 3.5.1.1, 3.5.1.2, 3.5.1.3, 3.5.1.4, 3.5.1.5, 3.5.1.6, 3.5.1.7, 3.5.1.8, 3.5.1.9, 3.5.1.10, 3.5.2.1, 3.5.2.2, 3.5.2.3, 3.5.2.4, 3.5.2.5, 3.5.2.6, 3.5.2.7, 3.5.2.8, 3.5.2.9, 3.5.2.10, 3.5.3.1, 3.5.3.2, 3.5.3.3, 3.5.3.4, 3.5.3.5, 3.5.3.6, 3.5.3.7, 3.5.3.8, 3.5.3.9, 3.5.3.10, 3.5.4.1, 3.5.4.2, 3.5.4.3, 3.5.4.4, 3.5.4.5, 3.5.4.6, 3.5.4.7, 3.5.4.8, 3.5.4.9, 3.5.4.10, 3.5.5.1, 3.5.5.2, 3.5.5.3, 3.5.5.4, 3.5.5.5, 3.5.5.6, 3.5.5.7, 3.5.5.8, 3.5.5.9, 3.5.5.10, 3.5.6.1, 3.5.6.2, 3.5.6.3, 3.5.6.4, 3.5.6.5, 3.5.6.6, 3.5.6.7, 3.5.6.8, 3.5.6.9, 3.5.6.10, 3.5.7.1, 3.5.7.2, 3.5.7.3, 3.5.7.4, 3.5.7.5, 3.5.7.6, 3.5.7.7, 3.5.7.8, 3.5.7.9, 3.5.7.10, 3.5.8.1, 3.5.8.2, 3.5.8.3, 3.5.8.4, 3.5.8.5, 3.5.8.6, 3.5.8.7, 3.5.8.8, 3.5.8.9, 3.5.8.10, 3.5.9.1, 3.5.9.2, 3.5.9.3, 3.5.9.4, 3.5.9.5, 3.5.9.6, 3.5.9.7, 3.5.9.8, 3.5.9.9, 3.5.9.10, 3.5.10.1, 3.5.10.2, 3.5.10.3, 3.5.10.4, 3.5.10.5, 3.5.10.6, 3.5.10.7, 3.5.10.8, 3.5.10.9, 3.5.10.10, 3.6.1.1, 3.6.1.2, 3.6.1.3, 3.6.1.4, 3.6.1.5, 3.6.1.6, 3.6.1.7, 3.6.1.8, 3.6.1.9, 3.6.1.10, 3.6.2.1, 3.6.2.2, 3.6.2.3, 3.6.2.4, 3.6.2.5, 3.6.2.6, 3.6.2.7, 3.6.2.8, 3.6.2.9, 3.6.2.10, 3.6.3.1, 3.6.3.2, 3.6.3.3, 3.6.3.4, 3.6.3.5, 3.6.3.6, 3.6.3.7, 3.6.3.8, 3.6.3.9, 3.6.3.10, 3.6.4.1, 3.6.4.2, 3.6.4.3, 3.6.4.4, 3.6.4.5, 3.6.4.6, 3.6.4.7, 3.6.4.8, 3.6.4.9, 3.6.4.10, 3.6.5.1, 3.6.5.2, 3.6.5.3, 3.6.5.4, 3.6.5.5, 3.6.5.6, 3.6.5.7, 3.6.5.8, 3.6.5.9, 3.6.5.10, 3.6.6.1, 3.6.6.2, 3.6.6.3, 3.6.6.4, 3.6.6.5, 3.6.6.6, 3.6.6.7, 3.6.6.8, 3.6.6.9, 3.6.6.10, 3.6.7.1, 3.6.7.2, 3.6.7.3, 3.6.7.4, 3.6.7.5, 3.6.7.6, 3.6.7.7, 3.6.7.8, 3.6.7.9, 3.6.7.10, 3.6.8.1, 3.6.8.2, 3.6.8.3, 3.6.8.4, 3.6.8.5, 3.6.8.6, 3.6.8.7, 3.6.8.8, 3.6.8.9, 3.6.8.10, 3.6.9.1, 3.6.9.2, 3.6.9.3, 3.6.9.4, 3.6.9.5, 3.6.9.6, 3.6.9.7, 3.6.9.8, 3.6.9.9, 3.6.9.10, 3.6.10.1, 3.6.10.2, 3.6.10.3, 3.6.10.4, 3.6.10.5, 3.6.10.6, 3.6.10.7, 3.6.10.8, 3.6.10.9, 3.6.10.10, 3.7.1.1, 3.7.1.2, 3.7.1.3, 3.7.1.4, 3.7.1.5, 3.7.1.6, 3.7.1.7, 3.7.1.8, 3.7.1.9, 3.7.1.10, 3.7.2.1, 3.7.2.2, 3.7.2.3, 3.7.2.4, 3.7.2.5, 3.7.2.6, 3.7.2.7, 3.7.2.8, 3.7.2.9, 3.7.2.10, 3.7.3.1, 3.7.3.2, 3.7.3.3, 3.7.3.4, 3.7.3.5, 3.7.3.6, 3.7.3.7, 3.7.3.8, 3.7.3.9, 3.7.3.10, 3.7.4.1, 3.7.4.2, 3.7.4.3, 3.7.4.4, 3.7.4.5, 3.7.4.6, 3.7.4.7, 3.7.4.8, 3.7.4.9, 3.7.4.10, 3.7.5.1, 3.7.5.2, 3.7.5.3, 3.7.5.4, 3.7.5.5, 3.7.5.6, 3.7.5.7, 3.7.5.8, 3.7.5.9, 3.7.5.10, 3.7.6.1, 3.7.6.2, 3.7.6.3, 3.7.6.4, 3.7.6.5, 3.7.6.6, 3.7.6.7, 3.7.6.8, 3.7.6.9, 3.7.6.10, 3.7.7.1, 3.7.7.2, 3.7.7.3, 3.7.7.4, 3.7.7.5, 3.7.7.6, 3.7.7.7, 3.7.7.8, 3.7.7.9, 3.7.7.10, 3.7.8.1, 3.7.8.2, 3.7.8.3, 3.7.8.4, 3.7.8.5, 3.7.8.6, 3.7.8.7, 3.7.8.8, 3.7.8.9, 3.7.8.10, 3.7.9.1, 3.7.9.2, 3.7.9.3, 3.7.9.4, 3.7.9.5, 3.7.9.6, 3.7.9.7, 3.7.9.8, 3.7.9.9, 3.7.9.10, 3.7.10.1, 3.7.10.2, 3.7.10.3, 3.7.10.4, 3.7.10.5, 3.7.10.6, 3.7.10.7, 3.7.10.8, 3.7.10.9, 3.7.10.10, 3.8.1.1, 3.8.1.2, 3.8.1.3, 3.8.1.4, 3.8.1.5, 3.8.1.6, 3.8.1.7, 3.8.1.8, 3.8.1.9, 3.8.1.10, 3.8.2.1, 3.8.2.2, 3.8.2.3, 3.8.2.4, 3.8.2.5, 3.8.2.6, 3.8.2.7, 3.8.2.8, 3.8.2.9, 3.8.2.10, 3.8.3.1, 3.8.3.2, 3.8.3.3, 3.8.3.4, 3.8.3.5, 3.8.3.6, 3.8.3.7, 3.8.3.8, 3.8.3.9, 3.8.3.10, 3.8.4.1, 3.8.4.2, 3.8.4.3, 3.8.4.4, 3.8.4.5, 3.8.4.6, 3.8.4.7, 3.8.4.8, 3.8.4.9, 3.8.4.10, 3.8.5.1, 3.8.5.2, 3.8.5.3, 3.8.5.4, 3.8.5.5, 3.8.5.6, 3.8.5.7, 3.8.5.8, 3.8.5.9, 3.8.5.10, 3.8.6.1, 3.8.6.2, 3.8.6.3, 3.8.6.4, 3.8.6.5, 3.8.6.6, 3.8.6.7, 3.8.6.8, 3.8.6.9, 3.8.6.10, 3.8.7.1, 3.8.7.2, 3.8.7.3, 3.8.7.4, 3.8.7.5, 3.8.7.6, 3.8.7.7, 3.8.7.8, 3.8.7.9, 3.8.7.10, 3.8.8.1, 3.8.8.2, 3.8.8.3, 3.8.8.4, 3.8.8.5, 3.8.8.6, 3.8.8.7, 3.8.8.8, 3.8.8.9, 3.8.8.10, 3.8.9.1, 3.8.9.2, 3.8.9.3, 3.8.9.4, 3.8.9.5, 3.8.9.6, 3.8.9.7, 3.8.9.8, 3.8.9.9, 3.8.9.10, 3.8.10.1, 3.8.10.2, 3.8.10.3, 3.8.10.4, 3.8.10.5, 3.8.10.6, 3.8.10.7, 3.8.10.8, 3.8.10.9, 3.8.10.10, 3.9.1.1, 3.9.1.2, 3.9.1.3, 3.9.1.4, 3.9.1.5, 3.9.1.6, 3.9.1.7, 3.9.1.8, 3.9.1.9, 3.9.1.10, 3.9.2.1, 3.9.2.2, 3.9.2.3, 3.9.2.4, 3.9.2.5, 3.9.2.6, 3.9.2.7, 3.9.2.8, 3.9.2.9, 3.9.2.10, 3.9.3.1, 3.9.3.2, 3.9.3.3, 3.9.3.4, 3.9.3.5, 3.9.3.6, 3.9.3.7, 3.9.3.8, 3.9.3.9, 3.9.3.10, 3.9.4.1, 3.9.4.2, 3.9.4.3, 3.9.4.4, 3.9.4.5, 3.9.4.6, 3.9.4.7, 3.9.4.8, 3.9.4.9, 3.9.4.10, 3.9.5.1, 3.9.5.2, 3.9.5.3, 3.9.5.4, 3.9.5.5, 3.9.5.6, 3.9.5.7, 3.9.5.8, 3.9.5.9, 3.9.5.10, 3.9.6.1, 3.9.6.2, 3.9.6.3, 3.9.6.4, 3.9.6.5, 3.9.6.6, 3.9.6.7, 3.9.6.8, 3.9.6.9, 3.9.6.10, 3.9.7.1, 3.9.7.2, 3.9.7.3, 3.9.7.4, 3.9.7.5, 3.9.7.6, 3.9.7.7, 3.9.7.8, 3.9.7.9, 3.9.7.10, 3.9.8.1, TABLE B-continued 3.9.8.2, 3.9.8.3, 3.9.8.4, 3.9.8.5, 3.9.8.6, 3.9.8.7, 3.9.8.8, 3.9.8.9, 3.9.8.10, 3.9.9.1, 3.9.9.2, 3.9.9.3, 3.9.9.4, 3.9.9.5, 3.9.9.6, 3.9.9.7, 3.9.9.8, 3.9.9.9, 3.9.9.10, 3.9.10.1, 3.9.10.2, 3.9.10.3, 3.9.10.4, 3.9.10.5, 3.9.10.6, 3.9.10.7, 3.9.10.8, 3.9.10.9, 3.9.10.10, 3.10.1.1, 3.10.1.2, 3.10.1.3, 3.10.1.4, 3.10.1.5, 3.10.1.6, 3.10.1.7, 3.10.1.8, 3.10.1.9, 3.10.1.10, 3.10.2.1, 3.10.2.2, 3.10.2.3, 3.10.2.4, 3.10.2.5, 3.10.2.6, 3.10.2.7, 3.10.2.8, 3.10.2.9, 3.10.2.10, 3.10.3.1, 3.10.3.2, 3.10.3.3, 3.10.3.4, 3.10.3.5, 3.10.3.6, 3.10.3.7, 3.10.3.8, 3.10.3.9, 3.10.3.10, 3.10.4.1, 3.10.4.2, 3.10.4.3, 3.10.4.4, 3.10.4.5, 3.10.4.6, 3.10.4.7, 3.10.4.8, 3.10.4.9, 3.10.4.10, 3.10.5.1, 3.10.5.2, 3.10.5.3, 3.10.5.4, 3.10.5.5, 3.10.5.6, 3.10.5.7, 3.10.5.8, 3.10.5.9, 3.10.5.10, 3.10.6.1, 3.10.6.2, 3.10.6.3, 3.10.6.4, 3.10.6.5, 3.10.6.6, 3.10.6.7, 3.10.6.8, 3.10.6.9, 3.10.6.10, 3.10.7.1, 3.10.7.2, 3.10.7.3, 3.10.7.4, 3.10.7.5, 3.10.7.6, 3.10.7.7, 3.10.7.8, 3.10.7.9, 3.10.7.10, 3.10.8.1, 3.10.8.2, 3.10.8.3, 3.10.8.4, 3.10.8.5, 3.10.8.6, 3.10.8.7, 3.10.8.8, 3.10.8.9, 3.10.8.10, 3.10.9.1, 3.10.9.2, 3.10.9.3, 3.10.9.4, 3.10.9.5, 3.10.9.6, 3.10.9.7, 3.10.9.8, 3.10.9.9, 3.10.9.10, 3.10.10.1, 3.10.10.2, 3.10.10.3, 3.10.10.4, 3.10.10.5, 3.10.10.6, 3.10.10.7, 3.10.10.8, 3.10.10.9, 3.10.10.10, 4.1.1.1, 4.1.1.2, 4.1.1.3, 4.1.1.4, 4.1.1.5, 4.1.1.6, 4.1.1.7, 4.1.1.8, 4.1.1.9, 4.1.1.10, 4.1.2.1, 4.1.2.2, 4.1.2.3, 4.1.2.4, 4.1.2.5, 4.1.2.6, 4.1.2.7, 4.1.2.8, 4.1.2.9, 4.1.2.10, 4.1.3.1, 4.1.3.2, 4.1.3.3, 4.1.3.4, 4.1.3.5, 4.1.3.6, 4.1.3.7, 4.1.3.8, 4.1.3.9, 4.1.3.10, 4.1.4.1, 4.1.4.2, 4.1.4.3, 4.1.4.4, 4.1.4.5, 4.1.4.6, 4.1.4.7, 4.1.4.8, 4.1.4.9, 4.1.4.10, 4.1.5.1, 4.1.5.2, 4.1.5.3, 4.1.5.4, 4.1.5.5, 4.1.5.6, 4.1.5.7, 4.1.5.8, 4.1.5.9, 4.1.5.10, 4.1.6.1, 4.1.6.2, 4.1.6.3, 4.1.6.4, 4.1.6.5, 4.1.6.6, 4.1.6.7, 4.1.6.8, 4.1.6.9, 4.1.6.10, 4.1.7.1, 4.1.7.2, 4.1.7.3, 4.1.7.4, 4.1.7.5, 4.1.7.6, 4.1.7.7, 4.1.7.8, 4.1.7.9, 4.1.7.10, 4.1.8.1, 4.1.8.2, 4.1.8.3, 4.1.8.4, 4.1.8.5, 4.1.8.6, 4.1.8.7, 4.1.8.8, 4.1.8.9, 4.1.8.10, 4.1.9.1, 4.1.9.2, 4.1.9.3, 4.1.9.4, 4.1.9.5, 4.1.9.6, 4.1.9.7, 4.1.9.8, 4.1.9.9, 4.1.9.10, 4.1.10.1, 4.1.10.2, 4.1.10.3, 4.1.10.4, 4.1.10.5, 4.1.10.6, 4.1.10.7, 4.1.10.8, 4.1.10.9, 4.1.10.10, 4.2.1.1, 4.2.1.2, 4.2.1.3, 4.2.1.4, 4.2.1.5, 4.2.1.6, 4.2.1.7, 4.2.1.8, 4.2.1.9, 4.2.1.10, 4.2.2.1, 4.2.2.2, 4.2.2.3, 4.2.2.4, 4.2.2.5, 4.2.2.6, 4.2.2.7, 4.2.2.8, 4.2.2.9, 4.2.2.10, 4.2.3.1, 4.2.3.2, 4.2.3.3, 4.2.3.4, 4.2.3.5, 4.2.3.6, 4.2.3.7, 4.2.3.8, 4.2.3.9, 4.2.3.10, 4.2.4.1, 4.2.4.2, 4.2.4.3, 4.2.4.4, 4.2.4.5, 4.2.4.6, 4.2.4.7, 4.2.4.8, 4.2.4.9, 4.2.4.10, 4.2.5.1, 4.2.5.2, 4.2.5.3, 4.2.5.4, 4.2.5.5, 4.2.5.6, 4.2.5.7, 4.2.5.8, 4.2.5.9, 4.2.5.10, 4.2.6.1, 4.2.6.2, 4.2.6.3, 4.2.6.4, 4.2.6.5, 4.2.6.6, 4.2.6.7, 4.2.6.8, 4.2.6.9, 4.2.6.10, 4.2.7.1, 4.2.7.2, 4.2.7.3, 4.2.7.4, 4.2.7.5, 4.2.7.6, 4.2.7.7, 4.2.7.8, 4.2.7.9, 4.2.7.10, 4.2.8.1, 4.2.8.2, 4.2.8.3, 4.2.8.4, 4.2.8.5, 4.2.8.6, 4.2.8.7, 4.2.8.8, 4.2.8.9, 4.2.8.10, 4.2.9.1, 4.2.9.2, 4.2.9.3, 4.2.9.4, 4.2.9.5, 4.2.9.6, 4.2.9.7, 4.2.9.8, 4.2.9.9, 4.2.9.10, 4.2.10.1, 4.2.10.2, 4.2.10.3, 4.2.10.4, 4.2.10.5, 4.2.10.6, 4.2.10.7, 4.2.10.8, 4.2.10.9, 4.2.10.10, 4.3.1.1, 4.3.1.2, 4.3.1.3, 4.3.1.4, 4.3.1.5, 4.3.1.6, 4.3.1.7, 4.3.1.8, 4.3.1.9, 4.3.1.10, 4.3.2.1, 4.3.2.2, 4.3.2.3, 4.3.2.4, 4.3.2.5, 4.3.2.6, 4.3.2.7, 4.3.2.8, 4.3.2.9, 4.3.2.10, 4.3.3.1, 4.3.3.2, 4.3.3.3, 4.3.3.4, 4.3.3.5, 4.3.3.6, 4.3.3.7, 4.3.3.8, 4.3.3.9, 4.3.3.10, 4.3.4.1, 4.3.4.2, 4.3.4.3, 4.3.4.4, 4.3.4.5, 4.3.4.6, 4.3.4.7, 4.3.4.8, 4.3.4.9, 4.3.4.10, 4.3.5.1, 4.3.5.2, 4.3.5.3, 4.3.5.4, 4.3.5.5, 4.3.5.6, 4.3.5.7, 4.3.5.8, 4.3.5.9, 4.3.5.10, 4.3.6.1, 4.3.6.2, 4.3.6.3, 4.3.6.4, 4.3.6.5, 4.3.6.6, 4.3.6.7, 4.3.6.8, 4.3.6.9, 4.3.6.10, 4.3.7.1, 4.3.7.2, 4.3.7.3, 4.3.7.4, 4.3.7.5, 4.3.7.6, 4.3.7.7, 4.3.7.8, 4.3.7.9, 4.3.7.10, 4.3.8.1, 4.3.8.2, 4.3.8.3, 4.3.8.4, 4.3.8.5, 4.3.8.6, 4.3.8.7, 4.3.8.8, 4.3.8.9, 4.3.8.10, 4.3.9.1, 4.3.9.2, 4.3.9.3, 4.3.9.4, 4.3.9.5, 4.3.9.6, 4.3.9.7, 4.3.9.8, 4.3.9.9, 4.3.9.10, 4.3.10.1, 4.3.10.2, 4.3.10.3, 4.3.10.4, 4.3.10.5, 4.3.10.6, 4.3.10.7, 4.3.10.8, 4.3.10.9, 4.3.10.10, 4.4.1.1, 4.4.1.2, 4.4.1.3, 4.4.1.4, 4.4.1.5, 4.4.1.6, 4.4.1.7, 4.4.1.8, 4.4.1.9, 4.4.1.10, 4.4.2.1, 4.4.2.2, 4.4.2.3, 4.4.2.4, 4.4.2.5, 4.4.2.6, 4.4.2.7, 4.4.2.8, 4.4.2.9, 4.4.2.10, 4.4.3.1, 4.4.3.2, 4.4.3.3, 4.4.3.4, 4.4.3.5, 4.4.3.6, 4.4.3.7, 4.4.3.8, 4.4.3.9, 4.4.3.10, 4.4.4.1, 4.4.4.2, 4.4.4.3, 4.4.4.4, 4.4.4.5, 4.4.4.6, 4.4.4.7, 4.4.4.8, 4.4.4.9, 4.4.4.10, 4.4.5.1, 4.4.5.2, 4.4.5.3, 4.4.5.4, 4.4.5.5, 4.4.5.6, 4.4.5.7, 4.4.5.8, 4.4.5.9, 4.4.5.10, 4.4.6.1, 4.4.6.2, 4.4.6.3, 4.4.6.4, 4.4.6.5, 4.4.6.6, 4.4.6.7, 4.4.6.8, 4.4.6.9, 4.4.6.10, 4.4.7.1, 4.4.7.2, 4.4.7.3, 4.4.7.4, 4.4.7.5, 4.4.7.6, 4.4.7.7, 4.4.7.8, 4.4.7.9, 4.4.7.10, 4.4.8.1, 4.4.8.2, 4.4.8.3, 4.4.8.4, 4.4.8.5, 4.4.8.6, 4.4.8.7, 4.4.8.8, 4.4.8.9, 4.4.8.10, 4.4.9.1, 4.4.9.2, 4.4.9.3, 4.4.9.4, 4.4.9.5, 4.4.9.6, 4.4.9.7, 4.4.9.8, 4.4.9.9, 4.4.9.10, 4.4.10.1, 4.4.10.2, 4.4.10.3, 4.4.10.4, 4.4.10.5, 4.4.10.6, 4.4.10.7, 4.4.10.8, 4.4.10.9, 4.4.10.10, 4.5.1.1, 4.5.1.2, 4.5.1.3, 4.5.1.4, 4.5.1.5, 4.5.1.6, 4.5.1.7, 4.5.1.8, 4.5.1.9, 4.5.1.10, 4.5.2.1, 4.5.2.2, 4.5.2.3, 4.5.2.4, 4.5.2.5, 4.5.2.6, 4.5.2.7, 4.5.2.8, 4.5.2.9, 4.5.2.10, 4.5.3.1, 4.5.3.2, 4.5.3.3, 4.5.3.4, 4.5.3.5, 4.5.3.6, 4.5.3.7, 4.5.3.8, 4.5.3.9, 4.5.3.10, 4.5.4.1, 4.5.4.2, 4.5.4.3, 4.5.4.4, 4.5.4.5, 4.5.4.6, 4.5.4.7, 4.5.4.8, 4.5.4.9, 4.5.4.10, 4.5.5.1, 4.5.5.2, 4.5.5.3, 4.5.5.4, 4.5.5.5, 4.5.5.6, 4.5.5.7, 4.5.5.8, 4.5.5.9, 4.5.5.10, 4.5.6.1, 4.5.6.2, 4.5.6.3, 4.5.6.4, 4.5.6.5, 4.5.6.6, 4.5.6.7, 4.5.6.8, 4.5.6.9, 4.5.6.10, 4.5.7.1, 4.5.7.2, 4.5.7.3, 4.5.7.4, 4.5.7.5, 4.5.7.6, 4.5.7.7, 4.5.7.8, 4.5.7.9, 4.5.7.10, 4.5.8.1, 4.5.8.2, 4.5.8.3, 4.5.8.4, 4.5.8.5, 4.5.8.6, 4.5.8.7, 4.5.8.8, 4.5.8.9, 4.5.8.10, 4.5.9.1, 4.5.9.2, 4.5.9.3, 4.5.9.4, 4.5.9.5, 4.5.9.6, 4.5.9.7, 4.5.9.8, 4.5.9.9, 4.5.9.10, 4.5.10.1, 4.5.10.2, 4.5.10.3, 4.5.10.4, 4.5.10.5, 4.5.10.6, 4.5.10.7, 4.5.10.8, 4.5.10.9, 4.5.10.10, 4.6.1.1, 4.6.1.2, 4.6.1.3, 4.6.1.4, 4.6.1.5, 4.6.1.6, 4.6.1.7, 4.6.1.8, 4.6.1.9, 4.6.1.10, 4.6.2.1, 4.6.2.2, 4.6.2.3, 4.6.2.4, 4.6.2.5, 4.6.2.6, 4.6.2.7, 4.6.2.8, 4.6.2.9, 4.6.2.10, 4.6.3.1, 4.6.3.2, 4.6.3.3, 4.6.3.4, 4.6.3.5, 4.6.3.6, 4.6.3.7, 4.6.3.8, 4.6.3.9, 4.6.3.10, 4.6.4.1, 4.6.4.2, 4.6.4.3, 4.6.4.4, 4.6.4.5, 4.6.4.6, 4.6.4.7, 4.6.4.8, 4.6.4.9, 4.6.4.10, 4.6.5.1, 4.6.5.2, 4.6.5.3, 4.6.5.4, 4.6.5.5, 4.6.5.6, 4.6.5.7, 4.6.5.8, 4.6.5.9, 4.6.5.10, 4.6.6.1, 4.6.6.2, 4.6.6.3, 4.6.6.4, 4.6.6.5, 4.6.6.6, 4.6.6.7, 4.6.6.8, 4.6.6.9, 4.6.6.10, 4.6.7.1, 4.6.7.2, 4.6.7.3, 4.6.7.4, 4.6.7.5, 4.6.7.6, 4.6.7.7, 4.6.7.8, 4.6.7.9, 4.6.7.10, 4.6.8.1, 4.6.8.2, 4.6.8.3, 4.6.8.4, 4.6.8.5, 4.6.8.6, 4.6.8.7, 4.6.8.8, 4.6.8.9, 4.6.8.10, 4.6.9.1, 4.6.9.2, 4.6.9.3, 4.6.9.4, 4.6.9.5, 4.6.9.6, 4.6.9.7, 4.6.9.8, 4.6.9.9, 4.6.9.10, 4.6.10.1, 4.6.10.2, 4.6.10.3, 4.6.10.4, 4.6.10.5, 4.6.10.6, 4.6.10.7, 4.6.10.8, 4.6.10.9, 4.6.10.10, 4.7.1.1, 4.7.1.2, 4.7.1.3, 4.7.1.4, 4.7.1.5, 4.7.1.6, 4.7.1.7, 4.7.1.8, 4.7.1.9, 4.7.1.10, 4.7.2.1, 4.7.2.2, 4.7.2.3, 4.7.2.4, 4.7.2.5, 4.7.2.6, 4.7.2.7, 4.7.2.8, 4.7.2.9, 4.7.2.10, 4.7.3.1, 4.7.3.2, 4.7.3.3, 4.7.3.4, 4.7.3.5, 4.7.3.6, 4.7.3.7, 4.7.3.8, 4.7.3.9, 4.7.3.10, 4.7.4.1, 4.7.4.2, 4.7.4.3, 4.7.4.4, 4.7.4.5, 4.7.4.6, 4.7.4.7, 4.7.4.8, 4.7.4.9, 4.7.4.10, 4.7.5.1, 4.7.5.2, 4.7.5.3, 4.7.5.4, 4.7.5.5, 4.7.5.6, 4.7.5.7, 4.7.5.8, 4.7.5.9, 4.7.5.10, 4.7.6.1, 4.7.6.2, 4.7.6.3, 4.7.6.4, 4.7.6.5, 4.7.6.6, 4.7.6.7, 4.7.6.8, 4.7.6.9, 4.7.6.10, 4.7.7.1, 4.7.7.2, 4.7.7.3, 4.7.7.4, 4.7.7.5, 4.7.7.6, 4.7.7.7, 4.7.7.8, 4.7.7.9, 4.7.7.10, 4.7.8.1, 4.7.8.2, 4.7.8.3, 4.7.8.4, 4.7.8.5, 4.7.8.6, 4.7.8.7, 4.7.8.8, 4.7.8.9, 4.7.8.10, 4.7.9.1, 4.7.9.2, 4.7.9.3, 4.7.9.4, 4.7.9.5, 4.7.9.6, 4.7.9.7, 4.7.9.8, 4.7.9.9, 4.7.9.10, 4.7.10.1, 4.7.10.2, 4.7.10.3, 4.7.10.4, 4.7.10.5, 4.7.10.6, 4.7.10.7, 4.7.10.8, 4.7.10.9, 4.7.10.10, 4.8.1.1, 4.8.1.2, 4.8.1.3, 4.8.1.4, 4.8.1.5, 4.8.1.6, 4.8.1.7, 4.8.1.8, 4.8.1.9, 4.8.1.10, 4.8.2.1, 4.8.2.2, 4.8.2.3, 4.8.2.4, 4.8.2.5, 4.8.2.6, 4.8.2.7, 4.8.2.8, 4.8.2.9, 4.8.2.10, 4.8.3.1, 4.8.3.2, 4.8.3.3, 4.8.3.4, 4.8.3.5, 4.8.3.6, 4.8.3.7, 4.8.3.8, 4.8.3.9, 4.8.3.10, 4.8.4.1, 4.8.4.2, 4.8.4.3, 4.8.4.4, 4.8.4.5, 4.8.4.6, 4.8.4.7, 4.8.4.8, 4.8.4.9, 4.8.4.10, 4.8.5.1, 4.8.5.2, 4.8.5.3, 4.8.5.4, 4.8.5.5, 4.8.5.6, 4.8.5.7, 4.8.5.8, 4.8.5.9, 4.8.5.10, 4.8.6.1, 4.8.6.2, 4.8.6.3, 4.8.6.4, 4.8.6.5, 4.8.6.6, 4.8.6.7, 4.8.6.8, 4.8.6.9, 4.8.6.10, 4.8.7.1, 4.8.7.2, 4.8.7.3, 4.8.7.4, 4.8.7.5, 4.8.7.6, 4.8.7.7, 4.8.7.8, 4.8.7.9, 4.8.7.10, 4.8.8.1, 4.8.8.2, 4.8.8.3, 4.8.8.4, 4.8.8.5, 4.8.8.6, 4.8.8.7, 4.8.8.8, 4.8.8.9, 4.8.8.10, 4.8.9.1, 4.8.9.2, 4.8.9.3, 4.8.9.4, 4.8.9.5, 4.8.9.6, 4.8.9.7, 4.8.9.8, 4.8.9.9, 4.8.9.10, 4.8.10.1, 4.8.10.2, 4.8.10.3, 4.8.10.4, TABLE B-continued 4.8.10.5, 4.8.10.6, 4.8.10.7, 4.8.10.8, 4.8.10.9, 4.8.10.10, 4.9.1.1, 4.9.1.2, 4.9.1.3, 4.9.1.4, 4.9.1.5, 4.9.1.6, 4.9.1.7, 4.9.1.8, 4.9.1.9, 4.9.1.10, 4.9.2.1, 4.9.2.2, 4.9.2.3, 4.9.2.4, 4.9.2.5, 4.9.2.6, 4.9.2.7, 4.9.2.8, 4.9.2.9, 4.9.2.10, 4.9.3.1, 4.9.3.2, 4.9.3.3, 4.9.3.4, 4.9.3.5, 4.9.3.6, 4.9.3.7, 4.9.3.8, 4.9.3.9, 4.9.3.10, 4.9.4.1, 4.9.4.2, 4.9.4.3, 4.9.4.4, 4.9.4.5, 4.9.4.6, 4.9.4.7, 4.9.4.8, 4.9.4.9, 4.9.4.10, 4.9.5.1, 4.9.5.2, 4.9.5.3, 4.9.5.4, 4.9.5.5, 4.9.5.6, 4.9.5.7, 4.9.5.8, 4.9.5.9, 4.9.5.10, 4.9.6.1, 4.9.6.2, 4.9.6.3, 4.9.6.4, 4.9.6.5, 4.9.6.6, 4.9.6.7, 4.9.6.8, 4.9.6.9, 4.9.6.10, 4.9.7.1, 4.9.7.2, 4.9.7.3, 4.9.7.4, 4.9.7.5, 4.9.7.6, 4.9.7.7, 4.9.7.8, 4.9.7.9, 4.9.7.10, 4.9.8.1, 4.9.8.2, 4.9.8.3, 4.9.8.4, 4.9.8.5, 4.9.8.6, 4.9.8.7, 4.9.8.8, 4.9.8.9, 4.9.8.10, 4.9.9.1, 4.9.9.2, 4.9.9.3, 4.9.9.4, 4.9.9.5, 4.9.9.6, 4.9.9.7, 4.9.9.8, 4.9.9.9, 4.9.9.10, 4.9.10.1, 4.9.10.2, 4.9.10.3, 4.9.10.4, 4.9.10.5, 4.9.10.6, 4.9.10.7, 4.9.10.8, 4.9.10.9, 4.9.10.10, 4.10.1.1, 4.10.1.2, 4.10.1.3, 4.10.1.4, 4.10.1.5, 4.10.1.6, 4.10.1.7, 4.10.1.8, 4.10.1.9, 4.10.1.10, 4.10.2.1, 4.10.2.2, 4.10.2.3, 4.10.2.4, 4.10.2.5, 4.10.2.6, 4.10.2.7, 4.10.2.8, 4.10.2.9, 4.10.2.10, 4.10.3.1, 4.10.3.2, 4.10.3.3, 4.10.3.4, 4.10.3.5, 4.10.3.6, 4.10.3.7, 4.10.3.8, 4.10.3.9, 4.10.3.10, 4.10.4.1, 4.10.4.2, 4.10.4.3, 4.10.4.4, 4.10.4.5, 4.10.4.6, 4.10.4.7, 4.10.4.8, 4.10.4.9, 4.10.4.10, 4.10.5.1, 4.10.5.2, 4.10.5.3, 4.10.5.4, 4.10.5.5, 4.10.5.6, 4.10.5.7, 4.10.5.8, 4.10.5.9, 4.10.5.10, 4.10.6.1, 4.10.6.2, 4.10.6.3, 4.10.6.4, 4.10.6.5, 4.10.6.6, 4.10.6.7, 4.10.6.8, 4.10.6.9, 4.10.6.10, 4.10.7.1, 4.10.7.2, 4.10.7.3, 4.10.7.4, 4.10.7.5, 4.10.7.6, 4.10.7.7, 4.10.7.8, 4.10.7.9, 4.10.7.10, 4.10.8.1, 4.10.8.2, 4.10.8.3, 4.10.8.4, 4.10.8.5, 4.10.8.6, 4.10.8.7, 4.10.8.8, 4.10.8.9, 4.10.8.10, 4.10.9.1, 4.10.9.2, 4.10.9.3, 4.10.9.4, 4.10.9.5, 4.10.9.6, 4.10.9.7, 4.10.9.8, 4.10.9.9, 4.10.9.10, 4.10.10.1, 4.10.10.2, 4.10.10.3, 4.10.10.4, 4.10.10.5, 4.10.10.6, 4.10.10.7, 4.10.10.8, 4.10.10.9, 4.10.10.10, 5.1.1.1, 5.1.1.2, 5.1.1.3, 5.1.1.4, 5.1.1.5, 5.1.1.6, 5.1.1.7, 5.1.1.8, 5.1.1.9, 5.1.1.10, 5.1.2.1, 5.1.2.2, 5.1.2.3, 5.1.2.4, 5.1.2.5, 5.1.2.6, 5.1.2.7, 5.1.2.8, 5.1.2.9, 5.1.2.10, 5.1.3.1, 5.1.3.2, 5.1.3.3, 5.1.3.4, 5.1.3.5, 5.1.3.6, 5.1.3.7, 5.1.3.8, 5.1.3.9, 5.1.3.10, 5.1.4.1, 5.1.4.2, 5.1.4.3, 5.1.4.4, 5.1.4.5, 5.1.4.6, 5.1.4.7, 5.1.4.8, 5.1.4.9, 5.1.4.10, 5.1.5.1, 5.1.5.2, 5.1.5.3, 5.1.5.4, 5.1.5.5, 5.1.5.6, 5.1.5.7, 5.1.5.8, 5.1.5.9, 5.1.5.10, 5.1.6.1, 5.1.6.2, 5.1.6.3, 5.1.6.4, 5.1.6.5, 5.1.6.6, 5.1.6.7, 5.1.6.8, 5.1.6.9, 5.1.6.10, 5.1.7.1, 5.1.7.2, 5.1.7.3, 5.1.7.4, 5.1.7.5, 5.1.7.6, 5.1.7.7, 5.1.7.8, 5.1.7.9, 5.1.7.10, 5.1.8.1, 5.1.8.2, 5.1.8.3, 5.1.8.4, 5.1.8.5, 5.1.8.6, 5.1.8.7, 5.1.8.8, 5.1.8.9, 5.1.8.10, 5.1.9.1, 5.1.9.2, 5.1.9.3, 5.1.9.4, 5.1.9.5, 5.1.9.6, 5.1.9.7, 5.1.9.8, 5.1.9.9, 5.1.9.10, 5.1.10.1, 5.1.10.2, 5.1.10.3, 5.1.10.4, 5.1.10.5, 5.1.10.6, 5.1.10.7, 5.1.10.8, 5.1.10.9, 5.1.10.10, 5.2.1.1, 5.2.1.2, 5.2.1.3, 5.2.1.4, 5.2.1.5, 5.2.1.6, 5.2.1.7, 5.2.1.8, 5.2.1.9, 5.2.1.10, 5.2.2.1, 5.2.2.2, 5.2.2.3, 5.2.2.4, 5.2.2.5, 5.2.2.6, 5.2.2.7, 5.2.2.8, 5.2.2.9, 5.2.2.10, 5.2.3.1, 5.2.3.2, 5.2.3.3, 5.2.3.4, 5.2.3.5, 5.2.3.6, 5.2.3.7, 5.2.3.8, 5.2.3.9, 5.2.3.10, 5.2.4.1, 5.2.4.2, 5.2.4.3, 5.2.4.4, 5.2.4.5, 5.2.4.6, 5.2.4.7, 5.2.4.8, 5.2.4.9, 5.2.4.10, 5.2.5.1, 5.2.5.2, 5.2.5.3, 5.2.5.4, 5.2.5.5, 5.2.5.6, 5.2.5.7, 5.2.5.8, 5.2.5.9, 5.2.5.10, 5.2.6.1, 5.2.6.2, 5.2.6.3, 5.2.6.4, 5.2.6.5, 5.2.6.6, 5.2.6.7, 5.2.6.8, 5.2.6.9, 5.2.6.10, 5.2.7.1, 5.2.7.2, 5.2.7.3, 5.2.7.4, 5.2.7.5, 5.2.7.6, 5.2.7.7, 5.2.7.8, 5.2.7.9, 5.2.7.10, 5.2.8.1, 5.2.8.2, 5.2.8.3, 5.2.8.4, 5.2.8.5, 5.2.8.6, 5.2.8.7, 5.2.8.8, 5.2.8.9, 5.2.8.10, 5.2.9.1, 5.2.9.2, 5.2.9.3, 5.2.9.4, 5.2.9.5, 5.2.9.6, 5.2.9.7, 5.2.9.8, 5.2.9.9, 5.2.9.10, 5.2.10.1, 5.2.10.2, 5.2.10.3, 5.2.10.4, 5.2.10.5, 5.2.10.6, 5.2.10.7, 5.2.10.8, 5.2.10.9, 5.2.10.10, 5.3.1.1, 5.3.1.2, 5.3.1.3, 5.3.1.4, 5.3.1.5, 5.3.1.6, 5.3.1.7, 5.3.1.8, 5.3.1.9, 5.3.1.10, 5.3.2.1, 5.3.2.2, 5.3.2.3, 5.3.2.4, 5.3.2.5, 5.3.2.6, 5.3.2.7, 5.3.2.8, 5.3.2.9, 5.3.2.10, 5.3.3.1, 5.3.3.2, 5.3.3.3, 5.3.3.4, 5.3.3.5, 5.3.3.6, 5.3.3.7, 5.3.3.8, 5.3.3.9, 5.3.3.10, 5.3.4.1, 5.3.4.2, 5.3.4.3, 5.3.4.4, 5.3.4.5, 5.3.4.6, 5.3.4.7, 5.3.4.8, 5.3.4.9, 5.3.4.10, 5.3.5.1, 5.3.5.2, 5.3.5.3, 5.3.5.4, 5.3.5.5, 5.3.5.6, 5.3.5.7, 5.3.5.8, 5.3.5.9, 5.3.5.10, 5.3.6.1, 5.3.6.2, 5.3.6.3, 5.3.6.4, 5.3.6.5, 5.3.6.6, 5.3.6.7, 5.3.6.8, 5.3.6.9, 5.3.6.10, 5.3.7.1, 5.3.7.2, 5.3.7.3, 5.3.7.4, 5.3.7.5, 5.3.7.6, 5.3.7.7, 5.3.7.8, 5.3.7.9, 5.3.7.10, 5.3.8.1, 5.3.8.2, 5.3.8.3, 5.3.8.4, 5.3.8.5, 5.3.8.6, 5.3.8.7, 5.3.8.8, 5.3.8.9, 5.3.8.10, 5.3.9.1, 5.3.9.2, 5.3.9.3, 5.3.9.4, 5.3.9.5, 5.3.9.6, 5.3.9.7, 5.3.9.8, 5.3.9.9, 5.3.9.10, 5.3.10.1, 5.3.10.2, 5.3.10.3, 5.3.10.4, 5.3.10.5, 5.3.10.6, 5.3.10.7, 5.3.10.8, 5.3.10.9, 5.3.10.10, 5.4.1.1, 5.4.1.2, 5.4.1.3, 5.4.1.4, 5.4.1.5, 5.4.1.6, 5.4.1.7, 5.4.1.8, 5.4.1.9, 5.4.1.10, 5.4.2.1, 5.4.2.2, 5.4.2.3, 5.4.2.4, 5.4.2.5, 5.4.2.6, 5.4.2.7, 5.4.2.8, 5.4.2.9, 5.4.2.10, 5.4.3.1, 5.4.3.2, 5.4.3.3, 5.4.3.4, 5.4.3.5, 5.4.3.6, 5.4.3.7, 5.4.3.8, 5.4.3.9, 5.4.3.10, 5.4.4.1, 5.4.4.2, 5.4.4.3, 5.4.4.4, 5.4.4.5, 5.4.4.6, 5.4.4.7, 5.4.4.8, 5.4.4.9, 5.4.4.10, 5.4.5.1, 5.4.5.2, 5.4.5.3, 5.4.5.4, 5.4.5.5, 5.4.5.6, 5.4.5.7, 5.4.5.8, 5.4.5.9, 5.4.5.10, 5.4.6.1, 5.4.6.2, 5.4.6.3, 5.4.6.4, 5.4.6.5, 5.4.6.6, 5.4.6.7, 5.4.6.8, 5.4.6.9, 5.4.6.10, 5.4.7.1, 5.4.7.2, 5.4.7.3, 5.4.7.4, 5.4.7.5, 5.4.7.6, 5.4.7.7, 5.4.7.8, 5.4.7.9, 5.4.7.10, 5.4.8.1, 5.4.8.2, 5.4.8.3, 5.4.8.4, 5.4.8.5, 5.4.8.6, 5.4.8.7, 5.4.8.8, 5.4.8.9, 5.4.8.10, 5.4.9.1, 5.4.9.2, 5.4.9.3, 5.4.9.4, 5.4.9.5, 5.4.9.6, 5.4.9.7, 5.4.9.8, 5.4.9.9, 5.4.9.10, 5.4.10.1, 5.4.10.2, 5.4.10.3, 5.4.10.4, 5.4.10.5, 5.4.10.6, 5.4.10.7, 5.4.10.8, 5.4.10.9, 5.4.10.10, 5.5.1.1, 5.5.1.2, 5.5.1.3, 5.5.1.4, 5.5.1.5, 5.5.1.6, 5.5.1.7, 5.5.1.8, 5.5.1.9, 5.5.1.10, 5.5.2.1, 5.5.2.2, 5.5.2.3, 5.5.2.4, 5.5.2.5, 5.5.2.6, 5.5.2.7, 5.5.2.8, 5.5.2.9, 5.5.2.10, 5.5.3.1, 5.5.3.2, 5.5.3.3, 5.5.3.4, 5.5.3.5, 5.5.3.6, 5.5.3.7, 5.5.3.8, 5.5.3.9, 5.5.3.10, 5.5.4.1, 5.5.4.2, 5.5.4.3, 5.5.4.4, 5.5.4.5, 5.5.4.6, 5.5.4.7, 5.5.4.8, 5.5.4.9, 5.5.4.10, 5.5.5.1, 5.5.5.2, 5.5.5.3, 5.5.5.4, 5.5.5.5, 5.5.5.6, 5.5.5.7, 5.5.5.8, 5.5.5.9, 5.5.5.10, 5.5.6.1, 5.5.6.2, 5.5.6.3, 5.5.6.4, 5.5.6.5, 5.5.6.6, 5.5.6.7, 5.5.6.8, 5.5.6.9, 5.5.6.10, 5.5.7.1, 5.5.7.2, 5.5.7.3, 5.5.7.4, 5.5.7.5, 5.5.7.6, 5.5.7.7, 5.5.7.8, 5.5.7.9, 5.5.7.10, 5.5.8.1, 5.5.8.2, 5.5.8.3, 5.5.8.4, 5.5.8.5, 5.5.8.6, 5.5.8.7, 5.5.8.8, 5.5.8.9, 5.5.8.10, 5.5.9.1, 5.5.9.2, 5.5.9.3, 5.5.9.4, 5.5.9.5, 5.5.9.6, 5.5.9.7, 5.5.9.8, 5.5.9.9, 5.5.9.10, 5.5.10.1, 5.5.10.2, 5.5.10.3, 5.5.10.4, 5.5.10.5, 5.5.10.6, 5.5.10.7, 5.5.10.8, 5.5.10.9, 5.5.10.10, 5.6.1.1, 5.6.1.2, 5.6.1.3, 5.6.1.4, 5.6.1.5, 5.6.1.6, 5.6.1.7, 5.6.1.8, 5.6.1.9, 5.6.1.10, 5.6.2.1, 5.6.2.2, 5.6.2.3, 5.6.2.4, 5.6.2.5, 5.6.2.6, 5.6.2.7, 5.6.2.8, 5.6.2.9, 5.6.2.10, 5.6.3.1, 5.6.3.2, 5.6.3.3, 5.6.3.4, 5.6.3.5, 5.6.3.6, 5.6.3.7, 5.6.3.8, 5.6.3.9, 5.6.3.10, 5.6.4.1, 5.6.4.2, 5.6.4.3, 5.6.4.4, 5.6.4.5, 5.6.4.6, 5.6.4.7, 5.6.4.8, 5.6.4.9, 5.6.4.10, 5.6.5.1, 5.6.5.2, 5.6.5.3, 5.6.5.4, 5.6.5.5, 5.6.5.6, 5.6.5.7, 5.6.5.8, 5.6.5.9, 5.6.5.10, 5.6.6.1, 5.6.6.2, 5.6.6.3, 5.6.6.4, 5.6.6.5, 5.6.6.6, 5.6.6.7, 5.6.6.8, 5.6.6.9, 5.6.6.10, 5.6.7.1, 5.6.7.2, 5.6.7.3, 5.6.7.4, 5.6.7.5, 5.6.7.6, 5.6.7.7, 5.6.7.8, 5.6.7.9, 5.6.7.10, 5.6.8.1, 5.6.8.2, 5.6.8.3, 5.6.8.4, 5.6.8.5, 5.6.8.6, 5.6.8.7, 5.6.8.8, 5.6.8.9, 5.6.8.10, 5.6.9.1, 5.6.9.2, 5.6.9.3, 5.6.9.4, 5.6.9.5, 5.6.9.6, 5.6.9.7, 5.6.9.8, 5.6.9.9, 5.6.9.10, 5.6.10.1, 5.6.10.2, 5.6.10.3, 5.6.10.4, 5.6.10.5, 5.6.10.6, 5.6.10.7, 5.6.10.8, 5.6.10.9, 5.6.10.10, 5.7.1.1, 5.7.1.2, 5.7.1.3, 5.7.1.4, 5.7.1.5, 5.7.1.6, 5.7.1.7, 5.7.1.8, 5.7.1.9, 5.7.1.10, 5.7.2.1, 5.7.2.2, 5.7.2.3, 5.7.2.4, 5.7.2.5, 5.7.2.6, 5.7.2.7, 5.7.2.8, 5.7.2.9, 5.7.2.10, 5.7.3.1, 5.7.3.2, 5.7.3.3, 5.7.3.4, 5.7.3.5, 5.7.3.6, 5.7.3.7, 5.7.3.8, 5.7.3.9, 5.7.3.10, 5.7.4.1, 5.7.4.2, 5.7.4.3, 5.7.4.4, 5.7.4.5, 5.7.4.6, 5.7.4.7, 5.7.4.8, 5.7.4.9, 5.7.4.10, 5.7.5.1, 5.7.5.2, 5.7.5.3, 5.7.5.4, 5.7.5.5, 5.7.5.6, 5.7.5.7, 5.7.5.8, 5.7.5.9, 5.7.5.10, 5.7.6.1, 5.7.6.2, 5.7.6.3, 5.7.6.4, 5.7.6.5, 5.7.6.6, 5.7.6.7, 5.7.6.8, 5.7.6.9, 5.7.6.10, 5.7.7.1, 5.7.7.2, 5.7.7.3, 5.7.7.4, 5.7.7.5, 5.7.7.6, 5.7.7.7, 5.7.7.8, 5.7.7.9, 5.7.7.10, 5.7.8.1, 5.7.8.2, 5.7.8.3, 5.7.8.4, 5.7.8.5, 5.7.8.6, 5.7.8.7, 5.7.8.8, 5.7.8.9, 5.7.8.10, 5.7.9.1, 5.7.9.2, 5.7.9.3, 5.7.9.4, 5.7.9.5, 5.7.9.6, 5.7.9.7, 5.7.9.8, 5.7.9.9, 5.7.9.10, 5.7.10.1, 5.7.10.2, 5.7.10.3, 5.7.10.4, 5.7.10.5, 5.7.10.6, 5.7.10.7, 5.7.10.8, 5.7.10.9, 5.7.10.10, 5.8.1.1, 5.8.1.2, 5.8.1.3, 5.8.1.4, 5.8.1.5, 5.8.1.6, 5.8.1.7, 5.8.1.8, 5.8.1.9, 5.8.1.10, 5.8.2.1, 5.8.2.2, 5.8.2.3, 5.8.2.4, 5.8.2.5, 5.8.2.6, 5.8.2.7,

TABLE B-continued 5.8.2.8, 5.8.2.9, 5.8.2.10, 5.8.3.1, 5.8.3.2, 5.8.3.3, 5.8.3.4, 5.8.3.5, 5.8.3.6, 5.8.3.7, 5.8.3.8, 5.8.3.9, 5.8.3.10, 5.8.4.1, 5.8.4.2, 5.8.4.3, 5.8.4.4, 5.8.4.5, 5.8.4.6, 5.8.4.7, 5.8.4.8, 5.8.4.9, 5.8.4.10, 5.8.5.1, 5.8.5.2, 5.8.5.3, 5.8.5.4, 5.8.5.5, 5.8.5.6, 5.8.5.7, 5.8.5.8, 5.8.5.9, 5.8.5.10, 5.8.6.1, 5.8.6.2, 5.8.6.3, 5.8.6.4, 5.8.6.5, 5.8.6.6, 5.8.6.7, 5.8.6.8, 5.8.6.9, 5.8.6.10, 5.8.7.1, 5.8.7.2, 5.8.7.3, 5.8.7.4, 5.8.7.5, 5.8.7.6, 5.8.7.7, 5.8.7.8, 5.8.7.9, 5.8.7.10, 5.8.8.1, 5.8.8.2, 5.8.8.3, 5.8.8.4, 5.8.8.5, 5.8.8.6, 5.8.8.7, 5.8.8.8, 5.8.8.9, 5.8.8.10, 5.8.9.1, 5.8.9.2, 5.8.9.3, 5.8.9.4, 5.8.9.5, 5.8.9.6, 5.8.9.7, 5.8.9.8, 5.8.9.9, 5.8.9.10, 5.8.10.1, 5.8.10.2, 5.8.10.3, 5.8.10.4, 5.8.10.5, 5.8.10.6, 5.8.10.7, 5.8.10.8, 5.8.10.9, 5.8.10.10, 5.9.1.1, 5.9.1.2, 5.9.1.3, 5.9.1.4, 5.9.1.5, 5.9.1.6, 5.9.1.7, 5.9.1.8, 5.9.1.9, 5.9.1.10, 5.9.2.1, 5.9.2.2, 5.9.2.3, 5.9.2.4, 5.9.2.5, 5.9.2.6, 5.9.2.7, 5.9.2.8, 5.9.2.9, 5.9.2.10, 5.9.3.1, 5.9.3.2, 5.9.3.3, 5.9.3.4, 5.9.3.5, 5.9.3.6, 5.9.3.7, 5.9.3.8, 5.9.3.9, 5.9.3.10, 5.9.4.1, 5.9.4.2, 5.9.4.3, 5.9.4.4, 5.9.4.5, 5.9.4.6, 5.9.4.7, 5.9.4.8, 5.9.4.9, 5.9.4.10, 5.9.5.1, 5.9.5.2, 5.9.5.3, 5.9.5.4, 5.9.5.5, 5.9.5.6, 5.9.5.7, 5.9.5.8, 5.9.5.9, 5.9.5.10, 5.9.6.1, 5.9.6.2, 5.9.6.3, 5.9.6.4, 5.9.6.5, 5.9.6.6, 5.9.6.7, 5.9.6.8, 5.9.6.9, 5.9.6.10, 5.9.7.1, 5.9.7.2, 5.9.7.3, 5.9.7.4, 5.9.7.5, 5.9.7.6, 5.9.7.7, 5.9.7.8, 5.9.7.9, 5.9.7.10, 5.9.8.1, 5.9.8.2, 5.9.8.3, 5.9.8.4, 5.9.8.5, 5.9.8.6, 5.9.8.7, 5.9.8.8, 5.9.8.9, 5.9.8.10, 5.9.9.1, 5.9.9.2, 5.9.9.3, 5.9.9.4, 5.9.9.5, 5.9.9.6, 5.9.9.7, 5.9.9.8, 5.9.9.9, 5.9.9.10, 5.9.10.1, 5.9.10.2, 5.9.10.3, 5.9.10.4, 5.9.10.5, 5.9.10.6, 5.9.10.7, 5.9.10.8, 5.9.10.9, 5.9.10.10, 5.10.1.1, 5.10.1.2, 5.10.1.3, 5.10.1.4, 5.10.1.5, 5.10.1.6, 5.10.1.7, 5.10.1.8, 5.10.1.9, 5.10.1.10, 5.10.2.1, 5.10.2.2, 5.10.2.3, 5.10.2.4, 5.10.2.5, 5.10.2.6, 5.10.2.7, 5.10.2.8, 5.10.2.9, 5.10.2.10, 5.10.3.1, 5.10.3.2, 5.10.3.3, 5.10.3.4, 5.10.3.5, 5.10.3.6, 5.10.3.7, 5.10.3.8, 5.10.3.9, 5.10.3.10, 5.10.4.1, 5.10.4.2, 5.10.4.3, 5.10.4.4, 5.10.4.5, 5.10.4.6, 5.10.4.7, 5.10.4.8, 5.10.4.9, 5.10.4.10, 5.10.5.1, 5.10.5.2, 5.10.5.3, 5.10.5.4, 5.10.5.5, 5.10.5.6, 5.10.5.7, 5.10.5.8, 5.10.5.9, 5.10.5.10, 5.10.6.1, 5.10.6.2, 5.10.6.3, 5.10.6.4, 5.10.6.5, 5.10.6.6, 5.10.6.7, 5.10.6.8, 5.10.6.9, 5.10.6.10, 5.10.7.1, 5.10.7.2, 5.10.7.3, 5.10.7.4, 5.10.7.5, 5.10.7.6, 5.10.7.7, 5.10.7.8, 5.10.7.9, 5.10.7.10, 5.10.8.1, 5.10.8.2, 5.10.8.3, 5.10.8.4, 5.10.8.5, 5.10.8.6, 5.10.8.7, 5.10.8.8, 5.10.8.9, 5.10.8.10, 5.10.9.1, 5.10.9.2, 5.10.9.3, 5.10.9.4, 5.10.9.5, 5.10.9.6, 5.10.9.7, 5.10.9.8, 5.10.9.9, 5.10.9.10, 5.10.10.1, 5.10.10.2, 5.10.10.3, 5.10.10.4, 5.10.10.5, 5.10.10.6, 5.10.10.7, 5.10.10.8, 5.10.10.9, 5.10.10.10, 6.1.1.1, 6.1.1.2, 6.1.1.3, 6.1.1.4, 6.1.1.5, 6.1.1.6, 6.1.1.7, 6.1.1.8, 6.1.1.9, 6.1.1.10, 6.1.2.1, 6.1.2.2, 6.1.2.3, 6.1.2.4, 6.1.2.5, 6.1.2.6, 6.1.2.7, 6.1.2.8, 6.1.2.9, 6.1.2.10, 6.1.3.1, 6.1.3.2, 6.1.3.3, 6.1.3.4, 6.1.3.5, 6.1.3.6, 6.1.3.7, 6.1.3.8, 6.1.3.9, 6.1.3.10, 6.1.4.1, 6.1.4.2, 6.1.4.3, 6.1.4.4, 6.1.4.5, 6.1.4.6, 6.1.4.7, 6.1.4.8, 6.1.4.9, 6.1.4.10, 6.1.5.1, 6.1.5.2, 6.1.5.3, 6.1.5.4, 6.1.5.5, 6.1.5.6, 6.1.5.7, 6.1.5.8, 6.1.5.9, 6.1.5.10, 6.1.6.1, 6.1.6.2, 6.1.6.3, 6.1.6.4, 6.1.6.5, 6.1.6.6, 6.1.6.7, 6.1.6.8, 6.1.6.9, 6.1.6.10, 6.1.7.1, 6.1.7.2, 6.1.7.3, 6.1.7.4, 6.1.7.5, 6.1.7.6, 6.1.7.7, 6.1.7.8, 6.1.7.9, 6.1.7.10, 6.1.8.1, 6.1.8.2, 6.1.8.3, 6.1.8.4, 6.1.8.5, 6.1.8.6, 6.1.8.7, 6.1.8.8, 6.1.8.9, 6.1.8.10, 6.1.9.1, 6.1.9.2, 6.1.9.3, 6.1.9.4, 6.1.9.5, 6.1.9.6, 6.1.9.7, 6.1.9.8, 6.1.9.9, 6.1.9.10, 6.1.10.1, 6.1.10.2, 6.1.10.3, 6.1.10.4, 6.1.10.5, 6.1.10.6, 6.1.10.7, 6.1.10.8, 6.1.10.9, 6.1.10.10, 6.2.1.1, 6.2.1.2, 6.2.1.3, 6.2.1.4, 6.2.1.5, 6.2.1.6, 6.2.1.7, 6.2.1.8, 6.2.1.9, 6.2.1.10, 6.2.2.1, 6.2.2.2, 6.2.2.3, 6.2.2.4, 6.2.2.5, 6.2.2.6, 6.2.2.7, 6.2.2.8, 6.2.2.9, 6.2.2.10, 6.2.3.1, 6.2.3.2, 6.2.3.3, 6.2.3.4, 6.2.3.5, 6.2.3.6, 6.2.3.7, 6.2.3.8, 6.2.3.9, 6.2.3.10, 6.2.4.1, 6.2.4.2, 6.2.4.3, 6.2.4.4, 6.2.4.5, 6.2.4.6, 6.2.4.7, 6.2.4.8, 6.2.4.9, 6.2.4.10, 6.2.5.1, 6.2.5.2, 6.2.5.3, 6.2.5.4, 6.2.5.5, 6.2.5.6, 6.2.5.7, 6.2.5.8, 6.2.5.9, 6.2.5.10, 6.2.6.1, 6.2.6.2, 6.2.6.3, 6.2.6.4, 6.2.6.5, 6.2.6.6, 6.2.6.7, 6.2.6.8, 6.2.6.9, 6.2.6.10, 6.2.7.1, 6.2.7.2, 6.2.7.3, 6.2.7.4, 6.2.7.5, 6.2.7.6, 6.2.7.7, 6.2.7.8, 6.2.7.9, 6.2.7.10, 6.2.8.1, 6.2.8.2, 6.2.8.3, 6.2.8.4, 6.2.8.5, 6.2.8.6, 6.2.8.7, 6.2.8.8, 6.2.8.9, 6.2.8.10, 6.2.9.1, 6.2.9.2, 6.2.9.3, 6.2.9.4, 6.2.9.5, 6.2.9.6, 6.2.9.7, 6.2.9.8, 6.2.9.9, 6.2.9.10, 6.2.10.1, 6.2.10.2, 6.2.10.3, 6.2.10.4, 6.2.10.5, 6.2.10.6, 6.2.10.7, 6.2.10.8, 6.2.10.9, 6.2.10.10, 6.3.1.1, 6.3.1.2, 6.3.1.3, 6.3.1.4, 6.3.1.5, 6.3.1.6, 6.3.1.7, 6.3.1.8, 6.3.1.9, 6.3.1.10, 6.3.2.1, 6.3.2.2, 6.3.2.3, 6.3.2.4, 6.3.2.5, 6.3.2.6, 6.3.2.7, 6.3.2.8, 6.3.2.9, 6.3.2.10, 6.3.3.1, 6.3.3.2, 6.3.3.3, 6.3.3.4, 6.3.3.5, 6.3.3.6, 6.3.3.7, 6.3.3.8, 6.3.3.9, 6.3.3.10, 6.3.4.1, 6.3.4.2, 6.3.4.3, 6.3.4.4, 6.3.4.5, 6.3.4.6, 6.3.4.7, 6.3.4.8, 6.3.4.9, 6.3.4.10, 6.3.5.1, 6.3.5.2, 6.3.5.3, 6.3.5.4, 6.3.5.5, 6.3.5.6, 6.3.5.7, 6.3.5.8, 6.3.5.9, 6.3.5.10, 6.3.6.1, 6.3.6.2, 6.3.6.3, 6.3.6.4, 6.3.6.5, 6.3.6.6, 6.3.6.7, 6.3.6.8, 6.3.6.9, 6.3.6.10, 6.3.7.1, 6.3.7.2, 6.3.7.3, 6.3.7.4, 6.3.7.5, 6.3.7.6, 6.3.7.7, 6.3.7.8, 6.3.7.9, 6.3.7.10, 6.3.8.1, 6.3.8.2, 6.3.8.3, 6.3.8.4, 6.3.8.5, 6.3.8.6, 6.3.8.7, 6.3.8.8, 6.3.8.9, 6.3.8.10, 6.3.9.1, 6.3.9.2, 6.3.9.3, 6.3.9.4, 6.3.9.5, 6.3.9.6, 6.3.9.7, 6.3.9.8, 6.3.9.9, 6.3.9.10, 6.3.10.1, 6.3.10.2, 6.3.10.3, 6.3.10.4, 6.3.10.5, 6.3.10.6, 6.3.10.7, 6.3.10.8, 6.3.10.9, 6.3.10.10, 6.4.1.1, 6.4.1.2, 6.4.1.3, 6.4.1.4, 6.4.1.5, 6.4.1.6, 6.4.1.7, 6.4.1.8, 6.4.1.9, 6.4.1.10, 6.4.2.1, 6.4.2.2, 6.4.2.3, 6.4.2.4, 6.4.2.5, 6.4.2.6, 6.4.2.7, 6.4.2.8, 6.4.2.9, 6.4.2.10, 6.4.3.1, 6.4.3.2, 6.4.3.3, 6.4.3.4, 6.4.3.5, 6.4.3.6, 6.4.3.7, 6.4.3.8, 6.4.3.9, 6.4.3.10, 6.4.4.1, 6.4.4.2, 6.4.4.3, 6.4.4.4, 6.4.4.5, 6.4.4.6, 6.4.4.7, 6.4.4.8, 6.4.4.9, 6.4.4.10, 6.4.5.1, 6.4.5.2, 6.4.5.3, 6.4.5.4, 6.4.5.5, 6.4.5.6, 6.4.5.7, 6.4.5.8, 6.4.5.9, 6.4.5.10, 6.4.6.1, 6.4.6.2, 6.4.6.3, 6.4.6.4, 6.4.6.5, 6.4.6.6, 6.4.6.7, 6.4.6.8, 6.4.6.9, 6.4.6.10, 6.4.7.1, 6.4.7.2, 6.4.7.3, 6.4.7.4, 6.4.7.5, 6.4.7.6, 6.4.7.7, 6.4.7.8, 6.4.7.9, 6.4.7.10, 6.4.8.1, 6.4.8.2, 6.4.8.3, 6.4.8.4, 6.4.8.5, 6.4.8.6, 6.4.8.7, 6.4.8.8, 6.4.8.9, 6.4.8.10, 6.4.9.1, 6.4.9.2, 6.4.9.3, 6.4.9.4, 6.4.9.5, 6.4.9.6, 6.4.9.7, 6.4.9.8, 6.4.9.9, 6.4.9.10, 6.4.10.1, 6.4.10.2, 6.4.10.3, 6.4.10.4, 6.4.10.5, 6.4.10.6, 6.4.10.7, 6.4.10.8, 6.4.10.9, 6.4.10.10, 6.5.1.1, 6.5.1.2, 6.5.1.3, 6.5.1.4, 6.5.1.5, 6.5.1.6, 6.5.1.7, 6.5.1.8, 6.5.1.9, 6.5.1.10, 6.5.2.1, 6.5.2.2, 6.5.2.3, 6.5.2.4, 6.5.2.5, 6.5.2.6, 6.5.2.7, 6.5.2.8, 6.5.2.9, 6.5.2.10, 6.5.3.1, 6.5.3.2, 6.5.3.3, 6.5.3.4, 6.5.3.5, 6.5.3.6, 6.5.3.7, 6.5.3.8, 6.5.3.9, 6.5.3.10, 6.5.4.1, 6.5.4.2, 6.5.4.3, 6.5.4.4, 6.5.4.5, 6.5.4.6, 6.5.4.7, 6.5.4.8, 6.5.4.9, 6.5.4.10, 6.5.5.1, 6.5.5.2, 6.5.5.3, 6.5.5.4, 6.5.5.5, 6.5.5.6, 6.5.5.7, 6.5.5.8, 6.5.5.9, 6.5.5.10, 6.5.6.1, 6.5.6.2, 6.5.6.3, 6.5.6.4, 6.5.6.5, 6.5.6.6, 6.5.6.7, 6.5.6.8, 6.5.6.9, 6.5.6.10, 6.5.7.1, 6.5.7.2, 6.5.7.3, 6.5.7.4, 6.5.7.5, 6.5.7.6, 6.5.7.7, 6.5.7.8, 6.5.7.9, 6.5.7.10, 6.5.8.1, 6.5.8.2, 6.5.8.3, 6.5.8.4, 6.5.8.5, 6.5.8.6, 6.5.8.7, 6.5.8.8, 6.5.8.9, 6.5.8.10, 6.5.9.1, 6.5.9.2, 6.5.9.3, 6.5.9.4, 6.5.9.5, 6.5.9.6, 6.5.9.7, 6.5.9.8, 6.5.9.9, 6.5.9.10, 6.5.10.1, 6.5.10.2, 6.5.10.3, 6.5.10.4, 6.5.10.5, 6.5.10.6, 6.5.10.7, 6.5.10.8, 6.5.10.9, 6.5.10.10, 6.6.1.1, 6.6.1.2, 6.6.1.3, 6.6.1.4, 6.6.1.5, 6.6.1.6, 6.6.1.7, 6.6.1.8, 6.6.1.9, 6.6.1.10, 6.6.2.1, 6.6.2.2, 6.6.2.3, 6.6.2.4, 6.6.2.5, 6.6.2.6, 6.6.2.7, 6.6.2.8, 6.6.2.9, 6.6.2.10, 6.6.3.1, 6.6.3.2, 6.6.3.3, 6.6.3.4, 6.6.3.5, 6.6.3.6, 6.6.3.7, 6.6.3.8, 6.6.3.9, 6.6.3.10, 6.6.4.1, 6.6.4.2, 6.6.4.3, 6.6.4.4, 6.6.4.5, 6.6.4.6, 6.6.4.7, 6.6.4.8, 6.6.4.9, 6.6.4.10, 6.6.5.1, 6.6.5.2, 6.6.5.3, 6.6.5.4, 6.6.5.5, 6.6.5.6, 6.6.5.7, 6.6.5.8, 6.6.5.9, 6.6.5.10, 6.6.6.1, 6.6.6.2, 6.6.6.3, 6.6.6.4, 6.6.6.5, 6.6.6.6, 6.6.6.7, 6.6.6.8, 6.6.6.9, 6.6.6.10, 6.6.7.1, 6.6.7.2, 6.6.7.3, 6.6.7.4, 6.6.7.5, 6.6.7.6, 6.6.7.7, 6.6.7.8, 6.6.7.9, 6.6.7.10, 6.6.8.1, 6.6.8.2, 6.6.8.3, 6.6.8.4, 6.6.8.5, 6.6.8.6, 6.6.8.7, 6.6.8.8, 6.6.8.9, 6.6.8.10, 6.6.9.1, 6.6.9.2, 6.6.9.3, 6.6.9.4, 6.6.9.5, 6.6.9.6, 6.6.9.7, 6.6.9.8, 6.6.9.9, 6.6.9.10, 6.6.10.1, 6.6.10.2, 6.6.10.3, 6.6.10.4, 6.6.10.5, 6.6.10.6, 6.6.10.7, 6.6.10.8, 6.6.10.9, 6.6.10.10, 6.7.1.1, 6.7.1.2, 6.7.1.3, 6.7.1.4, 6.7.1.5, 6.7.1.6, 6.7.1.7, 6.7.1.8, 6.7.1.9, 6.7.1.10, 6.7.2.1, 6.7.2.2, 6.7.2.3, 6.7.2.4, 6.7.2.5, 6.7.2.6, 6.7.2.7, 6.7.2.8, 6.7.2.9, 6.7.2.10, 6.7.3.1, 6.7.3.2, 6.7.3.3, 6.7.3.4, 6.7.3.5, 6.7.3.6, 6.7.3.7, 6.7.3.8, 6.7.3.9, 6.7.3.10, 6.7.4.1, 6.7.4.2, 6.7.4.3, 6.7.4.4, 6.7.4.5, 6.7.4.6, 6.7.4.7, 6.7.4.8, 6.7.4.9, 6.7.4.10, 6.7.5.1,

TABLE B-continued 6.7.5.2, 6.7.5.3, 6.7.5.4, 6.7.5.5, 6.7.5.6, 6.7.5.7, 6.7.5.8, 6.7.5.9, 6.7.5.10, 6.7.6.1, 6.7.6.2, 6.7.6.3, 6.7.6.4, 6.7.6.5, 6.7.6.6, 6.7.6.7, 6.7.6.8, 6.7.6.9, 6.7.6.10, 6.7.7.1, 6.7.7.2, 6.7.7.3, 6.7.7.4, 6.7.7.5, 6.7.7.6, 6.7.7.7, 6.7.7.8, 6.7.7.9, 6.7.7.10, 6.7.8.1, 6.7.8.2, 6.7.8.3, 6.7.8.4, 6.7.8.5, 6.7.8.6, 6.7.8.7, 6.7.8.8, 6.7.8.9, 6.7.8.10, 6.7.9.1, 6.7.9.2, 6.7.9.3, 6.7.9.4, 6.7.9.5, 6.7.9.6, 6.7.9.7, 6.7.9.8, 6.7.9.9, 6.7.9.10, 6.7.10.1, 6.7.10.2, 6.7.10.3, 6.7.10.4, 6.7.10.5, 6.7.10.6, 6.7.10.7, 6.7.10.8, 6.7.10.9, 6.7.10.10, 6.8.1.1, 6.8.1.2, 6.8.1.3, 6.8.1.4, 6.8.1.5, 6.8.1.6, 6.8.1.7, 6.8.1.8, 6.8.1.9, 6.8.1.10, 6.8.2.1, 6.8.2.2, 6.8.2.3, 6.8.2.4, 6.8.2.5, 6.8.2.6, 6.8.2.7, 6.8.2.8, 6.8.2.9, 6.8.2.10, 6.8.3.1, 6.8.3.2, 6.8.3.3, 6.8.3.4, 6.8.3.5, 6.8.3.6, 6.8.3.7, 6.8.3.8, 6.8.3.9, 6.8.3.10, 6.8.4.1, 6.8.4.2, 6.8.4.3, 6.8.4.4, 6.8.4.5, 6.8.4.6, 6.8.4.7, 6.8.4.8, 6.8.4.9, 6.8.4.10, 6.8.5.1, 6.8.5.2, 6.8.5.3, 6.8.5.4, 6.8.5.5, 6.8.5.6, 6.8.5.7, 6.8.5.8, 6.8.5.9, 6.8.5.10, 6.8.6.1, 6.8.6.2, 6.8.6.3, 6.8.6.4, 6.8.6.5, 6.8.6.6, 6.8.6.7, 6.8.6.8, 6.8.6.9, 6.8.6.10, 6.8.7.1, 6.8.7.2, 6.8.7.3, 6.8.7.4, 6.8.7.5, 6.8.7.6, 6.8.7.7, 6.8.7.8, 6.8.7.9, 6.8.7.10, 6.8.8.1, 6.8.8.2, 6.8.8.3, 6.8.8.4, 6.8.8.5, 6.8.8.6, 6.8.8.7, 6.8.8.8, 6.8.8.9, 6.8.8.10, 6.8.9.1, 6.8.9.2, 6.8.9.3, 6.8.9.4, 6.8.9.5, 6.8.9.6, 6.8.9.7, 6.8.9.8, 6.8.9.9, 6.8.9.10, 6.8.10.1, 6.8.10.2, 6.8.10.3, 6.8.10.4, 6.8.10.5, 6.8.10.6, 6.8.10.7, 6.8.10.8, 6.8.10.9, 6.8.10.10, 6.9.1.1, 6.9.1.2, 6.9.1.3, 6.9.1.4, 6.9.1.5, 6.9.1.6, 6.9.1.7, 6.9.1.8, 6.9.1.9, 6.9.1.10, 6.9.2.1, 6.9.2.2, 6.9.2.3, 6.9.2.4, 6.9.2.5, 6.9.2.6, 6.9.2.7, 6.9.2.8, 6.9.2.9, 6.9.2.10, 6.9.3.1, 6.9.3.2, 6.9.3.3, 6.9.3.4, 6.9.3.5, 6.9.3.6, 6.9.3.7, 6.9.3.8, 6.9.3.9, 6.9.3.10, 6.9.4.1, 6.9.4.2, 6.9.4.3, 6.9.4.4, 6.9.4.5, 6.9.4.6, 6.9.4.7, 6.9.4.8, 6.9.4.9, 6.9.4.10, 6.9.5.1, 6.9.5.2, 6.9.5.3, 6.9.5.4, 6.9.5.5, 6.9.5.6, 6.9.5.7, 6.9.5.8, 6.9.5.9, 6.9.5.10, 6.9.6.1, 6.9.6.2, 6.9.6.3, 6.9.6.4, 6.9.6.5, 6.9.6.6, 6.9.6.7, 6.9.6.8, 6.9.6.9, 6.9.6.10, 6.9.7.1, 6.9.7.2, 6.9.7.3, 6.9.7.4, 6.9.7.5, 6.9.7.6, 6.9.7.7, 6.9.7.8, 6.9.7.9, 6.9.7.10, 6.9.8.1, 6.9.8.2, 6.9.8.3, 6.9.8.4, 6.9.8.5, 6.9.8.6, 6.9.8.7, 6.9.8.8, 6.9.8.9, 6.9.8.10, 6.9.9.1, 6.9.9.2, 6.9.9.3, 6.9.9.4, 6.9.9.5, 6.9.9.6, 6.9.9.7, 6.9.9.8, 6.9.9.9, 6.9.9.10, 6.9.10.1, 6.9.10.2, 6.9.10.3, 6.9.10.4, 6.9.10.5, 6.9.10.6, 6.9.10.7, 6.9.10.8, 6.9.10.9, 6.9.10.10, 6.10.1.1, 6.10.1.2, 6.10.1.3, 6.10.1.4, 6.10.1.5, 6.10.1.6, 6.10.1.7, 6.10.1.8, 6.10.1.9, 6.10.1.10, 6.10.2.1, 6.10.2.2, 6.10.2.3, 6.10.2.4, 6.10.2.5, 6.10.2.6, 6.10.2.7, 6.10.2.8, 6.10.2.9, 6.10.2.10, 6.10.3.1, 6.10.3.2, 6.10.3.3, 6.10.3.4, 6.10.3.5, 6.10.3.6, 6.10.3.7, 6.10.3.8, 6.10.3.9, 6.10.3.10, 6.10.4.1, 6.10.4.2, 6.10.4.3, 6.10.4.4, 6.10.4.5, 6.10.4.6, 6.10.4.7, 6.10.4.8, 6.10.4.9, 6.10.4.10, 6.10.5.1, 6.10.5.2, 6.10.5.3, 6.10.5.4, 6.10.5.5, 6.10.5.6, 6.10.5.7, 6.10.5.8, 6.10.5.9, 6.10.5.10, 6.10.6.1, 6.10.6.2, 6.10.6.3, 6.10.6.4, 6.10.6.5, 6.10.6.6, 6.10.6.7, 6.10.6.8, 6.10.6.9, 6.10.6.10, 6.10.7.1, 6.10.7.2, 6.10.7.3, 6.10.7.4, 6.10.7.5, 6.10.7.6, 6.10.7.7, 6.10.7.8, 6.10.7.9, 6.10.7.10, 6.10.8.1, 6.10.8.2, 6.10.8.3, 6.10.8.4, 6.10.8.5, 6.10.8.6, 6.10.8.7, 6.10.8.8, 6.10.8.9, 6.10.8.10, 6.10.9.1, 6.10.9.2, 6.10.9.3, 6.10.9.4, 6.10.9.5, 6.10.9.6, 6.10.9.7, 6.10.9.8, 6.10.9.9, 6.10.9.10, 6.10.10.1, 6.10.10.2, 6.10.10.3, 6.10.10.4, 6.10.10.5, 6.10.10.6, 6.10.10.7, 6.10.10.8, 6.10.10.9, 6.10.10.10, 7.1.1.1, 7.1.1.2, 7.1.1.3, 7.1.1.4, 7.1.1.5, 7.1.1.6, 7.1.1.7, 7.1.1.8, 7.1.1.9, 7.1.1.10, 7.1.2.1, 7.1.2.2, 7.1.2.3, 7.1.2.4, 7.1.2.5, 7.1.2.6, 7.1.2.7, 7.1.2.8, 7.1.2.9, 7.1.2.10, 7.1.3.1, 7.1.3.2, 7.1.3.3, 7.1.3.4, 7.1.3.5, 7.1.3.6, 7.1.3.7, 7.1.3.8, 7.1.3.9, 7.1.3.10, 7.1.4.1, 7.1.4.2, 7.1.4.3, 7.1.4.4, 7.1.4.5, 7.1.4.6, 7.1.4.7, 7.1.4.8, 7.1.4.9, 7.1.4.10, 7.1.5.1, 7.1.5.2, 7.1.5.3, 7.1.5.4, 7.1.5.5, 7.1.5.6, 7.1.5.7, 7.1.5.8, 7.1.5.9, 7.1.5.10, 7.1.6.1, 7.1.6.2, 7.1.6.3, 7.1.6.4, 7.1.6.5, 7.1.6.6, 7.1.6.7, 7.1.6.8, 7.1.6.9, 7.1.6.10, 7.1.7.1, 7.1.7.2, 7.1.7.3, 7.1.7.4, 7.1.7.5, 7.1.7.6, 7.1.7.7, 7.1.7.8, 7.1.7.9, 7.1.7.10, 7.1.8.1, 7.1.8.2, 7.1.8.3, 7.1.8.4, 7.1.8.5, 7.1.8.6, 7.1.8.7, 7.1.8.8, 7.1.8.9, 7.1.8.10, 7.1.9.1, 7.1.9.2, 7.1.9.3, 7.1.9.4, 7.1.9.5, 7.1.9.6, 7.1.9.7, 7.1.9.8, 7.1.9.9, 7.1.9.10, 7.1.10.1, 7.1.10.2, 7.1.10.3, 7.1.10.4, 7.1.10.5, 7.1.10.6, 7.1.10.7, 7.1.10.8, 7.1.10.9, 7.1.10.10, 7.2.1.1, 7.2.1.2, 7.2.1.3, 7.2.1.4, 7.2.1.5, 7.2.1.6, 7.2.1.7, 7.2.1.8, 7.2.1.9, 7.2.1.10, 7.2.2.1, 7.2.2.2, 7.2.2.3, 7.2.2.4, 7.2.2.5, 7.2.2.6, 7.2.2.7, 7.2.2.8, 7.2.2.9, 7.2.2.10, 7.2.3.1, 7.2.3.2, 7.2.3.3, 7.2.3.4, 7.2.3.5, 7.2.3.6, 7.2.3.7, 7.2.3.8, 7.2.3.9, 7.2.3.10, 7.2.4.1, 7.2.4.2, 7.2.4.3, 7.2.4.4, 7.2.4.5, 7.2.4.6, 7.2.4.7, 7.2.4.8, 7.2.4.9, 7.2.4.10, 7.2.5.1, 7.2.5.2, 7.2.5.3, 7.2.5.4, 7.2.5.5, 7.2.5.6, 7.2.5.7, 7.2.5.8, 7.2.5.9, 7.2.5.10, 7.2.6.1, 7.2.6.2, 7.2.6.3, 7.2.6.4, 7.2.6.5, 7.2.6.6, 7.2.6.7, 7.2.6.8, 7.2.6.9, 7.2.6.10, 7.2.7.1, 7.2.7.2, 7.2.7.3, 7.2.7.4, 7.2.7.5, 7.2.7.6, 7.2.7.7, 7.2.7.8, 7.2.7.9, 7.2.7.10, 7.2.8.1, 7.2.8.2, 7.2.8.3, 7.2.8.4, 7.2.8.5, 7.2.8.6, 7.2.8.7, 7.2.8.8, 7.2.8.9, 7.2.8.10, 7.2.9.1, 7.2.9.2, 7.2.9.3, 7.2.9.4, 7.2.9.5, 7.2.9.6, 7.2.9.7, 7.2.9.8, 7.2.9.9, 7.2.9.10, 7.2.10.1, 7.2.10.2, 7.2.10.3, 7.2.10.4, 7.2.10.5, 7.2.10.6, 7.2.10.7, 7.2.10.8, 7.2.10.9, 7.2.10.10, 7.3.1.1, 7.3.1.2, 7.3.1.3, 7.3.1.4, 7.3.1.5, 7.3.1.6, 7.3.1.7, 7.3.1.8, 7.3.1.9, 7.3.1.10, 7.3.2.1, 7.3.2.2, 7.3.2.3, 7.3.2.4, 7.3.2.5, 7.3.2.6, 7.3.2.7, 7.3.2.8, 7.3.2.9, 7.3.2.10, 7.3.3.1, 7.3.3.2, 7.3.3.3, 7.3.3.4, 7.3.3.5, 7.3.3.6, 7.3.3.7, 7.3.3.8, 7.3.3.9, 7.3.3.10, 7.3.4.1, 7.3.4.2, 7.3.4.3, 7.3.4.4, 7.3.4.5, 7.3.4.6, 7.3.4.7, 7.3.4.8, 7.3.4.9, 7.3.4.10, 7.3.5.1, 7.3.5.2, 7.3.5.3, 7.3.5.4, 7.3.5.5, 7.3.5.6, 7.3.5.7, 7.3.5.8, 7.3.5.9, 7.3.5.10, 7.3.6.1, 7.3.6.2, 7.3.6.3, 7.3.6.4, 7.3.6.5, 7.3.6.6, 7.3.6.7, 7.3.6.8, 7.3.6.9, 7.3.6.10, 7.3.7.1, 7.3.7.2, 7.3.7.3, 7.3.7.4, 7.3.7.5, 7.3.7.6, 7.3.7.7, 7.3.7.8, 7.3.7.9, 7.3.7.10, 7.3.8.1, 7.3.8.2, 7.3.8.3, 7.3.8.4, 7.3.8.5, 7.3.8.6, 7.3.8.7, 7.3.8.8, 7.3.8.9, 7.3.8.10, 7.3.9.1, 7.3.9.2, 7.3.9.3, 7.3.9.4, 7.3.9.5, 7.3.9.6, 7.3.9.7, 7.3.9.8, 7.3.9.9, 7.3.9.10, 7.3.10.1, 7.3.10.2, 7.3.10.3, 7.3.10.4, 7.3.10.5, 7.3.10.6, 7.3.10.7, 7.3.10.8, 7.3.10.9, 7.3.10.10, 7.4.1.1, 7.4.1.2, 7.4.1.3, 7.4.1.4, 7.4.1.5, 7.4.1.6, 7.4.1.7, 7.4.1.8, 7.4.1.9, 7.4.1.10, 7.4.2.1, 7.4.2.2, 7.4.2.3, 7.4.2.4, 7.4.2.5, 7.4.2.6, 7.4.2.7, 7.4.2.8, 7.4.2.9, 7.4.2.10, 7.4.3.1, 7.4.3.2, 7.4.3.3, 7.4.3.4, 7.4.3.5, 7.4.3.6, 7.4.3.7, 7.4.3.8, 7.4.3.9, 7.4.3.10, 7.4.4.1, 7.4.4.2, 7.4.4.3, 7.4.4.4, 7.4.4.5, 7.4.4.6, 7.4.4.7, 7.4.4.8, 7.4.4.9, 7.4.4.10, 7.4.5.1, 7.4.5.2, 7.4.5.3, 7.4.5.4, 7.4.5.5, 7.4.5.6, 7.4.5.7, 7.4.5.8, 7.4.5.9, 7.4.5.10, 7.4.6.1, 7.4.6.2, 7.4.6.3, 7.4.6.4, 7.4.6.5, 7.4.6.6, 7.4.6.7, 7.4.6.8, 7.4.6.9, 7.4.6.10, 7.4.7.1, 7.4.7.2, 7.4.7.3, 7.4.7.4, 7.4.7.5, 7.4.7.6, 7.4.7.7, 7.4.7.8, 7.4.7.9, 7.4.7.10, 7.4.8.1, 7.4.8.2, 7.4.8.3, 7.4.8.4, 7.4.8.5, 7.4.8.6, 7.4.8.7, 7.4.8.8, 7.4.8.9, 7.4.8.10, 7.4.9.1, 7.4.9.2, 7.4.9.3, 7.4.9.4, 7.4.9.5, 7.4.9.6, 7.4.9.7, 7.4.9.8, 7.4.9.9, 7.4.9.10, 7.4.10.1, 7.4.10.2, 7.4.10.3, 7.4.10.4, 7.4.10.5, 7.4.10.6, 7.4.10.7, 7.4.10.8, 7.4.10.9, 7.4.10.10, 7.5.1.1, 7.5.1.2, 7.5.1.3, 7.5.1.4, 7.5.1.5, 7.5.1.6, 7.5.1.7, 7.5.1.8, 7.5.1.9, 7.5.1.10, 7.5.2.1, 7.5.2.2, 7.5.2.3, 7.5.2.4, 7.5.2.5, 7.5.2.6, 7.5.2.7, 7.5.2.8, 7.5.2.9, 7.5.2.10, 7.5.3.1, 7.5.3.2, 7.5.3.3, 7.5.3.4, 7.5.3.5, 7.5.3.6, 7.5.3.7, 7.5.3.8, 7.5.3.9, 7.5.3.10, 7.5.4.1, 7.5.4.2, 7.5.4.3, 7.5.4.4, 7.5.4.5, 7.5.4.6, 7.5.4.7, 7.5.4.8, 7.5.4.9, 7.5.4.10, 7.5.5.1, 7.5.5.2, 7.5.5.3, 7.5.5.4, 7.5.5.5, 7.5.5.6, 7.5.5.7, 7.5.5.8, 7.5.5.9, 7.5.5.10, 7.5.6.1, 7.5.6.2, 7.5.6.3, 7.5.6.4, 7.5.6.5, 7.5.6.6, 7.5.6.7, 7.5.6.8, 7.5.6.9, 7.5.6.10, 7.5.7.1, 7.5.7.2, 7.5.7.3, 7.5.7.4, 7.5.7.5, 7.5.7.6, 7.5.7.7, 7.5.7.8, 7.5.7.9, 7.5.7.10, 7.5.8.1, 7.5.8.2, 7.5.8.3, 7.5.8.4, 7.5.8.5, 7.5.8.6, 7.5.8.7, 7.5.8.8, 7.5.8.9, 7.5.8.10, 7.5.9.1, 7.5.9.2, 7.5.9.3, 7.5.9.4, 7.5.9.5, 7.5.9.6, 7.5.9.7, 7.5.9.8, 7.5.9.9, 7.5.9.10, 7.5.10.1, 7.5.10.2, 7.5.10.3, 7.5.10.4, 7.5.10.5, 7.5.10.6, 7.5.10.7, 7.5.10.8, 7.5.10.9, 7.5.10.10, 7.6.1.1, 7.6.1.2, 7.6.1.3, 7.6.1.4, 7.6.1.5, 7.6.1.6, 7.6.1.7, 7.6.1.8, 7.6.1.9, 7.6.1.10, 7.6.2.1, 7.6.2.2, 7.6.2.3, 7.6.2.4, 7.6.2.5, 7.6.2.6, 7.6.2.7, 7.6.2.8, 7.6.2.9, 7.6.2.10, 7.6.3.1, 7.6.3.2, 7.6.3.3, 7.6.3.4, 7.6.3.5, 7.6.3.6, 7.6.3.7, 7.6.3.8, 7.6.3.9, 7.6.3.10, 7.6.4.1, 7.6.4.2, 7.6.4.3, 7.6.4.4, 7.6.4.5, 7.6.4.6, 7.6.4.7, 7.6.4.8, 7.6.4.9, 7.6.4.10, 7.6.5.1, 7.6.5.2, 7.6.5.3, 7.6.5.4, 7.6.5.5, 7.6.5.6, 7.6.5.7, 7.6.5.8, 7.6.5.9, 7.6.5.10, 7.6.6.1, 7.6.6.2, 7.6.6.3, 7.6.6.4, 7.6.6.5, 7.6.6.6, 7.6.6.7, 7.6.6.8, 7.6.6.9, 7.6.6.10, 7.6.7.1, 7.6.7.2, 7.6.7.3, 7.6.7.4, 7.6.7.5, TABLE B-continued 7.6.7.6, 7.6.7.7, 7.6.7.8, 7.6.7.9, 7.6.7.10, 7.6.8.1, 7.6.8.2, 7.6.8.3, 7.6.8.4, 7.6.8.5, 7.6.8.6, 7.6.8.7, 7.6.8.8, 7.6.8.9, 7.6.8.10, 7.6.9.1, 7.6.9.2, 7.6.9.3, 7.6.9.4, 7.6.9.5, 7.6.9.6, 7.6.9.7, 7.6.9.8, 7.6.9.9, 7.6.9.10, 7.6.10.1, 7.6.10.2, 7.6.10.3, 7.6.10.4, 7.6.10.5, 7.6.10.6, 7.6.10.7, 7.6.10.8, 7.6.10.9, 7.6.10.10, 7.7.1.1, 7.7.1.2, 7.7.1.3, 7.7.1.4, 7.7.1.5, 7.7.1.6, 7.7.1.7, 7.7.1.8, 7.7.1.9, 7.7.1.10, 7.7.2.1, 7.7.2.2, 7.7.2.3, 7.7.2.4, 7.7.2.5, 7.7.2.6, 7.7.2.7, 7.7.2.8, 7.7.2.9, 7.7.2.10, 7.7.3.1, 7.7.3.2, 7.7.3.3, 7.7.3.4, 7.7.3.5, 7.7.3.6, 7.7.3.7, 7.7.3.8, 7.7.3.9, 7.7.3.10, 7.7.4.1, 7.7.4.2, 7.7.4.3, 7.7.4.4, 7.7.4.5, 7.7.4.6, 7.7.4.7, 7.7.4.8, 7.7.4.9, 7.7.4.10, 7.7.5.1, 7.7.5.2, 7.7.5.3, 7.7.5.4, 7.7.5.5, 7.7.5.6, 7.7.5.7, 7.7.5.8, 7.7.5.9, 7.7.5.10, 7.7.6.1, 7.7.6.2, 7.7.6.3, 7.7.6.4, 7.7.6.5, 7.7.6.6, 7.7.6.7, 7.7.6.8, 7.7.6.9, 7.7.6.10, 7.7.7.1, 7.7.7.2, 7.7.7.3, 7.7.7.4, 7.7.7.5, 7.7.7.6, 7.7.7.7, 7.7.7.8, 7.7.7.9, 7.7.7.10, 7.7.8.1, 7.7.8.2, 7.7.8.3, 7.7.8.4, 7.7.8.5, 7.7.8.6, 7.7.8.7, 7.7.8.8, 7.7.8.9, 7.7.8.10, 7.7.9.1, 7.7.9.2, 7.7.9.3, 7.7.9.4, 7.7.9.5, 7.7.9.6, 7.7.9.7, 7.7.9.8, 7.7.9.9, 7.7.9.10, 7.7.10.1, 7.7.10.2, 7.7.10.3, 7.7.10.4, 7.7.10.5, 7.7.10.6, 7.7.10.7, 7.7.10.8, 7.7.10.9, 7.7.10.10, 7.8.1.1, 7.8.1.2, 7.8.1.3, 7.8.1.4, 7.8.1.5, 7.8.1.6, 7.8.1.7, 7.8.1.8, 7.8.1.9, 7.8.1.10, 7.8.2.1, 7.8.2.2, 7.8.2.3, 7.8.2.4, 7.8.2.5, 7.8.2.6, 7.8.2.7, 7.8.2.8, 7.8.2.9, 7.8.2.10, 7.8.3.1, 7.8.3.2, 7.8.3.3, 7.8.3.4, 7.8.3.5, 7.8.3.6, 7.8.3.7, 7.8.3.8, 7.8.3.9, 7.8.3.10, 7.8.4.1, 7.8.4.2, 7.8.4.3, 7.8.4.4, 7.8.4.5, 7.8.4.6, 7.8.4.7, 7.8.4.8, 7.8.4.9, 7.8.4.10, 7.8.5.1, 7.8.5.2, 7.8.5.3, 7.8.5.4, 7.8.5.5, 7.8.5.6, 7.8.5.7, 7.8.5.8, 7.8.5.9, 7.8.5.10, 7.8.6.1, 7.8.6.2, 7.8.6.3, 7.8.6.4, 7.8.6.5, 7.8.6.6, 7.8.6.7, 7.8.6.8, 7.8.6.9, 7.8.6.10, 7.8.7.1, 7.8.7.2, 7.8.7.3, 7.8.7.4, 7.8.7.5, 7.8.7.6, 7.8.7.7, 7.8.7.8, 7.8.7.9, 7.8.7.10, 7.8.8.1, 7.8.8.2, 7.8.8.3, 7.8.8.4, 7.8.8.5, 7.8.8.6, 7.8.8.7, 7.8.8.8, 7.8.8.9, 7.8.8.10, 7.8.9.1, 7.8.9.2, 7.8.9.3, 7.8.9.4, 7.8.9.5, 7.8.9.6, 7.8.9.7, 7.8.9.8, 7.8.9.9, 7.8.9.10, 7.8.10.1, 7.8.10.2, 7.8.10.3, 7.8.10.4, 7.8.10.5, 7.8.10.6, 7.8.10.7, 7.8.10.8, 7.8.10.9, 7.8.10.10, 7.9.1.1, 7.9.1.2, 7.9.1.3, 7.9.1.4, 7.9.1.5, 7.9.1.6, 7.9.1.7, 7.9.1.8, 7.9.1.9, 7.9.1.10, 7.9.2.1, 7.9.2.2, 7.9.2.3, 7.9.2.4, 7.9.2.5, 7.9.2.6, 7.9.2.7, 7.9.2.8, 7.9.2.9, 7.9.2.10, 7.9.3.1, 7.9.3.2, 7.9.3.3, 7.9.3.4, 7.9.3.5, 7.9.3.6, 7.9.3.7, 7.9.3.8, 7.9.3.9, 7.9.3.10, 7.9.4.1, 7.9.4.2, 7.9.4.3, 7.9.4.4, 7.9.4.5, 7.9.4.6, 7.9.4.7, 7.9.4.8, 7.9.4.9, 7.9.4.10, 7.9.5.1, 7.9.5.2, 7.9.5.3, 7.9.5.4, 7.9.5.5, 7.9.5.6, 7.9.5.7, 7.9.5.8, 7.9.5.9, 7.9.5.10, 7.9.6.1, 7.9.6.2, 7.9.6.3, 7.9.6.4, 7.9.6.5, 7.9.6.6, 7.9.6.7, 7.9.6.8, 7.9.6.9, 7.9.6.10, 7.9.7.1, 7.9.7.2, 7.9.7.3, 7.9.7.4, 7.9.7.5, 7.9.7.6, 7.9.7.7, 7.9.7.8, 7.9.7.9, 7.9.7.10, 7.9.8.1, 7.9.8.2, 7.9.8.3, 7.9.8.4, 7.9.8.5, 7.9.8.6, 7.9.8.7, 7.9.8.8, 7.9.8.9, 7.9.8.10, 7.9.9.1, 7.9.9.2, 7.9.9.3, 7.9.9.4, 7.9.9.5, 7.9.9.6, 7.9.9.7, 7.9.9.8, 7.9.9.9, 7.9.9.10, 7.9.10.1, 7.9.10.2, 7.9.10.3, 7.9.10.4, 7.9.10.5, 7.9.10.6, 7.9.10.7, 7.9.10.8, 7.9.10.9, 7.9.10.10, 7.10.1.1, 7.10.1.2, 7.10.1.3, 7.10.1.4, 7.10.1.5, 7.10.1.6, 7.10.1.7, 7.10.1.8, 7.10.1.9, 7.10.1.10, 7.10.2.1, 7.10.2.2, 7.10.2.3, 7.10.2.4, 7.10.2.5, 7.10.2.6, 7.10.2.7, 7.10.2.8, 7.10.2.9, 7.10.2.10, 7.10.3.1, 7.10.3.2, 7.10.3.3, 7.10.3.4, 7.10.3.5, 7.10.3.6, 7.10.3.7, 7.10.3.8, 7.10.3.9, 7.10.3.10, 7.10.4.1, 7.10.4.2, 7.10.4.3, 7.10.4.4, 7.10.4.5, 7.10.4.6, 7.10.4.7, 7.10.4.8, 7.10.4.9, 7.10.4.10, 7.10.5.1, 7.10.5.2, 7.10.5.3, 7.10.5.4, 7.10.5.5, 7.10.5.6, 7.10.5.7, 7.10.5.8, 7.10.5.9, 7.10.5.10, 7.10.6.1, 7.10.6.2, 7.10.6.3, 7.10.6.4, 7.10.6.5, 7.10.6.6, 7.10.6.7, 7.10.6.8, 7.10.6.9, 7.10.6.10, 7.10.7.1, 7.10.7.2, 7.10.7.3, 7.10.7.4, 7.10.7.5, 7.10.7.6, 7.10.7.7, 7.10.7.8, 7.10.7.9, 7.10.7.10, 7.10.8.1, 7.10.8.2, 7.10.8.3, 7.10.8.4, 7.10.8.5, 7.10.8.6, 7.10.8.7, 7.10.8.8, 7.10.8.9, 7.10.8.10, 7.10.9.1, 7.10.9.2, 7.10.9.3, 7.10.9.4, 7.10.9.5, 7.10.9.6, 7.10.9.7, 7.10.9.8, 7.10.9.9, 7.10.9.10, 7.10.10.1, 7.10.10.2, 7.10.10.3, 7.10.10.4, 7.10.10.5, 7.10.10.6, 7.10.10.7, 7.10.10.8, 7.10.10.9, 7.10.10.10, 8.1.1.1, 8.1.1.2, 8.1.1.3, 8.1.1.4, 8.1.1.5, 8.1.1.6, 8.1.1.7, 8.1.1.8, 8.1.1.9, 8.1.1.10, 8.1.2.1, 8.1.2.2, 8.1.2.3, 8.1.2.4, 8.1.2.5, 8.1.2.6, 8.1.2.7, 8.1.2.8, 8.1.2.9, 8.1.2.10, 8.1.3.1, 8.1.3.2, 8.1.3.3, 8.1.3.4, 8.1.3.5, 8.1.3.6, 8.1.3.7, 8.1.3.8, 8.1.3.9, 8.1.3.10, 8.1.4.1, 8.1.4.2, 8.1.4.3, 8.1.4.4, 8.1.4.5, 8.1.4.6, 8.1.4.7, 8.1.4.8, 8.1.4.9, 8.1.4.10, 8.1.5.1, 8.1.5.2, 8.1.5.3, 8.1.5.4, 8.1.5.5, 8.1.5.6, 8.1.5.7, 8.1.5.8, 8.1.5.9, 8.1.5.10, 8.1.6.1, 8.1.6.2, 8.1.6.3, 8.1.6.4, 8.1.6.5, 8.1.6.6, 8.1.6.7, 8.1.6.8, 8.1.6.9, 8.1.6.10, 8.1.7.1, 8.1.7.2, 8.1.7.3, 8.1.7.4, 8.1.7.5, 8.1.7.6, 8.1.7.7, 8.1.7.8, 8.1.7.9, 8.1.7.10, 8.1.8.1, 8.1.8.2, 8.1.8.3, 8.1.8.4, 8.1.8.5, 8.1.8.6, 8.1.8.7, 8.1.8.8, 8.1.8.9, 8.1.8.10, 8.1.9.1, 8.1.9.2, 8.1.9.3, 8.1.9.4, 8.1.9.5, 8.1.9.6, 8.1.9.7, 8.1.9.8, 8.1.9.9, 8.1.9.10, 8.1.10.1, 8.1.10.2, 8.1.10.3, 8.1.10.4, 8.1.10.5, 8.1.10.6, 8.1.10.7, 8.1.10.8, 8.1.10.9, 8.1.10.10, 8.2.1.1, 8.2.1.2, 8.2.1.3, 8.2.1.4, 8.2.1.5, 8.2.1.6, 8.2.1.7, 8.2.1.8, 8.2.1.9, 8.2.1.10, 8.2.2.1, 8.2.2.2, 8.2.2.3, 8.2.2.4, 8.2.2.5, 8.2.2.6, 8.2.2.7, 8.2.2.8, 8.2.2.9, 8.2.2.10, 8.2.3.1, 8.2.3.2, 8.2.3.3, 8.2.3.4, 8.2.3.5, 8.2.3.6, 8.2.3.7, 8.2.3.8, 8.2.3.9, 8.2.3.10, 8.2.4.1, 8.2.4.2, 8.2.4.3, 8.2.4.4, 8.2.4.5, 8.2.4.6, 8.2.4.7, 8.2.4.8, 8.2.4.9, 8.2.4.10, 8.2.5.1, 8.2.5.2, 8.2.5.3, 8.2.5.4, 8.2.5.5, 8.2.5.6, 8.2.5.7, 8.2.5.8, 8.2.5.9, 8.2.5.10, 8.2.6.1, 8.2.6.2, 8.2.6.3, 8.2.6.4, 8.2.6.5, 8.2.6.6, 8.2.6.7, 8.2.6.8, 8.2.6.9, 8.2.6.10, 8.2.7.1, 8.2.7.2, 8.2.7.3, 8.2.7.4, 8.2.7.5, 8.2.7.6, 8.2.7.7, 8.2.7.8, 8.2.7.9, 8.2.7.10, 8.2.8.1, 8.2.8.2, 8.2.8.3, 8.2.8.4, 8.2.8.5, 8.2.8.6, 8.2.8.7, 8.2.8.8, 8.2.8.9, 8.2.8.10, 8.2.9.1, 8.2.9.2, 8.2.9.3, 8.2.9.4, 8.2.9.5, 8.2.9.6, 8.2.9.7, 8.2.9.8, 8.2.9.9, 8.2.9.10, 8.2.10.1, 8.2.10.2, 8.2.10.3, 8.2.10.4, 8.2.10.5, 8.2.10.6, 8.2.10.7, 8.2.10.8, 8.2.10.9, 8.2.10.10, 8.3.1.1, 8.3.1.2, 8.3.1.3, 8.3.1.4, 8.3.1.5, 8.3.1.6, 8.3.1.7, 8.3.1.8, 8.3.1.9, 8.3.1.10, 8.3.2.1, 8.3.2.2, 8.3.2.3, 8.3.2.4, 8.3.2.5, 8.3.2.6, 8.3.2.7, 8.3.2.8, 8.3.2.9, 8.3.2.10, 8.3.3.1, 8.3.3.2, 8.3.3.3, 8.3.3.4, 8.3.3.5, 8.3.3.6, 8.3.3.7, 8.3.3.8, 8.3.3.9, 8.3.3.10, 8.3.4.1, 8.3.4.2, 8.3.4.3, 8.3.4.4, 8.3.4.5, 8.3.4.6, 8.3.4.7, 8.3.4.8, 8.3.4.9, 8.3.4.10, 8.3.5.1, 8.3.5.2, 8.3.5.3, 8.3.5.4, 8.3.5.5, 8.3.5.6, 8.3.5.7, 8.3.5.8, 8.3.5.9, 8.3.5.10, 8.3.6.1, 8.3.6.2, 8.3.6.3, 8.3.6.4, 8.3.6.5, 8.3.6.6, 8.3.6.7, 8.3.6.8, 8.3.6.9, 8.3.6.10, 8.3.7.1, 8.3.7.2, 8.3.7.3, 8.3.7.4, 8.3.7.5, 8.3.7.6, 8.3.7.7, 8.3.7.8, 8.3.7.9, 8.3.7.10, 8.3.8.1, 8.3.8.2, 8.3.8.3, 8.3.8.4, 8.3.8.5, 8.3.8.6, 8.3.8.7, 8.3.8.8, 8.3.8.9, 8.3.8.10, 8.3.9.1, 8.3.9.2, 8.3.9.3, 8.3.9.4, 8.3.9.5, 8.3.9.6, 8.3.9.7, 8.3.9.8, 8.3.9.9, 8.3.9.10, 8.3.10.1, 8.3.10.2, 8.3.10.3, 8.3.10.4, 8.3.10.5, 8.3.10.6, 8.3.10.7, 8.3.10.8, 8.3.10.9, 8.3.10.10, 8.4.1.1, 8.4.1.2, 8.4.1.3, 8.4.1.4, 8.4.1.5, 8.4.1.6, 8.4.1.7, 8.4.1.8, 8.4.1.9, 8.4.1.10, 8.4.2.1, 8.4.2.2, 8.4.2.3, 8.4.2.4, 8.4.2.5, 8.4.2.6, 8.4.2.7, 8.4.2.8, 8.4.2.9, 8.4.2.10, 8.4.3.1, 8.4.3.2, 8.4.3.3, 8.4.3.4, 8.4.3.5, 8.4.3.6, 8.4.3.7, 8.4.3.8, 8.4.3.9, 8.4.3.10, 8.4.4.1, 8.4.4.2, 8.4.4.3, 8.4.4.4, 8.4.4.5, 8.4.4.6, 8.4.4.7, 8.4.4.8, 8.4.4.9, 8.4.4.10, 8.4.5.1, 8.4.5.2, 8.4.5.3, 8.4.5.4, 8.4.5.5, 8.4.5.6, 8.4.5.7, 8.4.5.8, 8.4.5.9, 8.4.5.10, 8.4.6.1, 8.4.6.2, 8.4.6.3, 8.4.6.4, 8.4.6.5, 8.4.6.6, 8.4.6.7, 8.4.6.8, 8.4.6.9, 8.4.6.10, 8.4.7.1, 8.4.7.2, 8.4.7.3, 8.4.7.4, 8.4.7.5, 8.4.7.6, 8.4.7.7, 8.4.7.8, 8.4.7.9, 8.4.7.10, 8.4.8.1, 8.4.8.2, 8.4.8.3, 8.4.8.4, 8.4.8.5, 8.4.8.6, 8.4.8.7, 8.4.8.8, 8.4.8.9, 8.4.8.10, 8.4.9.1, 8.4.9.2, 8.4.9.3, 8.4.9.4, 8.4.9.5, 8.4.9.6, 8.4.9.7, 8.4.9.8, 8.4.9.9, 8.4.9.10, 8.4.10.1, 8.4.10.2, 8.4.10.3, 8.4.10.4, 8.4.10.5, 8.4.10.6, 8.4.10.7, 8.4.10.8, 8.4.10.9, 8.4.10.10, 8.5.1.1, 8.5.1.2, 8.5.1.3, 8.5.1.4, 8.5.1.5, 8.5.1.6, 8.5.1.7, 8.5.1.8, 8.5.1.9, 8.5.1.10, 8.5.2.1, 8.5.2.2, 8.5.2.3, 8.5.2.4, 8.5.2.5, 8.5.2.6, 8.5.2.7, 8.5.2.8, 8.5.2.9, 8.5.2.10, 8.5.3.1, 8.5.3.2, 8.5.3.3, 8.5.3.4, 8.5.3.5, 8.5.3.6, 8.5.3.7, 8.5.3.8, 8.5.3.9, 8.5.3.10, 8.5.4.1, 8.5.4.2, 8.5.4.3, 8.5.4.4, 8.5.4.5, 8.5.4.6, 8.5.4.7, 8.5.4.8, 8.5.4.9, 8.5.4.10, 8.5.5.1, 8.5.5.2, 8.5.5.3, 8.5.5.4, 8.5.5.5, 8.5.5.6, 8.5.5.7, 8.5.5.8, 8.5.5.9, 8.5.5.10, 8.5.6.1, 8.5.6.2, 8.5.6.3, 8.5.6.4, 8.5.6.5, 8.5.6.6, 8.5.6.7, 8.5.6.8, 8.5.6.9, 8.5.6.10, 8.5.7.1, 8.5.7.2, 8.5.7.3, 8.5.7.4, 8.5.7.5, 8.5.7.6, 8.5.7.7, 8.5.7.8, 8.5.7.9, 8.5.7.10, 8.5.8.1, 8.5.8.2, 8.5.8.3, 8.5.8.4, 8.5.8.5, 8.5.8.6, 8.5.8.7, 8.5.8.8, 8.5.8.9, 8.5.8.10, 8.5.9.1, 8.5.9.2, 8.5.9.3, 8.5.9.4, 8.5.9.5, 8.5.9.6, 8.5.9.7, 8.5.9.8, 8.5.9.9,

TABLE B-continued 8.5.9.10, 8.5.10.1, 8.5.10.2, 8.5.10.3, 8.5.10.4, 8.5.10.5, 8.5.10.6, 8.5.10.7, 8.5.10.8, 8.5.10.9, 8.5.10.10, 8.6.1.1, 8.6.1.2, 8.6.1.3, 8.6.1.4, 8.6.1.5, 8.6.1.6, 8.6.1.7, 8.6.1.8, 8.6.1.9, 8.6.1.10, 8.6.2.1, 8.6.2.2, 8.6.2.3, 8.6.2.4, 8.6.2.5, 8.6.2.6, 8.6.2.7, 8.6.2.8, 8.6.2.9, 8.6.2.10, 8.6.3.1, 8.6.3.2, 8.6.3.3, 8.6.3.4, 8.6.3.5, 8.6.3.6, 8.6.3.7, 8.6.3.8, 8.6.3.9, 8.6.3.10, 8.6.4.1, 8.6.4.2, 8.6.4.3, 8.6.4.4, 8.6.4.5, 8.6.4.6, 8.6.4.7, 8.6.4.8, 8.6.4.9, 8.6.4.10, 8.6.5.1, 8.6.5.2, 8.6.5.3, 8.6.5.4, 8.6.5.5, 8.6.5.6, 8.6.5.7, 8.6.5.8, 8.6.5.9, 8.6.5.10, 8.6.6.1, 8.6.6.2, 8.6.6.3, 8.6.6.4, 8.6.6.5, 8.6.6.6, 8.6.6.7, 8.6.6.8, 8.6.6.9, 8.6.6.10, 8.6.7.1, 8.6.7.2, 8.6.7.3, 8.6.7.4, 8.6.7.5, 8.6.7.6, 8.6.7.7, 8.6.7.8, 8.6.7.9, 8.6.7.10, 8.6.8.1, 8.6.8.2, 8.6.8.3, 8.6.8.4, 8.6.8.5, 8.6.8.6, 8.6.8.7, 8.6.8.8, 8.6.8.9, 8.6.8.10, 8.6.9.1, 8.6.9.2, 8.6.9.3, 8.6.9.4, 8.6.9.5, 8.6.9.6, 8.6.9.7, 8.6.9.8, 8.6.9.9, 8.6.9.10, 8.6.10.1, 8.6.10.2, 8.6.10.3, 8.6.10.4, 8.6.10.5, 8.6.10.6, 8.6.10.7, 8.6.10.8, 8.6.10.9, 8.6.10.10, 8.7.1.1, 8.7.1.2, 8.7.1.3, 8.7.1.4, 8.7.1.5, 8.7.1.6, 8.7.1.7, 8.7.1.8, 8.7.1.9, 8.7.1.10, 8.7.2.1, 8.7.2.2, 8.7.2.3, 8.7.2.4, 8.7.2.5, 8.7.2.6, 8.7.2.7, 8.7.2.8, 8.7.2.9, 8.7.2.10, 8.7.3.1, 8.7.3.2, 8.7.3.3, 8.7.3.4, 8.7.3.5, 8.7.3.6, 8.7.3.7, 8.7.3.8, 8.7.3.9, 8.7.3.10, 8.7.4.1, 8.7.4.2, 8.7.4.3, 8.7.4.4, 8.7.4.5, 8.7.4.6, 8.7.4.7, 8.7.4.8, 8.7.4.9, 8.7.4.10, 8.7.5.1, 8.7.5.2, 8.7.5.3, 8.7.5.4, 8.7.5.5, 8.7.5.6, 8.7.5.7, 8.7.5.8, 8.7.5.9, 8.7.5.10, 8.7.6.1, 8.7.6.2, 8.7.6.3, 8.7.6.4, 8.7.6.5, 8.7.6.6, 8.7.6.7, 8.7.6.8, 8.7.6.9, 8.7.6.10, 8.7.7.1, 8.7.7.2, 8.7.7.3, 8.7.7.4, 8.7.7.5, 8.7.7.6, 8.7.7.7, 8.7.7.8, 8.7.7.9, 8.7.7.10, 8.7.8.1, 8.7.8.2, 8.7.8.3, 8.7.8.4, 8.7.8.5, 8.7.8.6, 8.7.8.7, 8.7.8.8, 8.7.8.9, 8.7.8.10, 8.7.9.1, 8.7.9.2, 8.7.9.3, 8.7.9.4, 8.7.9.5, 8.7.9.6, 8.7.9.7, 8.7.9.8, 8.7.9.9, 8.7.9.10, 8.7.10.1, 8.7.10.2, 8.7.10.3, 8.7.10.4, 8.7.10.5, 8.7.10.6, 8.7.10.7, 8.7.10.8, 8.7.10.9, 8.7.10.10, 8.8.1.1, 8.8.1.2, 8.8.1.3, 8.8.1.4, 8.8.1.5, 8.8.1.6, 8.8.1.7, 8.8.1.8, 8.8.1.9, 8.8.1.10, 8.8.2.1, 8.8.2.2, 8.8.2.3, 8.8.2.4, 8.8.2.5, 8.8.2.6, 8.8.2.7, 8.8.2.8, 8.8.2.9, 8.8.2.10, 8.8.3.1, 8.8.3.2, 8.8.3.3, 8.8.3.4, 8.8.3.5, 8.8.3.6, 8.8.3.7, 8.8.3.8, 8.8.3.9, 8.8.3.10, 8.8.4.1, 8.8.4.2, 8.8.4.3, 8.8.4.4, 8.8.4.5, 8.8.4.6, 8.8.4.7, 8.8.4.8, 8.8.4.9, 8.8.4.10, 8.8.5.1, 8.8.5.2, 8.8.5.3, 8.8.5.4, 8.8.5.5, 8.8.5.6, 8.8.5.7, 8.8.5.8, 8.8.5.9, 8.8.5.10, 8.8.6.1, 8.8.6.2, 8.8.6.3, 8.8.6.4, 8.8.6.5, 8.8.6.6, 8.8.6.7, 8.8.6.8, 8.8.6.9, 8.8.6.10, 8.8.7.1, 8.8.7.2, 8.8.7.3, 8.8.7.4, 8.8.7.5, 8.8.7.6, 8.8.7.7, 8.8.7.8, 8.8.7.9, 8.8.7.10, 8.8.8.1, 8.8.8.2, 8.8.8.3, 8.8.8.4, 8.8.8.5, 8.8.8.6, 8.8.8.7, 8.8.8.8, 8.8.8.9, 8.8.8.10, 8.8.9.1, 8.8.9.2, 8.8.9.3, 8.8.9.4, 8.8.9.5, 8.8.9.6, 8.8.9.7, 8.8.9.8, 8.8.9.9, 8.8.9.10, 8.8.10.1, 8.8.10.2, 8.8.10.3, 8.8.10.4, 8.8.10.5, 8.8.10.6, 8.8.10.7, 8.8.10.8, 8.8.10.9, 8.8.10.10, 8.9.1.1, 8.9.1.2, 8.9.1.3, 8.9.1.4, 8.9.1.5, 8.9.1.6, 8.9.1.7, 8.9.1.8, 8.9.1.9, 8.9.1.10, 8.9.2.1, 8.9.2.2, 8.9.2.3, 8.9.2.4, 8.9.2.5, 8.9.2.6, 8.9.2.7, 8.9.2.8, 8.9.2.9, 8.9.2.10, 8.9.3.1, 8.9.3.2, 8.9.3.3, 8.9.3.4, 8.9.3.5, 8.9.3.6, 8.9.3.7, 8.9.3.8, 8.9.3.9, 8.9.3.10, 8.9.4.1, 8.9.4.2, 8.9.4.3, 8.9.4.4, 8.9.4.5, 8.9.4.6, 8.9.4.7, 8.9.4.8, 8.9.4.9, 8.9.4.10, 8.9.5.1, 8.9.5.2, 8.9.5.3, 8.9.5.4, 8.9.5.5, 8.9.5.6, 8.9.5.7, 8.9.5.8, 8.9.5.9, 8.9.5.10, 8.9.6.1, 8.9.6.2, 8.9.6.3, 8.9.6.4, 8.9.6.5, 8.9.6.6, 8.9.6.7, 8.9.6.8, 8.9.6.9, 8.9.6.10, 8.9.7.1, 8.9.7.2, 8.9.7.3, 8.9.7.4, 8.9.7.5, 8.9.7.6, 8.9.7.7, 8.9.7.8, 8.9.7.9, 8.9.7.10, 8.9.8.1, 8.9.8.2, 8.9.8.3, 8.9.8.4, 8.9.8.5, 8.9.8.6, 8.9.8.7, 8.9.8.8, 8.9.8.9, 8.9.8.10, 8.9.9.1, 8.9.9.2, 8.9.9.3, 8.9.9.4, 8.9.9.5, 8.9.9.6, 8.9.9.7, 8.9.9.8, 8.9.9.9, 8.9.9.10, 8.9.10.1, 8.9.10.2, 8.9.10.3, 8.9.10.4, 8.9.10.5, 8.9.10.6, 8.9.10.7, 8.9.10.8, 8.9.10.9, 8.9.10.10, 8.10.1.1, 8.10.1.2, 8.10.1.3, 8.10.1.4, 8.10.1.5, 8.10.1.6, 8.10.1.7, 8.10.1.8, 8.10.1.9, 8.10.1.10, 8.10.2.1, 8.10.2.2, 8.10.2.3, 8.10.2.4, 8.10.2.5, 8.10.2.6, 8.10.2.7, 8.10.2.8, 8.10.2.9, 8.10.2.10, 8.10.3.1, 8.10.3.2, 8.10.3.3, 8.10.3.4, 8.10.3.5, 8.10.3.6, 8.10.3.7, 8.10.3.8, 8.10.3.9, 8.10.3.10, 8.10.4.1, 8.10.4.2, 8.10.4.3, 8.10.4.4, 8.10.4.5, 8.10.4.6, 8.10.4.7, 8.10.4.8, 8.10.4.9, 8.10.4.10, 8.10.5.1, 8.10.5.2, 8.10.5.3, 8.10.5.4, 8.10.5.5, 8.10.5.6, 8.10.5.7, 8.10.5.8, 8.10.5.9, 8.10.5.10, 8.10.6.1, 8.10.6.2, 8.10.6.3, 8.10.6.4, 8.10.6.5, 8.10.6.6, 8.10.6.7, 8.10.6.8, 8.10.6.9, 8.10.6.10, 8.10.7.1, 8.10.7.2, 8.10.7.3, 8.10.7.4, 8.10.7.5, 8.10.7.6, 8.10.7.7, 8.10.7.8, 8.10.7.9, 8.10.7.10, 8.10.8.1, 8.10.8.2, 8.10.8.3, 8.10.8.4, 8.10.8.5, 8.10.8.6, 8.10.8.7, 8.10.8.8, 8.10.8.9, 8.10.8.10, 8.10.9.1, 8.10.9.2, 8.10.9.3, 8.10.9.4, 8.10.9.5, 8.10.9.6, 8.10.9.7, 8.10.9.8, 8.10.9.9, 8.10.9.10, 8.10.10.1, 8.10.10.2, 8.10.10.3, 8.10.10.4, 8.10.10.5, 8.10.10.6, 8.10.10.7, 8.10.10.8, 8.10.10.9, 8.10.10.10, 9.1.1.1, 9.1.1.2, 9.1.1.3, 9.1.1.4, 9.1.1.5, 9.1.1.6, 9.1.1.7, 9.1.1.8, 9.1.1.9, 9.1.1.10, 9.1.2.1, 9.1.2.2, 9.1.2.3, 9.1.2.4, 9.1.2.5, 9.1.2.6, 9.1.2.7, 9.1.2.8, 9.1.2.9, 9.1.2.10, 9.1.3.1, 9.1.3.2, 9.1.3.3, 9.1.3.4, 9.1.3.5, 9.1.3.6, 9.1.3.7, 9.1.3.8, 9.1.3.9, 9.1.3.10, 9.1.4.1, 9.1.4.2, 9.1.4.3, 9.1.4.4, 9.1.4.5, 9.1.4.6, 9.1.4.7, 9.1.4.8, 9.1.4.9, 9.1.4.10, 9.1.5.1, 9.1.5.2, 9.1.5.3, 9.1.5.4, 9.1.5.5, 9.1.5.6, 9.1.5.7, 9.1.5.8, 9.1.5.9, 9.1.5.10, 9.1.6.1, 9.1.6.2, 9.1.6.3, 9.1.6.4, 9.1.6.5, 9.1.6.6, 9.1.6.7, 9.1.6.8, 9.1.6.9, 9.1.6.10, 9.1.7.1, 9.1.7.2, 9.1.7.3, 9.1.7.4, 9.1.7.5, 9.1.7.6, 9.1.7.7, 9.1.7.8, 9.1.7.9, 9.1.7.10, 9.1.8.1, 9.1.8.2, 9.1.8.3, 9.1.8.4, 9.1.8.5, 9.1.8.6, 9.1.8.7, 9.1.8.8, 9.1.8.9, 9.1.8.10, 9.1.9.1, 9.1.9.2, 9.1.9.3, 9.1.9.4, 9.1.9.5, 9.1.9.6, 9.1.9.7, 9.1.9.8, 9.1.9.9, 9.1.9.10, 9.1.10.1, 9.1.10.2, 9.1.10.3, 9.1.10.4, 9.1.10.5, 9.1.10.6, 9.1.10.7, 9.1.10.8, 9.1.10.9, 9.1.10.10, 9.2.1.1, 9.2.1.2, 9.2.1.3, 9.2.1.4, 9.2.1.5, 9.2.1.6, 9.2.1.7, 9.2.1.8, 9.2.1.9, 9.2.1.10, 9.2.2.1, 9.2.2.2, 9.2.2.3, 9.2.2.4, 9.2.2.5, 9.2.2.6, 9.2.2.7, 9.2.2.8, 9.2.2.9, 9.2.2.10, 9.2.3.1, 9.2.3.2, 9.2.3.3, 9.2.3.4, 9.2.3.5, 9.2.3.6, 9.2.3.7, 9.2.3.8, 9.2.3.9, 9.2.3.10, 9.2.4.1, 9.2.4.2, 9.2.4.3, 9.2.4.4, 9.2.4.5, 9.2.4.6, 9.2.4.7, 9.2.4.8, 9.2.4.9, 9.2.4.10, 9.2.5.1, 9.2.5.2, 9.2.5.3, 9.2.5.4, 9.2.5.5, 9.2.5.6, 9.2.5.7, 9.2.5.8, 9.2.5.9, 9.2.5.10, 9.2.6.1, 9.2.6.2, 9.2.6.3, 9.2.6.4, 9.2.6.5, 9.2.6.6, 9.2.6.7, 9.2.6.8, 9.2.6.9, 9.2.6.10, 9.2.7.1, 9.2.7.2, 9.2.7.3, 9.2.7.4, 9.2.7.5, 9.2.7.6, 9.2.7.7, 9.2.7.8, 9.2.7.9, 9.2.7.10, 9.2.8.1, 9.2.8.2, 9.2.8.3, 9.2.8.4, 9.2.8.5, 9.2.8.6, 9.2.8.7, 9.2.8.8, 9.2.8.9, 9.2.8.10, 9.2.9.1, 9.2.9.2, 9.2.9.3, 9.2.9.4, 9.2.9.5, 9.2.9.6, 9.2.9.7, 9.2.9.8, 9.2.9.9, 9.2.9.10, 9.2.10.1, 9.2.10.2, 9.2.10.3, 9.2.10.4, 9.2.10.5, 9.2.10.6, 9.2.10.7, 9.2.10.8, 9.2.10.9, 9.2.10.10, 9.3.1.1, 9.3.1.2, 9.3.1.3, 9.3.1.4, 9.3.1.5, 9.3.1.6, 9.3.1.7, 9.3.1.8, 9.3.1.9, 9.3.1.10, 9.3.2.1, 9.3.2.2, 9.3.2.3, 9.3.2.4, 9.3.2.5, 9.3.2.6, 9.3.2.7, 9.3.2.8, 9.3.2.9, 9.3.2.10, 9.3.3.1, 9.3.3.2, 9.3.3.3, 9.3.3.4, 9.3.3.5, 9.3.3.6, 9.3.3.7, 9.3.3.8, 9.3.3.9, 9.3.3.10, 9.3.4.1, 9.3.4.2, 9.3.4.3, 9.3.4.4, 9.3.4.5, 9.3.4.6, 9.3.4.7, 9.3.4.8, 9.3.4.9, 9.3.4.10, 9.3.5.1, 9.3.5.2, 9.3.5.3, 9.3.5.4, 9.3.5.5, 9.3.5.6, 9.3.5.7, 9.3.5.8, 9.3.5.9, 9.3.5.10, 9.3.6.1, 9.3.6.2, 9.3.6.3, 9.3.6.4, 9.3.6.5, 9.3.6.6, 9.3.6.7, 9.3.6.8, 9.3.6.9, 9.3.6.10, 9.3.7.1, 9.3.7.2, 9.3.7.3, 9.3.7.4, 9.3.7.5, 9.3.7.6, 9.3.7.7, 9.3.7.8, 9.3.7.9, 9.3.7.10, 9.3.8.1, 9.3.8.2, 9.3.8.3, 9.3.8.4, 9.3.8.5, 9.3.8.6, 9.3.8.7, 9.3.8.8, 9.3.8.9, 9.3.8.10, 9.3.9.1, 9.3.9.2, 9.3.9.3, 9.3.9.4, 9.3.9.5, 9.3.9.6, 9.3.9.7, 9.3.9.8, 9.3.9.9, 9.3.9.10, 9.3.10.1, 9.3.10.2, 9.3.10.3, 9.3.10.4, 9.3.10.5, 9.3.10.6, 9.3.10.7, 9.3.10.8, 9.3.10.9, 9.3.10.10, 9.4.1.1, 9.4.1.2, 9.4.1.3, 9.4.1.4, 9.4.1.5, 9.4.1.6, 9.4.1.7, 9.4.1.8, 9.4.1.9, 9.4.1.10, 9.4.2.1, 9.4.2.2, 9.4.2.3, 9.4.2.4, 9.4.2.5, 9.4.2.6, 9.4.2.7, 9.4.2.8, 9.4.2.9, 9.4.2.10, 9.4.3.1, 9.4.3.2, 9.4.3.3, 9.4.3.4, 9.4.3.5, 9.4.3.6, 9.4.3.7, 9.4.3.8, 9.4.3.9, 9.4.3.10, 9.4.4.1, 9.4.4.2, 9.4.4.3, 9.4.4.4, 9.4.4.5, 9.4.4.6, 9.4.4.7, 9.4.4.8, 9.4.4.9, 9.4.4.10, 9.4.5.1, 9.4.5.2, 9.4.5.3, 9.4.5.4, 9.4.5.5, 9.4.5.6, 9.4.5.7, 9.4.5.8, 9.4.5.9, 9.4.5.10, 9.4.6.1, 9.4.6.2, 9.4.6.3, 9.4.6.4, 9.4.6.5, 9.4.6.6, 9.4.6.7, 9.4.6.8, 9.4.6.9, 9.4.6.10, 9.4.7.1, 9.4.7.2, 9.4.7.3, 9.4.7.4, 9.4.7.5, 9.4.7.6, 9.4.7.7, 9.4.7.8, 9.4.7.9, 9.4.7.10, 9.4.8.1, 9.4.8.2, 9.4.8.3, 9.4.8.4, 9.4.8.5, 9.4.8.6, 9.4.8.7, 9.4.8.8, 9.4.8.9, 9.4.8.10, 9.4.9.1, 9.4.9.2, 9.4.9.3, 9.4.9.4, 9.4.9.5, 9.4.9.6, 9.4.9.7, 9.4.9.8, 9.4.9.9, 9.4.9.10, 9.4.10.1, 9.4.10.2, 9.4.10.3, 9.4.10.4, 9.4.10.5, 9.4.10.6, 9.4.10.7, 9.4.10.8, 9.4.10.9, 9.4.10.10, 9.5.1.1, 9.5.1.2, 9.5.1.3, 9.5.1.4, 9.5.1.5, 9.5.1.6, 9.5.1.7, 9.5.1.8, 9.5.1.9, 9.5.1.10, 9.5.2.1, TABLE B-continued 9.5.2.2, 9.5.2.3, 9.5.2.4, 9.5.2.5, 9.5.2.6, 9.5.2.7, 9.5.2.8, 9.5.2.9, 9.5.2.10, 9.5.3.1, 9.5.3.2, 9.5.3.3,
9.5.3.4, 9.5.3.5, 9.5.3.6, 9.5.3.7, 9.5.3.8, 9.5.3.9, 9.5.3.10, 9.5.4.1, 9.5.4.2, 9.5.4.3, 9.5.4.4, 9.5.4.5,
9.5.4.6, 9.5.4.7, 9.5.4.8, 9.5.4.9, 9.5.4.10, 9.5.5.1, 9.5.5.2, 9.5.5.3, 9.5.5.4, 9.5.5.5, 9.5.5.6, 9.5.5.7,
9.5.5.8, 9.5.5.9, 9.5.5.10, 9.5.6.1, 9.5.6.2, 9.5.6.3, 9.5.6.4, 9.5.6.5, 9.5.6.6, 9.5.6.7, 9.5.6.8, 9.5.6.9,
9.5.6.10, 9.5.7.1, 9.5.7.2, 9.5.7.3, 9.5.7.4, 9.5.7.5, 9.5.7.6, 9.5.7.7, 9.5.7.8, 9.5.7.9, 9.5.7.10, 9.5.8.1,
9.5.8.2, 9.5.8.3, 9.5.8.4, 9.5.8.5, 9.5.8.6, 9.5.8.7, 9.5.8.8, 9.5.8.9, 9.5.8.10, 9.5.9.1, 9.5.9.2, 9.5.9.3,
9.5.9.4, 9.5.9.5, 9.5.9.6, 9.5.9.7, 9.5.9.8, 9.5.9.9, 9.5.9.10, 9.5.10.1, 9.5.10.2, 9.5.10.3, 9.5.10.4,
9.5.10.5, 9.5.10.6, 9.5.10.7, 9.5.10.8, 9.5.10.9, 9.5.10.10, 9.6.1.1, 9.6.1.2, 9.6.1.3, 9.6.1.4, 9.6.1.5,
9.6.1.6, 9.6.1.7, 9.6.1.8, 9.6.1.9, 9.6.1.10, 9.6.2.1, 9.6.2.2, 9.6.2.3, 9.6.2.4, 9.6.2.5, 9.6.2.6, 9.6.2.7,
9.6.2.8, 9.6.2.9, 9.6.2.10, 9.6.3.1, 9.6.3.2, 9.6.3.3, 9.6.3.4, 9.6.3.5, 9.6.3.6, 9.6.3.7, 9.6.3.8, 9.6.3.9,
9.6.3.10, 9.6.4.1, 9.6.4.2, 9.6.4.3, 9.6.4.4, 9.6.4.5, 9.6.4.6, 9.6.4.7, 9.6.4.8, 9.6.4.9, 9.6.4.10, 9.6.5.1,
9.6.5.2, 9.6.5.3, 9.6.5.4, 9.6.5.5, 9.6.5.6, 9.6.5.7, 9.6.5.8, 9.6.5.9, 9.6.5.10, 9.6.6.1, 9.6.6.2, 9.6.6.3,
9.6.6.4, 9.6.6.5, 9.6.6.6, 9.6.6.7, 9.6.6.8, 9.6.6.9, 9.6.6.10, 9.6.7.1, 9.6.7.2, 9.6.7.3, 9.6.7.4, 9.6.7.5,
9.6.7.6, 9.6.7.7, 9.6.7.8, 9.6.7.9, 9.6.7.10, 9.6.8.1, 9.6.8.2, 9.6.8.3, 9.6.8.4, 9.6.8.5, 9.6.8.6, 9.6.8.7,
9.6.8.8, 9.6.8.9, 9.6.8.10, 9.6.9.1, 9.6.9.2, 9.6.9.3, 9.6.9.4, 9.6.9.5, 9.6.9.6, 9.6.9.7, 9.6.9.8, 9.6.9.9,
9.6.9.10, 9.6.10.1, 9.6.10.2, 9.6.10.3, 9.6.10.4, 9.6.10.5, 9.6.10.6, 9.6.10.7, 9.6.10.8, 9.6.10.9,
9.6.10.10, 9.7.1.1, 9.7.1.2, 9.7.1.3, 9.7.1.4, 9.7.1.5, 9.7.1.6, 9.7.1.7, 9.7.1.8, 9.7.1.9, 9.7.1.10, 9.7.2.1,
9.7.2.2, 9.7.2.3, 9.7.2.4, 9.7.2.5, 9.7.2.6, 9.7.2.7, 9.7.2.8, 9.7.2.9, 9.7.2.10, 9.7.3.1, 9.7.3.2, 9.7.3.3,
9.7.3.4, 9.7.3.5, 9.7.3.6, 9.7.3.7, 9.7.3.8, 9.7.3.9, 9.7.3.10, 9.7.4.1, 9.7.4.2, 9.7.4.3, 9.7.4.4, 9.7.4.5,
9.7.4.6, 9.7.4.7, 9.7.4.8, 9.7.4.9, 9.7.4.10, 9.7.5.1, 9.7.5.2, 9.7.5.3, 9.7.5.4, 9.7.5.5, 9.7.5.6, 9.7.5.7,
9.7.5.8, 9.7.5.9, 9.7.5.10, 9.7.6.1, 9.7.6.2, 9.7.6.3, 9.7.6.4, 9.7.6.5, 9.7.6.6, 9.7.6.7, 9.7.6.8, 9.7.6.9,
9.7.6.10, 9.7.7.1, 9.7.7.2, 9.7.7.3, 9.7.7.4, 9.7.7.5, 9.7.7.6, 9.7.7.7, 9.7.7.8, 9.7.7.9, 9.7.7.10, 9.7.8.1,
9.7.8.2, 9.7.8.3, 9.7.8.4, 9.7.8.5, 9.7.8.6, 9.7.8.7, 9.7.8.8, 9.7.8.9, 9.7.8.10, 9.7.9.1, 9.7.9.2, 9.7.9.3,
9.7.9.4, 9.7.9.5, 9.7.9.6, 9.7.9.7, 9.7.9.8, 9.7.9.9, 9.7.9.10, 9.7.10.1, 9.7.10.2, 9.7.10.3, 9.7.10.4,
9.7.10.5, 9.7.10.6, 9.7.10.7, 9.7.10.8, 9.7.10.9, 9.7.10.10, 9.8.1.1, 9.8.1.2, 9.8.1.3, 9.8.1.4, 9.8.1.5,
9.8.1.6, 9.8.1.7, 9.8.1.8, 9.8.1.9, 9.8.1.10, 9.8.2.1, 9.8.2.2, 9.8.2.3, 9.8.2.4, 9.8.2.5, 9.8.2.6, 9.8.2.7,
9.8.2.8, 9.8.2.9, 9.8.2.10, 9.8.3.1, 9.8.3.2, 9.8.3.3, 9.8.3.4, 9.8.3.5, 9.8.3.6, 9.8.3.7, 9.8.3.8, 9.8.3.9,
9.8.3.10, 9.8.4.1, 9.8.4.2, 9.8.4.3, 9.8.4.4, 9.8.4.5, 9.8.4.6, 9.8.4.7, 9.8.4.8, 9.8.4.9, 9.8.4.10, 9.8.5.1,
9.8.5.2, 9.8.5.3, 9.8.5.4, 9.8.5.5, 9.8.5.6, 9.8.5.7, 9.8.5.8, 9.8.5.9, 9.8.5.10, 9.8.6.1, 9.8.6.2, 9.8.6.3,
9.8.6.4, 9.8.6.5, 9.8.6.6, 9.8.6.7, 9.8.6.8, 9.8.6.9, 9.8.6.10, 9.8.7.1, 9.8.7.2, 9.8.7.3, 9.8.7.4, 9.8.7.5,
9.8.7.6, 9.8.7.7, 9.8.7.8, 9.8.7.9, 9.8.7.10, 9.8.8.1, 9.8.8.2, 9.8.8.3, 9.8.8.4, 9.8.8.5, 9.8.8.6, 9.8.8.7,
9.8.8.8, 9.8.8.9, 9.8.8.10, 9.8.9.1, 9.8.9.2, 9.8.9.3, 9.8.9.4, 9.8.9.5, 9.8.9.6, 9.8.9.7, 9.8.9.8, 9.8.9.9,
9.8.9.10, 9.8.10.1, 9.8.10.2, 9.8.10.3, 9.8.10.4, 9.8.10.5, 9.8.10.6, 9.8.10.7, 9.8.10.8, 9.8.10.9,
9.8.10.10, 9.9.1.1, 9.9.1.2, 9.9.1.3, 9.9.1.4, 9.9.1.5, 9.9.1.6, 9.9.1.7, 9.9.1.8, 9.9.1.9, 9.9.1.10, 9.9.2.1,
9.9.2.2, 9.9.2.3, 9.9.2.4, 9.9.2.5, 9.9.2.6, 9.9.2.7, 9.9.2.8, 9.9.2.9, 9.9.2.10, 9.9.3.1, 9.9.3.2, 9.9.3.3,
9.9.3.4, 9.9.3.5, 9.9.3.6, 9.9.3.7, 9.9.3.8, 9.9.3.9, 9.9.3.10, 9.9.4.1, 9.9.4.2, 9.9.4.3, 9.9.4.4, 9.9.4.5,
9.9.4.6, 9.9.4.7, 9.9.4.8, 9.9.4.9, 9.9.4.10, 9.9.5.1, 9.9.5.2, 9.9.5.3, 9.9.5.4, 9.9.5.5, 9.9.5.6, 9.9.5.7,
9.9.5.8, 9.9.5.9, 9.9.5.10, 9.9.6.1, 9.9.6.2, 9.9.6.3, 9.9.6.4, 9.9.6.5, 9.9.6.6, 9.9.6.7, 9.9.6.8, 9.9.6.9,
9.9.6.10, 9.9.7.1, 9.9.7.2, 9.9.7.3, 9.9.7.4, 9.9.7.5, 9.9.7.6, 9.9.7.7, 9.9.7.8, 9.9.7.9, 9.9.7.10, 9.9.8.1,
9.9.8.2, 9.9.8.3, 9.9.8.4, 9.9.8.5, 9.9.8.6, 9.9.8.7, 9.9.8.8, 9.9.8.9, 9.9.8.10, 9.9.9.1, 9.9.9.2, 9.9.9.3,
9.9.9.4, 9.9.9.5, 9.9.9.6, 9.9.9.7, 9.9.9.8, 9.9.9.9, 9.9.9.10, 9.9.10.1, 9.9.10.2, 9.9.10.3, 9.9.10.4,
9.9.10.5, 9.9.10.6, 9.9.10.7, 9.9.10.8, 9.9.10.9, 9.9.10.10, 9.10.1.1, 9.10.1.2, 9.10.1.3, 9.10.1.4,
9.10.1.5, 9.10.1.6, 9.10.1.7, 9.10.1.8, 9.10.1.9, 9.10.1.10, 9.10.2.1, 9.10.2.2, 9.10.2.3, 9.10.2.4,
9.10.2.5, 9.10.2.6, 9.10.2.7, 9.10.2.8, 9.10.2.9, 9.10.2.10, 9.10.3.1, 9.10.3.2, 9.10.3.3, 9.10.3.4,
9.10.3.5, 9.10.3.6, 9.10.3.7, 9.10.3.8, 9.10.3.9, 9.10.3.10, 9.10.4.1, 9.10.4.2, 9.10.4.3, 9.10.4.4,
9.10.4.5, 9.10.4.6, 9.10.4.7, 9.10.4.8, 9.10.4.9, 9.10.4.10, 9.10.5.1, 9.10.5.2, 9.10.5.3, 9.10.5.4,
9.10.5.5, 9.10.5.6, 9.10.5.7, 9.10.5.8, 9.10.5.9, 9.10.5.10, 9.10.6.1, 9.10.6.2, 9.10.6.3, 9.10.6.4,
9.10.6.5, 9.10.6.6, 9.10.6.7, 9.10.6.8, 9.10.6.9, 9.10.6.10, 9.10.7.1, 9.10.7.2, 9.10.7.3, 9.10.7.4,
9.10.7.5, 9.10.7.6, 9.10.7.7, 9.10.7.8, 9.10.7.9, 9.10.7.10, 9.10.8.1, 9.10.8.2, 9.10.8.3, 9.10.8.4,
9.10.8.5, 9.10.8.6, 9.10.8.7, 9.10.8.8, 9.10.8.9, 9.10.8.10, 9.10.9.1, 9.10.9.2, 9.10.9.3, 9.10.9.4,
9.10.9.5, 9.10.9.6, 9.10.9.7, 9.10.9.8, 9.10.9.9, 9.10.9.10, 9.10.10.1, 9.10.10.2, 9.10.10.3, 9.10.10.4,
9.10.10.5, 9.10.10.6, 9.10.10.7, 9.10.10.8, 9.10.10.9, 9.10.10.10, 10.1.1.1, 10.1.1.2, 10.1.1.3, 10.1.1.4,
10.1.1.5, 10.1.1.6, 10.1.1.7, 10.1.1.8, 10.1.1.9, 10.1.1.10, 10.1.2.1, 10.1.2.2, 10.1.2.3, 10.1.2.4,
10.1.2.5, 10.1.2.6, 10.1.2.7, 10.1.2.8, 10.1.2.9, 10.1.2.10, 10.1.3.1, 10.1.3.2, 10.1.3.3, 10.1.3.4,
10.1.3.5, 10.1.3.6, 10.1.3.7, 10.1.3.8, 10.1.3.9, 10.1.3.10, 10.1.4.1, 10.1.4.2, 10.1.4.3, 10.1.4.4,
10.1.4.5, 10.1.4.6, 10.1.4.7, 10.1.4.8, 10.1.4.9, 10.1.4.10, 10.1.5.1, 10.1.5.2, 10.1.5.3, 10.1.5.4,
10.1.5.5, 10.1.5.6, 10.1.5.7, 10.1.5.8, 10.1.5.9, 10.1.5.10, 10.1.6.1, 10.1.6.2, 10.1.6.3, 10.1.6.4,
10.1.6.5, 10.1.6.6, 10.1.6.7, 10.1.6.8, 10.1.6.9, 10.1.6.10, 10.1.7.1, 10.1.7.2, 10.1.7.3, 10.1.7.4,
10.1.7.5, 10.1.7.6, 10.1.7.7, 10.1.7.8, 10.1.7.9, 10.1.7.10, 10.1.8.1, 10.1.8.2, 10.1.8.3, 10.1.8.4,
10.1.8.5, 10.1.8.6, 10.1.8.7, 10.1.8.8, 10.1.8.9, 10.1.8.10, 10.1.9.1, 10.1.9.2, 10.1.9.3, 10.1.9.4,
10.1.9.5, 10.1.9.6, 10.1.9.7, 10.1.9.8, 10.1.9.9, 10.1.9.10, 10.1.10.1, 10.1.10.2, 10.1.10.3, 10.1.10.4,
10.1.10.5, 10.1.10.6, 10.1.10.7, 10.1.10.8, 10.1.10.9, 10.1.10.10, 10.2.1.1, 10.2.1.2, 10.2.1.3, 10.2.1.4,
10.2.1.5, 10.2.1.6, 10.2.1.7, 10.2.1.8, 10.2.1.9, 10.2.1.10, 10.2.2.1, 10.2.2.2, 10.2.2.3, 10.2.2.4,
10.2.2.5, 10.2.2.6, 10.2.2.7, 10.2.2.8, 10.2.2.9, 10.2.2.10, 10.2.3.1, 10.2.3.2, 10.2.3.3, 10.2.3.4,
10.2.3.5, 10.2.3.6, 10.2.3.7, 10.2.3.8, 10.2.3.9, 10.2.3.10, 10.2.4.1, 10.2.4.2, 10.2.4.3, 10.2.4.4,
10.2.4.5, 10.2.4.6, 10.2.4.7, 10.2.4.8, 10.2.4.9, 10.2.4.10, 10.2.5.1, 10.2.5.2, 10.2.5.3, 10.2.5.4,
10.2.5.5, 10.2.5.6, 10.2.5.7, 10.2.5.8, 10.2.5.9, 10.2.5.10, 10.2.6.1, 10.2.6.2, 10.2.6.3, 10.2.6.4,
10.2.6.5, 10.2.6.6, 10.2.6.7, 10.2.6.8, 10.2.6.9, 10.2.6.10, 10.2.7.1, 10.2.7.2, 10.2.7.3, 10.2.7.4,
10.2.7.5, 10.2.7.6, 10.2.7.7, 10.2.7.8, 10.2.7.9, 10.2.7.10, 10.2.8.1, 10.2.8.2, 10.2.8.3, 10.2.8.4,
10.2.8.5, 10.2.8.6, 10.2.8.7, 10.2.8.8, 10.2.8.9, 10.2.8.10, 10.2.9.1, 10.2.9.2, 10.2.9.3, 10.2.9.4,
10.2.9.5, 10.2.9.6, 10.2.9.7, 10.2.9.8, 10.2.9.9, 10.2.9.10, 10.2.10.1, 10.2.10.2, 10.2.10.3, 10.2.10.4,
10.2.10.5, 10.2.10.6, 10.2.10.7, 10.2.10.8, 10.2.10.9, 10.2.10.10, 10.3.1.1, 10.3.1.2, 10.3.1.3, 10.3.1.4,
10.3.1.5, 10.3.1.6, 10.3.1.7, 10.3.1.8, 10.3.1.9, 10.3.1.10, 10.3.2.1, 10.3.2.2, 10.3.2.3, 10.3.2.4,
10.3.2.5, 10.3.2.6, 10.3.2.7, 10.3.2.8, 10.3.2.9, 10.3.2.10, 10.3.3.1, 10.3.3.2, 10.3.3.3, 10.3.3.4,
10.3.3.5, 10.3.3.6, 10.3.3.7, 10.3.3.8, 10.3.3.9, 10.3.3.10, 10.3.4.1, 10.3.4.2, 10.3.4.3, 10.3.4.4,
10.3.4.5, 10.3.4.6, 10.3.4.7, 10.3.4.8, 10.3.4.9, 10.3.4.10, 10.3.5.1, 10.3.5.2, 10.3.5.3, 10.3.5.4,
10.3.5.5, 10.3.5.6, 10.3.5.7, 10.3.5.8, 10.3.5.9, 10.3.5.10, 10.3.6.1, 10.3.6.2, 10.3.6.3, 10.3.6.4,
10.3.6.5, 10.3.6.6, 10.3.6.7, 10.3.6.8, 10.3.6.9, 10.3.6.10, 10.3.7.1, 10.3.7.2, 10.3.7.3, 10.3.7.4,
10.3.7.5, 10.3.7.6, 10.3.7.7, 10.3.7.8, 10.3.7.9, 10.3.7.10, 10.3.8.1, 10.3.8.2, 10.3.8.3, 10.3.8.4,
10.3.8.5, 10.3.8.6, 10.3.8.7, 10.3.8.8, 10.3.8.9, 10.3.8.10, 10.3.9.1, 10.3.9.2, 10.3.9.3, 10.3.9.4,

TABLE B-continued 10.3.9.5, 10.3.9.6, 10.3.9.7, 10.3.9.8, 10.3.9.9, 10.3.9.10, 10.3.10.1, 10.3.10.2, 10.3.10.3, 10.3.10.4,
10.3.10.5, 10.3.10.6, 10.3.10.7, 10.3.10.8, 10.3.10.9, 10.3.10.10, 10.4.1.1, 10.4.1.2, 10.4.1.3, 10.4.1.4,
10.4.1.5, 10.4.1.6, 10.4.1.7, 10.4.1.8, 10.4.1.9, 10.4.1.10, 10.4.2.1, 10.4.2.2, 10.4.2.3, 10.4.2.4,
10.4.2.5, 10.4.2.6, 10.4.2.7, 10.4.2.8, 10.4.2.9, 10.4.2.10, 10.4.3.1, 10.4.3.2, 10.4.3.3, 10.4.3.4,
10.4.3.5, 10.4.3.6, 10.4.3.7, 10.4.3.8, 10.4.3.9, 10.4.3.10, 10.4.4.1, 10.4.4.2, 10.4.4.3, 10.4.4.4,
10.4.4.5, 10.4.4.6, 10.4.4.7, 10.4.4.8, 10.4.4.9, 10.4.4.10, 10.4.5.1, 10.4.5.2, 10.4.5.3, 10.4.5.4,
10.4.5.5, 10.4.5.6, 10.4.5.7, 10.4.5.8, 10.4.5.9, 10.4.5.10, 10.4.6.1, 10.4.6.2, 10.4.6.3, 10.4.6.4,
10.4.6.5, 10.4.6.6, 10.4.6.7, 10.4.6.8, 10.4.6.9, 10.4.6.10, 10.4.7.1, 10.4.7.2, 10.4.7.3, 10.4.7.4,
10.4.7.5, 10.4.7.6, 10.4.7.7, 10.4.7.8, 10.4.7.9, 10.4.7.10, 10.4.8.1, 10.4.8.2, 10.4.8.3, 10.4.8.4,
10.4.8.5, 10.4.8.6, 10.4.8.7, 10.4.8.8, 10.4.8.9, 10.4.8.10, 10.4.9.1, 10.4.9.2, 10.4.9.3, 10.4.9.4,
10.4.9.5, 10.4.9.6, 10.4.9.7, 10.4.9.8, 10.4.9.9, 10.4.9.10, 10.4.10.1, 10.4.10.2, 10.4.10.3, 10.4.10.4,
10.4.10.5, 10.4.10.6, 10.4.10.7, 10.4.10.8, 10.4.10.9, 10.4.10.10, 10.5.1.1, 10.5.1.2, 10.5.1.3, 10.5.1.4,
10.5.1.5, 10.5.1.6, 10.5.1.7, 10.5.1.8, 10.5.1.9, 10.5.1.10, 10.5.2.1, 10.5.2.2, 10.5.2.3, 10.5.2.4,
10.5.2.5, 10.5.2.6, 10.5.2.7, 10.5.2.8, 10.5.2.9, 10.5.2.10, 10.5.3.1, 10.5.3.2, 10.5.3.3, 10.5.3.4,
10.5.3.5, 10.5.3.6, 10.5.3.7, 10.5.3.8, 10.5.3.9, 10.5.3.10, 10.5.4.1, 10.5.4.2, 10.5.4.3, 10.5.4.4,
10.5.4.5, 10.5.4.6, 10.5.4.7, 10.5.4.8, 10.5.4.9, 10.5.4.10, 10.5.5.1, 10.5.5.2, 10.5.5.3, 10.5.5.4,
10.5.5.5, 10.5.5.6, 10.5.5.7, 10.5.5.8, 10.5.5.9, 10.5.5.10, 10.5.6.1, 10.5.6.2, 10.5.6.3, 10.5.6.4,
10.5.6.5, 10.5.6.6, 10.5.6.7, 10.5.6.8, 10.5.6.9, 10.5.6.10, 10.5.7.1, 10.5.7.2, 10.5.7.3, 10.5.7.4,
10.5.7.5, 10.5.7.6, 10.5.7.7, 10.5.7.8, 10.5.7.9, 10.5.7.10, 10.5.8.1, 10.5.8.2, 10.5.8.3, 10.5.8.4,
10.5.8.5, 10.5.8.6, 10.5.8.7, 10.5.8.8, 10.5.8.9, 10.5.8.10, 10.5.9.1, 10.5.9.2, 10.5.9.3, 10.5.9.4,
10.5.9.5, 10.5.9.6, 10.5.9.7, 10.5.9.8, 10.5.9.9, 10.5.9.10, 10.5.10.1, 10.5.10.2, 10.5.10.3, 10.5.10.4,
10.5.10.5, 10.5.10.6, 10.5.10.7, 10.5.10.8, 10.5.10.9, 10.5.10.10, 10.6.1.1, 10.6.1.2, 10.6.1.3, 10.6.1.4,
10.6.1.5, 10.6.1.6, 10.6.1.7, 10.6.1.8, 10.6.1.9, 10.6.1.10, 10.6.2.1, 10.6.2.2, 10.6.2.3, 10.6.2.4,
10.6.2.5, 10.6.2.6, 10.6.2.7, 10.6.2.8, 10.6.2.9, 10.6.2.10, 10.6.3.1, 10.6.3.2, 10.6.3.3, 10.6.3.4,
10.6.3.5, 10.6.3.6, 10.6.3.7, 10.6.3.8, 10.6.3.9, 10.6.3.10, 10.6.4.1, 10.6.4.2, 10.6.4.3, 10.6.4.4,
10.6.4.5, 10.6.4.6, 10.6.4.7, 10.6.4.8, 10.6.4.9, 10.6.4.10, 10.6.5.1, 10.6.5.2, 10.6.5.3, 10.6.5.4,
10.6.5.5, 10.6.5.6, 10.6.5.7, 10.6.5.8, 10.6.5.9, 10.6.5.10, 10.6.6.1, 10.6.6.2, 10.6.6.3, 10.6.6.4,
10.6.6.5, 10.6.6.6, 10.6.6.7, 10.6.6.8, 10.6.6.9, 10.6.6.10, 10.6.7.1, 10.6.7.2, 10.6.7.3, 10.6.7.4,
10.6.7.5, 10.6.7.6, 10.6.7.7, 10.6.7.8, 10.6.7.9, 10.6.7.10, 10.6.8.1, 10.6.8.2, 10.6.8.3, 10.6.8.4,
10.6.8.5, 10.6.8.6, 10.6.8.7, 10.6.8.8, 10.6.8.9, 10.6.8.10, 10.6.9.1, 10.6.9.2, 10.6.9.3, 10.6.9.4,
10.6.9.5, 10.6.9.6, 10.6.9.7, 10.6.9.8, 10.6.9.9, 10.6.9.10, 10.6.10.1, 10.6.10.2, 10.6.10.3, 10.6.10.4,
10.6.10.5, 10.6.10.6, 10.6.10.7, 10.6.10.8, 10.6.10.9, 10.6.10.10, 10.7.1.1, 10.7.1.2, 10.7.1.3, 10.7.1.4,
10.7.1.5, 10.7.1.6, 10.7.1.7, 10.7.1.8, 10.7.1.9, 10.7.1.10, 10.7.2.1, 10.7.2.2, 10.7.2.3, 10.7.2.4,
10.7.2.5, 10.7.2.6, 10.7.2.7, 10.7.2.8, 10.7.2.9, 10.7.2.10, 10.7.3.1, 10.7.3.2, 10.7.3.3, 10.7.3.4,
10.7.3.5, 10.7.3.6, 10.7.3.7, 10.7.3.8, 10.7.3.9, 10.7.3.10, 10.7.4.1, 10.7.4.2, 10.7.4.3, 10.7.4.4,
10.7.4.5, 10.7.4.6, 10.7.4.7, 10.7.4.8, 10.7.4.9, 10.7.4.10, 10.7.5.1, 10.7.5.2, 10.7.5.3, 10.7.5.4,
10.7.5.5, 10.7.5.6, 10.7.5.7, 10.7.5.8, 10.7.5.9, 10.7.5.10, 10.7.6.1, 10.7.6.2, 10.7.6.3, 10.7.6.4,
10.7.6.5, 10.7.6.6, 10.7.6.7, 10.7.6.8, 10.7.6.9, 10.7.6.10, 10.7.7.1, 10.7.7.2, 10.7.7.3, 10.7.7.4,
10.7.7.5, 10.7.7.6, 10.7.7.7, 10.7.7.8, 10.7.7.9, 10.7.7.10, 10.7.8.1, 10.7.8.2, 10.7.8.3, 10.7.8.4,
10.7.8.5, 10.7.8.6, 10.7.8.7, 10.7.8.8, 10.7.8.9, 10.7.8.10, 10.7.9.1, 10.7.9.2, 10.7.9.3, 10.7.9.4,
10.7.9.5, 10.7.9.6, 10.7.9.7, 10.7.9.8, 10.7.9.9, 10.7.9.10, 10.7.10.1, 10.7.10.2, 10.7.10.3, 10.7.10.4,
10.7.10.5, 10.7.10.6, 10.7.10.7, 10.7.10.8, 10.7.10.9, 10.7.10.10, 10.8.1.1, 10.8.1.2, 10.8.1.3, 10.8.1.4,
10.8.1.5, 10.8.1.6, 10.8.1.7, 10.8.1.8, 10.8.1.9, 10.8.1.10, 10.8.2.1, 10.8.2.2, 10.8.2.3, 10.8.2.4,
10.8.2.5, 10.8.2.6, 10.8.2.7, 10.8.2.8, 10.8.2.9, 10.8.2.10, 10.8.3.1, 10.8.3.2, 10.8.3.3, 10.8.3.4,
10.8.3.5, 10.8.3.6, 10.8.3.7, 10.8.3.8, 10.8.3.9, 10.8.3.10, 10.8.4.1, 10.8.4.2, 10.8.4.3, 10.8.4.4,
10.8.4.5, 10.8.4.6, 10.8.4.7, 10.8.4.8, 10.8.4.9, 10.8.4.10, 10.8.5.1, 10.8.5.2, 10.8.5.3, 10.8.5.4,
10.8.5.5, 10.8.5.6, 10.8.5.7, 10.8.5.8, 10.8.5.9, 10.8.5.10, 10.8.6.1, 10.8.6.2, 10.8.6.3, 10.8.6.4,
10.8.6.5, 10.8.6.6, 10.8.6.7, 10.8.6.8, 10.8.6.9, 10.8.6.10, 10.8.7.1, 10.8.7.2, 10.8.7.3, 10.8.7.4,
10.8.7.5, 10.8.7.6, 10.8.7.7, 10.8.7.8, 10.8.7.9, 10.8.7.10, 10.8.8.1, 10.8.8.2, 10.8.8.3, 10.8.8.4,
10.8.8.5, 10.8.8.6, 10.8.8.7, 10.8.8.8, 10.8.8.9, 10.8.8.10, 10.8.9.1, 10.8.9.2, 10.8.9.3, 10.8.9.4,
10.8.9.5, 10.8.9.6, 10.8.9.7, 10.8.9.8, 10.8.9.9, 10.8.9.10, 10.8.10.1, 10.8.10.2, 10.8.10.3, 10.8.10.4,
10.8.10.5, 10.8.10.6, 10.8.10.7, 10.8.10.8, 10.8.10.9, 10.8.10.10, 10.9.1.1, 10.9.1.2, 10.9.1.3, 10.9.1.4,
10.9.1.5, 10.9.1.6, 10.9.1.7, 10.9.1.8, 10.9.1.9, 10.9.1.10, 10.9.2.1, 10.9.2.2, 10.9.2.3, 10.9.2.4,
10.9.2.5, 10.9.2.6, 10.9.2.7, 10.9.2.8, 10.9.2.9, 10.9.2.10, 10.9.3.1, 10.9.3.2, 10.9.3.3, 10.9.3.4,
10.9.3.5, 10.9.3.6, 10.9.3.7, 10.9.3.8, 10.9.3.9, 10.9.3.10, 10.9.4.1, 10.9.4.2, 10.9.4.3, 10.9.4.4,
10.9.4.5, 10.9.4.6, 10.9.4.7, 10.9.4.8, 10.9.4.9, 10.9.4.10, 10.9.5.1, 10.9.5.2, 10.9.5.3, 10.9.5.4,
10.9.5.5, 10.9.5.6, 10.9.5.7, 10.9.5.8, 10.9.5.9, 10.9.5.10, 10.9.6.1, 10.9.6.2, 10.9.6.3, 10.9.6.4,
10.9.6.5, 10.9.6.6, 10.9.6.7, 10.9.6.8, 10.9.6.9, 10.9.6.10, 10.9.7.1, 10.9.7.2, 10.9.7.3, 10.9.7.4,
10.9.7.5, 10.9.7.6, 10.9.7.7, 10.9.7.8, 10.9.7.9, 10.9.7.10, 10.9.8.1, 10.9.8.2, 10.9.8.3, 10.9.8.4,
10.9.8.5, 10.9.8.6, 10.9.8.7, 10.9.8.8, 10.9.8.9, 10.9.8.10, 10.9.9.1, 10.9.9.2, 10.9.9.3, 10.9.9.4,
10.9.9.5, 10.9.9.6, 10.9.9.7, 10.9.9.8, 10.9.9.9, 10.9.9.10, 10.9.10.1, 10.9.10.2, 10.9.10.3, 10.9.10.4,
10.9.10.5, 10.9.10.6, 10.9.10.7, 10.9.10.8, 10.9.10.9, 10.9.10.10, 10.10.1.1, 10.10.1.2, 10.10.1.3,
10.10.1.4, 10.10.1.5, 10.10.1.6, 10.10.1.7, 10.10.1.8, 10.10.1.9, 10.10.1.10, 10.10.2.1, 10.10.2.2,
10.10.2.3, 10.10.2.4, 10.10.2.5, 10.10.2.6, 10.10.2.7, 10.10.2.8, 10.10.2.9, 10.10.2.10, 10.10.3.1,
10.10.3.2, 10.10.3.3, 10.10.3.4, 10.10.3.5, 10.10.3.6, 10.10.3.7, 10.10.3.8, 10.10.3.9, 10.10.3.10,
10.10.4.1, 10.10.4.2, 10.10.4.3, 10.10.4.4, 10.10.4.5, 10.10.4.6, 10.10.4.7, 10.10.4.8, 10.10.4.9,
10.10.4.10, 10.10.5.1, 10.10.5.2, 10.10.5.3, 10.10.5.4, 10.10.5.5, 10.10.5.6, 10.10.5.7, 10.10.5.8,
10.10.5.9, 10.10.5.10, 10.10.6.1, 10.10.6.2, 10.10.6.3, 10.10.6.4, 10.10.6.5, 10.10.6.6, 10.10.6.7,
10.10.6.8, 10.10.6.9, 10.10.6.10, 10.10.7.1, 10.10.7.2, 10.10.7.3, 10.10.7.4, 10.10.7.5, 10.10.7.6,
10.10.7.7, 10.10.7.8, 10.10.7.9, 10.10.7.10, 10.10.8.1, 10.10.8.2, 10.10.8.3, 10.10.8.4, 10.10.8.5,
10.10.8.6, 10.10.8.7, 10.10.8.8, 10.10.8.9, 10.10.8.10, 10.10.9.1, 10.10.9.2, 10.10.9.3, 10.10.9.4,
10.10.9.5, 10.10.9.6, 10.10.9.7, 10.10.9.8, 10.10.9.9, 10.10.9.10, 10.10.10.1, 10.10.10.2, 10.10.10.3,
10.10.10.4, 10.10.10.5, 10.10.10.6, 10.10.10.7, 10.10.10.8, 10.10.10.9, 10.10.10.10

Additional exemplary formula B compound groups include the following compound groups disclosed below. Unless otherwise specified, the configurations of all hydrogen atoms and R groups for the following compound groups are as defined for the group 1 compounds of formula B above. As is apparent from the description, each of the compound groups disclose a significant number of unique compounds or generic structures. The compounds or generic structures specifically described in any of the compound groups are thus exemplary only and the remaining compounds or structures in each group are described by Tables A and B as noted in each group.

As used in the description of compounds in the compound groups, the definitive structure of compounds in the various compound groups is specified only by the structure defining portion of the compound group and in Tables A and B, which together definitively name or specifies individual compound or genus structures. The structure defining portion of the compound groups is generally contained in the first sentence the compound groups below. This applies regardless of any name or structure, including chemical names in the exemplary compounds that are named in some of the compound groups. Thus, any name or structure for any compound or compound genus that refers to a compound or genus in a compound group and is given anywhere in the disclosure is intended only to refer to the compound or genus that is definitively specified by the compound groups together with Tables A and B.

Group 2. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10}$ r is hydrogen in the β-configuration. As examples, group 2 compound 1.2.7.1 is 3β,7β-dihydroxy-16-oxo-17β-amino-5β-androstane and compound 1.1.4.1 is 3β-hydroxy-16α-fluoro-17β-amino-5β-androstane.

Group 3. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 5-6 position is present. Thus, group 3 compound 1.2.7.1 is 3β,7β-dihydroxy-16-oxo-17β-aminoandrost-5-ene and compound 1.1.4.1 is 3β-hydroxy-16α-fluoro-17β-aminoandrost-5-ene.

Group 4. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus as described for group 1 compounds, except that double bonds at the 1-2- and 5-6 positions are present. Thus, group 4 compound 1.2.7.1 is 3β,7β-dihydroxy-16-oxo-17β-aminoandrost-1,5-diene and compound 1.1.4.1 is 3β-hydroxy-16α-fluoro-17β-aminoandrost-1,5-diene.

Group 5. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 1-2 position is present. Thus, group 5 compound 1.2.7.1 is 3β,7β-dihydroxy-16-oxo-17β-aminoandrost-1-ene and compound 1.1.4.1 is 3β-hydroxy-16α-fluoro-17β-aminoandrost-1-ene.

Group 5A. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 1-2 position is present and hydrogen at the 5-position is in the β-configuration. Thus, group 5A compound 1.2.7.1 is 3β,7β-dihydroxy-16-oxo-17-amino-5β-androst-1-ene and 5A compound 1.1.4.1 is 3β-hydroxy-16α-fluoro-17β-amino-5β-androst-1-ene.

Group 6. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 4-5 position is present. Thus, group 6 compound 1.2.7.1 is 3β,7β-dihydroxy-16-oxo-17β-aminoandrost-4-ene and compound 1.1.4.1 is 3β-hydroxy-16α-fluoro-17β-aminoandrost-4-ene.

Group 7. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at both the 1-2 and 4-5 positions are present. Thus, group 7 compound 1.2.7.1 is 3β,7β-dihydroxy-16-oxo-17β-aminoandrost-1,4-diene and compound 1.1.4.1 is 3β-hydroxy-16α-fluoro-17β-aminoandrost-1,4-diene.

Group 8. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 16-17 position is present. For this group and other compound groups that contain a 16-17 double bond, the $R^3$ and $R^4$ moieties will only be single bonded. Moieties such as =O are thus not included as $R^3$ or $R^4$ substituents in the compound group, since this would give rise to a pentavalent carbon at the 16- or 17-position. Thus, group 8 compound 1.2.7.1 does not represent any compound since a 16-17 double bond and an 1 5=O at 16 can not both be present at the same time, while group 8 compound 1.1.4.1 is 3β-hydroxy-16-fluoro-17-aminoandrost-16-ene.

Group 8A. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 16-17 position is present and hydrogen at the 5-position is in the β-configuration. Thus, group 8A compound 1.2.7.1 is 3β,7β-dihydroxy-16-oxo-17β-amino-5β-androst-16-ene and 8A compound 1.1.4.1 is 3β-hydroxy-16α-fluoro-17β-amino-5β-androst-16-ene.

Group 9. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at the 16-17 and 5-6 positions are present. Thus, group 9 compound 1.1.4.1 is 3β-hydroxy-16-fluoro-17-aminoandrost-5,16-diene.

Group 10. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at the 16-17 and 1-2 positions are present. Thus, group 10 compound 1.1.4.1 is 3β-hydroxy-16-fluoro-17-aminoandrost-1,16-diene.

Group 10A. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 16-17 and 1-2 positions are present and hydrogen at the 5-position is in the β-configuration. Thus, group 10A compound 1.2.7.1 is 3β,7β-dihydroxy-16-oxo-17β-amino-5β-androst-1,16-diene and 10A compound 1.1.4.1 is 3β-hydroxy-16α-fluoro-17β-amino-5β-androst-1,16-diene.

Group 11. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at the 16-17 and 45 positions are present. Thus, group 11 compound 1.1.4.1 is 3βhydroxy-16-fluoro-17-aminoandrost-4,16-diene.

Group 12. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at the 1-2, 16-17 and 4-5 positions are present. Thus, group 12 compound 1.1.4.1 is 3β-hydroxy-16-fluoro-17-aminoandrost-1,4,16-triene.

Group 13. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at the 1-2, 16-17 and 5-6 positions are present. Thus, group 12 compound 1.1.4.1 is 3β-hydroxy-16-fluoro-17-aminoandrost-1,5,16-triene.

Group 14. This group contains compounds from groups 1-13 above wherein, for single bonded $R^1$, $R^2$, $R^3$ and $R^4$ moieties, $R^1$, $R^2$, $R^3$ and $R^4$ respectively are in the α,β,α,β, β,β,α,α, β,α,α,β, α,α,α,β, β,β,β,β, β,β,β,α, α,β,β,β, β,α,α,α, α, β,α,β,β, α,α,α,α, β,α,β,α, α,β,β,α, α,α,β,α, α,β,α,α or α,α,β,β configurations. Thus, $R^1$, $R^2$, $R^3$ and $R^4$ respectively are in the α,β,α,β configurations, group 14 compound 1.2.7.1 from group 3 (also referred to as group 14-3 compound 1.2.7.1) is 3α,7β-dihydroxy-16-oxo-17β-aminoandrost-5-ene and compound 1.1.4.1 from group 3 (also referred to as group 14-3 compound 1.1.4.1) is 3α-hydroxy-16α-fluoro-17β-aminoandrost-5-ene. When $R^1$, $R^2$, $R^3$ and $R^4$ respectively are in the α,β,α,β configurations, group 14 compound 1.2.7.1 from group 1 (also referred to as group 14-1 compound 1.2.7.1) is 3α,7β-dihydroxy-16-oxo-17β-aminoandrostane and group 14-1 compound 1.1.4.1 is 3α-hydroxy-16α-fluoro-17β-aminoandrostane. Similarly, when $R^1$, $R^2$, $R^3$ and $R^4$ respectively are in the α,β,α,β configurations, group 14-6 compound 1.2.7.1 is 3α,7β-dihydroxy-16-oxo-17β-aminoandrost-4-ene and group 14-6 compound 1.1.4.1 is 3α-hydroxy-16α-fluoro-17β-aminoandrost-4-ene.

Group 15. This group contains compounds in groups 1-14 above wherein $R^{10F}$, $R^{10G}$ and $R^{10H}$ respectively are in the β,α,β, β,β,α, α,β,β, β,β,β, α,α,α, α,β,α or α,α,β configurations. Thus, when $R^{10F}$, $R^{10G}$ and $R^{10H}$ respectively can be in the β,α,β configurations, group 15 compound 1.2.7.1 from group 3 is 3β,7β-dihydroxy-16-oxo-17β-amino-14β-androst-5-ene and compound 1.1.4.1 from group 3 is 3β-hydroxy-16α-fluoro-17β-amino-14β-androst-5-ene. When $R^{10E}$, $R^{10F}$, $R^{10G}$ and $R^{10H}$ respectively are in the α,β,α,β configurations, group 15 compound 1.2.7.1 from group 1 is 3α,7β-dihydroxy-16-oxo-17β-amino-14β-androstane and compound 1.1.4.1 from group 1 is 3α-hydroxy-16α-fluoro-17β-amino-14β-androstane. When $R^{10F}$, $R^{10G}$ and $R^{10H}$ respectively are in the β,α,β configurations and $R^1$, $R^2$, $R^3$ and $R^4$ respectively are in the α,β,α,β configurations as included in group 14, group 15-14-3 compound 1.2.7.1 (compound 1.2.7.1 from groups 14 and 3) is 3α,7β-dihydroxy-16-oxo-17β-amino-14β-androst-5-ene and group 15-14-3 compound 1.1.4.1 is 3α-hydroxy-16α-fluoro-17β-amino-14β-androst-5-ene. When $R^{10G}$ is —F in the α-configuration and $R^{10F}$ and $R^{10H}$ are —H in the β- and α-configurations respectively, group 15-3 compound 1.1.4.1 is 3β-hydroxy-9α,16α-difluoro-17β-aminoandrost-5-ene and 15-3 compound 1.1.5.1 is 3β-hydroxy-9α-fluoro-17β-aminoandrost-5-ene.

Group 16. This group contains compounds in groups 1-15 above wherein 1 or 2 of $R^{10A}$, $R^{10B}$, $R^{10C}$ and $R^{10D}$ are not —H and are an independently chosen moiety as defined herein, e.g., optionally substituted alkyl, —$CH_3$, halogen, —$SR^{PR}$ or —$R^{PR}$, wherein each $R^{10A}$, $R^{10B}$, $R^{10C}$ and $R^{10D}$ is independently in the α-configuration or the β-configuration and $R^{PR}$ independently are —H or a protecting group. Thus, when $R^{10C}$ and $R^{10D}$ are both not —H, they can be in the β,β,β,α, α,β or α,α configurations respectively. Similarly, when $R^{10B}$ and $R^{10D}$ are both not —H, they can be in the β,β,β,α, α,β or α,α configurations respectively, or, when $R^{10B}$ is not —H and $R^{10A}$, $R^{10C}$ and $R^{10D}$ are all —H, $R^{10B}$ can be in the α-configuration or the β-configuration. Thus, when $R^{10C}$ is —Cl in the α-configuration, group 16-3 compound 1.2.7.1 is 3β,7β-dihydroxy-6-chloro-16-oxo-17β-aminoandrost-5-ene and group 16-3 compound 1.1.4.1 is 3β-hydroxy-6-chloro-16α-fluoro-17β-aminoandrost-5-ene. When $R^{10C}$ is —Br in the α-configuration, group 16-1 compound 1.2.7.1 is 3β,7β-dihydroxy-6α-bromo-16-oxo-17β-aminoandrostane and group 16-1 compound 1.1.4.1 is 3β-hydroxy-6α-bromo-16α-fluoro-17β-aminoandrostane.

Group 17. This group contains compounds in groups 1-16 above wherein (1) one or both of $R^5$ and $R^6$ are not —$CH_3$ and they independently are a moiety as defined herein, and (2) $R^5$ and $R^6$ are in the β,β,β,α, α,β or α,α configurations respectively. Thus, $R^5$ and $R^6$ independently can be —H, —$CH_3$, —$C_2H_5$, —$C_3H_7$, optionally substituted alkyl, —OH, —F, —Cl, —Br, —I or another single bonded moiety as defined herein in the β,β,β,α, α,βor α,α configurations. When, for example, $R^5$ is —$CH_3$, $R^6$ is —H and both are in the β-configuration, group 17-1 compound 1.2.7.1 is 3β,7β-dihydroxy-16-oxo-17β-amino-19-norandrostane and group 17-1 compound 1.1.4.1 is 3β-hydroxy-16α-fluoro-17β-amino-19-norandrostane. When $R^5$ is —$CH_3$, $R^6$ is —H and both are in the β-configuration, group 17-3 compound 1.2.7.1 is 3β,7β-dihydroxy-16-oxo-17β-amino-19-norandrost-5-ene and group 17-3 compound 1.1.4.1 is 3β-hydroxy-16α-fluoro-17β-amino-19-norandrost-5-ene. When $R^5$ is —$CH_3$, $R^6$ is —H and both are in the β-configuration, $R^{10G}$ is —F in the α-configuration and $R^{10F}$ and $R^{10H}$ are —H in the β- and α-configurations respectively, group 17-15-3 compound 1.1.4.1 is 3β-hydroxy-9α,16β-difluoro-17β-amino-19-norandrost-5-ene and 17-15-3 compound 1.1.5.1 is 3β-hydroxy-9α-fluoro-17β-amino-19-norandrost-5-ene.

Group 18. This group contains compounds in groups 1-17 above wherein $R^7$ is not —$CH_2$— and is another $R^7$ moiety defined herein, e.g., —O—, —NH—, —S—, —$CH_2$—$CH_2$— or —$C(R^{10})_2$— where each $R^{10}$ is an independently chosen moiety described herein. Exemplary $R^7$ include —C(halogen)$_2$- such as —$CF_2$—, —CH(α-optionally substituted alkyl), —CH(β-optionally substituted alkyl), —CH(α-OH), —CH(β-OH) or —C(optionally substituted alkyl)$_2$- such as —$C(CH_3)_2$— or —$C(C_2H_5)(CH_3)$—. Each optionally substituted alkyl group can contain 1, 2, 3, 4, 5, 6, 7, 8 or more carbon atoms as defined previously.

Group 19. This group contains compounds in groups 1-18 above wherein $R^8$ is not —$CH_2$— and is another $R^8$ moiety defined herein, e.g., —O—, —NH—, —S— or —$C(R^{10})_2$— where each $R^{10}$ is an independently chosen moiety described herein. Exemplary $R^8$ include —C(halogen)$_2$- such as —$CF_2$—, —CH(α-optionally substituted alkyl), —CH(, optionally substituted alkyl) or —C(optionally substituted alkyl)$_2$- such as —$C(CH_3)_2$— or —$C(C_2H_5)(CH_3)$—. Each optionally substituted alkyl group can contain 1, 2, 3, 4, 5, 6, 7, 8 or more carbon atoms as defined previously. In some embodiments, when one or both $R^{10}$ at $R^8$ is —OH, —SH, =O, an ester, a thioester, or another moiety that can give rise to a hydroxyl group by metabolism or hydrolysis, $R^2$ and/or $R^{10D}$ is not —H. As examples, group 19-3 compound 1.1.4.1 is 3β-hydroxy-11-oxa-16α-fluoro-17β-aminoandrost-5-ene and 19-3 compound 1.1.5.1 is 3β-hydroxy-11-oxa-17β-aminoandrost-5-ene. When $R^8$ is —O—, $R^5$ is —$CH_3$, $R^6$ is —H and both are in the β-configuration, $R^{10G}$ is —F in the α-configuration and $R^{10F}$ and $R^{10H}$ are —H in the β- and α-configurations respectively, group 19-17-15-3 compound 1.1.4.1 is 3β-hydroxy-9α,16α-difluoro-11-oxa-17β-amino-19-norandrost-5-ene and 19-17-15-3 compound 1.1.5.1 is 3β-hydroxy-9α-fluoro-11-oxa-17β-amino-19-norandrost-5-ene.

Group 20. This group contains compounds in groups 1-19 above wherein $R^9$ is not —$CH_2$— and is another $R^9$ moiety defined herein, e.g., —O—, —NH—, —S— or —$C(R^{10})_2$— where each $R^{10}$ is an independently chosen moiety as defined herein. Exemplary $R^9$ include —$C(halogen)_2$- such as —$CF_2$—, —$CH(\alpha\text{-OH})$, —$CH(\beta\text{-OH})$ or —C(optionally substituted alkyl)$_2$-such as —$C(CH_3)_2$— or —$C(C_2H_5)$(CH)—. Each optionally substituted alkyl group can contain 1, 2, 3, 4, 5, 6, 7, 8 or more carbon atoms as defined previously. For groups that contain a double bond at the 1-2 position such as groups 5 and 7, $R^9$ can be —N═, but $R^9$ will not be —O— or —S— due to improper bonding, i.e., —O↑ and —S═ are not present in the steroid ring.

Group 21. This group contains compounds in groups 1-20 above where $R^4$ substituents 1-10 listed in Table A are replaced with the following groups: 1 -optionally substituted amine, 2 -optionally substituted amide, 3 -optionally substituted oxime, 4 -optionally substituted alkyl, 5 -optionally substituted alkenyl, 6 -optionally substituted alkynyl, 7 -optionally substituted aryl, 8 -optionally substituted heterocycle, 9-ether, e.g., methoxy, ethoxy or methoxymethyl and 10 -ester, e.g., acetate, propionate, enanthate or trifluoroacetate. Any of these groups can be a moiety defined herein for that group. Thus, for Table A substituent 1, optionally substituted amine, the $R^4$ group includes moieties such as —$NH_3^+$ $Cl^-$, —$NH_3^+Br^-$, —$NH_3^+I^-$, optionally substituted alkylamine, di-optionally substituted alkylamine, —$NHR^{PR}$, —$N(R^{PR})_2$ and —NH—$CH_3$, where $R^{PR}$ are a protecting group. Similarly, optionally substituted amide includes moieties such as —$C(O)NH_2$, —C(O)—NH—$C(CH_3)_3$ and —C(O)—$NH_2$, which are described herein. Other $R^4$ moieties include ═N—$OCH_3$, ═N—$OC_2H_5$, ═N—$OC_3H_7$ and ═N—O-optionally substituted alkyl. Group 21-3 compound 1.1.6.1 (i.e., group 21 compound 1.1.6.1 from group 3) is 3β,16α-dihydroxy-17β-optionally substituted amine-androst-5-ene and 21-3 compound 1.1.4.1 is 3β-hydroxy-16α-fluoro-17β-optionally substituted amine-androst-5-ene, where the optionally substituted amine is a moiety described herein such as an amine salt, an optionally substituted alkylamine or an optionally substituted dialkylamine like —$NH_3^+$ $Cl^-$, —$NHCH_3$, —$N(CH_3)_2$ and —$NH_4$—$(CH_2)_2$—OH. Similarly, group 21-1 compound 1.1.6.1 (i.e., group 21 compound 1.1.6.1 from group 1) is 3β,16α-dihydroxy-17β-optionally substituted amine-androstane and 21-1 compound 1.1.4.1 is 3β-hydroxy-16α-fluoro-17β-optionally substituted amine-androstane.

Group 22. This group contains compounds in groups 1-20 above where $R^4$ substituents 1-10 listed in Table A are replaced with the following groups: 1 -acyl, 2 -thioester, 3 -thioether, 4 -thioacyl, 5 -epoxide, 6 -optionally substituted cyclopropyl, 7 —O—Si(C1-C6 alkyl)$_3$, 8 -phosphate, 9 -phosphate ester and 10 -phosphate ether. Any of these groups can be a moiety defined herein for that group. Thus, for Table A substituent 1, acyl, the $R^4$ group includes moieties such as —$C(O)CH_3$, —$C(O)C_2H_5$, —$C(O)CH_2OH$, —$C(O)CH_2$-halogen and —C(O)-optionally substituted alkyl. Similarly, thioester includes moieties such as —C(O)—$SCH_3$, —C(O)—$SC_2H_5$, —S—C(O)-optionally substituted alkyl and —C(O)—S-optionally substituted alkyl. The epoxide and optionally substituted cyclopropyl moieties for substituents 5 and 6 respectively can be at the 16-17 positions or at the 17-18 positions.

Group 23. This group contains compounds in groups 1-20 above where $R^4$ substituents 1-10 listed in Table A are replaced with the following groups: 1 -phosphate thioether, 2 -thionoester, 3-amino acid, 4 -peptide, 5 -dipeptide, 6 -optionally substituted heterocycle, 7 -optionally substituted carboxyl, 8 -carbonate, 9 -carbamate and 10 -phosphothioester. Amino acids for substituent 3 are as described herein and include, e.g., —NH—$CH_2$—C(O)OH, —NH—$CH_2$—C(O)OR$^{PR}$, —NH—CH—$CH_2$—(O)OH, —NH—$CH_2$—$CH_2$—C(O)OR$^{PR}$, —NH—$CH(CH_3)$—C(O)OH, —NH—CH($CH_3$)—$CH_2$—C(O)OH, —NH—CH($CH_3$)—$CH_2$—C(O)OR$^{PR}$, —NH—$CH_2$—$CH_2$—$CH_2$—C(O)OH, —NH—$CH_2$—CHCH$_2$—C(O)OR$^{PR}$—O—C(O)—$CH_2$—$NH_2$, —O—C(O)—$CH_2$—NHR$^{PR}$, —O—C(O)—$CH_2$—$CH_2$—$NH_2$, —O—C(O)—$CH_2$—$CH_2$—NHR$^{PR}$ or for ionizable groups such as free carboxyls or amines, a salt such as a Na$^+$ or K$^+$ salt for carboxyls or a salt such as HCl or HBr salt for amines.

Group 24. This group contains compounds in groups 1-20 above where $R^4$ substituents 1-10 listed in Table A are replaced with the following groups: 1 -thiophosphate, 2 -phosphothioether, 3 -thiophosphate thioether, 4 -phosphonoester, 5 -phosphonate, 6 -phosphonate ester, 7 -phosphonate ether, 8 -phosphonate thioether, 9 —O—S(O)(O)—OH or a -sulfate salt, e.g., —O—S(O)(O)—O$^+$Na$^-$, 10 —F, —Cl, —Br or —I.

Group 25. This group contains compounds in groups 1-20 above where $R^4$ substituents 1-10 listed in Table A are replaced with the following groups: 1 -sulfate ester, 2 -sulfate ether, 3 -sulfate thioether, 4 —O—S(O)—OH, 5 -sulfite salt, e.g., —O—S(O)—O$^+$Na$^-$, 6 -sulfite ester, 7 -sulfite ether, 8 -sulfoxide, 9 —O—S(O)(O)—OR$^{PR}$ and 10 —O—S(O)(O)—OCH$_3$.

Group 26. This group contains compounds in groups 1-20 above where $R^4$ substituents 1-10 listed in Table A are replaced with the following groups: 1 -sulfonamide, 2 -sulfonamide derivative, e.g., —S(O)(O)—NHR$^{PR}$ or —S(O)(O)—NH-optionally substituted alkyl, 3 -sulfamate, 4 -sulfamate derivative, e.g., —O—S(O)(O)—NHR$^{PR}$, —O—S(O)(O)—N(RD)$_2$ or —S(O)(O)—NH-optionally substituted alkyl, 5 -sulfonate, 6 -sulfamide, 7 -sulfinamide, 8 -sulfurous diamide, 9 -optionally protected monosaccharide, e.g., D-, L- or DL-glucose, fructose, rhamnose or glucuronic acid, 10 -optionally protected oligosaccharide, e.g., D-, L- or DL-galactose-galactose, -galactose-mannose or -glucuronic acid-glucose.

Group 26A. This group contains compounds in groups 1-20 above where $R^4$ substituents 1-10 listed in Table A are replaced with the following groups: 1 —N-pyrrolidine, 2 —N1-pyrazolone, 3 —N2-pyrazolone, 4 —N-imidazolidin-2-one, 5 —N1-imidazole, 6 —N-1,4,5-dihydroimidazole, 7 —N-morpholine, 8 —N1-pyridine, 9 —N-piperidine, 10 —N-piperazine. As examples, group 26A-3 compound 1.1.6.1 (i.e., group 26A compound 1.1.6.1 from group 3) is 3β,16α-dihydroxy-17β-N-pyrrolidinylandrost-5-ene, 26A-3 compound 1.1.4.1 is 3β-hydroxy-16α-fluoro-17β-N-pyrrolidinylandrost-5-ene, group 26A-4 compound 1.1.6.1 (i.e., group 26A compound 1.1.6.1 from group 4) is 3β,16α-dihydroxy-17β-N-pyrrolidinylandrost-1,5-diene and 26A-4 compound 1.1.4.1 is 3β-hydroxy-16α-fluoro-17β-N-pyrrolidinylandrost-1,5-diene.

Group 26B. This group contains compounds in groups 1-20 above where $R^4$ substituents 1-10 listed in Table A are replaced with the following groups: 1 —N-piperazine substituted at N4 with optionally substituted alkyl, 2 —N-indole, 3 —N-indoline, 4 —N-quinolidine, 5 —NH—C(O)—$CH_2$—$CH_2$—C(O)—OH, 6 —NH—C(O)—$CH_2$—C(O)—OH, 7 —NH—C(O)—$CH_2$—$CH_2$—C(O)—OR$^{PR}$, 8 —NH—C(O)—$CH_2$—C(O)—OR$^{PR}$, 9 —NH—C(O)—$(CH_2)_3$—C(O)—OH, 10 —NH—C(O)—$(CH)_3$—C(O)—OR$^{PR}$. Ionizable moieties such as free carboxyl groups include salts, e.g., Na$^+$ or K$^+$. $R^{PR}$ is a protecting group.

Group 26C. This group contains compounds in groups 1-20 above where $R^4$ substituents 1-10 listed in Table A are replaced with the following groups: 1 —NH—CH($CH_3$)—C(O)OH, 2 —NH—CH($CH_3$)—C(O)$OR^{PR}$, 3 —NH—CH($CH_2OH$)—C(O)OH, 4 —NH—CH($CH_2OH$)—C(O)$OR^{PR}$, 5 —NH—$CH_2$—$CH_2$—C(O)—OH, 6 —NH—$CH_2$—C(O)—OH, 7 —NH—$CH_2$—$CH_2$—C(O)—$OR^{PR}$, 8 —NH—$CH_2$—C(O)—$OR^{PR}$, 9 —NH—$(CH_2)_3$—C(O)—OH, 10 —NH—$(CH_2)_3$—C(O)—$OR^{PR}$. Ionizable moieties such as free carboxyl groups include salts, e.g., $Na^+$ or $K^+$. $R^{PR}$ is a protecting group.

Group 26D. This group contains compounds in groups 1-20 above where $R^4$ substituents 1-10 listed in Table A are replaced with the following groups: 1 —NH—CH($CH_3$)—C(O)OH, 2 —NH—NH—C(O)$CH_3$, 3 —NH—NH—C(O)$OCH_3$, 4 —NH—NH—C(O)$C_2H_5$, 5 —NH—NH—C(O)$OC_2H_5$, 6 —NH—NH—C(O)$C_3H_7$, 7 —NH—NH—C(O)-optionally substituted alkyl, 8 —NH—C(NH-optionally substituted alkyl)=N-optionally substituted alkyl, 9 —NH—C(NH—$CH_3$)=N—$CH_3$, 10 —NH—C(NH—$C_2H_5$)=N—$C_2H_5$.

Group 26E. This group contains compounds in groups 1-20 above where $R^4$ substituents 1-10 listed in Table A are replaced with the following groups: 1 spiro β-$NH_4$—$(CH_2)_2$—O-α, 2 spiro α-NH—$(CH_2)_2$—O-β, 3 spiro β-$NH_4$—$(CH_2)_2$—NH-α, 4 spiro α-NH—$(CH_2)_2$—NH-β, 5 spiro β-NH—CH=N—$CH_2$-α, 6 spiro α-NH—CH=N—$CH_2$-β, 7 spiro β-NH—$CHR^{10}$—$CHR^{10}$—O-α, 8 spiro α-NH—$CHR^{10}$—$CHR^{10}$—O-β, 9 spiro β-NH—$CHR^{10}$—$CHR^{10}$—NH-α, 10 spiro α-NH—$CHR^{10}$—$CHR^{10}$—NH-β. Each $R^{10}$ is independently chosen and has the meaning given above, e.g., —H, —OH, =O, —SH, =S, halogen or optionally substituted alkyl.

Group 27. This group contains compounds in groups 1-20 above where $R^4$ substituents 1-10 listed in Table A are replaced with the following groups: 1-glycol, e.g., propylene glycol or ethylene glycol, 2-polyethylene glycol, e.g., PEG 100 or PEG 200, 3 -an acetal ring, 4 -a spiro ring, 5 -a thioacetal ring, 6 spiro —O—$CH_2$—, 7 spiro —O—$(CH_2)_2$—O—, 8 spiro —NH—$(CH_2)_2$—O—, 9 —NH—C(O)—$(CH_2)_2$—C(O)O—$CH_3$, 10 —NH—C(O)—$(CH_2)_2$—C(O)—OH.

Group 28. This group contains compounds in groups 1-27 above where $R^1$ substituents 1-10 listed in Table A are replaced with the following groups: 1 -optionally substituted amine, 2 -optionally substituted amide, 3 -optionally substituted oxime, 4 -optionally substituted alkyl, 5 -optionally substituted alkenyl, 6 -optionally substituted alkynyl, 7 -optionally substituted aryl, 8 -optionally substituted heterocycle, 9 -ether and 10 -ester. Any of these groups can be a moiety defined herein for that group. Thus, for Table A substituent 1, optionally substituted amine, the $R^1$ group includes moieties such as —$NH_3^+Cl^-$, —$NH_3+Br^-$, —$NH_3^+I^-$, optionally substituted alkylamine, di-optionally substituted alkylamine and —NH—$CH_3$.

Group 29. This group contains compounds in groups 1-27 above where $R^1$ substituents 1-10 listed in Table A are replaced with the following groups: 1 -acyl, 2 -thioester, 3 -thioether, 4 -thioacyl, 5 -epoxide, 6 -optionally substituted cyclopropyl, 7 —O—Si(C1-C6 alkyl)$_3$, 8 -phosphate, 9 -phosphate ester and 10 -phosphate ether. Any of these groups can be a moiety defined herein for that group. Thus, for Table A substituent 1, acyl, the $R^1$ group includes moieties such as —C(O)$CH_3$, —C(O)$C_2H_5$, —C(O)$CH_2OH$, —C(O)$CH_2$-halogen and —C(O)-optionally substituted alkyl. Similarly, thioester includes moieties such as —C(O)—$SCH_3$, —S—C(O)-optionally substituted alkyl and —C(O)—S-optionally substituted alkyl. The epoxide and optionally substituted cyclopropyl moieties for substituents 5 and 6 respectively can be at the 2-3 positions or at the 3-4 positions in the α- or β-configuration.

Group 30. This group contains compounds in groups 1-27 above where $R^1$ substituents 1-10 listed in Table A are replaced with the following groups: 1 -phosphate thioether, 2 -thionoester, 3 -amino acid, 4 -peptide, 5 -dipeptide, 6 -optionally substituted heterocycle, 7 -optionally substituted carboxyl, 8 -carbonate, 9 -carbamate and 10 -phosphothioester.

Group 31. This group contains compounds in groups 1-27 above where $R^1$ substituents 1-10 listed in Table A are replaced with the following groups: 1 -thiophosphate, 2 -phosphothioether, 3 -thiophosphate thioether, 4 -phosphonoester, 5 -phosphonate, 6 -phosphonate ester, 7 -phosphonate ether, 8 -phosphonate thioether, 9 —O—S(O)(O)—OH and 10 -sulfate salt, e.g., —O—S(O)(O)—$O^+Na^-$.

Group 32. This group contains compounds in groups 1-27 above where $R^1$ substituents 1-10 listed in Table A are replaced with the following groups: 1 -sulfate ester, 2 -sulfate ether, 3 -sulfate thioether, 4 —O—S(O)—OH, 5 -sulfite salt, e.g., —O—S(O)—$O^+Na^-$, 6 -sulfite ester, 7 -sulfite ether, 8 -sulfoxide, 9 —O—S(O)(O)—OH or a sulfate salt, e.g., —O—S(O)(O)—$O^+Na^-$, 10 —F, —Cl, —Br or —I.

Group 33. This group contains compounds in groups 1-27 above where $R^1$ substituents 1-10 listed in Table A are replaced with the following groups: 1-sulfonamide, 2 -sulfonamide derivative, e.g., —S(O)(O)—$NHR^{PR}$ or —S(O)(O)—NH-optionally substituted alkyl, 3 -sulfamate, 4 -sulfamate derivative, e.g., —O—S(O)(O)—$NHR^{PR}$, —O—S(O)(O)—N(RD)$_2$ or O—S(O)(O)—NH-optionally substituted alkyl, 5 -sulfonate, 6 -sulfamide, 7 -sulfinamide, 8 -sulfurous diamide, 9 -optionally protected monosaccharide, e.g., D-, L- or DL-glucose, fructose, rhamnose or glucuronic acid, 10 -optionally protected oligosaccharide, e.g., D-, L- or DL-galactose-galactose, -galactose-mannose or -glucuronic acid-glucose.

Group 33A. This group contains compounds in groups 1-27 above where $R^1$ substituents 1-10 listed in Table A are replaced with the following groups: 1 —N-pyrrolidine, 2 —N-1-pyrazolone, 3 —N2-pyrazolone, 4 —N-imidazolidin-2-one, 5 —N1-imidazole, 6 —N-1-4,5-dihydroimidazole, 7 —N-morpholine, 8 —N1-pyridine, 9 —N-piperidine, 10 —N-piperazine. As examples, group 33A-3 compound 1.1.6.9 (i.e., group 33A compound 1.1.6.9 from group 3) is 3β-N-pyrrolidinyl-16α,17β-dihydroxyandrost-5-ene and 33A-3 compound 1.1.4.9 is 3β-N-pyrrolidinyl-16α-fluoro-17β-hydroxyandrost-5-ene, group 33A-4 compound 1.1.6.9 (i.e., group 26A compound 1.1.6.9 from group 4) is 3β-N-pyrrolidiny-16α,17β-dihydroxyandrost-1,5-diene and 26A-4 compound 1.1.4.9 is 3β-N-pyrrolidinyl-16α-fluoro-17β-hydroxyandrost-1,5-diene.

Group 33B. This group contains compounds in groups 1-27 above where $R^1$ substituents 1-10 listed in Table A are replaced with the following groups: 1 —N-piperazine substituted at N4 with optionally substituted alkyl, 2 —N4-indole, 3 —N4-indoline, 4-N-quinolidine, 5 —NH—C(O)—$CH_2$—$CH_2$—C(O)—OH, 6 —NH—C(O)—$CH_2$—C(O)—OH, 7 —NH—C(O)—$CH_2$—$CH_2$—C(O)—$OR^{PR}$, 8 —NH—C(O)—$CH_2$C(O)—$OR^{PR}$, 9 —NH—C(O)—$(CH_2)_3$—C(O)—OH, 10 —NH—C(O)—$(CH)_3$—C(O)—$OR^{PR}$. Ionizable moieties such as free carboxyl groups include salts, e.g., $Na^+$ or $K^+$. $R^{PR}$ is a protecting group.

Group 33C. This group contains compounds in groups 1-27 above where $R^1$ substituents 1-10 listed in Table A are replaced with the following groups: 1 —NH—CH($CH_3$)—C(O)OH, 2 —NH—CH($CH_3$)—C(O)$OR^{PR}$, 3 —NH—CH (CH$_2$OH)—C(O)OH, 4 —NH—CH(CH$_2$OH)—C(O)OR$^{PR}$, 5 —NH—CH$_2$—CH$_2$—C(O)—OH, 6 —NH—CH$_2$—C(O)—OH, 7 —NH—CH$_2$—CH$_2$—C(O)—OR$^{PR}$, 8 —NH—CH$_2$—C(O)—OR$^{PR}$, 9 —NH—(CH$_2$)$_3$—C(O)—OH, 10 —NH—(CH$_2$)$_3$—C(O)—OR$^{PR}$. Ionizable moieties such as free carboxyl groups include salts, e.g., Na$^+$ or K$^+$. R$^{PR}$ is a protecting group.

Group 33D. This group contains compounds in groups 1-27 above where R$^1$ substituents 1-10 listed in Table A are replaced with the following groups: 1 —NH—CH(CH$_3$)—C(O)OH, 2 —NH—NH—C(O)CH$_3$, 3 —NH—NH—C(O)OCH$_3$, 4 —NH—NH—C(O)C$_2$H$_5$, 5 —NH—NH—C(O)OC$_2$H$_5$, 6 —NH—NH—C(O)C$_3$H$_7$, 7 —NH—NH—C(O)-optionally substituted alkyl, 8 —NH—C(NH-optionally substituted alkyl)=N-optionally substituted alkyl, 9 —NH—C(NH—CH$_3$)=N—CH$_3$, 10 —NH—C(NH—C$_2$H$_5$)=N—C$_2$H$_5$.

Group 33E. This group contains compounds in groups 1-27 above where R$^1$ substituents 1-10 listed in Table A are replaced with the following groups: 1 spiro β-NH—(CH$_2$)$_2$—O-α, 2 spiro α-NH—(CH$_2$)$_2$—O-β, 3 spiro β-NH—(CH$_2$)$_2$—NH-α, 4 spiro α-NH—(CH$_2$)$_2$—NH-β, 5 spiro β-NH—CH=N—CH$_2$-α, 6 spiro α-NH—CH=N—CH$_2$-β, 7 spiro β-NH—CHR$^{10}$—CHR$^{10}$—O-α, 8 spiro α-NH—CHR$^{10}$—CHR$^{10}$—O-β, 9 spiro β-NH—CHR$^{10}$—CHR$^{10}$—NH-α, 10 spiro α-NH—CHR$^{10}$—CHR$^{10}$—NH-β. Each R$^{10}$ is independently chosen and has the meaning given above, e.g., —H, —OH, =O, —SH, =S, halogen or optionally substituted alkyl.

Group 34. This group contains compounds in groups 1-27 above where R$^1$ substituents 1-10 listed in Table A are replaced with the following groups: 1 -glycol, e.g., propylene glycol or ethylene glycol, 2 -polyethylene glycol, e.g., PEG 100 or PEG 200, 3 -an acetal ring, 4 -a spiro ring, 5 -a thioacetal ring, 6 spiro —O—CH$_2$—, 7 spiro —O—(CH$_2$)$_2$—O—, 8 spiro —NH—(CH$_2$)$_2$—O—, 9 —NH—C(O)—(CH$_2$)$_2$—C(O)O—CH$_3$, 10 —NH—C(O)—(CH$_2$)—C(O)—OH.

Group 35. This group contains compounds in groups 1-34 above where R$^3$ substituents 1-10 listed in Table A are replaced with the following groups: 1 -optionally substituted amine, 2 -optionally substituted amide, 3 -optionally substituted oxime, 4 -optionally substituted alkyl, 5 -optionally substituted alkenyl, 6 -optionally substituted alkynyl, 7 -optionally substituted aryl, 8 -optionally substituted heterocycle, 9 -ether and 10 -ester. Any of these groups can be a moiety defined herein for that group.

Group 36. This group contains compounds in groups 1-34 above where R$^3$ substituents 1-10 listed in Table A are replaced with the following groups: 1 -acyl, 2 -thioester, 3 -thioether, 4 -thioacyl, 5 -epoxide, 6 -optionally substituted cyclopropyl, 7 —O—Si(C1-C6 alkyl)$_3$, 8 -phosphate, 9 -phosphate ester and 10 -phosphate ether. Any of these groups can be a moiety defined herein for that group. The epoxide and optionally substituted cyclopropyl moieties for substituents 5 and 6 respectively can be at the 15-16 positions or at the 16-17 positions in the α- or β-configuration.

Group 37. This group contains compounds in groups 1-34 above where R$^3$ substituents 1-10 listed in Table A are replaced with the following groups: 1 -phosphate thioether, 2 -thionoester, 3 -amino acid, 4 -peptide, 5 -dipeptide, 6 -optionally substituted heterocycle, 7 -optionally substituted carboxyl, 8 -carbonate, 9 -carbamate and 10 -phosphothioester.

Group 38. This group contains compounds in groups 1-34 above where R$^3$ substituents 1-10 listed in Table A are replaced with the following groups: 1 -thiophosphate, 2 -phosphothioether, 3 -thiophosphate thioether, 4 -phosphonoester, 5 -phosphonate, 6 -phosphonate ester, 7 -phosphonate ether, 8 -phosphonate thioether, 9 —O—S(O)(O)—OH and 10 -sulfate salt, e.g., —O—S(O)(O)—O$^+$Na$^-$.

Group 39. This group contains compounds in groups 1-34 above where R$^3$ substituents 1-10 listed in Table A are replaced with the following groups: 1 -sulfate ester, 2 -sulfate ether, 3 -sulfate thioether, 4 —O—S(O)—OH, 5 -sulfite salt, e.g., —O—S(O)—O$^+$Na$^-$, 6 -sulfite ester, 7 -sulfite ether, 8 -sulfoxide, 9 —O—S(O)(O)—OR$^{PR}$ and 10 —O—S(O)(O)—OCH$_3$.

Group 40. This group contains compounds in groups 1-34 above where R$^3$ substituents 1-10 listed in Table A are replaced with the following groups: 1 -sulfonamide, 2 -sulfonamide derivative, e.g., —S(O)(O)—NHR$^{PR}$ or —S(O)(O)—NH-optionally substituted alkyl, 3 -sulfamate, 4 -sulfamate derivative, e.g., —O—S(O)(O)—NHR$^{PR}$, —O—(O)(O)—N(RD)$_2$ or O—S(O)(O)—NH-optionally substituted alkyl, 5 -sulfonate, 6 -sulfamide, 7 -sulfinamide, 8 -sulfurous diamide, 9 -optionally protected monosaccharide, e.g., D-, L- or DL-glucose, fructose, rhamnose or glucuronic acid, 10 -optionally protected oligosaccharide, e.g., D-, L- or DL-galactose-galactose, -galactose-mannose or -glucuronic acid-glucose.

Group 40A. This group contains compounds in groups 1-34 above where R$^3$ substituents 1-10 listed in Table A are replaced with the following groups: 1 —N-pyrrolidine, 2 —N1-pyrazolone, 3 —N2-pyrazolone, 4 —N4-imidazolidin-2-one, 5 —N1-imidazole, 6 —N-1-4, 5 -dihydroimidazole, 7 —N-morpholine, 8 —N-1-pyridine, 9 —N-piperidine, 10 —N-piperazine.

Group 40B. This group contains compounds in groups 1-34 above where R$^3$ substituents 1-10 listed in Table A are replaced with the following groups: 1 —N-piperazine substituted at N4 with optionally substituted alkyl, 2 —N4-indole, 3 —N4-indoline, 4-N-quinolidine, 5 —NH—C(O)—CH$_2$—CH$_2$—C(O)—OH, 6 —NH—C(O)—CH$_2$—C(O)—OH, 7 —NH—C(O)—CH$_2$—CH$_2$—C(O)—OR$^{PR}$, 8 —NH—C(O)—CH—C(O)—OR$^{PR}$, 9 —NH—C(O)—(CH$_2$)$_3$—C(O)—OH, 10 —NH—C(O)—(CH$_2$)$_3$—C(O)—OR$^{PR}$. Ionizable moieties such as free carboxyl groups include salts, e.g., Na$^+$ or K$^+$. R$^{PR}$ is a protecting group.

Group 40C. This group contains compounds in groups 1-34 above where R$^3$ substituents 1-10 listed in Table A are replaced with the following groups: 1 —NH—CH(CH$_3$)—C(O)OH, 2 —NH—CH(CH$_3$)—C(O)OR$^{PR}$, 3 —NH—CH(CH$_2$OH)—C(O)OH, 4 —NH—CH(CH$_2$OH)—C(O)OR$^{PR}$, 5 —NH—CH$_2$—CH$_2$—C(O)—OH, 6 —NH—CH$_2$—C(O)—OH, 7 —NH—CH$_2$—CH$_2$—C(O)—OR$^{PR}$, 8 —NH—CH$_2$—C(O)—OR$^{PR}$, 9 —NH—(CH$_2$)$_3$—C(O)—OH, 10 —NH—(CH$_2$)$_3$—C(O)—OR$^{PR}$. Ionizable moieties such as free carboxyl groups include salts, e.g., Na$^+$ or K$^+$. R$^{PR}$ is a protecting group.

Group 40D. This group contains compounds in groups 1-34 above where R$^3$ substituents 1-10 listed in Table A are replaced with the following groups: 1 —NH—CH(CH$_3$)—C(O)OH, 2 —NH—NH—C(O)CH$_3$, 3 —NH—NH—C(O)OCH$_3$, 4 —NH—NH—C(O)C$_2$H$_5$, 5 —NH—NH—C(O)OC$_2$H$_5$, 6 —NH—NH—C(O)C$_3$H$_7$, 7 —NH—NH—C(O)-optionally substituted alkyl, 8 —NH—C(NH-optionally substituted alkyl)=N-optionally substituted alkyl, 9 —NH—C(NH—CH$_3$)=N—CH$_3$, 10 —NH—C(NH—C$_2$H$_5$)=N—C$_2$H$_5$.

Group 40E. This group contains compounds in groups 1-34 above where R$^3$ substituents 1-10 listed in Table A are replaced with the following groups: 1 spiro β-NH—(CH$_2$)$_2$—O-α, 2 spiro α-NH—(CH$_2$)$_2$—O—, 3 spiro β-NH—(CH$_2$)—NH-α, 4 spiro α-NH—(CH$_2$)$_2$—NH—β, 5 spiro β-NH—

CH=N—CH$_2$-α, 6 spiro α-NH—CH=N—CH$_2$-β, 7 spiro β-NH—CHR$^{10}$—CHR$^{10}$—O-α, 8 spiro α-NH—CHR$^{10}$—CHR$^{10}$—O—β, 9 spiro β-NH—CHR$^{10}$—CHR$^{10}$—NH-α, 10 spiro α-NH—CHR$^{10}$—CHR$^{10}$—NH—P. Each R$^{10}$ is independently chosen and has the meaning given above, e.g., —H, —OH, =O, —SH, =S, halogen or optionally substituted alkyl.

Group 41. This group contains compounds in groups 1-34 above where R$^3$ substituents 1-10 listed in Table A are replaced with the following groups: 1 -glycol, e.g., propylene glycol or ethylene glycol, 2 -polyethylene glycol, e.g., PEG 100 or PEG 200, 3 -an acetal ring, 4 -a spiro ring, 5 -a thioacetal ring, 6 spiro —O—CH$_2$—O—, 7 spiro —O—(CH$_2$)$_2$—O—, 8 spiro —NH—(CH$_2$)$_2$—O—, 9 —NH—C(O)—(CH$_2$)$_2$—C(O)O—CH$_3$, 10 —NH—C(O)—(CH$_2$)$_2$—C(O)—OH.

Group 42. This group contains compounds in groups 1-41 above where R$^2$ substituents 1-10 listed in Table A are replaced with the following groups: 1 -optionally substituted amine, 2 -optionally substituted amide, 3 -optionally substituted oxime, 4 -optionally substituted alkyl, 5 -optionally substituted alkenyl, 6 -optionally substituted alkynyl, 7 -optionally substituted aryl, 8 -optionally substituted heterocycle, 9 -ether and 10 -ester. Any of these groups can be a moiety defined herein for that group.

Group 43. This group contains compounds in groups 1-41 above where R$^2$ substituents 1-10 listed in Table A are replaced with the following groups: 1 -acyl, 2 -thioester, 3 -thioether, 4 -thioacyl, 5 -epoxide, 6 -optionally substituted cyclopropyl, 7 —O—Si(C1-C6 alkyl)$_3$, 8 -phosphate, 9 -phosphate ester and 10 -phosphate ether. Any of these groups can be a moiety defined herein for that group. The epoxide and optionally substituted cyclopropyl moieties for substituents 5 and 6 respectively can be at the 6-7 positions or at the 7-8 positions in the α- or β-configuration.

Group 44. This group contains compounds in groups 1-41 above where R$^2$ substituents 1-10 listed in Table A are replaced with the following groups: 1 -phosphate thioether, 2 -thionoester, 3 -amino acid, 4 -peptide, 5 -dipeptide, 6 -optionally substituted heterocycle, 7 -optionally substituted carboxyl, 8 -carbonate, 9 -carbamate and 10 -phosphothioester.

Group 45. This group contains compounds in groups 1-41 above where R$^2$ substituents 1-10 listed in Table A are replaced with the following groups: 1 -thiophosphate, 2 -phosphothioether, 3 -thiophosphate thioether, 4 -phosphonoester, 5 -phosphonate, 6 -phosphonate ester, 7 -phosphonate ether, 8 -phosphonate thioether, 9 —O—S(O)(O)—OH and 10 -sulfate salt, e.g., —O—S(O)(O)—O$^+$Na$^-$.

Group 46. This group contains compounds in groups 1-41 above where R$^2$ substituents 1-10 listed in Table A are replaced with the following groups: 1 -sulfate ester, 2 -sulfate ether, 3 -sulfate thioether, 4 —O—S(O)—OH, 5 -sulfite salt, e.g., —O—S(O)—O$^+$Na$^-$, 6 -sulfite ester, 7 -sulfite ether, 8 -sulfoxide, 9 —O—S(O)(O)—OR$^{PR}$ and 10 —O—S(O)(O)—OCH$_3$.

Group 47. This group contains compounds in groups 1-41 above where R$^2$ substituents 1-10 listed in Table A are replaced with the following groups: 1 -sulfonamide, 2 -sulfonamide derivative, e.g., —S(O)(O)—NHR$^{PR}$ or —S(O)(O)—NH-optionally substituted alkyl, 3 -sulfamate, 4 -sulfamate derivative, e.g., —O—S(O)(O)—NHR$^{PR}$, —O—(O)(O)—N(RD)$_2$ or —S(O)(O)—NH-optionally substituted alkyl, 5 -sulfonate, 6 -sulfamide, 7 -sulfinamide, 8 -sulfurous diamide, 9 -optionally protected monosaccharide, e.g., D-, L- or DL-glucose, fructose, rhamnose or glucuronic acid, 10 -optionally protected oligosaccharide, e.g., D-, L- or DL-galactose galactose, -galactose-man nose or -glucuronic acid-glucose.

Group 47A. This group contains compounds in groups 1A41 above where R$^2$ substituents 1-10 listed in Table A are replaced with the following groups: 1 —N-pyrrolidine, 2 —N-1-pyrazolone, 3 —N2-pyrazolone, 4 —N-imidazolidin-2-one, 5 —N1-imidazole, 6 —N-1-4,5-dihydroimidazole, 7 —N-morpholine, 8 —N-1-pyridine, 9 —N-piperidine, 10 —N-piperazine.

Group 47B. This group contains compounds in groups 1-41 above where R$^2$ substituents 1-10 listed in Table A are replaced with the following groups: 1 —N-piperazine substituted at N4 with optionally substituted alkyl, 2 —N-indole, 3 —N-indoline, 4-N-quinolidine, 5 —NH—C(O)—CH$_2$—CH$_2$—C(O)—OH, 6 —NH—C(O)—CH$_2$—C(O)—OH, 7 —NH—C(O)—CH$_2$—CH$_2$—C(O)—OR$^{PR}$, 8 —NH—C(O)—CH$_2$—C(O)—OR$^{PR}$, 9 —NH—C(O)—(CH$_2$)$_3$—C(O)—OH, 10 —NH—C(O)—(CH$_2$)$_3$—C(O)—OR$^{PR}$. Ionizable moieties such as free carboxyl groups include salts, e.g., Na$^+$ or K$^+$. R$^{PR}$ is a protecting group.

Group 47C. This group contains compounds in groups 1-41 above where R$^2$ substituents 1-10 listed in Table A are replaced with the following groups: 1 —NH—CH(CH$_3$)—C(O)OH, 2 —NH—CH(CH$_3$)—C(O)OR$^{PR}$, 3 —NH—CH(CH$_2$OH)—C(O)OH, 4 —NH—CH(CH$_2$OH)—C(O)OR$^{PR}$, 5 —NH—CH$_2$—CH$_2$—C(O)—OH, 6 —NH—CH$_2$—C(O)—OH, 7 —NH—CH$_2$—CH$_2$—C(O)—OR$^{PR}$, 8 —NH—CH$_2$—C(O)—OR$^{PR}$, 9 —NH—(CH$_2$)$_3$—C(O)—OH, 10—NH—(CH$_2$)$_3$—C(O)—OR$^{PR}$. Ionizable moieties such as free carboxyl groups include salts, e.g., Na$^+$ or K$^+$. R$^{PR}$ is a protecting group.

Group 47D. This group contains compounds in groups 1-41 above where R$^2$ substituents 1-10 listed in Table A are replaced with the following groups: 1 —NH—CH(CH$_3$)—C(O)OH, 2 —NH—NH—C(O)CH$_3$, 3 —NH—NH—C(O)OCH$_3$, 4 —NH—NH—C(O)C$_2$H$_5$, 5 —NH—NH—C(O)OC$_2$H$_5$, 6 —NH—NH—C(O)C$_3$H$_7$, 7—NH—NH—C(O)-optionally substituted alkyl, 8 —NH—C(NH-optionally substituted alkyl)=N-optionally substituted alkyl, 9 —NH—C(NH—CH$_3$)=N—CH$_3$, 10 —NH—C(NH—C$_2$H$_5$)=N—C$_2$H$_5$.

Group 47E. This group contains compounds in groups 1-41 above where R$^2$ substituents 1-10 listed in Table A are replaced with the following groups: 1 spiro —NH—(CH$_2$)$_2$O-α, 2 spiro α-NH—(CH$_2$)$_2$O—, 3 spiro β-NH—(CH$_2$)$_2$—NH—, 4 spiro α—NH—(CH$_2$)$_2$—NH-β, 5 spiro β-NH—CH=N—CH$_2$-α, 6 spiro α-NH—CH=N—CH$_2$—O, 7 spiro β-NH—CHR$^{10}$—CHR$^{10}$—O-α, 8 spiro α-NH—CHR$^{10}$—CHR$^{10}$—O-β, 9 spiro β-NH—CHR$^{10}$—CHR$^{10}$—NH-α, 10 spiro α-NH—CHR$^{10}$—CHR$^{10}$—NH-β. Each R$^{10}$ is independently chosen and has the meaning given above, e.g., —H, —OH, =O, —SH, =S, halogen or optionally substituted alkyl.

Group 48. This group contains compounds in groups 1-41 above where R$^2$ substituents 1-10 listed in Table A are replaced with the following groups: 1 -glycol, e.g., propylene glycol or ethylene glycol, 2 -polyethylene glycol, e.g., PEG 100 or PEG 200, 3 -an acetal ring, 4 -a spiro ring, 5 -a thioacetal ring, 6 spiro —O—CH$_2$—O—, 7 spiro —O—(CH$_2$)$_2$—O—, 8 spiro —NH—(CH$_2$)$_2$—O—, 9 —NH—C(O)—(CH$_2$)$_2$—C(O)O—CH$_3$, 10 —NH—C(O)—(CH$_2$)$_2$—C(O)—OH.

Group 49. This group contains compounds in groups 1-48 above wherein R$^4$ is single bonded and a second R$^4$ that is not —H is present. The second R⁴ can be a moiety defined herein for R⁴, e.g., optionally substituted alkyl, halogen, —SH or —OH.

Group 50. This group contains compounds in groups 1-49 above wherein R¹ is single bonded and a second R¹ that is not —H is present. The second R¹ can be a moiety defined herein for R¹, e.g., optionally substituted alkyl, halogen, —SH or —OH.

Group 51. This group contains compounds in groups 1-50 above wherein R³ is single bonded and a second R³ that is not —H is present. The second R³ can be a moiety defined herein for R³, e.g., optionally substituted alkyl, halogen, —SH or —OH.

Group 52. This group contains compounds in groups 1-51 above wherein R² is single bonded and a second R² that is not —H is present. The second R² can be a moiety defined herein for R², e.g., optionally substituted alkyl, halogen, —SH or —OH.

Metabolites. The invention includes the therapeutic or other uses disclosed herein of metabolites of F1C, which include biologically active metabolites. Metabolites can arise from in vivo or in vitro metabolism. Metabolites of F1C include products that are new. Metabolites may result for example from the oxidation, reduction, hydrolysis, amidation, esterification, glycosidation and the like of the administered formula 1 compound, due to enzymatic or chemical processes. Metabolites may be generated in vivo in a subject or they may arise ex vivo from cells or tissues, e.g., from a mammal such as a human, rodent or a primate. Accordingly, the invention includes new F1Cs produced by a process comprising contacting an F1C with a subject or a subject's cells or tissue for a period of time sufficient to yield detectable amounts of a metabolic product thereof. Such products typically are identified by preparing a radiolabeled or mass labeled F1C that comprises, e.g., 1, 2, 3 or more $^{13}C$, $^{14}C$, $^{3}H$, $^{2}H$, $^{131}I$, $^{32}P$, $^{35}S$ or $^{99}Tc$ atoms bonded to the compound, and administering it as a trace labeled compound along with the unlabeled compound. The labeled and unlabeled compounds are administered by any suitable route (by, e.g., a buccal, sublingual, parenteral, topical or oral route) in a detectable dose (e.g. greater than about 0.1 µg/kg, or at least about 10 µg/kg or at least about 0.5 mg/kg of the labeled compound) to a subject, e.g., an animal or mammal such as rat, mouse, guinea pig, primate, or to a human. After administration sufficient time is allowed for metabolism to occur (typically about 30 seconds to 30 hours) and conversion products are isolated from one or more of the urine, blood, plasma, feces or other suitable biological sources. The amount of labeled formula 1 compound that is administered to a subject will vary with the specific activity of the labeled compound. Exemplary metabolic conversions of formula 1 compounds include modification of hydrogen atoms or other moieties that are bonded to, e.g., one or more of the 1, 2, 3, 4, 6, 7, 11, 15, 16 or 17 positions. Exemplary conversions at these one or more of positions include hydroxylation of ring atoms, e.g., ring carbon atoms, conjugation of hydroxyl groups that are bonded to one or more of those positions with moieties such as sulfate, phosphate or a monosaccharide or disaccharide such as glucuronic acid and hydrolysis of moieties such as esters or alkoxy groups.

Analytical characterization and reference standards. Individual F1Cs described or disclosed herein are suitable for use as standards for determining chemical or physical properties using one, two or more analytical methods, e.g., for use in HPLC, reverse phase HPLC, MS (mass spectrometry), quadrupole MS, GC-MS, LC-MS, NMR (nuclear magnetic resonance spectrometry), $^{2}H$-NMR, $^{3}H$-NMR, $^{13}C$-NMR, $^{14}C$-NMR, infrared spectrometry (IR), Fourier transform-IR, optical rotary dispersion, loss on drying for water and solvent measurement, Karl Fisher titration for water determination, differential scanning calorimetry, melting point, density, refractive index, solubility characteristics in organic solvents, aqueous systems or aqueous-organic solvent mixtures, for water and solvent measurement, Karl Fisher titration for water determination, differential scanning calorimetry, melting point, density, refractive index, solubility characteristics in organic solvents, aqueous systems or aqueous-organic solvent mixtures, the partition coefficient in immiscible solvent systems, e.g., octanol:water partition coefficient, heat stability or epimerization rate or characteristics of a given enantiomer. These analytical or chemical properties of each F1C are collectively referred to as analytical characteristics. For general methods, see, e.g., H. L. J. Makin et al., eds. *Steroid Analysis* 1995, Chapman & Hall, ISBN 0751401285. Thus, to aid in the determination of, e.g., the structure of a metabolite of a F1C or a structurally related compound, the parent compound or another structurally related F1C could be used as a standard. Metabolism of F1Cs will often include one or more of oxidation, reduction, hydroxylation or conjugation, e.g., oxidation or reduction to a —OH or =O moiety, or conjugation with a moiety such as sulfate, phosphate, amino acid, dipeptide or a monosaccharide such as glucuronic acid at, e.g., the 2, 3, 6, 7, 11, 15, 16, 17 or other positions on the steroid nucleus. In these embodiments, the appropriate use of a F1C of known structure as a standard can aid in or verify the identification of metabolites that are projected to have closely related structures. Information regarding the identification can be useful or sometimes is necessary for, e.g., obtaining regulatory approval to market a therapeutic agent such as a F1C or understanding the potential biological role that a F1C or its metabolite can play in one of the applications disclosed herein or in a cited reference. To facilitate such uses, the F1C may be labeled as appropriate, e.g., using a F1C with, e.g., one or more $^{2}H$, $^{3}H$, $^{13}C$, $^{14}C$, $^{15}N$, $^{18}O$, $^{18}F$, $^{35}S$, $^{32}P$ or $^{123}I$, at 1, 2 or more of the 1, 2, 3, 4, 5, 6, 7, 8, 9, 10, 11, 12, 13, 14, 15, 16, 17, 18, 19, 20, 21, 22 or other positions in any formula 1 steroid. Radiolabel or heavy isotope atoms may be directly bonded to, or for carbon atoms, replace a steroid nucleus atom, or they may be bonded through one, two or more intervening atoms, e.g., steroid-O—$^{32}P(O)(OH)(OH)$. Suitably labeled compounds include any of the F1Cs disclosed herein. Such labeled compounds may comprise, e.g., a $^{13}C$ at the 18 or 19 positions and 1, 2, 3 or 4 $^{3}H$ may be bonded to the $^{13}C$ atom(s) or to a ring carbon(s). Other formula 1 compounds may comprise one or two $^{2}H$ or $^{3}H$ atoms bonded to one or more of the 1, 2, 4, 5, 6, 11 or 12 positions and optionally a $^{13}C$ at the 18 or 19 position(s). F1Cs and their metabolites are isolated or characterized using radiolabeled or mass labeled atoms. F1Cs are also optionally isolated by the use of antibodies capable of binding to epitopes in F1Cs or in metabolites.

In general, analysis of F1C metabolites is accomplished in the same way as conventional drug metabolism studies, which are known to those skilled in the art. The conversion products, especially when they are not otherwise found in vivo, are useful in diagnostic assays for therapeutic dosing of the formula 1 compounds even if they possess only limited therapeutic activity of their own.

Embodiments include a method (the "characterization method") to characterize or at least partially characterize a formula 1 compound that is at least partially uncharacterized for one or more given chemical or analytical properties, e.g., a known or potential metabolite of a parent formula 1 compound, comprising (a) providing a formula 1 compound having one, two or more known characteristics, e.g., a known or at least partially known or characterized chemical structure, XRD spectrum or melting point (a "CF1C"), and a formula 1 compound that is unknown or at least partially uncharacterized, i.e., is uncharacterized for at least one of the same analytical characteristics (a "UCF1C"), (b) obtaining one, two or more analytical characteristics of the UCF1C, and (c) comparing the 1, 2 or more analytical characteristics of the CF1C with the analytical characteristics of the UCF1C. The steps in this method may be conducted in any suitable order, e.g., analytical or chemical data for the CF1C will usually be obtained before or at about the same time as one obtains the analytical or chemical data for the UCF1C. Usually the CF1C will be more completely characterized than the UCF1C, particularly with regard to its chemical structure or its relative degree of purity or with regard to the analytical or chemical data that is being sought. This method allows further characterization of the UCF1C, e.g., by confirming the UCF1C's chemical structure or by determining the UCF1C's stability under various storage or temperature conditions or in various formulations or by determining other analytical or chemical properties of interest. In this method, the CF1C itself may not be completely characterized, however, for the one, two or more analytical characteristics of interest, the CF1C will usually have a known or confirmed property or properties, while the UCF1C is unknown or at least unconfirmed for the same property or properties.

In some embodiments the characterization method is conducted by comparing dissimilar analytical characteristics. For example, the CF1C may be well characterized by GC-MS or by NMR, while an insufficient amount of the UCF1C is available for analysis with the same technique. In these cases, one can then, e.g., compare the GC-MS of the CF1C with the NMR of the UCF1C to obtain the same or essentially the same information for the UCF1C. Other examples of where this can be done is where DSC data is available for the CF1C, and only melting point data is available for the UCF1C. In this case, the CF1C DSC data is compared to the UCF1C's melting point data. Also, in conducting the characterization method, one can optionally derivatize or chemically modify the CF1C and/or the UCF1C to facilitate analysis of the compound(s). For example, in conducting MS, GC-MS or NMR analysis, one or more free hydroxyl or ketone moieties on the CF1C and/or the F2C can be silylated using, e.g., trimethylsilyl chloride, t-butyl-dimethylsilyl chloride or other suitable silylating agents. Similarly, the UCF1C may be treated or incubated with a cell line or tissue or with a glucuronidase, sulfatase, phosphatase, esterase, lipase, oxidoreductase or other enzyme and then characterized. This treatment may in some cases convert the UCF1C into the CF1C, but this conversion would usually be confirmed by one, two or more suitable analytical methods. Such treatments will usually generate additional data about the structure, properties or origin of the UCF1C.

Embodiments include modifications of the characterization method that use a CF1C and a second formula 1 compound that is believed or known to have a related structure or empirical formula. In these modifications, the CF1C is used as described and a second formula 1 compound or a UCF1C that is believed or known to be, e.g., an epimer or a salt, of the CF1C is compared to the CF1C. Invention embodiments include other modifications of the characterization method such as (1) comparing analytical or chemical data from a single CF1C with 2, 3, 4 or more UCF1C, (2) comparing analytical or chemical data from 2, 3, 4 or more CF1C with a single UCF1C and (3) comparing analytical or chemical data from 2, 3, 4 or more CF1C with 2, 3, 4 or more UCF1C. In these modifications, the CF1C or UCF1C are used essentially as described for the characterization method, except that data is obtained for the added formula 1 compounds.

Typically, when the 1, 2 or more analytical characteristics of a CF1C or a UCF1C are obtained, which may be for use in the characterization method or for other purposes, each compound is analyzed under the same or essentially the same analytical conditions using the same or essentially the same analytical technique or instrument. Variations in an analytical technique may be used where the properties of a CF1C or a UCF1C require slightly different handling or specimen preparation. An example of a variation in analytical conditions is the comparison of a property of a CF1C, e.g., its stability to heat, humidity or prolonged storage at a given temperature, with the same property of the CF1C in a composition containing an excipient(s) or in a formulation (where the CF1C in a composition is then considered the UCF1C for the characterization method). This allows the determination of the stability of the CF1C as a pure compound compared to its stability in any desired composition.

When characterizing a CF1C by MS, particularly by GC-MS, one will usually conduct an initial characterization of a formula 1 compound or a CF1C in the characterization method using a known GC-MS method (e.g., H. L. J. Makin et al., *Mass Spectra and GC Data of Steroids: Androgens and Estrogens* 1999 John Wiley & Sons, pages XIII-XIV) or a suitable variation of this method. For F1Cs that contain free hydroxyls or oxo groups, the hydroxyl groups can be derivatized to an ester such as acetate, hydroxyl and oxo or groups can be derivatized to trimethylsilyl ether, i.e., —O—Si$(CH_3)_3$, and oxo groups can be derivatized to a an oxime such as =N—O—$CH_3$ before GC-MS analysis. Other functional groups can also be suitably derivatized. For embodiments of the characterization method that use a GC-MS analysis method, the CF1C or the UCF1C is analyzed by the GC-MS method or a suitable variation to obtain or to confirm chemical structure information about the CF1C or the UCF1C. Suitable variations include, e.g., a change in the carrier gas from helium to hydrogen to increase the sensitivity of detection or a decrease in the ionization from 70 eV to 50 eV can give a better parent mass ion.

As is apparent from the present disclosure, the F1C may be prepared synthetically and typical embodiments will utilize purified a F1C. Purified F1C can be free, essentially free or partially free, of other F1C or other compounds such as excipients. Thus, any given purified F1C can be present as a solid that contains, e.g., less than about 15% w/w or less than about 10% w/w or less than about 8% w/w or less than about 5% w/w or less than about 3% w/w or less than about 1% w/w of one, two or more other F1Cs, excipients, synthetic by-products, decomposition products or synthesis or purification reactants or reagents. Similarly, the F1C can be present in a solution or suspension that contains at least about 90% w/w or at least about 95% w/w or at least about 97% w/w of the F1C and one or more excipients and less than about 10% or 8% or 5% or 3% w/w or 1% w/w of one, two or more other F1Cs, excipients, synthetic by-products, decomposition products or synthesis or purification reactants or reagents.

Various groups that F1Cs contain as described herein, e.g., hydroxyl groups or ketones bonded to the steroid nucleus, or substituted alkyl groups, substituted heterocycles, amino acids and peptides, which can contain one or more reactive moieties such as hydroxyl, oxo, carboxyl, amino or thiol moieties. Intermediates used to make F1Cs may be protected as is apparent in the art, e.g., using suitable $R^{PR}$ moieties. Noncyclic and cyclic protecting groups and corresponding cleavage reactions are described in "Protective Groups in Organic Chemistry", Theodora W. Greene (John Wiley & Sons, Inc., New York, 1991, ISBN 0-471-62301-6) (hereafter "Greene") and will not be detailed here. In the context of the present invention, these protecting groups are groups that can be removed from a F1C without irreversibly changing the covalent bond structure or oxidation/reduction state of the remainder of the molecule. For example, the protecting group, —R$^{PR}$, that is bonded to an —OR$^{PR}$ or —NHR$^{PR}$ group can be removed to form —OH or —NH$_2$, respectively, without affecting other covalent bonds in the molecule. Protecting groups for carbonyl or ketone moieties include ethylene ketals, e.g., —O—CH$_2$—CH$_2$—O—. At times, when desired, more than one protecting group can be removed at a time, or they can be removed sequentially. In F1Cs containing more than one protecting group, the protecting groups are the same or different.

Protecting groups are removed by known procedures, although it will be understood that the protected intermediates fall within the scope of this invention. The removal of the protecting group may be arduous or straightforward, depending upon the economics and nature of the conversions involved. In general, one will use a protecting group with exocyclic amines or with carboxyl groups during synthesis of a F1C. For most therapeutic applications amine groups should be deprotected. Protecting groups commonly are employed to protect against covalent modification of a sensitive group in reactions such as alkylation or acylation. Ordinarily, protecting groups are removed by, e.g. hydrolysis, elimination or aminolysis. Thus, simple functional considerations will suffice to guide the selection of a reversible or an irreversible protecting group at a given locus on the F1Cs. Suitable protecting groups and criteria for their selection are described in T. W. Greene and P. G. M. Wuts, Eds. "Protective Groups in Organic Synthesis" 2nd edition, Wiley Press, at pps. 10-142, 143-174, 175-223, 224-276, 277-308, 309-405 and 406-454.

Characterization of a protecting group is made in the conventional manner, e.g., as described by Kocienski, Philip J.; "*Protecting Groups*" (Georg Thieme Verlag Stuttgart, N.Y., 1994) (hereafter "Kocienski"), Section 1.1, page 2, and Greene Chapter 1, pages 1-9. In particular, a group is a protecting group if when, based on mole ratio, 90% of that protecting group has been removed by a deprotection reaction, no more than 50%, typically 25%, more typically 10%, of the deprotected product molecules have undergone changes to their covalent bond structure or oxidation/reduction state other than those occasioned by the removal of the protecting group. When multiple protecting groups of the same type are present in the molecule, the mole ratios are determined when all of the groups of that type are removed. When multiple protecting groups of different types are present in the molecule, each type of protecting group is treated (and the mole ratios are determined) independently or together with others depending on whether the deprotection reaction conditions pertinent to one type are also pertinent to the other types present. In one embodiment, a group is a protecting group if when, based on mole ratio determined by conventional techniques, 90% of that protecting group has been removed by a conventional deprotection reaction, no more than 50%, typically 25%, more typically 10%, of the deprotected product molecules have undergone irreversible changes to their covalent bond structure or oxidation/reduction state other than those occasioned by the removal of the protecting group. Irreversible changes require chemical reactions (beyond those resulting from aqueous hydrolysis, acid/base neutralization or conventional separation, isolation or purification) to restore the covalent bond structure or oxidation/reduction state of the deprotected F1C.

Protecting groups are also described in detail together with general concepts and specific strategies for their use in Kocienski, Philip J.; "Protecting Groups" (Georg Thieme Verlag Stuttgart, N.Y., 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184, Chapter 6, Amino Protecting Groups, pages 185-243, Chapter 7, Epilog, pages 244-252, and Index, pages 253-260, are incorporated with specificity in the context of their contents. More particularly, Sections 2.3 Silyl Ethers, 2.4 Alkyl Ethers, 2.5 Alkoxyalkyl Ethers (Acetals), 2.6 Reviews (hydroxy and thiol protecting groups), 3.2 Acetals, 3.3 Silylene Derivatives, 3.4 1,1,3,3-Tetraisopropyldisiloxanylidene Derivatives, 3.5 Reviews (diol protecting groups), 4.2 Esters, 4.3 2,6,7-Trioxabicyclo[2.2.2]octanes [OBO] and Other Ortho Esters, 4.4 Oxazolines, 4.5 Reviews (carboxyl protecting groups), 5.2 O,O-Acetals, 5.3 S,S-Acetals, 5.4 O,S-Acetals, 5.5 Reviews (carbonyl protecting groups), 6.2 N-Acyl Derivatives, 6.3 N-Sulfonyl Derivatives, 6.4 N-Sulfenyl Derivatives, 6.5 N-Alkyl Derivatives, 6.6 N-Silyl Derivatives, 6.7 Imine Derivatives, and 6.8 Reviews (amino protecting groups), are each incorporated with specificity where protection/deprotection of the requisite functionalities is discussed. Further still, the tables "Index to the Principal Protecting Groups" appearing on the inside front cover and facing page, "Abbreviations" at page xiv, and "reagents and Solvents" at page xv are each incorporated in their entirety herein at this location.

Typical hydroxy protecting groups are described in Greene at pages 14-118 and include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy) methyl, 2-(Trimethylsilyl)ethoxymethyl, Tetrahydropyranyl, 3-Bromotetrahydropyranyl, Tetrahydropthiopyranyl, 1-Methoxycyclohexyl, 4-methoxytetrahydropyranyl, 1,4-Dioxan-2-yl, Tetrahydrofuranyl, Tetrahydrothiofuranyl); Substituted Ethyl Ethers (1-Ethoxyethyl, 1-(2-Chloroethoxy) ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl) ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, 1,3-Benzodithiolan-2-yl, Benzisothiazolyl, S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate; Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-

Dimethoxybenzyl, o-Nitrobenzyl, p-Nitrobenzyl); Groups With Assisted Cleavage (2-Iodobenzoate, 4-Azidobutyrate, 4-Nitro-4-methyl pentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Other Esters (2,6-Dichloro-4-methyl phenoxyacetate, 2,6-Dichloro-4-(1,1,3,3-tetramethyl-butyl)phenoxyacetate, Isobutyrate, Monosuccinoate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitro-phenylsulfenate); and Sulfonates (Sulfate, Methanesulfonate (Mesylate), Benzylsulfonate, Tosylate (Tos)). More typically hydroxy protecting groups include substituted methyl ethers, substituted benzyl ethers, silyl ethers, and esters including sulfonic acid esters, still more typically, esters, trialkylsilyl ethers and tosylates, such as acetates, trimethylsilyl and methoxymethyl.

Typical 1,2- and 1,3-diol protecting groups are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, alpha-Methoxybenzylidene, 1-(N,N-Dimethylamino)ethylidene Derivative, alpha-(N,N-Dimethylamino)benzylidene Derivative, 2-Oxacyclopentylidene); and Silyl Derivatives (Di-t-butylsilylene Group, 1,3-(1,1,3,3-Tetraiso-propyldisiloxanylidene) Derivative, Tetra-t-butoxydisiloxane-1,3-diylidene Derivative, Cyclic Carbonates, Cyclic Boronates, Ethyl Boronate, Phenyl Boronate). More typically, 1,2- and 1,3-diol protecting groups include epoxides and acetonides.

Typical amino protecting groups are described in Greene at pages 315-385 and include Carbamates (Methyl and Ethyl, 9-Fluorenylmethyl, 9(2-Sulfo)fluoroenylmethyl, 9-(2,7-Dibromo)fluorenylmethyl, 2,7-Di-t-buthyl-[9-(10,10-dioxo-10,10,10,10-tetrahydrothioxanthyl)]-methyl, 4-Methoxyphenacyl); Substituted Ethyl (2,2,2-Trichloroethyl, 2-Trimethylsilylethyl, 2-Phenylethyl, 1-(1-Adamantyl)-1-methylethyl, 1,1-Dimethyl-2-haloethyl, 1,1-Dimethyl-2,2-dibromoethyl, 1,1-Dimethyl-2,2,2-trichloroethyl, 1-Methyl-1-(4-biphenylyl)ethyl, 1-(3,5-Di-t-butylphenyl)-1-methylethyl, 2-(2'- and 4'-Pyridyl)ethyl, 2-(N,N-Dicyclohexylcarboxamido)ethyl, t-Butyl, 1-Adamantyl, Vinyl, Allyl, 1-Isopropylallyl, Cinnamyl, 4-Nitrocinnamyl, 8-Quinolyl, N-Hydroxypiperidinyl, Alkyldithio, Benzyl, p-Methoxybenzyl, p-Nitrobenzyl, p-Bromobenzyl, p-Chorobenzyl, 2,4-Dichlorobenzyl, 4-Methylsulfinylbenzyl, 9-Anthrylmethyl, Diphenylmethyl); Groups With Assisted Cleavage (2-Methylthioethyl, 2-Methylsulfonylethyl, 2-(p-Toluenesulfonyl)ethyl, [2-(1,3-Dithianyl)]methyl, 4-Methylthiophenyl, 2,4-Dimethylthiophenyl, 2-Phosphonioethyl, 2-Triphenylphosphonioisopropyl, 1,1-Dimethyl-2-cyanoethyl, m-Choro-p-acyloxybenzyl, p-(Dihydroxyboryl)benzyl, 5-Benzisoxazolylmethyl, 2-(Trifluoromethyl)-6-chromonyl methyl); Groups Capable of Photolytic Cleavage (m-Nitrophenyl, 3,5-Dimethoxybenzyl, o-Nitrobenzyl, 3,4-Dimethoxy-6-nitrobenzyl, Phenyl(o-nitrophenyl)methyl); Urea-Type Derivatives (Phenothiazinyl)-(10)-carbonyl Derivative, N'-p-Toluenesulfonylaminocarbonyl, N'-Phenylaminothiocarbonyl); Other Carbamates (t-Amyl, S-Benzyl Thiocarbamate, p-Cyanobenzyl, Cyclobutyl, Cyclohexyl, Cyclopentyl, Cyclopropylmethyl, p-Decyloxybenzyl, Diisopropylmethyl, 2,2-Dimethoxycarbonylvinyl, o-(N,N-Dimethyl-carboxamido)benzyl, 1,1-Dimethyl-3-(N,N-dimethylcarboxamido)propyl, 1,1-Dimethylpropynyl, Di(2-pyridyl)methyl, 2-Furanylmethyl, 2-Iodoethyl, Isobutyl, Isonicotinyl. More typically, amino protecting groups include carbamates and amides, still more typically, N-acetyl groups.

Groups capable of biological cleavage typically include prodrugs. Some exemplary groups are described in "Design of Prodrugs", Hans Bundgaard (Elsevier, N.Y., 1985, ISBN 0-444-80675-X) (Bundgaard) and will not be detailed here. In particular, Bundgaard, at pages 1-92, describes prodrugs and their biological cleavage reactions for a number of functional group types. Prodrugs for carboxyl and hydroxyl groups are detailed in Bundgaard at pages 3 to 10, for amides, imides and other NH-acidic compounds at pages 10 to 27, amines at pages 27 to 43, and cyclic prodrugs at pages 62 to 70. These moieties are optionally bonded to the steroid at one, two or more of the variable groups that are bonded to the rings in the F1Cs, e.g., one or more $R^1$-$R^6$, $R^{10}$, $R^{15}$, $R^{17}$ and $R^{18}$.

In some embodiments one or more F1Cs or groups of F1Cs may be excluded from one or more of the uses disclosed herein. For example, if the subject has or is susceptible to developing a memory impairing neurological disorder or memory impairment condition, excluded compounds can include 5-androstene-3β-ol-7,17-dione or 5-androstene-3β, 7-diol-17-one or a derivative of these compounds that can has a group at the 7-position that can convert to —OH or =O by hydrolysis. In other cases, the F1Cs can exclude one or more of 4-pregnene-11β,17α,21-triol-3,20-dione, 17α,21-dihydroxypregn-4-ene-3,11,20-trione, 11β,21-dihydroxy-3,20-dioxopregn-4-en-18-al, 11β,17α,21-trihydroxypregna-1,4-diene-3,20-dione, 17α,21-dihydroxypregna-1,4-diene-3,11,20-trione, 3β-hydroxypregn-5-ene-20-one, 3β-hydroxyandrost-5-ene-17-one, pregn-4-ene-3,20-dione, 21-hydroxypregn-4-ene-3,20-dione, 9-fluoro-11β,16α,21-trihydroxy-16-methylpregna-1,4-diene-3,20-dione, 9-fluoro-11β,16α,17,21-tetrahydroxypregna-1,4-diene-3, 20-dione, 9-fluoro-11β,17α,21-trihydroxy-16-methylpregna-1,4-diene-3,20-dione, dehydroepiandrosterone-3-sulfate, 1,4-pregnadiene-17α,21-diol-3,11,20-trione, androsterone, androsterone acetate, androsterone propionate, androsterone benzoate, androst-5-ene-3β,17β-diol, androst-5-ene-3β,17β-diol-3-acetate, androst-5-ene-3β,17β-diol-17-acetate, androst-5-ene-3β,17β-diol-3β,17-diacetate, androst-5-ene-3β,17β-diol-17-benzoate, androst-5-ene-3β,17β-diol-3-acetate-17-benzoate, androst-4-ene-3β,17-dione, androst-5-ene-3β,7β,17β-triol, androst-5-ene-3β,7α,17β-triol, dehydroepiandrosterone, 4-dihydrotestosterone, 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol, testosterone, methyl testosterone, testolactone, oxymetholone, fluoxymesterone, acetoxypregnenolone, allylestrenol, anagestone acetate, chlormadinone acetate, cyproterone, cyproterone acetate, desogestrel, dihydrogesterone, dimethisterone, ethisterone (17α-ethynyltestosterone), ethynodiol diacetate, fluorogestone acetate, gestadene, hydroxyprogesterone, hydroxyprogesterone acetate, hydroxyprogesterone caproate, 3-ketodesogestrel, hydroxymethylprogesterone, hydroxymethylprogesterone acetate, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone, progesterone, cyproterone acetate, norethindrone, norethindrone acetate, levonorgestrel, an ester of any of the foregoing compounds (e.g., acetate, enanthate, propionate, isopropionate, cyclopropionate, isobutyrate, butyrate, valerate, caproate, isocaproate, hexanoate, heptanoate, octanoate, nonanoate, decanoate, undecanoate, phenylacetate or benzoate esters, e.g., hydroxyl esters), a naturally occurring glucorcorticoid, a species disclosed herein or a derivative of any of these that can convert to these molecules by hydrolysis or metabolism, e.g., a metabolizable or hydrolyzable ester or ether such as a cyclic ketal, an acetate, a diacetete, a proprionate, a diproprionate, or an O-alkyl, an acyl, e.g., —C(O)—C1-C6 alkyl or another moiety that is bonded at, e.g., a variable group such as for $R^1$-$R^6$.

Dosages of F1C and dosing protocols or methods. In treating any of the conditions or symptoms disclosed herein, one can continuously or intermittently administer the F1C(s) to a subject having or susceptible to developing the condition or symptom. In treating a condition such as an infection, a hyperproliferation condition, an inflammation condition or another condition disclosed herein with a F1C using an intermittent dosing can avoid or ameliorate some of the undesired aspects normally associated with discontinuous dosing. Such undesired aspects include development of resistance of a pathogen such as a pathogen disclosed herein, e.g., a virus or bacterium such as HIV or *Staphylococcus aureus* or a parasite such as a *Plasmodium parasite*, to the therapeutic agent, failure of the patient or subject to adhere to a daily dosing regimen or reduction of the dosages of other therapeutic agents and/or their associated unwanted side effects or toxicities, e.g., reduction or a toxic effect of a chemotherapy or radiation exposure. In any of the continuous or intermittent dosing protocols described herein, other appropriate treatments can be applied as the subject's clinical situation dictates. Suitable other appropriate treatments or therapeutic agents are described elsewhere herein and in the cited references.

In any of the continuous or in any step(s) in the intermittent dosing protocols described herein, or in treating any of the diseases, conditions or symptoms described herein, the F1C(s) can be administered by one or more suitable routes, e.g., oral, buccal, sublingual, intramuscular (i.m.), subcutaneous (s.c.), intravenous (i.v.), intradermal, another parenteral route or by an aerosol. The effective daily dose in such methods will typically comprise about 0.05 mg/kg/day to about 200 mg/kg/day, or about 0.1 to about 100 mg/kg/day, including about 0.2 mg/kg/day, 0.5 mg/kg/day, about 1 mg/kg/day, about 2 mg/kg/day, about 4 mg/kg/day, about 6 mg/kg/day, about 10 mg/kg/day, about 20 mg/kg/day, about 40 mg/kg/day or about 100 mg/kg/day. Higher dosages, e.g., about 250 mg/kg/day, about 300 mg/kg/day or about 350 mg/kg/day can also be utilized, e.g., in veterinary applications. One can administer the F1C(s) orally using about 4 to about 60 mg/kg/day, usually about 6-30 mg/kg/day. In some embodiments, the intermittent dosing methods exclude dosing protocols that are commonly used to deliver contraceptive steroids to, e.g., human females, such as daily dosing for 21 days, followed by no dosing for 7 days. For humans, dosing is generally about 0.005 mg/kg/day to about 30 mg/kg/day, typically about 0.5-5 mg/kg/day. Low dosages for humans such as about 0.005 mg/kg/day to about 0.2 mg/kg/day or about 0.25-10 mg/day, can be used with, e.g., local, topical, transmucosal or intravenous administration and higher dosages such as about 0.1 mg/kg/day to about 20 mg/kg/day or about 5-200 mg/day, can be used, e.g., for oral, subcutaneous or other systemic or local administration route. For non-human subjects, e.g., mammals such as rodents or primates, the effective daily dosage may comprise about 0.05 mg/kg/day to about 350 mg/kg/day. F1C formulation dosages or daily doses or unit doses or subdoses for subjects such as humans and mammals include, e.g., about 1, 5, 10, 15, 20, 25, 50, 75, 100, 125, 150, 175, 200, 225, 250, 275, 300, 325, 350, 400 or 450 mg of the F1C.

An effective dosage or an effective amount of a F1C(s) is one that is sufficient to result in, e.g., a detectable change in a symptom or an immune parameter such as one described herein. An effective dosage (or daily dosage) may be administered to a subject over a period of time, e.g., at least about 1-14 days before a symptom change or an immune parameter detectably changes. Effective amounts of a F1C can be delivered using the dosages and dosing protocols described herein.

In some embodiments, F1C are used to treat, ameliorate, prevent or slow the progression of a condition or disease described herein by continuous daily dosing of the F1C for 1 day to 1, 2, 3 years or more. In related embodiments, F1C are used to treat, ameliorate, prevent or slow the progression of a condition or disease described herein by continuous dosing the F1C every other day or dosing every third, fourth, fifth, sixth, seventh or $14^{th}$ day over a time period of 3 days to 1, 2, 3 years or more, e.g., dosing for about 2, 3, 4, 5, 6 or 7 days or about 1, 2, 3, 4, 6, 8, 10, 12, 16, 20, 24 or more weeks. Daily doses in any of these dosing regimens or protocols may be subdivided into 2 or 3 subdoses.

Intermittent dosing protocols include administration of a F1C, e.g., orally, topically or parenterally as follows: (1) daily dosing or dosing every other day or dosing every third day or dosing every fourth day or dosing every fifth day or dosing every seventh day for about 2, 3, 4, 5, 6, 7, 8, 9, 10, 11, 12, 13, 14, 15, 16, 17, 18, 19, 20, 21 or 28 days to about 190 days or more, e.g., 1 or 2 years, (2) no dosing of the F1C for 1 to about 190 consecutive days (e.g., about 2, 3, 4, 5, 6, 7, 8, 9, 10, 11 or 12 days to about 20 days), (3) daily dosing for about 3 to about 190 days (e.g., about 3 to about 20 days), and (4) optionally repeating step (2) or a variation of step (2) and (5) optionally repeating the steps (1), (2), (3) and (4) 1, 2, 3, 4, 5, 6, 10, 15, 20, 30 or more times. In some embodiments, the dosing of steps (1) and (3) are the same, while in others, step (1) dosing is for a longer time than step (3). Less frequently, step (1) dosing will be for a shorter time. In some embodiments, steps (1)-(4) or (1)-(5) of the dosing protocol described above where step (4) is included, is repeated at least one time, e.g., at least 2, 3, 4, 5 or 6 times. For conditions that tend to remain chronic, e.g., HIV infection or other chronic conditions described herein, any of these intermittent dosing protocols can be maintained over a relatively long time period, e.g., for at least about 4 months or 6 months to about 5 or more years.

In some embodiments, the number of days of dosing in steps (1) and (3) is the same in each round of treatment, i.e., each time period in step (1) and (3) is the same in the initial and subsequent rounds of the method. In other embodiments they differ. Thus, in some embodiments, step (1) may comprise dosing of about 1 mg/day to about 1500 mg/day of a F1C for 1, 2, 3, 4, 5, 6, 7, 8, 9 or 10 or more consecutive days. Then, step (2) may comprise not administering any F1C for at least about 2, 3, 4, 5, 6, 7, 14, 21, 28, 42, 56, 84, 98, 112 or more consecutive days. Step (3) could comprise dosing of a F1C for 1, 2, 3, 4, 5, 6, 7, 8, 9, 10 or more consecutive days. When step (4) is included it is typically about 1 day to about 3 months, usually 3 days to about 6 weeks. On days when the F1C is administered to the subject, it may be delivered in a single dose or in two, three or more subdoses at, e.g., about 12 hour or about 8 hour time intervals.

Exemplary embodiments comprise (1) administering a F1C(s) once every (as a single dose or as 2 or 3 daily subdoses) 2 days, every 3 days or every 4 days or once per week for about 3, 5, 7, 9, 11, 13, 14, 15, 21, 28 or more days, followed by (2) no dosing for about 2, 3, 4, 5, 6, 10, 14, 15, 21, 20, 25, 28, 30, 35, 40, 42, 45, 49, 56, 60, 70, 77, 84, 98, 112 or more days and then (3) administering the F1C(s) at least once more on one day, e.g., administering the F1C(s) as described in step (1), (4) not dosing for 2, 3, 4, 5, 7 or more days, e.g., as described in step (2) for 1, 2, 3, 4, 5, 6, 7 or 8 weeks, and (5) optionally repeating steps (1), (2), (3) and (4) 1, 2, 3, 4, 5 or 6 times or more.

Other embodiments comprise (1) administering a F1C(s) once every day (as a single dose or as 2 or 3 daily subdoses) for 3-15 or about 8-12 days, followed by (2) no dosing for 1, 2, 3, 4, 5, 6, 10, 15, 20, 25, 30, 35, 40, 45, 50, 56, 70, 84, 98, 112 or more days and then (3) administering the F1C(s) at least once more on one day, e.g., administering the F1C(s) once per day for about 3-15 or about 8-12 consecutive days essentially as described in step (1) and (4) optionally repeating steps (1), (2) and (3) 1, 2, 3, 4, 5 or 6 times or more. In a subset of these embodiments (1) comprises administering a F1C(s) once every day for about 5, 6, 7, 8, 9 or 10 days, followed by (2) no dosing for about 1040 days, (3) administering the F1C(s) at least once more on one day, e.g., administering the F1C(s) once per day for about 10 days (4) repeating step (2) or a variation, e.g., no dosing for about 5-45 days, and (5) optionally repeating steps (1), (2), (3) and (4) or a variation thereof those steps 1, 2, 3, 4, 5 or 6 times or more.

One aspect of invention intermittent dosing is monitoring the subject's response to a particular dosing regimen or schedule, e.g., to any intermittent administration method disclosed herein. For example, while dosing a subject who has a viral infection (e.g., HCV, HIV, SIV, SHIV), one can measure the subject's or pathogen's response, e.g., amelioration of one or more symptoms or a change in infectious particles or viral DNA or RNA in the serum or a change in an immune parameter of interest. Once a response is observed dosing can be continued for one, two or three additional days, followed by discontinuing the dosing for at least one day (at least 24 hours), usually for at least about 2, 3, 4, 5, 6, 7, 14, 21, 28, 42, 56, 70, 84, 98, 112 or more days. Once the subject's response shows signs of remission (e.g., a symptom begins to intensify, viral serum DNA or RNA begins to increase or an immune parameter, e.g., as described herein, begins to deteriorate), dosing can be resumed for another course. An aspect of the subject's response to F1C(s) is that the subject may show a measurable response within a short time, usually about 5-10 days, which allows straightforward tracking of the subject's response, e.g., by monitoring viral titer in peripheral white blood cells ("PBMC"), by measuring viral nucleic acid levels in the blood or by measuring a white blood cell population(s) or expression of a cytokine or interleukin by e.g., white blood cells or a subset(s) thereof. One may monitor one or more immune cell subsets, e.g., NK, LAK, dendritic cells or cells that mediate ADCC immune responses, during and after intermittent dosing to monitor the subject's response and to determine when further administration of the F1C is indicated. These cell subsets are monitored as described herein, e.g., by flow cytometry.

For any of the treatments or methods described herein, prolonged beneficial effects or a sustained immune response by a subject may result from a single administration or short course, e.g, about 1-5 days or about 8 days to about 4 months, of continuous or intermittent administration of a F1C. A single administration means that a F1C is administered to the subject in one, two, three or more doses within a 24 hour period and no further administration of any F1C to the subject occurs for at least about 4-90 days, e.g., about for at least about 30 days to about 2 months, or for about 1.5, 2, 3, 4, 5, 6 or more months. Prolonged beneficial effects or immune responses may also persist after a short course of treatment has been completed (e.g., daily dosing for 2, 3, 4, 5 or 6 days) and the subject is no longer receiving any F1C, or, in some cases, any other therapeutic treatment to treat the primary cause of the subject's pathological condition. Such beneficial effects can persist for more than about 5-30 days, e.g., for at least about 21, 28, 42, 56, 70, 84, 98, 112 or more days. Thus, administration of a F1C provides a method to help protect a subject against progression of an infection or against adverse consequences of unwanted immune reactions, e.g., inflammation or immunosuppression or as disclosed herein, without any dosing of the compound for at least 1, 2 or 3 months after an initial dosing protocol.

Other intermittent dosing embodiments comprise administering to a subject having or susceptible to a condition as described herein an effective amount of a F1C using an initial induction or high dosing regimen. The high dosing regimen may comprise, e.g., 1, 2, 3, 4, 5, 6, 7 or more daily doses of about 4 to about 40 mg/kg that are administered daily, every other day, every $3^{rd}$ day, every $4^{th}$ day or every $5^{th}$ day. Then, the subject is not dosed with a F1C for a period, e.g., of about 5, 7, 14, 21, 28, 42, 56, 70, 84, 98, 112 or more consecutive days. Then a lower daily dosing regimen is administered to the subject, e.g., about 0.2 mg/kg to about 4 or about 6 mg/kg, essentially as described for the high dosing regimen. Alternatively, this low dosing regimen may comprise 1, 2, 3, 6 or more rounds of a low to moderate initial level, e.g., about 2 to about 10 mg/kg/day, optionally followed by subsequent rounds of daily dosing that decrease the initial low to moderate level by about 10%, 20%, 30%, 40% or more in each subsequent round of treatment, which is continued until administration is discontinued. These embodiments can be used with any of the dosing protocols described herein.

Dosages of the F1C, continuous or intermittent dose protocols, routes of administration and the use of combination therapies with other standard therapeutic agents or treatments could be applied essentially as described above for any of the diseases or conditions that are disclosed herein. Thus, the F1Cs may be administered prophylactically or therapeutically in chronic or acute conditions. In acute conditions, the F1Cs may also be administered at the time of occurrence or relatively soon after an acute event such as the onset of surgery, a migraine or the occurrence of trauma, e.g., a central nervous system injury, a cerebral stroke or myocardial infarction. For acute events, a F1C may thus be administered concurrently, e.g., within about 15 minutes or about 30 minutes or about 45 minutes of the onset or occurrence of the acute event, or at a later time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours after the onset or occurrence of the acute event or at any range of times defined by any two of these later times. The F1Cs may thus be administered at about 4-120 hours, about 6-120 hours, about 8-48 hours, 8-24 hours, 8-12 hours, 10-12 hours, 10-14 hours, 10-16 hours, about 10-24 hours, 12-14 hours or about 12-16 hours after an acute event starts, occurs or is believed to have begun, e.g., after a surgical procedure has been completed or after a radiation treatment has ended or after a cytotoxic chemotherapy or a myelosuppressive cancer chemotherapy has been administered to the subject.

Alternatively, the F1Cs may be administered before, e.g., within about 15 minutes, about 30 minutes or about 45 minutes before the onset or occurrence of a planned or anticipated acute event, or at an earlier time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours before the onset or occurrence of the acute event. The F1Cs may thus be administered at about 6-120 hours, about 8-48 hours, about 10-24 hours, about 10-16, or about 12-16 hours before the planned or anticipated acute event, e.g., before a planned surgery or a radiation treatment starts or occurs.

Formulations and compositions for preparing formulations. Invention embodiments include formulations described here and elsewhere in this disclosure. While it is possible for the F1C(s) to be administered to a subject or incubated with a subject's cells in vitro as the compound alone, it is usual to use F1C in a formulation or at least in a composition that contains 1, 2, 3, 4, 5, 6 or more excipients. The formulations, which are useful for veterinary or human pharmaceutical use, comprise at least one F1C, together with 1, 2, 3, 4, 5, 6 or more excipients and optionally one or more additional therapeutic ingredients.

The invention includes compositions comprising one or more pharmaceutically acceptable excipients or carriers. The compositions are used to prepare formulations suitable for human or animal use. Formulations may be designed or intended for oral, rectal, nasal, topical or transmucosal (including buccal, sublingual, ocular, vaginal and rectal) and parenteral (including subcutaneous, intramuscular, intravenous, intradermal, intrathecal, intraocular and epidural) administration. In general, aqueous and non-aqueous liquid or cream formulations are delivered by a parenteral, oral or topical route. In other embodiments, the F1C(s) may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal or intramuscular depot or a rectal or vaginal suppository. The preferred route may vary with, for example, the subject's pathological condition or weight or the subject's response to therapy with a F1C or other therapy that is used or that is appropriate to the circumstances. The F1C formulations can also be administered by two or more routes, e.g., subcutaneous injection and buccal or sublingual, where these delivery methods are essentially simultaneous or they may be essentially sequential with little or no temporal overlap in the times at which the compound is administered to the subject.

The formulations include those suitable for the foregoing administration routes. The formulations may conveniently be presented in unit dosage form and may be prepared by any of the methods known in the art of pharmacy. Techniques, excipients and dosage forms are found in, e.g., *Remington's Pharmaceutical Sciences*, Mack Publishing Co., Easton, Pa. 1985, 17$^{th}$ edition; Nema et al., *PDA J. Pharm. Sci. Tech.* 1997 51:166-171; *Pharmaceutical Coating Technology*, 1995, G. Cole, et al., editors, Taylor & Francis, ISBN 0 136628915; *Pharmaceutical Dosage Forms*, 1992 2$^{nd}$ revised edition, volumes 1 and 2, H. A. Lieberman, et al., editors, Marcel Dekker, ISBN 0824793870; *Pharmaceutical Preformulation*, 1998, pages 1-306, J. T. Carstensen, Technomic Publishing Co. ISBN 1566766907; and *Encyclopedia of Pharmaceutical Technology*, volumes 1, 2 and 3, 2$^{nd}$ edition, 2002, J. Swarbrick and J. C Boylan, editors, Marcel Dekker, Inc., New York, N.Y.

Methods to make invention formulations include the step of bringing into association or contacting a F1C(s) with one or more excipient, such as one described herein or in the cited references. In general the formulations are prepared by uniformly and intimately bringing into association the F1C(s) with liquid excipients or finely divided solid excipients or both, and then, if appropriate, shaping the product.

Formulations suitable for oral administration are prepared as discrete units such as capsules, soft gelatin capsules (softgels), cachets, tablets or caplets each containing a predetermined amount of the F1C(s). F1C formulations can also be present as a powder or granules or as a solution or a suspension, colloid or gel in an aqueous liquid or base or in a non-aqueous liquid or base; or as an oil-in-water liquid emulsion or a water-in-oil liquid emulsion. The F1C formulations may also be a bolus, electuary or paste. Suspension formulations will typically contain about 0.5% w/w or about 1% w/w to about 5%, 10%, 15% or 20% w/w of the F1C, which can be for parenteral use or for other routes of administration, e.g., oral softgels.

A tablet is made by compression or molding, optionally with one or more accessory ingredients. Compressed tablets may be prepared by compressing in a suitable machine the F1C(s) in a free-flowing form such as a powder or granules, optionally mixed with a binder, lubricant, inert diluent, preservative, surface active or dispersing agent. Molded tablets may be made by molding in a suitable machine a mixture of the powdered or granulated F1C and one or more excipients, which are optionally moistened, with an inert liquid diluent or excipient. The tablets may optionally be coated or scored and optionally are formulated so as to provide slow or controlled release of the F1C(s) therefrom. An exemplary tablet or caplet formulation suitable for buccal or sublingual delivery of a F1C to a subject's tissues comprises about 25 or 50 mg of a F1C comprising per 25 mg of the F1C about 6.2 mg povidone, about 0.62 mg magnesium stearate, about 45 mg mannitol and about 48 mg of compressible sucrose.

For infections of the eye or other external tissues e.g., the mouth or skin, the formulations are typically applied as a topical ointment or cream containing the F1C(s) in an amount of, for example, about 0.075 to about 20% w/w (including F1C(s) in a range between about 0.1% and 20% in increments of 0.1% w/w such as about 0.6% w/w, about 0.7% w/w, about 1% w/w, about 1.5% w/w, about 2% w/w, about 2.5 w/w, about 3% w/w, about 5% w/w, about 7% w/w, about 10% w/w etc.), including about 0.2 to 15% w/w and about 0.5 to 10% w/w. When formulated in an ointment, the F1C(s) may be employed with either a paraffinic or a water-miscible ointment base. Alternatively, they may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, butane 1,4-diol, mannitol, sorbitol, glycerol and a polyethylene glycol (including, e.g., PEG 300 and PEG 400) and mixtures thereof. The topical formulations may include a compound that enhances absorption or penetration of the F1C(s) through the skin or other affected areas. Examples of such dermal penetration enhancers include dimethyl sulphoxide and related analogs.

The oily phase of the emulsion formulations may be constituted from known excipients in a known manner. While the phase may comprise an emulsifier or emulgent, it typically comprises a mixture of at least one emulsifier with a fat or an oil or with both a fat and an oil. A hydrophilic emulsifier may be included together with a lipophilic emulsifier, which acts as a stabilizer. Some embodiments include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulations include Tween60™, Span80™, cetostearyl alcohol, benzyl alcohol, myristyl alcohol, glyceryl monostearate and sodium lauryl sulfate. Other excipients include emulsifying wax, propyl gallate, citric acid, lactic acid, polysorbate 80, sodium chloride, isopropyl palmitate, glycerin and white petrolatum.

The choice of suitable oils or fats for the formulation is based on achieving the desired cosmetic properties. Creams are generally a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils are used.

Formulations suitable for topical administration to the eye include eye drops, which are usually sterile, wherein the F1C(s) is dissolved or suspended in a suitable excipient(s), including an aqueous solvent for a F1C(s) that comprise at least about 0.5, one, two or more charges at pH values near neutrality, e.g., about pH 6-8. The F1C(s) is typically present in such formulations in a concentration of about 0.5-20% w/w, about 1-10% w/w or about 2-5% w/w.

Formulations suitable for topical administration to oral mucosa include lozenges or tablets comprising the F1C(s) in a flavored basis or a monosaccharide or disaccharide such as sucrose, lactose or glucose and acacia or tragacanth; pastilles comprising the F1C(s) in an inert basis such as gelatin and glycerin, or sucrose and acacia; and mouthwashes comprising the F1C(s) in a suitable liquid excipient(s). In some embodiments, the lozenges or tablets optionally comprise the property of rapid dissolution or disintegration, e.g., disintegration within about 15 seconds to about 2 minutes, while in others, the lozenges or tablets comprise the property of slower dissolution or disintegration, e.g., disintegration within about 2 minutes to about 10 minutes or more.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the F1C(s) such excipients as are known in the art to be appropriate.

Formulations suitable for parenteral administration include aqueous and non-aqueous sterile injection solutions which may contain anti-oxidants, buffers, bacteriostats, salts (e.g., NaCl, potassium or sodium carbonate or bicarbonate or potassium or sodium phosphates) and solutes which render the formulation isotonic with the blood of the intended subject; and aqueous and non-aqueous sterile suspensions which may include suspending agents or thickening agents. In general, the F1C that is present in liquid compositions or formulations is completely dissolved in aqueous or non-aqueous excipients. However, in some embodiments, e.g., transient compositions or some formulations, the F1C is partially dissolved while the remaining portion is present as a solid, which can be a suspension or a colloid.

Formulations suitable for parenteral delivery of F1Cs to subjects such as humans or animals typically comprise 1, 2, 3, 4, 5, 6 or more excipients. Exemplary embodiments include (1) any two, three or four of propylene glycol, PEG200, PEG300, ethanol, benzyl alcohol and benzyl benzoate and (2) any two, three or four of propylene glycol, PEG100, PEG200, PEG300, PEG400, benzyl alcohol and benzyl benzoate. Typically such formulations will contain both propylene glycol and one or more PEGs, e.g., PEG100, PEG200, PEG300 or PEG400, which enhance the solubility of the F1C by a cosolvent effect.

Formulations, or compositions disclosed herein for use to make formulations suitable for administration by the routes disclosed herein optionally comprise an average particle size in the range of about 0.01 to about 500 microns, about 0.1 to about 100 microns or about 0.5 to about 75 microns. Average particle sizes include a range between 0.01 and 500 microns in 0.05 micron or in 0.1 micron or other increments, e.g., an average particle size of about 0.05, 0.1, 0.2, 0.3, 0.4, 0.5, 0.7, 1, 1.5, 2.0, 2.5, 3.0, 3.5, 4.0, 4.5, 5.0, 5.5, 6, 7, 8, 9, 10, 15, 20, 25, 30, 35, 40, 50, 60, 75, 85, 100, 120, 150, etc. microns). The F1C itself that is used to make a formulation can have one, two or more of these average particle sizes. When F1Cs or compositions that comprise a F1C are used as intermediates to make a formulation, they may comprise one, two, three or more of these average particle sizes, or size ranges. In preparing any of the compositions or formulations that are disclosed herein and that comprise a F1C (and optionally one or more excipients), one may optionally mill, sieve or otherwise granulate the compound or composition to obtain a desired particle size, e.g., as described above.

Milling or micronization by any other method may occur before or after the F1C is contacted with one or more excipients. For example, one may mill a F1C to obtain an average particle size (or diameter) of about 0.05-50 µM or about 0.5-10 µM (e.g., about 0.02, 0.04, 0.05, 0.07, 0.1, 0.5, 1, 1.5, 2, 2.5, 5, 10, 15, 20, 30, 40, 50, 60, 80, 100 or 120 µM average particle size or diameter) before contacting the milled F1C with a liquid or solid excipient. In some cases the F1C is milled or sieved to obtain an average particle size of about 5 µm or about 10 µm before it is contacted with a solid or liquid excipient(s) to obtain a solution or suspension or a powder suitable for making a tablet, capsule or other dosage form as described herein or in the cited references. Micronized compound may be prepared using any suitable process for obtaining small particles, e.g., controlled precipitation from a solution, micronizing or milling, a number of which are known in the art. The micronized particles may include a percentage of particles that are less than or equal to about 0.1-20 µm in diameter. Ranges of average particle sizes include F1Cs of about 0.04-0.6 µm, about 0.04-1.0 µm, about 0.05-0.6 µm, about 0.05-1.0 µm, about 0.1-0.4 µm, about 0.5-1 µm, about 1-20 µm or about 2-50 µm.

As used herein, reference to an average particle size or an average particle diameter means that the material, e.g., a F1C(s), an excipient(s) or a composition that comprises both, is ground, milled, sieved or otherwise treated so as to comprise the specified average size. It is to be understood that some particles may be larger or smaller, but the composition or the F1C(s) will comprise a significant proportion of the material with the specified size or within an acceptable range of the specified size, e.g., at least about 70% or about 80% of the particles within about 30% to about 50% of the average size or diameter. Micronization methods include milling by ball mills, pin mills, jet mills (e.g., fluid energy jet mills) and grinding, sieving and precipitation of a compound(s) from a solution, see, e.g., U.S. Pat. Nos. 4,919,341, 5,202,129, 5,271,944, 5,424,077 and 5455049. Average particle size is determined by known methods, e.g., transmission electron microscopy, scanning electron microscopy, light microscopy, X-ray diffractometry, light scattering methods or Coulter counter analysis.

Thus, the F1Cs may comprise a powder that consists of one, two or more of these average particle sizes and the powder may be contacted with a solid excipient(s), suitably mixed and optionally compressed or formed into a desired shape. Alternatively, such a F1C(s) is contacted with a liquid excipient(s) to prepare a liquid formulation or a liquid composition that is incorporated into a solid formulation. Suitable micronized formulations thus include aqueous or oily solutions or suspensions of the F1C(s).

Formulations suitable for aerosol administration typically will comprise a fine powder, e.g., having an average particle size of about 0.1 to about 20 microns or any one, two or more of the average particle sizes within this range that are described above. The powder is typically delivered by rapid inhalation through the nasal passage or by inhalation through the mouth so as to reach the bronchioles or alveolar sacs of the lungs.

Formulations suitable for aerosol, dry powder or tablet administration may be prepared according to conventional methods and may be delivered with other therapeutic agents such as compounds heretofore used in the treatment or prophylaxis of viral or other infections as described herein. Such formulations may be administered, e.g., orally, parenterally (e.g., intravenous, intramuscular, subcutaneous, intradermal, intrathecal), topically, sublingually or by a buccal or sublingual route.

Micronized F1C is useful, e.g., to facilitate mixing, dissolution or uniform suspension of the F1C in one or more liquid or solid excipients, e.g., a PEG such as PEG 300 or PEG 400, propylene glycol, benzyl benzoate, a complexing agent, such as a cyclodextrin (e.g., an α-, β- or γ-cyclodextrin such as hydroxypropyl-β-cyclodextrin). Micronized F1C is also useful to facilitate uniformly distributing drug substance when the micronized compound is contacted with one or more solid excipients (e.g., a filler, a binder, a disintegrant, complexing agent (e.g., a cyclodextrin such as hydroxypropyl-β-cyclodextrin), a preservative, a buffer or a lubricant).

In related embodiments, suitable compositions or formulations comprise a F1C that is present in two or more physical forms. For example, a liquid composition or formulation may comprise a F1C that is present in solution and as undissolved particles, which may be milled as described herein. Alternatively, a solid composition or formulation may comprise a F1C that is present as an amorphous form and as a crystal or in an encapsulated granule. Such encapsulated granules may comprise a slow release type formulation and the F1C that is present may be in one or more physical forms, e.g., liquids or solids as described herein, but usually as a solid in tablets or other solid formulations.

The formulations are presented in unit-dose or multi-dose containers, for example sealed ampules and vials, and may be stored in a freeze-dried (lyophilized) condition requiring only the addition of the sterile liquid excipient, for example water for injection, immediately prior to use. In general, solid, liquid or other formulations or compositions that comprise a F1C, e.g., unit dosages for solid or liquid formulations, are stored in a sealed container, which may optionally be opaque or nearly opaque (e.g., amber or blue glass or brown plastic) to reduce the amount of light that reaches the formulation or composition. Such containers are also optionally sealed, e.g., hermetically sealed, to prevent or limit exchange of air, water or other gases between the container's contents and air. Extemporaneous injection solutions and suspensions are prepared from sterile powders, granules and tablets as described above. Unit dosage formulations are those containing a daily dose or unit daily sub-dose, as recited herein, or an appropriate fraction thereof, of the F1C(s).

It should be understood that in addition to the ingredients particularly mentioned above the formulations of this invention may include other agents or excipients conventional in the art having regard to the type of formulation in question, for example those suitable for oral administration may include flavoring agents. Excipients include liquids, such as benzyl benzoate, cottonseed oil, N,N-dimethylacetamide, a $C_{2-12}$ alcohol (e.g., ethanol), glycerol, peanut oil, vitamin E, poppyseed oil, safflower oil, sesame oil, soybean oil and vegetable oil. Excipients may optionally exclude one or more excipient, e.g., chloroform, dioxane, vegetable oil, DMSO, other excipients or any combination of these. Other excipients are components typically used in the pharmaceutical formulation arts, e.g., one, two or more of fillers, binders, disintegrants, dispersants, preservatives, glidants and lubricants, e.g., povidone, crospovidone, corn starch, carboxymethyl cellulose, hydroxypropyl methylcellulose, microcrystalline cellulose, gum arabic, polysorbate 80, butylparaben, propylparaben, methylparaben, BHA, EDTA, sodium lauryl sulfate, sodium chloride, potassium chloride, titanium dioxide, magnesium stearate, castor oil, olive oil, vegetable oil, buffering agents such as sodium hydroxide, monobasic sodium phosphate, dibasic sodium phosphate, potassium hydroxide, monobasic potassium phosphate, dibasic potassium phosphate, tribasic potassium phosphate, potassium carbonate, potassium bicarbonate, ammonium hydroxide, ammonium chloride, saccharides such as mannitol, glucose, fructose, sucrose or lactose any of which may be compressible or any of which may be spray dried, milled, micronized or otherwise treated to obtained desired characteristics.

Formulations made from or comprising a F1C are optionally stored under conditions that limit the amount of light or water that reaches the formulation, e.g., in a sealed container that holds a formulation or unit dosage form and optionally contains silica gel or activated carbon. Water permeation characteristics of containers have been described, e.g., Containers—Permeation, Chapter, USP 23, 1995, U.S. Pharmacopeial Convention, Inc., Rockville, Md., p. 1787. Storage of BrEA hemihydrate or formulations that contain it is typically at about 4-30° C.

The invention further provides veterinary compositions comprising at least one F1C together with a veterinary excipient(s) therefor. Veterinary excipients are materials useful for the purpose of administering the composition and may be solid, liquid or gaseous materials that are otherwise inert or acceptable in the veterinary art and are compatible with the F1C(s). These veterinary compositions may be administered orally, parenterally or by any other desired route.

Invention formulations include controlled release or slow release formulations containing a F1C(s) in which the release of the F1C(s) is controlled or regulated to allow less frequency dosing or to improve the pharmacokinetic or toxicity profile of a given F1C(s). Polymers and other materials that are suitable to prepare controlled release formulations that comprise a F1C have been described, e.g., U.S. Pat. Nos. 4,652,443, 4,800,085, 4,808,416, 5,013,727, 5,188,840.

Formulations may thus contain microcapsules, granules or other shaped forms and may comprise a F1C and a slow release polymer or polymer matrix that comprises or consists of one or more of ethylene dimethacrylate, diethylene glycol dimethacrylate, diethylene glycol diacrylate, triethylene glycol dimethacrylate, triethylene glycol diacrylate, tetrathylene glycol dimethacrylate, tetraethylene glycol diacrylate, polyethylene glycol dimethacrylate, polyethylene glycol diacrylate, diethylaminoethyl dimethacrylate, glycidyl methacrylate, epoxy acrylate, glycidyl acrylate, hydroxyethyl methacrylate, hydroxyethyl acrylate, hydroxypropyl methacrylate, hydroxypropyl acrylate, hydroxybutyl methacrylate, hydroxybutyl acrylate, hydroxyhexyl methacrylate, hydroxyhexyl acrylate, butanediol dimethacrylate, butanediol diacrylate, propanediol dimethacrylate, propanediol diacrylate, pentanediol dimethacrylate, pentanediol diacrylate, hexanediol dimethacrylate, hexanediol diacrylate, neopentyl glycol dimethacrylate, neopentyl glycol diacrylate, trimethylopropane triacrylate, trimethylolpropane trimethacrylate, trimethyloethane triacrylate, trimethylolethane trimethacrylate, polypropyleneglycol diacrylate, and polypropylene glycol dimethacrylate.

Formulations may comprise a liposome or lipid complex that comprises or contains a F1C(s). Such formulations are prepared according to known methods, e.g., U.S. Pat. Nos. 4,427,649, 5,043,165, 5,714,163, 5,744,158, 5,783,211, 5,795,589, 5,795,987, 5,798,348, 5,811,118, 5,820,848, 5,834,016 and 5882678. The liposomes optionally contain an additional therapeutic agent(s), e.g., amphotericin B, cis-platin, adriamycin, a protease inhibitor, a nucleoside or a nucleotide analog, such as one of those mentioned herein. Formulations that comprise liposomes can be delivered to a subject by any standard route, e.g., oral, aerosol or parenteral (e.g., s.c., i.v. or i.m.).

Liposome formulations can be used to enhance delivery of the F1C(s) to certain cell types such as tumor cells (see e.g., U.S. Pat. No. 5,714,163) or to cells of the reticuloendothelial system ("RES"). The RES includes macrophages, mononuclear phagocytic cells, Kupfer cells, cells lining the sinusoids of the spleen, lymph nodes, and bone marrow, and the fibroblastic reticular cells of hematopoietic tissues. In general, RES cells are phagocytic and they are targets for targeted delivery of a F1C(s) in vitro or in vivo using liposomes, or other compositions or formulations. Thus, one can deliver F1C to a neoplasm that is derived from reticuloendothelial tissue (reticuloendothelioma). The liposomes may optionally comprise a peptide from an infectious agent such as a malaria parasite, a virus or a tumor associated antigen. The peptides may facilitate the generation of a MHC class II and B cell response. In other cases a liposomal F1C formulation is useful to obtain suspension F1C formulations.

Invention embodiments include the product made by a process of combining, mixing or otherwise contacting a F1C and one, two or more excipients. Such products are produced by routine methods of contacting the ingredients. Such products optionally contain a diluent, a disintegrant, a lubricant, a binder, or other excipients described herein or in references cited herein.

Other embodiments include compositions that transiently occur when a method step or operation is performed. For example, when a F1C, containing less than about 3% w/w water is contacted with an excipient, e.g., a PEG, an alcohol, propylene glycol benzyl alcohol or benzyl benzoate, the composition before addition of one ingredient with another is a non-homogenous mixture. As the ingredients are contacted, the mixture's homogeneity increases and the proportion of ingredients relative to each other approaches a desired value. Thus, invention compositions, which contain less than about 3% w/w or less than about 2% w/w or less than about 1% w/w or less than about 0.5% w/w water can comprise about 0.0001-99% w/w of a F1C and 1, 2, 3 or more excipients. These transient compositions are intermediates that necessarily arise when one makes an invention composition or formulation and they are included in invention embodiments.

When a F1C and an excipient(s) is contacted or mixed, the final composition may comprise a homogenous mixture or it may comprise a mixture that is not homogenous for one or more of the compounds that are present in the composition. Compositions and formulations that are either homogenous or non-homogenous are included in the scope of the invention. Non-homogenous compositions can be used, e.g., to make controlled release formulations.

Invention embodiments include compositions and formulations that comprise less than about 3% water, a F1C and a compound that is not generally considered suitable for human use but is useful to make an invention formulation for veterinary use. Veterinary formulations are compositions useful for the purpose of administering invention compositions to primates, cats, dogs, horses, cows, rabbits and other subjects and may contain excipients acceptable in the veterinary art and are compatible with F1Cs. These veterinary compositions may not always be suitable for human use because they contain an excipient that is not suitable for human use, e.g., an alcohol other than ethanol such as methanol, propanol or butanol. Typically such excipients will be present at relatively low levels, e.g., about 1-30%, usually about 1-5%.

Invention embodiments include non-aqueous compositions and formulations, e.g., unit dosage forms and sterile solutions or suspensions, that comprise about 1-25% w/w of a F1C, about 20-60% w/w propylene glycol, about 15-55% w/w of more or more PEGs, e.g., PEG100 or PEG200, about 0-5% w/w benzyl benzoate, about 0-5% w/w benzyl alcohol and optionally one or more additional excipients. These non-aqueous formulations will usually contain less than about 3%, 2%, 1%, 0.8%, 0.5%, 0.4%, 0.3%, 0.2% or 0.1% w/w of water. In formulations that contain non-aqueous excipients, the F1C will usually be relatively hydrophobic and will usually not contain any easily charged or ionizable moieties such as free carboxyl groups.

F1Cs may be administered to subjects by transmucosal dosing, e.g., by buccal or sublingual administration. The buccal area generally refers to the subject's mouth and pharynx, and the buccal mucosa includes the mucosa of the mouth and pharynx. The sublingual area refers generally to the mucosa below and adjacent to the tongue. Formulations suitable for buccal or sublingual administration typically comprise about 1-100 mg of F1C per unit dose, often about 2-60 mg. Transmucosal dosages may comprise a slow release or a rapid release formulation or tablet that contains about 1, 5, 10, 15, 20, 25, 30, 35, 40, 50 or 60 mg of a F1C. Slow release formulations will generally degrade or release the F1C from the dosage over a period of about 2 minutes to about 60 minutes or more. Rapid release formulations will generally release the F1C over a period of about 4 seconds to about 2 minutes, typically over about 0.1 to about 1 minute. Solid and liquid buccal or sublingual formulations optionally include one, two, three or more excipients such as fillers, binders, lubricants, antioxidants, preservatives, flavoring agents or disintegrants, e.g., lactose, sucrose, mannitol, Tween-80, magnesium stearate, butylated hydroxyanisole, butylated hydroxytoluene, cyclodextrins (e.g., α-cyclodextrins, β-cyclodextrins, γ-cyclodextrins, hydroxypropyl-β-cyclodextrin, β-cyclodextrin ether comprising one or more hydroxybutyl sulfonate moieties, cyclodextrins as described in U.S. Pat. No. 6,610,671 or U.S. Pat. No. 6,566,347), carbomers, hydrolyzed polyvinylalcohol, polyethylene oxide, polyacrylates, hydroxypropylmethylcellulose, hydroxypropylcellulose, and combinations thereof. Such formulations may be a unit solid such as a tablet or powder or a liquid. Buccal tablets may comprise a concave surface for contacting the buccal mucosa and adhering to it. A buccal or sublingual dosage may comprise a compressed tablet of a substantially uniform mixture of a bioerodible polymeric carrier, which on sustained contact with the oral mucosa, substantially or completely erodes within a predetermined period in the range of about 10 minutes to about 24 hours. In some embodiments, the F1C is administered by a method for administering the compound to the subject, e.g., to a mammal or a human, comprising affixing a unit dosage or tablet to the subject's buccal mucosa in a region at or near the upper gum between the first bicuspid on the left and the first bicuspid on the right (or an alternative location for the dosage unit is the inner lip area opposing the this upper gum area) and optionally allowing the tablet to remain in place until erosion thereof is complete or nearly complete. Exemplary excipients may comprise a combination of polyethylene oxide and a carbomer, e.g., wherein the polyethylene oxide and the carbomer are in an approximately 1:5 to 5:1 ratio by weight.

Tablets or unit dosages for buccal or sublingual delivery may be about 5 mm in diameter and 2 mm in height, so that the unit dosage occupies about 40 mm$^3$. Such dosages will typically weigh less than about 100 mg (e.g., about 5 to 60 mg), with a contact surface area of about 10-30 mm$^2$, e.g., about 15-20 mm$^2$. Such dosages will generally be about 4-10 mm in diameter and about 1-3 mm in height. When a polymer excipient is used, it optionally comprises a polymer having sufficient tack to ensure that the dosage unit adheres to the buccal mucosa for a sufficient time period, e.g., the time period during which drug is to be delivered to the buccal mucosa. The polymeric excipient is gradually "bioerodible," and it hydrolyzes, dissolves, erodes or disintegrates (collectively "erodes") at a predetermined rate upon contact with water or saliva. The polymeric carrier is generally sticky when moist, but not when dry, for convenience in handling. The average molecular weight of the polymer may be about 400 to 1,000,000, or about 1,000 to 100,000. Higher the molecular weight polymers generally erode more slowly.

For these buccal and sublingual dosages, a pharmaceutically acceptable polymer(s) can be used. Such polymers will provide a suitable degree of adhesion and the desired drug release profile, and are generally compatible with the drug to be administered and any other components that may be present in the buccal dosage unit. The polymeric carriers optionally comprise hydrophilic (water-soluble and water-swellable) polymers that adhere to the wet surface of the buccal mucosa. Examples of polymeric carriers that are useful herein include acrylic acid polymers, e.g., those known as "carbomers" (Carbopol™, which may be obtained from B.F. Goodrich, is one such polymer). Other suitable polymers include hydrolyzed polyvinylalcohol; polyethylene oxides (e.g., Sentry Polyox™ water soluble resins, available from Union Carbide); polyacrylates (e.g., Gantrez™, which may be obtained from GAF); vinyl polymers and copolymers; polyvinylpyrrolidone; dextran; guar gum; pectins; starches; and cellulosic polymers such as hydroxypropyl methylcellulose, (e.g., Methocel™, which may be obtained from the Dow Chemical Company), hydroxypropyl cellulose (e.g., Klucel™, which may be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methylcellulose, ethyl cellulose, cellulose acetate phthalate, cellulose acetate butyrate, and the like. The carrier may also comprise two or more suitable polymers in combination, for example, a carbomer combined in an approximately 1:5 to 5:1 ratio, by weight, with a polyethylene oxide.

Buccal dosages may contain only the F1C and the polymer(s). However, it may be desirable in some cases to include one or more additional excipients. For example, a lubricant may be included to facilitate the process of manufacturing the dosage units; lubricants may also optimize erosion rate and drug flux. If a lubricant is present, it may optionally represent about 0.01 wt. % to about 2 wt. %, or about 0.01 wt. % to 0.5 wt. %, of the dosage unit. Suitable lubricants include, but are not limited to, magnesium stearate, calcium stearate, stearic acid, sodium stearylfumarate, talc, hydrogenated vegetable oils and polyethylene glycol. However, modulating the particle size of the components in the dosage unit and/or the density of the unit can provide a similar effect, e.g., improved manufacturability, and optimization of erosion rate and drug flux without addition of a lubricant.

Other excipients are also optionally incorporated into buccal unit dosages. Such additional optional excipients include, one or more disintegrants, diluents, binders, enhancers, or the like. Examples of disintegrants that may be used include, but are not limited to, cross-linked polyvinylpyrrolidones, such as crospovidone (e.g., Polyplasdone™ XL, which may be obtained from GAF), cross-linked carboxylic methylcelluloses, such as croscarmelose (e.g., Ac-di-sol™, which may be obtained from FMC), alginic acid, and sodium carboxymethyl starches (e.g., Explotab™, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab™, which may be obtained from Stauffer), sugars that have been processed by cocrystallization with dextrin (e.g., co-crystallized sucrose and dextrin such as Di-Pak™, which may be obtained from Amstar), lactone, calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Permeation enhancers may also be present in the novel dosage units in order to increase the rate at which the active agent passes through the buccal mucosa. Examples of permeation enhancers include, but are not limited to, polyethylene glycol monolaurate ("PEGML"), glycerol monolaurate, lecithin, the 1-substituted azacycloheptan-2-ones, particularly 1-n-dodecylcyclaza-cycloheptan-2-one (available under the trademark Azone™ from Nelson Research & Development Co., Irvine, Calif.), lower alkanols (e.g., ethanol), SEPA™ (available from Macrochem Co., Lexington, Mass.), cholic acid, taurocholic acid, bile salt type enhancers, and surfactants such as Tergitol™, Nonoxynol-9™ and TWEEN-80™.

Flavorings are optionally included in buccal or sublingual formulations. Any suitable flavoring may be used, e.g., one or more of mannitol, sucrose, glucose, lactose, lemon, lemon lime, orange, menthol or artificial sweeteners such as aspartame, saccharin sodium, dipotassium glycyrrhizinate, stevia and thaumatin. Some sweeteners such as sucrose may also aid in dissolution or erosion of solid formulations. Coloring agents may also be added, e.g., any of the water soluble FD&C dyes or mixtures thereof, e.g., one or more of FD&C Yellow No. 5, FD&C RED No. 2, FD&C Blue No. 2, etc., food lakes or red iron oxide. In addition such formulations dosages may be formulated with one or more preservatives or bacteriostatic agents, e.g., methyl hydroxybenzoate, propyl hydroxybenzoate, chlorocresol, benzalkonium chloride, or the like.

Other embodiments include solid buccal or sublingual formulations comprising (i) a F1C and (ii) erythritol, (iii) crystalline cellulose and (iv) a disintegrant, e.g., crospovidone. These formulations are capable of buccal disintegration or dissolution and may further comprise mannitol. These formulations may dissolve completely in solely saliva within about 1-10 minutes of administration to a subject. The erythritol is optionally contained in a proportion of about 5-90 parts by weight, based on 100 parts by weight of the solid buccal formulation. The crystalline cellulose is optionally contained in a proportion of about 3-50 parts by weight, based on 100 parts by weight of the formulation. The disintegrant is optionally contained in a proportion of 1-10 parts by weight. In any of the solid buccal or sublingual formulations the ingredients are generally uniformly mixed, although non-uniform mixtures may be used. An exemplary formulation comprises a solid capable of buccal disintegration or dissolution, which comprises (i) about 0.3-50 parts by weight of a F1C, (ii) about 50-80 parts by weight of erythritol, (iii) about 5-20 parts by weight of crystalline cellulose and (iv) about 3-7 parts by weight of a disintegrant, which optionally is one or more of crospovidone, croscarmellose, croscarmellose sodium, carmellose calcium, carboxymethylstarch sodium, low substituted hydroxypropyl cellulose or corn starch. Examples of the crystalline cellulose include products of various grade such as CEOLUS KG801, avicel PH101, avicel PH102, avicel PH301, avicel PH302, avicel RC-591 (crystalline cellulose carmellose sodium) and so on. One crystalline cellulose may be used or two or more species may be used in combination. The disintegrant, e.g., crospovidone, may be used singly or in combination with other disintegrants. Crospovidone includes any cross-linked 1-ethenyl-2-pyrrolidinone homopolymer, and may comprise a polymer of molecular weight of 1,000,000 or more. Examples of commercially available crospovidone include Cross-linked povidone, Kollidon CL, Polyplasdone XL, Polyplasdone XL-10, INF-10 (manufactured by ISP, Inc.), polyvinylpolypyrrolidone, PVPP and 1-vinyl-2-pyrrolidinone homopolymer. The disintegrants are optionally incorporated in a proportion of about 1-15 parts by weight, or about 1-10 parts by weight, or about 3-7 parts by weight, based on 100 parts by weight of the solid formulation.

Some embodiments include a solid buccal or sublingual formulation containing a F1C where unit doses of the formulation substantially or completely disintegrates or erodes within about 20-120 seconds in water at 37° C. or on insertion of the unit dose into the buccal area or upon placement under the tongue. Such formulations may comprise a swellable hydrophilic excipient, a water-soluble or a water-dispersible excipient, e.g., one or more of partially hydrolyzed gelatin, hydrolyzed dextran, dextrin, mannitol, alginates, polyvinyl alcohol, polyvinyl pyrrolidine, water soluble cellulose derivatives, methylcellulose, ethyl cellulose, carboxymethyl cellulose, hydroxymethylcellulose, hydroxypropyl methylcellulose, microcrystalline cellulose, alginates, gelatin, guar gum, gum tragacanth, gum acacia, polyacrylic acid, polymethacrylic acid, polysilicic acid, polylactic acid, polymaleic acid, polyvinyl alcohol, polyethylene glycol, polyvinyl pyrrolidone, nonionic blocked polymers, carbomers, polycarbophils, a water soluble starch, dicalcium phosphate, calcium carbonate, silica or polyethyleneglycol, e.g., PEG1000, PEG2000 or a polyethylene oxide ("PEO"), PEO1000, PEO100000 or PEO5000000.

Other embodiments include the product obtained by storing invention compositions or formulations, e.g., unit dosage forms or compositions used to make formulations, at about 4-40° C. for at least about 30 days, e.g., storage at ambient temperature for about 1-24 months. Invention formulations will typically be stored in hermetically or induction sealed containers for these time periods. Compositions and formulations that comprise a F1C will typically be held in closed or sealed containers, particularly when the composition is a formulation for pharmaceutical or veterinary use.

Typical containers for storage of compositions and formulations that comprise a F1C will limit the amount of water that reaches the materials contained therein. Typically, formulations are packaged in hermetically or induction sealed containers. The containers are usually induction sealed. Water permeation characteristics of containers have been described, e.g., Containers—Permeation, chapter, USP 23 <671>, United States Pharmacopeial Convention, Inc., 12601 Twinbrook Parkway, Rockville, Md. 20852, pp.: 1787 et seq. (1995).

Immune modulation. The F1Cs, or the biologically active substances produced from these compounds by hydrolysis or metabolism in vivo, have a number of clinical and non-clinical applications. The compounds are generally useful to correct immune dysregulation, e.g., imbalanced immune responses to disease conditions, pathogens or the like, suppression of an innate or acquired immune response(s) and inflammation conditions in vertebrate or mammalian subjects, e.g., as disclosed herein. Thus, while the compounds will generally enhance a deficient immune response in a given clinical condition, they will generally reduce the same immune response when it is too active in a different clinical condition. For example, they can enhance insufficient or suboptimal Th1 immune responses, reduce excess or undesirable Th2 immune responses, reduce excess or undesirable Th1 immune responses or enhance insufficient or suboptimal Th2 immune responses or they can reduce excess or undesirable inflammation or one or more of its symptoms. The compounds will generally also modulate dysregulated Tc1 and Tc2 immune responses (associated with $CD8^+$ T cells) in a similar manner, e.g., excessive Tc1 or Tc2 responses will be detectably decreased and deficient or suboptimal Tc1 or Tc2 responses will generally be detectably enhanced.

Invention embodiments include a method to modulate a subject's innate immunity, Th1 immune responses, Tc1 immune responses, Th2 immune responses or Tc2 immune responses comprising administering an effective amount of a F1C to a subject or delivering the F1C to the subject's tissues. Other methods include modulating an immune or cellular response in a subject in need thereof comprising administering to the subject, or delivering to the subject's tissues, an effective amount of a compound of formula 1. Immune and cellular response modulation includes enhancing Th1 immune responses, reducing Th2 immune responses, reducing Th1 immune responses, enhancing Th2 immune responses, reducing unwanted or pathological inflammation, enhancing hematopoiesis or modulating the synthesis, level or a biological activity of a biomolecule such as (1) a transcription factor such as a nuclear hormone receptor or an associated receptor factor, (2) a purine such as adenosine, (3) a nucleotide cofactor such as NADPH, (4) a cytokine or interleukin or a receptor for a cytokine or interleukin, or (5) another biomolecule as disclosed herein. Such enhancements, reductions, levels or activities are usually in an easily detectable range, e.g., a change compared to a suitable control of at least about 5%, 10%, 20%, 30%, 40%, 50%, 60%, 70%, 80%, 90%, 95% or a range that is between about any two of these values. Typically the subject is in need of such treatment, e.g., by having a clinical condition disclosed herein or being subject to developing such a condition, e.g., having been exposed or potentially exposed to a pathogen or having a predisposing condition such as precancer.

In modulating one or more activities of Th1, Th2, Tc1 or Tc2 cells or their function(s), the F1Cs will typically detectably modulate one, two, three or more factors, e.g., immune cell subsets or populations, cytokines, interleukins, surface antigens such as a CD molecule(s) and/or their receptors that affect the development, migration, numbers or biological function(s) of such cells. When a Th1 or Tc1 cell or population is affected, the F1Cs will typically increase or decrease the synthesis or level of one, two or more of an associated effector factor, e.g., IFNγ, IL-2, IL-12, IL-18, T-bet, PPARα and PPARγ or a cell surface molecule, e.g., as disclosed herein or in the cited references, that is associated with or needed for normal, optimal or enhanced Th1 or Tc1 cells or cell function. Such molecules are generally associated with development or enhancement of Th1 or Tc1 cells or their biological function(s). When a Th2 or Tc2 cell or population is affected, the F1Cs will typically increase or decrease the synthesis or level of one, two or more of an associated effector factor, e.g., IL-4, IL-5, IL-6, IL-8, IL-10, IL-13, GATA-3, COX-2 or a cell surface molecule, e.g., as disclosed herein or in the cited references, that is associated with or needed for normal, optimal or enhanced Th2 or Tc2 cells or cell function(s). Such molecules are generally associated with development or enhancement of Th2 or Tc2 cells or their biological function(s).

Similarly, when a subject has or is subject to developing an unwanted or excessive inflammation, the F1Cs will generally detectably modulate one or more relevant effector factors for inflammation, e.g., a detectable decrease of one, two, three or more of IL-1α, IL-1β, TNFα, TNF-β, MIP-1α, MIP-2, TGF-01, IP-10, LT-β, γIFN, IL-6, IL-8, IL-10 and COX-2, lipoxygenase, or an increase of one or more suppressor factors or antagonists of inflammation. Such modulation can comprise increases or decreases of at least about 2%, 5%, 10%, 15%, 20%, 25%, 30%, 40%, 50%, 60%, 70%, 75%, 80%, 85%, 90%, 95%, 98%, 100%, 200%, 300%, 500%, 1000%, 5000% or within a range between any two of these values, e.g., between about 5-95%, about 10-90%, about 5-60% or about 40-95%. In general, such changes leads to a detectable amelioration of an inflammation-associated disease, condition, symptom or to the detectable slowing of the progression thereof or to a detectably reduced incidence or severity of or susceptibility to developing an unwanted inflammatory response.

In conditions where an unwanted or excessive Th1, Tc1, Th2 or Tc2 response is associated with or causes a disease(s), disease(s) progression, disease(s) state maintenance, condition(s) or symptom(s), the F1Cs will generally decrease the level or one or more biological activity of one, two or more of their respective associated effector molecules. In conditions where a deficient or suboptimal Th1, Tc1, Th2 or Tc2 response is associated with or causes a disease(s), disease(s) progression, disease(s) state maintenance, condition(s) or symptom(s), the F1Cs will generally increase the level or one or more biological activity of one, two, three or more of their respective associated effector molecules. Such changes in the level or biological activity(ies) the associated effector molecules is generally detectable using standard methods and is typically an increase (when a response is insufficient) or a decrease (when a response is in excess) of at least about 2%, 5%, 10%, 15%, 20%, 25%, 30%, 40%, 50%, 60%, 70%, 75%, 80%, 85%, 90%, 95%, 98% or within a range between any two of these values, e.g., between about 5-95%, about 10-90%, about 5-60% or about 40-95%. In general, such changes leads to a detectable amelioration of a disease, condition, symptom or to the detectable slowing of the progression thereof or to a detectably reduced incidence or severity of or susceptibility to developing a disease(s) or the occurrence of a symptom(s) for a at least a portion of subjects that are treated with a F1C, e.g., at least about 5%, 10%, 20%, 40%, 60% or 80% of treated subjects. The F1Cs may facilitate the clinical cure of a disease(s), prolong remission of a disease(s) or eliminate or ameliorate a clinically detectable symptom(s).

The F1C will generally also affect the function of other immune cell subsets in a similar manner. Thus, when an insufficient macrophage, dendritic cell or neutrophil response is associated with the establishment, maintenance or progression of a disease, symptom or a condition, the F1Cs will generally enhance of the level or a biological activity(ies) of one or more effector molecule associated with or needed for an optimal or more normal response or immune function that is mediated by the macrophages, dendritic cells or neutrophils. Similarly, when the subject suffers from a excessive or pathological activity associated with macrophages, dendritic cells or neutrophils, which is associated with the establishment, maintenance or progression of a disease, symptom or a condition, the F1Cs will generally detectably reduce the level or a biological activity(ies) of one or more effector molecule associated with or needed for an optimal or more normal response or immune function that is mediated by the macrophages, dendritic cells or neutrophils. Such effector molecules are as described herein or in the cited references.

As used herein, reference to Th1 or Th2 immune responses means such responses as observed in mammals generally and not as observed in the murine system, from which the Th1 and Th2 terminology originated. Thus, in humans, Th1 cells are $CD4^+$ T lymphocytes and they usually preferentially display chemokine receptors CXCR3 and CCR5, while Th2 cells are $CD4^+$ T lymphocytes and usually preferentially express the CCR4, CCR8 and/or CXCR4 chemokine receptor molecule(s) and generally a smaller amount of CCR3, see, e.g., U. Syrbe et al., *Springer Semin. Immunopathol.* 1999 21:263-285, S. Sebastiani et al., *J. Immunol.* 2001 166:996-1002. Tc1 and Tc2 immune responses are mediated by $CD8^+$ lymphocytes and means to identify these cells and their associated lymphokines, cell specific antigens and biological activities have been described, see, e.g., M. B. Faries et al., *Blood* 2001 98:2489-2497, W. L. Chan et al., *J. Immunol.* 2001 167:1238-1244, C. Prezzi et al., *Eur. J. Immunol.* 2001 31:894-906, H. Ochi et al., *J. Neuroimmunol.* 2001 119:297-305, D. H. Fowler and R. E. Gress, *Leukemia and Lymphoma* 2000 38:221-234.

The F1Cs are useful in reestablishing normal immune function in various immune dysregulation or immune suppression conditions. For example, they are useful to treat, slow progression of or to ameliorate one or more symptoms associated with one or more of an autoimmune condition(s), a inflammation condition(s), an infection(s), a cancer(s), a precancer(s), a chemotherapy(ies), radiation therapy, a burn(s), a trauma(s), a surgery(ies), a pulmonary condition, a cardiovascular disease(s) and a neurological or neurodegenerative disease(s). Without being limited to any theory, the F1Cs are believed to act through several mechanisms, including by directly or indirectly modulating nuclear hormone receptor activity or by affecting or modulating other biological targets such as transcription factors, steroid binding proteins or enzymes in at least some of the diseases, conditions or symptoms disclosed herein.

The F1Cs are useful to modulate delayed-type hypersensitivity ("DTH") responses and anergic conditions in subjects having to subject to developing abnormal DHT responses or anergy. Means to measure such responses and conditions are known and can be used to characterize the effects of the F1Cs on these responses and conditions. See, e.g., A. E. Brown, et al., *J. Med. Assoc. Thailand* 83:633-639 2000, R. A. Smith et al., *J. Adolesc. Health* 27:384-390 2000, N. M. Ampel, *Med. Mycology* 37:245-250 1999. The compounds will generally detectably enhance or restore DTH in immune suppression conditions. They will also generally detectably reduce or eliminate anergy in subjects having significantly reduced or no immune response to, e.g., specific antigens or pathogens.

The invention provides a method to detectably enhance an antigen specific immune response, cell mediated immune response or a delayed-type hypersensitivity immune response in a subject having impaired or negligible antigen specific immune response, cell mediated immune response or delayed-type hypersensitivity immune response, comprising administering to the subject, or delivering to the subject's tissues, an effective amount of a F1C. The antigen specific immune response, cell-mediated immune response or delayed-type hypersensitivity immune response can be enhanced at least about 25%, at least about 40%, at least about 50%, at least about 60%, at least about 75% or at least about 90%. Some of the subjects may have an antigen specific immune response, cell mediated immune response or a delayed-type hypersensitivity immune response that is impaired or negligible, e.g., about 50% or less or about 30% or less or about 10% or less of the response that an otherwise normal subject would be expected to have. Such subjects may not detectably respond to at least 1 antigen out of 2, 3, 4 or 5 antigens that a normal subject would respond to. In some embodiments, the subject is an HIV-infected human having a $CD4^+$ T cell count of about 0-150 cells/$mm^3$ or about 2-100 cells/$mm^3$ and/or wherein the antigen specific immune response, cell mediated immune response or delayed-type hypersensitivity immune response is an enhanced response to a viral, bacterial, parasite or fungal antigen such as an HIV, HCV, HBV or CMV antigen such as a viral or HIV core antigen or HIV p24 antigen or a viral or HIV envelope antigen, a *Candida antigen*, a viral, bacterial, parasite or fungal antigen essentially as described herein or to phytohemagglutinin. The responses to treatment with a F1C may be quantitated by, e.g., mixed lymphocyte reaction, ELIspot analysis or flow cytometric analysis of, e.g., circulating blood cells such as $CD4^+$ or $CD8^+$ T cells or for levels of cytokines (e.g., IL-2, TNFα or IFNγ) in such cells. Such analyses have been described, e.g., V. P. Badovinac and J. T. Hardy, *J. Immunol. Methods* 2000, 238:107-117, N. Favre et al., *J. Immunol. Methods* 1997, 204:57-66, E. Hagiwara et al., *Cytokine* 1995, 7:815-822, N. W. Lukacs et al., *Blood* 1993, 82:3668-3674, M. Umemoto et al., *Clin. Exp. Immunol.* 1998, 112:459-463, A. Fietta et al., *Gerontology* 1994, 40:237-245, C. H. Orteu et al., *J. Immunol.* 1998, 161:1619-1629.

Clinical indications that have an association with or have a symptom(s) that is consistent or associated with an excessive or unwanted Th2 immune response include, e.g., fatigue, pain, fever or an increased incidence of infection, schizophrenia, acute myelitis, tumor progression, progressive systemic sclerosis, Omenn's syndrome, atopic disease, atopy, allergen hypersensitivity, atopic asthma, atopic dermatitis, burns, trauma (e.g., bone fracture, hemorrhage, surgery), immune responses to xenotransplantation, chronic periodontitis, SLE (systemic lupus erythematosus), discoid lupus erythematosus, osteoporosis, myasthenia gravis, Graves disease, mite-associated ulcerative dermatitis, rheumatoid arthritis and osteoarthritis. Excessive Th2 immune responses are also associated with an unwanted symptom or pathology, e.g., fatigue, pain, fever or an increased incidence of infection, that is associated with aging, allergy and inflammation conditions such as allergic bronchopulmonary aspergillosis in cystic fibrosis patients, allergic respiratory disease, allergic rhinitis, atopic dermatitis, subepithelial fibrosis in airway hyperresponsiveness, chronic sinusitis, perennial allergic rhinitis, fibrosing alveolitis (lung fibrosis). This common underlying immune component is at least part of the pathology or symptoms of all of these conditions. This allows a F1C to be effectively used to prevent or treat the condition or to treat or ameliorate one or more symptoms that are associated with these conditions. Thus, in some embodiments, an unwanted or excessive Th2 response is present and amelioration of one or more symptoms associated with this condition is accomplished by administering an effective amount of a F1C according to the methods described herein, e.g., F1C is administered using a formulation and a route of administration essentially as described herein on an intermittent or a daily basis.

Typically, unwanted Th2 immune responses are associated with, or caused by, increased expression of one or more cytokines or interleukins such as one, two, three or more of cortisol, IL-4, IL-5, IL-6, IL-10 and IL-13. Administration of a F1C will generally reduce the expression of one or more of the Th2-associated cytokines or interleukins. At the same time, the compounds generally enhance the expression of one or more cytokines or interleukins associated with Th1 immune responses. Because of their capacity to modulate or to balance Th1 and Th2 immune responses, the compounds are useful for a variety of clinical conditions, e.g., infection, immunosuppression or cancer, where an enhanced Th1 immune response is desired. Effects of the F1Cs in treating, preventing or slowing the progression of the clinical conditions described herein can include one or more of (1) enhancing the Th1 character of a subject's immune response or immune status, (2) increasing the intensity of a Th1 or a Th2 immune response or both and (3) decreasing inflammation or a symptom thereof.

Exemplary conditions where an immune imbalance or an excessive Th1 immune response is involved include autoimmune diseases such as multiple sclerosis, Crohn's disease (regional enteritis), ulcerative colitis, inflammatory bowel disease, rheumatoid arthritis, reactive arthritis, acute allograft rejection, sarcoidosis, type 1 diabetes mellitus, *Helicobacter pylori* associated peptic ulcer, graft versus host disease and Hashimotos' thyroiditis. Because these conditions are associated with a similar type immune dysfunction, a F1C can be effectively used to prevent or treat these conditions or to treat or ameliorate one or more symptoms associated therewith. Thus, in some embodiments, an unwanted or excessive Th1 response is present and amelioration of one or more symptoms associated with this condition is accomplished by administering an effective amount of a F1C according to the methods described herein, e.g., F1C is administered using a formulation and a route of administration essentially as described herein on an intermittent or a daily basis. In other embodiments, an deficient Th1 response is enhanced, which is optionally observed as a detectable increase in one or more of IFNγ, IL-2, IL-12 or IL-18 in Th1 cells or in accessory cells such as a dendritic cell or macrophage. In all of the conditions where an insufficient or excess Th1, Th2, Tc1 or Tc2 response is present, amelioration of one or more symptoms associated with the condition is accomplished by administering an effective amount of a F1C according to the methods described herein.

Aspects of the invention include the use or administration of compositions or formulations that comprise a carrier and an amount of at least one F1C effective to detectably modulate an immune parameter. For example, to enhance the relative proportion of a desired immune cell subset, e.g., $CD4^+$ T cells, $CD8^+$ T cells, NK cells, LAK cells, neutrophils, granulocytes, basophils, eosinophils or dendritic cells, or to modulate (detectably increase or decrease) one or more functions of immune cell subsets. The F1Cs can modulate the expression of CD molecules or alter the proportion of cell subsets, e.g., $CD4^+$ or $CD8^+$ T cells, or their relative numbers in a subject's blood or tissues. CD and related molecules participate in the function of various immune cell subsets and can be useful as markers for immune function in vivo. In some aspects, the F1Cs activate immune cells which generally alters (increases or decreases) expression of, or changes the numbers of cells that express one or more of, CD4, CD6, CD8, CD25, CD27, CD28, CD30, CD36, CD38, CD39, CD43, CD45RA, CD45RO, CD62L, CD69, CD71, CD90 or HLA-DR molecules. Often, the numbers of cells that express these molecules are increased, e.g., CD25, CD36, CD16 or CD69. Typically, such increases are observed as an increased proportion of circulating white blood cells that express one or more of these molecules or white blood cells, e.g., T cells or dendritic cells, that express CXCR3, CCR5, CCR4, CCR8 and/or CXCR4. In some cases the number of such molecules per cell is detectably altered.

Expression of one or more adhesion molecules CD2, CD5, CD8, CD11a, CD11b, CD11c, CD18, CD29, CD31, CD36, CD44, CD49a, CD49b, CD49c, CD49d, CD49e, CD49f, CD50, CD54, CD58, CD103 or CD104 are also detectably modulated after administration of the F1Cs to a subject. Often, the numbers of cells that express these molecules are increased, e.g., CD5 or CD56. The adhesion molecules function in various aspects of immune responses, such as binding to class I MHC molecules, transducing signals between cells or binding to molecules in the extracellular matrix associated with endothelial or other cell types. Administration of the F1Cs to a subject also affects the numbers of certain immune cell subsets, e.g., NK cells (e.g., $CD8^-$, $CD56^+$ or $CD8^+$, $CD56^+$) or lymphokine activated killer cells (LAK). Increased circulating NK or LAK cells are typically observed, which is reflected in increased numbers of cells that express one or more of CD16, CD38, CD56, CD57 or CD94. Also, increased numbers of circulating dendritic cell precursors are observed, as shown by increases in cells that express one or more of CD11c, CD80, CD83, CD106 or CD123. Although one can observe an increased proportion of circulating white blood cells that express one or more of these molecules, in some instances the number of such molecules per cell is detectably altered. Both the cell numbers and the density of CD molecule per cell can also be detectably modulated. Modulation of immune cell subsets typically occurs on intermittent dosing of a F1C, but will arise from any suitable dosing regimen, e.g., as described herein.

Expression of one or more homing or other receptors or receptor subunits such as CD62L, CLA-1, LFA1, CD44, ICAM, VCAM or ECAM may also be detectably affected after administration of the F1Cs to a subject. The numbers of cells that express these molecules, or the relative amounts per cell of, e.g., CD44 or CD62L, may be increased where a desired immune response is desired, e.g., migration of T cells to mucosal tissues or exposure of naïve T cells to antigen in lymph nodes. Alternatively, numbers of cells that express these molecules, or the relative amounts per cell of, e.g., CLA-1, may be decreased where inhibition of an undesired immune response, such as an inflammatory response is desired. The subject's response to such enhanced expression includes migration of cells such as movement of naïve T cells to peripheral lymph nodes in response to modulation of CD62L or other homing receptor expression. Thus, the F1Cs can also facilitate migration of various immune cell types, e.g., dendritic cells, NK cells, LAK cells, macrophages or lymphocytes, from one location to another within a subject. For example, the compounds can enhance dendritic cell or lymphocyte migration from areas such as the skin tissues to the gut associated lymphoid tissue ("GALT"), lymph nodes or spleen. Such migration may facilitate the function of those cell types by increasing their transit to tissues where their effector functions, e.g., antigen presentation by dendritic cells, normally occur. The migration period is often relatively transient (e.g., observable over about 1-7 days) or occasionally longer (e.g., occurring for about 8-40 days), depending on the dosing regimen and other factors. This migration can be observed by standard methods, e.g., by cell staining, by PCR analyses or by determining the presence of a given cell type in circulation or determining a decrease in the number circulating cells. A decrease would generally reflect sequestration of an immune cell population(s) in a tissue(s) where the immune cell normally exercises its effector functions.

Thus, in some embodiments, the migration of one or more immune cell subsets such as $CD11C^+$ cells from tissue such as skin or lung through the blood to immune tissue such as lymph nodes or GALT is seen as a transient increase in the level of circulating $CD11C^+$ cells in response to exposure of the subject's tissues to a suitable amount of a F1C. Thus, the level of $CD11C^+$ cells in the blood will generally detectably increase, e.g., a statistically significant increase, plateau and then decrease as migration of the cells to immune tissue subsides. In these embodiments, the proportion of the cells of the affected immune cell subset is typically relatively low in most physiological immune states, e.g., normal or abnormal immune conditions, compared to the total white blood cell population in circulation. In other embodiments, the migration of one or more immune cell subsets such as $CD123^+$ cells from the circulation to immune tissue such as lymph nodes or GALT results in a decrease. In these embodiments, the decrease in the numbers of circulating immune cells reflects the migration of the immune cells from the blood to immune tissue such as lymph nodes or GALT. Such a decrease may be transient and followed by recovery of the affected immune cell subset(s) over about 2 to 24 weeks. In conducting these embodiments, administration of the F1C to the subject is accomplished using the formulations or the methods as described herein.

Thus, an aspect of the invention is a method to enhance the migration of one or more immune cell types in a subject from one location (e.g., bone marrow, circulating blood or a tissue such as the skin, liver, central nervous system or lung) to another (e.g., to the blood or to a lymphoid tissue such as a lymph node, spleen or a mucosal tissue such as GALT) by administration to a subject as described herein of an effective amount of a F1C essentially as described by any of the methods disclosed herein. A related aspect is the monitoring, e.g., by suitable blood counts or tissue biopsy, of the subject's response to determine the timing and extent of such immune cell migration.

Other CD molecules that are modulated by the presence of the F1Cs in a subject include cytokine receptor molecules such as one or more of CD115, CDW116, CD117, CD118, CDW119, CD120a, CD120b, CD121a, CD121b, CD122, CD123, CD124, CD125 CD126, CDW127, CDW128 or CDW130. Often, the numbers of receptor molecules per cell will be modulated. For example, receptors for cytokines that mediate or facilitate Th1 immune responses or innate immune responses (e.g., one or more of IL-1α, IL-1β, IL-2, IL-4, IL-12, γIFN or α-interferon) will typically increase in or on cells that mediate Th1 or innate immune responses. Modulation of these molecules may be by direct interactions with a receptor(s) in the cell that expresses the cytokine receptor or indirectly by modulation of cytokine synthesis in the affected cells or in other cells, typically immune cells that may interact with the cells whose receptor synthesis is being modulated.

Thus, autocrine or paracrine mechanisms may underlie some of the effects associated with administration of a F1C(s) such as altered cytokine profiles in immune cells or altered immune cell populations. Endocrine cytokine mechanisms may also contribute to desired immune responses.

Treatment of a subject with a F1C can result in a change of at least about 20-80% or about 25-50% above or below (e.g., at least 30% or at least 40% above or below) the control or basal level of affected immune cell subsets. For example, increases of more than about 30% in the total numbers of activated CD8$^+$ T cells, e.g., CD8$^+$, CD69$^+$, CD25$^+$ T cells, CD8$^+$, CD69$^+$, CD25$^-$ T cells or CD8$^+$, CD69$^-$, CD25$^+$ T cells, can occur by 7 days after a single dose of a F1C to a subject. Such increases may be greater than 50%, 60% or 100% in the total numbers of activated CD8$^+$ T cells or subsets of activated CD8$^+$ T cells in individual subjects. Typically such increases are about in the total numbers of activated CD8$^+$ T cells or subsets of activated CD8$^+$ T cells averages about 30-40%, with individual subjects experiencing increases over 100% in the numbers of activated CD8$^+$ T cells per unit blood volume compared to the basal level.

Administration of the F1Cs can affect other immune cell subsets. For example, the concentration of circulating CD4$^+$, CD69$^+$, CD25$^-$ (Th1 helper cells) and CD8$^+$, CD16$^+$, CD38$^+$ LAK cells or CD8$^-$, CD16$^+$, CD38$^+$ LAK cells typically increases during or after the course of dosing a subject with a F1C. Also, CD8$^-$, CD16$^+$, CD38$^+$ and CD8$^+$, CD16$^+$, CD38$^+$ (ADCC effector cells) and low side scatter Lin$^-$, DR$^+$, CD123$^+$ (dendritic precursors) or low side scatter Lin$^-$, DR$^+$, CD11c$^+$ (dendritic cells or precursors) may show modest to significant increases.

In subjects that are immunosuppressed, e.g., from certain infections (e.g., viral (HIV, HCV), bacterial infection or parasite infection) or from chemotherapy (e.g., an antiviral therapy, a cancer chemotherapy or a radiation therapy), administration of the F1Cs to the subject results in a favorable shift in the balance of Th1 or Th2 responses the subject can mount in the face of immunosuppression. When Th1 responses are suboptimal or insufficient, treatment with a F1C results in enhancement of Th1 responses or a reduction in Th2 responses. Conversely, when Th2 responses are suboptimal or insufficient, treatment with a F1C results in enhancement of Th2 responses, which may occur with a concomitant modulation (increase or decrease) in Th1 responses. The F1Cs can thus be used to shift the nature of a subject's immune response to result in a more balanced immune response from immunosuppression. Alternatively, the compounds can selectively suppress inappropriate or unwanted immune responses. Enhanced Th1 responses appears to be at least partly due to one or more of (i) a reduction in biological restraints, e.g., high levels of IL-4 or IL-10, on Th1 functions by preexisting primed Th1 effector cells, (ii) enhanced differentiation of Th0 cells to Th1 cells or enhanced responses mediated by Th1 cells, (iii) enhanced function of accessory cell function, e.g., antigen presentation by dendritic cells, dendritic precursor or progenitor cells or by macrophages or their precursors or progenitors, (iv) enhanced proliferation and differentiation of Th1 precursor or progenitor cells, (v) enhanced IL-12 expression in dendritic cells or their precursors, which results in enhanced differentiation of Th1 cells from Th0 precursors, (vi) enhanced expression or activity of factors associated with Th1 functions, e.g., IL-2, gamma interferon (γIFN or IFNγ), IL-18 or lymphotoxin.

An aspect of the invention methods is an alteration in the expression of IL-4 or IL-10 that occurs after administration of a F1C to a subject. A consistent observation is that extracellular IL-4 or IL-10 levels rapidly decrease to levels that are undetectable by ELISA. Intracellular IL-10 levels are reduced to levels that are near or below the limits of detection by flow cytometry. The administration of a F1C to a subject thus provides a means to inhibit either or both of these interleukins. Such inhibition may be associated with enhancement of Th1 immune responses relative to Th2 or Th0 responses, e.g., in subjects where Th1 responses are suppressed (e.g., from viral, bacterial or parasite infection (HIV, HCV, etc) or chemotherapy) or are otherwise suboptimal. In many subjects, levels of either IL-4 or IL-10, usually IL-10, before dosing with a F1C is low or undetectable. In these subjects, dosing with the F1C results in a rapid drop in the interleukin that is detectable, usually IL-4.

Clinical conditions are described in more detail below where the F1Cs are useful for treating, preventing, slowing the progression of, or ameliorating one or more symptoms associated with the described conditions. In any these conditions, any F1C disclosed herein can be used according to one or more of the dosing methods that are disclosed herein. For these conditions, dosages for the F1Cs, formulations and routes of administration are as described herein. Additional information regarding these and other clinical conditions or symptoms that can be treated, prevented or ameliorated with the F1Cs are found at e.g., *The Merck Manual*, 17$^{th}$ edition, M. H. Beers and R. Berkow editors, 1999, Merck Research Laboratories, Whitehouse Station, N.J., ISBN 0911910-10-7, or in other references cited herein.

Responses to treatment of a subject having a condition disclosed herein with a F1C is optionally monitored by observing changes in one or more immune or other appropriate clinical parameters, e.g., as described herein or in D. S. Jacobs et al., editors, Laboratory Test Handbook, 4$^{th}$ edition, pages 11-686, Lexi-Comp Inc., Hudson, Ohio, ISBN 0-916589-36-6, or in any of the references cited herein, or by monitoring the progression or severity of the underlying condition according to known methods, e.g., J. B. Peter, editor, *Use and Interpretation of Laboratory Tests in Infectious Disease*, 5$^{th}$ Edition, pages 1-309, 1998, Specialty Laboratories, Santa Monica, Calif., ISBN 1-889342-13-0.

Infection treatments. In some embodiments, the F1C(s) is administered to a subject who has a pathogen infection, such as a viral, bacterial, fungal, yeast, intracellular parasite or extracellular parasite infection. The F1Cs can be considered for use in a broad scope of infections (see, e.g., J. B. Peter, editor, *Use and Interpretation of Laboratory Tests in Infectious Disease*, 5$^{th}$ edition, Specialty Laboratories, Santa Monica, Calif. 90404, 1998, pages 1-271), since the compounds generally enhance Th1 immune responses and/or reduce Th2 immune responses and/or reduce inflammation or its symptoms. Difficulty in treating many infections, e.g., progressive toxoplasmic encephalitis, malaria, tuberculosis, Leishmaniasis and schistosomiasis, often appear to be associated with one or more of an unwanted Th2 immune responses, a suboptimal Th1 response or the development of resistance of the infectious agent to antimicrobial agents. For example, in disseminated or diffuse tuberculosis, a reduced Th2 response would be desirable to allow a patient to slow progression of the disease or to clear infected cells more efficiently. In treating chloroquine resistant or sensitive malaria, the F1Cs have essentially the same activity.

Exemplary viral infections that the F1Cs can be used to treat, prevent or ameliorate include infections by one or more DNA or RNA viruses, or a symptom(s) associated with such infection(s), such as a genogroup, clade, serotype, serotype subtypes, isolate, strain, subtype or so forth of influenza viruses (e.g., a human influenza A virus, a human influenza B virus, an avian (e.g., chicken, duck, goose) influenza virus, a swine influenza virus or a recombinant avian-swine influenza virus), respiratory syncytial viruses, Rotaviruses, Hantaviruses, animal or human Papillomaviruses (e.g., HPV-1, HPV-2, HPV-6, HPV-7, HPV-10, HPV-11, HPV-13, HPV-16, HPV-18, HPV-32, HPV-33, HPV-35, HPV-39, HPV-42, HPV-43, HPV-44, HPV-45, HPV-61, HPV-72 or HPV-83), Poxviruses, Poliovirus, rabies viruses, human and animal Retroviruses (e.g., HIV-1, HIV-2, LAV, human T-cell leukemia virus I ("HTLV I"), HTLV II, HTLV II, SIV, SHIV, FIV or FeLV), Togaviruses and Flaviviruses (e.g., West Nile Virus, Yellow Fever Virus, Dengue viruses), Herpesviruses (e.g., CMV, EBV, Varicella Zoster Virus (human Herpesvirus 3), Herpes simplex virus 1 ("HSV-1"), Herpes simplex virus 2 ("HSV-2"), human Herpesvirus 6 ("HHV-6"), human Herpesvirus 7, human Herpesvirus 8 ("HHV-8")), measles viruses, mumps viruses, rubella virus, Hepadnaviruses or hepatitis viruses, Adenoviruses, Retroviruses, Togaviruses, Alphaviruses, Arboviruses, Coronaviruses (e.g., human severe acute respiratory syndrome virus, Urbani SARS-associated coronavirus, human respiratory coronaviruses such as HCV-229E or HCV-OC43, including serogroups, genotypes, strains or variants of any of these viruses), Flaviviruses, Filoviruses, Rhinoviruses, Picornavi ruses, Papovavi ruses, Bunyaviruses, Picornaviruses, Poxviruses, Parvoviruses (e.g., human B19 parvovirus) and/or Pestiviruses.

Specific viruses, including their genogroups, clades, isolates, serotypes, serotype subtypes, strains and so forth, that may establish a virus infection susceptible to the treatment methods disclosed herein include one or more of human hepatitis C virus ("HCV"), human hepatitis B virus ("HBV"), human hepatitis A virus ("HAV"), human hepatitis delta virus, human hepatitis E virus, duck hepatitis virus, woodchuck hepatitis virus, one or more of human herpesviruses 1, 2, 3, 4, 5, 6A, 6B, 7 or 8, human SARS virus, one or more of human papilloma viruses 1-60, e.g., HPV 6, HPV 11, HPV 16, HPV 18, HPV 31, HPV 45, animal papilloma viruses, poliovirus 1, poliovirus 2, poliovirus 3, one or more of Dengue virus types 1, 2, 3 or 4, one or more of foot-and-mouth disease virus 1-7, including serotypes O, A, C, SAT 1, SAT 2, SAT 3 and ASIA 1, one or more of coxsackievirus A1-A22, A24, and B1-B6, one or more of human echovirus 1-9, 11-27 and 29-34, one or more of human enterovirus 68-71, one or more of adenovirus 1-49, one or more of Parainfluenza viruses 1, 2, 3 or 4, Human respiratory coronaviruses 229E and OC43, one or more of Human rotaviruses, BK virus, Bunyamwera virus, California Encephalitis Virus, Central European Encephalitis Virus, encephalomyocarditis virus, Colorado tick fever virus, Cowpox virus, Eastern equine encephalitis virus, Venezuelan equine encephalitis virus, Argentine hemorrhagic fever virus, Bolivian hemorrhagic fever virus, Lacrosse virus, Hantaan virus, JC virus, Lassa virus, Lymphocytic choriomeningitis virus, Kyasanur forest virus, Marburg virus, Measles virus, Mokola virus, Monkeypox virus, Molluscum contagiosum virus, Mumps virus, Murray Valley encephalitis virus, Norwalk virus, O'nyong-nyong virus, Omsk hemmorhagic virus, Orf virus, Rabies virus, RA-1 virus, Western equine encephalitis virus, Japanese encephalitis virus, Yellow Fever Virus, West Nile virus, Variola (smallpox) virus, cowpox virus, Vaccinia virus, Ebola virus, Respiratory syncytial virus, human cytomegalovirus, Rhinoviruses 1-113, Rift Valley fever virus, Ros river virus, Rubella virus, Russian spring-summer encephalitis virus, Sandfly fever viruses, St. Louis encephalitis virus, SV40 virus, vaccinia virus, Varicella-zoster virus, Vesicular stomatitis viruses and Bovine Viral Diarrhea Virus. These and other exemplary viruses have been described. See, for example B. N. Fields, et al., editors, *Fundamental Virology,* 3rd edition, 1996, Lippencott-Raven Publishers, see chapter 2 at pages 23-57, including table 4 at pages 26-27, table 5 at pages 28-29, chapter 17 at pages 523-539, chapters 26-27 at pages 763-916, chapter 32 at pages 1043-1108 and chapter 35 at pages 1199-1233, T. G. Ksiazek et al., New Engl. J. Med., electronic publication on Apr. 10, 2003.

In related embodiments, the F1Cs are used to treat, prevent or ameliorate Arbovirus infections, Arenavirus infections, Hantavirus infections and hemorrhagic fever virus infections, or a symptom(s) or complication(s) thereof, in subjects such as humans. In these infections the F1Cs can treat, prevent or ameliorate one or more symptoms including fever, headache, drowsiness, vomiting, stiff neck, mental confusion, muscle trembling, convulsions, and coma. Hemorrhagic fevers in humans are associated with infection by Hantaviruses and Filoviruses such as Ebola and Marburg viruses, which can cause infections that include Korean, Bolivian and Argentinean hemorrhagic fevers, Congo fever and Lassa fever.

Hantavirus infection is a viral disease that rodents can transmit to humans and the infection is associated with serious lung or kidney infection. Symptoms of Hantavirus infection of the lungs include one or more of fever, muscle pain, myalgia, headache, abdominal pain, conjunctival bleeding, diarrhea, or coughing. Hantavirus kidney infection may be mild or severe and is associated with fever, headache, backache, abdominal pain, small bruise-like patches on the whites of the eyes, abdominal rash, impaired kidney function, nausea, loss of appetite, fatigue and intracranial bleeding.

The F1Cs can also be used to treat, prevent or ameliorate infections caused by members of the Poxyiridae family, e.g., members of the Orthopoxvirus genus in subjects such as mammals or humans. The compounds can be used to treat, ameliorate or prevent one or more symptoms associated with Orthopoxvirus infections. For example, the variola or smallpox virus causes a serious infection with symptoms that include fever, chills, backache, headache, skin lesions and death. In treating Orthopoxvirus infections such as a variola infection, the F1Cs can result in enhanced efficacy of host factors such as cytokines or interferons such as IFN-α or IFN-γ. The subject may also be optionally treated with another agent such as IFN-γ, a nucleoside analog or a nucleotide analog such as one described herein or in the cited references. Treatment of a subject such as a human who is anticipated to potentially come in contact with a virus, e.g., an Orthopoxvirus such as the variola virus or the vaccinia virus is accomplished by administering a F1C to the subject by, e.g., daily or intermittent dosing, beginning at about 1-14 days before an anticipated potential exposure.

Parasites that can be treated using a F1C(s) include malaria parasites, sleeping sickness parasites and parasites associated with gastrointestinal infections. Exemplary parasite, fungi, yeast and bacterial infections that can be treated, prevented or ameliorated in subjects such as mammals or humans, include ones caused by or associated with species, groups, genotypes, serotypes, strains, genomovars or isolates of gastrointestinal helminths, microsporidia, isospora, cryptococci, cryptosporidia (*Cryptosporidium parvum*), *Trypanosoma* sp. (e.g., *T. brucei, T. gambiense, T. cruzi, T. evansi*), *Leishmania* sp. (e.g., *L. donovani, L. major, L. braziliensis*), *Plasmodium* sp. (e.g., *P. falciparum, P. knowlesi, P. vivax, P. berghei, P. yoelli*), *Ehrlichia* sp. (e.g., *E. canis, E. chaffeensis, E. phagocytophila, E. equi, E. sennetsu*), *Entamoeba* sp., *Babesia microti, Bacillus anthracis, Borrelia* sp. (e.g., *B. burgdorferi*), *Brucella* sp. (e.g., *B. militensis, B. abortus*), *Bartonella* sp. (*B. henselae*), *Bordetella* sp. (e.g., *B. bronchiseptica, B. pertussis*), *Burkholderia* sp., (e.g., *B. pseudomallei, B. cepacia*), *Campylobacter* sp., *Clostridium* sp. (e.g., *C. perfringens, C.*

*difficile, C. tetani, C. septicum*), *Chlamidya* sp. (e.g., *C. pneumoniae*), *Francisella* sp. (e.g., *F. tularensis*), *Enterococcus* sp. (e.g., *E. faecalis, E. faecium*), *Enterobacter* sp., *Bacteroides* sp. (e.g., *B. fragilis, B. thetaiomicron*), *Prevotella* sp., *Fusobacterium* sp., *Porphyromonas* sp., *Erysipelothrix rhusiopathiae, Escherichia* sp. (*E. coli*), *Gardnerella vaginalis, Haemophilus* sp. (e.g., *H. somnus, H. influenzae, H. parainfluenzae*), *Klebsiella* sp. (*K. pneumoniae*), *Leptospira* sp., *Legionella pneumonia, Listeria* (e.g., *L. monocytogenes, L. ivanovii*), *Morganella* sp. (e.g., *M. morganii*), *Mycobacterium* sp. (e.g., *M. avium, M. bovis, M. Ieprae, M. tuberculosis, M. pneumoniae. M. penetrans*), *Mycoplasma* sp. (e.g., *M. fermentans, M. penetrans, M. pneumoniae*), *Neisseria* (e.g., *N. gonorrhoeae, N. meningitidis*), *Nocardia asteroides, Proteus* sp. (e.g., *P. mirabilis, P. vulgaris, P. myxofaciens*), *Providencia* sp. (e.g., *P. rettgeri, P. stuartii*), *Pseudomonas* sp. (*P. aeruginosa*), *Salmonella* sp. (e.g., *S. typhimurium, S. tyhpi, S. paratyhpi, S. dublin, S. enteritidis, S. schottmuelleri, S. hirschfeldii*), *Serratia* sp., *Shigella* sp. (e.g., *S. flexneri, S. sonnei, S. dysenteriae*), *Streptococcus* sp. (e.g., *S. pneumoniae, S. pyogenes, S. faecalis, S. faecium, S. agalactiae, S. mutans, S. sanguis*), *Staphylococcus* sp. (e.g., *S. aureus*), *Rickettsia* sp. (e.g., *R. rickettsii, R. prowazekii, R. tsutsugamushi*), *Treponema* sp. (e.g., *T. pallidum, T. carateum*), *Vibrio* sp. (e.g., *V. cholerae, V. parahaemolyticus, V. mimicus*), *Yersinia* sp. (e.g., *Y. enterocolitica, Y. pestis*), *Pneumocystis* sp. (e.g., *P. carinii*), *Aspergillus* sp. (e.g., *A. fumigatus, A. terreus, A. flavus*), *Candida* sp. (e.g., *C. albicans, C. krusei, C. tropicalis*), *Chlamidya* sp. (e.g., *C. trachomatis*), *Schistosoma* sp. (e.g., *S. mansoni, S. japonicum, S. haematobium*), *Strongyloides stercoralis, Wucheria bancrofti, Brugia* sp. (e.g., *B. malayi, B. timori*), *Trichomonas* sp., (e.g., *T. vaginalis*) and *Taenia* sp., (e.g., *T. pedis, T. solium*).

Human *Aspergillus* infections that can be treated include invasive aspergilliosis, allergic bronchopulmonary aspergillosis, aspergilloma and chronic necrotizing aspergillosis. Bacterial infections that can be treated, prevented or ameliorated thus include infections by intracellular or extracellular gram positive bacteria, gram-negative bacteria, acid fast bacteria, Mycoplasma or rickettsial infections (e.g., a rickettsial spotted fever infection or a rickettsial typhus or scrib typhus infection). Other pathogens that are amenable to F1C treatments are as described. See, e.g., J. B. Peter, editor, *Use and Interpretation of Laboratory Tests in Infectious Disease,* 5$^{th}$ Edition, pages 1-309, 1998, Specialty Laboratories, Santa Monica, Calif., ISBN 1-889342-13-0.

For any of the infections disclosed herein, a subject who has the infection, or is susceptible of developing the infection, e.g., by suspected or potential exposure to an infectious agent, is treated by administering an effective amount of a F1C to the subject. Such subjects may have, or be susceptible to developing another condition, e.g., an autoimmune condition, inflammation condition, cardiovascular condition or a cancer or precancer as described herein, such as rheumatoid arthritis, systemic lupus erythematosis, Crohn's disease, ulcerative colitis, type 1 diabetes, type 2 diabetes, peptic ulcers, skin ulcers, oral cavity ulcers, asthma, multiple sclerosis, coronary artery disease, acute or chronic rheumatuc heart disease, atherosclerosis, stroke or lung cancer, that can be related to or exacerbated by the infection. In these embodiments, the F1Cs can function by one or more mechanisms, including enhancing innate immune responses, modulating, e.g., detectably increase or decrease, the level or activity of one or more of the transcription factors, enzymes or other biomolecules described herein, e.g., IL-1α, IL-1β, TNFα, TNF-β, IL-6, IL-8, IL-10, gro-α, IFN-γ, IFN-α, MCP-1, MIP-1α, MIP-1β, MIP-2, IP-10, LT-β, GM-CSF, RANTES or their isotypes or homologs or cortisol. For example, molecules such as IL1α, TNFα, MIP-1α or MCP-1 are generally decreased in infections where there is an overexpression of one or more of these molecules. A detectable decrease of one or more of these molecules often occurs.

In an exemplary embodiment, a subject such as a human that is known or suspected of having been exposed to *B. anthracis* spores or cells is treated with a F1C. The subject may have overt symptoms of either cutaneous or pulmonary infection. The F1C is administered at a dosage disclosed herein, e.g., about 0.05-10 mg/kg/day or about 0.1-5 mg/kg/day by buccal delivery or by a parenteral route such as subcutaneous, intramuscular or intravenous injection, for about 5-14 consecutive days. An oral dosage would be about 10-25 mg/kg/day of a F1C for about 5-14 consecutive days. Dosing with the F1C will typically begin at about the time that the infection is suspected or is diagnosed, or shortly thereafter, e.g., within about 1-12 hours.

During or after treatment, the patient is optionally monitored and the amelioration of one or more symptoms or a slowed disease progression is observed. Such symptoms can include one or more of a red-brown bump with swelling at the edges, blisters, formation of a black scab or eschar at the site of skin infection and edema. Symptoms of cutaneous anthrax that can be ameliorated include fever, headache, muscle ache, nausea, and vomiting. In treating *B. anthracis* infections, the F1Cs will typically decrease tissue damage associated with inflammation, enhance innate immune responses, enhance humoral immune responses, reduce TNFα, IL-1α or IL-1β levels or activity or enhance killing or phagocytosis of pathogen in the infected subject or the subject's immune cells, e.g., monocytes, neutrophils or macrophages.

For a pulmonary anthrax infection, amelioration of one or more of fever, bleeding and necrosis of lymph nodes near the lung, local chest infection, shock, coma or death can occur. Infection of the brain and meningoencephalitis may occur and is treated in a similar manner, although an increased dosage can be utilized, e.g., about 20-50 mg/kg/day of the F1C is administered by a parenteral, e.g., intravenous, sublingual or buccal route. In any of these skin, pulmonary or gastrointestinal infections, the subject is also optionally treated using one or more standard antibiotics and routes of administration, e.g., procaine penicillin G, of streptomycin, tetracycline, erythromycin, ciprofloxacin, doxycycline, levofloxacin, norfloxacin or oxofloxacin.

The use of the F1Cs will generally ameliorate the inflammation, sepsis or shock that can occur when antibiotics are administered to subjects having a systemic or pulmonary *B. anthracis* infection. A potential adverse effect of antibiotic use to treat a systemic or pulmonary *B. anthracis* infection is serious or potentially lethal inflammation, sepsis and/or shock that results from release of anthrax lethal toxin or factor or other inflammatory molecules on lysis of the bacteria. Release of bacterial lethal factor from lysed bacterial cells is associated with an intense inflammation, which is at least partially mediated by one or more inflammatory factors such as TNFα, IL-1β, IL-1α, IL-6, IL-8 or COX-2. The F1Cs detectably reduce the level and/or biological effects of such inflammatory factors and can also detectably maintain or facilitate macrophage viability or one or more desired macrophage function(s) at the same time.

Similarly, the F1Cs can be used to treat, prevent or ameliorate an infection by one or more gram-negative bacteria, e.g., gram-negative enteric bacteria. Such bacteria are commonly members of the *Bartonella, Brucella, Campylobacter, Enterobacter, Escherichia, Francisella, Klebsiella, Morganella, Proteus, Providencia, Pseudomonas, Salmonella,*

*Serratia, Vibrio* or *Yersinia genera*. Use of F1C can reduce the adverse effects of bacterial lipopolysaccharide or endotoxin that is associated with these organisms. For example, the F1Cs are therapeutically useful for infection by *Yersinia pestis*, which causes plague. Several forms of plague can exist, i.e., bubonic, pneumonic, septicemic, or pestis minor. The compounds ameliorate one or more of the symptoms associated with these infections. For example, in a bubonic plague infection, symptoms typically arise several days after exposure to *Y. pestis*, and can include a fever of up to 106° F., chills, rapid weak heartbeat, low blood pressure, lymph node swelling accompanied by tenderness, restlessness, confusion, uncoordinated movements, liver and spleen swelling. Symptoms associated with pneumonic plague include high fever, chills, rapid heartbeat, severe headache, coughing, blood-tinged sputum and rapid and labored breathing.

In septicemic or pneumonic *Y. pestis* infections, the subject is optionally treated using one or more standard antibiotics and routes of administration, e.g., streptomycin, tetracycline, gentamycin or chloramphenicol according to standard doses and dosing routes.

In a subject having a *V. cholerae* infection, symptoms typically arise several days after exposure to the pathogen, and can include a fever, chills, diarrhea, which can be serious or fatal if untreated, oliguria, muscle cramps and hypovolemia. In *V. cholerae* infections, the subject is treated with a F1C and optionally with one or more standard therapies, e.g., intravenous and/or oral replacement of water, glucose and electrolytes, tetracycline, doxycycline, erythromycin, furazolidone norfloxacin, trimethoprim and/or sulfamethoxazole, according to standard dosages and routes of administration.

In any of these bacterial infections, the subject is optionally treated with a suitable or appropriate antibacterial agent(s). Such agents include one, two or more antibacterial agents selected from an aminoglycoside, an amphenicol, an ansamycin, a H lactam, a lincosamide, a macrolide, a peptide, a tetracycline, a 2,4-diaminopyrimidine, a nitrofuran, a quinolone, a sulfonamide, a sulfone, cycloserine, mupirocin and tuberin. Aminoglycosides include dihdrostreptomycin, gentamicin, kanamycin, neomycin, and streptomycin and the amphenicols include chloramphenicol and chloramphenicol palmitate. β-Lactams include cefadroxil, cefamandole, cefatrizine, cefazedone, cefazolin, cefixime, ceftibuten, ceftizoxime, cefuroxime, cephalexin, cephalosporin, cephalothin, amoxicillin, carbenicillin and a penicillin G. Macrolides or other abtibiotics include clarithromycin, erythromycin, tetracycline, doxycycline, ciprofloxacin and dapsone.

Symptoms and conditions associated with infections that the F1C can treat include one or more of sepsis, septicemia, fever, e.g., moderate to high fever, inflammation, pain, e.g., chest pain, muscle pain, joint pain, back pain or headache, chills, itching, rash, skin lesions, erythema, e.g., peripheral erythema, lymphadenopathy, e.g., local, regional or systemic lymphadenopathy, nausea, vomiting, cyanosis, shock, coma, necrosis, hemorrhage, encephalitis, meningoencephalitis, cramping, mild to severe diarrhea, cough, weakness, splenomegaly, anorexia and weight loss. Other symptoms that can be treated are known. See, e.g., *The Merck Manual*, 17$^{th}$ edition, M. H. Beers and R. Berkow editors, 1999, Merck Research Laboratories, Whitehouse Station, N.J., ISBN 0911910-10-7, J. B. Peter, editor, *Use and Interpretation of Laboratory Tests in Infectious Disease*, 5$^{th}$ Edition, pages 1-309, 1998, Specialty Laboratories, Santa Monica, Calif., ISBN 1-889342-13-0.

The F1Cs can reduce rate or severity of coinfection and/or the rate of progression of an opportunistic or a latent infection in subjects having a retrovirus infection. In this embodiment of the invention, subjects such as humans infected with HIV1 or HIV2 are treated continuously or intermittently over a period of about 100-180 days. After treatment for this period of time, the rate of occurrence of new opportunistic infections is reduced or the rate of progression or re-occurrence of a pre-existing opportunistic or latent infection is reduced. Such opportunistic and latent infections can be one or more of e.g., a symptomatic infection by HSV-1, HSV-2, HHV-6, HHV-8, CMV, HCV, HBV, an oral bacterium, a human papillomavoirus such as HPV type 16, a *Mycobacterium, Pneumocystis carinii, Candida, Cryptosporidium, Toxoplasma, Cryptococcus, Staphylococcus, Salmonella, Plasmodium* or a cardiac viral, fungal or bacterial infection. The reduced rate of the incidence, severity or progression of opportunistic or latent infections is maintained during the time at which the F1C is dosed to the subject and for a period of time after dosing has ended, e.g., for about 2, 3, 4, 5, 6, 7 or 8 weeks after dosing has terminated. In cases where the F1C is administered to the subject by an intermittent dosing method, the time at which the occurrence of new opportunistic infections or emergence of latent infections is generally reached after 2, 3 or 4 rounds of intermittent dosing is completed. Such intermittent dosing can comprise administering 1-6 daily doses over a 1 week period, e.g., one dose on a single day, 2 consecutive daily doses, 5 consecutive daily doses or 2, 3 or 4 doses given every other day for a week, followed by no dosing for about 1, 2, 3, 4, 5, 6, 7 or 8 weeks, which is then followed by one or more rounds of dosing and no dosing. Reduced opportunistic and latent infections will be particularly pronounced in patients who are susceptible to such infections, e.g., humans having a CD4$^+$ T cell count of about 25-100 cells/mm$^3$, but who are not acutely or critically compromised by the retroviral infection at the time dosing with the F1C is initiated. Other effects that are observed at this time include decreased levels of pro-inflammatory cytokines and decreased tissue damage associated with inflammation, e.g., cardiac damage. F1Cs such as 3α,16α-dihydroxyandrostane-17-one, 3β,16α-dihydroxyandrostane-17-one, 3α,17β-dihydroxyandrostane-16-one, 3β,17β-dihydroxyandrostane-16-one and 3β,16α,17β-trihydroxyandrostane can be used in these methods.

For subjects who have a viral or parasite infection and are in the course of a F1C treatment, other treatments can also be administered to the subject, e.g., nucleoside analogs for viral infections or an antimalarial(s) agent such as one or more of artemisinin, dihydroartemisinin, a artemisinin analog (e.g., as disclosed in J. Han et al., *J. Nat. Products* 64:2101-1205 2001 or G. A. Balint *Pharmacol. Ther.* 90:261-265 2001), dapsone, sulfadoxin, pyrimethamine, chloroquine, mefloquine, halofantrine, proguanil, proguanil hydrochloride, cycloguanil, chlorocycloguanil, atovaquone, quinine, berberine, and/or primaquine for subjects having or subject to developing a malaria infection. Subjects suffering from or subject to developing a fungal infection can optionally be treated with a F1C and an antifungal agent, e.g., an azole or a polyene such as ketoconazole, fluconazole, anidalfungin, amphotericin B or a liposomal formulation that comprises an azole or polyene such as amphotericin B. Exemplary antiviral agents suitable for use in the method include reverse transcriptase or polymerase inhibitors such as AZT (zidovudine or 3'-azido-3'-deoxythymidine), 3TC, D4T, ddI, ddC, 2',3'-dideoxynucleosides such as 2',3'-didoxycytidine, 2',3'-dideoxyadenosine, 2',3'-didoxyinosine, 2',3'-didehydrothymidine, carbovir and acyclic nucleosides, e.g., acyclovir, ganciclovir. Exemplary protease inhibitors, fusion inhibitors or other antiviral or anti-retroviral agents that may be used in a combination therapy with a F1C include lamivudine, indinavir, nelfinavir, amprenavir, ritonavir, crixivan, sequanavir, nevirapine, stavudine, a HIV fusion inhibitor, efavirenz, co-trimoxazole, adefovir dipivoxil, 9-[2-(R)-[[bis[[(isopropoxy-carbonyl) oxy]-methoxy]phosphinoyl]methoxy]propyl]adenine, (R)-9-[2-(phosphonomethoxy)-propyl]adenine, tenofivir disoproxil and its salts (including the fumarate salt), TAT inhibitors such as 7-chloro-5-(2-pyrryl)-3H-1,4-benzodiazepin-2(H)-one or nucleic acids that comprise one or more unmethylated CpG sequences essentially as disclosed in, e.g., U.S. Pat. No. 6,194,388.

The antiviral or antimicrobial agents or treatments in combination therapies with a F1C will be or are used essentially according to new or to known dosing and administration methods for those agents or treatments. Their use may precede, overlap or be coincident in time with or follow a treatment protocol with a F1C. In some embodiments, the other therapeutic agents or treatments will overlap and will thus be administered on one or more of the same days on which a F1C is administered to a subject having a viral infection, or subject to a viral infection. In other embodiments, the other therapeutic agents or treatments will be administered to such a subject within about 1 day to about 180 days before or after a treatment protocol or a dosing period with a F1C begins or ends. In exemplary embodiments, the other suitable treatment or agent is administered within 1 day, 2 days, 3 days, 4 days, about 7 days, about 14 days, about 28 days or about 60 days before or after a treatment protocol or a dosing period with a F1C begins or ends.

Although the forgoing combination therapies have been described in the context of viral or other infections, the protocols and methods that employ a F1C can be used in conjunction with any suitable new or known therapeutic agent(s) or treatment protocol(s) for other any other clinical condition described herein. Any of these additional treatments can be coupled with the administration of any of the F1Cs in any of the embodiments described herein. Exemplary conditions include one or more of a non-viral pathogen infection(s), a cancer(s), a precancer(s), an inflammation condition(s), an autoimmune condition(s), an immunosuppression condition(s), a neurological disorder(s), a cardiovascular disorder(s), a neurological disorder(s), diabetes, obesity, wasting, anorexia, anorexia nervosa, a cancer chemotherapy(ies) side-effect(s), a side-effect(s) of a chemotherapy(ies) or a radiation therapy(ies) of any other clinical condition disclosed herein or in the cited references, or the like. Thus, invention embodiments include the use of a F1C before, during or after a treatment that uses another suitable therapeutic agent(s) or therapeutic treatment(s) for any of the diseases or conditions disclosed herein, any of which diseases or conditions may be acute, chronic, severe, mild, moderate, stable or progressing.

Examples of such agents, treatments or chemotherapies include the use of one or more adrenergic agents, adrenocortical suppressants, aldosterone antagonists, anabolics, analeptics, analgesics, anesthesia, anthelmintics, antiacne agents, anti-adrenergics, anti-allergics, anti-amebics, anti-androgens, antianginals, anti-anxiety agents, anti-arthritics, anti-asthmatic agents, anti-atherosclerotic agents, antibacterials, anticholinergics, anticoagulants, anticonvulsants, antidepressants, antidiabetics, antidiarrheals, antidiuretics, antiemetics, anti-epileptics, anti-estrogens, antifibrinolytics, antifungals, antihistamines, antihyperlipidemia agents, antihyperlipoproteinemic agents, antihypertensive agents, antihypotensives, anti-infectives, anti-inflammatory agents such as entanercept (a dimeric fusion comprising a portion of the human TNF receptor linked to the Fc protion of human IgG1 containing the $C_H2$ and $C_H3$ domain and hinge regions of IgG1) or a COX-2 inhibitor such as celexicob (4-5-[-(4-methylphenyl)-3-(trifluoromethyl)-1H-pyrazole-1-yl]benzenesulfonamide) or rofecoxib (4-[4-methylsulfonyl)phenyl]-3-phenyl-2(5H)-furanone), antimalarial agents, antimicrobials, antimigraine agents, antimycotic agents, antinausea agents, antineoplastic agents, antiparasitics, antiparkinsonian agents, antiproliferatives, antiprostatic hypertrophy agents, antiprotozoals, antipruritics, antipsychotics, antirheumatics, antischistosomals (e.g., praziquantel, artemisinin), blood glucose regulators, bone resorption inhibitors, bronchodilators, cardiac depressants, cardioprotectants, choleretics, depressants, diuretics, dopaminergic agents, enzyme inhibitors, free oxygen radical scavengers, glucocorticoids, peptide hormones, steroid hormones, hypocholesterolemics, hypoglycemics, hypolipidemics, hypotensives, immunomodulators, liver disorder treatments, mucosal protective agents, nasal decongestants, neuromuscular blocking agents, plasminogen activators, platelet activating factor antagonists, platelet aggregation inhibitors, post-stroke and post-head trauma treatments, progestins, psychotropics, radioactive agents, relaxants, sclerosing agents, sedatives, sedative-hypnotics, selective adenosine A1 antagonists, serotonin antagonists, serotonin inhibitors, serotonin receptor antagonists, thyroid inhibitors, thyromimetics, tranquilizers, vasoconstrictors, vasodilators, wound healing agents, xanthine oxidase inhibitors or a treatment(s) or therapeutic agent(s) for amyotrophic lateral sclerosis, ischemia, e.g., cereberal ischemia, cardiac ischemia or cardiovascular ischemia, or unstable angina. The selection and use of these agents for a particular subject will typically use dosing methods, dosages and routes of administration essentially according to known methods, dosages and routes of administration. Such methods, dosages and routes of administration are described in detail at, e.g., *Textbook of Autoimmune Diseases*, R. G. Lahita, editor, Lippincott Williams & Wikins, Philadelphia, Pa., 2000, ISBN 0-7817-1505-9, pages 81-851, *Holland•Frei Cancer Medicine* $^{e.}$5, $5^{th}$ edition, R. C. Bast et al., editors, 2000, ISBN 1-55009-113-1, pages 168-2453, B. C. Becker Inc. Hamilton, Ontario, Canada, *Hematology, Basic Principles and Practice*, 3rd edition, R. Hoffman, et al., editors, 2000, ISBN 0-443-77954-4, pages 115-2519, Churchill Livingstone, Philadelphia, Pa., *Rheumatology*, $2^{nd}$ edition, J. H. Klippel et al., editors, 1998, ISBN 0-7234-2405-5, volume 1, sections 1-5 and volume 2, sections 6-8, Mosby International, London, UK, *Alzheimer's Disease and Related Disorders: Etiology, Pathogenesis and Therapeutics*, K. Iqbal, et al., editors, 1999, ISBN 0-471986386, John Wiley & Son Ltd, and *Cardiovascular Medicine*, E. J. Topol, editor, Lippincott Williams & Wikins, Philadelphia, Pa., 1998, ISBN 0781716810.

In some infections, the F1C(s) effects an improvement of one or more of the symptoms associated with the infection or a symptom thereof. For example, treatment of subjects who are immune suppressed, e.g., from a retrovirus infection, cancer chemotherapy or other cause, generally show improvement of one or more associated symptoms, such as weight loss, fever, anemia, pain, fatigue or reduced infection symptoms that are associated with a secondary infection(s), e.g., HSV-1, HSV-2, papilloma, human cytomegalovirus ("CMV"), *Pneumocystis* (e.g., *P. carinii*) or *Candida* (*C. albicans, C. krusei, C. tropicalis*) infections.

In some embodiments, the F1C(s) is administered as a nonaqueous liquid formulation as described herein or the F1C(s) is administered according to any of the intermittent dosing protocols described herein using a solid or liquid formulation(s). In the case of a subject who has a retroviral infection, e.g., a human with an HIV infection, with symptoms that include one or more of, a relatively low CD4 count (e.g., about 10-200, or about 20-100 or about 20-50), one or more additional pathogen infections (HSV-1, HSV-2, HHV-6, HHV-8, CMV, HCV, a HPV, *P. carinii* or *Candida* infection) and one or more of anemia, fatigue, Kaposi's sarcoma, fever or involuntary weight loss (at least about 5% of body weight), administration of about 0.1 to about 10 mg/kg/day (usually about 0.4 to about 5 mg/kg/day) of a F1C(s) to the subject typically results in noticeable improvement of one or more of the symptoms within about 1-4 weeks. In other embodiments, the F1C(s) is administered to a subject who has a condition that appears to be associated with a viral infection, e.g., pneumonia or retinitis associated with CMV, nasopharyngeal carcinoma or oral hairy leukoplakia associated with Epstein-Barr virus, progressive pancephalitis or diabetes associated with Rubella virus or aplastic crisis in hemolytic anemia associated with Parvovirus 19.

One or more intermittent dosing protocols disclosed herein or one or more of the liquid non-aqueous formulations described herein can be applied by routine experimentation to any of the uses or applications described herein. For a F1C(s) that is a new compound per se, the compound(s) can be administered to a subject according to an invention intermittent dosing protocol(s) or by other protocols, e.g., continuous daily dosing of a single dose or two or more subdoses per day. In addition any of the F1Cs, e.g., one or more F1Cs that are new per se, can be present in any solid or liquid formulation described herein. These formulations and dosing protocols can be applied by routine methods to any of the uses or applications described herein.

Antibodies, vaccines and vaccine adjuvants. The F1Cs can be used to enhance cellular or humoral responses to vaccination against, e.g., infectious agents or malignant cells. F1Cs can also be used to make antibodies that bind to the F1Cs themselves or their metabolic products. Antibodies that bind to the F1Cs can be used, e.g., in diagnostic, quality control, or the like, methods or in assays for the F1Cs or their metabolites. In addition, the F1Cs are useful for raising antibodies against otherwise non-immunogenic polypeptides, in that the compounds may serve as haptenic sites stimulating an immune response against the polypeptide.

Immunogens that are used to make antibodies that bind to a F1C comprise a F1C that has 1 or more epitopes and optionally another immunogenic substance. The immunogenic substance can be covalently bonded to the F1C to form an immunogenic conjugate or it can be in a mixture of non-covalently bonded materials, or a combination of the above. Immunogenic substances include adjuvants such as Freund's adjuvant, immunogenic proteins such as viral, bacterial, yeast, plant and animal polypeptides, including keyhole limpet hemocyanin, serum albumin, bovine thyroglobulin or soybean trypsin inhibitor, and immunogenic polysaccharides. Typically, the F1C having one, two or more epitopes is covalently conjugated to an immunogenic polypeptide or polysaccharide by the use of a polyfunctional (ordinarily bifunctional) cross-linking agent. Methods for the manufacture of immunogens that comprise one or more haptens are conventional per se. Methods for conjugating haptens to immunogenic polypeptides or the like are used here. Such conjugates are prepared in conventional fashion. For example, the cross-linking agents N-hydroxysuccinimide, succinic anhydride or $C_{2-8}$ alkyl-N=C=N—$C_{2-8}$ alkyl are useful in preparing the conjugates. The conjugates comprise a F1C that is attached by a bond or a linking group of 1-100, typically, 1-25, more typically about 1-10 carbon atoms to the immunogenic substance. Typically a polypeptide, polysaccharide or other suitable immunogenic moiety is conjugated to a site on a F1C in a location that is distant from the epitope on the F1C to be recognized. The conjugates are separated from starting materials and by-products using chromatography or the like, and then are optionally sterile filtered, or otherwise sterilized, or are optionally vialed for storage. Synthetic methods to prepare hapten-carrier immunogens have been described, see e.g., G. T. Hermanson, Bioconjugate Techniques Academic Press, 1996, pages 419-493.

Animals or mammals are typically immunized once, twice or more times against the immunogenic conjugates that comprise a F1C and an immunogen. Polyclonal antisera or monoclonal antibodies are prepared in conventional fashion. In some embodiments, about 0.0001 mg/kg to about 1 mg/kg, e.g., about 0.001 or about 0.01 or about 0.1 mg/kg, of immunogenic conjugate or derivative is used on one, two, three or more occasions to immunize the subject as described herein. The immunogenic conjugates are administered, orally, topically or parenterally as described herein, e.g., by i.m. or s.c. injection. Methods to prepare antibodies, including methods to obtain antibodies that bind to steroids have been described, see, e.g., R. O, Neri et al., *Endocrinology* 74:593-598 1964, M. Ferin et al., *Endocrinology* 85:1070-1078 1969, J. Vaitukaitis et al., *J. Clin. Endocr. Metab.* 33:988-991 1971 and M. Ferin et al., *Endocrinology* 94:765-775 1974. Such methods can be used essentially as described to prepare antibodies or monoclonal antibodies that bind to a F1C. Embodiments include serum or other preparations that comprise any polyclonal or monoclonal antibodies that bind to a F1C(s), methods to make such antibodies and compounds or compositions that are used in conducting these methods.

In other embodiments the F1Cs are used as adjuvants to enhance a subject's immune response to antigens such as proteins, peptides, polysaccharides, glycoproteins or killed or attenuated viruses or cell preparations. In these methods, an effective amount of the F1C is administered at about the same time that the antigen is delivered to the subject, e.g., within about 1, 2, 3, 4, 5, 6, or 7 days of when the antigen is administered to the subject. In some embodiments, the F1C is administered 1, 2, 3, 4 or more times (usually once or twice per day) at 1, 2, 3 or 4 days before or after the antigen is administered to the subject. In other embodiments, the F1C is administered on the same day that the antigen is administered to the subject, e.g., within about 1-4 hours. Such immunization methods may be repeated once, twice or more as needed. The F1C can be administered to the subject using any of the formulations or delivery methods described herein or in the references cited herein. Subjects suitable for these vaccinations include young and elderly mammals, including humans, e.g., humans about 3-36 months of age or older and humans about 60, 65, 70, 75 years of age or older. The amount of antigen used can be about 0.01 µg/kg to about 20 mg/kg, typically about 1-100 µg/kg. Dosages of the F1C used in these vaccinations is essentially as described herein, e.g., about 5 mg to about 1000 mg of a F1C is used per day on days when it is administered as part of the vaccination method.

Related embodiments include compositions or formulations that comprise a F1C, an antigen(s) or antigen(s) preparation and optionally one or more excipients. The antigen is essentially as disclosed herein or in a cited reference. Antigen preparations may comprise one or more of (1) lethally or sublethally radiated cells or pathogens, (2) disrupted cells or viruses or such as attenuated viruses, (3) a nucleic acid or DNA vaccine, (4) an antigenic protein, glycoprotein, polysaccharide or a fragment or derivative of any of these molecules, (5) chemically treated cells or pathogens, e.g., formalin or detergent treated cells, viruses or cell or virus extracts and (6) genetically engineered viral or bacterial vectors that express one or more antigens or antigen fragments. Pathogens include prions or the etiologic agents of, e.g., Creutzfelt-Jacob disease, bovine spongiform encephalopathy and scrapie in sheep, goats or mice. Where cells or disrupted are present in an antigen preparation, they may by genetically modified, e.g., to express one or more antigens or epitopes against which an immune response is desired. Antigens in these embodiments are moieties that can elicit a detectable immune response when it is administered to a subject. In some embodiments, the antigen is foreign to the subject. For foreign antigens, the subject to be vaccinated may not encode or express the antigen, while the antigen is usually part of or expressed by a pathogen or by a subject or mammal of a different species. In other embodiments, antigens are endogenous or non-foreign to the subject, e.g., they are usually encoded or expressed by the subject or another subject of the same species. Endogenous antigens are suitable for use in, e.g., tumor vaccination methods.

Exemplary tumors from which a suitable antigen(s) may be obtained are as described herein or in the cited references. A DNA vaccine as used here typically comprises a nucleic acid, usually DNA, that encodes one or more antigens or epitopes that a pathogen, e.g., a parasite, fungus, virus or bacterium, or a tumor encodes or can express. Tumor antigens that are suitable for use in vaccination methods that employ a F1C include tumor-associated antigens and tumor-specific antigens. These molecules typically comprise one or more protein, glycoprotein, carbohydrate or glycolipid. Vaccinations that employ a tumor antigen(s) may comprise autologous tumor cells or allogenic tumor cells, which are optionally disrupted and optionally used with a non-formula 1 adjuvant, such as bacillus Calmette-Guerin (BCG), purified protein derivative, Freund's complete adjuvant, *Corynebacterium parvum, Mycobacterium vaccae*, oligonucleotides that consist of or comprise an unmethylated CpG dimer or an alum precipitate. In some embodiments, tumor cells treated with neuraminidase comprise all or part of the tumor antigen source. The non-formula 1 adjuvants are also optionally used in any of the vaccination methods disclosed herein. As used here, tumor associated antigens, e.g., the carcinoembryonic antigen, α-fetoprotein or the prostate specific antigen, are molecules that are often associated with or detectably expressed by premalignant or malignant cells or cell populations and also with some normal tissues during at least part of the subject's life cycle.

Other suitable antigens include STn, sialyl Tn-KLH, carbohydrate conjugates, carcinogenic embryonic antigen, MAGE-1, MUC-1, HER-2/neu, prostate specific antigen, p53, T/Tn, bacterial flagella antigens or capsular polysaccharide antigens (e.g., *Staphylococcus aureus* capsular polysaccharide antigens) and antigenic fragments or antigenic synthetic derivatives of any of these molecules, e.g., a fragment or derivative that retains at least about 20% or 30% of the antigenicity of the native or intact molecule. See, e.g., L. A. Holmberg et al., *Bone Marrow Transplant.* 2000 25:1233-1241, J. W. Hadden, *Int. J. Immunopharmacology* 1999 21:79-101, G. Ragupathi et al., *Glycoconj. J.* 1998 15:217-221, A. I. Fattom et al., *Infect. Immun.* 1998 66:4588-4592, U.S. Pat. Nos. 5,770,208, 5,866,140 and 6194161 and citations elsewhere herein, including the preceding paragraph.

An antigenic protein, peptide or glycoprotein can be identified by standard methods, e.g., protein or nucleic acid sequencing, for any of the infectious agents or tumors that are described herein or in the cited references. Thus, in some embodiments, an effective amount of a F1C and an antigen are administered to a subject, or delivered to the subject's tissues, to stimulate an immune response against the antigen. The antigen may comprise one, two or more antigenic epitopes, which may come from one, two or more genes. In some embodiments, the subject is optionally monitored to follow or determine the immune, dendritic cell, B cell, T cell, antibody or cytokine response, such as one disclosed herein, e.g., modulation or increase in γIFN, IL-2 or IL-12 levels or measurement of the production of one or more immunoglobulin types or subtypes. The subject may also be monitored by in vitro cell assays, e.g., for activation of T cells or subsets of T cells or other relevant white blood cell types. Such assays include measuring T cell activation using chromium release assays, or mixed lymphocyte assays. The subject is optionally treated with one or more additional booster vaccinations, when this is called for under the circumstances.

Nucleic acid or DNA vaccines as used here will typically comprise a nucleic acid comprising an expressible region that encodes one, two or more suitable antigens or epitopes, e.g., all or an antigenic portion of a viral, bacterial, fungal or parasite protein or glycoprotein. The expressible region will usually comprise a transcription promoter and optionally other control sequences that are operatively linked to the antigen coding region where the promoter and control sequences are transcriptionally active in the intended subject or tissue. Suitable control sequences include enhancers, recognition sequences for transcription factors and termination sequences. Such expression vectors may optionally comprise one, two or more expressible genes or gene fragments, which may each comprise their attendant operatively linked expression sequences. Suitable methods and expression vectors to deliver nucleic acids for vaccine purposes have been described, e.g., U.S. Pat. Nos. 5,223,263, 5,580,859, 5,703, 055, 5,846,946 and 5910488.

Vaccinations that utilize a F1C and an antigen(s) are generally suitable for eliciting or enhancing desired immune responses in conjunction with exposure of a subject to an antigen(s), compared to vaccination without the compound. Antigen specific humoral antibody responses or antigen specific T cell responses may be enhanced or elicited. Typically vaccination using a F1C and a suitable antigen is conducted to prevent a potential infection or to reduce the severity of a future infection. However, in some cases the vaccination is conducted in a subject that has an infection such as a chronic or a latent infection such as a parasite or a retrovirus or herpesvirus infection, which may be latent or in relapse. In other cases the subject may have a cancer or precancer. Thus, the subject may be exposed to, or contain, one or more of the antigens that are used in one of these vaccination procedures. Such vaccinations are included within the scope of the invention.

In related embodiments, the F1Cs are useful to facilitate preparation of hybridoma clones that express monoclonal antibodies. In these methods, a suitable amount of a F1C, e.g., about 100 µg to about 2 mg for a small mammal, is administered to a subject, e.g., a mouse, to enhance the immune response to the desired antigen, which is also administered to the subject. After antigen challenge, suitable cells are recovered from the subject, e.g., anti-antigen immunoglobulin expressing HPRT$^+$ spleen cells from a mouse. These cells are then fused with suitable immortal cells (e.g., mouse melanoma cells) using, e.g., PEG or Sendai virus, and selected in suitable selection growth medium, e.g., tissue culture medium that contains hypoxanthine, aminopterin and thymidine, to obtain a group or panel of hybridomas that express anti-antigen monoclonal antibodies. The hybridoma panel is used to generate individual clones, which are optionally screened to determine the antibody specificity and antigen binding properties. About one, 100, 1000, 10,000, 100,000 or more individual clones are screened by standard methods. The monoclonal antibodies may be from any suitable source, e.g., murine, human, human-murine hybrid or the like. Methods to obtain human, human-murine hybrid or related monoclonal antibodies have been described, e.g., U.S. Pat. Nos. 5,562,903, 5,461,760, 5,705,154, 5,854,400, 5,858,728, 5,874,082, 5,874,540, 5,877,293, 5,882,644, 5,886,152, 5,889,157, 5,891,996, 5,916,771, 5,939,598, 5,985,615, 5,998,209, 6,013,256, 6,075,181, 6,901,001, 6,114,143, 6,114,598, 6,117,980. The F1Cs can be used in any of the methods disclosed in these references to facilitate generation or recovery of hybridoma panels and clones that express monoclonal antibodies.

An aspect of these methods comprise a product, i.e., a hybridoma panel or a hybridoma clone, that is obtained by the process of contacting a subject (such as a mouse) with (1) a suitable amount of a F1C and (2) a suitable amount of an antigen, allowing sufficient time to generate an immune response in the subject against the antigen and then fusing suitable anti-antigen immunoglobulin producing cells from the subject, e.g., the subject's spleen cells, with a suitable immortal cell line (e.g., a HPRT$^+$ mouse myeloma). The antigen or immunogen is as described above, e.g., a suitable protein, protein fragment or glycoprotein such as an interleukin, cytokine or antigen from an infectious agent. In these methods, a mouse is typically the subject, but other mammals, e.g., humans or other rodents, are also suitable according to known methods.

The amount of antigen for immunization used in preparing monoclonal antibodies in a human or a mammal will typically be about 1 μg to about 1000 μg, e.g., about 2 μg, 5 μg, 10 μg, 50 μg or 100 μg of antigen. The antigens are essentially as described in the vaccination methods described above, e.g., disrupted cell, a protein or glycoprotein, which is optionally combined with a suitable amount of an adjuvant such as Freund's complete adjuvant, alum precipitate, a bacterial lipopolysaccharide or BCG.

Related embodiments include a method comprising administering to a subject (e.g., a mammal such as a human or a primate), or delivering to the subject's tissues, an effective amount of a F1C and a specific antigen. Immune responses that are enhanced include a mucosal immune response to an antigen such as a protein, peptide, polysaccharide, microorganism, tumor cell extract or lethally radiated tumor or pathogen cells (e.g., antigens or cells from melanoma, renal cell carcinoma, breast cancer, prostate cancer, benign prostatic hyperplasia, virus or bacteria, or other tumor or pathogen as disclosed herein). Aspects of these embodiments include enhancement of the subject's immune response when an antigen or immunogen is administered intranasally or orally. In these aspects, the F1C is administered about simultaneously with the antigen or within about 3 hours to about 6 days of antigen administration. The use of immune modulating agents to enhance immune responses to a vaccine has been described, e.g., U.S. Pat. No. 5,518,725.

Other uses for the F1C(s) include administering the compound(s) to a subject who suffers from a pathological condition(s). The treatment may treat or ameliorate the source of the condition(s) and/or symptoms associated with the pathological condition(s) such as infection with a pathogen(s) (viruses, bacteria, fungi), a malignancy, unwanted immune response, i.e., an immune response that causes pathology and/or symptoms, e.g., autoimmune conditions or allergy or conditions such as hypoproliferation conditions, e.g., normal or impaired tissue growth, or wound healing or burn healing, or in immunosuppression conditions, e.g., conditions characterized by an absence of a desired response and/or an inadequate degree of a desired response.

Enhanced antibody responses include detectable enhancement of antibody titer or a shift in the antibody, e.g., an antibody response from a Th2 biased response to an increased Th1 biased component of the response. In such antibody shifts, the Th1 and Th2 character of the response is determined by known methods. For example, a relatively low ratio of IgG1 (or the analogous antibody subclass in humans and other subjects) to IgG2a (or the analogous antibody subclass in humans and other subjects), e.g., about 6:1 to about 12:1, that is generated after exposure of a subject (a mouse for the IgG1 and IgG2a subclasses) to an antigen indicates a Th1 biased antibody response. Conversely a higher ratio, e.g., about 20:1 to about 30:1 indicates a Th1 biased antibody response. Generation of antigen-specific IgG1 generation involves T-helper type 2 (Th2) cells, and for IgG2a, T-helper type 1 (Th1) cells. The F1Cs can detectably increase the Th1 character of an antibody response to an antigen or they can increase the magnitude of both the Th1 and Th2 response.

Exemplary pathogens or cells that are suitable sources for antigens or a gene(s) that encode suitable antigens include pathogens described herein or in the cited references.

Cancer and hyrerproliferation conditions. Many cancers, precancers, malignancies or hyperproliferation conditions are associated with an unwanted Th2 immune response, a deficient Th1 response or unwanted inflammation. An insufficient Th1 immune response may play a role in the capacity of malignant or premalignant cells to escape immune surveillance. Any of the F1Cs disclosed herein, may thus be used to treat, prevent or slow the progression of one or more cancers, precancers or cell hyperproliferation conditions or they may be used to ameliorate one or more symptoms thereof. In these conditions, the F1Cs are useful to enhance the subject's Th1 responses or to reestablish a more normal Th1-Th2 balance in the subject's immune responses. The F1Cs may function at least in part by decreasing inflammation or inflammation associated markers such as IL-6 and/or by enhancing hematopoiesis in many of these conditions.

These conditions include cancers or precancers comprising carcinomas, sarcomas, adenomas, blastoma, disseminated tumors and solid tumors such as one associated with or arising from prostate, lung, breast, ovary, skin, stomach, intestine, pancreas, neck, larynx, esophagus, throat, tongue, lip, oral cavity, oral mucosa, salivary gland, testes, liver, parotid, biliary tract, colon, rectum, cervix, uterus, vagina, pelvis, endometrium, kidney, bladder, central nervous system, glial cell, astrocyte, squamous cell, blood, bone marrow, muscle or thyroid cells or tissue. The F1Cs are thus useful to treat, prevent, slow the progression of, or ameliorate one or more symptoms of a precancer, cancer or related hyperproliferation condition such as myelodysplastic syndrome, actinic keratoses, endometriosis, Barrett's esophagus, leiomyoma, fibromyoma, benign or precancerous intestinal or bowel polyps or benign prostatic hyperplasia. The compounds can also be used to treat, prevent, slow the progression of, slow the replication or growth of, or to ameliorate one or more symptoms of a primary tumor, a metastasis, an advanced malignancy, a blood born malignancy, a leukemia or a lymphoma. Any of these conditions may be in an early or mild form or can be moderate or advanced in the existent or progression of the disease or a symptom.

In treating endometriosis, the use of an F1C will slow the rate of disease progression and decrease the severity or frequency of one or more symptoms such as irregular menstrual periods, infertility abdominal pain or cramping and pain in the lower back or pelvic area, which may precede menstruation or may accompany sexual intercourse or bowel movements. Beneficial effects from F1C treatment will be mediated in patients with endometriosis at least partially by increasing the patient's Th1 immune responses and/or by decreasing anti-endometrial antibodies or aberrent Th2 immune responses. Treatment of emdometriosis could be accompanied by other suitable treatments, e.g., treatment with one or more of estrogen, progesterone, danazol, follicle stimulating hormone antagonists, leutinizing hormone antagonists, gonadotropin-releasing hormone antagonists such as nafarelin acetate or analgesics such as codeine, tylenol or aspirin.

The F1Cs can be used to treat paraneoplastic syndromes or conditions such as ones associated with lung or breast cancers that secrete calcitonin or that enhance osteoclast activity. Such conditions include hypercalcemia, Cushing's syndrome, acromegaly and non-islet cell tumor hypoglycemia. The compounds are used to decrease osteoclast activity or other symptoms associated with such conditions.

Hyperproliferation conditions that can be treated include melanoma, Kaposi's sarcoma, leiomyosarcoma, non-small cell lung cancer, small cell lung cancer, bronchogenic carcinoma, renal cell cancer or carcinoma, glioma, glioblastoma, pancreatic or gastric adenocarcinoma, gastrointestinal adenocarcinoma, human papillomavirus associated cervical intraepithelial neoplasia, cervical carcinoma, hepatoma, hepatocellular carcinoma, hepatocellular adenoma, cutaneous T-cell lymphoma (mycosis fungoides, Sezary syndrome), colorectal cancer, chronic lymphocytic leukemia, chronic myelogenous leukemia, ALL or follicular lymphoma, multiple myeloma, carcinomas with p53 mutations, colon cancer, cardiac tumors, adrenal tumors, pancreatic cancer, retinoblastoma, a small cell lung cancer, a non-small cell lung cancer, intestinal cancer, testicular cancer, stomach cancer, neuroblastoma, neuroma, myxoma, myoma, endothelioma, osteoblastoma, osteoclastoma, osteosarcoma, chondrosarcoma, adenoma, breast cancer, prostate cancer, Kaposi's sarcoma, ovarian cancer, squamous cell carcinoma of the gastrointestinal tract and non-myeloid tumors. Treating a subject with a F1C can ameliorate one or more side effects of chemotherapy or cancer symptoms such as alopecia, pain, fever, malaise, chronic fatigue and cachexia or weight loss. Other cancers, precancers or their symptoms that can be treated, prevented or ameliorated are described in, e.g., *Holland•Frei Cancer Medicine*$^{e.}$5, 5$^{th}$ edition, R. C. Bast et al., editors, 2000, ISBN 1-55009-113-1, pages 168-2453, B. C. Becker Inc. Hamilton, Ontario, Canada or *The Merck Manual*, 17$^{th}$ edition, M. H. Beers and R. Berkow editors, 1999, Merck Research Laboratories, Whitehouse Station, N.J., ISBN 0911910-10-7.

In some of these embodiments, the subject's hyperproliferation or malignant condition may be associated with or caused by one or more pathogens. Such conditions include hepatocellular carcinoma associated with HCV or HBV, Kaposi's sarcoma associated with HIV-1 or HIV-2, T cell leukemia associated with HTLV I, Burkitt's lymphoma associated with Epstein-Barr virus or papillomas or carcinoma associated with papilloma viruses (e.g., human HPV 6, HPV 11, HPV 16, HPV 18, HPV 31, HPV 45) or gastric adenocarcinoma, gastric MALT lymphoma or gastric inflammation associated with *Helicobacter pylori*, lactobacillus, enterobacter, staphylococcus or propionibacteria infection.

In some of these embodiments, the F1Cs may be used to treat, prevent or slow the progression of or ameliorate one or more conditions in a subject having or subject to developing a hyperproliferation condition where angiogenesis contributes to the pathology. Abnormal or unwanted angiogenesis or neovascularization contributes to the development or progression of solid tumor growth and metastases, as well as to arthritis, some types of eye diseases such as diabetic retinopathy, retinopathy of prematurity, macular degeneration, corneal graft rejection, neovascular glaucoma, rubeosis, retinoblastoma, uvietis and pterygia or abnormal blood vessel growth of the eye, and psoriasis. See, e.g., Moses et al., *Biotech.* 9:630-634 1991, Folkman et al., *N. Engl. J. Med.*, 333:1757-1763 1995, and Auerbach et al., *J. Microvasc. Res.* 29:401-411 1985.

Dosages of the F1C, routes of administration and the use of combination therapies with other standard therapeutic agents or treatments could be applied essentially as described above for cancer or hyperproliferation conditions or other conditions as disclosed herein. Thus, in some embodiments, the use of the F1C is optionally combined with one, two or more additional therapies for a cancer or precancer(s), e.g., one, two or more of surgery and treatment with an antiandrogen or an antiestrogen as described herein or in the cited references, an antineoplastic agent such as an alkylating agent, a nitrogen mustard, a nitrosourea, an antimetabolite, a cytotoxic agent, a cytostatic agent, platinum agents, anthracyclines, taxanes or treatment with an analgesic such as propoxyphene napsylate, acetaminophen, morphine or codeine. Exemplary anticancer and adjunct agents include tamoxifen, paclitaxel, taxol, docetaxil, methotrexate, vincristine, vinblastine, 5-fluorouracil, thioguanine, mercaptopurine, adriamycin, chlorambucil, cyclophosphamide, cisplatin, carboplatin, transplatinum, irinotecan, procarbazine, hydroxyurea, erythropoietin, G-CSF, bicalutamide, anastrozole, fludarabine phosphate, doxorubicin and any suitable form of any of these agents, e.g., salts and solvates. Such therapies would be used essentially according to standard protocols and they would precede, be essentially concurrent with and/or follow treatment with a F1C. In some embodiments, such additional therapies will be administered at the same time that a F1C is being used or within about 1 day to about 16 weeks before or after at least one round of treatment with the F1C is completed. In other embodiments, a course of therapy is administered to the subject, e.g., treatment with a myelosuppressive amount of a myelosuppressive agent such as 5-fluorouracil, cyclophosphamide or a platinum compound such as cisplatin, followed within about 1, 2, 3, 4, 5 or 6 days by administration of one or more courses of treatment with a F1C. Other suitable exemplary therapeutic agents and their use have been described in detail, see, e.g., *Physicians Desk Reference* 54$^{th}$ edition, 2000, pages 303-3250, ISBN 1-56363-330-2, Medical Economics Co., Inc., Montvale, N.J. One or more of these exemplary agents can be used in combination with a F1C to ameliorate, slow the establishment or progression of, prevent or treat any of the appropriate cancers, precancers or related conditions described herein, or any of their symptoms.

In treating cancers or hyperproliferation conditions, the F1Cs may detectably modulate, e.g., decrease or increase, the expression or level or activity of one or more biomolecules associated with the prevention, establishment, maintenance or progression of the cancer or hyperproliferation condition. Such biomolecules include one or more of carcinoembryonic antigen, prostate specific antigen, her2/neu, Bcl-XL, bcl-2, p53, IL-1$\alpha$, IL-1$\beta$, IL-6, or TNF$\alpha$, GATA-3, COX-2, NF$\kappa$B, IkB, an IkB kinase, e.g., IkB kinase-$\alpha$, IkB kinase-$\beta$ or IkB kinase-$\gamma$, NFAT, calcineurin, calmodulin, a ras protein such as H-ras or K-ras, cyclin D, cyclin E, xanthine oxidase, or their isoforms, orthologs, homologs or mutant forms, which may be observed as either reduced or increased levels or biological activity(ies). Biomolecule levels or their activity(ies) that can be at least transiently detectably increased include one or more IL-2, IFN$\gamma$, IL-12, T-bet, 06-methylguanine-DNA-methyltransferase, calcineurin, calmodulin, a superoxide dismutase (e.g., Mn, Zn or Cu), a tumor suppressor protein such as the retinoblastoma protein (Rb) or CDKN2A (p16), BRCA1, BRCA2, MeCP2, MBD2, PTEN, NBR1, NBR2 or the isoforms, orthologs, homologs or mutant forms, which may have either attenuated or enhanced biological activity(ies), of any of these molecules. In treating a cancer described herein such as prostate cancer, one or more of ELAC2, 2',5'-oligoadenylate dependent RNAse L (RNASEL), macrophage scavenger receptor 1 (MSR1), BRCA2 can be modulated or decreased.

The F1Cs can modulate the synthesis or a biological activity of one or more other gene products such as transcription factors, enzymes or steroid or other receptors that are associated with the establishment, progression or maintenance of a cancer or precancer or associated symptom. The compounds can inhibit AIB-1 coactivator or HER2/neu synthesis or activity in breast cancer cells or breast cancer conditions. They can enhance the synthesis or an activity of an estrogen receptor such as ERα, ERβ1 or ERβ2 or progesterone receptor in breast cancer or colon cancer cells or conditions. These effects can include modulation of the expression or one or more biological activities of proteins or enzymes that contribute to disease establishment or progression. Thus, the compounds can decrease IL-4, IL-6 or IL-13 expression by stromal cells or immune cells that are in proximity to or adjacent to solid or diffuse tumor cells in a subject such as a human or another mammal. In the cancers or precancers described herein, the compounds can thus directly or indirectly modulate (e.g., decrease) the activity or expression of relevant enzymes such as STAT-6, neutral endopeptidase, a hydroxysteroid dehydrogenase, such as a 17β-hydroxysteroid dehydrogenase, 11β-hydroxysteroid dehydrogenase, 7β-hydroxysteroid dehydrogenase or a 3β-hydroxysteroid dehydrogenase.

In some embodiments, the F1Cs are used to treat tumors or cancers wherein proliferation of the tumor or cancer cells is enhanced in response to sex steroids such as natural or synthetic androgens or estrogens. In other embodiments, the tumor or cancer cells are not responsive to such hormones or they are only slightly responsive to the presence of such compounds.

Cardiovascular applications. Any of the F1Cs disclosed herein, may be used to treat, prevent or slow the progression of one or more of congenital heart defects, cardiovascular diseases, disorders, abnormalities and/or conditions, or to ameliorate one or more symptoms thereof in a subject. These include peripheral artery disease, arterio-arterial fistula, arteriovenous fistula, cerebral arteriovenous malformations, aortic coarctation, cor triatum, coronary vessel anomalies, patent ductus arteriosus, Ebstein's anomaly, hypoplastic left heart syndrome, levocardia, transposition of great vessels, double outlet right ventricle, tricuspid atresia, persistent truncus arteriosus, and heart septal defects, such as aortopulmonary septal defect, endocardial cushion defects, Lutembacher's Syndrome, ventricular heart septal defects, cardiac tamponade, endocarditis (including bacterial), heart aneurysm, cardiac arrest, congestive heart failure, congestive cardiomyopathy, paroxysmal dyspnea, cardiac edema, post-infarction heart rupture, ventricular septal rupture, heart valve diseases, myocardial diseases, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, cardiovascular syphilis, cardiovascular tuberculosis, arrhythmias such as sinus arrhythmia, atrial fibrillation, atrial flutter, bradycardia, extrasystole, Adams-Stokes Syndrome, bundle-branch block, sinoatrial block, long QT syndrome, parasystole, sick sinus syndrome, ventricular fibrillations, tachycardias such as paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia and heart valve diseases such as aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

The F1Cs can be used to treat, prevent or ameliorate one or more symptoms of myocardial diseases or pathological myocardial or vascular conditions such as alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, myocardial fibrosis, endomyocardial fibrosis, Kearns Syndrome, myocardial reperfusion injury, myocarditis, cardiovascular or vascular diseases such as dissecting aneurysms, false aneurysms, infected aneurysms, ruptured aneurysms, aortic aneurysms, cerebral aneurysms, coronary aneurysms, heart aneurysms, and iliac aneurysms, angiodysplasia, angiomatosis, bacillary angiomatosis, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, thrombosis, erythromelalgia, hemorrhoids, hepatic veno-occlusive disease, hypertension, hypotension, idiopathic pulmonary fibrosis, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, venous insufficiency and arterial occlusive diseases such as arteriosclerosis, intermittent claudication, carotid stenosis, fibromuscular dysplasias, mesenteric vascular occlusion, Moyamoya disease retinal artery occlusion, thromboangiitis obliterans or atherosclerosis, any of which may be at an early stage or at a more advanced or late stage.

The F1Cs can also be used to treat, prevent or ameliorate one or more symptoms of cerebrovascular diseases, thrombosis, and/or conditions such as carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subarachnoid hemorrhage, cerebral infarction, cerebral ischemia (including transient), subclavian steal syndrome, periventricular leukomalacia, vascular headache, cluster headache, migraine, vertebrobasilar insufficiency, air embolisms, embolisms such as cholesterol embolisms, fat embolisms, pulmonary embolisms or amniotic fluid embolism, thromoboembolisms, thrombosis such as coronary thrombosis, hepatic vein thrombosis, retinal vein occlusion, carotid artery thrombosis, sinus thrombosis, Wallenberg's syndrome, and thrombophlebitis.

The F1Cs can also be used to treat, prevent or ameliorate one or more symptoms of vascular ischemia or myocardial ischemias, vasculitis and coronary diseases, including angina pectoris, coronary aneurysm, coronary arteriosclerosis, coronary thrombosis, coronary vasospasm, myocardial infarction and myocardial stunning, cerebral ischemia, ischemic colitis, compartment syndromes, anterior compartment syndrome, myocardial ischemia, reperfusion injuries, peripheral limb ischemia, aortitis, arteritis, Behcet's Syndrome, mucocutaneous lymph node syndrome, thromboangiitis obliterans, hypersensitivity vasculitis, Schoenlein-Henoch purpura, allergic cutaneous vasculitis, Wegener's granulomatosis or metabolic syndrome, which may be accompanied by one, two or more of obesity, insulin resistance, dyslipidemia, hypertension or other related symptoms or conditions.

Exemplary symptoms that the use of the F1Cs can ameliorate include one or more of pain such as arm, jaw or chest pain, edema or swelling, high blood pressure, shortness of breath or dyspnea, e.g., on exertion or while prone, fatigue or malaise and low cardiac injection fraction. In treating a cardiovascular condition in a subject or in improving one or more symptoms thereof, the F1Cs may accomplish one or more of increasing cardiac ejection volume or fraction, decreasing levels of IL-6, decreasing levels of C reactive protein, fibrinogen, cardiac creatinine kinase, increasing fatty acid metabolism or utilization by cardiac tissue, increasing carnityl palmitoyl fatty acid transferase or other cardiac metabolic enzymes, activating potassium dependent calcium channels, vasodilating or enhancing oxygen delivery to ischemic tissues or decreasing levels of scarring or plaque formation that occurs, e.g., after vascular damage. Symptoms associated with a cardiovascular condition such as ischemia that can be ameliorated also include acidosis, expression of one or more immediate early genes in, e.g., glial cells, vascular smooth muscle cells or endothelial cells, neuronal membrane depolarization and increased neuronal extracellular calcium and glutamate concentration. Other biological effects associated with treatment using a F1C may also be monitored, e.g., and increase or decrease of a cell surface antigen, a cytokine or an interleukin as disclosed herein.

Useful biological effects of the F1Cs in cardiovascular indications such as myocardial ischemias also include preventing or reducing heart or vascular cell death and subsequent fibrosis. These effects are associated with a decreased oxidative capacity of heart cells or myocytes, which is associated with a decreased capacity of the cells to metabolize fatty acids efficiently. The compounds enhance fatty acid metabolism and ameliorate the deleterious effects of a limited oxidative capacity.

The F1Cs also can limit inflammation or cell injury that is associated with ischemia or oxygen reperfusion after ischemia. Ischemia, which is a detrimental decrease in oxygenated blood delivery to affected cells or tissues, may arise from a cardiovascular condition or event such as an infarction, or from thermal injury or burns. Ischemia may also arise from accidental or surgical trauma. Reperfusion after cells have become hypoxic for a sufficient period of time can lead to tissue or cell injury that varies from slight to lethal. The compounds can reduce cell or tissue injury or death associated with ischemia and reperfusion, by, e.g., reducing inflammation or the level of a molecule associated with inflammation. Thus, levels of a proinflammatory cytokine or molecule such as leukotriene B4, platelet activating factor or levels of extracellular P-selectin may result from administration of a F1C to a subject who may experience reperfusion injury. Thus, the compounds can reduce injury or death of, e.g., neuron, cardiac, vascular endothelium, myocardial, pulmonary, hepatic or renal cells or tissues. Without wishing to be bound by any theory, the compounds may act in part by reducing one or more of neutrophil activation, platelet activation, platelet aggregation, endothelial cell activation and neutrophil adherence or adhesion to endothelial cells in these conditions.

The F1Cs are useful to treat autoimmune or metabolic conditions or disorders, or their symptoms, in subjects such as mammals or humans, that relate to impaired insulin synthesis or use or that relate to abnormal or pathological lipid or cholesterol metabolism or levels. Such conditions and symptoms include polycystic ovarian syndrome, Type 1 diabetes (including Immune-Mediated Diabetes Mellitus and Idiopathic Diabetes Mellitus), Type 2 diabetes (including forms with (1) predominant or profound insulin resistance, (2) predominant insulin deficiency and some insulin resistance, (3) forms intermediate between these), obesity, hyperglycemia and dyslipidemia, unwanted hyperlipidemia conditions such as hypertriglyceridemia and hypercholesterolemias such as hyper-LDL cholesterolemia, (4) unwanted hypolipidemias, e.g., hypo-HDL cholesterolemia or low HDL cholesterol levels and (5) angina pectoris. In diabetes, the compounds are useful to (1) enhance β-cell function in the islets of Langerhans (e.g., increase insulin secretion), (2) reduce the rate of islet cell damage, (3) increase insulin receptor levels or activity to increase cell sensitivity to insulin and/or (4) modulate glucocorticoid receptor activity to decrease insulin resistance in cells that are insulin resistant. The compounds are thus useful to treat, prevent, ameliorate or slow the progression of a metabolic or cardiovascular condition such as diabetes or hyperglycemia, or a related symptom or condition such as a dyslipidemia in a subject such as a human or a mammal.

Beneficial effects that can the F1Cs can exert on such related symptoms or conditions include improved glucose tolerance, improved glucose utilization, decreased severity or slowed progression of vascular disease (e.g., microvascular or macrovascular disease, including nephropathy, neuropathy, retinopathy, hypertension, cerebrovascular disease and coronary heart disease) or a decreased severity or slowed progression of atherosclerosis, an arteriosclerosis condition (e.g., coronary arteriosclerosis, hyperplastic arteriosclerosis, peripheral arteriosclerosis or hypertensive arteriosclerosis), decreased severity or slowed progression of diabetic osteoarthropathy, skin lesions, rhabdomyolysis, ketosis, detectably decreased generation of islet cell autoantibodies, decreased levels or activity of inflammatory macrophages (foam cells) in atherosclerotic plaques, or detectably decreased expression or levels of one or more of human (or mammalian) angiopoietin-like 3 gene product, apolipoprotein C-1, inducible or constitutive nitric oxide synthase, e.g., in endothelial cells, macrophages or the like, pyruvate dehydrogenase kinase 4, carboxyl ester lipase, cholesteryl ester transfer protein, endothelial lipase, vascular wall lipoprotein lipase, antilipoprotein lipase autoantibodies, triglyceride-rich lipoproteins, LDL cholesterol, C-reactive protein, high sensitivity C-reactive protein, fibrinogen, plasma homocysteine, VCAM-1, IL-1 (e.g., IL-1β), IL-6, a TNF (e.g., TNFα), AP-1, NF-κB, and IFN-γ. In these any of these diseases or conditions, the F1Cs can also modulate, e.g., detectably increase, the activity or level of one, two or more of human (or mammalian) LOX-1, apolipoprotein A-1, apolipoprotein A-2, LPDL lipase, hormone sensitive lipase, paraoxonase, brain natriuretic peptide, a brain natriuretic peptide receptor, e.g., Npr1 or Npr3, hepatic lipase, LDL receptor, HDL apoliporpotein E, HDL apoliporpotein J, HDL cholesterol, VLDL receptor, ATP-binding cassette transporter 1, leukemia inhibitory factor, CD36, LXRα, LXRβ, CARβ, RXR, PPARα, PPARβ, PPARγ or a lipoprotein lipase, e.g., marophage lipoprotein lipase. As used herein, obesity includes a human with a body mass index of at least about 25, 26, 27, 28, 29, 30, 31, 32, 33, 34, 35, 36 or greater. Obese humans that are treated with a F1C may have one or more of the conditions described here.

The F1Cs are useful in treating insulin resistance and associated symptoms and conditions. Insulin resistance is typically observed as a diminished ability of insulin to exert its biological action across a broad range of concentrations. This leads to less than the expected biologic effect for a given level of insulin. Insulin resistant subjects or human have a diminished ability to properly metabolize glucose or fatty acids and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, hypertension, obesity, atherosclerosis and a variety of other disorders. Insulin resistant individuals can progress to a diabetic state. The compounds can also be used in the treatment or amelioration of one or more condition associated with insulin resistance or glucose intolerance including an increase in plasma triglycerides and a decrease in high-density lipoprotein cholesterol, high blood pressure, hyperuricemia, smaller denser low-density lipoprotein particles, and higher circulating levels of plasminogen activator inhibitor-1. Such diseases and symptoms have been described, see, e.g., G. M. Reaven, *J. Basic Clin. Phys. Pharm.* 1998, 9: 387-406, G. M. Reaven, *Physiol. Rev.* 1995, 75: 473-486 and J. Flier, *J. Ann. Rev. Med.* 1983, 34:145-60.

The compounds can thus be used in diabetes, obesity, hyperlipidemia or hypercholesterolemia conditions to reduce body fat mass, increase muscle mass or to lower one or more of serum or blood low density lipoprotein, triglyceride, cholesterol, apolipoprotein B, free fatty acid or very low density lipoprotein compared to a subject that would otherwise be considered normal for one or more of these characteristics. These beneficial effects are typically obtained with little or no effect on serum or blood high density lipoprotein levels. The F1Cs are useful to reduce or slow the rate of myocardial tissue or myocyte damage, e.g., fibrosis, or to enhance cardiac fatty acid metabolism in conditions, such as inflammation, where fatty acid metabolism is depressed or decreased. Elevated cholesterol levels are often associated with a number of other disease states, including coronary artery disease, angina pectoris, carotid artery disease, strokes, cerebral arteriosclerosis, and xanthoma, which the F1Cs can ameliorate or slow the progression or severity of. Abnormal lipid and cholesterol conditions that can be treated include exogenous hypertriglyceridemia, familial hypercholesterolemia, polygenic hypercholesterolemia, biliary cirrhosis, familial combined hyperlipidemia, dysbetalipoproteinemia, endogenous hypertriglyceridemia, mixed hypertriglyceridemia and hyperlipidemia or hypertriglycidemia secondary to alcohol consumption, diabetic lipemia, nephrosis or drug treatments, e.g., corticosteroid, estrogen, colestipol, cholestyramine or retinoid treatments. Dosages, routes of administration and dosing protocols for the F1Cs are essentially as described herein. Where the condition is chronic, the F1Cs will generally be administered to a subject such as a human for a relatively long time period, e.g., for about 3 months to about 10 years or more. Dosages, routes of administration and dosing protocols for the F1Cs are essentially as described herein. Dosing of the compound can be daily or intermittent using a dosing protocol using dosages as described herein, e.g., about 0.01 to about 20 mg/kg of a F1C administered to a subject once or twice per day daily or intermittently. The use of the F1Cs can be combined with one, two or more other suitable treatments, e.g., treatment for cessation of smoking, diet control, e.g., caloric restriction or reduced fat intake, or treatment with fibrates, non-steroidal anti-inflammatory drugs, angiotensin-converting enzyme inhibitors or HMG-CoA reductase inhibitors such as aspirin, clofibrate, fenofibrate, ciprofibrate, gemfibrozil, Simvastatin™, Pravastatin™, Mevastatin™ or Lovastatin™.

The use of any F1C or species in any genus of F1Cs disclosed herein to treat, prevent or ameliorate any of these cardiovascular or metabolic disorders or symptoms will generally use one or more of the routes of administration, dosages and dosing protocols as disclosed herein. Thus, in exemplary embodiments, about 0.5 to about 100 mg/kg or about 1 to about 25 mg/kg, of the F1C will be administered per day by an oral, buccal, sublingual or parenteral route. Such administration can be, e.g., daily for about 5 to about 60 days in acute conditions or it can be intermittent for about 3 months to about 2 years or more for chronic conditions. Alternatively, intermittent dosing can be used essentially as described herein for acute cardiovascular conditions. In some embodiments, for conditions such as ischemia or trauma, administration of the F1C is provided before or as soon after the ischemic or traumatic event as possible, e.g., within about 6 hours of an ischemic or traumatic event or about 12-24 hours before an anticipated ischemic or traumatic event. In other embodiments, administration of the F1C can be delayed for, e.g., about 6, 7, 8, 9, 10, 11, 12, 13, 14, 15, 16, 18, 19, 20, 21, 24, 28, 32, 36, 40, 48 or more hours after an ischemic or traumatic event has occurred and a course of daily or intermittent dosing is initiated at one of these times, or in a range between any of these times after the event. Thus, administration of the F1C can begin at about 10-14 hours, at about 11-13 hours or at about 8-16 hours after the ischemic or traumatic event.

In another aspect of the invention, the F1Cs can be used to prevent, treat or to reduce the severity of vascular or microvascular occlusions in human sickle cell diseases (SCD). SCD is heterogenous and includes subgroups with high transcranial velocities, which is a group with an increased risk of infarctive stroke or cereberal thrombosis. SCD types also include sickle cell-$\beta^+$ thalassemia, sickle cell-$\beta^\circ$ thalassemia, sickle cell-$\delta\beta^\circ$ thalassemia and sickle cell-HPFH (hereditary of persistent fetal hemoglobin). Another subgroup of SCD patients is characterized by the presence of a *Plasmodium* parasite infection. SCD is usually accompanied by acute vaso-occlusive episodes such as microvascular occlusions, ischemia and infarctions that arise from adhesion of sickle cells and other blood cell types, e.g., platelets or leukocytes, to vascular endothelial cells. Reduced sickle cell adhesion in response to treatment with a F1C and related responses is facilitated at least in part by decreased production or activity of one or more biological response mediators such as one, two, three or more of thrombospondin, von Willebrand factor, epinephrine, C reactive protein, cAMP, basal cell adhesion molecule/Lutheran (BCAM/Lu), P-selectin, L-selectin, E-selectin, VCAM-1, ICAM-1, fibronectin, annexin V, placenta growth factor, superoxide, CD11a, CD11b, CD11c, CD15, CD18, CD31, CD36, TNF$\alpha$, NF-$\kappa$B, IL-1$\beta$ or IL-6 by endothelial cells or one or more immune cell types as described herein. In treating sickle cell disease, the F1Cs will also increase the activity or levels of one, two or more desired response mediators including fetal hemoglobin, erythropoietin, heme oxygenase, nitric oxide, PPAR$\alpha$, PPAR$\gamma$ or GM-CSF. The F1Cs will thus ameliorate one or more symptoms of sickle cell disease such as anemia, stroke, pain, e.g., chest or abdominal pain, skin ulcers, dyspnea, organ damage, retinopathy or the level of infected red cells in *Plasmodium*-infected subjects. Treatment of acute SCD episodes or of chronic SCD with F1Cs can be combined with other suitable therapies, e.g., inhaled nitric oxide, hydroxyurea treatment, anti-adhesion molecule antibody treatment or analgesic use such as morphine, oxycodone, or codeine. The F1Cs can also be used to reduce cellular damage from reactive oxygen species associated with hydroxyurea treatment, since the F1Cs will enhance cellular antioxidant capacity.

As is apparent from the foregoing, the use of the F1C is optionally combined with one or more additional therapies for cardiovascular or related disorders, e.g., insulin therapy, vascular surgery, cardiac surgery, angioplasty, or treatment with andrenergic blockers, coronary vasodilators, calcium channel blockers, nitrates, angiotensin converting enzyme inhibitors, anti-hypertensives, anti-inflammatory agents, diuretics, anti-arrhythmia agents, thrombolytic agents, enzyme inhibitors such as hydroxymethylglutaryl CoA reductase inhibitors or xanthine oxidase inhibitors. Exemplary hydroxymethylglutaryl CoA reductase inhibitors include statins such as mevastatin, lovastatin, pravastatin, simvastatin or compounds described in U.S. Pat. No. 4,346,227, 4,448,979, 4,739,073, 5,169,857, 5,006,530 or 5401746. Other therapies that can be applied include diet control, dietary calorie restriction or diet modification for subjects who are or who are susceptible to developing a cardiovascular or related condition such as pulmonary hypertension, diabetes, a dyslipidemia or obesity, e.g., humans having a body mass index of 27, 28, 29, 30, 31, 32, 33, 34, 35, 36 or greater. Diet modifications include limiting or restricting salt, alcohol, caffeine, cigarette, drugs, e.g., opiate, hallucinogen, sedative, narcotic or amphetamine, sugar, refined sugar and/ or fat or cholesterol intake, use or abuse. Additional therapies include treatment with one or more of digoxin, nitroglycerin, doxazosin mesylate, nifedipine, enalapril maleate, indomethicin, tissue plasminogin activator, urokinase, acetylsalicylic acid or the like. Any of such additional therapies would be used essentially according to standard protocols and such therapies would precede, be concurrent with or follow treatment with a F1C. In some embodiments, such additional therapies will be administered at the same time that a F1C is being used or within about 1 day to about 16 weeks before or after at least one round of treatment with the F1C is completed. Other exemplary therapeutic agents and their use have been described in detail, see, e.g., *Physicians Desk Reference* 54th edition, 2000, pages 303-3251, ISBN 1-56363-330-2, Medical Economics Co., Inc., Montvale, N.J.; *Harrison's Principles of Internal Medicine,* 15th edition, 2001, E. Braunwald, et al., editors, McGraw-Hill, New York, N.Y., ISBN 0-07-007272-8, especially chapters 231, 241-248 and 258-265 at pages 1309-1318, 1377-1442 and 1491-1526. One or more of these exemplary agents or treatments can be used in combination with a F1C to treat any of the appropriate cardiovascular and related disorders described herein and in the references cited herein.

Respiratory and pulmonary conditions. F1Cs can be used to treat, ameliorate, prevent or slow the progression of a number of pulmonary conditions or their symptoms such as 1, 2, 3 or more of cystic fibrosis, bronchiectasis, cor pulmonale, pneumonia, lung abscess, acute bronchitis, chronic bronchitis, chronic obstructive pulmonary diseases, emphysema, pneumonitis, e.g., hypersensitivity pneumonitis or pneumonitis associated with radiation exposure, alveolar lung diseases and interstitial lung diseases, e.g., associated with asbestos, fumes or gas exposure, aspiration pneumonia, pulmonary hemorrhage syndromes, amyloidosis, connective tissue diseases, systemic sclerosis, ankylosing spondylitis, allergic granulomatosis, granulomatous vasculitides, asthma, e.g., acute asthma, chronic asthma, atopic asthma, allergic asthma or idiosyncratic asthma, cystic fibrosis and associated conditions, e.g., allergic bronchopulmonary aspergillosis, chronic sinusitis, pancreatic insufficiency, inflammation or *Haemophilus influenzae, S. aureus* or *Pseudomonas aeruginosa* infection. In some of these conditions where inflammation plays a role in the pathology of the condition, the F1Cs can ameliorate or slow the progression of the condition by reducing damage from inflammation. In other cases, the F1Cs act to limit pathogen replication or pathogen-associated lung tissue damage.

For these conditions, the severity of the disease or the type or severity of associated symptoms can vary. For example, in humans having pediatric, e.g., infants or children of about 1 month or about 4 months of age to about 16 or 17 years of age, or adult cystic fibrosis ("CF"), the disease may be associated with the presence of one or more symptoms, syndromes, genetic mutations or the like. Symptoms or syndromes that can be observed in human CF patients include 1, 2, 3, 4 or more of *Staphylococcus* (e.g., *S. aureus*), *Haemophilus influenzae, Pseudomonas* or *Burkholderia* respiratory tract or lung infection or propensity to develop detectable infection or colonization, coughing, wheezing, cyanosis, bronchiolitis, bronchospasm, pneumothorax, hemoptysis, pancreatic exocrine insufficiency, bronchiectatic lung disease, atelectasis-consolidation, pulmonary edema, increased lung vascular hydrostatic pressure, increased lung vascular permeability, sinusitis, respiratory insufficiency, bronchial wall or interlobular septa thickening, reduction of forced expiratory volume in 1 second, dyspnea, impaired male fertility, elevated sweat chloride (e.g., >60 mmol/L), mucous plugging, tree-in-bud sign, mosaic perfusion pattern, glucose intolerance or abnormal elevation of one or more of IL-4, IL-8, RANTES, neutrophil elastase, eosinophils, macrophages, neutrophils, eosinophil cationic protein or cysteinyl leukotrienes. Any of these symptoms or syndromes can be acute, intermittent or chronic and/or mild, moderate or severe. Relevant mutations include, e.g., a homozygous or heterozygous, dominant or recessive deletion, insertion and/or point mutation in (1) the cationic trypsinogen gene or (2) the cystic fibrosis transmembrane conductance regulator (CFTR) gene, such as one, two or more of, a CFTR F508del deletion mutation or CFTR lacking phe508, 3272-26A>G/F508del, 3659delC, 394delTT, S1455X or Δ26, I1234V, 2183AA>G, 2043delG, 548A>T, I148T, R334W, S1196X, 4041C>G, 1161delC, 1756G>T or 3120+1G>A mutation.

The use of a F1C to treat, ameliorate or slow the progression of conditions such as CF can be optionally combined with other suitable treatments. For CF, this includes, e.g., one, two or more of oral or aerosol corticosteroid treatment, ibuprofen treatment, DNAse or IL-10 treatment, diet control, e.g., vitamin E supplementation, vaccination against pathogens, e.g., *Haemophilus influenzae,* or chest physical therapy, e.g., chest drainage or percussion.

Humans or other subjects who have one or more of these conditions can be treated with other suitable therapeutics. Pulmonary conditions that can be treated with the F1Cs and other therapeutic methods and agents that can be used in conjunction with the F1Cs have been described in detail, see, e.g., *Harrison's Principles of Internal Medicine,* 15th edition, 2001, E. Braunwald, et al., editors, McGraw-Hill, New York, N.Y., ISBN 0-07-007272-8, especially chapters 252-265 at pages 1456-1526; Physicians Desk Reference 54th edition, 2000, pages 303-3251, ISBN 1-56363-330-2, Medical Economics Co., Inc., Montvale, N.J. One or more of these exemplary agents or treatments can be used in combination with a F1C to treat any of the appropriate cardiovascular and related disorders described herein and in the references cited herein.

Treatment of any of these respiratory and pulmonary conditions using a F1C is accomplished using the treatment regimens described herein. For chronic conditions, intermittent dosing of the F1C can be used to reduce the frequency of treatment. Intermittent dosing protocols are as described herein.

Applications in autoimmunity, allergy, inflammation and related conditions. As mentioned above, the F1Cs may be used to treat, prevent or slow the progression of one or more autoimmune allergic or inflammatory diseases, disorders, or conditions, or to ameliorate one or more symptoms thereof in a subject. These diseases and conditions include Addison's Disease, autoimmune hemolytic anemia, autoimmune sensorineural hearing loss, antiphospholipid syndrome, acute or chronic rheumatoid arthritis and other synovial disorders, an osteoarthritis including post-traumatic osteoarthritis and hypertrophic pulmonary osteoarthropathy, psoriatic arthritis, polyarthritis, epichondylitis, type I diabetes, type II diabetes, rheumatic carditis, bursitis, ankylosing spondylitis, multiple sclerosis, a dermatitis such as contact dermatitis, atopic dermatitis, exfoliative dermatitis or seborrheic dermatitis, mycosis fungoides, allergic encephalomyelitis, autoimmune glomerulonephritis, Goodpasture's Syndrome, Graves' Disease, Hashimoto's Thyroiditis, multiple sclerosis, myasthenia gravis, neuritis, bullous pemphigoid, pemphigus, polyendocrinopathies, purpura, Reiter's Disease, autoimmune thyroiditis, systemic lupus erythematosus, scleroderma, fibromyalgia, chronic fatigue syndrome, autoimmune pulmonary inflammation, Guillain-Barre Syndrome, type 1 or insulin dependent diabetes mellitus, autoimmune inflammatory eye disease, hepatitis C virus associated autoimmunity, postinfectious autoimmunity associated with, e.g., virus or bacterial infection such as a parvovirus such as human parvovirus B19 or with rubella virus, autoimmune skin and muscle conditions such as pemphigus vulgaris, pemphigus foliaceus, systemic dermatomyositis or polymyositis or another inflammatory myopathy, myocarditis, asthma such as allergic asthma, allergic encephalomyelitis, allergic rhinitis, a vasculitis condition such as polyarteritis nodosa, giant cell arteritis or systemic necrotizing vasculitis, chronic and an acute or chronic inflammation condition such as chronic prostatitis, granulomatous prostatitis and malacoplakia, ischemia-reperfusion injury, endotoxin exposure, complement-mediated hyperacute rejection, nephritis, cytokine or chemokine induced lung injury, cachexia, sarcoidosis, inflammatory bowel disease, regional enteritis, ulcerative colitis, Crohn's disease, inflammatory bowel disease or inflammation associated with an infection, e.g., septic shock, sepsis, or systemic inflammatory response syndrome. Any of these diseases or conditions or their symptoms may be acute, chronic, mild, moderate, severe, stable or progressing before, during or after the time administration of the F1C to a subject such as a human, is initiated. In general, a detectable improvement is observed in the subject within a period of about 3 days to about 12 months after initiation of a dosing protocol, e.g., the severity of the disease or condition will detectably decrease, the rate of progression will detectably slow or the severity of a symptom(s) will detectably decrease.

As used herein, acute inflammation conditions are characterized as an inflammation that typically has a fairly rapid onset, quickly becomes moderate or severe and usually lasts for only a few days or for a few weeks. Chronic inflammation conditions as used herein are characterized as an inflammation that may begin with a relatively rapid onset or in a slow, or even unnoticed manner, tends to persist for at least several weeks, e.g., about 3-6 weeks, months, or years and may have a vague or indefinite termination. Chronic inflammation may result when the injuring agent (or products resulting from its presence) persists in the lesion, and the subject's tissues respond in a manner (or to a degree) that is not sufficient to overcome completely the continuing effects of the injuring agent. Other exemplary conditions are described in, e.g., *Textbook of Autoimmune Diseases*, R. G. Lahita, editor, Lippincott Williams & Wikins, Philadelphia, Pa., 2000, ISBN 0-7817-1505-9, pages 175-851 and *Rheumatology*, $2^{nd}$ edition, J. H. Klippel et al., editors, 1998, ISBN 0-7234-2405-5, volume 1, sections 1-5 and volume 2, sections 6-8, Mosby International, London, UK.

A F1C can be used to inhibit or ameliorate one or more inappropriate immune responses or their symptoms in autoimmunity, inflammation, allergy or related conditions. The effects of the F1Cs include detectably ameliorating one or more of (1) the proliferation, differentiation or chemotaxis of T cells, (2) reducing unwanted cytotoxic T cell responses, (3) reducing unwanted autoantibody or other antibody synthesis, e.g., an unwanted IgA, IgE, IgG or IgM, in allergy, asthma or another autoimmune or inflammation condition, (4) inhibiting the development, proliferation or unwanted activity of autoreactive T or B cells, (5) altering the expression of one or more cytokines, interleukins or cell surface antigens, e.g., a cytokine, interleukin or cell surface antigen described herein (decreasing IL-8 in an autoimmune condition, decreasing the level of acute phase proteins such as C reactive protein or fibrinogen in inflammation conditions, (6) decreasing eosinophilia in allergy conditions, (7) detectably decreasing the level or activity of one or more of ICAM-1, IL-1α, IL-1β, TNFα, IL-6 or IL-8 in, e.g., inflammation conditions or in autoimmune conditions such as an arthritis or a myocarditis condition such as osteoarthritis, rheumatoid arthritis, toxic myocarditis, indurative myocarditis or idiopathic myocarditis, (8) decreasing the level or biological activity of one or more of anti-islet antibody, TNF, IFN-γ, IL-1, an arthritis symptom(s), nephritis, skin rash, photosensitivity, headache frequency or pain, migraine frequency or pain, abdominal pain, nausea or anti-DNA antibodies in, e.g., insulin dependent diabetes mellitus or an autoimmune or inflammation condition such as systemic lupus erythematosus, rheumatoid arthritis or Crohn's disease, (9) reducing induction of arachidonic acid metabolism or reducing eicosanoid metabolites such as thromboxanes or prostaglandins in, e.g., inflammation, asthma or allergy, (10) reducing IL-4, IL-8 or IL-10 synthesis, levels or activity in, e.g., allergy or inflammation such as idiopathic pulmonary fibrosis or allergic asthma or (11) reducing or interfering with neutrophil chemotaxis by, e.g., reducing thioredoxin release from affected cells in conditions such as cancer, infections, inflammation or autoimmunity.

Exemplary symptoms that the use of the F1Cs can ameliorate in these autoimmune, inflammatory and allergy conditions include one or more of pain such as shoulder, hip, joint, abdominal or spine pain, joint stiffness or gelling, bursitis, tendonitis, edema or swelling, fatigue or malaise, headache, dyspnea, skin rash, fever, night sweats, anorexia, weight loss, skin or intestine ulceration, muscle weakness, pericarditis, coronary occlusion, neuropathy and diarrhea. In treating one of these conditions in a subject or in improving one or more symptoms thereof, the F1Cs may accomplish one or more of decreasing levels of one or more of IL-1, IL-4, IL-6 or TNFα, decreasing levels of C reactive protein, fibrinogen or creatinine kinase. Other biological effects associated with treatment using a F1C may also be monitored or observed, e.g., an increase or decrease of a cell surface antigen, a cytokine or an interleukin as disclosed herein.

In another aspect of the invention, the F1Cs can be used to treat or to reduce the severity of chronic allergies or atopic diseases such as allergic rhinitis, psoriasis, eczema, gastrointestinal allergies, atopic dermatitis conditions, allergic asthma, food allergies and hay fever. These conditions are typically characterized by the presence of elevated levels of allergen specific antibodies of the IgE isotype. In treating or ameliorating these conditions, the F1Cs reduce the generation of IgE by "isotype switching", which is increasing allergen-specific IgA production and/or decreasing IgE production from preexisting allergen-primed cells. Allergen specific IgG may also be increased from new cells that might otherwise have responded to allergen exposure by generating unwanted IgE.

The IgA and IgG are allergen specific, which will enhance clearance of allergen from mucosa or other tissue and reduction of chronic or late phase allergic responses. The F1C can thus also be used to increase the biological clearance of allergens from tissue and mucosa. Reduced generation of the levels or activity of IgE by B cells in response to treatment with a F1C and related responses is facilitated at least in part by decreased production of one or more biological response mediators, e.g., cytokines or response mediators such as protein kinase A inhibitors, substance P neuropeptide, thymus- and activation-regulated chemokine, e.g., by airway smooth muscle cells, proteinase activated receptor-2 by neurons, intracellular signal-transducing protein-6 (STAT6), Janus kinase 1, Janus kinase 6, CD40, CD86 and/or NF-kB by B cells, CD154 in T cells, and suppressor of cytokine signalling-3, phosphodiesterase 4, TNF-$\alpha$, MCP-1, RANTES, CXCL10, CXCL8 (IL-8), prostaglandin E2 receptor, IL-1$\beta$, IL-4, IL-5, IL-6, IL-9, IL-10, IL-13, and IL-23, by one or more other cell types such as immune cells as described herein, airway smooth muscle cells, mucosal cells or keratinocytes. In these treatments, the F1Cs will also increase the activity or levels of one or more desired response mediators including soluble CD23, cathepsin E, epidermal growth factor receptor, IFN$\gamma$, IL-2, IL-12 or IL-18. In treating these conditions, Treatment can be combined with other suitable therapies, e.g., corticosteroids such as fluticasone propionate. The F1Cs can also be used to reduce rebound phenomena following withdrawal of corticosteroid therapies, since the F1Cs have an anti-inflammatory effect without having immunosuppressive side effects. Use of the F1Cs to generate any of these biological responses or treatments can be by daily or intermittent administration of the F1C to the subject.

In a related embodiment, the F1Cs are used in allergen vaccination protocols to enhance levels or activity of allergen specific IgA or IgG, which contributes to reducing IgE responses to allergen exposure. Such protocols are used to decrease a subject's sensitivity to allergen exposure. Typically such allergies are chronic or atopic. In these applications, the vaccination protocol typically uses the allergen(s) or an active fragment(s) of the allergen that is associated with the allergy or atopic condition. In these methods, a F1C is administered to a subject who has an IgE mediated allergy or atopy condition in conjunction with administration of the allergen. Allergens typically used include dermatophagoides, house dust, cat allergen and pollen. In any of these methods isotype switching or vaccination methods, the F1C is typically administered as described herein, e.g., by administering the F1C about 1, 2, 3, 4, 5, 6, 7, 8, or more days before the allergen is administered to the subject. The subject may receive about 1-20 mg/kg of a F1C at 2, 3 and 4 days before the allergen is administered or injected. The F1C treatment increases allergen specific IgA or IgG responses or levels relative to untreated controls. The use of F1C with allergens will reduce the total number of anti-allergic vaccinations that are needed, increase the quality or length of an effective response and/or increase the proportion of subjects in which allergy shots are effective. An effective response is seen in about 55%, 60%, 65%, 70%, 75%, 80% or more of vaccinated patients who also receive the F1C compared to about 40-50% of vaccinated patients who do not receive the F1C.

In treating inflammation or any condition described herein where inflammation contributes to the condition, the F1Cs may detectably modulate, e.g., decrease or increase, the expression or level or activity of one or more biomolecules associated with the prevention, establishment, maintenance or progression of the inflammation condition. Such biomolecules include one or more of carcinoembryonic antigen, prostate specific antigen, her2/neu, Bcl-XL, bcl-2, p53, IL-1$\alpha$, IL-1, IL-6, or TNF$\alpha$, GATA-3, COX-2, NF$\kappa$B, IkB, an IkB kinase, e.g., IkB kinase-$\alpha$, IkB kinase-$\beta$ or IkB kinase-$\gamma$, NFAT, a ras protein such as H-ras or K-ras, cyclin D, cyclin E xanthine oxidase, or their isoforms, orthologs, homologs or mutant forms, which may have either reduced or enhanced biological activity(ies), and which may be detectably decreased. Biomolecules that can be detectably increased include IL-2, IFN$\gamma$, IL-12, T-bet, 06-methylguanine-DNA-methyltransferase, calcineurin, calmodulin, a superoxide dismutase (e.g., Mn, Zn or Cu), a tumor suppressor protein such as the retinoblastoma protein (Rb) or CDKN2A (p16), BRCA1, BRCA2, MeCP2, MBD2, PTEN, NBR1, NBR2 or the isoforms, orthologs, homologs or mutant forms, which may have either attenuated or enhanced biological activity(ies), of any of these molecules. One or more of these biomolecules may be modulated in any inflammation condition described herein.

The use of any F1C or species in any genus of F1Cs disclosed herein to treat, prevent or ameliorate any of these autoimmune, inflammatory or allergy conditions or symptoms will generally use one or more of the routes of administration, dosages and dosing protocols as disclosed herein. Thus, in exemplary embodiments, about 0.5 to about 100 mg/kg or about 1 mg/kg to about 15 mg/kg, of the F1C will be administered per day by, e.g., an oral, buccal, sublingual, topical or parenteral route. Such administration can be, e.g., daily for about 5 to about 60 days in acute conditions or it can be intermittent for about 3 months to about 2 years or more for chronic conditions. Alternatively, intermittent dosing can be used essentially as described herein for acute autoimmune, inflammatory and allergy conditions.

In another aspect of the invention, the F1Cs can be used to treat or to reduce the severity of chronic allergies or atopic diseases such as allergic rhinitis, psoriasis, eczema, gastrointestinal allergies, atopic dermatitis conditions, allergic asthma, food allergies and hay fever. These conditions are typically characterized by the presence of elevated levels of the IgE isotype and of B cells that generate IgE. In treating or ameliorating these conditions, the F1Cs reduce the generation of IgE by facilitating an isotype switch from B cells that produce IgE to cells that produce antigen-specific IgA and/or IgG4. The IgA and IgG4 are allergen specific, which will facilitate clearance of allergen from mucosa or other tissue and reduction of chronic or late phase allergic responses. The F1c can thus be used to increase the biological clearance of allergens from tissue. Reduced generation of the levels or activity of IgE by B cells in response to treatment with a F1C and related responses is facilitated at least in part by decreased production of one or more biological response mediators, e.g., cytokines or response mediators such as protein kinase A inhibitors, substance P neuropeptide, thymus- and activation-regulated chemokine, e.g., by airway smooth muscle cells, proteinase activated receptor-2 by neurons, intracellular signal-transducing protein-6 (STAT6), Janus kinase 1, Janus kinase 6, CD40, CD86 and/or NF-κB by B cells, CD154 in T cells, and suppressor of cytokine signalling-3, phosphodiesterase 4, TNF-α, MCP-1, RANTES, CXCL10, CXCL8 (IL-8), prostaglandin $E_2$ receptor, IL-1β, IL-4, IL-5, IL-6, IL-10, IL-13 and IL-18 by one or more other cell types such as immune cells as described herein, airway smooth muscle cells, mucosal cells or keratinocytes. In these treatments, the F1Cs will also increase the activity or levels of one or more desired response mediators including cathepsin E, epidermal growth factor receptor, IFNγ, IL-2, IL-12. In treating these conditions, Treatment can be combined with other suitable therapies, e.g., corticosteroids such as fluticasone propionate. The F1Cs can also be used to reduce rebound phenomena following withdrawal of corticosteroid therapies, since the F1Cs have an anti-inflammatory effect without having immunosuppressive side-effects. Use of the F1Cs to effect any of these biological responses or treatments can be by daily or intermittent administration of the F1C to the subject.

In a related embodiment, the F1Cs are used to enhance isotype switching from IgE to IgG in these chronic allergies or atopic diseases in vaccination protocols that use the allergen(s) or an active fragment(s) of the allergen that is associated with the allergy or atopic condition. In these methods, a F1C is administered to a subject who has an elevated IgE allergy or atopy condition in conjunction with administration of the allergen. The subject's response to the allergen is an enhanced proportion of B cells that produce IgG compared to B cells that generate IgE. Allergens typically used include *dermatophagoides*, house dust, cat allergen and pollen. In these methods, the F1C is typically administered about 1, 2, 3, 4, 5, 6, 7, 8, or more days before the allergen is administered to the subject, e.g., the subject receives about 1-20 mg/kg of a F1C at 2, 3 and 4 days before the allergen is administered or injected. The F1C facilitates isotype switching to IgG. The use of F1C with allergens will reduce the total number of anti-allergic vaccinations that are needed, increase the quality or length of an effective response and/or increase the proportion of subjects in which allergy shots are effective, e.g., an effective response is seen in about 55%, 60%, 65%, 70%, 75%, 80% or more of vaccinated patients who also receive the F1C compared to about 40-50% of vaccinated patients who do not receive the F1C.

The F1Cs are suitable for enhancing immune responses in aging in subjects such as humans or primates. In humans at about 50 to 60 years of age and later, one or more aspects of immune responses will typically decrease by a detectable amount compared to typical immune responses at younger ages, e.g., at about 18-50 years of age. The F1Cs can be used on an intermittent basis or continuously in aged subjects. Intermittent administration of a F1C can occur as described herein, e.g., daily dosing or dosing every other day or every third day for about 1, 2, 3, 4, 5, 6, 7, 8 or 9 days, followed by about 2, 3, 4, 5, 6, 7, 8, 9 or 10 weeks of no dosing, optionally followed by about 1, 2, 3, 4, 5, 6, 7 or 8 days of daily dosing or dosing every other day or every third day and then followed by about 2, 3, 4, 5, 6, 7, 8, 9 or 10 weeks of no dosing. Such dosing cycles can be repeated indefinitely or as needed. Such treatments can be used prophylactically or therapeutically. In prophylaxis the F1C are administered, e.g., before or during influenza outbreaks, or in aged patients in hospitals or in aged patients in long term living or care facilities such as retirement communities or nursing homes. In therapeutic applications, the F1C are used to treat trauma, e.g., bone fractures or active infections. The F1C treatments in these embodiments will result in enhanced immune responses, including increased innate and specific responses to, e.g., infectious agents. These treatments will typically also have other beneficial effects including enhancing bone marrow production of blood cells or blood components such as neutrophils or improving levels of dysregulated immune response mediators, e.g., decreasing elevated cortisol, IL-6, IL-10, COX-2 or C reactive protein levels or increasing low IL-2 or IL-12 levels.

In related embodiments, the use of the F1C is optionally combined with one or more additional known or experimental therapies for an autoimmune, inflammatory or allergy disorder(s), e.g., one or more of surgery and treatment with a corticosteroid or glucocorticoid such as hydrocortisone, hydrocortisone acetate, fludrocortisone, prednisone, prednisolone, prednisolone acetate, methylprednisolone, dexamethasone, dexamethasone acetate or triamcinolone acetonide, leflunomide, an antibody, e.g., a human or humanized monoclonal antibody, that decreases the activity or level of C5 complement, TNFα or TNFα receptor, an antirheumatic drug such as methorexate, D-penicillamine, sodium aurothiomalate, sulfasalazine or hydroxychloroquine, immunosuppressive agents such as 6-thioguanylic acid, chlorambucil, cyclophosphamide or cyclosporin, a non-steroidal antiinflammatory agent such as celecoxib, ibuprofin, piroxicam or naproxin, an antihistamine such as loratidine or promethazine hydrochloride, an analgesic such as propoxyphene napsylate, acetaminophen or codeine or administration of vitamins (e.g., multivitamins, individual vitamins), antioxidants or other agents (e.g., vitamin E, folinic acid, carnitine, a C2-8 alkanoyl carnitine such as acetyl or propionyl L-carnitine) or nutritional supplements (e.g., liquid protein or carbohydrate preparations). Such therapies would be used essentially according to standard protocols and such they would precede, be concurrent with or follow treatment with a F1C. In some embodiments, such additional therapies will be administered at the same time that a F1C is being used or within about 1 day to about 16 weeks before or after at least one round of treatment with the F1C is completed. Other exemplary therapeutic agents and their use have been described in detail, see, e.g., *Physicians Desk Reference* 54th edition, 2000, pages 303-3267, ISBN 1-56363-330-2, Medical Economics Co., Inc., Montvale, N.J. One or more of these exemplary agents can be used in combination with a F1C to ameliorate, prevent or treat any of the appropriate autoimmune, inflammatory or allergy conditions or disorders described herein or any of their symptoms.

Where a natural or synthetic antiinflammatory glucocorticoid is used to treat one more of the conditions disclosed herein or wherein endogenous levels of glucocorticoid such as cortisol are elevated to an unwanted level in a subject, the use of a F1C will ameliorate unwanted side-effects of such glucocorticoid use or excess. Typically the F1C will be administered during, before and/or after glucocorticoid levels are elevated or during, before and/or after a therapeutic glucocorticoid is administered to the subject, e.g., within about 1, 2, 3, 4, 5, 6 or 7 days or within about 2, 3, 4, 5, 6, 7, 8, 9, 10, 11, 12, 14, 16, 20 or 24 weeks before or after glucocorticoid use or elevated glucocorticoid levels exist. Typically, the use of the F1C to counteract unwanted side-effects of therapeutic glucocorticoid use in these embodiments, will reduce or ameliorate the onset, severity or progression of one or more unwanted side-effects of glucocorticoid therapy such as a detectable immune suppression, an increased occurrence or incidence of infection, an undesirable alteration of mood (e.g., increased anxiety, depression or schizophrenia) or a detectable loss or alteration of memory.

Regeneration and wound healing. The F1Cs can be used to facilitate cell differentiation, proliferation or repair where regeneration of tissues is desired. The regeneration of tissues could be used to repair, replace, protect or limit the effects of tissue damaged by congenital defects, trauma (wounds, burns, incisions, or ulcers), age, disease (e.g. osteoporosis, osteoarthritis, periodontal disease, liver failure), surgery, including cosmetic plastic surgery, fibrosis, reperfusion injury, toxin exposure or systemic cytokine damage. Ulcers or skin lesions can arise from ionizing radiation exposure, cytotoxic chemotherapy or pressure, e.g., a pressure or decubitis ulcer or vascular insufficiency, e.g., associated with diabetes or vascular occlusion. Tissues for which regeneration may be enhanced include organs (e.g., pancreas, liver, lung, intestine, kidney, skin, endothelium, oral mucosa, gut or intestinal mucosa), muscle (e.g., smooth, skeletal or cardiac), vasculature (including vascular and lymphatics), central or peripheral nervous tissue, hematopoietic tissue, and skeletal tissue (e.g., bone, cartilage, tendon, and ligament). Decreased scarring or an increased rate or quality of healing may accompany these effects.

The F1Cs are thus useful to enhance healing or tissue repair in a subject having a bone fracture(s), e.g., a simple or compound skull, spine, hip, arm or leg bone fracture. Similarly, nerve or brain tissue treatment using a F1C allows treating, slowing the progression of, ameliorating or preventing diseases such as central and peripheral nervous system diseases, neuropathies, or mechanical and traumatic diseases, disorders, and/or conditions (e.g., spinal cord disorders, head trauma, cerebrovascular disease, and stoke). The compounds are useful to treat diseases associated with peripheral nerve injuries, peripheral neuropathy (e.g., resulting from chemotherapy, radiation exposure or therapy or other medical therapies), localized neuropathies, and central nervous system diseases such as Alzheimer's disease, Parkinson's disease, Huntington's disease and amyotrophic lateral sclerosis. The subjects undergoing treatment in these conditions may be elderly, e.g., a human at least about 55, 60, 65 or 70 years of age. Where the condition is acute, e.g., a bone fracture or a burn, the treatment may comprise administration of a F1C to the subject on a daily or intermittent basis for about 3 days to about 12 months, e.g., administration for about 2-12 weeks beginning after the subject sustains an injury.

An aspect of the F1Cs is their capacity to facilitate wound or trauma healing by increasing the proliferation or self-renewal of stem cells and pluripotent derivatives of stem cells and/or the rate of differentiation of stem cells or their pluripotent derivatives to mature cell types. Thus, the F1Cs can increase the numbers, rate of differentiation or activity of stem cells in, e.g., skin, central or nervous system tissue, blood vessels, heart tissue, lung, liver, pancreas, kidney, thymus, spleen, oral mucosa, intestine or bone marrow, some of which is discussed elsewhere herein. Increased numbers of mature cell types typically is observed beginning at about 2-28 days after treatment with a F1C is started, usually after about 2-21 days. Thus, the F1Cs can enhance the numbers, activities or differentiation of, e.g., crypt cells in intestinal mucosa, skin stem cells in the oral mucosa or cardiac precursor cells after damage to those cells or tissues. Such damage can arise, e.g., from trauma, infection, ionizing radiation exposure, toxin exposure and/or cytotoxic chemotherapy. Optimal modulation of stem cell survival, self-renewal and differentiation in these embodiments is usually obtained by dosing the F1C at a time period near the time that the subject is exposed to an agent, event or treatment that can cause significant tissue damage. Typically this time period is about 1, 2, 3, 4 or 5 days before, on the same day as or within 1, 2, 3, 4 or 5 days after the damaging event or exposure occurs. For chronic toxin exposure, e.g., alcohol, chronic continuous or intermittent administration of the F1C can be used. Dosages of the F1Cs, routes of administration and dosing protocols for these embodiments are as described herein.

As noted above, the F1Cs are useful to enhance healing in a subject who has experienced or who is expected to experience one or more traumas or acute injuries such as a wound, burn, bone fracture, nervous system tissue trauma, gastrointestinal damage or intestinal cell damage or other traumatic events. In some embodiments, such subjects have experienced a trauma and who are immune suppressed or are anticipated to become immune suppressed. The immune suppression may arise from, e.g., a myelosuppressive cancer therapy, a glucocorticoid therapy or from radiation exposure. Thus, in some cases a subject such as a human or a primate who has experienced a trauma, e.g., a bone fracture, a chemical or thermal burn, a cut or a laceration, is also exposed to, e.g., an ionizing radiation as described herein such as γ-radiation, β-radiation, X-radiation or neutron radiation in an immune suppressive amount or dose, e.g., about 0.3 Gy ("gray") to about 30 Gy, typically about 0.5 Gy to about 12 Gy or about 0.7 Gy to about 8 Gy. The subject's radiation exposure can be localized or whole body and can occur rapidly, e.g., over a period of up to about 20 minutes, or more slowly, e.g., over a period of about 5-25 minutes to about 5-72 hours or more. A Gy of radiation is 1 joule per kg of absorbed ionizing radiation. The trauma event and the radiation exposure event may occur at about the same time, e.g., on the same day, or within a time period of about 1, 2, 3, 4, 5 or 6 days to about 1, 2, 3 or 4 weeks, when detectable clinical effects of both events are present. Treatment with the F1C will use the dosing protocols, dosages and routes of F1C administration as described herein, e.g., dosing daily or every other day for about 1-12 days using dosages of about 0.1 mg/kg to about 30 mg/kg, depending on the route of administration and the subject's condition. Dosing of the F1C will usually commence within a few days of the radiation exposure event, e.g., within 0, 1, 2, 3 or 4 days. Similarly, such healing or repair of traumas in subjects who are or are expected to become immune suppressed, e.g., from an immunosuppressive chemotherapy, cancer, stress, infection or from aging, can be treated in the same manner.

Neurological conditions. Nervous system diseases, disorders, conditions, or their symptoms (collectively 'neurological conditions') that can be ameliorated, treated or prevented with any of the F1Cs disclosed herein include, but are not limited to, nervous system trauma or injury, and neurological conditions that result in an unwanted pathology or symptom, e.g., demyelination, pain, impairment of cognitive function, discernable memory loss, depression, anxiety, a disconnection of axons, a diminution of neuron, astrocyte or glia function or degeneration or death of nervous system cells or tissues such as one or more of those described herein.

Neurological conditions, including nervous system lesions that may be treated, prevented, or ameliorated in a subject include but are not limited to, the following lesions of either the central (including spinal cord, brain) or peripheral nervous systems. Exemplary neurological conditions include (1) ischemic lesions, in which a lack of oxygen in a portion of the nervous system results in neuronal injury or death, including cerebral infarction, ischemia or stroke, or spinal cord infarction or ischemia, (2) traumatic lesions, including lesions caused by physical injury or associated with surgery, for example, lesions which sever a portion of the nervous system, or compression injuries, (3) malignant lesions, in which a portion of the nervous system is destroyed or injured by malignant tissue which is either a nervous system associated malignancy or a malignancy derived from non-nervous system tissue, (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis or syphilis, (5) degenerative lesions or conditions, in which a portion of the nervous system is destroyed or injured as a result of a degenerative process including but not limited to degeneration associated with Parkinson's disease, Alzheimer's disease, Huntington's chorea, AIDS associated dementia, epileptic dementia, presenile dementia, senile dementia, vascular dementia, post stroke dementia, post traumatic dementia or amyotrophic lateral sclerosis (ALS), (6) lesions associated with nutritional diseases, disorders, and/or conditions, in which a portion of the nervous system is destroyed or injured by a nutritional disorder or disorder of metabolism including but not limited to, vitamin B 12 deficiency, folic acid deficiency, Wernicke disease, tobacco-alcohol amblyopia, Marchiafava-Bignami disease (primary degeneration of the corpus callosum), and alcoholic cerebellar degeneration, (7) neurological lesions associated with systemic diseases including, but not limited to, diabetes (diabetic neuropathy, Bell's palsy), systemic lupus erythematosus, carcinoma, or sarcoidosis, (8) lesions caused by toxic substances including alcohol, lead, or neurotoxins, (9) demyelinated lesions in which a portion of the nervous system is destroyed or injured by a demyelinating disease including, but not limited to, multiple sclerosis, human immunodeficiency virus-associated myelopathy, progressive multifocal leukoencephalopathy, and central pontine myelinolysis or a myelopathy, e.g., diabetic meylopathy or a transverse myelopathy, (10) neurological conditions such as insomnia (e.g., transient or chronic), epilepsy, schizophrenia, psychosis, delusion, a unipolar mood disorder, a bipolar mood disorder, psychomotor dysfunction, depression, anxiety, addiction to or abuse of a drug substance such as tobacco, nicotine, caffeine, alcohol, a barbiturate, a tranquilizer, a narcotic such as hydromorphone HCl, propoxyphene napsylate, meperidine HCl, valium, codeine, cocaine, morphine, heroin or methadone, (11) cognitive dysfunction conditions or diseases such as one or more of impaired long-term or short-term memory, impaired concentration, impaired attention or impaired learning, where the cognitive dysfunction condition or disease is optionally associated with chemotherapy, radiation therapy or exposure, aging, trauma, e.g., CNS trauma, or neurodegeneration and (12) genetic disorders with a neurological pathology or component such as Down's syndrome or Tay Sach's disease.

The F1Cs are useful to ameliorate, treat or prevent the onset, severity or length of other neurological diseases or conditions such as headache or a migraine condition or symptom such as classic migraine, cluster headache, abdominal migraine, common migraine, hemiplegic migraine, ocular migraine, fulminating migraine, complicated migraine or a symptom of any of these such as head pain, vertigo, nausea, vomiting or potophobia.

In some embodiments, the F1C is used to protect neural cells from the damaging effects of cerebral hypoxia, cerebral ischemia or neural cell injury associated with cerebral infarction, heart attack, stroke or elevated levels of glucocorticoids such as cortisol. The compounds that are also useful for treating or preventing a nervous system disorder may be selected, e.g., by assaying their biological activity in promoting the survival or differentiation of neurons. For example, and not by way of limitation, the F1Cs can be used to elicit any of the following useful effects: (1) increased survival time of neurons in culture, (2) increased sprouting of neurons in culture or in vivo, (3) increased production of a neuron-associated molecule in culture or in vivo, e.g., dopamine or choline acetyltransferase or acetylcholinesterase with respect to motor neurons or (4) decreased symptoms of neuron dysfunction in vivo. Such effects may be measured by any method known in the art. Increased survival of neurons may be measured using known methods, such as, for example, the method set forth in Arakawa et al. (*J. Neurosci.* 10:3507-3515 1990); increased sprouting of neurons may be detected by methods known in the art, such as the methods set forth in Pestronk et al. (*Exp. Neurol.* 70:65-82 1980) or Brown et al. (*Ann. Rev. Neurosci.* 4:17-42 1981). Increased production of neuron-associated molecules may be measured by, e.g., bioassay, enzymatic assay, antibody binding or Northern blot assay, using techniques known in the art and depending on the molecule to be measured. Motor neuron dysfunction may be measured by assessing the physical manifestation of motor neuron disorder, e.g., weakness, motor neuron conduction velocity, or functional disability. Motor neuron conditions may arise from infarction, cancer, infection, exposure to toxin, trauma, surgical damage or a degenerative disease that affects motor neurons as well as other components of the nervous system.

Other neurological conditions that can be treated using F1Cs include conditions that selectively affect neurons or adjacent tissues such as amyotrophic lateral sclerosis, progressive spinal muscular atrophy, progressive bulbar palsy, primary lateral sclerosis, infantile and juvenile muscular atrophy, poliomyelitis and the post polio syndrome, hereditary motorsensory neuropathy, spinal cord compression and a myelitis such as necrotizing myelitis, transverse myelitis, ascending myelitis, bulbar myelitis, concussion myelitis, demyelinated myelitis, postinfectious myelitis, systemic myelitis or transverse myelitis.

In some neurological conditions such as mood changes, depression, anxiety, memory loss or motor function impairment, the F1Cs can modulate one or more biological activities of a transcription factor or a nuclear hormone receptor such as ERα in tissue such as the hypothalamus or amygdala or ERβ in tissue such as the hippocampus, thalamus or entorhinal cortex.

In neurological conditions or other conditions where loss or damage to nervous system cells or tissue is typically present, e.g., multiple sclerosis, cerebral infarction, cerebral trauma, elevated glucocorticoid levels or Alzheimer's disease, use of the F1Cs can lead to detectable repair of damaged cells or replacement of at least some killed cells. Elevated glucocorticoids can result from endogenous production of natural glucocorticoids, e.g., cortisol or hydrocortisone, or from administration of synthetic glucocorticoids, e.g., dexamethasone, triamcinolone, betamethasone or other synthetic agents disclosed herein or in the cited references. Repair or replacement can occur for cell types that are present in nervous system tissues, e.g., neurons, Schwann cells, glial cells, astrocytes, oligodendrocytes, macroglia cells, endothelial cells, or stem or progenitor cells of any of these cell types. The cells may reside in discrete regions of nervous organs, e.g., hippocampus, cerebrum or cerebellum, or they may reside in multiple regions. Any of the neurological conditions that can be treated with the F1Cs may be acute, subacute or chronic and they may be subclinical (having few or no overt symptoms), mild, moderate or severe.

In treating neurological conditions, the F1Cs will generally enhance function, self renewal and/or differentiation of stem or progenitor cells and/or they will reduce the severity of cell damage or impairment compared to similar subjects that are not treated with the F1Cs. In cases where myelin damage or nerve death occurs, the F1Cs can reduce the rate at which damage or death occurs or they can detectably reverse damage or enhance replacement of killed cells, particularly where the extent of such damage or killing is mild or moderate. Without wishing to be bound to any theory, the F1Cs may exert these properties (1) by directly acting as a hormone, growth factor or modulator of a biomolecule disclosed herein such as an enzyme, a glucocorticoid receptor, PPARα, a neural stem cell helix-loop-helix transcription factor such as HES1 or an estrogen receptor to enhance replication, synaptogenesis or other repair or maintenance functions, (2) by enhancing recruitment and/or differentiation of cells involved in cell or tissue repair, e.g., enhanced recruitment and differentiation of oligodendrocyte cells to a demyelinated lesion in multiple sclerosis and/or (3) indirectly by modulating the level or activity of autocrine, paracrine or endocrine factors such as one or more inflammatory cytokines or markers as disclosed herein that can modulate disease progression, e.g., cortisol, IL-1α, IL-1β, TNF-α, IL-6, a thromboxane, a prostaglandin or a neuregulin.

In treating chronic or progressive disorders such as multiple sclerosis or Alzheimer's disease, the F1Cs will typically slow the rate of progression of the disease. The F1Cs act at least in part by decreasing the activity or levels of chemokines and/or pro-inflammatory cytokines, e.g., one, two or more of MCP-1, MIP-1, ICAM, V-CAM, E-selectin, RANTES, IL-1α, IL-1β, IL-6, IL-8 and TNF-α. This reduction can be accompanied by a reduced rate of deposition of amyloid-β (AJ3) protein, which results in slowed disease progression and in reduced severity and/or frequency of one or more symptoms such as short term memory loss, impaired concentration, impaired judgement, episodes of disorientation or confusion and periods of mood or behavior changes such as irritability, anxiety or aggression. Treatment of chronic or progressive disorders such as Alzheimer's disease with a F1C is optionally accompanied by other suitable treatments, e.g., treatment with one or more non-steroidal anti-inflammatory drugs or other palliative measures.

Factors such as increased levels of cortisol or thromboxane, that are associated with increased cell or tissue damage or with inhibition of cell growth or differentiation are generally decreased or reregulated to express in a normal manner by the appropriate cells such as neurons, astrocytes, glial cells or their stem or precursor cells. Factors that facilitate normal differentiation or repair, e.g., basic fibroblast growth factor 2 or neuregulin, are generally increased or reregulated to express in a normal manner by the appropriate cells such as neurons, astrocytes, glial cells or their stem or precursor cells.

Because of these properties, the F1Cs can be used in various protocols or methods to enhance differentiation or proliferation of these cell types in vivo or in vitro. Typically, the concentration of the F1Cs will exert one or more of these beneficial effects at extracellular concentrations of about $1 \times 10^{-12}$ M to about $5 \times 10^{-6}$ M, e.g., about $1 \times 10^{-11}$ M to about $5 \times 10^{-7}$ M or about $1 \times 10^{-10}$ M to about $1 \times 10^{-7}$ M. Such concentrations can suitably be established transiently, e.g., for about 10 minutes to about 6 hours or about 12 hours once or twice per day on one, two or more days. Alternatively, such concentrations may be maintained more or less constantly, e.g., within these ranges for at least about 12 hours per day for one, two or more days, particularly for in vitro use to enhance cell or tissue growth, differentiation or viability in tissue culture. Methods to administer the F1Cs for in vivo use are essentially as described herein.

For any of these neurological conditions or their associated symptoms, the presence of the condition or its pathological manifestation, e.g., cell or tissue damage, or symptom may be determined by suitable objective or subjective means, e.g., assays to detect tissue damage, levels of diagnostic markers or an etiological agent, performance of histopathological examination of cells or tissues, patient questionnaires or behavior performance tests, measurement of a diagnostic marker(s), e.g., an enzyme, hormone, cytokine or drug substance in blood or tissue, electroencephalography, imaging methods such as X-ray, MRI scan or CAT scan, observation and diagnosis of clinical features or symptoms or biopsy of affected tissue or cells, e.g., aspiration biopsy, needle biopsy, incision biopsy or punch biopsy of tissue or cells. Neurological conditions, diseases and symptoms, which the F1Cs can be used to treat or ameliorate and methods to diagnose and characterize such conditions or diseases have been described. See, e.g., Ph. Demaerel, A. L. Baert et al., eds. *Recent Advances in Diagnostic Neuroradiology (Medical Radiology: Diagnostic Imaging)* 2001 Springer Verlag, ISBN: 3504657231, W. G. Bradley et al., *Neurology in Clinical Practice: Principles of Diagnosis and Management* 1995, see, e.g., vol. 1 Ch. 1-55 and vol. 2. Ch. 1-66, Butterworth-Heinemann Medical, ISBN 0750694777, H. J. M. Barnett et al., eds. *Stroke: Pathophysiology, Diagnosis and Management* $3^{rd}$ edition, 1998, see, e.g., pages 10-1450, Churchill Livingstone, ISBN 0443075514, P. J. Vinken et al., eds. *Neurodystrophies and Neurolipidoses* $2^{nd}$ ed. 1996, see, e.g., pages 8-780, Elsevier Science, ISBN 0444812857, P. L. Peterson and J. W. Phillis eds. *Novel Therapies for CNS Injuries: Rationales and Results* 1995, see, e.g., pages 8-380, CRC Press, ISBN 0849376521, D. Schiffer, *Brain Tumors: Pathology and Its Biological Correlates* $2^{nd}$ ed. 1997, see, e.g., pages 5-450, Springer Verlag, ISBN 3540616225 and E. Niedermeyer and F. Lopes Da Silva, eds. *Electroencephalography: Basic Principles, Clinical Applications and Related Fields* $4^{th}$ ed. 1999 see, e.g., pages 13-1238, Lippincott, Williams & Wilkins, ISBN 0683302841.

The use of the F1Cs in these conditions is optionally combined with one or more of the therapeutic treatments that are described in these references. The F1C may be administered before, during or after another treatment is employed to prevent, treat or ameliorate a given neurological condition or symptom thereof. Any of these neurological conditions or symptoms may be mild or at an early stage, moderate or severe or advanced.

Dosages of the F1C, routes of administration and the use of combination therapies with other standard therapeutic agents or treatments could be applied essentially as described above for cardiovascular conditions or as disclosed elsewhere herein. Thus, the F1Cs may be administered prophylactically or therapeutically in chronic conditions or they may be administered at the time of or relatively soon before or after an acute event such as an epileptic seizure, onset of a migraine or occurrence of trauma, before, during or after surgery, accidental head or central nervous system injury or a cerebral stroke or infarction. For acute events, the formula 1 compounds may thus be administered concurrently, e.g., within about 15 minutes or about 30 minutes of the onset or occurrence of the acute event, or at a later time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours after the onset or occurrence of the acute event. The F1Cs may thus be administered at about 6-120 hours, or about 8-48 hours, about 10-24 hours or about 12-16 hours after an acute event starts or occurs. In other embodiments, the F1C can be administered before an expected acute event such as a planned surgery. In these cases, the F1Cs may be administered before, e.g., within about 15 minutes or about 30 minutes of the onset or occurrence of the acute event, or at an earlier time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours before the onset or occurrence of the acute event.

Skin treatments. The affect of the F1Cs on immune function permits their use to improve the function of organs or organ systems that rely on the optimal functioning of one or more immune responses. Thus, the F1Cs can be administered to a subject to prevent, treat, ameliorate, slow the progression of or enhance the healing of certain skin conditions such as skin inflammation, lesions, atrophy or rash. Conditions that can give rise to skin pathology or an unwanted skin condition include autoimmune diseases, inflammation, allergy, age, exposure to sunlight, cancer, infection or the like.

As used here, skin includes external skin and internal skin or surfaces such as oral, intestinal and rectal mucosa. These conditions include lesions, rashes or inflammation associated with, e.g., burns, infections and the thinning or general degradation of the dermis often characterized by a decrease in collagen or elastin as well as decreased number, size and doubling potential of fibroblast cells. Such skin conditions include keratoses such as actinic keratosis, psoriasis, eczema, warts such as papillomavirus-induced warts, ulcers or lesions such as herpesvirus-induced ulcers or lesions or diabetes associated ulcers or lesions, discoid lupus erythematosus, erythema nodosum, erythema multiform, cutaneous T cell lymphoma, atopic dermatitis, inflammatory vasculitis, relapsing polychondritis, exfoliative dermatitis, sarcoidosis, burns, melanoma, rash or irritation from poison oak, poison ivy or poison Sumac, blemished or hyperpigmented skin, hyperkeratotic skin, dry skin, dandruff, acne, inflammatory dermatoses, scarring such as from a chemical or thermal burn and age-related skin changes. In these embodiments, treatment with the F1Cs is optionally combined with other appropriate treatments or therapies essentially as described herein, e.g., one or more of a corticosteroid such as hydrocortisone or cortisol, prednisone, or prednisolone, an α-hydroxybenzoic acid or an α-hydroxycarboxylic acid(s) is coadministered with a F1C to treat, prevent or ameliorate a skin condition such as atrophy or a lesion. α-Hydroxybenzoic acids and α-hydroxycarboxylic acids suitable for use in these embodiments are described in, e.g., U.S. Pat. Nos. 5,262,407, 5,254,343, 4,246,261, 4,234,599 and 3,984,566. The F1C can be used to minimize cutaneous atrophy caused by corticosteroids, a side effect of their application to the skin.

In these embodiments that address skin conditions, dosages, routes of administration and dosing protocols for the F1Cs are essentially as described herein. In some embodiments, the F1C is administered to the subject in the form of a topical cream, ointment, spray, foam or gel. These topical formulations will optionally comprise about 0.1% w/w to about 20% w/w, or about 0.2% w/w to about 10% w/w of a F1C in a composition that comprises one or more excipients that are suitable for such topical formulations, including, e.g., one or more agents that enhance penetration or delivery of the F1C into the skin. Such topical formulations can be administered, e.g., once, twice or three times per day using about 0.1 g to about 8 g or about 0.2 g to about 5 g of the topical formulation on each occasion. Administration may be daily for about 1 to about 28 days, or it may be intermittent and used as needed. The amount of a topical formulation that can be administered may be higher, e.g., about 15 g or about 20 g, if the size of the area to be treated is relatively large, e.g., at least about 30 cm$^2$ to about 100 cm$^2$ or more. Alternatively, systemic administration of the F1C such as oral, parenteral, sublingual or buccal delivery may be used, particularly when the area of the skin to be treated is relatively large. In some cases, both topical and systemic administration of a F1C can be used. Excipients that topical or other formulations may contain include those described herein, or agents that enhance permeation or solubilization of the F1C, e.g., DMSO or an alkylalkanol, such as a 2-alkylalkanol or a 3-alkyloctanol that comprises about 8-36 carbon atoms (e.g., 8, 9, 10, 11, 12, 13, 14, 15, 16, 17, 18, 19 or 20 carbon atoms) such as 2-ethyloctanol, 2-propyloctanol, 2-octyldodecanol, 2-butyloctanol, 2-hexyldecanol, 2-pentylnonanol, 3-ethyloctanol, 3-propyloctanol, 3-octyldodecanol, 3-butyloctanol, 3-hexyldecanol, 3-pentylnonanol, isostearyl alcohol, isocetyl alcohol, or mixtures thereof. Such alkylalkanol moieties include those having the structure HO—CH$_2$—(CH$_2$)$_{0-4}$—CH(C1-10 alkyl)-(CH$_2$)$_{0-6}$—CH$_3$, any of which are optionally substituted at the alkanol or the alkyl moiety with one, two, three or more independently selected substituents as described herein, e.g., with one, two, three or more independently selected —O—, —F, —OH, —CN or —CH=CH— moieties. Such formulations can be used in therapeutic applications described herein or in cosmetic applications.

Enhancement of hematopoiesis. The invention includes methods to modulate hematopoiesis by administering a F1C to a subject, which can be used to treat or prevent various blood cell deficiencies such as thrombocytopenia ("TP") or neutropenia ("NP"). Hematopoiesis or hemopoiesis is the formation and development of the various types of blood cells and their progenitor cells. Mature cells are found in circulation or tissues such as the lymph nodes, spleen or the thymus. Many of the stem cells that give rise to mature forms reside in the bone marrow, although some may circulate in the blood for some time. Clinical blood cell deficiencies such as thrombocytopenia, neutropenia or erythropenia can arise from causes such as impaired hematopoiesis or abnormal loss or destruction of mature or immature blood cells.

Without being bound to any theory, the treatment methods at least in part result in enhanced hematopoiesis, enhanced movement of blood cells into the circulation and/or in reduced loss of blood cells such as platelets or neutrophils. The F1Cs can enhance self-renewal or numbers of hematopoietic stem cells, precursor cells, mature blood cells and/or they can enhance or accelerate differentiation of stem or any progenitor cell that can give rise to a mature blood cell. The stem or progenitor cells include early lineage cells showing little or no characteristics of fully differentiated blood cells and/or they can be partially differentiated. Increased platelet or neutrophil production, enhanced survival or reduced loss is typically observed as increased circulating blood cell counts. Increases in blood cells appear to arise from enhanced proliferation of precursor cells and/or from enhanced or accelerated differentiation of precursor cells. Increased cell numbers, e.g., platelets or neutrophils, can also arise from reduced loss or death of such cells, increased demargination of cells such as neutrophils from the vasculature into circulating blood or other tissues and/or shorter transit time of mature or precursor cells from the bone marrow into blood.

Thus, invention embodiments comprise a method to treat or prevent a blood cell deficiency such as TP or NP in a subject in need thereof, comprising administering to the subject, or delivering to the subject's tissues, an effective amount of a F1C. Related embodiments include a method to increase self-renewal of hematopoietic stem cells or hematopoietic progenitor cells or to increase the commitment of such cells to transition to a more differentiated blood precursor cell or mature blood cell. In other embodiments, the invention provides a method for stimulating the proliferation or differentiation of neutrophil precursors or to increase demargination of neutrophils or to reduce transit time from bone marrow to blood in a subject having or susceptible to developing NP comprising administering an effective amount of a F1C to the subject in need thereof. The F1C treatment will stimulate the activity of, e.g., neutrophils, or enhance their production from progenitor cells, enhance their survival and/or limit their loss. Hematopoietic stem cells, e.g., GEMM cells, are pluripotent and can give rise to more than one type of mature blood cell, while hematopoietic progenitor cells are usually not pluripotent, but are bipotent or monopotent. Hematopoietic progenitor cells reside primarily in bone marrow, but can also be found in blood, spleen or lymph tissue or fluids.

Normal ranges of various white blood cells or blood components in adult (about 18-49 years of age) human blood are as follows. Total adult white blood cell counts average about 7500/mm$^3$, with an approximate normal range of about 4.5–11.0×10$^3$/mm$^3$. The normal basophil level is about 35/mm$^3$, with a normal range of about 10/mm$^3$ to about 100/mm$^3$. The normal adult neutrophil level is about 4400/mm$^3$, with a normal range of about 2000-7700/mm$^3$. The normal eosinophil level is about 275/mm$^3$, with a normal range of about 150-300/mm$^3$. The normal monocyte level is about 540/mm$^3$, with a normal range of about 300-600/mm$^3$. The normal adult platelet level is about 2.5×10$^5$/mm$^3$, with a normal range of about 2.1×10$^5$–2.9×10$^5$/mm$^3$. The normal human adult red cell mass corresponds to about 4.6×10$^{12}$ red cells/L in females and about 5.2×10$^{12}$ red cells/L in males.

A human patient in need of treatment will typically have, or be subject to developing, a cell count below these values. For example, the subject may have a cell count that is about 2% to about 90% below the lower or upper values of these ranges, e.g., about 5%, about 10%, about 20%, about 30%, about 50% or about 70% below any of these values. As used herein, neutropenia means generally a circulating neutrophil count of less than about 2000/mm$^3$, typically less than about 1500/mm$^3$ or usually less than about 1300/mm$^3$. Under the common terminology criteria for adverse events, version 3.0, published at http://ctep.cancer.gov, grade 1 neutropenia in humans is the lower limit of normal to 1500 neutrophils/mm$^3$, less than 1500 to 1000 neutrophils/mm$^3$ is grade 2 neutropenia, about 1000-500 neutrophils/mm$^3$ is grade 3 neutropenia and less than about 500 neutrophils/mm$^3$ is considered to be grade 4 neutropenia. Febrile NP is NP accompanied by a fever, e.g., about 39.5° C. to about 43° C. or more, that is at least transient, e.g., lasting about 2 or more hours.

Thrombocytopenia generally means a circulating platelet count of less than the normal circulating range, e.g., less than about 1.6×10$^5$/mm$^3$, less than about 1.5×10$^5$/mm$^3$, less than about 1.3×10$^5$/mm$^3$ or less than about 1.0×10$^5$/mm$^3$. Under the common terminology criteria for adverse events, version 3.0, grade 1 thrombocytopenia is the lower normal limit to 75,000 platelets/mm$^3$, grade 2 thrombocytopenia is <75,000-50,000 platelets/mm$^3$, grade 3 thrombocytopenia is <50,000-25,000 platelets/mm$^3$ and grade 4 is <25,000 platelets/mm$^3$. Anemia generally means a red cell mass corresponding to less than about 4.0×10$^{12}$ red cells/L in adult females and less than about 4.5×10$^{12}$ red cells/L in adult males (a hemoglobin level of less than about 12.0 g/dL in adult females and less than about 13.5 g/dL in adult males).

In some cases, the diagnosis of a deficiency may cover a cell count that falls outside these ranges, due, e.g., to individual variations in a subject's age, sex, race, animal strain or normal blood cell status for the individual. Such variations are identified by known means such as by identification of a change from the subject's normal status or by multiple cell measurements over time that reveal a deficiency. See, e.g., Hematology—Basic Principles and Practice, 2$^{nd}$ edition, R. Hoffman, E. J. Benz Jr. et al., editors, Churchill Livingstone, N.Y., 1995. Subjects with an identified or identifiable deficiency outside these standard ranges are included in the definition of a blood cell deficiency or a subject in need of treatment, as used herein.

In exemplary embodiments, use of the F1Cs for treating subjects including primates or humans who are subject to developing a NP condition will typically result in a decreased in the severity and/or duration of NP. Typically, the F1C treatment will comprise treating the subject daily, every other day or every third day for about 1, 2, 3, 4, 5, 6, 7, 8, 9, 10, 11 or 12 days with about 0.1 mg/kg to about 5 mg/kg, usually about 0.5 mg/kg to about 4 mg/kg. For these dosages, the F1C is typically administered by parenteral, e.g., intravenous, subcutaneous or intramuscular, or transmucosal delivery. Oral administration will generally use dosages that are about 3-25 mg/kg higher, e.g., about 4-30 mg/kg of the F1C. Human unit dosages will typically comprise about 1-1500 mg, usually about 10-150 mg, which can be subdivided, e.g., into two or three subdoses. Treatment of subjects who may develop a NP condition from a chronic or slow onset condition will generally begin when reduced neutrophil counts are observed, e.g., when the subject has grade 1 or 2 NP. In situations where NP can arise over a short time period, e.g., from an inducing event such as a chemotherapy, an acute infection or radiation exposure, treatment with the F1C will generally begin at about the time of the inducing event. Thus, for subjects who will be subjected a chemotherapy or radiation therapy, dosing with the F1C can begin about 1, 2, 3 or 4 days before, during (essentially simultaneous with or on the same day as) or about 1, 2, 3 or 4 after the inducing event. Typically dosing the F1C begins in a period from 2 days before to 2 days after the subject is exposed to the NP inducing event.

Treatment with a F1C will reduce the severity of NP, e.g., by preventing the development of grade 3 or 4 NP or febrile NP in subjects who would otherwise be expected to develop or susceptible to developing grade 3 or 4 NP. The F1C will also typically reduce the duration of, e.g., grade 3 or 4 NP, in subjects who would otherwise be expected to develop or susceptible to developing such NP. The reduction in the duration of NP, grade 3 or 4 NP, can range from 100% to a detectable level, e.g., a reduction of at least about 10%. Typically, the reduction of the period during which a subject has grade 3 or 4 NP or febrile NP is about 25% to about 85%, e.g., about 30%, 40%, 50%, 60%, 70%, 80% or more.

Individual responses can vary depending on factors such as the subject's initial neutrophil status, when dosing with the F1C is initiated, dosage of the F1C and the route of administration of the F1C. NP in subjects susceptible to developing NP can arise from conditions or treatments as described herein, e.g., autoimmune conditions, cancer, cancer chemotherapy, an infection, antimicrobial chemotherapy, bone marrow transplantation, an immunosuppressive therapy, bone marrow damage or exposure to or treatment with an ionizing radiation such as one or more of γ-radiation, X-rays, fast neutrons, β-radiation or α-radiation.

TP, abnormally low platelet counts, can arise from impaired platelet production, sequestration of platelets in the spleen or abnormal loss of circulating platelets. Impaired production can result from causes such as chemotherapy, radiation exposure, e.g., a radiation therapy, or an from autoimmune condition. Abnormal loss of circulating platelets is often associated with autoreactive antibodies that bind to platelets and reduce their life span. These underlying causes give rise to the various clinical forms of TP, such as autoimmune neonatal TP, immune thrombocytopenic purpura, radiation induced TP, chemotherapy induced TP and amegakaryocytic TP.

Other conditions that are amenable to prophylaxis or treatment by the invention methods include the acquired blood cell deficiencies. Exemplary deficiencies or groups of deficiencies that can be treated are neonatal alloimmune TP, immune TP, immune thrombocytopenic purpura, thrombotic thrombocytopenic purpura, post-transfusion purpura, radiation associated TP, chemotherapy associated TP (e.g., an anticancer, antiviral, antibacterial, antifungal or antiparasite therapy, NSAID treatments such as with indomethicin, ibuprofen, naproxen, phenylbutazone, piroxicam or zompirac, or β-lactam antibiotic treatments such as with ampicillin, carbenicillin, penicillin G, ticarcillin, or cephalosporin treatments such as with cefazolin, cefoxitin or cephalothin, anticoagulant treatments such as heparin, hirudin, lepirudin or aspirin, treatment with plasma expanders or psychotropic drugs), amegakaryocitic TP, radiation associated TP, TP associated with solid organ allograft or xenograft rejection or immune suppression therapy in solid organ or other tissue transplants (e.g., liver, lung, kidney, heart, bone marrow, hematopoietic stem cell or endothelial cell transplant, implant or transfusion), cardiopulmonary bypass surgery, cardiovascular disease or therapy associated TP (e.g., congenital cyanotic heart disease, valvular heart disease, pulmonary embolism, pulmonary hypertension disorders or diltiazem, nifedipine, nitroglycerin or nitroprusside therapy), TP associated with chronic or acute renal failure or treatment for these conditions (e.g., dialysis), TP associated with infection such as a virus or bacterial infection. NP conditions that can be treated include postinfective NP, autoimmune NP, chronic idiopathic NP, basophilic leukopenia, eosinophilic leukopenia, monocytic leukopenia, neutrophilic leukopenia, cyclic NP, periodic NP, chemotherapy associated NP, radiation associated NP, NP associated with solid organ allograft or xenograft rejection or immune suppression therapy in solid organ or other tissue transplants (e.g., liver, lung, kidney, heart, bone marrow, hematopoietic stem cell or endothelial cell transplant, implant or transfusion), chemotherapy associated leukopenia, radiation associated leukopenia, leukopenia associated with solid organ allograft or xenograft rejection or immune suppression therapy in solid organ or other tissue transplants (e.g., liver, lung, kidney, heart, bone marrow, hematopoietic stem cell or endothelial cell transplant, implant or transfusion), immune hemolytic anemias, anemia associated with chronic or acute renal failure or treatment for these conditions (e.g., dialysis), anemia associated with chemotherapy (e.g., isoniazid, prednisone) or anemia associated with radiation exposure.

The F1Cs are thus useful to facilitate or speed up immune system recovery in autologous bone marrow transplant or stem cell transplant situations. In many cases it would be medically sound to continue the treatment associated with causing or exacerbating the blood cell deficiency. Thus, in some embodiments a F1C treatment is conducted with subjects who are undergoing another therapy at the same time or near the same time, e.g., within about 1, 2, 3, 4 or several days to within about 1-6 months. Such subjects typically will have an identified blood cell deficiency such as a NP or a TP, e.g., as disclosed herein. However, the F1Cs can be generally suitable for preventing the onset or reducing the severity of such deficiencies, and they can thus be used prophylactically in these indications, e.g., by administering a F1C beginning at about 1-60 days before administering another therapy that could lead to a cytopenia condition such as TP or NP.

In conditions such as NP, the F1Cs will typically function at least in part by modulating, e.g., increasing, the level or activity of biomolecules such as IL-1β, G-CSF, GM-CSF or one or more of their receptors, that can enhance generation or survival of a desired cell type such as neutrophils. In this regard, the F1Cs can act as inducers of endogenous growth or differentiation factors that facilitate increased production or survival of neutrophils or other blood cell types. This aspect of the F1Cs allows one to eliminate or reduce the use of such molecules in treating conditions such as NP.

Use of a F1C in treating cytopenia conditions is thus optionally combined with the use of an effective amount of one or more growth factors or cytokines as a means to further enhance the effect of the F1Cs for their intended uses or to modulate, e.g., enhance, their effects or efficacy. Suitable growth factors and cytokines are as described herein or in the cited references. For example, when one administers the F1C to enhance generation of platelets in humans or other subjects, or their precursor cells such as CFU-blast cells, multipotent thymic precursor cells ($CD34^+$, $CD38^+$, $CD7^+$, $CD44^+$, $CD33^+$, $CD2^-$, $CD5^-$, $CD1a^-$), Pro-DC2 cells, immature DC2 cells, immature NK cells, CFU-GEMM, BFU-Mk, CFU-Mk, CFU-G, CFU-GM, immature megakaryocytes or mature postmitotic megakaryocytes, one can also administer one or more of G-CSF, GM-CSF, SCF, Steel factor ("SF"), leukemia inhibitory factor ("LIF"), interkeukin-1α, ("IL-1α"), IL-3, IL-6, IL-11, TPO, EPO, their isoforms, their derivatives (e.g., linked to a PEG or fusions such as PIXY321) or their isoforms, orthologs or homologs for other species. Similarly, administration of the F1C to enhance the generation or function of myelomonocytic cells such as neutrophils, basophils or monocytes in humans or other subjects, can also be combined with administration of one or more of G-CSF, GM-CSF, M-CSF, LIF, TPO, SF, interleukin-1 ("IL-1"), IL-2, IL-3, IL-4, interleukin-5 ("IL-5"), IL-6, IL-11, interleukin-12 ("IL-12"), interleukin-13 ("IL-13"), FLT3 ligand, their isoforms, orthologs, homologs or derivatives (e.g., linked to a PEG or fusions such as PIXY321) or their isoforms, orthologs or homologs for other species. To enhance generation of red cells or their precursor cells such as CFU-GEMM, BFU-E or CFU-E in humans being treated with a F1C, one can co-administer one or more of G-CSF, GM-CSF, IL-1, IL-3, IL-6, TPO, EPO, transforming growth factor-β1, their isoforms, their derivatives (e.g., linked to a PEG or fusions such as PIXY321) or their isoforms, orthologs or homologs for other species. See, e.g., *Hematology—Basic Principles and Practice*, $3^{rd}$ edition, R. Hoffman, E. J. Benz Jr. et al., editors, Churchill Livingstone, N.Y., 2000 (see, e.g., Chapters 14-17 at pages 154-260). The co-administration of such factors in these methods is intended to enhance the efficacy of the F1C treatment, which is optionally measured by taking suitable blood or tissue, e.g., bone marrow, samples at one or more times before and after the compounds have been administered. Such co-administration will generally be compatible with a subject's condition and other therapeutic treatments. Co-administration of such factors can precede, be simultaneous with, or follow the times of administration of the F1C(s) to the subject. Dosages of such growth factors would generally be similar to those previously described, e.g., typically an initial course of treatment comprises administering about 1.0 to about 20 µg/kg/d for about 1-10 days, or as described in, e.g., *Hematology—Basic Principles and Practice*, $3^{rd}$ edition, R. Hoffman, E. J. Benz Jr. et al., editors, Churchill Livingstone, N.Y., 2000 (see, e.g., Chapter 51 at pages 939-979 and the references cited therein).

In cases where a subject's blood cell deficiency is caused by, or associated with another therapy, the invention contemplates that the other therapy will continue, if this is reasonable under the circumstances. The timing of other therapies can precede, be simultaneous with, or follow the times of administration of the F1C(s) to the subject. For example, chemotherapy for some malignancies is accompanied by myelosuppression or a deficiency in one or more blood cell types, e.g., TP or NP. Continued treatment would be called for in some cases, and then the invention methods would be employed to deliver to the subject an effective amount of a F1C. Thus, alkylating agents, antimicrotubule agents, antimetabolites, vinca alkaloids, topoisomerase I or II inhibitors, or platinum compounds such as one or more of mechlorethamine, vincristine, vinblastine, bleomycin, doxorubicin, epirubicin, tamoxifen, cyclophosphamide, etoposide, methotrexate, ifosfamide, melphalan, chlorambucil, busulfan, carmustine, lomustine, streptozocin, dacarbazine, vinorelbine, paclitaxel (taxol), docetaxel, cytosine arabinoside, hydroxyurea, fludarabine, 2'-chlorodeoxyadenosine, 2'-deoxycoformycin, 6-thioguanine, 6-mercaptopurine, 5-azacytidine, gemcitabine, arabinofuranosylguanine, daunorubicin, mitoxantrone, amsacrine, topotecan, irinotecan, cisplatin, carboplatin, pilcamycin, procarbazine, aspariginase, aminoglutethimide, actinomycin D, azathioprine and gallium nitrate may be administered in conjunction with administration of any F1C(s) that is disclosed herein. Treatments with other therapeutic agents such as heparin or nucleoside analogs such as 3-thiacytosine, azidothymidine or dideoxycytosine, or other antimicrobials such as cephalosporin, quinine, quinidine, gold salts (e.g., aurothioglucose), a fluoroquinolone (e.g., ciprofloxacin), clarithromycin, fluconazole, fusidic acid, gentamycin, nalidixic acid, penicillins, pentamidine, rifampicin, sulfa antibiotics, suramin or vancomycin may result in a blood cell deficiency(s) and they can thus be combined with administration of a F1C to treat the deficiency, or to ameliorate a symptom thereof. Similarly, anti-inflammatory drugs (e.g., salicylates, entanercept (a dimeric fusion comprising a portion of the human TNF receptor linked to the Fc portion of human IgG1 containing the $C_H2$ and $C_H3$ domain and hinge regions of IgG1) or a COX-2 inhibitor such as celexicob (4-5[-(4-methylphenyl)-3-(trifluoromethyl)-1H-pyrazole-1-yl]benzenesulfonamide) or rofecoxib (4-[4-methylsulfonyl)phenyl]-3-phenyl-2(5H)-furanone) or an IL-1 receptor antagonist such as anakinra), cardiac drugs (e.g., digitoxin), β-blockers or antihypertensive drugs (e.g., oxprenolol or captopril), diuretics (e.g., spironolactone), benzodiazepines, (e.g., diazepam) or antidepressants (e.g., amitriptyline, doxepin). Any of these methods also optionally include co-administration of one or more of the growth factors described above, e.g., IL-3, G-CSF, GM-CSF or TPO.

Other therapies for treating a blood cytopenia such as TP or NP also include administering one or more of glucocorticoid steroids (e.g., prednisone, prednisolone), human IgG antibodies, anti-Rh(D)$^+$ antibodies for Rh(D)$^+$ patients, an androgen such as danazol, vinca alkaloids (e.g., vincristine, vinblastine), thrombopoietin and immunosuppresants (e.g., azathioprine, cyclophosphamide, FK506 or cyclosporin). Splenectomy may also be indicated, for example when first line treatments fail. The goal of treatment for TP in humans is typically to increase platelet counts to at least about 20,000/mm$^3$ or more typically to at least about 50,000/mm$^3$ and to maintain these levels.

Although the treatment options to increase platelet levels are generally known, they usually have a number of drawbacks. For example, infusion of IgG antibodies is not always effective and the treatment is relatively expensive. Other treatments, such as prednisone are also not always effective and they typically are discontinued or tapered off after several weeks due to toxicity or unwanted side effects. Splenectomy, which is relatively expensive and invasive, is also not always effective. The sources of thrombocytopenia and treatment options have been described. See, e.g., *Hematology—Basic Principles and Practice*, 3$^{rd}$ edition, R. Hoffman, E. J. Benz Jr. et al., editors, Churchill Livingstone, N.Y., 2000 (see, e.g., Chapters 126-129 and 131 at pages 2096-2154 and 2172-2186), PCT publication WO 200035466.

Neutropenia ("NP"), is considered to exist clinically when neutrophils drop to below a level considered normal. NP can arise from impaired production of neutrophil precursors or mature neutrophils, movement of neutrophils from the circulation to tissue, abnormal circulating neutrophil loss or a combination of these causes. Impaired neutrophil production can be acquired from, e.g., treatment with a cytotoxic or cytostatic drug, chemotherapy, radiation therapy or an autoimmune response as described herein. The abnormal loss of circulating neutrophils in autoimmunity is typically associated with autoreactive antibodies that bind to the cells and reduce their life span. These underlying causes give rise to the various clinical forms of NP, such as postinfectious NP, drug-induced NP, autoimmune NP, or chronic idiopathic NP. The sources of NP and treatment options have been described. See, e.g., *Hematology—Basic Principles and Practice*, 3$^{rd}$ edition, R. Hoffman, E. J. Benz Jr. et al., editors, Churchill Livingstone, N.Y., 2000 (see, e.g., Chapters 19, 41, 51, 79, 134 and 137 at pages 297-331, 720-762, 939-979, 1443-1500, 2220-2248 and 2257-2263).

In some embodiments, the F1Cs that are used to enhance hematopoiesis or to treat associated conditions such as a TP or a NP disease or condition as disclosed herein, are characterized by having a lack of appreciable androgenicity. In these embodiments, the F1Cs are characterized by having about 15% or less, about 10% or less, about 5% or less, about 2% or less, about 1% or less or about 0.5% or less of the androgenicity of a reference androgen such as testosterone, testosterone proprionate, dihydrotestosterone or dihydrotestosterone proprionate as measured in a suitable assay using suitable positive and/or negative controls. F1Cs having, e.g., a substitution at the 6- or 7-position or having no double bond at the 4-5 or 5-6 positions, will generally have relatively low levels of androgen activity. Suitable assays for androgenicity of various compounds have been described, e.g., J. R. Brooks, et al., *Prostate* 1991, 18:215-227, M. Gerrity et al., *Int. J. Androl.* 1981 4:494-504, S. S. Rao et al., *Indian J. Exp. Biol.* 1969 7:20-22, O. Sunami et al., *J. Toxicol. Sci.* 2000 25:403-415, G. H. Deckers et al., *J. Steroid Biochem. Mol. Biol.* 2000 74:83-92. The androgenicity of the F1Cs are optionally determined as described or essentially as described in one or more of these assays or any other assay. Thus, one such embodiment comprises a method to enhance hematopoiesis or to treat TP or NP comprising administering to a subject in need thereof an effective amount of a F1C, or delivering to the subject's tissues an effective amount of a F1C, wherein the F1C has about 30% or less, about 20% or less, about 10% or less or about 5% or less of the androgenicity of an androgen such as testosterone, testosterone proprionate, dihydrotestosterone or dihydrotestosterone proprionate as measured in a suitable assay, e.g., as described in the citations above. In conducting such methods, the subjects, e.g., rodents, humans or primates, are optionally monitored for e.g., amelioration, prevention or a reduced severity of a disease, condition or symptom. Such monitoring can optionally include measuring one or more of cytokines (e.g., TNFα, IL-1β), WBCs, platelets, granulocytes, neutrophils, RBCs, NK cells, macrophages or other immune cell types, e.g., as described herein or in the cited references, in circulation at suitable times, e.g., at baseline before treatment is started and at various times during or after treatment with a F1C, e.g., at about 2-45 days after treatment with a F1C has ended.

In conducting any of these methods, one can monitor the subject's clinical condition at any relevant time before, during or after administration of the F1Cs, which treatments are optionally combined with any of the other agents or treatments described above. The subject's blood can be drawn on one, two or more occasions in advance of treatment to, e.g., obtain a baseline or initial level of white or red blood cells, to verify a presumptive diagnosis of a blood cell deficiency or to determine a blood parameter such as circulating myelomonocyte counts, circulating neutrophil counts or circulating platelet counts. then, during the course of treatment or thereafter the subject's blood can be drawn on one, two or more occasions to follow the subject's response, e.g., once treatment with a F1C has ended.

Invention embodiments include methods that comprise administering to a subject in need thereof an effective amount of a F1C and an effective amount of at least one form of interferon, such as γ-Interferon or a growth factor or interleukin such as G-CSF or IL-6. Interferons can enhance the biological activity of the white cells that arise from increased hematopoiesis. This can be particularly useful when the subject's circulating blood cell deficiency is associated with, e.g., an infection or a chemotherapy that suppresses hematopoiesis. Administration of a growth factor or an interleukin such as IL-6 can facilitate hematopoiesis by stimulating quiescent stem cells or other progenitors that give rise to deficient cell types. Related embodiments replace growth factor or interferon administration partially or completely by increasing endogenous production in the subject using conventional methods, e.g., administering double stranded RNA to stimulate γ-IFN.

In these embodiments, the subject may have thrombocytopenia or neutropenia or the subject's circulating platelets, red cells, mature myelomonocytic cells, or their precursor cells, in circulation or in tissue may be detectably increased. In some cases the subject has renal failure. These methods may further comprise the steps of obtaining blood from the subject before administration of the F1C and measuring the subject's white or red cell counts and optionally, on one, two, three or more occasions, measuring the subject's circulating white cell or red cell counts after administration of the F1C, e.g., within about 12 weeks after an initial administration of a F1C or during or within about 12 weeks after a course of treatment as described herein.

Delayed radiation effects. Invention embodiments include a method to prevent, treat or ameliorate a symptom or condition associated with one or more delayed adverse effect, symptom or condition from ionizing radiation exposure in a subject in need thereof comprising administering to the subject, or delivering to the subject's tissues, an effective amount of a F1C. In these embodiments, administration of the F1C commences at least 2 weeks after the subject has been exposed to a dose or subdose of radiation that could give rise to a delayed radiation effect. Dosing with the F1C can thus begin at 14 days to about 2 years or more after ionizing radiation exposure. Typically dosing will begin at about 2 weeks, 3 weeks, or 1, 2, 3 or 4 months after exposure of the subject to sufficient ionizing radiation to potentially cause delayed effects. Radiation exposure may arise from a radiation therapy where exposure is intentional, or it may arise from an accidental exposure.

Radiation therapy ("RT") can generate a number of late delayed-onset conditions or symptoms. Delayed radiation effects are conditions or symptoms that generally arise or become detectable to the subject or to a health care provider at least about 1 month after exposure to radiation. Thus the conditions or symptoms may be detectable at about 2 months, about 3 months, about 4 months, about 5 months, about 1 year, about 20 years or more after radiation exposure. For example, transient nervous system symptoms may develop early after RT, but progressive, permanent, often disabling nervous system damage may appear months or years later. The total radiation dose, size of the fractions, duration of RT, and volume of tissue irradiated influence the probability of the injury and its severity. Individual patient and tissue susceptibility to delayed injuries is variable, which factors into the selection of safe and effective radiation doses for RT. Total radiation doses that a subject may receive may comprise single doses or 2, 3, 4, or more doses within a range of about 1 to about 400 Gy, e.g., about 1, 1.4, 1.6, 1.8, 2, 2.5, 3, 5, 10, 20, 40, 50, 80, 100, 130, 150, 180, 200, 250, 300, 400 Gy. Typical doses are about 1-12 Gy or about 1-8 Gy. Such doses in a given course of treatment may be the same or different and can occur over a period of time, e.g., over 1 day to about 1 or 2 years.

In some embodiments, the total radiation dose occurs on a single exposure that occurs in a relatively short time period, e.g., about 1-20 minutes to about 12 hours. In other embodiments, the total dose is delivered to the subject in multiple doses or over a longer time, e.g., over about 2 days to about 12 months or more in multiple doses in, e.g., 2, 3, 4, 6, 8, 10 or more individual doses. Ameliorating a side effect may comprise detectably slowing the progression of a symptom or condition or detectably reducing the ultimate expected severity of a symptom or condition. The affected condition or symptom may be detectably reduced as determined by the subject or the health care provider. Thus, after administration of a F1C, the target symptom or condition may be moderately reduced, slightly reduced, essentially nonexistent or subclinical, e.g., present at a low level that is not deemed significant by the subject or the health care provider. Amelioration of one or more conditions or symptoms that can be suitably quantified may be observed as a decrease of about 5% or more, e.g., at least about 10%, at least about 20%, at least about 30%, at least about 40%, at least about 50%, at least about 70%, at least about 80% or at least about 90% in the relative expected or potential severity or extent of the condition or symptom.

For example, in lung pneumonitis, administration of a F1C can lead to detectably increased oxygen saturation in the subject's blood by about 5% or by about 10% or more, e.g., oxygen saturation can rise from about 83% to about 88%, which would typically be detectable by the subject and the health care provider. Such decreased severity of a condition or symptom may be objectively measured in some instances, e.g., by determining the number or activity of circulating platelets or neutrophils or by evaluation of fever, severity or frequency of diarrhea or blood oxygen saturation levels. For other symptoms or conditions, prevention may be subjectively observed by a significant or detectable improvement in a relevant score, e.g., decreased fever or pain or a decreased need for treatment of fever, pain or inflammation.

Symptoms or conditions of radiation exposure that can be treated also include encephalopathy, myelopathy, nausea, diarrhea, acute inflammation, chronic inflammation, edema, pain, fever, headache, depression, malaise, weakness, hair loss, skin atrophy, skin ulceration, skin lesion, keratosis, telangiectasia, infection, e.g., bacterial, viral, fungal or yeast infection, hypoplasia, atrophy, marrow hypoplasia, hemorrhage, fibrosis, e.g., lung fibrosis, pneumonitis, bone marrow hypoplasia, hemorrhage or cytopenia, e.g., anemia, leukopenia or thrombocytopenia, edema, fibrosis or hemorrhage or the need for edema, fibrosis or hemorrhage treatment. Such symptoms or conditions may arise from one or more radiation-damaged tissues or cells, including lymphoid cells, bowel or intestinal epithelium or tissue, bone marrow, testicles, ovaries, brain tissue, spinal cord tissue or skin epithelium.

Exemplary symptoms or conditions associated with late effects of radiation exposure include (1) acute or chronic radiation-induced enteritis or diarrhea, e.g., in patients receiving pelvic radiotherapy, (2) pseudomembranous inflammation, (3) perivascular fibrosis, (4) endothelial cell damage or death, e.g., associated with vascular radiation therapy, (5) cardiac tissue inflammation or damage or pericardial disease, e.g., in pediatric or adult patients receiving radiation therapy for a leukemia, thoracic neoplasm or other malignancy, (6) pulmonary tissue inflammation or damage, (7) hematopoietic or marrow cell inflammation or damage, e.g., in wide field radiation therapy, (8) endocrine or thyroid dysfunction, e.g., in thalamic or hypothalamic tumors in pediatric or other patients, (9) decreased growth or decreased bone development or density, e.g., in pediatric patients receiving radiation therapy for a childhood leukemia or other malignancy, (10) central nervous system inflammation or damage, e.g., in pediatric or adult patients receiving radiation therapy for a leukemia (e.g., CNS acute lymphocytic leukemia) or other malignancy, (11) connective tissue damage after radiation therapy, (12) incidence or severity of a secondary leukemia such as acute myelogenous leukemia or myelodysplasia and (13) gastric ulceration, bleeding, small bowel obstruction or fistula formation in, e.g., patients receiving radiation therapy to the gastrointestinal tract. These symptoms or conditions are treated or ameliorated using the F1Cs essentially as disclosed herein.

In treating such symptoms or conditions, slowing the progression of a symptom, condition or side effect will detectably reduce the rate at which the condition, symptom or side effect worsens or intensifies. In some embodiments, pronounced slowing of the rate of progression is, e.g., the time needed to progress to an expected or a measurable point, which may be increased by a period of about 1, 2, 3, 4, 5, 10, 20, 30 or more days to a period of about 1, 2, 3, 4, 6, 8, 10, 12, 18, 24, 36, 48, 72 or more months.

Radiation-associated brain damage can give rise to acute encephalopathy with symptoms such as headache, nausea, vomiting, somnolence, depression, disorientation, and worsening neurologic signs. The encephalopathy may arise from the first, second or a subsequent radiation fraction, e.g., when high intracranial pressure has not been treated with, e.g., corticosteroids. Late-delayed radiation damage to the brain or nervous system can arise at about 2, 3, 4, 5, 6, 7, 8, 9, or 10 months to 1, 2, 3 or more years after leukemia prophylaxis in children or after brain tumor prophylaxis or treatment in adults. Symptoms often include pain or headache and progressive dementia without focal signs and adults typically also develop an unsteady gait. Cerebral atrophy appears on CT scans in some cases. Late-delayed damage can arise at about 1 week, about 2 weeks about 2 months or about 1-2 years after irradiation of extracranial tumors or high-dose irradiation of intracranial tumors, e.g., brachytherapy or radiosurgery, although the symptoms are generally more focal. The invention method would be used during the time period when such symptoms would be expected to arise, e.g., commencing at about 1-5 days or about 7-60 days after radiation exposure and ending at about 0.5, 1, 2, 3, 4, 5 or more years later. Exemplary brachytherapies and unsealed source therapies include prostate $^{125}$I seed implants in prostate conditions such as prostate cancer, $^{90}$Yt conjugated to monoclonal antibodies or in endovascular brachial radiotherapy.

Early-delayed radiation spinal cord myelopathy follows radiation therapy to the spinal cord, neck, upper thorax or lumbar region or and it is often characterized by Lhermitte's sign, i.e., an electric shock-like sensation radiating down the back and into the legs on neck flexion. Late-delayed radiation myelopathy can arise months or years after therapy for extraspinal tumors, e.g., Hodgkin's disease. Other symptoms can include progressive weakness and sensory loss, such as a Brown-Séquard type, i.e., a proprioceptive sensory loss and weakness on one side of the body and loss of temperature and pain sensation on the other side. Progression times vary, but many human patients suffering from late-delayed radiation spinal cord myelopathy become paraplegic. Late-delayed radiation neuropathy may produce brachial neuropathy, e.g., after treatment for breast or lung cancer. Radiation can also give rise to gliomas, meningiomas, or peripheral nerve sheath tumors at about 1, 2, 3, 4, 5 or more years after therapy. The F1Cs will generally be administered at about the time period when these symptoms would be expected to arise, e.g., commencing at about 1-5 days, or about 7-60 days or about 6 or 12 months after radiation exposure and ending at about 3, 4, 6 months later or about 1, 2, 3, 4, 5, 6 or more years later. In some embodiments, the F1C is administered to the subject on the same day that a planned or accidental radiation exposure occurs and dosing is continued for about 1, 2, 3, 4, 8, 12 or more weeks to about 2, 3, 4, 5, 6 or more years, or for a time as disclosed elsewhere herein.

Early-delayed encephalopathy often arises or is detectable at about 2, 3 or 4 months after radiation therapy. This encephalopathy in adults, is distinguished from worsening or recurrent brain tumor by, e.g., computed tomography (CT) or magnetic resonance imaging (MRI). The condition in children can occur as a somnolence syndrome, e.g., after whole-brain irradiation for leukemia. The condition in children typically improves spontaneously over several days to weeks. Such encephalopathies can be prevented, delayed in onset, recede more rapidly and/or be less severe when a F1C is administered to the subject throughout the period when encephalopathy can arise, e.g., beginning about a week, two weeks or a month before the expected onset of a symptom or condition and ending about a week or month or two months after it would be expected to arise or to resolve.

In some embodiments, a radiation late effect is a symptom or condition that may arise months or years after radiation exposure, treatment with the F1C can commence shortly, e.g., about 0.5, 1, 2, 3, 4, 5, 10, 14, 21 or 28 days, after the radiation exposure or after initiation of a radiation treatment. In other embodiments, the invention treatment method can commence after radiation exposure has terminated, e.g., about 1-30 days or about 1-72 months or more after radiation exposure. In these embodiments, the treatment method can be administered over a period of months or years, e.g., about 0.5, 1, 2, 3, 4, 5, 6, 12, 18, 24, 36, 48, 72, 96 or more months. In some embodiments, dosing of the subject will occur for a period of about 2-12 months or for a period of about 4-6 months. Occasionally, treatment for radiation late effects will commence on the day of or before initiation of a planned radiation treatment, e.g., at about 1, 2, 3, 4, 5, 7, 14, 21, 28 or more days before a planned exposure to radiation of a sufficient dose to a subject that will potentially generate, or is likely to generate, one or more radiation late effects, symptoms or conditions in the subject, e.g., any radiation-associated symptom or condition disclosed herein. In any of these embodiments, dosing of the subject with the F1C can be on a daily dosing basis or on an intermittent basis, e.g., using a treatment protocol essentially as described herein or in the cited references.

The F1Cs can be used to prevent, ameliorate, slow the progression and/or reduce the ultimate severity of marrow hypoplasia, hemorrhage, e.g., brainstem hemorrhage, cerebral hemorrhage or gastric hemorrhage or cytopenia, e.g., a blood cell count about 4-25% or more below the low end of a normal range for the subject, e.g., one or more of anemia (e.g., less than about $4.0 \times 10^{12}$ red cells/L for adult human females and less than about $4.5 \times 10^{12}$ red cells/L in adult human males or a hemoglobin level of less than about 12.0 g/dL in adult human females and less than about 13.5 g/dL in adult human males), late effect leukopenia (e.g., adult human white blood cell counts less than about 3,800, 4,000 or 4,300 mm$^{-3}$; adult human basophil counts less than about 10 or 15 mm$^{-3}$; adult human neutrophil counts less than about 1,600, 1,800 or 2,000 mm$^{-3}$; human eosinophil level less than about 100, 120 or 150 mm$^{-3}$; monocyte level less than about 260 or 300 mm$^{-3}$) or late effect thrombocytopenia (e.g., human platelet counts less than about 15,000, 18,000 or 20,000 mm$^{-3}$).

In some embodiments, an effective amount of a F1C is administered to a subject, or delivered to the subject's tissues, wherein the subject has received or has been exposed to a total radiation dose of at least about 0.5 Gy to about 100 Gy or more. The radiation dosage may comprise a single dose or two, three, four, five, six, 10 or more divided doses or subdoses. Thus, in exemplary embodiments, the subject may have received a total radiation dose in ranges of about 0.2-300 Gy, about 0.2-100 Gy, about 0.2-80 Gy 0.2-60 Gy, about 0.2-40 Gy, about 0.2-20 Gy, about 0.2-12 Gy, about 0.2-10 Gy, about 0.2-8 Gy, about 0.2-6 Gy or about 0.2-4 Gy. Subdivided doses may be administered on 1, 2, 3, 4, 5, 6, 7, 8, 9, 10 or more occasions and such doses may be, e.g., about 0.05, 0.1, 0.3, 0.5, 0.8, 1, 2, 3, 4, 5, 6 or more Gy per subdose. The subject may be exposed to radiation subdoses over a period of about one day or over several days, e.g., about 2, 3, 4, 5, 6, 8, 10, 20 or 25 days, or over a period of months, e.g., about 1, 2, 3, 4, 5, 6, 8, 10, 12, 15, 18, 24, 36, 48 or more months. When a subject is exposed to a full dose or a subdose of radiation, the exposure will occur over a period of about 1 minute to about 48 hours, typically about 2-120 minutes or about 4-60 minutes. Radiation doses or subdoses may be, e.g., about 0.01, 0.05, 0.1, 0.2, 0.5, 0.8, 1, 1.5, 2, 2.5, 3, 4, 5, 6 or 8 Gy per dose or subdose.

Administration of the F1C will typically commence at about 1 day to about 6 months after a subject has received a total radiation exposure, e.g., any dose or dose range disclosed herein. Typically, the F1C is used in the invention method commencing at about 2-120 days after radiation exposure or at about the time that radiation delayed effects become apparent to the subject or the subject's health care provider, e.g., within about 1-30 days after a condition or symptom is detected. Administration of the F1C may continue for a period of about 5 days to about 60 days for conditions or symptoms that tend to resolve over a relatively short time period. In other embodiments, the F1C is administered for a period of 2, 3, 4, 5, 6, 8, 10, 12, 15, 18, 24, 36, 48, 60 or more months for conditions or symptoms that tend to be chronic (e.g., neurological damage or inflammation), arise over a long time period (e.g., secondary cancers or neurological damage) or to progress over a relatively long time, e.g., about 1-5 years or more (e.g., cancers or neurological damage).

In any of the radiation exposure embodiments or dosing protocols disclosed herein, the F1C can be administered to the subject daily or on an intermittent basis, e.g., on about 1-5 days/week or about 2-10 days/month. In daily dosing embodiments, the F1C is administered to the subject daily for about 3 days to about 5 years or longer. Exemplary daily dosing embodiments include daily administration of a F1C for about 14, 30, 60, 90, 120, 180, 360 or more days. Daily doses may be administered in a single dose or as divided subdoses that are given, e.g., twice, three times, four times or more per day. In intermittent dosing embodiments, the F1C can be administered to the subject on 1, 2, 3, 4 or 5 days within a one week period, followed by a period of about 1, 2, 3, 4, 5, 6, 7, 8, 9, 10, 12, 16, 20, 24, 28 or 32 weeks without administration of the F1C, followed by administration of the F1C to the subject on 1, 2, 3, 4 or 5 days within a one week period. In other intermittent dosing embodiments, the F1C is administered to the subject every other day, every two days, every three days, every 4 days or every seven days.

For any radiation exposure situation where delayed radiation effects may arise, e.g., a radiation exposure as disclosed herein, daily administration may comprise administering about 0.01 mg/kg to about 500 mg/kg of the F1C to a subject per day. Exemplary dosages are about 0.1-100 mg/kg/day and about 0.2-30 mg/kg/day. Exemplary unit doses comprise about 1, 5, 10, 15, 20, 25, 30, 40, 50, 75, 100, 200, 300 or 500 mg of a F1C in a suitable formulation. Exemplary unit dosages for humans or other subjects disclosed herein comprise a formulation that comprises about 1-1000 mg of a F1C or about 5-400 mg or about 10-300 mg, e.g., about 5, 10, 20, 25, 30, 40, 50, 60 75, 100, 150, 200, 250, 300, 400 or 500 mg. Larger unit or daily dosages, e.g., about 5-400 mg, will generally be used with larger subjects such as humans, while smaller subjects such as rodents or dogs will generally utilize lower unit or daily dosages, e.g., about 0.3-25 mg.

Modulation of transcription factors, receptors and gene expression. In treating any of the diseases, conditions or symptoms disclosed herein, the F1Cs can modulate, i.e., detectably enhance or increase or detectably inhibit or decrease, the expression or a biological activity(ies) of one or more transcription factors or receptors. This can lead to detectable modulation of target gene activity or expression as part of the treatment or amelioration of the disease, condition or symptom. Such modulation can arise from changes in the capacity of a transcription factor or receptor to bind to or form a complex with other natural ligands such as a target DNA sequence(s), another transcription factor(s), a transcription cofactor, a receptor such as a nuclear hormone receptor or cell membrane receptor (e.g., a lipid, peptide, protein or glycoprotein receptor such as an interleukin receptor or a growth factor receptor), a receptor cofactor or an enzyme such as a polymerase, kinase, phosphatase or transferase. The effects of F1Cs on these biomolecules can be exerted in immune cells or in non-immune tissue, e.g., cells or tissue adjacent to diseased tissue such as infected or malignant cells. The F1Cs may directly or indirectly modulate the capacity of any of these molecules to transduce signals that are part of normal signal transduction processes.

In many of the clinical conditions described herein, e.g., in cancers, infections, acute inflammation, chronic inflammation, trauma, neurological conditions or autoimmunity, the F1Cs can modulate, e.g., detectably decrease or increase, a biological activity(ies), protein or molecule level or RNA level of 1, 2, 3, 4, 5, 6 or more biomolecules that are involved in establishment, maintenance or progression of a disease, condition or symptom. Such biomolecules include 1, 2, 3, 4, 5, 6 or more of AP-1, a cyclooxygenase such as mammalian or human cyclooxygenase-1 (COX-1) or cyclooxygenase-2 (COX-2), a mammalian or human lipoxygenase, e.g., 5-lipoxygenase, TNFα, TNFα receptor 1, TNFα receptor 2, TNF receptor-associated factor, TNFβ, TNFβ receptor, MIP-1α, monocyte chemoattractant-1 (MCP-1), interferon gamma (IFNγ or γIFN), IL-1α, IL-1β, IL-1α receptor, IL-1β receptor, IL-2, IL-3, IL-4, IL-4 receptor (IL-4R), IL-5, IL-6, IL-6 receptor (IL-6R), IL-8, IL-8 receptor (IL-8R), IL-10, IL-10 receptor (IL-10R), IL-12, an IL-12 receptor, (e.g., IL-12Rβ2), IL-13, IL-15, IL-17, IL-18, nuclear factor kappa B (NFκB), AP-1, c-maf, v-maf, mafB, NrI, mafK, mafG, the maf family protein p18, reactive oxygen species, e.g., peroxynitrite, hydrogen peroxide or superoxide ion (collectively ROS), a 17β-hydroxysteroid dehydrogenase (17β-HSD) or an 11β-hydroxysteroid dehydrogenase (11β-HSD), e.g., 11β-HSD type 1, 11β-HSD type 2, 17β-HSD type 1, 17β-HSD type 2 or 17β-HSD type 5, a steroid aromatase, e.g., cytochrome P450 aromatase, steroid 5α-reductase, serum or blood cortisol, cytosolic phospholipase A2 (cPLA2), calcium-independent phospholipase A2 (iPLA2), a prostaglandin, e.g., prostaglandin E2 (PGE2) or prostaglandin D2 (PGD2), a leukotriene, e.g., leukotriene B4, inducible nitric oxide synthetase (iNOS), nitric oxide (NO), GM-CSF, RANTES (regulated on activation, normal T cells expressed and secreted), eotaxin, GATA-3, CCR1, CCR3, CCR4, CCR5, CXCR4, in, e.g., a subject's cell(s) or tissue(s) or in enzyme, tissue or cell-based assays. In these subjects, the levels of other biomolecules, their RNAs or the level of their activity can be detectably modulated include IFNα, INFα receptor, PPARα, PPARγ, PPARδ or a transcription factor such as T-bet is detectably increased. Other biomolecules or their isoforms, polymorphs, orthologs, or homologs that the F1Cs directly or indirectly modulate include one or more of, e.g., Janus kinase 1 (JAK1), Janus kinase 2 (JAK2), Janus kinase 3 (JAK3), signal transducer and activator of transcription 1 (STAT1), signal transducer and activator of transcription 2 (STAT2) and signal transducer and activator of transcription 3 (STAT3). The F1Cs can modulate the other biologically active analogs of any these enzymes, chemokines, cytokines, their receptors or ligands, including their isoforms, polymorphs, orthologs or homologs. In some cells or tissues, one or more of these biomolecules may be detectably increased, while in other cells or tissues, the same biomolecule may be detectably decreased. Thus, the biomolecules that the F1Cs can modulate, e.g., detectably increase or decrease, include the intracellular or extracellular level or biological activity of one or more enzyme, cytokine, cytokine receptor, chemokine and/or chemokine receptor. Exemplary chemokine receptors include one, two or more of CCR-1, CCR-2, CCR-2A, CCR-2B, CCR-3, CCR-4, CCR-5, CXCR-3 and CXCR-4.

The F1Cs can modulate the activity of certain biomolecules that mediate various biological responses that affect establishment or progression of a disease or that enhance or inhibit specific immune responses. Thus, in conditions where unwanted inflammation is present, the F1Cs can reduce inflammation, while enhancing Th1 or Tc1 immune responses at the same time. The biomolecules that the F1Cs can modulate include, e.g., transcription factors or receptors, including orphan nuclear receptors, and the homologs, isoforms, orthologs and co-factors (e.g., co-repressors, co-activators, transcription factors, gene promoter regions, sequences or messenger moieties such as calcium ions, potassium ions or cAMP) of any of these molecules and related molecules that participate in their function. The compounds can directly or indirectly from complexes with such molecules or they can modulate (detectably increase or decrease) the synthesis, level or one or more biological activities of those molecules. These complexes include receptors or transcription factor complexes, which can comprise heterodimers, homodimers and trimer, tetramer, pentamer or higher homo or hetero complexes. A number of the orphan receptors or their isoforms, orthologs or homologs, e.g., PPARα, PPARβ, PPARγ, PPARγ1, PPARγ2, PPARγ3, LXRα, LXRβ, SXR, PXR, CARα and CARβ, can form heterodimers with one or more of RXRα, RXRβ and RXRγ.

Exemplary mammalian, human or other biomolecules include steroidogenic factor-1 (SF-1), steroidogenic acute regulatory protein (StAR), a chicken ovalbumin upstream promoter-transcription factor (COUP-TF), chicken ovalbumin upstream promoter-transcription factor (COUP-TFI) and its mammalian isoforms, orthologs and homologs, silencing mediator for retinoid and thyroid hormone receptor (SMRT) and its mammalian isoforms, orthologs and homologs, sterol regulatory element binding protein (SREBP) 1a (SREBP-1a), SREBP-1c, SREPB-2, NF-E3, FKHR-L1, COUP-TFII and its mammalian isoforms, orthologs and homologs, and the isoforms, orthologs and homologs of IκB, IκBα, AML-3, PEBP2αA1, Osf2, Cbfa1, RUNX2, activating transcription factor 2 (ATF2), c-Jun, c-Fos, a mitogen activated kinase (MAP) such as p38 or JNK, a mitogen activated kinase kinase (MKK), a p160 or steroid receptor coactivator-1 family (SRC-1, SRC-1/serum response factor), SRC-2, SRC-3, SET, nerve growth factor inducible protein B, StF-IT, NFAT, NFAT interacting protein 45 (NIP45), IkB, an IkB kinase, NFATp, NFAT4, an AP-1 family protein, a p300 protein, CREB, CREB-binding protein (CPB), p300/CBP, p300/CPB-associated factor, SWI/SNF and their human and other homologs, BRG-1, OCT-1/OAF, AP-1, AF-2, Ets, androgen receptor associated protein 54 (ARA54), androgen receptor associated protein 55 (ARA55), androgen receptor associated protein 70 (ARA70), androgen receptor-interacting protein 3 (ARIP3), ARIP3/PIASx α complex, PIASx α, Miz1, Miz1/PIASx β complex, PIASx β, PIAS1, PIAS3, GBP, GBP/PIAS1 complex, RAC3/ACTR complex, SRC-1α, receptor interacting protein-140 (RIP-140), transcription factor activator protein-1, activation function-2, glucocorticoid receptor-interacting protein-1 (GRIP-1), receptor interacting protein-160 (RIP-160), suppressor of gal4D lesions (SUG-1), transcription intermediary factor-1 (TIF-1), transcription intermediary factor-2 (TIF-2), SMRT, N-CoR, N-CoA-1, p/CIP, p65 (RelA), the 120 KD rel-related transcription factor, heat shock proteins (HSP) such as HSP90, HSP70 and HSP72, heat shock factor-1, Vpr encoded by the human immunodeficiency virus and its isoforms and homologs thereof, testicular orphan receptor 2 (TR2), testicular orphan receptor 4 (TR4), a thyroid hormone receptor α, thyroid hormone receptor α1 (TRα1), thyroid hormone receptor α2 (TRα2), thyroid hormone receptor β (TRβ), retinoid X receptor α (RXRα), retinoid X receptor β (RXRβ), retinoid X receptor γ (RXRβ), TR α1/RXR α heterodimer, direct repeat-4 thyroid hormone response element (DR4-TRE), an estrogen receptor (ER) such as ERα or ERβ, estrogen receptor related receptor α (ERRα or EER1), estrogen receptor related receptor β (ERRβ or EER2), estrogen receptor related receptor γ (ERRγ or EER3), steroid xenobiotic receptor (SXR), a hepatocyte nuclear factor 4 (HNF-4), hepatocyte nuclear factor 4γ (HNF-4γ), hepatocyte nuclear factor 3 (HNF-3), liver X receptors (LXRs), LXRα, LXRβ, estrogen receptor α (ERα), constitutive androstane receptor-α (CAR-α), constitutive androstane receptor-β (CAR-β), RXR/CAR-β heterodimer, short heterodimer partner (SHP; NR0B2), SHP/ERα heterodimer, estrogen receptor α, SHP/ERβ heterodimer, testicular orphan receptor TR4, TR2/TR4 heterodimer, pregnane X receptor (PXR) and isoforms, cytochrome P-450 monooxygenase 3A4, including its gene promoter region and isoforms thereof, HNF-4/cytochrome P-450 monooxygenase 3A4 gene promoter region and isoforms complex, HIV-1 long terminal repeat (LTR), HIV-2 LTR, TR2/HIV-1 LTR complex, TR4/HIV-1 LTR complex, TR4/HIV-1 LTR complex, TR α1/TR4/HIV-1 LTR complex, TR2 isoforms (TR2-5, TR7, TR9, TR11), DAX-1 (NR0B1), DAX-1/steroidogenic acute regulatory protein gene promoter region, RevErb, ReverbA α, Rev-erb β, steroid receptor coactivator amplified in breast cancer (AIB 1), p300/CREB binding protein-interacting protein (p/CIP), thyroid hormone receptor (TR, T3R), thyroid hormone response elements (T3RES), retinoblastoma protein (Rb), tumor suppressor factor p53, transcription factor E2F, mammalian acute phase response factor (APRF), constitutive androstane receptor (CAR), *Xenopus* xSRC-3 and mammalian (e.g., human) isoforms, orthologs and homologs, TAK1, TAK1/peroxisome proliferator-activated receptor α (PPARα) complex, PPARα/RXRα complex, peroxisome proliferator-activated receptor β (PPARβ), peroxisome proliferator-activated receptor γ (PPARγ), peroxisome proliferator-activated receptor δ (PPARδ), farnesoid X receptor, retina X receptor, TAK-1/RIP-140 complex, a retinoic acid receptor (RAR), retinoic acid receptor-β (RARβ), retinoic acid receptors (RARγ), TR4/RXRE complex, SF-1/steroid hydroxylase gene promoter region, SF-1/oxytocin, including its gene promoter region, a bile acid receptor (FXR), nuclear receptor corepressor (NcoR), liver receptor homologous protein-1 (LRH-1; NR5A2), SF-1/ACTH receptor gene promoter region, rat Ear-2 and mammalian homologs, human TR3 orphan receptor (TR3), RLD-1, OR-1, androgen receptor, glucocorticoid receptor, estrogen receptor, progesterone receptor, mineralcorticoid receptor, aldosterone receptor, E6-associated protein (E6-AP), OR1, OR1/RXRα complex, TIF-1, CBP/P300 complex, TRIP1/SUG-1 complex, RIP-140, steroid receptor coactivator 1 (SRC1), SRC1α/P160 complex and TIF-2/GRIP-1 complex, RAR/N-CoR/RIP13 complex, RAR/SMRT/TRAC-2 complex and protein X of hepatitis B virus. The homologs, orthologs and isoforms of these transcription factors, receptors and other molecules are included among the molecules that the F1Cs can modulate the synthesis or one or more biological activities of. Such factors are biologically active or function in one or more of a number of cell types such as T cells, B cells, macrophages, dendritic cells, platelets, monocytes, neutrophils, neurons, epithelial cells, endothelial cells, cartilage cells, osteoblasts, osteoclasts, splenocytes, thymocytes and GALT associated cells. Methods to identify these molecules and their biological activities have been described, e.g., U.S. Pat. Nos. 6,248,781, 6,242,253, 6,180,681, 6,174,676, 6,090,561, 6,090,542, 6,074,850, 6,063,583, 6,051,373, 6,024,940, 5,989,810, 5,958,671, 5,925,657, 5,958,671, 5,844,082, 5,837,840, 5,770,581, 5,756,673, and PCT publication Nos. WO 00/24245, WO 0073453 and WO 97/39721.

In one aspect, the compounds are used to treat, prevent or to ameliorate conditions or symptoms that are associated with unwanted or expression or activity of one or more of these molecules in conditions such as, e.g., acute inflammation, chronic inflammation or their symptoms, acute allergy, chronic allergy or their symptoms, e.g., allergic rhinitis or acute or chronic asthma, psoriatic arthritis, osteoporosis, osteoarthritis, rheumatoid arthritis, neurological dysfunction or their symptoms, e.g., dementias such as Alzheimer's Disease, Parkinson's Disease, or memory loss conditions, in osteoporosis or in cancer such as breast cancer. The compounds can prevent NFκB from translocating from the cytoplasm into the nucleus and thus can increase the ratio of cytoplasmic NFκB to nuclear NFκB. The F1Cs may inhibit activation of NFκB-mediated transcription while NFκB is bound to target DNA sequences in the nucleus. Alternatively, the F1Cs can activate or enhance the expression of or one or more activity of a transcription factor such as T-bet in, e.g., a subject's cell(s) or tissue(s) or in enzyme or cell-based assays. In this aspect the compounds are used to treat, prevent or to ameliorate conditions or symptoms that are associated with deficient expression or activity of T-bet in conditions such as immune dysfunction in an immunosuppression condition, aging, an infection, a cancer or precancer as described herein or in the cited references.

The invention provides methods to identify compounds to regulate immune or other biological responses in a context-sensitive manner. Such compounds modulate differential expression in a cell of the level of or an activity of, eg., 4, 5, 6, 7, 8 or more genes or gene products, comprising administering an effective amount of a F1C. The genes or gene products are USF1, c-Fos, EGR1, Cul1, RIPK2, IκBα, IκBKb, NF-κB, NF-κB2, NF-κB1 p50, Fn14 (fibroblast growth factor-inducible 14), TWEAK (TNF-like weak inducer of apoptosis), NEMO (NF-κB essential modifier), FCAR, c-Fos/C/EBPβ, RANTES, ICAM1, TSG (TNFAIP6), IL-2 receptor α, GRO2, GRO3, HO1, Jun B, c-Fos/JunB complex, JunB/ATF3 complex, c-Jun, c-Fos/c-Jun complex, ATF-3, MMP1, TSG-6 (TNFAIP3), AP-1, EGR1, TGFβ, ATF-3/c-Jun complex, c-Fos, MMP3, IL-8, STAT5A, STAT5B, CDKN1A, IFNγ receptor 2 (IFNγR2), T-bet, C reactive protein, immunoglobulin E, an AP-1 family protein, GATA-3, Jak2, Tyk2, stat1, stat3, stat4, stat5, MIP-1α, MIP-2, IP-10, MCP-1, TNF-α, TNF-β, LT-β, IFN-α, IFN-β, TGF-β1, NF-κB, IL-1α, IL-1β, IL-4, IL-6, IL-10, IL-12 receptor β1, IL-12p35, IL-12p40, IL-23, IL-23 receptor or another gene or gene product disclosed herein, including in Table 1. The compounds identified by the screening methods modulate the expression of dysregulated genes and restore or enhance normal immune responses in conditions where unwanted dysregulation contributes to the establishment or progression a pathological condition such as an infection, an autoimmune disorder, a cardiovascular condition or a neurological condition.

Thus, in some embodiments, the level or a biological activity of 4, 5, 6, 7, 8, 9, 10, 11, 12, 13, 14, 15 or more of COX-2, IL-1β, TNFα, TNFα receptor 1, TNFα receptor 2, TNF receptor-associated factor, MIP-1α, MCP-1, IFNγ, IL-4, IL-4R, IL-6, IL-6R, IL-8, IL-8R, IL-10, IL-10R, IL-12, IL-12R, IL-18, IL-18R NFκB, IkBα, AP-1, GATA-3, 11β-HSD1, cPLA2, iPLA2, cortisol, ROS, PGE2, PGD2, leukotriene A4, leukotriene B4, leukotriene C4, iNOS or GM-CSF are optionally measured and they are generally detectably reduced, e.g., RNA or protein levels are reduced by about 10-95% or about 20-95% or more compared to suitable untreated controls. In these embodiments, the level or a biological activity of 4, 5, 6 or more of IFNα, INFα receptor, IL-12, an IL-12 receptor, (e.g., IL-12Rβ2), PPARα, PPARγ, and T-bet are optionally measured and they are generally detectably increased. In a chronic infection condition, e.g., HIV in humans, autoimmunity, a chronic fungal or parasite infection or in a precancer or cancer condition, e.g., benign prostatic hyperplasia, the progression of the condition may be slowed over a period of 1, 2, 3, 4, 5 or more years. In these embodiments, the subject's condition becomes more manageable with a reduced incidence or severity of side effects, e.g., a detectable halt, slowing, reversal or decreased incidence of wasting, dementia, CD4 cell count decreases or viral load increases, which tend to occur over time in HIV infected humans or a halt, slowing or reversal of pathogen or precancer or cancer cell replication.

These effects are typically observed after administration of an effective amount of a F1C using, e.g., a method or dose essentially as disclosed herein. The simultaneous reduction of multiple biomolecules provides a method to modulate immune responses by modulating multiple pathways that lead to a common condition such as inflammation. This provides a method to treat or ameliorate, e.g., acute or chronic inflammation, a cancer, an infection or a symptom associated therewith, or to slow the progression of or reduce the severity of these conditions or their symptoms.

Previously described methods can be used to measure the amount, activity or cellular location of various biomolecules such as cytokines or transcription factors. See, e.g., U.S. Pat. Nos. 6,107,034, 5,925,657, 5,658,744, 4,016,043 and 3,850,752, S. Szabo et al., *Cell* 2000 100:655-669, Y. Nakamura et al., *J. Allergy Clin. Immunol.* 1999 103(2 pt. 1):215-222, R. V. Hoch et al., *Int. J. Cancer* 1999 84:122-128. These methods can be used to measure the effects of the F1Cs on transcription factors or receptors in cells or tissues that have been exposed to the compounds.

Without wishing to be bound to any theory, the F1Cs may modulate multiple biomolecules in a microenvironment sensitive manner or context. The effects of the compounds can provide a decrease in a particular molecule such as IFNγ and a decrease in inflammation associated with elevated IFNγ levels or activity without eliminating beneficial effects of the molecule. This effect arises from decreasing the level or activity of a biomolecule such as IFNγ in cells that are dysregulated, while allowing normal immune cells to produce sufficient amounts of the same molecule to perform normal immune functions. In locations where the biomolecule is needed for activity, e.g., in lymph nodes or spleen cells, sufficient amounts of the modulated molecule are present to elicit a desired response, while the level of the molecule in cells in circulation decreases. The compounds can increase IL-13, IL-15, IL-17 or IL-18 in conditions where a subject has a deficient Th1 immune response, e.g., in infection or cancer. Conversely, the compounds can decrease IL-13, IL-15 or IL-18 in conditions such as allergy or autoimmune conditions, e.g., multiple sclerosis, where an excess Th1 immune status may prevail.

In general, the F1Cs will detectably decrease the synthesis or one or more biological activity of one or more of these molecules (or other transcription factors or receptors disclosed herein) when such synthesis or activities is associated with the establishment, maintenance, progression or enhanced severity of a clinical condition or symptom disclosed herein. Conversely, the F1Cs will generally detectably increase the synthesis or one or more biological activities of one or more of these molecules (or other transcription factors or receptors disclosed herein) when such synthesis or activity is associated with the treatment, prevention, cure or amelioration of a clinical condition or symptom disclosed herein.

These decreases or increases compared to suitable controls can be relatively small, including changes near the lower limits of delectability for such molecules using known or new assays, e.g., a decrease or increase in the synthesis or biological activity of at least about 2%, about 5%, about 10% or about 20%. Such changes can be modest or relatively large, e.g., at least about a 50% change, at least about a 90% change, or at least about a 200% change, up to about a 5-fold, about a 10-fold, about a 100-fold or greater decrease or increase in the synthesis or biological activity of the affected molecule(s) compared to suitable controls. These changes are typically measured relative to controls that lack a F1C or that use known agonists or antagonists of one or more relevant molecules. Assays can be based on measuring decreases or increases in, e.g., one or more of protein levels, RNA or mRNA levels, a ligand binding activity, transcription of a target gene(s) and the like. Suitable assay protocols include any suitable polymerase chain reaction assay to measure an RNA or mRNA, any suitable blotting protocol for nucleic acid or for protein such as a Northern or Western blot method or any transcription assay, including DNA footprinting or a gene expression or gene function assay. Typically the F1Cs will effect detectable changes in the synthesis or one or more biological activities in a concentration range of about $0.5 \times 10^{-9}$ M to about $3 \times 10^{-5}$ M. Exemplary compositions that comprise a F1C for use in, e.g., in vivo animal assays, in vitro cell or tissue culture assays or in cell free assays, will comprise one or more suitable solvents or vehicles including DMSO, ethanol, water and a suitable tissue culture medium.

One or more of these transcription factors, receptors or complexes can be a component in methods when, e.g., they are used with a F1C in cell-free assays or in tissue culture assays. Formation of these complexes in cells or analysis of the effects of F1Cs on one or more of their biological activities is facilitated by inserting into the cells a DNA construct(s) that expresses one or more of these proteins, e.g., mammalian or yeast cells containing a stable DNA construct or a construct used for transient transfection assays. Methods to perform assays or to induce biological responses in vitro or in vivo using the F1Cs as agonists, antagonists or as reference standards are essentially as described, see, e.g., U.S. Pat. Nos. 5,080,139, 5,696,133, 5,932,431, 5,932,555, 5,935,968, 5,945,279, 5,945,404, 5,945,410, 5,945,412, 5,945,448, 5,952,319, 5,952,371, 5,955,632, 5,958,710, 5,958,892 and 5,962,443; International Publication Numbers WO 96/19458, WO 99/41257 and WO 99/45930. The complexes or assay systems, that comprise a F1C and one or more of these molecules are embodiments of the invention, as are the use of these compositions when employed in the practice of any of the assay methods or in any of the clinical treatment methods disclosed herein or in the cited references.

Invention embodiments include a method comprising contacting a F1C(s) with a cell(s), whereby the F1C(s) forms a complex with a steroid hormone receptor or results directly or indirectly in the modulation of a biological activity of the steroid hormone receptor or a gene that it regulates. The steroid hormone receptor may be an orphan nuclear hormone receptor or a characterized receptor such as the glucocorticoid receptor, estrogen receptor or the androgen receptor that displays a moderate or high binding affinity for the F1C(s). In some embodiments, the nuclear hormone receptor is a known receptor. Biological effects from interaction of a F1C and a receptor can lead to interference with the replication or development of a pathogen or the cell(s) itself, e.g., detectably inhibited proliferation of cancer cells. For example, expression of HIV transcripts in HIV-infected cells may be altered. The receptor-F1C complex may directly interfere with LTR-dependent transcription of HIV genes, leading to reduced viral replication. Alternatively, such effects can include the decreased synthesis or biological activity of a protein or gene product that is associated with the establishment, maintenance or progression of a disease condition described herein or in the cited references.

An aspect of F1C biological activity is their capacity to modulate the capacity of cells or tissues described herein to express one or more enzymes that mediate phase II detoxification and reduction of damaging or reactive species such as xenobiotics, including electrophiles and chemical carcinogens, and superoxide radicals or hydrogen peroxide. Modulation of these genes is mediated by one or more transcription factors or complexes of factors that include bZip transcription factors such as Nrf2 (NF-E2 related factor 2, Unigene symbol Nfe2L2) and Maf proteins such as MafG, MafK or MafF. These factors bind to cis-elements such as EpRE (electrophile response element) or ARE (antioxident response element). EpRE and/or ARE elements present in the promoters of phase II detoxification enzymes including NAD(P)H:quinine oxidoreductase-1 (NQO1) and glutathione-S-transferase (GST)

as well as cellular defensive enzymes such as thioredoxins, heme oxygenase 1 (HO 1, or HMOX1), the catalytic and regulatory subunit γ-glutamylcycleine syhthetase (γGCS or GCLM) and xCT (SLC7A11), a subunit of the cystine/glutamate exchange transporter. EpRE and ARE mediate upregulation of these genes following exposure of the cells to many xenobiotics. In situations where enhanced expression of these genes or transcription factors is desirable, the F1C upregulate the activity or levels of one or more of these factors and/or enzymes.

Thus, in some embodiments the F1C are used to modulate the level or activity of one or more of Nrf2, a thioredoxin, NQO1, GST, HO 1, the catalytic subunit of γGCS, the regulatory subunit of γGCS and xCT in cells or tissues that are exposed to a F1C. In some embodiments, the cells or tissues are treated with a F1C when an unwanted acute or chronic condition such as toxin exposure or elevated oxidative stress is present in the cells or tissues. Such conditions can occur, e.g., as described elsewhere herein, including in acute or chronic pathological inflammation conditions, acute or chronic infections and trauma conditions. The effect of the F1Cs is restoration of normal expression or establishment of desired levels of expression of one or more of these transcription factors or enzymes, e.g., decreased expression in situations where chronic over-expression occurs. Thus, the F1C can be used to modulate these or other genes described herein, e.g., to decrease expression or mRNA levels or protein levels of one or more of these or other genes in clinical conditions where excess or unwanted expression or levels of the gene is associated with establishment, maintenance, severity or progression of the clinical condition resulting in clinical improvement in the disease or an unwanted symptom.

Other genes in cells or tissues in vitro or in vivo that the F1Cs can modulate include 1, 2, 3, 4, 5, 6 or more of the following genes (which are listed by their Unigene symbols): LOC55967, 37149, LOC64148, LOC57823, AGPAT1, PHACS, OAS1, OAS3, OASL, IFRG28, C(27)-3BETA-HSD, LOC55831, HMGCR, HMGCS1, PDPK1, HPD, AIRP, PFKFB3, DHCR7, OGG1, ADAM9, ADAMTS1, ADAMTS10, AKAP1, AKAP10, AKAP3, AKAP4, AKAP8, TOB3, ABO, AIM1, LOC55902, ACAT2, ASMTL, ACP5, OA48-18, ACO1, ACO1, ACR, ABLIM, ACF7, LOC81569, ARPC4, ACTC, ACTG2, ACTL6, ALCAM, PC4, ATF1, ATF3, ATF4, AICDA, ABR, ACVR1, ACVR2, ACADS, ACOX1, ACOX2, AOAH, ACYP1, AD-003, LOC55829, AP1B1, AP1G2, AP1S1, AP2M1, AP3B2, AP3M1, ADD3, ADORA2A, ADORA2B, ADA, ADAR, ADAT1, AMPD1, ADCY3, ADCY7, AK1, ADSL, ARF4, ARF4L, ARF6, ARL4, ADPRTL2, ART3, LOC51578, ADRB2, ADRB3, ADM, ADMR, AGER, AFG3L1, AFG3L2, AGC1, AGRP, ALDH1A1, ALDH1B1, ALDH2, AKR1C1, AKR1C2, AKR1C3, AKR7A2, AKR7A3, ALDOC, ALG5, ALPI, ALPL, ABH, AF1Q, AIF1, KIAA1017, ATRX, A2M, A2M, AMACR, ASPSCR1, ABP1, ACCN1, ACCN2, AOC2, ACY1, ALAD, ALAS1, LOC64167, AMPH, AGL, APPBP1, ALS2CR2, AGTRL1, ANK2, ASB1, ASB2, ANXA1, ANXA11, ANXA9, MOX2, KIN, AMHR2, KIAA0106, APELIN, APG5L, API5L1, APXL, APOARGC, APOC4, LOC51275, APAF1, APAF1, APEXL2, AQP1, AQP2, LOC51326, HSU52521, ARG2, AVPR1B, ARMET, ASS, ALX3, ALX4, ACTR3, ARTN, ARNTL, AIP, ARSA, ARSB, ARSD, ASH2L, AMSH, AKNA, ACLY, ATP5F1, ATP5I, ATP5J, ATP5A1, ATP5C1, ATP50, ATP2A1, ATP2B1, ATP2B2, ATP2C1, ATP7B, ATP6D, ABCA3, ABCA4, ABCA5, ABCA7, ABCC5, ABCD1, ABCE1, ABCF1, ABCF2, ABCG4, AUH, BAL, B29, B7-H3, BPI, BIRC1, BIRC3, BIRC4, BIRC7, BIRC8, BAF53A, BAIAP2, BARX2, BHLHB2, BLZF1, BATF, BTEB1, BCL11A, BCL2, BCL3, BCL6, BCL7A, BCL9, BTG1, BBC3, BMF, BMF, BNIP3, BAG2, BIK, BCL2L1, BCL2L11, BOKL, SBBI42, BFSP1, BBP, ICAT, GAL3ST-4, BACE, BACE2, BACE2, BTRC, BF, BID, BIC, BLVRA, BTD, BPHL, BM88, BN51T, BPOZ, BRI3, BAI2, BSMAP, BCAT2, BCK-DHB, BCRP2, BCAR3, BIG1, BIG2, BAZ1A, BAZ2A, BAZ2B, BP75, BRD1, BRD2, BRD3, BRUNOL5, BRUNOL6, BTK, BTBD2, BTG2, BUB3, BUP, BRF2, BBOX1, BTN3A1, BYSL, LOC81558, C2F, ZFP26, C6.1A, C9orf10, CABP1, CHP, CACNB1, CALM2, CAPN1, CAPN2, CAPN5, LOC57118, H_GS165L15.1, CHST2, CA3, CA11, CA12, CPM, CLC, CROT, CBL, CSNK2A2, CSN2, CFLAR, CASP10, CASP2, CASP6, CASP8, CARD14, CECR5, CECR6, CAT56, CTSC, CTSE, CTSL, CTSS, CTSW, CTSZ, LOC56996, CITED1, CEBPE, CBF2, CNOT2, CD14, CD1A, CD1D, CD2AP, CD33, CD36L1, CD3D, ASE-1, CD3G, CD4, CD44, CD5L, CD69, CD72, CD79A, CD8A, CD8B1, CD83, CD84, CDC14A, CKS2, CEP2, CDC45L, CLK2, TOK-1, CDV-1, CDC25A, CDC25C, CGR19, GP110, CREG, CRABP1, CENTA1, CENTB2, CENTG1, CETN3, CENPA, CENPB, CENPF, CEP1, CER1, CCM1, LOC51148, CLN2, CLN3, FIGF, LOC50999, CGI-152, CGI-152, CHES1, CCR1, CCR8, CCRL2, CX3CR1, CMKLR1, CHN1, CLCN2, CLCN3, CLCA1, CLCA4, CLIC1, CHK, CHKL, LOC56994, CHRNA3, CHRNA4, C4S-2, C4ST, CSPG4, CSPG6, CHAC, CGB8, CSH1, CHAF1B, CBX4, CHD1L, CHD3, CHD3, C11orf14, C21orf11, C22orf5, CTRL, CIG30, CIZ1, LUC7A, CS, CLTCL1, CLDN12, CLDN15, CLDN17, CPSF3, CPSF5, CPSF6, CLU, MERTK, LOC55907, VI, IRLB, JPO1, CIA, CLP, F3, F9, F8, F8A, LOC51137, COPA, CKN1, COQ7, CRSP6, CRSP7, CIAS1, CLPS, COL2A1, COL4A3BP, COL5A3, COL7A1, COL19A1, COL15A1, COL16A1, COL18A1, MIC1, CSF1R, CSF3, C1QA, C1R, C2, C5R1, C8A, C8G, CPLX2, GJA10, CGTHBA, CHUK, CNTN5, CNTNAP1, COPS4, CPNE3, CBFB, CBFA2T3, CORO2A, COX10, CPXCR1, CRY1, CRYGA, CRYZL1, CSK, CTDP1, CLECSF6, CLECSF9, LOC51266, CUGBP2, CUL1, CUL2, CUL3, CUL4B, CUL5, HUMMHCWLA, CNGB1, CCNB3, DMTF1, CCNE2, CCNG2, CNNM2, CNNM4, CDK10, CDK3, CDK7, CDKNLA, CDKNLB, CDKN2B, CDKN2C, CDKN2D, CDKN3, CTH, CBS, CST8, CSTA, CST3, CSRP1, CSRP3, CHORDC1, CCBL1, CRIP2, CHIC2, CYSLT1, CARS, CTNS, CMAH, CYB5, HCS, COX5A, COX7C, LOC57404, CYP51, CYP1A1, CYP1B1, CYP2A6, CYP2D6, CYP2E, CYP2J2, CYP4F3, CYPL1B1, CYP21A2, CYP24, CYP27B1, CRLF2, CREME9, CNK, N-PAC, KIAA0068, PIR121, #22, LOC81501, DRIL2, DDXBP1, DDX10, DDX16, DDX19, DDX8, DELGEF, DAF, DEFB2, DSS1, DLL1, DLL3, DSIPI, KIAA1365, DRPLA, DNASE1, DTYMK, #23, D4ST-1, #24, DDEF1, DRG2, DGKZ, DGAT, DIAPH1, DEF6, DGS-D, DGS-H, DHODH, DPYSL2, DPYD, HUM2DD, DDAH1, DDAH2, HSA249128, DTR, DLG4, DISC1, SAS10, DLX2, UBD, DKFZP434A236, DKFZP434B103, DKFZP434B168, DKFZP434C212, DKFZP434I216, DKFZP434N014, DKFZP434N043, DKFZP434N161, DKFZP564C1940, DKFZP564M1416, DKFZP5640123, DKFZP566C134, DKFZP566F0546, DKFZP566F2124, DKFZP566K023, DC8, CTRP5, DKFZP586M1523, DKFZP727C091, DNMT1, DNMT2, DNMT3B, DFFB, DNAJA1, DNAJB11, DNAJB4, DNAJB5, DNAJB6, DNAJB6, DNAJB9, DNAJC3, DOK2, DPM1, DO, DRD1, DRD5, DUX4, DORFIN, ADAR3, DSCR4, DONSON, DUOX1, DUSP1, DUSP11, DUSP12, DUSP2, DUSP3, DUSP4, DUSP5, DUSP7, DYRK3, DYRK4, DNCI1, DKC1, DMWD, EP300, E2F5, SMURF1, ELF1, EAF1, EAP30, EBF, EDR1, EGR1, EGR2, EGR4, EVI2A, EVI2B, ENC1, ENTPD1, ENTPD2, EMR1, EMR3, EGLN1, EHD1, EHD2, ETFB, HSA277841, ELK4, EMK1, ELKS, ELL, EVC, ELL2, ELOVL4, EMD, KIAA0709, ENG, PODLX2, ERO1-L(BETA), ENDOFIN, EDG4, EPAS1, EZFIT, EDN1, ET(B)R-LP-2, EN1, HEF1, ERH, EZH1, ENO3, ENO1B, EFNA2, EFNB1, LOC84648, EPS15R, EPM2A, EPIM, EMP2, EPLIN, DD96, EPHX1, EBI3, ERGL, EPB41L2, EPB72, LOC51145, EPOR, ECRG4, EBAG9, EBBP, ETV1, ETV5, EEF1B2, EIF1AY, EIF2S3, EIF3S10, EIF3S7, EIF4G3, EIF4B, EIF4EL3, EIF5, EIF5A, EIF5A2, ETF1, EXTL1, EXTL2, LAK-4P, KIAA0165, EMILIN-2, XLKD1, ECM2, EYA2, FGD1, FHR5, FANCE, FANCF, FNTA, FNTB, FADD, FABP5, FADS3, FAAH, FACL2, FACL3, FACL5, FOSB, FBXL11, FBXL3A, FBXL4, FBXL9, FBXW2, FBXW3, FBXO11, FBXO2, FBXO22, FBXO24, FBXO3, FBXO7, FBXO8, FBX30, FCAR, FCGBP, FCGR2B, FCGR3A, FE65L2, FES, FER, FTHL17, FTL, FALZ, HSRNAFEV, #25, FOP, FHOS, FBN1, FGL1, FGF11, FGF9, FGFR1, FGFRL1, FLRT1, FBLN1, FLNB, FLNC, M83, FRAP1, LOC51303, LOC51661, FKSG42, FKSG58, FKSG64, FKSG87, FMO1, FMO3, FMO5, LOC51167, FLJ00005, LOC51066, FLT3LG, FLT4, FOLR2, FSTL1, FSTL3, FOXC2, FOXF1, FOXG1A, FOXO1A, FOXO3A, FPRL1, FS, FOSL2, FOSL1, FHL1, FHL2, FHIT, FRDA, FPGT, FUCA1, FUT5, FUT8, FUSIP2, FXYD1, FYN, FYB, FZR1, ZSIG37, #26, RDC1, GPR19, GPR31, GPR34, GPR35, GPR41, GPR50, GPR61, GPR64, GPR65, GPR68, GPR7, GPR84, GPR91, GPRC5C, GPRC5D, GSPT2, GTSE1, LOC51161, G5C, G6C, GABARAPL1, GABARAPL2, GAJ, GLA, GALR2, LOC85329, HSY11339, GGCX, GGH, GDAP1, GJA3, GJA8, GJB2, FGR, GRPR, GATA2, GATA6, GCN1L1, GCN2, GMDS, LOC51291, #27, HSA250839, #28, RES4-25, GOA, GTF2A1, GTF2B, GTF2F1, GTF2F2, GTF3C1, GPHN, GGPS1, LOC51087, LOC64396, LOC51738, #29, GK003, GL002, GMFB, GBAS, GLTSCR1, GLP1R, GMEB2, #30, GPI, GLUT11, G6PC, G6PD, GAD1, GLUD1, GLUD2, GRIP1, GRIA2, GRIN1, GRIN2A, GRIN2C, GRM4, GRM6, GCLM, GLS, GLRX, GCDH, GPX2, GPX3, GSTA2, GSTA4, GSTM1, GSTM2, GSTM5, GSTP1, GSTT1, GSS, GAPDS, GNPAT, GATM, GCAT, GNMT, GYS1, GYG2, GYPA, GYPE, GP3ST, GP1BB, GP9, GARS, GLO1, GPC1, GLG1, GOLGA1, GOLGA2, GOLGA4, GOLGB1, GOLPH2, GOLPH4, GOSR1, GOLTC1, KIAA0855, GLP, GNRH1, GNRHR, GNLY, GZMB, GAB2, GRO1, GRO2, GRO3, PLA2G13, GADD45B, GRB10, GFER, LOC84649, HUMGT198A, GTF21RD1, GCH1, GRAF, GEM, RAGB, GTT1, GNAL, GNAI1, GNAZ, GNB5, GNAQ, GNG10, KIAA0277, GUCY1B2, GUCA1A, GUCA2B, #31, #32, $H_1F_2$, $H_1F_4$, HLX1, $H_2BFQ$, $H_2BFR$, $H_3FD$, $H_3FK$, $H_3FM$, $H_3F_3B$, H326, $H_4FH$, $H_4FM$, HRY, HP, LOC51773, #33, HCR, #34, #35, HSP105B, HSPE1, HSPB7, HSPA1A, HSPA1B, HSPA6, HSPA1L, HSPCB, APG-1, HIP, KIAA0054, HELLS, KIAA0928, HEM1, HHEX, HMOX1, HMOX2, HEBP, HBE1, HPX, HCK, HS3ST3B1, HS6ST, HSPG2, HPSE, XIP, LOC63928, LOC51339, HPS, HHLA2, HNRPA0, HNRPA2B1, HNRPF, HNRPM, HNRPU, HDLBP, HGRG8, HMG14, HMG2, HMGIY, HIRIP3, HIRIP5, HRH1, HRH2, HBOA, #36, HDAC7A, HRB, HTATIP, BAT8, TCF-3, HNK-1ST, HESX1, HOXA1, HOXA11, HOXA6, HOXA7, HOXB5, HOXC10, #37, HERPUD1, RRS1, HOOK2, HOOK3, HCF-2, HP1-BP74, LOC51202, HRASLS, HSKM-B, HSPBP1, HSPC018, HSPCO22, HSPCO25, HSPCO30, LOC51669, HSPCO39, LOC51125, LOC51122, HSPCO49, HSPCO55, HSPCO63, HSPC071, HSPC073, HSPC125, HSPC142, HSPC144, HSPC154, HSPC156, HT014, HTGN29, LOC58514, #38, HYPK, HMMR, HYAL3, HSD11B2, CG018, FLJ00060, LOC54557, LOC51235, HSPC228, HSPC192, #39, LOC56270, AF140225, BK1048E9.5, 13CDNA73, DJ1057B20.2, DJ1181N3.1, DJ465N24.2.1, DJ796117.1, FELL, DKFZP434F0272, DKFZp434G0522, DKFZP434K046, DKFZP434N1429, DKFZP434N185, DKFZp434P1115, DKFZP566G1424, DKFZP761L0424, DKFZp762B226, KIAA1630, DKFZp7620076, FLJ00001, FLJ10074, FLJ10081, FLJ10201, FLJ10357, FLJ10407, FLJ10420, FLJ10512, FLJ10656, FLJ10697, FLJ10707, FLJ10719, FLJ10826, FLJ10830, FLJ11113, FLJ11183, FLJ11560, FLJ12221, FLJ12572, FLJ12895, FLJ20033, FLJ20097, FLJ20203, FLJ20281, FLJ20297, FLJ20333, FLJ20689, FLJ20793, FLJ20886, FLJ20986, FLJ21877, FLJ22035, FLJ22263, FLJ22341, FLJ22376, FLJ22593, FLJ22955, FLJ23059, FLJ23119, FLJ23132, FLJ23316, FLJ23563, MGC10485, MGC14961, MGC20255, MGC20496, MGC4856, MGC5618, PRO1546, LOC63923, HIF1A, HIG2, IDN3, IDS, LNIR, IK, IKKE, ILVBL, IER3, HIVEP2, IGHM, ISLR, IGSF2, IPW, INHBA, INHBC, IBTK, ID1, ING1, ING3, IKBKB, IKBKAP, ITPR1, ITPR2, ITPKA, ITPKB, INPP4B, INPP5B, INSIG1, LOC55971, IGF1R, IGF2AS, IGFBP6, IGFBP4, INSM1, ITM1, ITGA1, ITGA2B, ITGA3, ITGA5, ITGA6, ITGB3, ITGB4, ITGB7, ITGB7, ICAM1, ICAM2, ICAM5, ICSBP1, IFNGR1, IFNGR2, IRF1, IRF2, IRF4, ISG20, IFNA17, IFNA6, IF127, IF130, IF141, IF141, IFRD1, IL1RN, IL1RL2, IL1A, IL1B, FIL1(EPSILON), FILL, IL10, IL10RA, IL11RA, IL13RA1, IL15RA, IL17E, IL18BP, IL18R1, IL18RAP, IL2RA, IL2RB, #40, IL23A, IL6, IL7R, IL8, IL8RA, IL1HY2, #41, SYNCOILIN, ITSN1, 1HABP4, INVS, IRX5, IDI1, ICMT, IVD, JDP1, JAG1, JAG2, SSI-1, JAK1, JM4, JUNB, JUND, KLK4, KLK6, KLK8, KLKB1, KAI1, KPNB2, KPNA3, KATNA1, KATNB1, #42, AB026190, KEL, KRT3, KRT6A, KAP4.10, KAP4.2, KRTHB1, KRTHB6, KIAA1274, KIAA0007, KIAA0008, KIAA0009, KIAA0014, KIAA0020, KIAA0036, KIAA0074, KIAA0100, KIAA0101, KIAA0133, KIAA0135, KIAA0140, KIAA0143, KIAA0146, KIAA0166, KIAA0172, KIAA0185, KIAA0189, KIAA0191, KIAA0194, KIAA0196, KIAA0202, KIAA0211, KIAA0225, KIAA0229, KIAA0232, KIAA0240, KIAA0244, stab1, KIAA0247, KIAA0251, KIAA0256, KIAA0265, KIAA0268, KIAA0290, KIAA0295, KIAA0306, KIAA0321, KIAA0323, KIAA0328, KIAA0332, KIAA0335, KIAA0342, KIAA0346, KIAA0356, KIAA0365, KIAA0368, KIAA0370, KIAA0404, KIAA0408, KIAA0410, KIAA0417, KIAA0418, KIAA0419, KIAA0429, KIAA0430, KIAA0433, KIAA0467, KIAA0469, KIAA0470, KIAA0535, KIAA0552, KIAA0561, LOC114659, KIAA0586, KIAA0590, KIAA0595, KIAA0605, KIAA0615, KIAA0618, KIAA0635, KIAA0637, KIAA0645, KIAA0649, KIAA0663, KIAA0671, KIAA0680, KIAA0685, KIAA0710, KIAA0711, KIAA0713, KIAA0716, KIAA0726, KIAA0728, KIAA0737, KIAA0752, KIAA0769, KIAA0773, KIAA0775, KIAA0792, MAST205, KIAA0843, KIAA0860, KIAA0871, KIAA0872, KIAA0874, KIAA0893, KIAA0907, KIAA0913, KIAA0914, KIAA0922, KIAA0924, KIAA0939, KIAA0945, KIAA0957, KIAA0963, KIAA0964, KIAA0971, KIAA0982, KIAA0990, KIAA1001, KIAA1008, KIAA1009, KIAA1018, KIAA1023, KIAA1041, KIAA1042, KIAA1043, KIAA1049, RAP140, KIAA1116, KIAA1128, KIAA1143, KIAA1150, KIAA1171, KIAA1199, KIAA1203, KIAA1204, KIAA1224, KIAA1228, KIAA1234, KIAA1235, KIAA1237, KIAA1240, KIAA1243, KIAA1244, KIAA1246, KIAA1253, KIAA1255, KIAA1266, KIAA1271, KIAA1278, KIAA1288, KIAA1292, KIAA1295, KIAA1298, KIAA1301, KIAA1303, KIAA1305, KIAA1306, KIAA1311, KIAA1320, KIAA1332, KIAA1337, KIAA1339, KIAA1340, KIAA1345, KIAA1350, KIAA1363, KIAA1376, KIAA1387, KIAA1388, KIAA1402, KIAA1409, KIAA1414, KIAA1424, KIAA1430, KIAA1441, KIAA1451, KIAA1457, KIAA1460, KIAA1464, KIAA1467, KIAA1483, KIAA1484, KIAA1485, KIAA1486, KIAA1509, KIAA1512, KIAA1513, KIAA1522, KIAA1524, KIAA1527, KIAA1528, KIAA1535, KIAA1538, KIAA1542, KIAA1547, KIAA1549, KIAA1553, KIAA1554, KIAA1557, KIAA1559, KIAA1563, KIAA1571, KIAA1587, KIAA1598, KIAA1599, KIAA1617, KIAA1638, KIAA1641, KIAA1656, KIAA1666, KIAA1668, KIAA1673, KIAA1677, FLJ10898, KIAA1694, KIAA1698, KIAA1701, KIAA1705, KIAA1708, KIAA1710, KIAA1725, KIAA1726, KIAA1727, KIAA1728, KIAA1737, KIAA1741, KIAA1742, KIAA1758, KIAA1762, KIAA1771, KIAA1785, KIAA1789, KIAA1795, KIAA1798, KIAA1802, KIAA1811, KIAA1813, KIAA1814, KIAA1819, KIAA1821, KIAA1832, KIAA1842, KIAA1858, KIAA1862, KIAA1870, KIAA1887, KIAA1896, KIAA1899, KIAA1908, KIAA1917, KIAA1919, KIAA1937, KIAA1938, KIR3DL1, KIR3DL2, KIR3DS1, KIR2DL4, KIR2DS5, KLRF1, KIF13A, KIF13B, KIF1C, KIF3A, KIF5B, KIFC3, KIF1B, KNSL5, CENPH, KITLG, KR18, SZF1, SERHL, KRML, LOC51045, KLF1, KLF4, ZK1, KUB3, KCNIP2, KYNU, KMO, HADHSC, LDHL, LMNA, LMNB1, LMNB2, LAMA2, LAMA5, LTBP1, LTBP3, LTBP4, LBP-9, LCHN, LOC51157, LGALS3, LGALS3BP, LGALS9, KIAA0821, HSOBRGRP, LRRFIP2, LZTFL1, LETM1, LRPPRC, LRRC3, RNO2, LZTR1, LIF, LILRA3, ILT10, LILRB2, LILRB4, IRC1, LENG1, LENG3, LAIR2, LIG3, LIG4, KIAA0175, FLJ23293, KIAA0203, SLY, SV2, E2-230K, DKFZP564M112, ARV1, LASP1, LDB2, LIMK2, LMO2, LMO4, LMO6, LHX2, LIM, LIN-7-C, LIN-7B, LIPA, LPIN2, LHFP, LHFPL2, LSR7, NUDE1, LIV-1, LOC88523, LDLR, #43, LDLB, LDLC, LRP3, QP-C, #44, LSM1, LUC7L, LFNG, LABH1, T1A-2, LW-1, LOC51088, LNK, LY117, LY64, LCP2, LBC, LRMP, LTB, LPAAT-delta, LYSAL1, LALP1, LAPTM5, LOXL3, LOC51300, HML2, MACMARCKS, MARCO, MST1, MADH4, MADH7, MAD2L1, MADP-1, MEF2A, MAGEF1, FLJ20798, MAGOH, LOC51678, HLA-DRB5, MVP, KIAA0936, MPI, MPDU1, MAN2A2, MGAT1, MGAT3, MKP-7, MPN, MRG, MAML1, MMP1, MMP10, MMP11, MMP14, MMP15, MMP19, MMP2, MMP3, MMP7, MMP8, MNT, MAD, MAX, MBLR, MEFV, MRE11A, MEIS2, MEIS1, MC1R, MAGEA6, MAGED1, MAGEE1, MDA5, MS4A1, MS4A4A, MS4A6A, MS4A7, LOC51336, LOC51337, MSLN, CPX-1, MTF1, MSRA, MBD4, MTHFD2, MGST1, MAP4, MAPT, MAPRE2, MAPRE3, MIP-T3, MID2, LOC55972, LOC56993, MRP63, MRP64, MRPL1, MRPL12, MRPL13, MRPL15, MRPL16, MRPL17, MRPL32, MRPS24, MRPS25, MRPS33, MRPS36, TOP1 MT, MTRF1, MAPK1, MAPK7, MAPK8, MAP2K4, MAP3K1, MAP3K13, MAP3K14, MAP3K2, MAP3K5, MAP3K6, MAP3K8, MAP3K9, MAP4K1, MAP4K2, MKP-L, MLN51, MRF-1, MAIL, MAOA, MAOB, MMD, MRG15, MDM4, MPHOSPH9, #45, FLJ00029, #46, #47, #48, #49, #50, #51, #52, #53, #54, #55, #56, #57, #58, #59, #60, #61, #62, #63, MSTP031, MSTP043, MUC6, MCOLN1, MALT1, MADCAM1, MUL, MEN1, MINPP1, BMI1, MLH1, MAG, MPZL1, MNDA, MLL, MLLT1, MLLT6, MLLT7, MYOC, MB, MYO1E, MYO9B, MIR, MYO10, MYL5, MYL6, MLCB, MYBPC3, MYBPH, MTMR1, MYOZ, MACS, MX1, NAGA, HSA242910, NAT2, NDUFA4, NDUFA5, NDUFA7, NDUFA9, NDUFB1, NDUFB2, NDUFB3, NDUFB4, NDUFB6, NDUFS6, NDUFV3, NOX1, JFC1, #64, NPPA, CD244, BY55, NAP4, NDRG4, WWP2, LOC51667, NAF1, NEO1, NESCA, NESH, NAPG, LOC51162, LOC84687, NEDD4, NXPH2, NBL1, NAG, NEUD4, NF1, NEUROD1, NEUROD2, NEUROD4, NEUROD6, NGB, NRGN, NLGN2, NMU, NPAS1, NPAS2, NRP2, NTRK3, NSMAF, NCF2, NNT, NPC2, NBS1, NEK2, NEK3, NIN, NINJ1, NIT2, KIR-023 GB, NME7, NMNAT, NDRG3, NMT2, NOD2, NIMP, #65, NOT56L, NOTCH$_3$, HSNOV1, DJ434014.5, NSP1, NSP3, SGSH, NTHL1, NTT5, GS2NA, SP140, NFE2, NFE2L2, NFAT5, NFATC3, NFKB1, NFKB2, NFKBIA, NFKBIE, NFKBIL1, P84, MDM1, NRBF-2, NCOA1, NCOA4, AIB3, NR1D1, NR1D2, NR1H3, NR2C1, NR2F6, NR3C1, NR4A1, NR4A2, NR5A2, NRF1, NXF2, NXF3, NFYA, NFYB, NFX1, SC65, NOL3, NOLA2, NOLA3, NPM1, NSBP1, NUMBL, NRM, NYD-SP12, LOC51133, OA1, OR11A1, OR12D3, OR2C1, OR7E24P, OGT, OSM, OIP5, OPRL1, OPRM1, OPN1LW, OPN1SW, ORC2L, OAZ2, OAZIN, ORNT2, ORM1, OSRF, OSF-2, OSTF1, OCIA, OXR1, RODH, OLR1, OSBP, OSBPL2, FLJ10217, BITE, PAK6, PCAF, PIGPC1, p53DINP1, p53R2, P53AIP1, PAI-RBP1, PACE, PAX1, PAX4, PILR(BETA), PMX1, PRX2, PITX1, KIAA0992, PANX1, PAPA-1, PRCC, LOC55893, PARD6A, HUMPPA, PON2, PTMS, POR1, PVALB, PAXIP1L, PCQAP, PC3-96, PSIP1, PSIP2, PAF65A, PAF65B, PCTK3, PDLIM1, PDZK1, PDZ-GEF1, LOC51735, TOPK, PTX3, PMPCB, PYY2, PDI2, PAM, PPIL2, PPIF, PRF1, PCM1, PLIN, PRAX-1, PEX11A, PEX16, PXMP3, PEX1, PPARA, PPARG, PPARGC1, PET112L, PHF1, PMAIP1, MDS019, PCYT2, PPAP2A, PIK4CA, PICALM, PIGB, PIGC, PIGF, PIGH, PIP5K1B, PIP5K2B, PDE1B, PDE1C, PDE2A, PDE4B, PDE4D, PDE5A, PDE6A, PDE6C, PDE8A, PDE8B, PGAM1, PGAM2, PIK3CG, PIK3C2A, PIK3C2B, PIK3R1, P101-PI3K, PEPP3, PLA2G6, PLCE, PLCG1, PLD1, PLD2, PLSCR1, PLSCR3, LHPP, C8FW, #66, PSPH, PIM1, PIM2, PINX1, LOC96626, PIR, PTTG3, PL6, PGCP, PLAT, PLAU, PLGL, PLS1, PAFAH2, PDGFA, PDGFB, PDGFRA, PLEK, PSD, PLEKHA1, PSCD2, PSCDBP, PHLDA1, PHLDA3, PLEC1, PLAGL1, PLAGL2, PLXNB2, PLXNB3, PLXNC1, #67, #68, #69, #70, PVRL2, PAPOLA, PABPC1, PKD2L1, PQBP1, POLI, POLK, POLA, POLD3, POLL, POLM, POLQ, POLS, POLR2D, POLR2E, POLR2K, RPC39, POLR3K, #71, PMSCL2, POP4, POP2, POP3, MG61, PMS2, PMS2L3, CRIPT, HERG-3, KCNK15, KCNK3, KCNK5, KCNK9, KCNN2, KCNN3, KCNJ1, KCNJ11, KCNJ15, KCNJ16, KCNJ5, KCNJ6, KCNK4, KCNMB3, KCNMB1, KCNS1, KCNQ1, KCNQ2, KCNQ3, KCNA10, KCNA3, KCNA5, KCND1, KCNH3, POU2F1, POU6F1, #72, PRDM13, PRDM2, PRDM8, SET07, PBEF, PRAME, PFDN2, OKL38, PRP17, PSEN1, PRIM1, PRO0233, PRO0365, PRO0641, PRO0644, PRO1073, #73, PRO1900, PRO2000, #74, #75, PCOLCE2, PLOD, PGRMC1, PDCD4, PDCD5, PDCD6, PDCD61P, PDCD7, PIP, B4-2, PML, PPBP, PCSK7, PTGDR, PTGER2, PTGER4, PTGES, PTGIR, PTGIS, PART1, PSK, #76, LOC85414, PRM1, PRM2, PRSS11, PRSS16, SPUVE, PSMD4, PSMD9, PSMA3, PSMA5, PSMA6, PSMB10, AWP1, PCCX2, PDI, PIAS3, PKIG, PACSIN2, PRKCABP, PRKCG, PRKCQ, PRKCZ, PRKCL2, PKD2, NJMU-R1, NYD-SP15, PRKAA1, PRKACA, PRKAR2B, PRKWNK1, P3, LOC51207, PPP1CB, PPP1R12A, PPP1R14C, PPP1R15A, PPP1R2, PPP1R3B, PPM1G, PPP2R3, PPP2R5B, PR48, PPP3CA, PPP3CC, PPP4R1, PME-1, PPEF1, HSU79274, LOC84518, PRO51, PTK9, PTPN11, PTPN12, PTPN3, PPFIA1, PTPRG, PTPRO, PTPLA, LOC51184, PRKRIR, PCMT1, POMT1, AD013, PRG1, PRG2, LOC51685, U5-100K, PTDO11, PPFIBP2, #77, P2RX2, P2RX7, PURA, HM74, M96, #78, GPR, GPCR150, #79, SH120, PHTF1, KIAA0436, M6A, MRS3/4, N6AMT1, HRIHFB2122, LOC51051, C3F, LOC51086, P2Y10, RABEX5, RNASE3L, FJX1, SIG11, LOC64172, HS1-2, P2RY6, PC, PDHB, PDK3, QDPR, RABL2B, RAB11B, RAB33A, RAB38, RAB3IL1, RAB5B, RAB5C, GAPCENA, RAB6C, RAB7, RAB7L1, #80, RAB5EP, RAD23B, RAD51C, PIR51, RAD54L, RAD54B, RAD9, RSP3, RDX, RAE1, RALGPS1A, REPS2, LOC83859, RGL, RANBP1, RANBP6, EPAC, RAP1GDS1, RPIP8, RAMP, LOC54453, #81, ARHF, ARHH, RIN1, GAP11P4BP, RASAL1, RASAL2, RASGRF1, RREB1, G3BP, RIS1, RAC3, RRP22, LOC51655, RBAK, REST, RLF, RAMP3, RIPK1, RIPK2, RIPK3, RBPSUHL, RCV1, RECQL, RECQL4, RGPR, RGS14, RGS16, RGS8, RFX4, RFX5, RFXAP, RSC1A1, RNTRE, RENBP, RFC3, RFC4, RFC5, RIP60, RPA3, RSN, RFP, RFP2, RFPL2, RCN2, RTN2, RTN4, LOC51170, RP1, RP2, RPGR, RBBP1, RBBP4, RAIl, RAI15, RAI2, RARA, RARB, RARG, LOC51036, RXRG, RDH5, RDHL, RBP1, REV1L, REV3L, RECK, RGC32, RHAG, RTKN, RNASEH1, RNASEHI, RPP14, RPP38, RNASE1, RNASE4, RPN1, RPIA, RPL14, RPL19, RPL21, RPL23, RPL23A, RPL24, RPL26, RPL27, RPL4, RPL44, RPL8, RPS12, RPS14, RPS15, RPS21, RPS23, RPS25, RPS27A, RPS6 KB1, RPS6KA1, RPS6KA3, RPS6KA4, RIT, RING1, RNF17, RNF2, RNF20, RNF23, RNF24, RNF25, RNF30, RYBP, LOC51285, RNMT, RPC, RBM10, RBM7, RBM8A, RBM9, RBMS1, RBMS2, LOC84549, RNAHP, RNUT1, RNU17D, RNPS1, RMP, RU2, RUNX1, RUNX2, RUVBL1, RUVBL2, RYR2, RYK, S100A10, S100A12, S100A13, S100A3, S100A5, LOC57402, SAC2, AHCY, SAMHD1, SAMSN1, SARCOSIN, SBBI31, SAFB, SCHIP1, SOST, SEC10L1, SEC13L1, SEC22A, SEC22L1, SEC24A, FLJ10578, SEC61G, SFRP5, SCAMP3, SEL1L, SEPN1, SEMA3B, SEMA3C, SEMA4B, SEMA4D, SEMA4F, SEMA4G, SEMA4C, SEMG2, SENP2, 37137, SQSTM1, SERPINB4, SERPINB8, SERPIND1, SERPINE1, SERPINF2, SERPING1, SERPINH1, SR-A1, SDS, SHMT1, SPTLC2, SPINK5, SPINT1, SPINLW1, SRR, NDR, STK10, STK11, STK13, STK16, STK17A, STK17B, STK18, STK19, STK2, STK6, MST4, MGC4809, SDCCAG10, SDCCAG28, SDCCAG3, SDCCAG31, PK428, SES2, SETDB1, SET, SIAH2, SCML2, SRY, HSSEXGENE, SRPK1, SH2D2A, SPAP1, SH3BGR, SH3BGRL2, SH3BP2, SH3GL2, SH3GLB2, SHB, HRIHFB2072, SHOX2, HEP27, SIT, SIGLEC10, SIGLEC11, SIGLEC8, SIGLEC9, NEU2, SN, STHM, SIAT1, SIAT4B, SIAT4C, SIAT6, SIAT8D, SIAT8B, SIAT8A, SIAT8C, SIAT9, SRP19, SRPR, SSR1, SSR2, STAT2, STAT5A, STAT5B, STAT6, SIPA1, SLAM, SILV, #82, #83, LOC57168, KEO4, #84, #85, #86, MGC14386, #87, Rpo1-2, #88, #89, LOC92797, #90, #91, #92, #93, #94, #95, #96, #97, #98, #99, LOC91151, #100, #101, #102, #103, #104, #105, #106, #107, #108, #109, #110, #110, #112, LOC90522, #113, #114, #115, #116, #117, #118, #119, #120, #121, #122, #123, #124, #125, HS1119D91, LOC57167, #126, #126A, UPF3A, UPF3B, #127, #128, SAP30, SIX2, SIM1, SSBP2, SIRT2, SIRT5, SSA1, SSB, XP5, #129, SMA3, HspB9, SCYA1, SCYA3, SCYA4, SCYA5, SCYA16, SCYA18, SCYA20, SCYA22, SCYA24, SCYA8, SCYB10, SCYB14, SCYB6, SMP1, SNRPA1, SNRPE, SNRPF, SNRPG, SOLH, SHARP, SMCX, SMOH, SNAI1, SNAPAP, SRCAP, SCNN1A, SCNN1G, SLC1A6, SLC12A4, SLC12A6, SLC12A5, SLC13A3, SLC16A5, SLC18A2, SLC19A1, SLC2A1, SLC2A3, SLC2A6, SLC20A1, SLC21A12, SLC21A9, SLC22A8, SLC22A1, SLC22A1LS, SLC22A5, SLC24A3, SLC25A20, SLC25A5, SLC25A6, SLC25A10, SLC26A2, SLC27A4, SLC28A3, SLC29A1, SLC29A2, SLC3A2, SLC3A1, SLC30A1, SLC30A4, SLC4A1AP, SLC4A7, SLC4A10, SLC5A3, SLC6A8, SLC6A1, SLC6A13, SLC6A9, SLC6A7, SLC6A6, SLC7A10, SLC7A11, SLC9A1, SLC9A5, SSTR5, SON, SOS1, SORL1, SNX12, SNX15, SNX16, SNX2, HSSOX6, SP2, SP3, SPOCK, SATB1, SSH3BP1, SPTAN1, SPTBN1, SPAG1, SPAG4, SPAG9, #130, STRBP, SPATA2, SAT, SKP2, SMPD1, SPHK2, SF3A1, SF3A2, SF3B1, SF3B2, SFRS10, SFRS3, SFRS5, SFRS6, SFRS7, SPON2, SPR1, SPRY1, SPRY2, SART-2, SLA, SOX13, SOX2, SOX22, SOX4, SSI-3, STATI2, CIS4, STMN3, SLK, SCGF, SLU7, ZAK, SREBF1, SREBF2, STG, STOML1, STCH, STAG1, SDF1, STIM1, SNT-1, SDHC, SDHD, SUOX, SULT2B1, STE, SUSP1, SOD2, SVIL, ST5, ST7, SUFU, SKD1, SKD3, SURF5, SURF6, SMARCAL1, SMARCB1, SMARCD1, SMARCF1, SYNE-1B, SV2B, SYNGR4, SYTL2, SDC4, SS18, STX10, STX11, STX16, STX5A, STX7, STXBP1, STXBP2, SNTB1, TACTILE, TRA@, TRD@, TRG@, TAF9L, S1L, TBK1, TARBP1, TOM1L2, TAS2R13, TAS2R14, TAS2R7, TAF1C, TAF2A, TAF2C2, TAF2N, TAX1 BP1, TBX21, TBX6, TAL1, TIAM1, TCP10, TEKT3, TEX13A, TEX13B, FLJ20499, TSGA10, TSGA14, TSKS, TETRAN, TSPAN1, TIAF1, TGIF, TGIF2, TH1L, TPMT, AOE372, TXNRD1, TR2, THBD, THBS3, TK2, TRIP10, TRIP11, TRIP12, TRIP13, TRIP3, TRIP4, TRIP6, THRA, TRAP240, TRHR, TIA1, TIAL1, TIGA1, TJP2, TSTA3, TLH29, TRAF1, TRAF3, GG2-1, TLR1, TLR2, TOP2A, TOP3A, TOP3B, TRF4-2, TPARL, AD022, TANK, KIAA0057, ICBP90, TCF17, TCF19, TCF3, TCF6L1, TFAP4, TFE3, TFCP2, TFEC, NRF, TCFL1, TCFL4, TCFL5, TTF1, TTF2, CROC4, ALY, TIF1, TReP-132, TOB1, TLE4, TF, TFRC, HSU53209, TGFB1I1, TAB1, TGFA, TGFB1, TGFBR3, TGM3, TGM5, TRPC6, TERE1, GC20, IF2, TIM17, TIMM8A, TIMM8B, KIAA0016, TOMM70A, TRAM, #134, TLOC1, TM4SF1, TM4SF5, TM7SF2, TACl, TMG4, TMEM1, TMEM2, TMEM5, TMEM7, TMPIT, TMEFF1, TAP1, LOC58486, #135, RAP1, THH, TREM1, TNRC11, TNRC12, TNRC4, TPI1, TRIM14, TRIM22, TRIM26, TRIM33, TRIM34, TRIM5, TRIM6, TPP2, TR10, TFG, IPT, SECP43, TGT, TRO, TROAP, TMOD2, TMOD3, TPM1, TPM2, TPM4, LOC51149, WARS2, TSFM, TSPYL, TTK, TUFM, TULP3, TSC2, TUBA3, TUBB, TDRKH, PCTAIRE2BP, TUFT1, HCC8, TEM8, TNFSF13, TNFSF15, TNFSF7, TNFSF9, TNF, FIP2, TNFRSF10D, TNFRSF21, TNFRSF4, TNFRSF6, TNFRSF6B, TNFAIP1, TNFAIP2, TNFAIP3, TNFAIP6, TPD52L1, TP53BP1, DLM1, TSSC1, TSSC3, TUCAN, TSG, 1-4, PSK-1, TYRO3, TYRP1, YWHAE, YWHAH, YWHAG, T1E, U2AF65, HPRP8BP, LSM5, LOC51691, UQCRB, USP10, USP12, USP14, USP16, USP18, USP9X, UBE4A, UBE2A, UBE2C, UBE2E1, UBE2E3, UBE2H, UBE2L3, UBE2N, UBL1, UBL3, NEDD4L, B4GALT5, B3GNT5, B3GNT6, UGCGL2, UGDH, GALNT2, GNE, UAP1, ULBP3, BM036, MDS028, MDS030, MDS032, HARP11, HT007, HT008, VDUP1, UCC1, UBTF, UREB1, USF1, UNG2, UMPH1, UP, UCN, UPK2, HSHUR7SEQ, V1RL1, ABL1, ABL2, VPS26, VPS4, AKT2, VCP, VARS2, VANGL2, VR1, OTRPC4, VNN3, VCY2, VCAM1, VEGFC, VIP, VIPR1, CRK, CRKL, VAX2, ERBB3, VAMP1, VAMP4, ETS1, ETS2, FOS, SCAM-1, VMD2, VIT1, MYB, MYBL1, MYC, KIAA1329, BRAF, RALA, RALB, REL, RELA, RELB, SKI, YES1, WASF1, WDR10, WDR3, WDR4, WDF2, WDR11, WHIP, KIAA0105, WAS, WHSC2, WW45, WWOX, MDS009, XAGE-1, XBP1, XPR1, XPA, XPN-PEP2, HSXQ280RF, XRCC2, YAF2, ZF5128, ZFP, ZNF-U69274, ZFD25, ZNF131, ZNF146, ZNF151, ZNF16, ZNF165, ZNF185, ZNF187, ZNF19, ZNF193, ZNF195, ZNF200, ZNF205, ZNF213, ZNF22, ZNF221, ZNF230, ZNF236, ZNF237, ZNF238, ZNF257, ZNF258, ZNF26, ZNF264, ZNF268, ZNF278, ZNF297, ZNF302, ZNF313, ZNF33B, ZNF36, ZNF44, ZNF45, ZNF79, ZNF83, ZNF85, ZNF9, ZNF91, ZFP161, ZNFN1A1, PEGASUS, ZFX, ZNRD1, ZHX1, ZYG and ZYX. Homologs of these genes or proteins in other species, e.g., primates, are also modulated by the F1C. Modulation of these genes can be observed, e.g., as increased expression or mRNA levels or protein levels of the biomolecules in clinical conditions where insufficient or suboptimal expression or levels of the gene is associated with establishment, maintenance, severity or progression of the clinical condition to produce a desired clinical improvement.

Other therapeutic and biological applications and activities. The F1Cs are useful for preventing, slowing the progression of or treating certain chronic conditions in a subject such as a mammal or a human. Chronic conditions include diseases and conditions that arise or develop over a relatively long time period, e.g., over about 3 months to 10 years or more. Such conditions include chronic renal failure, which may result from polycystic kidney disease, from, e.g., an autoimmune condition such as acute or chronic glomerulonephritis, or from diabetes, interstitial nephritis, hypertension and other conditions discussed elsewhere herein. Chronic conditions include chronic pulmonary conditions such as chronic bronchitis, lung fibrosis, right ventricular hypertrophy, pulmonary hypertension, emphysema, asthma and chronic obstructive pulmonary disease, which may be treated with a F1C. These conditions or their symptoms may be mild, moderate or severe. The subject may be suffering from the disease or condition or may be subject to developing the condition, e.g., the subject may display early signs or a predisposition to develop a chronic condition. Such treatment will generally facilitate prevention of the disease, delay the onset or severity of the disease or condition, ameliorate one or more symptoms, e.g., reduce shortness of breath, coughing or dyspnea, or slow progression of the disease or condition. In these and other chronic conditions described herein, the F1Cs will generally be administered to a subject such as a human for a relatively long time period, e.g., for at least about 3 months to about 10 years or more. Dosages, routes of administration and dosing protocols for the F1Cs are essentially as described herein. Dosing of the compound can be daily or intermittent using a dosing protocol using dosages as described herein, e.g., about 0.1 to about 20 mg/kg of a F1C administered to a subject once or twice per day daily or intermittently. The use of the F1Cs can be combined with other treatments, e.g., β-agonists such as metaproterenol or albuterol, or corticosteroids, e.g., prednisone, for asthma or chronic obstructive pulmonary disease.

The F1Cs can modulate the biological activity of cytokines or interleukins that are associated with various immune deficiency or dysregulation conditions, which may be transient or chronic. They can thus be used to ameliorate, treat or prevent naturally occurring age-related decline in immune function in a subject or immune deficiency or dysregulation resulting from trauma, stress, burns, surgery, autoimmunity or infections as described herein. Such immune deficiency dysregulation may be associated with, e.g., an age-related increase in production of one or more of IL-4, IL-5 and IL-6 or an age-related decrease in production of one or more of IL-2, IL-3, γ-IFN, GM-CSF or antibodies. In these embodiments, the F1C is administered to the subject to detectably decrease production or levels of one or more of IL-4, IL-5 and IL-6 or to detectably increase production or levels of one or more of IL-2, IL-3, IL-5, IL-12, GM-CSF and γ-IFN. These cytokine changes facilitate normalization of the subject's immune responses. Such normalization can be observed by various means. These means include monitoring appropriate cytokine RNA or protein level(s) in the subject or by measuring biological responses such as restoration or detectable improvement of contact hypersensitivity in a subject with depressed or suboptimal contact hypersensitivity response. The F1Cs can thus be used to enhance or restore a deficient or suboptimal immune response such as contact hypersensitivity response in a subject with a chronic or transient state of immune deficiency or dysregulation. In these embodiments, the F1C is administered using the dosages, routes of administration and dosing protocols for the F1Cs essentially as described herein. Treatment with the F1Cs is optionally combined with other appropriate treatments or therapies essentially as described herein, e.g., a antibacterial or antiviral agent(s) is coadministered with a F1C to treat, prevent or ameliorate an infection in an infected subject or a subject suffering from, e.g., a burn. Methods to measure changes in cytokine levels or contact hypersensitivity are known and can optionally be applied in these embodiments, see, e.g., U.S. Pat. Nos. 5,919,465, 5,837,269, 5,827,841, 5,478,566.

The capacity of the F1Cs to modulate immune functions permits their use for treating, preventing, slowing the progression of or alleviating the a symptom(s) of subjects with psychological disorders, metabolic disorders, chronic stress, sleep disorders, conditions associated with sexual senescence, aging, or premature aging. Metabolic disorders include parathyroidism, pseudoparathyroidism, hypoparathyroidism, hypercalcemia, hypocalcemia and detectable symptoms thereof such as fatigue, constipation, kidney stones and kidney malfunction. Chronic stress and related disorders include fibromyalgia, chronic fatigue syndrome, hypothalamic-pituitary axis dysregulation. Other related pathological conditions that can be treated with the F1Cs include hormone deficiency associated with aging or with a pathological condition, hypogonadism, vaginal atrophy, diminished libido, urinary incontinence, skin collagen loss, loss or impairment of skin, organ or joint connective tissue and menopause or its symptoms such as hot flashes, unwanted mood changes, fatigue and insomnia. In these embodiments, treatment of subjects with a F1C is optionally combined with other suitable agents such as triiodothyronine, tetraiodothyronine, an insulin-like growth factor, insulin-like growth factor binding protein-3, an estrogen or a progestin.

As noted above, in some embodiments a treatment with a F1C is combined with a corticosteroid or glucocorticoid. Corticosteroids are used in a number of clinical situations to, e.g., decrease the intensity or frequency of flares or episodes of inflammation or autoimmune reactions in conditions such as acute or chronic rheumatoid arthritis, acute or chronic osteoarthritis, ulcerative colitis, acute or chronic asthma, bronchial asthma, psoriasis, systemic lupus erythematosus, hepatitis, pulmonary fibrosis, type I diabetes, type II diabetes or cachexia. However, many corticosteroids have significant side effects or toxicities that can limit their use or efficacy. The F1Cs are useful to counteract such side effects or toxicities without negating all of the desired therapeutic capacity of the corticosteroid. This allows the continued use, or a modified dosage of the corticosteroid, e.g., an increased dosage, without an intensification of the side effects or toxicities or a decreased corticosteroid dosage. The side-effects or toxicities that can be treated, prevented, ameliorated or reduced include one or more of bone loss, reduced bone growth, enhanced bone resorption, osteoporosis, immunosuppression, increased susceptibility to infection, mood or personality changes, depression, headache, vertigo, high blood pressure or hypertension, muscle weakness, fatigue, nausea, malaise, peptic ulcers, pancreatitis, thin or fragile skin, growth suppression in children or preadult subjects, thromboembolism, cataracts, and edema. Dosages, routes of administration and dosing protocols for the F1C would be essentially as described herein. An exemplary dose of F1C of about 0.5 to about 20 mg/kg/day is administered during the period during which a corticosteroid is administered and optionally over a period of about 1 week to about 6 months or more after dosing with the corticosteroid has ended. The corticosteroids are administered essentially using known dosages, routes of administration and dosing protocols, see, e.g., *Physicians Desk Reference* 54$^{th}$ edition, 2000, pages 323-2781, ISBN 1-56363-330-2, Medical Economics Co., Inc., Montvale, N.J. However, the dosage of the corticosteroid may optionally be adjusted, e.g., increased about 10% to about 300% above the normal dosage, without a corresponding increase in all of the side effects or toxicities associated with the corticosteroid. Such increases would be made incrementally over a sufficient time period and as appropriate for the subject's clinical condition, e.g., daily corticosteroid dose increases of about 10% to about 20% to a maximum of about 300% over about 2 weeks to about 1 year.

Such corticosteroids include hydrocortisone (cortisol), corticosterone, aldosterone, ACTH, triamcinolone and derivatives such as triamcinolone diacetate, triamcinolone hexacetonide, and triamcinolone acetonide, betamethasone and derivatives such as betamethasone dipropionate, betamethasone benzoate, betamethasone sodium phosphate, betamethasone acetate, and betamethasone valerate, flunisolide, prednisone, fluocinolone and derivatives such as fluocinolone acetonide, diflorasone and derivatives such as diflorasone diacetate, halcinonide, dexamethasone and derivatives such as dexamethasone dipropionate and dexamethasone valerate, desoximetasone (desoxymethasone), diflucortolone and derivatives such as diflucortolone valerate), fluclorolone acetonide, fluocinonide, fluocortolone, fluprednidene, flurandrenolide, clobetasol, clobetasone and derivatives such as clobetasone butyrate, alclometasone, flumethasone, and fluocortolone.

In some applications, the F1C(s) may directly and/or indirectly interfere with replication, development or cell to cell transmission of a pathogen such as a virus or a parasite (malaria). Improvement in a subject's clinical condition may arise from a direct effect on an infectious agent or on a malignant cell. Interference with cellular replication can arise from inhibition of one or more enzymes that a parasite or an infected cell uses for normal replication or metabolism, e.g., glucose-6-phosphate dehydrogenase, which affects cellular generation of NADPH (see, e.g., Raineri et al., *Biochemistry* 1970 9: 2233-2243). This effect may contribute to cytostatic effects that some F1Cs can have. Modulation of cellular enzymes expression or activity may also interfere with replication or development of a pathogen, e.g., HIV or malaria parasites or with replication or development of neoplastic cells, e.g., inhibition of angiogenesis. Clinical improvement will also generally result from an enhanced immune response such as an improved Th1 response.

Administration of a F1C can lead to a decrease in adenosine levels in a subject's tissue(s), e.g., lung or central nervous system tissue. This effect can be used to treat, prevent, ameliorate one or more symptoms of or slow the progression of a disease(s) or clinical condition(s) where a relatively high level of adenosine is a factor in or can contribute to the disease or condition, e.g., in asthma.

Adenosine is associated with the symptoms of bronchial asthma, where it can induce bronchoconstriction or contraction of airway smooth muscle in asthmatic subjects, see, e.g., J. Thorne and K. Broadley, *American Journal of Respiratory & Critical Care Medicine* 149(2 pt. 1):392-399 1994, S. Ali et al., *Agents &Actions* 37:165-167 1992, Bjorck et al., *American Review of Respiratory Disease* 145:1087-1091 1992. This effect is not observed in non-asthmatic subjects. In the central nervous system, adenosine can inhibit the release of neurotransmitters such as acetylcholine, noradrenaline, dopamine, serotonin, glutamate, and GABA. It can also depress neurotransmission, reduce neuronal firing to induce spinal analgesia and it possesses anxiolytic properties, see, e.g., A. Pelleg and R. Porter, Pharmacotherapy 10:157 1990. In the heart, adenosine suppresses pacemaker activity, slows AV conduction, possesses antiarrhythmic and arrhythmogenic effects, modulates autonomic control and triggers the synthesis and release of prostaglandins. In addition, adenosine has vasodilatory effects and can modulate vascular tone.

The unwanted effects of excess adenosine can be ameliorated or reduced by administering sufficient amounts of a F1C to a subject who is subject to developing or who has an unwanted level of adenosine in one or more tissues or organs. In typical embodiments, one will administer about 10 mg/kg/day to about 100 mg/kg/day of a F1C to a subject over a period of about 1 week to about 4 months to effect detectable changes in adenosine levels or amelioration in one or more symptoms associated with high adenosine in one or more of the subject's tissues. Such changes may be determined by comparing the subject's adenosine levels before treatment with the F1C is started. Alternatively, for subjects with symptoms that are consistent with high adenosine levels, the decrease can be inferred by comparing the normal level of adenosine in the target tissue(s) for subjects of the same species and similar age or sex with the level that is observed after treatment. Methods to measure adenosine levels in mammalian tissue are known and can optionally be used in these embodiments, e.g., U.S. Pat. No. 6,087,351.

In some clinical conditions, the F1Cs can inhibit activated T lymphocytes in vivo, and they can inhibit the expression or biological activity of one or more of TNF-α, IFN-γ, IL-6, IL-8 or insulin like growth factor-1 receptor (IGF-1R) or IL-6 receptor. The compounds are thus useful to treat, prevent or ameliorate conditions where this is a component of pathology. Such conditions include inflammation conditions such as psoriasis, psoriatic arthritis, osteoarthritis, and rheumatoid arthritis. The compound can thus ameliorate the inflammation, e.g., by inhibiting expression of one or more of TNF-α, IFN-γ, IL-6, IL-8 or IGF-1R. Also, the compounds can inhibit unwanted T cell activity. They can thus ameliorate one or more psoriasis symptoms such as skin scaling, skin thickening, keratinocyte hyperproliferation, deficient filaggrin expression (B. Baker et al., *Br. J. Dermatol.* 1984, 111:702), deficient strateum corneum lipid deposition or they can improve a clinical assessment such as the Psoriasis Activity and Severity Index. The F1Cs can be delivered to a subject with psoriasis using topical or systemic formulations as described herein. Topical formulations include gels, lotions and creams, e.g., as described herein. Daily or intermittent administration of the compound can be used essentially as described herein. The use of the F1Cs is optionally combined with one more current psoriasis treatments, e.g., topical emollients or moisturizers, tars, anthralins, systemic or topical corticosteroids, vitamin D analogs such as calcitriol, methotrexate, etretinate, acitretin, cyclosporin, FK 506, sulfasalazine, ultraviolet B radiation optionally combined with one or more of a topical corticosteroid, tar, anthralin, emollient or moisturizer or ultraviolet A plus psoralen. Such additional treatments essentially would use known dosages and routes of administration, which are applied, e.g., within a month before, during or within a month after a treatment course with a F1C.

Other desirable modulation effects of the F1Cs on cells or tissues include (1) inhibition of one or more of bone resorption or calcium release or gp80, gp130, tumor necrosis factor (TNF), osteoclast differentiation factor (RANKL/ODF), RANKL/ODF receptor, IL-6 or IL-6 receptor expression or biological activity in, e.g., bone loss or osteoporosis conditions or in osteoclasts, or in cancers such as prostate cancer, metastatic breast cancer or metastatic lung cancer (e.g., with bone metastases), (2) inhibition of osteoclastogenesis or osteoclast development from progenitor cells, (3) enhancement of NFκB inhibition that is mediated by nuclear hormone receptors, e.g., enhanced inhibition of estrogen receptor-α or estrogen receptor-β mediated inhibition of NFκB in inflammation, rheumatoid arthritis or osteoporosis, (4) enhancement of osteoblastogenesis, osteoblast, bone callus or bone development, e.g., from progenitor cells in bone fractures, depressed bone healing situations (e.g., in a burn patient or in a patient being treated with a glucocorticoid), bone growth or osteoporosis or other bone loss conditions, by, e.g., modulation or enhancement of osteoblast replication or development or modulation or enhancement of the synthesis or biological activity of a transcription factor such as Cbfa1, RUNX2 or AML-3 (5) normalization of hypothalamic-pituitary-adrenal axis function in conditions where there is dysregulation such as in chronic inflammatory diseases, chronic asthma or rheumatoid arthritis (increased cortisol to ACTH ratio), (6) modulation of ligand-gated ion channels in neurons in, e.g., depression, sleep or memory disorders, (8) modulation of G-protein coupled receptors in neurons in, e.g., depression, sleep or memory disorders, (9) modulation, e.g., induction or inhibition, of the synthesis or biological activity of metabolic enzymes such as a cytochrome or a hydroxylase (e.g., 11β hydroxylase, a CYP enzyme such as CYP1A1, CYP2B1, CYP2b10, CYP4A, CYP7A, CYP7A1, CYP7B, CYP7B1, CYP11A1, CYP11B1, CYP17, P450 3A4, P450c17, P450scc, P450c21 or an isozyme, homolog or mutant of any of these) in cells or tissues such as liver cells, neurons, neuron precursor cells, brain, breast, testes or colon, (10) enhancement of collagen synthesis or levels in, e.g., skin in aging or skin damage from, e.g., trauma, thermal injury or solar radiation, (11) inhibition of nitric oxide production in cells or tissue, e.g., in nervous system tissue or in microglial cells in dementias such as Alzheimer's disease, (12) enhancing glucose-stimulated insulin synthesis in hyperglycemia or diabetes conditions, (13) modulation of gamma-aminobutyric acid (GABA), dopamine or N-methyl-D-aspartate (NMDA) receptor activity or levels in, e.g., brain tissue or neurons, (e.g., decreased GABA-mediated chloride currents or potentiation of neuronal response to NMDA in the hippocampus) in, e.g., conditions such as a dementia (Alzheimer's Disease), depression, anxiety, schizophrenia or memory loss due to, e.g., aging or another condition described herein, (14) modulating (e.g., enhancing) the expression or activity of a transcription factor(s), or a homolog(s) or isoform(s), such as SET, nerve growth factor inducible protein B, StF-IT, SF-1 in cells or tissues such as nerve cells, neuronal precursor cells or liver cells, (15) inhibition of eosinophil infiltration or reduction IgE levels in allergic responses or in lung or other tissue, (16) modulation, e.g., a decrease, in serum or blood of leptin levels in, e.g., obese subjects such as humans with a body mass index of about 27, 28, 29, 30, 31, 32, 33, 34 or greater, (17) increased corticotropin releasing hormone synthesis or activity in, e.g., elderly subjects such as humans at least about 60 years of age or at least about 70 years of age, (18) enhancement of memory or reduction of memory loss or disorientation in aging or dementias such as Alzheimer's Disease, (20) enhancement of the synthesis or activity of one or more enzymes responsible for thermogenesis, e.g., liver glycerol-3-phosphate dehydrogenase or malic enzyme, in subjects such as obese or diabetic humans, (21) modulation, e.g., reduction, of the synthesis or biological activity of the CXCR4 receptor or the CXCL12 chemokine in hyperproliferation conditions such as breast cancers or precancers, (22) modulation of the synthesis or biological activity of one or more of holocytochrome c, cytochrome c, second mitochondria-derived activator of caspase, Apaf-1, Bax, procaspase-9, caspase-9, procaspase-3, caspase-3, caspase-6 and caspase-7, e.g., enhanced translocation of these molecules from mitochondria to cytosol or activation of these molecules in the cytosol in cancer precancer cells, cancer cells or cells that mediate autoimmunity, (23) modulation of the synthesis or biological activity of one or more of tumor necrosis factor-α, interleukin-1β converting enzyme, IL-6, IL-8, caspase-4 and caspase-5, e.g., decreased activation of these molecules in injured cells or cells subject to injury from, e.g., ischemia or infarction (e.g., vascular, cardiac or cerebral), reperfusion of hypoxic cells or tissue or an inflammation condition such as rheumatoid arthritis, ulcerative colitis, viral hepatitis, alcoholic hepatitis, or another inflammation condition disclosed herein, (24) decrease of the synthesis, biological activity or activation of one or more of phospholipase A2, caspase-1, caspase-3 and procaspase-3 in neurodegeneration disorders or dementias such as Alzheimer's disease, Huntington's disease, or another neurological condition disclosed herein, (25) regulation or normalization of dysregulated protein kinase B, phosphatidylinositol 3-kinase and Forkhead transcription factors, e.g., a class 0 Forkhead transcription factor, in immune dysregulation or oxidative stress conditions such as immune suppression, allergy or autoimmune conditions. The F1Cs can thus be used where one or more of these conditions or their symptoms is present. Methods to measure the synthesis or biological activity of these molecules has been described, see, e.g., U.S. Pat. Nos. 6,200,969, 6,187,767, 6,174,901, 6,110,691, 6,083,735, 6,024,940, 5,919,465 and 5,891,924.

Specific Embodiments

Aspects of the invention and related subject matter include the following specific embodiments.

1. A method to prevent, treat, ameliorate or slow the progression of cystic fibrosis, sickle cell disease, neutropenia or thrombocytpoenia in a subject, or to treat a symptom of the neutropenia or thrombocytopenia, comprising administering to a subject, or delivering to the subject's tissues, an effective amount of a formula 1 compound having the structure 5, 6, 7, 8, 9, 10, 11, 12, 13 or 14

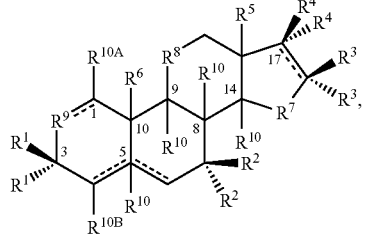

5

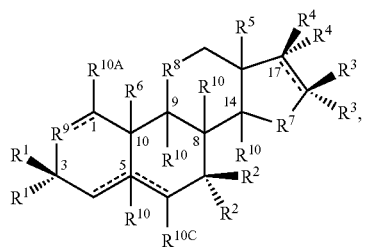

6

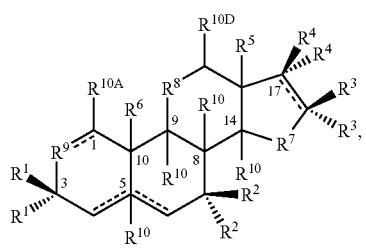

7

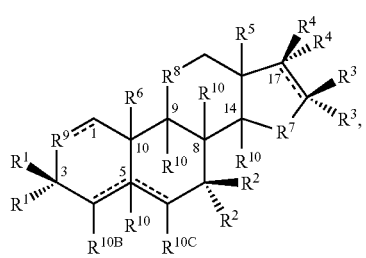

8

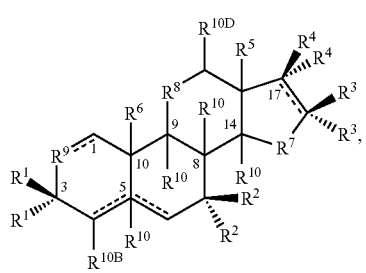

9

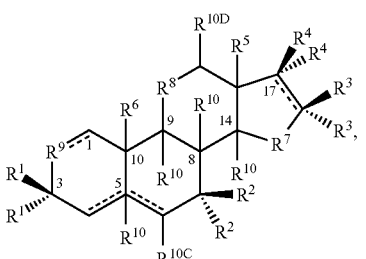

10

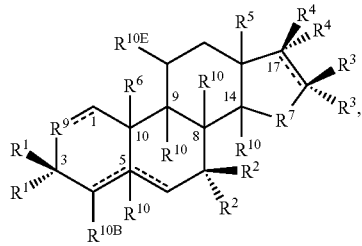

11

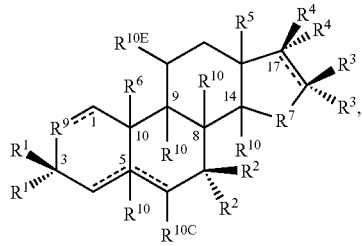

12

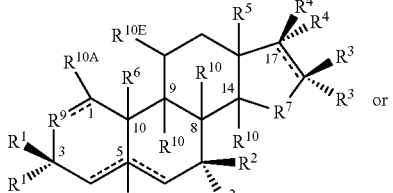

13

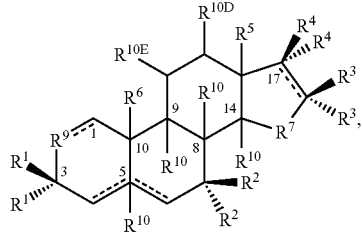

14 or a metabolic precursor or a metabolite thereof, wherein $R^{10}$ moieties at the 5 (if present), 8, 9 and 14 positions respectively are in the α,α,α,α, α,α,α,β, α,α,β,α, α,β,α,α, β,α,α,α, α,α,β,β, α,β,α,β, β,α,α,β, β,α,β,α, β,β,α,α, α,β,β, α, α,β,β,β, β,α,β,β, β,β,α,β, β,β,β,α or β,β,β,β configurations, wherein $R^{10A}$, $R^{10B}$, $R^{10C}$, $R^{10D}$ and $R^{10E}$ respectively are in the α or β,β configurations, wherein, each $R^1$, $R^2$, $R^3$, $R^4$, $R^5$, $R^6$, $R^{10}$, $R^{10A}$, $R^{10B}$, $R^{10C}$, $R^{10D}$ and $R^{10E}$ independently are —H, —OH, —OR$^{PR}$, —SR$^{PR}$, —N(R$^{PR}$)$_2$, —O—Si—(R$^{13}$)$_3$, —CHO, —CHS, —CN, —SCN, —NO$_2$, —NH$_2$, —COOH, —OSO$_3$H, —OPO$_3$H, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide, a polymer, or, one more of $R^1$, $R^2$, $R^3$, $R^4$, $R^5$, $R^6$, $R^{10}$, $R^{10A}$, $R^{10B}$, $R^{10C}$, $R^{10D}$ and $R^{10E}$ are =O, =S, =N—OH, =CH$_2$, =CH—

CH$_3$, or an independently selected spiro ring and the hydrogen atom or the second variable group that is bonded to the same carbon atom is absent, or, one or more of two adjacent R$^1$-R$^6$, R$^{10}$, R$^{10A}$, R$^{10B}$, R$^{10C}$, R$^{10D}$ and R$^{10E}$ comprise an independently selected epoxide, acetal, a thioacetal, ketal or thioketal;

R$^7$ is —C(R$^{10}$)$_2$—, —C(R$^{10}$)$_2$—C(R$^{10}$)$_2$—, —C(R$^{10}$)$_2$—C(R$^{10}$)$_2$—C(R$^{10}$)$_2$—, —C(R$^{10}$)$_2$—O—C(R$^{10}$)$_2$—, —C(R$^{10}$)$_2$—S—C(R$^{10}$)$_2$—, —C(R$^{10}$)$_2$—NR$^{PR}$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—;

R$^8$ and R$^9$ independently are —C(R$^{10}$)$_2$—, —C(R$^{10}$)$_2$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—, or one or both of R$^8$ or R$^9$ independently are absent, leaving a 5-membered ring;

R$^{13}$ independently is C$_{1-6}$ alkyl; and

R$^{PR}$ independently is —H or a protecting group, optionally provided that (1) one or two of R$^{10A}$, R$^{10B}$, R$^{10C}$, R$^{10D}$ and R$^{10E}$ are not hydrogen or (2) one R$^4$ is —NH$_2$, an optionally substituted amine, —N(R$^{PR}$)$_2$, =NOH, =NO-optionally substituted alkyl, an amide or an N-linked amino acid. In these embodiments, the subject may have or be subject to developing the listed condition and the subject can be a human or a primate.

2. The method of embodiment 1 wherein one each of R$^1$, R$^2$, R$^3$ and R$^4$ are —H, and, when no double bond links the second R$^1$, R$^2$, R$^3$ and R$^4$ to the ring to which it is bonded and no double bond is present at the 16-17 position, then the second R$^1$, R$^2$, R$^3$ and R$^4$ respectively are in the α,α,α,α, α,α,α,β, α,α,β,α, α,β,α,α, β,α,α,α, α,α,β,β, α,β,α,β, β,α,α,β, β,α,β,α, β,β,α,α, α,β,β,α, α,β,β,β, β,α,β,β, β,β,α,β, β,β,β,α or β,β,β,β configurations and the second R$^1$, R$^2$, R$^3$ and R$^4$ are optionally independently selected from —H, —F, —Cl, —Br, —I, —OH, —SH, —NH$_2$, —COOH, —CH$_3$, —C$_2$H$_5$, —C(CH$_3$)$_3$, —OCH$_3$, —OC$_2$H$_5$, —CF$_3$, —CH$_2$OH, —C(O)CH$_3$, —C(O)CH$_2$OH, —C(O)CH$_2$F, —C(O)CH$_2$Cl, —C(O)CH$_2$Br, —C(O)CH$_2$I, —C(O)CF$_3$, —C$_2$F$_5$, =O, =CH$_2$, =CHCH$_3$, amino acid, carbamate, carbonate, optionally substituted C1-C20 alkyl, optionally substituted C1-C20 ether, optionally substituted C1-C20 ester, optionally substituted C1-C20 thioether, optionally substituted C1-C20 thioester, optionally substituted monosaccharide, optionally substituted disaccharide, optionally substituted oligosaccharide.

3. The method of embodiment 1 or 2 wherein (a) R$^{10A}$ is bonded to the ring to which it is attached by a single bond and a double bond is present at (i) the 1-2 position, or (ii) the 1-2 and 16-17 positions; or (b) R$^{10B}$ is bonded to the ring to which it is attached by a single bond and a double bond is present at the 4-5 position; or (c) R$^{10c}$ is bonded to the ring to which it is attached by a single bond and a double bond is present at the 5-6 position; or (d) R$^{10A}$ and R$^{10B}$ are bonded to the rings to which they are attached by a single bond and a double bond is present at (i) the 1-2 and 4-5 positions, or (ii) the 1-2, 4-5 and 16-17 positions;

(e) R$^{10A}$ and R$^{10C}$ are bonded to the rings to which they are attached by a single bond and a double bond is present at (i) the 1-2 and 5-6 positions, or (ii) the 1-2, 5-6 and 16-17 positions; or (f) no double bond is present.

4. The method of embodiment 1, 2 or 3 wherein the compounds of structure 5, 6, 7, 8, 9, 10, 11 and 12 have the structure

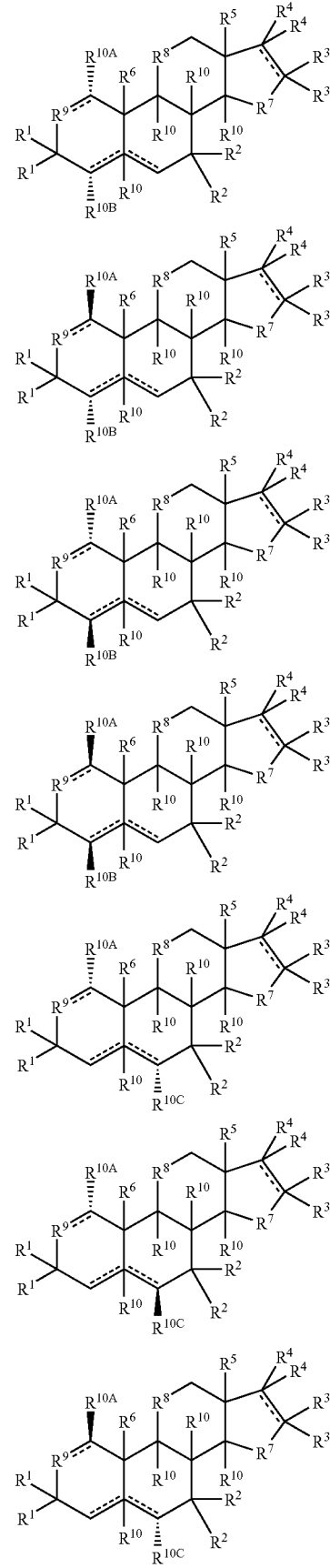

219
-continued
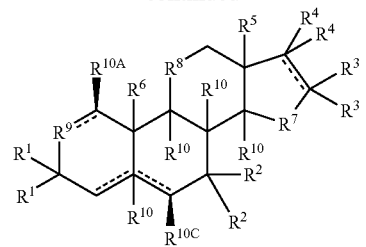
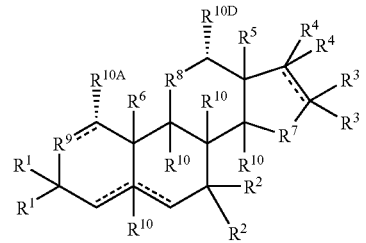
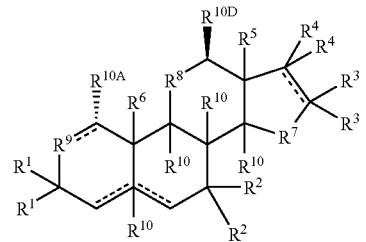
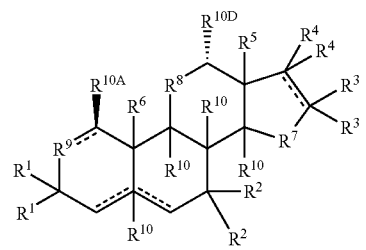
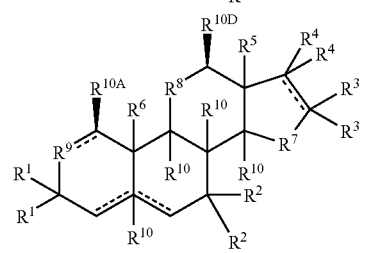
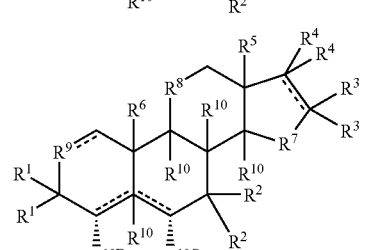
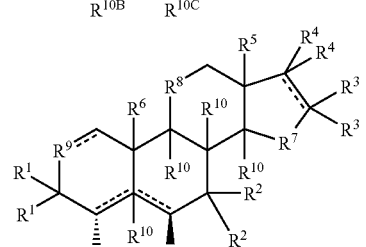
220
-continued
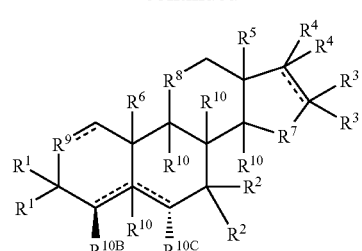
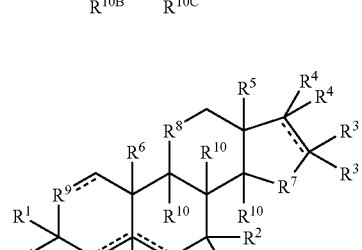
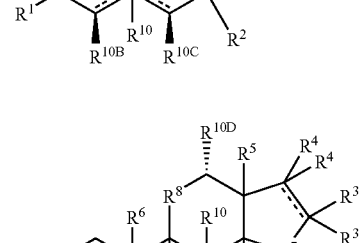
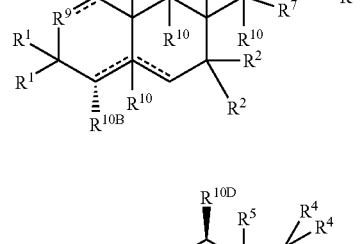
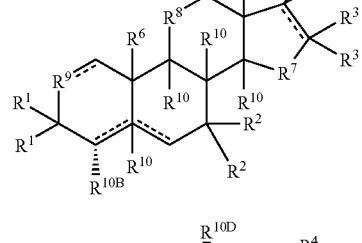
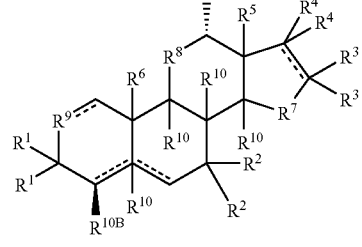
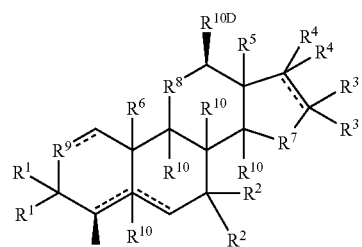

-continued

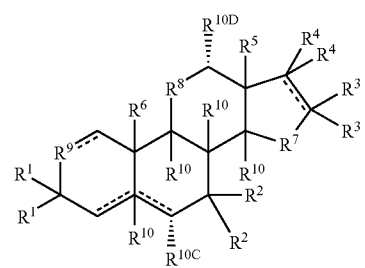
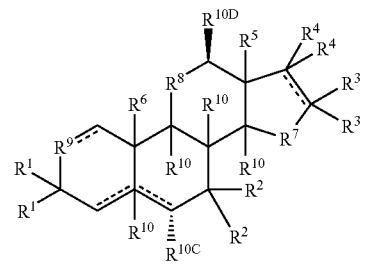
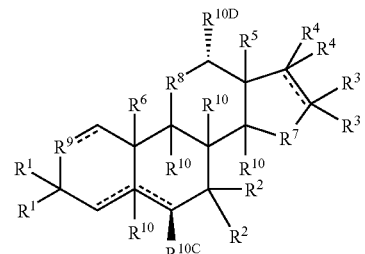
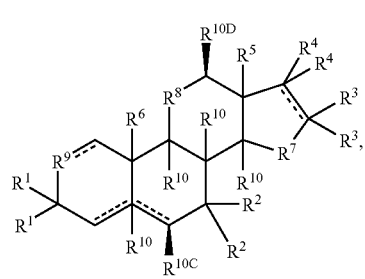
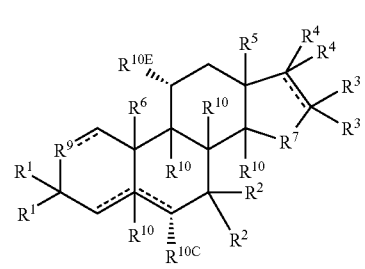
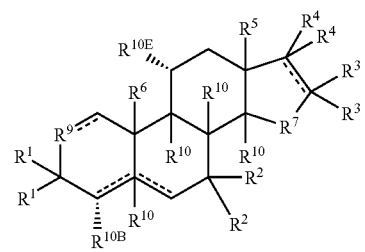

-continued

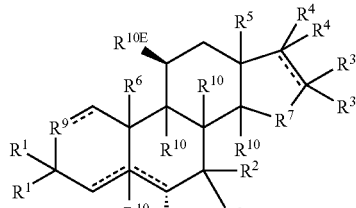
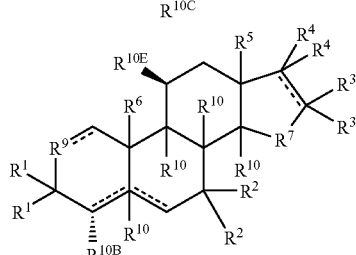
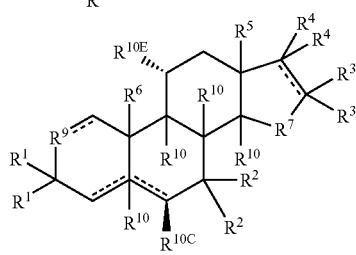
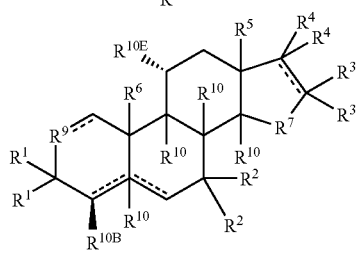
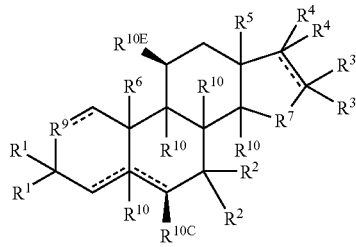
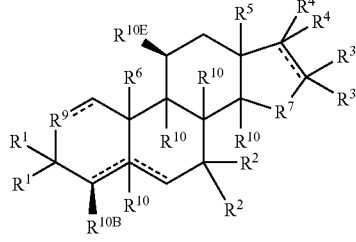

provided that if a double bond is present at the 1-2, 4-5 or 5-6 positions, then $R^{10A}$, $R^{10B}$ or $R^{10C}$ respectively are bonded to the ring to which they are linked by a single bond and wherein, when $R^1$, $R^2$, $R^3$ and $R^4$ are single bonded, one is in the 5-configuration and the other $R^1$, $R^2$, $R^3$ and $R^4$ is in the β-configuration.

5. The method of embodiment 1, 2, 3 or 4 wherein (1) $R^5$ and $R^6$ respectively are in the α,α, α,β, β,α or β,β configuration and $R^5$ and $R^6$ are optionally both —CH$_3$ or are optionally selected from —CH$_3$ and —CH$_2$OH or (2) R$^5$ and R$^6$ are both in the β-configuration and R$^5$ and R$^6$ are optionally both —CH$_3$ or are optionally —CH$_3$ and —CH$_2$OH.

6. The method of embodiment 1, 2, 3, 4 or 5 wherein R$^5$ and R$^6$ are optionally both in the β-configuration and are optionally independently selected from —H, —F, —Br, —CH$_3$, —C$_2$H$_5$, —C(CH$_3$)$_3$, —CH$_2$CH$_2$OH, —CH(O), —CH$_2$OH, —CH$_2$-ester, —CH$_2$-ether, —CH$_2$-amino acid, —CH$_2$-carbamate, —CH$_2$OR$^{PR}$, —CHS, —CH$_2$SH, —CH$_2$SR$^{PR}$, —CH$_2$-thioester, —CH$_2$-thioether, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—CO$_2$H, —CH$_2$OC(O)—(CH$_2$)$_n$—CO$_2$R$^{PR}$, —CH$_2$OC(O)—(CH$_2$)$_n$—C(O)SH, —CH$_2$OC(O)—(CH$_2$)$_n$—C(O)SR$^{PR}$, —CH$_2$OC(O)—(CH$_2$)$_n$—NH$_2$, —CH$_2$OC(O)—(CH$_2$)$_n$—NHR$^{PR}$, a monosaccharide, and an ester wherein n is 0, 1, 2, 3 or 4 and R$^{PR}$ are independently selected protecting groups for atoms to which they are bonded.

7. The method of embodiment 1, 2, 3, 4, 5 or 6 wherein one each of R$^1$, R$^2$, R$^3$ and R$^4$ are —H and wherein (i) no double bond is present at the 16-17 position, the second R$^1$, R$^2$, R$^3$ and R$^4$ respectively are bonded to the ring to which they are attached by a single bond in the β,β,α,β configurations (i.e., R$^1$ is in the β-configuration, R$^2$ is in the β-configuration, R$^3$ is in the α-configuration and R$^4$ is in the β-configuration when no double bond is present at 16-17), or (ii) a double bond is present at the 16-17 position and R$^1$ and R$^2$ respectively are in the β,β configurations (i.e., R$^1$ is in the β-configuration and R$^2$ is in the β-configuration when a double bond is present at 16-17).

8. The method of embodiment 1, 2, 3, 4, 5 or 6 wherein (i) no double bond is present at the 16-17 position, one each of R$^1$, R$^2$, R$^3$ and R$^4$ are —H, and the second R$^1$, R$^2$, R$^3$ and R$^4$ respectively are bonded to the ring to which they are attached by a single bond in the β,β,β,β configurations or (ii) one each of R$^1$, R$^2$ and R$^3$ are —H, no double bond is present at the 16-17 position, the second R$^1$, R$^2$ and R$^3$ respectively are bonded to the ring to which they are attached by a single bond in the β,β,β, β,β,α, β,α,β, α,β,β, β,α,α, α,β,α, α,α,β or α,α,α configurations and both R$^4$ together are bonded to the ring by a double bond (i.e., both R$^4$ together are a double bonded moiety described herein such as =O, =NOH, =CH$_2$ or =CH—CH$_3$).

9. The method of embodiment 1, 2, 3, 4, 5 or 6 wherein (i) no double bond is present at the 16-17 position, one each of R$^1$, R$^2$, R$^3$ and R$^4$ are —H and the second R$^1$, R$^2$, R$^3$ and R$^4$ respectively are bonded to the ring to which they are attached by a single bond in the β,β,β,α configurations or (ii) one each of R$^1$, R$^2$ and R$^4$ are —H, no double bond is present at the 16-17 position, the second R$^1$, R$^2$ and R$^4$ respectively are bonded to the ring to which they are attached by a single bond in the β,β,β, β,β,α, β,α,β, α,β,β, β,α,α, α,β,α, α,α,β or α,α,α configurations and both R$^3$ together are bonded to the ring by a double bond (i.e., both R$^3$ together are a double bonded moiety described herein such as =O, =NOH, =CH$_2$ or =CH—CH$_3$).

10. The method of embodiment 1, 2, 3, 4, 5 or 6 wherein no double bond is present at the 16-17 position, one each of R$^1$, R$^2$, R$^3$ and R$^4$ are —H and the second R$^1$, R$^2$, R$^3$ and R$^4$ respectively are bonded to the ring to which they are attached by a single bond in the β,β,α,α configurations.

11. The method of embodiment 1, 2, 3, 4, 5 or 6 wherein (i) no double bond is present at the 16-17 position, one each of R$^1$, R$^2$, R$^3$ and R$^4$ are —H, and the second R$^1$, R$^2$, R$^3$ and R$^4$ respectively are bonded to the ring to which they are attached by a single bond in the β,α,β,β configurations (i.e., R$^1$ is in the β-configuration, R$^2$ is in the α-configuration, R$^3$ is in the β-configuration and R$^4$ is in the β-configuration when no double bond is present at 16-17), or (ii) a double bond is present at the 16-17 position and R$^1$ and R$^2$ respectively are in the β,α configurations (i.e., R$^1$ is in the β-configuration and R$^2$ is in the α-configuration when a double bond is present at 16-17).

12. The method of embodiment 1, 2, 3, 4, 5 or 6 wherein (i) no double bond is present at the 16-17 position, one each of R$^1$, R$^2$, R$^3$ and R$^4$ are —H, and the second R$^1$, R$^2$, R$^3$ and R$^4$ respectively are bonded to the ring to which they are attached by a single bond in the β,α,β,α configurations or (ii) one each of R$^1$, R$^3$ and R$^4$ are —H, no double bond is present at the 16-17 position, the second R$^1$, R$^3$ and R$^4$ respectively are bonded to the ring to which they are attached by a single bond in the β,β,β, β,β,α, β,α,β, α,β,β, β,α,α, α,β,α, α,α,β or α,α,α configurations and both R$^2$ together are bonded to the ring by a double bond (i.e., both R$^2$ together are a double bonded moiety described herein such as =O, =NOH, =CH$_2$ or =CH—CH$_3$).

13. The method of embodiment 1, 2, 3, 4, 5 or 6 wherein (i) no double bond is present at the 16-17 position, one each of R$^1$, R$^2$, R$^3$ and R$^4$ are —H, and the second R$^1$, R$^2$, R$^3$ and R$^4$ respectively are bonded to the ring to which they are attached by a single bond in the β,α,α,β configurations or (ii) one each of R$^2$, R$^3$ and R$^4$ are —H, no double bond is present at the 16-17 position, the second R$^2$, R$^3$ and R$^4$ respectively are bonded to the ring to which they are attached by a single bond in the β,β,β, β,β,α, β,α,β, α,β,β, β,α,α, α,β,α, α,α,β or α,α,α configurations and both R$^1$ together are bonded to the ring by a double bond (i.e., both R$^1$ together are a double bonded moiety described herein such as =O, =NOH, =CH$_2$ or =CH—CH$_3$).

14. The method of embodiment 1, 2, 3, 4, 5 or 6 wherein no double bond is present at the 16-17 position, one each of R$^1$, R$^2$, R$^3$ and R$^4$ are —H, and the second R$^1$, R$^2$, R$^3$ and R$^4$ respectively are bonded to the ring to which they are attached by a single bond in the β,α,α,α configurations.

15. The method of embodiment 1, 2, 3, 4, 5 or 6 wherein (i) no double bond is present at the 16-17 position, one each of R$^1$, R$^2$, R$^3$ and R$^4$ are —H, the second R$^1$, R$^2$, R$^3$ and R$^4$ respectively are bonded to the ring to which they are attached by a single bond in the α,β,β,β configurations (i.e., R$^1$ is in the α-configuration, R$^2$ is in the β-configuration, R$^3$ is in the β-configuration and R$^4$ is in the β-configuration when no double bond is present at 16-17), or (ii) a double bond is present at the 16-17 position and R$^1$ and R$^2$ respectively are in the α,β configurations (i.e., R$^1$ is in the α-configuration and R$^2$ is in the β-configuration when a double bond is present at 16-17).

16. The method of embodiment 1, 2, 3, 4, 5 or 6 wherein (i) no double bond is present at the 16-17 position, one each of R$^1$, R$^2$, R$^3$ and R$^4$ are —H, and the second R$^1$, R$^2$, R$^3$ and R$^4$ respectively are bonded to the ring to which they are attached by a single bond in the α,β,α,β configurations or (ii) one each of R$^1$ and R$^3$ are —H, no double bond is present at the 16-17 position, the second R$^1$ and R$^3$ respectively are bonded to the ring to which they are attached by a single bond in the β,β, β,α, α,β or α,α configurations and both R$^2$ together and both R$^4$ together are bonded to the ring by a double bond (i.e., both R$^2$ together and both R$^4$ together are an independently selected double bonded moiety described herein such as =O, =NOH, =CH$_2$ or =CH—CH$_3$).

17. The method of embodiment 1, 2, 3, 4, 5 or 6 wherein (i) no double bond is present at the 16-17 position, one each of R$^1$, R$^2$, R$^3$ and R$^4$ are —H, and the second R$^1$, R$^2$, R$^3$ and R$^4$ respectively are bonded to the ring to which they are attached by a single bond in the α,β,β,α configurations or (ii) one each of $R^2$ and $R^3$ are —H, no double bond is present at the 16-17 position, the second $R^2$ and $R^3$ respectively are bonded to the ring to which they are attached by a single bond in the β,β, β,α, α,β or α,α configurations and both $R^1$ together and both $R^4$ together are bonded to the ring by a double bond (i.e., both $R^1$ together and both $R^4$ together are an independently selected double bonded moiety described herein such as =O, =NOH, =CH$_2$ or =CH—CH$_3$).

18. The method of embodiment 1, 2, 3, 4, 5 or 6 wherein no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the α,β,α,α configurations.

19. The method of embodiment 1, 2, 3, 4, 5 or 6 wherein (i) no double bond is present at the 16-17 position, one each of $R^1$, $R^2$, $R^3$ and $R^4$ are —H, the second $R^1$, $R^2$, $R^3$ and $R^4$ respectively are bonded to the ring to which they are attached by a single bond in the α,α,β,β configurations (i.e., $R^1$ is in the α-configuration, $R^2$ is in the α-configuration, $R^3$ is in the β-configuration and $R^4$ is in the β-configuration when no double bond is present at 16-17), or (ii) a double bond is present at the 16-17 position and $R^1$ and $R^2$ respectively are in the α,α configurations (i.e., $R^1$ and $R^2$ are both in the α-configuration when a double bond is present at 16-17).

20. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the α,α,α,β configurations or (ii) one each of $R^1$ and $R^4$ are —H, no double bond is present at the 16-17 position, the second $R^1$ and $R^4$ respectively are bonded to the ring to which they are attached by a single bond in the β,β, β,α, α,β or α,α configurations and both $R^2$ together and both $R^3$ together are bonded to the ring by a double bond (i.e., both $R^2$ together and both $R^3$ together are an independently selected double bonded moiety described herein such as =O, =NOH, =CH$_2$ or =CH—CH$_3$).

21. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the α,α,β,α configurations or (ii) one each of $R^2$ and $R^4$ are —H, no double bond is present at the 16-17 position, the second $R^2$ and $R^4$ respectively are bonded to the ring to which they are attached by a single bond in the β,β, β,α, α,β or α,α configurations and both $R^1$ together and both $R^3$ together are bonded to the ring by a double bond (i.e., both $R^1$ together and both $R^3$ together are an independently selected double bonded moiety described herein such as =O, =NOH, =CH$_2$ or =CH—CH$_3$).

22. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the α,α,α,α configurations or (ii) one each of $R^1$ and $R^2$ are —H, no double bond is present at the 16-17 position, the second $R^1$ and $R^2$ respectively are bonded to the ring to which they are attached by a single bond in the β,β, β,α, α,β or α,α configurations and both $R^3$ together and both $R^4$ together are bonded to the ring by a double bond (i.e., both $R^3$ together and both $R^4$ together are an independently selected double bonded moiety described herein such as =O, =NOH, =CH$_2$ or =CH—CH$_3$) or (iii) one each of $R^3$ and $R^4$ are —H, no double bond is present at the 16-17 position, the second $R^3$ and $R^4$ respectively are bonded to the ring to which they are attached by a single bond in the β,β, β,α, α,β or α,α configurations and both $R^1$ together and both $R^2$ together are bonded to the ring by a double bond (i.e., both $R^1$ together and both $R^2$ together are an independently selected double bonded moiety described herein such as =O, =NOH, =CH$_2$ or =CH—CH$_3$).

23. The method of any of embodiments 1 through 22 wherein no double bond is present at the 4-5 or the 5-6 positions and $R^{10}$ at the 5, 8, 9 and 14 positions respectively are in the α,β,α,α configurations or, if a double bond is present at the 4-5 or the 5-6 positions, then $R^{10}$ at the 8, 9 and 14 positions respectively are in the β,α,α configurations.

24. The method of any of embodiments 1 through 22 wherein no double bond is present at the 4-5 or the 5-6 positions and $R^{10}$ at the 5, 8, 9 and 14 positions respectively are in the β,β,α,α configurations.

25. The method of any of embodiments 1 through 22 wherein no double bond is present at the 4-5 or the 5-6 positions and $R^{10}$ at the 5, 8, 9 and 14 positions respectively are in the α,β,α,β configurations or, if a double bond is present at the 4-5 or the 5-6 positions, then $R^{10}$ at the 8, 9 and 14 positions respectively are in the β,α,β configurations.

26. The method of any of embodiments 1 through 22 wherein no double bond is present at the 4-5 or the 5-6 positions and $R^{10}$ at the 5, 8, 9 and 14 positions respectively are in the β,β,α,β configurations.

27. The method of any of embodiments 1 through 22 wherein no double bond is present at the 4-5 or the 5-6 positions and $R^{10}$ at the 5, 8, 9 and 14 positions respectively are in the α,β,β,α configurations or, if a double bond is present at the 4-5 or the 5-6 positions, then $R^{10}$ at the 8, 9 and 14 positions respectively are in the β,β,α configurations.

28. The method of any of embodiments 1 through 22 wherein no double bond is present at the 4-5 or the 5-6 positions and $R^{10}$ at the 5, 8, 9 and 14 positions respectively are in the β,β,β,α configurations.

29. The method of any of embodiments 1 through 22 wherein no double bond is present at the 4-5 or the 5-6 positions and $R^{10}$ at the 5, 8, 9 and 14 positions respectively are in the α,α,α,α configurations or, if a double bond is present at the 4-5 or the 5-6 positions, then $R^{10}$ at the 8, 9 and 14 positions respectively are in the α,α,α configurations.

30. The method of any of embodiments 1 through 22 wherein no double bond is present at the 4-5 or the 5-6 positions and $R^{10}$ at the 5, 8, 9 and 14 positions respectively are in the β,α,α,α configurations.

31. The method of any of embodiments 1 through 22 wherein no double bond is present at the 4-5 or the 5-6 positions and $R^{10}$ at the 5, 8, 9 and 14 positions respectively are in the α,α,α,β, α,α,β,α, α,α,β,β, β,α,α,β, β,α,β,α, α,β, β,β, β,α,β,β, or β,β,β,β configurations or, if a double bond is present at the 4-5 or the 5-6 positions, then $R^{10}$ at the 8, 9 and 14 positions respectively are in the α,α,β, α,β,α, α,β,β or β,β,β configurations.

32. The method of any of embodiments 1 through 31 wherein $R^{10}$ at the 5, 8, 9 and 14-positions are independently selected from —H, —F, —Cl, —Br, —I, —OH, —OR$^{PR}$, —SH, —NH$_2$, —COOH, —CH$_3$, —C$_2$H$_5$, —C(CH$_3$)$_3$, —CH$_2$OH, —CH$_2$OR$^{PR}$, —CH$_2$F, —CH$_2$Cl, —CH$_2$Br, —CH$_2$I, —CHO, —CHS, —CH$_2$SH, —CH$_2$SR$^{PR}$, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—CO$_2$H, —CH$_2$OC(O)—(CH$_2$)$_n$—CO$_2$R$^{PR}$, —CH$_2$OC(O)—(CH$_2$)—C(O)SH, —CH$_2$—C(O)—(CH$_2$)$_n$—C(O)SR$^{PR}$, —CH$_2$OC(O)—(CH$_2$)$_n$—NH$_2$, —CH$_2$OC(O)—(CH$_2$)$_n$—NHR$^{PR}$, a monosaccharide, an amino acid, a carbonate, a carbamate, an ester, optionally substituted C1-C20 alkyl optionally selected from —CH$_3$, —C$_2$H$_5$ and —C$_3$H$_7$, optionally substituted C1-C20 ether optionally selected from —OCH₃, —OC₂H₅ and —OC₃H₇, optionally substituted C1-C20 ester optionally selected from acetoxy and propionoxy, optionally substituted aryl optionally selected from —O-phenyl, —O—-(alkoxy)$_{1-3}$-phenyl where each alkoxy is optionally independently selected (e.g., methoxy or ethoxy) and —O-(halo)$_{1-3}$-phenyl where each halogen is optionally independently selected (e.g., —F or —Cl).

33. The method of any of embodiments 1 through 31 wherein $R^{10}$ at the 5, 8, 9 and 14-positions respectively are
   (1) —H, —H, —H, —H;
   (2) —H, —H, halogen (—F, —Cl, —Br or —I), —H;
   (3) —H, —H, —H, —OH;
   (4) —H, —H, halogen (—F, —Cl, —Br or —I), —OH;
   (5) -optionally substituted alkyl (e.g., —CH₃, —CH₂OH, —CH₂O-ester, —C₂H₅), —H, —H, —H;
   (6) -optionally substituted alkyl (e.g., —CH₃, —CH₂OH, —CH₂O-ester, —C₂H₅), —H, halogen (—F, —Cl, —Br or —I), —H;
   (7) -optionally substituted alkyl (e.g., —CH₃, —CH₂OH, —CH₂O-ester, —C₂H₅), —H, —H, —OH;
   (8) -acyl (e.g., —C(O)—(CH₂)$_{0-2}$—CH₃), —H, —H, —H;
   (9) -ester (e.g., acetoxy or propionoxy), —H, —H, —H;
   (10) -ether (e.g., —O—(CH₂)$_{0-2}$—CH₃), —H, —H, —H;
   (11) -ester (e.g., acetoxy, propionoxy, —O—C(O)—(CH₂)$_{1-6}$—H), —H, halogen (e.g., —F, —Cl, —Br), —H;
   (12) -ester (e.g., acetoxy or propionoxy), —H, —H, —OH;
   (13) —H, —H, —H, -acyl (e.g., —C(O)—(CH₂)$_{0-2}$—CH₃);
   (14) —H, —H, —H, -ester (e.g., acetoxy or propionoxy); or
   (15) —H, —H, —H, -ether (e.g., —O—(CH₂)$_{0-2}$—CH₃, —OCH₃, —OC₂H₅, —OCH₂OH, —OCH₂F, —OCH₂Br, —OCH₂COOH, —OCH₂NH₂, —OCH₂CH₂OH, —OCH₂CH₂F, —OCH₂CH₂Br, —OCH₂CH₂COOH or —OCH₂CH₂NH₂).

34. The method of any of embodiments 1 through 33 wherein $R^{10}$ at the 5-position is in the α-configuration and is optionally selected from —H, —F, —Cl, —Br, —I, —OH, —OR$^{PR}$, —CH₃, —C₂H₅, —C(CH₃)₃, —CH₂OH, —CH₂OR$^{PR}$, —CH₂F, —CH₂Cl, —CH₂Br, —CH₂I, —CH(O), —CH(S), —CH₂SH, —CH₂SR$^{PR}$, —CH₂NH₂, —CH₂NHR$^{PR}$, —CF₃, —CH₂CH₃, —CH₂CH₂F, —CH₂CF₃, —CH₂OC(O)—(CH₂)$_n$—CH₃, —CH₂OC(O)—(CH₂)$_n$—CO₂H, —CH₂OC(O)—(CH₂)$_n$—CO₂R$^{PR}$, —CH₂OC(O)—(CH₂)$_n$—C(O)SH, —CH₂OC(O)—(CH₂)$_n$—C(O)SR$^{PR}$, —CH₂OC(O)—(CH₂)$_n$—NH₂, —CH₂OC(O)—(CH₂)$_n$—NHR$^{PR}$, a monosaccharide, an amino acid, a carbonate, a carbamate and an ester.

35. The method of any of embodiments 1 through 33 wherein $R^{10}$ at the 5-position is in the β-configuration and is optionally selected from —H, —F, —Cl, —Br, —I, —OH, —OR$^{PR}$, —CH₃, —C₂H₅, —C(CH₃)₃, —CH₂OH, —CH₂R$^{PR}$, —CH₂F, —CH₂Cl, —CH₂Br, —CH₂I, —CHO, —CHS, —CH₂SH, —CH₂SR$^{PR}$, —CH₂NH₂, —CH₂NHR$^{PR}$, —CF₃, —CH₂CH₃, —CH₂CH₂F, —CH₂CF₃, —CH₂OC(O)—(CH₂)$_n$—CH₃, —CH₂OC(O)—(CH₂)$_n$—CO₂H, —CH₂OC(O)—(CH₂)$_n$—CO₂R$^{PR}$, CH₂OC(O)—(CH₂)$_n$—C(O)SH, —CH₂OC(O)—(CH₂)$_n$—C(O)SR$^{PR}$, —CH₂OC(O)—(CH₂)$_n$—NH₂, —CH₂OC(O)—(CH₂)$_n$—NHR$^{PR}$, a monosaccharide, an amino acid, a carbonate, a carbamate and an ester.

36. The method of any of embodiments 1 through 35 wherein $R^{10}$ at the 8-position is in the α-configuration and is optionally selected from —H, —F, —Cl, —Br, —I, —OH, —OR$^{PR}$, —CH₃, —C₂H₅, —C(CH₃)₃, —CH₂OH, —CH₂OR$^{PR}$, —CH₂F, —CH₂Cl, —CH₂Br, —CH₂I, —CHO, —CHS, —CH₂SH, —CH₂SR$^{PR}$, —CH₂NH₂, —CH₂NHR$^{PR}$, —CF₃, —CH₂CH₃, —CH₂CH₂F, —CH₂CF₃, —CH₂OC(O)—(CH₂)$_n$—CH₃, —CH₂OC(O)—(CH₂)$_n$—CO₂H, —CH₂OC(O)—(CH₂)$_n$—CO₂R$^{PR}$, —CH₂OC(O)—(CH₂)$_n$—C(O)SH, —CH₂OC(O)—(CH₂)$_n$—C(O)SR$^{PR}$, —CH₂OC(O)—(CH₂)$_n$—NH₂, —CH₂OC(O)—(CH₂)$_n$—NHR$^{PR}$, a monosaccharide, an amino acid, a carbonate, a carbamate and an ester.

37. The method of any of embodiments 1 through 35 wherein $R^{10}$ at the 8-position is in the β-configuration and is optionally selected from —H, —F, —Cl, —Br, —I, —OH, —OR$^{PR}$, —CH₃, —C₂H₅, —C(CH₃)₃, —CH₂OH, —CH₂R$^{PR}$, —CH₂F, —CH₂Cl, —CH₂Br, —CH₂I, —CHO, —CHS, —CH₂SH, —CH₂SR$^{PR}$, —CH₂NH₂, —CH₂NHR$^{PR}$, —CF₃, —CH₂CH₃, —CH₂CH₂F, —CH₂CF₃, —CH₂OC(O)—(CH₂)$_n$—CH₃, —CH₂OC(O)—(CH₂)$_n$—CO₂H, —CH₂OC(O)—(CH₂)$_n$—CO₂R$^{PR}$, —CH₂OC(O)—(CH₂)$_n$—C(O)SH, —CH₂OC(O)—(CH₂)$_n$—C(O)SR$^{PR}$, —CH₂OC(O)—(CH₂)$_n$—NH₂, —CH₂OC(O)—(CH₂)$_n$—NHR$^{PR}$, a monosaccharide, an amino acid, a carbonate, a carbamate and an ester.

38. The method of any of embodiments 1 through 37 wherein $R^{10}$ at the 9-position is in the α-configuration and is optionally selected from —H, —F, —Cl, —Br, —I, —OH, —OR$^{PR}$, —CH₃, —C₂H₅, —C(CH₃)₃, —CH₂OH, —CH₂OR$^{PR}$, —CH₂F, —CH₂Cl, —CH₂Br, —CH₂I, —CHO, —CHS, —CH₂SH, —CH₂SR$^{PR}$, —CH₂NH₂, —CH₂NHR$^{PR}$, —CF₃, —CH₂CH₃, —CH₂CH₂F, —CH₂CF₃, —CH₂OC(O)—(CH₂)$_n$—CH₃, —CH₂OC(O)—(CH₂)$_n$—CO₂H, —CH₂OC(O)—(CH₂)$_n$—CO₂R$^{PR}$, —CH₂OC(O)—(CH₂)$_n$—C(O)SH, —CH₂OC(O)—(CH₂)$_n$—C(O)SR$^{PR}$, —CH₂OC(O)—(CH₂)$_n$—NH₂, —CH₂OC(O)—(CH₂)$_n$—NHR$^{PR}$, a monosaccharide, an amino acid, a carbonate, a carbamate and an ester.

39. The method of any of embodiments 1 through 37 wherein $R^{10}$ at the 9-position is in the β-configuration and is optionally selected from —H, —F, —Cl, —Br, —I, —OH, —OR$^{PR}$, —CH₃, —C₂H₅, —C(CH₃)₃, —CH₂OH, —CH₂OR$^{PR}$, —CH₂F, —CH₂Cl, —CH₂Br, —CH₂I, —CHO, —CHS, —CH₂SH, —CH₂SR$^{PR}$, —CH₂NH₂, —CH₂NHR$^{PR}$, —CF₃, —CH₂CH₃, —CH₂CH₂F, —CH₂CF₃, —CH₂OC(O)—(CH₂)$_n$—CH₃, —CH₂OC(O)—(CH₂)$_n$—CO₂H, —CH₂OC(O)—(CH₂)$_n$—CO₂R$^{PR}$, —CH₂OC(O)—(CH₂)$_n$—C(O)SH, —CH₂OC(O)—(CH₂)$_n$—C(O)SR$^{PR}$, —CH₂OC(O)—(CH₂)$_n$—NH₂, —CH₂OC(O)—(CH₂)$_n$—NHR$^{PR}$, a monosaccharide, an amino acid, a carbonate, a carbamate and an ester.

40. The method of any of embodiments 1 through 39 wherein $R^{10}$ at the 14-position is in the α-configuration and is optionally selected from —H, —F, —Cl, —Br, —I, —OH, —OR$^{PR}$, —CH₃, —C₂H₅, —C(CH₃)₃, —CH₂OH, —CH₂OR$^{PR}$, —CH₂F, —CH₂Cl, —CH₂Br, —CH₂I, —CHO, —CHS, —CH₂SH, —CH₂SR$^{PR}$, —CH₂NH₂, —CH₂NHR$^{PR}$, —CF₃, —CH₂CH₃, —CH₂CH₂F, —CH₂CF₃, —CH₂OC(O)—(CH₂)$_n$—CH₃, —CH₂OC(O)—(CH₂)$_n$—CO₂H, —CH₂OC(O)—(CH₂)$_n$—CO₂R$^{PR}$, —CH₂OC(O)—(CH₂)$_n$—C(O)SH, —CH₂OC(O)—(CH₂)$_n$—C(O)SR$^{PR}$, —CH₂OC(O)—(CH₂)$_n$—NH₂, —CH₂OC(O)—(CH₂)$_n$—NHR$^{PR}$, a monosaccharide, an amino acid, a carbonate, a carbamate and an ester.

41. The method of any of embodiments 1 through 39 wherein $R^{10}$ at the 14-position is in the β-configuration and is optionally selected from —H, —F, —Cl, —Br, —I, —OH, —OR$^{PR}$, —CH₃, —C₂H₅, —C(CH₃)₃, —CH₂OH, —CH₂OR$^{PR}$, —CH₂F, —CH₂Cl, —CH₂Br, —CH₂I, —CHO, —CHS, —CH₂SH, —CH₂SR$^{PR}$, —CH₂NH₂, —CH₂NHR$^{PR}$, —CF₃, —CH₂CH₃, —CH₂CH₂F, —$CH_2CF_3$, —$CH_2OC(O)$—$(CH_2)_n$—$CH_3$, —$CH_2OC(O)$—$(CH_2)_n$—$CO_2H$, —$CH_2OC(O)$—$(CH_2)_n$—$CO_2R^{PR}$, —$CH_2OC(O)$—$(CH_2)_n$—$C(O)SH$, —$CH_2OC(O)$—$(CH_2)_n$—$C(O)SR^{PR}$, —$CH_2OC(O)$—$(CH_2)_n$—$NH_2$, —$CH_2OC(O)$—$(CH_2)_n$—$NHR^{PR}$, a monosaccharide, an amino acid, a carbonate, a carbamate and an ester.

42. The method of any of embodiments 1 through 41 wherein $R^7$ is —$CH_2$—, —CHOH—, —CH($\alpha R^{10}$)—, —CH(ester)-, —CH(alkoxy)- or —CH(halogen)- where the hydroxyl, ester or alkoxy group or the halogen atom is present in the $\alpha$-configuration and the alkoxy group is optionally selected from —$OCH_3$, —$OC_2H_5$ and —$OC_3H_7$ and the halogen atom is —F, —Cl, —Br or —I.

43. The method of any of embodiments 1 through 41 wherein $R^7$ is (i) —CHOH—, —$CF_2$—, —$C(R^{10})_2$—, —CH($\beta R^{10}$)—, —CH(ester)-, —CH(alkoxy)- or —CH(halogen)- where the hydroxyl, ester or alkoxy group or the halogen atom is present in the $\beta$-configuration and the alkoxy group is optionally selected from —$OCH_3$, —$OC_2H_5$ and —$OC_3H_7$ and the halogen atom is —F, —Cl, —Br or —I or (ii) wherein $R^7$ is —C($\beta CH_3$)($\alpha$OH)—, —C($\alpha CH_3$)($\beta$OH)—, —C($\beta CH_3$)($\alpha$F)—, —C($\alpha CH_3$)($\beta$F)—, —$CF_2$—, —C($\beta CH_3$)($\alpha$Cl)—, —C($\alpha CH_3$)($\beta$Cl)—, —$CCl_2$—, —C($\beta CH_3$)($\alpha$Br)—, —C($\alpha CH_3$)($\beta$Br)—, —$CBr_2$—, —C($\beta CH_3$)($\alpha$I)—, —C($\alpha CH_3$)($\beta$I)—, or —$Cl_2$—.

44. The method of any of embodiments 1 through 41 wherein $R^7$ is —C(O)—, —C($=CHCH_3$)—, —C($=CH_2$)—, —C($=CH$—$(CH_2)_n$—$CH_3$)—, —C($=CH$—$(CH_2)_n$—$CH_2OH$)—, —C($=CH$—$(CH_2)_n$—$CH_2F$)—, —C($=CH$—$(CH_2)_n$—$CH_2Cl$)—, —C($=CH$—$(CH_2)_n$—$CH_2Br$)—, —C($=CH$—$(CH_2)_n$—$CH_2I$)—, —C($=NOH$)—, —C($=NO$—$(CH_2)_n$—$CH_3$), wherein n is 0, 1, 2, 3 or 4.

45. The method of any of embodiments 1 through 44 wherein $R^3$ is —$CH_2$—, —CHOH—, —CH($\alpha R^{10}$)—, —CH(ester)-, —CH(alkoxy)- or —CH(halogen)- where the hydroxyl, ester or alkoxy group or the halogen atom is present in the $\alpha$-configuration and the alkoxy group is optionally selected from —$OCH_3$, —$OC_2H_5$ and —$OC_3H_7$ and the halogen atom is —F, —Cl, —Br or —I.

46. The method of any of embodiments 1 through 44 wherein $R^8$ is (i) —CHOH—, —$CF_2$—, —$C(R^{10})_2$—, —CH($\beta R^{10}$)—, —CH(ester)-, —CH(alkoxy)- or —CH(halogen)- where the hydroxyl, ester or alkoxy group or the halogen atom is present in the $\beta$-configuration and the alkoxy group is optionally selected from —$OCH_3$, —$OC_2H_5$ and —$OC_3H_7$ and the halogen atom is —F, —Cl, —Br or —I or (ii) wherein $R^3$—C($\beta CH_3$)($\alpha$OH)—, —C($\alpha CH_3$)($\beta$OH)—, —C($\beta CH_3$)($\alpha$F)—, —C($\alpha CH_3$)(OF)—, —$CF_2$—, —C($\beta CH_3$)($\alpha$Cl)—, —C($\alpha CH_3$)($\alpha$Cl)—, —$CCl_2$—, —C($\beta CH_3$)($\alpha$Br)—, —C($\alpha CH_3$)($\beta$Br)—, —$CBr_2$—, —C($\beta CH_3$)($\alpha$I)—, —C($\alpha CH_3$)($\beta$I)—, or —$Cl_2$—.

47. The method of any of embodiments 1 through 44 wherein $R^8$ is —C(O)—, —$CH_2$—, —C($=CHCH_3$)—, —C($=CH_2$)—, —C($=CH$—$(CH_2)_n$—$CH_3$)—, —C($=CH$—$(CH_2)_n$—$CH_2OH$)—, —C($=CH$—$(CH_2)_n$—$CH_2F$)—, —C($=CH$—$(CH_2)_n$—$CH_2Cl$)—, —C($=CH$—$(CH_2)_n$—$CH_2Br$)—, —C($=CH$—$(CH_2)_n$—$CH_2I$)—, —C($=NOH$)—, —C($=NO$—$(CH_2)_n$—$CH_3$), wherein n is 0, 1, 2, 3 or 4.

48. The method of any of embodiments 1 through 47 wherein $R^9$ is —$CH_2$—, —CHOH—, —CH($\alpha R^{10}$)—, —CH(ester)-, —CH(alkoxy)- or —CH(halogen)- where the hydroxyl, ester or alkoxy group or the halogen atom is present in the $\alpha$-configuration and the alkoxy group is optionally selected from —$OCH_3$, —$OC_2H_5$ and —$OC_3H_7$ and the halogen atom is —F, —Cl, —Br or —I.

49. The method of any of embodiments 1 through 47 wherein $R^9$ is (i) —CHOH—, —$CF_2$—, —$C(R^{10})_2$—, —CH($\beta R^{10}$)—, —CH(ester)-, —CH(alkoxy)- or —CH(halogen)- where the hydroxy, ester or alkoxy group or the halogen atom is present in the $\beta$-configuration and the alkoxy group is optionally selected from —$OCH_3$, —$OC_2H_5$ and —$OC_3H_7$ and the halogen atom is —F, —Cl, —Br or —I, or (ii) wherein $R^9$ is —C($\beta CH_3$)($\alpha$OH)—, —C($\alpha CH_3$)($\beta$OH)—, —C($\beta CH_3$)($\alpha$F)—, —C($\alpha CH_3$)(OF)—, —$CF_2$—, —C($\beta CH_3$)($\alpha$Cl)—, —C($\alpha CH_3$)($\beta$Cl)—, —$CCl_2$—, —C($\beta CH_3$)($\alpha$Br)—, —C($\alpha CH_3$)($\beta$Br)—, —$CBr_2$—, —C($\beta CH_3$)($\alpha$I)—, —C($\alpha CH_3$)($\beta$I)—, or —$Cl_2$—.

50. The method of any of embodiments 1 through 47 wherein $R^9$ is —C(O)—, —$CH_2$—, —C($=CHCH_3$)—, —C($=CH_2$)—, —C($=CH$—$(CH_2)_n$—$CH_3$)—, —C($=CH$—$(CH_2)_n$—$CH_2OH$)—, —C($=CH$—$(CH_2)_n$—$CH_2F$)—, —C($=CH$—$(CH_2)_n$—$CH_2Cl$)—, —C($=CH$—$(CH_2)_n$—$CH_2Br$)—, —C($=CH$—$(CH_2)_n$—$CH_2I$)—, —C($=NOH$)—, —C($=NO$—$(CH_2)_n$—$CH_3$), wherein n is 0, 1, 2, 3 or 4.

51. The method of any of embodiments 1 through 50 wherein the subject has, or is subject or susceptible to developing, neutropenia.

52. The method of any of embodiments 1-50 wherein the subject is a mammal.

53. The method of embodiment 52 wherein the mammal is a human.

54. The method of any preceeding embodiment wherein $R^7$ is —$CH_2$—, —C($\alpha$-OH, $\beta$H)—, —C($\beta$-OH, $\alpha$-H)— or —C(O)—.

55. The method of any preceeding embodiment wherein $R^3$ is —$CH_2$—, —C($\alpha$-OH, $\beta$-H)—, —C($\beta$-OH, $\alpha$-H)—, —C($\alpha$-OH, $\beta$-F)—, —C($\beta$-OH, $\alpha$-F)—, —C($\alpha$-F, $\beta$-H)—, —C($\beta$-F, $\alpha$-H)— or —C(O)—.

56. The method of any preceeding embodiment wherein $R^9$ is —$CH_2$—, —C($\alpha$-OH, —H)—, —C($\beta$-OH, $\alpha$-H)— or —C(O)—.

57. The method of any preceeding embodiment wherein $R^{10A}$ is —H, $\alpha$-OH, $\beta$-OH or =O.

58. The method of any preceeding embodiment wherein $R^{10B}$ is —H, $\beta$-OH, $\beta$-OH or =O.

59. The method of any preceeding embodiment wherein $R^{10C}$ is —H, $\alpha$-OH, $\beta$-OH or =O.

60. The method of any preceeding embodiment wherein $R^{10D}$ is —H, $\alpha$-OH, $\beta$-OH or =O.

61. The method of any preceeding embodiment wherein $R^{10E}$ is —H, $\alpha$-OH, $\beta$-OH or =O.

62. The method of any preceeding embodiment wherein $R^{14}$ are ($\alpha$-OH, $\beta$-H), ($\beta$-OH, $\alpha$-H), ($\alpha$-C(O)$CH_3$, $\beta$-H), ($\beta$-C(O)$CH_3$, $\alpha$-H), ($\alpha$-OH, $\beta$-F), ($\beta$-OH, $\alpha$-F), ($\alpha$-H, $\beta$-F), ($\beta$-H, $\alpha$-F), ($\alpha$-$NH_2$, $\beta$-H), ($\beta$-$NH_2$, ($\alpha$-H), =O, =$CH_2$ or =CH—$CH_3$.

63. The method of any preceeding embodiment wherein $R^1$ are (H, H), ($\alpha$-OH, $\beta$-H), ($\beta$-OH, $\alpha$-H) or =O.

64. The method of any preceeding embodiment wherein $R^2$ are (H, H), ($\alpha$-OH, $\beta$-H), ($\beta$-OH, $\alpha$-H) or =O.

65. The method of any preceeding embodiment wherein $R^3$ are (H, H), ($\alpha$-OH, $\beta$-H), ($\beta$-OH, $\alpha$-H), ($\alpha$-H, $\beta$-F), ($\beta$-H, $\alpha$-F) or =O.

66. The method of any of embodiments 1-65 wherein the formula 1 compound is 16$\alpha$-bromo-3$\beta$-hydroxy-5$\alpha$-androstan-17-one, 16$\alpha$-fluoro-3$\beta$-hydroxy-5$\alpha$-androstan-17-one, 16$\alpha$-chloro-3$\beta$-hydroxy-5$\alpha$-androstan-17-one, 16$\beta$-bromo-3$\beta$-hydroxy-5$\alpha$-androstan-17-one, 16$\beta$-fluoro-3$\beta$-hydroxy-5$\alpha$-androstan-17-one, 16$\beta$-chloro-3$\beta$-hydroxy-5$\alpha$-androstan-17-one, 16$\alpha$,3$\beta$-dihydroxy-5$\alpha$-androstan-17-one, 16$\beta$,3$\beta$-dihydroxy-5$\alpha$-androstan-17-one, 16$\alpha$,3$\alpha$-dihydroxy-5α-androstan-17-one, 16β,3α-dihydroxy-5α-androstan-17-one, 16α-bromo-3β-hydroxy-5α-androstan-17-one hemihydrate, 3α-hydroxy-16α-fluoroandrostane-17-one, 3β-hydroxy-16α-fluoroandrostane-17-one, 17α-hydroxy-16α-fluoroandrostane-3-one, 17β-hydroxy-16α-fluoroandrostane-3-one, 17α-hydroxy-16α-fluoroandrostane-4-one, 17β-hydroxy-16α-fluoroandrostane-4-one, 17α-hydroxy-16α-fluoroandrostane-6-one, 17β-hydroxy-16α-fluoroandrostane-6-one, 17α-hydroxy-16α-fluoroandrostane-7-one, 17β-hydroxy-16α-fluoroandrostane-7-one, 17α-hydroxy-16α-fluoroandrostane-11-one, 17β-hydroxy-16α-fluoroandrostane-11-one, 16α-fluoroandrost-5-ene-17-one, 7α-hydroxy-16α-fluoroandrost-5-ene-17-one, 7β-hydroxy-16α-fluoroandrost-5-ene-17-one, 4α-hydroxy-16α-fluoroandrost-5-ene-17-one, 3α-hydroxy-16α-fluoroandrost-5-ene-17-one, 3β-hydroxy-16α-fluoroandrost-5-ene-17-one, 4β-hydroxy-16α-fluoroandrost-5-ene-17-one, 6α-hydroxy-16β-fluoroandrost-5-ene-17-one, 6β-hydroxy-16α-fluoroandrost-5-ene-17-one, 11α-hydroxy-16α-fluoroandrost-5-ene-17-one, 11β-hydroxy-16α-fluoroandrost-5-ene-17-one, 4α,17β-dihydroxy-16α-fluoroandrost-5-ene, 4β,17β-dihydroxy-16α-fluoroandrost-5-ene, 6α,17β-dihydroxy-16α-fluoroandrost-5-ene, 6β,17β-dihydroxy-16α-fluoroandrost-5-ene, 11α,17β-dihydroxy-16α-fluoroandrost-5-ene, 11β,17β-dihydroxy-16α-fluoroandrost-5-ene, 4α,17α-dihydroxy-16α-fluoroandrost-5-ene, 4β,17α-dihydroxy-16α-fluoroandrost-5-ene, 6α,17α-dihydroxy-16α-fluoroandrost-5-ene, 6β,17α-dihydroxy-16α-fluoroandrost-5-ene, 11α,17α-dihydroxy-16α-fluoroandrost-5-ene, 11β,17α-dihydroxy-16α-fluoroandrost-5-ene, 7α,17β-dihydroxy-16α-fluoroandrost-5-ene, 7β,17β-dihydroxy-16α-fluoroandrost-5-ene, 3α,17β-dihydroxy-16α-fluoroandrost-5-ene, 3β,17β-dihydroxy-16α-fluoroandrost-5-ene, 3α,17α-dihydroxy-16α-fluoroandrost-5-ene, 3β,17α-dihydroxy-16α-fluoroandrost-5-ene, 1α,17β-dihydroxy-16α-fluoroandrost-5-ene, 1β,17β-dihydroxy-16α-fluoroandrost-5-ene, 2α,17β-dihydroxy-16α-fluoroandrost-5-ene, 2β,17β-dihydroxy-16α-fluoroandrost-5-ene, 12α,17β-dihydroxy-16α-fluoroandrost-5-ene, 12β,17β-dihydroxy-16α-fluoroandrost-5-ene, 1α,17α-dihydroxy-16α-fluoroandrost-5-ene, 1β,17α-dihydroxy-16α-fluoroandrost-5-ene, 2α,17α-dihydroxy-16α-fluoroandrost-5-ene, 2β,17α-dihydroxy-16α-fluoroandrost-5-ene, 12α,17α-dihydroxy-16α-fluoroandrost-5-ene, 12β,17α-dihydroxy-16α-fluoroandrost-5-ene, 15α,17β-dihydroxy-16α-fluoroandrost-5-ene, 15β,17β-dihydroxy-16α-fluoroandrost-5-ene, 17β,18-dihydroxy-16α-fluoroandrost-5-ene, 17β,19-dihydroxy-16α-fluoroandrost-5-ene, 15α,17β-dihydroxy-16α-fluoroandrost-5-ene, 15β,17α-dihydroxy-16α-fluoroandrost-5-ene, 17α,18-dihydroxy-16α-fluoroandrost-5-ene, 17α,19-dihydroxy-16α-fluoroandrost-5-ene, 16α-fluoroandrost-4-ene-17-one, 7α-hydroxy-16α-fluoroandrost-4-ene-17-one, 7β-hydroxy-16α-fluoroandrost-4-ene-17-one, 3α-hydroxy-16α-fluoroandrost-4-ene-17-one, 3β-hydroxy-16α-fluoroandrost-4-ene-17-one, 4α-hydroxy-16α-fluoroandrost-4-ene-17-one, 4β-hydroxy-16α-fluoroandrost-4-ene-17-one, 6α-hydroxy-16β-fluoroandrost-4-ene-17-one, 6β-hydroxy-16α-fluoroandrost-4-ene-17-one, 11α-hydroxy-16β-fluoroandrost-4-ene-17-one, 11β-hydroxy-16α-fluoroandrost-4-ene-17-one, 4α,17β-dihydroxy-16α-fluoroandrost-4-ene, 4β,17β-dihydroxy-16α-fluoroandrost-4-ene, 6α,17β-dihydroxy-16α-fluoroandrost-4-ene, 6β,17β-dihydroxy-16α-fluoroandrost-4-ene, 11α,17β-dihydroxy-16α-fluoroandrost-4-ene, 11β,17β-dihydroxy-16α-fluoroandrost-4-ene, 4α,17-dihydroxy-16α-fluoroandrost-4-ene, 4β,17α-dihydroxy-16α-fluoroandrost-4-ene, 6α,17α-dihydroxy-16α-fluoroandrost-4-ene, 6β,17α-dihydroxy-16α-fluoroandrost-4-ene, 11α,17α-dihydroxy-16α-fluoroandrost-4-ene, 11β,17α-dihydroxy-16α-fluoroandrost-4-ene, 7α,17β-dihydroxy-16α-fluoroandrost-4-ene, 7β,17β-dihydroxy-16α-fluoroandrost-4-ene, 3α,17β-dihydroxy-16α-fluoroandrost-4-ene, 3β,17β-dihydroxy-16α-fluoroandrost-4-ene, 3α,17α-dihydroxy-16α-fluoroandrost-4-ene, 3β,17α-dihydroxy-16α-fluoroandrost-4-ene, 1α,17β-dihydroxy-16α-fluoroandrost-4-ene, 1β,17β-dihydroxy-16α-fluoroandrost-4-ene, 2α,17β-dihydroxy-16α-fluoroandrost-4-ene, 2β,17β-dihydroxy-16α-fluoroandrost-4-ene, 12α,17β-dihydroxy-16α-fluoroandrost-4-ene, 12β,17β-dihydroxy-16α-fluoroandrost-4-ene, 1α,17α-dihydroxy-16α-fluoroandrost-4-ene, 1β,17α-dihydroxy-16α-fluoroandrost-4-ene, 2α,17α-dihydroxy-16α-fluoroandrost-4-ene, 2β,17α-dihydroxy-16α-fluoroandrost-4-ene, 12α,17α-dihydroxy-16α-fluoroandrost-4-ene, 12β,17α-dihydroxy-16α-fluoroandrost-4-ene, 15α,17β-dihydroxy-16α-fluoroandrost-4-ene, 15β,17β-dihydroxy-16α-fluoroandrost-4-ene, 17β,18-dihydroxy-16α-fluoroandrost-4-ene, 17β,19-dihydroxy-16α-fluoroandrost-4-ene, 15α,17α-dihydroxy-16α-fluoroandrost-4-ene, 15β,17α-dihydroxy-16α-fluoroandrost-4-ene, 17α,18-dihydroxy-16α-fluoroandrost-4-ene, 17α,19-dihydroxy-16α-fluoroandrost-4-ene, 3β,17β-dihydroxyandrost-5-ene, 3β-hydroxy-7,17-dioxoandrost-5-ene, 3α-hydroxy-7,17-dioxoandrost-5-ene, 3β,17-dioxoandrost-5-ene, 3β,17-dioxoandrost-4-ene, 3β,17-dioxoandrost-1,4-diene, 3β,7β,17β-trihydroxyandrost-5-ene, 3β,7β,17β-trihydroxyandrostane, 3β,16α-dihydroxy-17-oxoandrostane, 3α,16α-dihydroxy-17-oxoandrostane, 3β,16β-dihydroxy-17-oxoandrostane, 3α,16β-dihydroxy-17-oxoandrostane, 3β,16α,17β-trihydroxyandrostane, 3β,16β,17β-trihydroxyandrostane, 3β,16α,17α-trihydroxyandrostane, 3β,16β,17α-trihydroxyandrostane, 3α,16α,17β-trihydroxyandrostane, 3α,16β,17β-trihydroxyandrostane or an analog of any of the foregoing compounds that is suitably substituted to fall within the scope of the embodiment, e.g., wherein an $R^{10}$ is a hydroxyl, thiol, optionally substituted alkyl or a halogen such as fluorine or bromine at the 1-, 2-, 4-, 6-, 7-, 9-11-, 12-, 14-, 15- or 16-position, wherein the $R^{10}$ is present in the α-configuration or the β-configuration.

67. A method to treat, ameliorate or slow the progression of cystic fibrosis in a human comprising administering to the human an effective amount of a formula 1 compound of any preceeding embodiment.

68. The method of embodiment 67, wherein one or more symptoms or syndromes are ameliorated, or wherein the progression of the disease is reduced.

69. The method of embodiment 68, wherein the one or more symptoms or syndromes are 1, 2, 3 or more of *Staphylococcus* (e.g., *S. aureus*), *Haemophilus influenzae, Pseudomonas* or *Burkholderia* respiratory tract or lung infection or propensity to develop a detectable infection or colonization, coughing, wheezing, cyanosis, bronchiolitis, bronchospasm, pneumothorax, hemoptysis, pancreatic exocrine insufficiency, bronchiectatic lung disease, atelectasis-consolidation, pulmonary edema, increased lung vascular hydrostatic pressure, increased lung vascular permeability, sinusitis, respiratory insufficiency, bronchial wall or interlobular septa thickening, reduction of forced expiratory volume in 1 second, dyspnea, impaired male fertility, elevated sweat chloride, mucous plugging, tree-in-bud sign, mosaic perfusion pattern, glucose intolerance or abnormal elevation of one or more of IL-4, IL-8, RANTES, neutrophil elastase, eosinophils, macrophages, neutrophils, eosinophil cationic protein or cysteinyl leukotrienes.

70. The method of embodiment 67, 68 or 69 wherein the method further comprises another suitable CF treatment, which is optionally selected from oral or aerosol corticosteroid treatment, ibuprofen treatment, DNAse treatment, IL-10 treatment, diet control, vaccination against pathogens, or chest physical therapy.

71. The method of embodiment 67, 68, 69 or 70 wherein the F1C is 16α-bromoepiandrosterone, 16α-bromoepiandrosterone hemihydrate, 16α-hydroxyepiandrosterone, 16β-hydroxyepiandrosterone, 3α,17β-dihydroxyandrostane, 3β,17β-dihydroxyandrostane, 3α,16α,17β-trihydroxyandrostane, 3α,16β,17β-trihydroxyandrostane, 3β,16α,17β-trihydroxyandrostane, 3β,16β,17β-trihydroxyandrostane, or an ester, carbonate or other analog of any of these compounds that can convert to the compound by metabolism or hydrolysis.

72. A method to prevent, treat or ameliorate neutropenia in a human comprising administering to the human an effective amount of a formula 1 compound of any of embodiments 1-66, wherein the neutropenia is postinfectious neutropenia, autoimmune neutropenia, chronic idiopathic neutropenia or a neutropenia resulting from or potentially resulting result from a cancer chemotherapy, chemotherapy for an autoimmune disease, an antiviral therapy, radiation exposure, tissue or solid organ allograft or xenograft rejection or immune suppression therapy in tissue or solid organ transplantation or aging or immunesenescence.

73. The method of embodiment 72 wherein one $R^4$ is in the β-configuration or the α-configuration and is —$NH_2$, a substituted amine or an amide, which is optionally selected from —$NH_2$, —$NHCH_3$, —$N(CH_3)_2$, —$NHR^{PR}$, —NH—C(O)—H and —NH—C(O)-optionally substituted alkyl, e.g., —NH—C(O)—$CH_3$.

74. The method of embodiment 73 wherein the other $R^4$ is —H, optionally substituted alkyl, —CN, —SCN or —OH.

75. The method of embodiment 72 wherein the F1C is 3β-hydroxy-17β-aminoandrost-5-ene, 3β-hydroxy-16α-fluoro-17β-aminoandrost-5-ene, 3β-hydroxy-16β-fluoro-17β-aminoandrost-5-ene, 3β-hydroxy-16,16-difluoro-17β-aminoandrost-5-ene, 3β,16α-dihydroxy-17β-aminoandrost-5-ene, 3β,16β-dihydroxy-17β-aminoandrost-5-ene, 3β-hydroxy-16,16-dimethyl-17β-aminoandrost-5-ene, an ester or carbonate of any of these compounds or an analog of any of the foregoing compounds where the double bond at the 5-6 position is absent and a hydrogen or other $R^{10}$ moiety is present at the 5-position in the α- or β-configuration and/or wherein the hydroxyl group (or ester or carbonate analog) at the 3-position is present in the α-configuration.

76. A compound of formula 1 as defined in embodiment 1.

77. The compound of embodiment 76 wherein one $R^3$ is a halogen, the other $R^3$ is not a halogen and one $R^4$ is —$NH_2$, a substituted amine, an N-linked amino acid, —$N(R^{PR})_2$ or an amide, where $R^{PR}$ independently or together are —H or a protecting group.

78. The compound of embodiment 77 wherein one $R^4$ is —$NH_2$.

79. The compound of embodiment 77 wherein the compound is 3β-hydroxy-16α-fluoro-17β-aminoandrost-5-ene, 3β-hydroxy-16β-fluoro-17β-aminoandrost-5-ene, 3α-hydroxy-16α-fluoro-17β-aminoandrost-5-ene, 3α-hydroxy-16β-fluoro-17β-aminoandrost-5-ene, 3β-hydroxy-16α-fluoro-17β-aminoandrost-4-ene, 3β-hydroxy-16β-fluoro-17β-aminoandrost-4-ene, 3α-hydroxy-16α-fluoro-17β-aminoandrost-4-ene, 3α-hydroxy-16β-fluoro-17β-aminoandrost-4-ene, 3β-hydroxy-16α-fluoro-17β-aminoandrostane, 3β-hydroxy-16β-fluoro-17β-aminoandrostane, 3α-hydroxy-16β-fluoro-17β-aminoandrostane, 3α-hydroxy-16β-fluoro-17β-aminoandrostane, 3β-hydroxy-16α-fluoro-17β-amino-5β-androstane, 3β-hydroxy-16β-fluoro-17β-amino-5β-androstane, 3α-hydroxy-16α-fluoro-17β-amino-5β-androstane, 3α-hydroxy-16β-fluoro-17β-amino-5β-androstane or an analog of any of these compounds wherein (1) the compound is substituted with an $R^{10}$ moiety other than —H at the 1, 2, 4, 6, 7, 11, 12, 14 or 15 position and/or (2) the compound is substituted at one or two of the 2, 11 or 15 positions with an independently selected —O—, —S— or —NH— moiety that replaces the one or two —$CH_2$— moieties.

80. A composition comprising a compound of formula 1 as defined in any preceding embodiment and one, two, three, four, five or more excipients.

81. A method to treat or to reduce the severity of a chronic allergy or an atopic disease, or one or more symptoms of the chronic allergy or atopic disease in a subject in need thereof, comprising administering an effective amount of a formula 1 compound of embodiment 1, wherein
one $R^1$ is, or both $R^1$ together are, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and
one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

82. The method of embodiment 81 wherein the compound is 16α-bromoepiandrosterone, 16α-bromoepiandrosterone hemihydrate, 16α-iodoepiandrosterone, 16-oxoepiandrosterone, 16-oxoandrosterone, 3β,16α-dihydroxyandrostane-17-one, 3α,16α-dihydroxyandrostane-17-one, 3β,16β-dihydroxyandrostane-17-one, 3α,16β-dihydroxyandrostane-17-one, 3β,16α,17β-trihydroxyandrostane, 3α,16α,17β-trihydroxyandrostane, 3β,16β,17β-trihydroxyandrostane, 3α,16β,17β-trihydroxyandrostane, or an analog of any of these compounds that is (1) 2-oxa or 11-oxa substituted, (2) substituted at the 7-position with an α-halogen, β-halogen, α-hydroxyl, β-hydroxyl or oxo moiety, (3) a D-ring homo analog, (4) a 19-nor analog and/or (5) an analog of any of the foregoing compounds that is substituted with an $R^{10}$ substituent disclosed herein, e.g., wherein the $R^{10}$ is a hydroxyl, thiol, optionally substituted alkyl or a halogen such as fluorine or bromine at the 1-, 2-, 4-, 6-, 9-11-, 12-, 14-, 15- or 16-positions, wherein the $R^{10}$, e.g., the hydroxyl, thiol, optionally substituted alkyl or halogen is present in the α-configuration or the β-configuration.

83. The method of embodiment 81 or 82 wherein the level or activity of IgE in the subject is at least transiently detectably reduced, e.g., shortly after allergen exposure (such as within about 1 hour to about 1 week) or at one more later times.

84. A method to increase the efficacy of an immune response to dendritic cells in a subject, comprising (1) contacting for a sufficient time an effective amount of a formula 1 compound of any of embodiments 1-66 and an effective amount of a non-self antigen with the subject's dendritic cells in vitro, (2) optionally expanding the dendritic cells in vitro in the presence or absence of the formula 1 compound and/or the antigen, (3) infusing the dendritic cells into the subject, (4) optionally administering an effective amount of the formula 1 compound to the subject and/or optionally administering an effective amount of the non-self antigen to the subject.

85. The method of embodiment 84 wherein the non-self antigen comprises an antigen derived or obtained from an infectious agent or from a malignant cell or a pre-malignant cell, wherein the malignant or pre-malignant cell is from the subject or is from another individual of the same species as the subject.

86. The method of embodiment 84 or 85 wherein one $R^1$ is, or both $R^1$ together are, —H, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

87. The method of embodiment 86 wherein the compound is 3β,17β-dihydroxyandrost-5-ene, 3β,7β,17β-trihydroxyandrost-5-ene, 3β,17β-dihydroxyandrost-1,5-diene, 3β,7β,17β-trihydroxyandrost-1,5-diene, 3β,17β-dihydroxy-16-haloandrost-5-ene, 3β,7β,17β-trihydroxy-16-haloandrost-5-ene, 16α-fluoro-17-oxoandrost-5-ene, 3α-hydroxy-16α-fluoro-17-oxoandrost-5-ene, 3β-hydroxy-16α-fluoro-17-oxoandrost-5-ene, 3β,17β-dihydroxy-16α-fluoroandrost-5-ene, 3α,17β-dihydroxy-16α-fluoroandrost-5-ene, 16α-bromoepiandrosterone, 16α-bromoepiandrosterone hemihydrate, 16α-iodoepiandrosterone, 16-oxoepiandrosterone, 16-oxoandrosterone, 3β,16α-dihydroxyandrostane-17-one, 3α,16α-dihydroxyandrostane-17-one, 3β,16β-dihydroxyandrostane-17-one, 3α,16β-dihydroxyandrostane-17-one, 3β,16α,17β-trihydroxyandrostane, 3α,16α,17β-trihydroxyandrostane, 3β,16β,17β-trihydroxyandrostane, 3α,16β,17β-trihydroxyandrostane, or an analog of any of these compounds that is (1) 11-oxa substituted or 2-oxa substituted if no double bond is present at the 1-2 position, (2) substituted at the 7-position with an α-halogen, β-halogen, α-hydroxyl, β-hydroxyl or oxo moiety (3), (3) a D-ring homo analog, (4) a 19-nor analog and/or (5) an analog of any of the foregoing compounds that is substituted with an $R^{10}$ substituent disclosed herein, e.g., wherein the $R^{10}$ is a hydroxyl, thiol, optionally substituted alkyl or a halogen such as fluorine or bromine at the 1-, 2-, 4-, 6-, 9-11-, 12-, 14-, 15- or 16-positions, wherein the $R^{10}$, e.g., the hydroxyl, thiol, optionally substituted alkyl or halogen is present in the α-configuration or the β-configuration.

88. A method to increase the efficacy of allergy vaccinations in a subject having an allergy, comprising (1) at an effective time before or during vaccination of the subject with an allergen, administering to the subject an effective amount of a formula 1 compound of embodiment 1, (2) optionally administering to the subject an effective amount of the formula 1 compound daily or intermittently for 2, 3, 4, 5, 6, 7, 14 or more days after the vacination of step (1), (3) after passage of sufficient time, repeating step (1) and (4) after passage of sufficient time, optionally repeating steps (1), (3) and/or (2).

89. The method of embodiment 88 wherein the subject has a chronic allergy or atopic disease, optionally selected from allergic rhinitis, psoriasis, eczema, gastrointestinal allergies, atopic dermatitis conditions, allergic asthma, food allergies and hay fever and (1) wherein the level of IgE in the subject is at least transiently detectably reduced during or after exposure to the allergen, or (2) wherein the total number of antiallergic vaccinations that are needed to reduce allergy reactions or symptoms to allergen exposure is reduced or there is an increase in the quality or length of an effective response to allergen vaccination or there is an increase the proportion of subjects in which allergy vaccination is effective.

90. The method of embodiment 88 or 89 wherein one $R^1$ is, or both $R^1$ together are, —H, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

91. The method of embodiment 90 wherein the compound is 3β,17β-dihydroxyandrost-5-ene, 3β,7β,17β-trihydroxyandrost-5-ene, 3β,17β-dihydroxyandrost-1,5-diene, 3β,7β,17β-trihydroxyandrost-1,5-diene, 3β,17β-dihydroxy-16-haloandrost-5-ene, 3β,7β,17β-trihydroxy-16-haloandrost-5-ene, 16α-fluoro-17-oxoandrost-5-ene, 3α-hydroxy-16α-fluoro-17-oxoandrost-5-ene, 3β-hydroxy-16α-fluoro-17-oxoandrost-5-ene, 3β,17β-dihydroxy-16α-fluoroandrost-5-ene, 3α,17β-dihydroxy-16α-fluoroandrost-5-ene, 16α-bromoepiandrosterone, 16α-bromoepiandrosterone hemihydrate, 16α-iodoepiandrosterone, 16-oxoepiandrosterone, 16-oxoandrosterone, 3β,16α-dihydroxyandrostane-17-one, 3α,16α-dihydroxyandrostane-17-one, 3β,16β-dihydroxyandrostane-17-one, 3α,16β-dihydroxyandrostane-17-one, 3β,16α,17β-trihydroxyandrostane, 3α,16α,17β-trihydroxyandrostane, 3β,16β,17β-trihydroxyandrostane, 3α,16β,17β-trihydroxyandrostane, or an analog of any of these compounds that is $(1)_{1-1}$-oxa substituted or 2-oxa substituted if no double bond is present at the 1-2 position, (2) substituted at the 7-position with an α-halogen, β-halogen, α-hydroxyl, β-hydroxyl or oxo moiety, (3) a D-ring homo analog, (4) a 19-nor analog and/or (5) an analog of any of the foregoing compounds that is substituted with an $R^{10}$ substituent disclosed herein, e.g., wherein the $R^{10}$ is a hydroxyl, thiol, optionally substituted alkyl or a halogen such as fluorine or bromine at the 1-, 2-, 4-, 6-, 9-11-, 12-, 14-, 15- or 16-positions, wherein the $R^{10}$, e.g., the hydroxyl, thiol, optionally substituted alkyl or halogen is present in the α-configuration or the β-configuration.

92. A method to prevent, treat or to reduce the severity of vascular or microvascular occlusions in human sickle cell or thalassemia diseases, comprising administering to the patient an effective amount of a formula 1 compound of any of embodiments 1-66.

93. The method of embodiment 92 further comprising daily or intermittent administration of the formula 1 compound.

94. The method of embodiment 92 or 93 further comprising monitoring the subject's blood cell status to determine if further administration of the formula 1 compound is desirable, and, if further treatment is desirable, administering to the patient an effective amount of the formula 1 compound.

95. The method of embodiment 92, 93 or 94 wherein the frequency of observed vascular occlusion events in the subject or the severity of the subject's symptoms of vascular occlusions is at least transiently detectably reduced.

96. The method of embodiment 92, 93, 95 or 95 wherein one $R^1$ is, or both $R^1$ together are, —H, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

97. The method of embodiment 90 wherein the compound is 3β,17β-dihydroxyandrost-5-ene, 3β,7β,17β-trihydroxyandrost-5-ene, 3β,17β-dihydroxyandrost-1,5-diene, 3β,7β,17β-trihydroxyandrost-1,5-diene, 3β,17β-dihydroxy-16-haloandrost-5-ene, 3β,7β,17β-trihydroxy-16-haloandrost-5-ene, 16α-fluoro-17-oxoandrost-5-ene, 3α-hydroxy-16α-fluoro-17-oxoandrost-5-ene, 3β-hydroxy-16α-fluoro-17-oxoandrost-5-ene, 3β,17β-dihydroxy-16α-fluoroandrost-5-ene, 3α,17β-dihydroxy-16α-fluoroandrost-5-ene, 16α-bromoepiandrosterone, 16α-bromoepiandrosterone hemihydrate, 16α-iodoepiandrosterone, 16-oxoepiandrosterone, 16-oxoandrosterone, 3β,16α-dihydroxyandrostane-17-one, 3α,16α-dihydroxyandrostane-17-one, 3β,16β-dihydroxyandrostane-17-one, 3α,16β-dihydroxyandrostane-17-one, 3β,16α,17β-trihydroxyandrostane, 3α,16α,17β-trihydroxyandrostane, 3β,16β,17β-trihydroxyandrostane, 3α,16β,17β-trihydroxyandrostane, or an analog of any of these compounds that is $(1)_{1-1}$-oxa substituted or 2-oxa substituted if no double bond is present at the 1-2 position, (2) substituted at the 7-position with an α-halogen, β-halogen, α-hydroxyl, β-hydroxyl or oxo moiety, (3) a D-ring homo analog, (4) a 19-nor analog and/or (5) an analog of any of the foregoing compounds that is substituted with an $R^{10}$ substituent disclosed herein, e.g., wherein the $R^{10}$ is a hydroxyl, thiol, optionally substituted alkyl or a halogen such as fluorine or bromine at the 1-, 2-, 4-, 6-, 9-11-, 12-, 14-, 15- or 16-positions, wherein the $R^{10}$, e.g., the hydroxyl, thiol, optionally substituted alkyl or halogen is present in the α-configuration or the β-configuration.

98. A method to identify a compound that modulates the expression in a cell of the level of or an activity of 1, 2, 3, 4, 5, 6, 7, 8, 9, 10 or more genes or gene products or gene transcripts in the cell, comprising contacting an effective amount of the compound with the cell under suitable conditions and for a sufficient time to detectably modulate the activity or level of the genes, or gene products in the cell, wherein the compound is a compound of any of embodiments 1-65.

99. The method of embodiment 98 wherein the genes or gene products are optionally selected from the group consisting of the genes or gene products disclosed herein.

100. The method of embodiment 98 or 99 wherein the genes or gene products are selected from the group consisting of USF1, c-Fos, EGR1, Cul1, RIPK2, IκBα, IκBKb, NF-κB1 p50, FCAR, c-Fos/C/EBPβ, RANTES, ICAM1, TSG (TNFAIP6), IL-2 receptor α, GRO2, GRO3, HO1, Jun B, c-Fos/JunB complex, JunB/ATF3 complex, c-Jun, c-Fos/c-Jun complex, ATF-3, MMP1, TSG-6 (TNFAIP3), EGR1, TGFβ, ATF-3/c-Jun complex, c-Fos, MMP3, IL-8, STAT5A, STAT5B, CDKN1A, IFNγ receptor 2 (IFNγR2), T-bet, C reactive protein, immunoglobulin E, an AP-1 family protein, SOD2, GATA-3, Jak2, Tyk2, stat1, stat3, stat4, stat5, stat6, MIP-1α, MIP-2, IP-10, MCP-1, TNF-α, TNF-β, LT-β, IFN-α, IFN-β, TGF-β1, NF-κB, IL-1α, IL-1β, IL-4, IL-6, IL-10, IL-12 receptor β1, IL-12p35, IL-12p40, IL-23 and IL-23 receptor.

101. The method of embodiment 98, 99 or 100 wherein the level or activity of 1, 2, 3, 4, 5, 6, 7, 8, 9, 10, 11, 12, 13, 14, 15, 16, 17, 18, 19, 20, about 30, about 50, about 100, about 150, about 200, about 250, about 300, about 500, about 700 or about 1000 of the genes or gene products is detectably modulated at least transiently.

102. The method of any of embodiments 98-101 wherein the level or an activity of the gene product is a detectable increase in the level of the mRNA, the protein or one or more biological activities associated with the gene product.

103. The method of embodiment 102 wherein the increase is a transient increase of about 1 hour to about 12 hours.

104. The method of embodiment 102 wherein the level or an activity of the gene product is a detectable decrease in the level of the mRNA, the protein or one or more biological activities associated with the gene product.

105. The method of embodiment 104 wherein the increase is a transient decrease of about 1 hour to about 12 hours.

106. The method of any of embodiments 98-101 wherein the modulation is an increase or a decrease of at least about 2-fold to about 1000-fold in the level or an activity of the mRNA, the protein or at least one biological activity associated with the gene product.

107. The method of any of embodiments 98-106 wherein one $R^1$ is, or both $R^1$ together are, —H, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

108. The method of any of embodiments 98-106 wherein the formula 1 compound is 16α-bromo-3β-hydroxy-5α-androstan-17-one, 16α-bromo-3β-hydroxy-5α-androstan-17-one hemihydrate, 16α-fluoro-3β-hydroxy-5α-androstan-17-one, 16α-chloro-3β-hydroxy-5α-androstan-17-one, 16β-bromo-3β-hydroxy-5α-androstan-17-one, 16β-fluoro-3β-hydroxy-5α-androstan-17-one, 16β-chloro-3β-hydroxy-5α-androstan-17-one, 16α,3β-dihydroxy-5α-androstan-17-one, 16β,3β-dihydroxy-5α-androstan-17-one, 16α,3α-dihydroxy-5α-androstan-17-one, 16β,3α-dihydroxy-5α-androstan-17-one, 16α-bromo-3β-hydroxy-5α-androstan-17-one hemihydrate, 3α-hydroxy-16α-fluoroandrostane-17-one, 3β-hydroxy-16α-fluoroandrostane-17-one, 17α-hydroxy-16α-fluoroandrostane-3-one, 17β-hydroxy-16α-fluoroandrostane-3-one, 17α-hydroxy-16α-fluoroandrostane-4-one, 17β-hydroxy-16α-fluoroandrostane-4-one, 17α-hydroxy-16α-fluoroandrostane-6-one, 17β-hydroxy-16α-fluoroandrostane-6-one, 17α-hydroxy-16α-fluoroandrostane-7-one, 17β-hydroxy-16α-fluoroandrostane-7-one, 17β-hydroxy-16β-fluoroandrostane-11-one, 17β-hydroxy-16α-fluoroandrostane-11-one, 16α-fluoroandrost-5-ene-17-one, 7α-hydroxy-16α-fluoroandrost-5-ene-17-one, 7β-hydroxy-16α-fluoroandrost-5-ene-17-one, 4α-hydroxy-16α-fluoroandrost-5-ene-17-one, 3α-hydroxy-16α-fluoroandrost-5-ene-17-one, 3β-hydroxy-16α-fluoroandrost-5-ene-17-one, 4β-hydroxy-16α-fluoroandrost-5-ene-17-one, 6α-hydroxy-16α-fluoroandrost-5-ene-17-one, 6β-hydroxy-16α-fluoroandrost-5-ene-17-one, 11α-hydroxy-16α-fluoroandrost-5-ene-17-one, 11β-hydroxy-16α-fluoroandrost-5-ene-17-one, 4α,17β-dihydroxy-16α-fluoroandrost-5-ene, 4β,17β-dihydroxy-16α-fluoroandrost-5-ene, 6α,17β-dihydroxy-16α-fluoroandrost-5-ene, 6β,17β-dihydroxy-16α-fluoroandrost-5-ene, 11α,17β-dihydroxy-16α-fluoroandrost-5-ene, 11β,17β-dihydroxy-16α-fluoroandrost-5-ene, 4α,17-dihydroxy-16α-fluoroandrost-5-ene, 4β,17α-dihydroxy-16α-fluoroandrost-5-ene, 6α,17α-dihydroxy-16α-fluoroandrost-5-ene, 6β,17α-dihydroxy-16α-fluoroandrost-5-ene, 11α,17α-dihydroxy-16α-fluoroandrost-5-ene, 11β,17α-dihydroxy-16α-fluoroandrost-5-ene, 7α,17β-dihydroxy-16α-fluoroandrost-5-ene, 7β,17β-dihydroxy-16α-fluoroandrost-5-ene, 3α,17β-dihydroxy-16α-fluoroandrost-5-ene, 3β,17β-dihydroxy-16α-fluoroandrost-5-ene, 3α,17α-dihydroxy-16α-fluoroandrost-5-ene, 3β,17α-dihydroxy-16α-fluoroandrost-5-ene, 1α,17β-dihydroxy-16α-fluoroandrost-5-ene, 1β,17β-dihydroxy-16α-fluoroandrost-5-ene, 2α,17β-dihydroxy-16α-fluoroandrost-5-ene, 2β,17β-dihydroxy-16α-fluoroandrost-5-ene, 12α,17β-dihydroxy-16α-fluoroandrost-5-ene, 12β,17β-dihydroxy-16α-fluoroandrost-5-ene, 1α,17α-dihydroxy-16α-fluoroandrost-5-ene, 1β,17α-dihydroxy-16α-fluoroandrost-5-ene, 2α,17α-dihydroxy-16β-fluoroandrost-5-ene, 2β,17α-dihydroxy-16α-fluoroandrost-5-ene, 12α,17β-dihydroxy-16β-fluoroandrost-5-ene, 12β,17α-dihydroxy-16α-fluoroandrost-5-ene, 15α,17β-dihydroxy-16α-fluoroandrost-5-ene, 15β,17β-dihydroxy-16α-fluoroandrost-5-ene, 17β,18-dihydroxy-16α-fluoroandrost-5-ene, 17β,19-dihydroxy-16α-fluoroandrost-5-ene, 15α,17α-dihydroxy-16α-fluoroandrost-5-ene, 15β,17α-dihydroxy-16α-fluoroandrost-5-ene, 17α,18-dihydroxy-16α-fluoroandrost-5-ene, 17α,19-dihydroxy-16α-fluoroandrost-5-ene, 16α-fluoroandrost-4-ene-17-one, 7α-hydroxy-16α-fluoroandrost-4-ene-17-one, 7β-hydroxy-16α-fluoroandrost-4-ene-17-one, 3α-hydroxy-16α-fluoroandrost-4-ene-17-one, 3β-hydroxy-16α-fluoroandrost-4-ene-17-one, 4α-hydroxy-16α-fluoroandrost-4-ene-17-one, 4β-hydroxy-16α-fluoroandrost-4-ene-17-one, 6α-hydroxy-16α-fluoroandrost-4-ene-17-one, 6β-hydroxy-16α-fluoroandrost-4-ene-17-one, 11-hydroxy-16α-fluoroandrost-4-ene-17-one, 11β-hydroxy-16α-fluoroandrost-4-ene-17-one, 4α,17β-dihydroxy-16α-fluoroandrost-4-ene, 4β,17β-dihydroxy-16α-fluoroandrost-4-ene, 6α,17β-dihydroxy-16α-fluoroandrost-4-ene, 6β,17β-dihydroxy-16α-fluoroandrost-4-ene, 11α,17β-dihydroxy-16α-fluoroandrost-4-ene, 11β,17β-dihydroxy-16α-fluoroandrost-4-ene, 4α,17α-dihydroxy-16β-fluoroandrost-4-ene, 4β,17α-dihydroxy-16α-fluoroandrost-4-ene, 6α,17α-dihydroxy-16β-fluoroandrost-4-ene, 6β,17α-dihydroxy-16α-fluoroandrost-4-ene, 11α,17-dihydroxy-16α-fluoroandrost-4-ene, 11β,17α-dihydroxy-16α-fluoroandrost-4-ene, 7α,17β-dihydroxy-16α-fluoroandrost-4-ene, 7β,17β-dihydroxy-16α-fluoroandrost-4-ene, 3α,17β-dihydroxy-16α-fluoroandrost-4-ene, 3β,17β-dihydroxy-16α-fluoroandrost-4-ene, 3α,17α-dihydroxy-16β-fluoroandrost-4-ene, 3β,17α-dihydroxy-16α-fluoroandrost-4-ene, 1α,17β-dihydroxy-16α-fluoroandrost-4-ene, 1β,17β-dihydroxy-16α-fluoroandrost-4-ene, 2α,17β-dihydroxy-16α-fluoroandrost-4-ene, 2β,17β-dihydroxy-16α-fluoroandrost-4-ene, 12α,17β-dihydroxy-16α-fluoroandrost-4-ene, 12β,17β-dihydroxy-16α-fluoroandrost-4-ene, 1α,17α-dihydroxy-16α-fluoroandrost-4-ene, 1β,17α-dihydroxy-16α-fluoroandrost-4-ene, 2α,17α-dihydroxy-16β-fluoroandrost-4-ene, 2β,17α-dihydroxy-16α-fluoroandrost-4-ene, 12α,17α-dihydroxy-16α-fluoroandrost-4-ene, 12β,17α-dihydroxy-16α-fluoroandrost-4-ene, 15β,17β-dihydroxy-16α-fluoroandrost-4-ene, 15β,17β-dihydroxy-16α-fluoroandrost-4-ene, 17β,18-dihydroxy-16α-fluoroandrost-4-ene, 17β,19-dihydroxy-16α-fluoroandrost-4-ene, 15β,17α-dihydroxy-16α-fluoroandrost-4-ene, 15β,17α-dihydroxy-16α-fluoroandrost-4-ene, 17α,18-dihydroxy-16β-fluoroandrost-4-ene, 17α,19-dihydroxy-16β-fluoroandrost-4-ene, 3β,17β-dihydroxyandrost-5-ene, 3β-hydroxy-7,17-dioxoandrost-5-ene, 3α-hydroxy-7,17-dioxoandrost-5-ene, 3β,17-dioxoandrost-5-ene, 3β,17-dioxoandrost-4-ene, 3β,17-dioxoandrost-1,4-diene, 3β,7β,17β-trihydroxyandrost-5-ene, 3β,7β,17β-trihydroxyandrostane, 3β,16α-dihydroxy-17-oxoandrostane, 3α,16α-dihydroxy-17-oxoandrostane, 3β,16β-dihydroxy-17-oxoandrostane, 3α,16β-dihydroxy-17-oxoandrostane, 3β,16α,17β-trihydroxyandrostane, 3β,16β,17β-trihydroxyandrostane, 3β,16α,17α-trihydroxyandrostane, 3β,16β,17α-trihydroxyandrostane, 3α,16α,17β-trihydroxyandrostane, 3α,16β,17β-trihydroxyandrostane or an analog of any of these compounds that is (1) 11-oxa substituted or 2-oxa substituted if no double bond is present at the 1-2 position, (2) substituted at the 7-position with an α-halogen, β-halogen, α-hydroxyl, β-hydroxyl or oxo moiety, (3) a D-ring homo analog, (4) a 19-nor analog and/or (5) an analog of any of the foregoing compounds that is substituted with an $R^{10}$ substituent disclosed herein, e.g., wherein the $R^{10}$ is a hydroxyl, thiol, optionally substituted alkyl or a halogen such as fluorine or bromine at the 1-, 2-, 4-, 6-, 9-11-, 12-, 14-, 15- or 16-positions, wherein the $R^{10}$, e.g., the hydroxyl, thiol, optionally substituted alkyl or halogen is present in the α-configuration or the β-configuration.

109. A method to enhance the healing of a trauma or an acute injury in a subject who has experienced or who is expected to experience a trauma or an acute injury comprising administering an effective amount of a compound to the subject, wherein the compound is (1) 3β,17β-dihydroxyandrost-5-ene, 3β,7β,17β-trihydroxyandrost-5-ene, a 16-halo analog of either compound, a 16-hydroxy analog of either compound, an 11-oxa analog of either compound, a 2-oxa analog of either compound, an ester or a carbonate of either compound, a derivative of either compound that can convert to either compound by hydrolysis or by metabolism or (2) a formula 1 compound of any of embodiments 1-66.

110. The method of embodiment 109 wherein the subject will experience or has experienced an immune suppressive event within about 2-3 weeks or about 3-4 weeks of the occurrence of the trauma or acute injury, wherein the immune suppressive event is exposure of the subject to an immune suppressive amount of ionizing radiation.

111. The method of embodiment 110 wherein the ionizing radiation exposure is about 0.3 Gy to about 30 Gy of the ionizing radiation.

112. The method of embodiment 110 wherein the radiation exposure is about 0.5 Gy to about 8 Gy of the ionizing radiation.

113. The method of embodiment 109 wherein the subject has experienced an immune suppressive event within 3 weeks of the occurrence of the trauma or acute injury, wherein the immune suppressive event is selected from an immune suppressive amount of an immunosuppressive chemotherapy.

114. The method of embodiment 113 wherein the immunosuppressive chemotherapy is an immunosuppressive cancer chemotherapy, an immunosuppressive antimicrobial therapy or an immunosuppressive glucocorticoid therapy.

115. The method of embodiment 113 wherein the immunosuppressive cancer chemotherapy is treatment of the subject with an immunosuppressive amount of cyclophosphamide, 5-fluorouracil or a platinum compound optionally selected from cisplatin and carboplatin.

116. The method of embodiment 113 wherein the immunosuppressive glucocorticoid chemotherapy is treatment of the subject with an immunosuppressive amount of dexamethasone, prednisone, hydrocortisone or cortisol.

117. The method of any of embodiments 109-116 wherein the subject is a human or a primate.

118. The method of any of embodiments 109-117 wherein the formula 1 compound has the structure

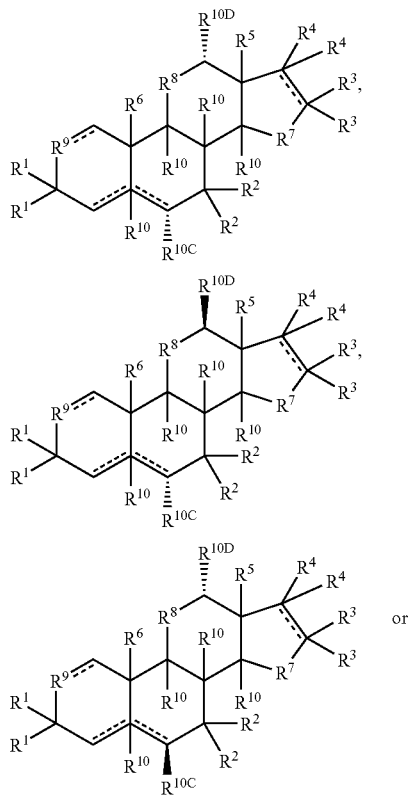

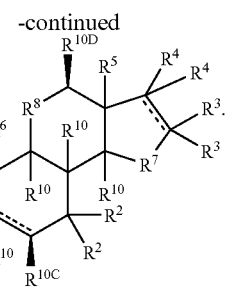

119. The method of embodiment 118 wherein the compound is 3β-hydroxy-17β-aminoandrost-5-ene.

120. The method of embodiment 118 wherein the compound is 3β-hydroxy-17β-amino-17α-optionally substituted alkyl-androst-5-ene, 3,8-hydroxy-9α-fluoro-17β-aminoandrost-5-ene or 3,8-hydroxy-17β-amino-19-norandrost-5-ene.

121. The method of any of embodiments 109-117 wherein the compound is 3β,17β-dihydroxyandrost-5-ene.

122. A method to modulate the expression of one or more transcription factors or enzymes in a subject who has a dysregulated oxidative stress condition comprising administering an effective amount of a compound to the subject, wherein the compound is (1) 3β,16α,17β-trihydroxyandrostane, 3α,16α,17β-trihydroxyandrostane, 3β,16α-dihydroxyandrostane-17-one, 3α,16α-dihydroxyandrostane-17-one, 3β,17β-dihydroxy-16α-haloandrostane, 3α,17β-dihydroxy-16α-haloandrostane, 3β,17β-dihydroxy-16α-bromoandrostane, 3α,17β-dihydroxy-16α-bromoandrostane, 3β-hydroxy-16α-bromoandrostane-17-one, 3β-hydroxy-16α-bromoandrostane-17-one hemihydrate, 3β,17β-dihydroxyandrost-5-ene, 3β,7β,17β-trihydroxyandrost-5-ene, 3β,17β-dihydroxy-16α-haloandrost-5-ene, 3α,17β-dihydroxy-16α-haloandrost-5-ene, 3β,16α,17β-trihydroxyandrost-5-ene, 3α,16α,17β-trihydroxyandrost-5-ene, an 11-oxa analog of any of these compounds, a 2-oxa analog of any of these compounds, a 19-nor analog of any of these compounds, a 9α-fluoro analog of any of these compounds, or an ester or a carbonate of any of these compounds or analogs, or (2) a derivative of any of these compounds or analogs that can convert to these compounds or analogs by hydrolysis or by metabolism, or (3) a formula 1 compound of any of embodiments 1-66.

123. The method of embodiment 122 wherein the compound modulates the level or activity of a transcription factor or enzyme selected from one or more of Nrf2, a Maf protein, a thioredoxin, NQO1, GST, HO 1, SOD2, the catalytic subunit of γGCS, the regulatory subunit of γGCS and xCT.

124. The method of embodiment 122 or 123 wherein the dysregulated oxidative stress condition is associated with exposure of the subject to a toxin that can cause cell or tissue damage or wherein elevated oxidative stress is present in one or more of the subject's cell types or tissues.

125. The method of embodiment 122, 123 or 124 wherein the subject has an acute or chronic inflammation condition, an acute or chronic infection or a trauma.

126. The method of embodiment 122, 123, 124 or 125 wherein the levels or activity of one, two or more of Nrf2, a Maf protein, a thioredoxin, NQO1, GST, HO 1, the catalytic subunit of γGCS, the regulatory subunit of γGCS and xCT is increased.

127. The method of embodiment 122, 123, 124, 125 or 126 wherein the compound is 3β,16α,17β-trihydroxyandrostane, 3α,16α,17β-trihydroxyandrostane, 3β,16α-dihydroxyandrostane-17-one or 3α,16-dihydroxyandrostane-17-one.

128. A product produced by the process of (1) contacting a F1C(s) and an excipient or (2) contacting a composition comprising a F1C(s) and one or more excipients with one or more additional excipients.

129. Use of a compound, composition, formulation or product of any of embodiments 1-129 or of any species or group of F1Cs disclosed herein for the preparation of a medicament. The medicament can be for the prophylaxis or treatment of a disease or condition disclosed herein in a subject having or susceptible to developing the disease or condition.

130. The use of a compound, composition, formulation or product of any of embodiments 1-129 or of any species or group of F1Cs disclosed herein to prepare a medicament for use to prevent or to treat, or to ameliorate one or more symptoms associated, with one, two or more acute or chronic diseases or conditions disclosed herein, e.g., an infection, an immunesuppression condition, an allergy, a cardiovascular condition, a metabolic disorder, a pulmonary condition, a skin condition, aging, a trauma such as a burn or a bone fracture, immune suppression, a neurological or centeral or peripheral nervous system condition or disorder, an unwanted or pathological inflammatory condition, toxicity or unwanted side-effects of a chemotherapy or of radiation exposure such as a glucocorticoid treatment or a cancer chemotherapy, an autoimmune disease or condition, a malignancy or cancer, a pre-malignant condition or to modulate a mammal's immune response, such as enhancing a Th1 response or decreasing a Th2 response, in a subject, e.g., a human or a mammal, having the acute or chronic disease or condition or subject to developing the acute or chronic disease or condition.

131. The use of embodiment 130, wherein the infection is a viral, bacterial, fungal, yeast or parasite infection, e.g., as described herein.

132. Use according to embodiment 130 or 131 wherein the medicament is for intermittently administering the F1C(s) to a subject or delivering to the subject's tissues the F1C(s), e.g., using an intermittent dosing protocol disclosed herein.

133. Use of a compound, composition, formulation or product of any of embodiments 1-129 or of any species or group of F1Cs disclosed herein to prepare a medicament for use to enhance a specific or an innate humoral or cellular response to vaccination or to the presence of 1, 2, 3, 4, 5, 6 or more endogenous antigens or epitopes associated with establishing or maintaining a disease or pathogenic agent such as a tumor antigen or an antigen associated with a pathogen.

134. Use according to embodiment 133 wherein the subject's innate immunity is enhanced.

135. Use according to embodiment 13 or 134 wherein the subject's innate or adaptive immunity is enhanced or wherein an unwanted immune response is decreased, or wherein number or activity of one, two or more of the subject's Th1 cells, tumor-infiltrating lymphocytes (TIL cells), NK cells, peripheral blood lymphocytes, phagocytes, monocytes, macrophage, neutrophils, eosinophils, dendritic cells, fibrocytes, astrocytes, gilal cells or stromal cells, e.g., bone marrow, lymph node or spleen stroma, are increased or activated at least transiently (e.g., for at least 10 minutes to 10 days or more), which is optionally as measured by, e.g., enhanced $^3$H-thymidine uptake compared to untreated controls or by an increase in the number of the cell type in circulation or demonstrable movement of the cell type from one tissue or compartment (e.g., skin or blood) to another tissue or compartment (e.g., blood, lymph node, spleen, Peyer's patches, GALT or thymus), or wherein the transcription rate, protein level or biological activity of one or more genes in the subject's NK cells, TIL cells, phagocytes, monocytes, macrophages, neutrophils, eosinophils, dendritic cells, fibrocytes, astrocytes, gilal cells or stromal cells are detectably modulated, e.g., increased (e.g., as measured by increased enzyme or biological activity of a biomolecule such as a nuclear hormone receptor such as an orphan nuclear hormone receptor, a transcription factor, a chemokine or a cytokine, which is optionally compared to suitable control cells or tissues).

136. A method to (a) modulate (detectably increase or decrease) the expression of at least one immune cell antigen by an immune cell in a subject, wherein the immune cell antigen is selected from CD3, CD11c, CD14, CD16, CD19, CD25, CD38, CD56, CD62L, CD69, CD45RA, CD45RO, CD123, HLA-DR, IL-1, IL-2, IL-4, IL-6, IL-8, IL-10, IL-12, TNFα, $IGF_1$ and γIFN, or (b) activate $CD8^+$ T cells or $CD8^-$ T cells in a subject, wherein the activation comprises at least transiently enhanced expression of CD25 or CD69 by the T cells, or (c) increase the proportion of $CD8^+$ or $CD8^-$ lymphokine activated killer cells in a subject's CD16+ cells (e.g., $CD8^+$, $CD16^+$, $CD38^+$ or cells $CD8^-$, $CD16^+$, $CD38^+$), or (d) increase the proportion of (i) $CD8^-$, $CD16^+$ natural killer cells, (ii) $CD8^+$, $CD16^+$ natural killer cells or (iii) $CD8^-$, $CD16^+$ cells that mediate antibody-dependent cell-mediated cytotoxicity, or (iv) $CD8^+$, $CD16^+$ cells that mediate antibody-dependent cell-mediated cytotoxicity, or (e) increase the proportion of dendritic cell precursors in a subject's circulating white blood cells (e.g., $Lin^-$, $HLA-DR^+$, $CD123^+$ or $Lin^-$ $HLA-DR^+$, $CD11c^+$ cells) or (f) increase the proportion of $CD45RA^+$ T cells or $CD45^+$, $R0^+$ T cells in a subject's circulating white blood cells, or (g) change (increase or decrease) the proportion or relative numbers of $CD62L^+$ T cells in a subject's circulating white blood cells, or (h) increase the proportion of $CD8^+$ or $CD4^+$ T cells that express CD62L in a subject's circulating $CD8^+$ or $CD4^+$ T cells, or (i) decrease the proportion of $CD8^+$ or $CD4^+$ T cells that express CD62L in a subject's circulating $CD8^+$ or $CD4^+$ T cells, or (j) increase the proportion of $HLA-DR^+$, $CD8^+$, $CD38^+$ cells in a subject's circulating white blood cells, or (k) decrease the level of IL-4 or IL-10 that is expressed by or present in a subject's white blood cells or in a subject's plasma (or that is expressed after the subject's white cells are stimulated in vitro), (l) at least transiently increase the number of dendritic cell precursors or dendritic cells that are present in a subject's white blood cells or in a subject's plasma, or (m) enhance the capacity of an immune cell, e.g., macrophages, $CD4^+$ T cells, $CD8^+$ T cells to express IL-2, IL-12 or γIFN or to activate such cells, the method comprising administering to the subject an effective amount of a F1C, which is optionally present in a composition or a formulation comprising 1, 2, 3, 4, 5, 6 or more pharmaceutically acceptable excipients. The F1c is any compound as described herein, e.g., a compound of embodiments 1-66 or in any chemical structure or any compound group.

137. A method to detect or to characterize a biological response (e.g., increased or decreased cytokine or cell surface antigen expression or activity, increased numbers of circulating neutrophils, increased phagocytic activity by phagocytic cells or modulation of a disease or symptom described herein) associated with the administration of a F1C to a subject comprising (1) obtaining a first biological sample from the subject and analyzing the sample to obtain a baseline value for the response, (2) administering the F1C to the subject to obtain a treated subject (3) within about 15 minutes to about 28 days after administering the F1C, obtaining a second biological sample from the treated subject and analyzing the sample to obtain a treated value for the response, and (4) optionally comparing the control information with the experimental information to detect the presence, absence, relative magnitude or absolute magnitude of the biological response.

138. The method of embodiment 137 wherein the biological response is modulation of $CD8^+$ T cells, $CD4^+$ T cells, $CD8^+$ lymphokine activated killer cells, $CD8^-$, $CD16^+$ natural killer cells, circulating dendritic cell precursors, circulating dendritic cells, tissue dendritic cell precursors, tissue dendritic cells, $CD8^+$ lymphokine activated killer cells, $CD8^-$ lymphokine activated killer cells, $CD8^-$, $CD16^+$ natural killer cells, $CD8^+$, $CD16^+$ natural killer cells, $CD8^-$, $CD16^+$ cells that mediate antibody-dependent cell-mediated cytotoxicity, $CD8^+$, $CD16^+$ cells that mediate antibody-dependent cell-mediated cytotoxicity, $CD45RA^+$ T cells, $CD45RA^+$, $CD45RO^+$ T cells, $CD45RO^+$ T cells, $CD8^+$, $CD62L^+$ T cells, $CD4^+$, $CD62L^+$ T cells or $HLA-DR^+$, $CD8^+$, $CD38^+$ T cells, monocytes, macrophages, glial cells or astrocytes, or wherein the biological response is at least transient modulation of an immune cell antigen or an immune accessory cell antigen (e.g., an adhesion molecule at the surface of endothelial cells or a cytokine receptor at the surface of T cells or B cells or a CD molecule, an interleukin or a cytokine, optionally selected from CD16, CD25, CD38, CD62L, CD69, CD45RA, CD45RO, IL-1, IL-2, IL-4, IL-6, IL-8, IL-10, TNFα, $IGF_1$ and γIFN).

139. A kit comprising a formulation that comprises a unit dosage or a multiple dosage comprising a F1C, e.g., any compound described or within any structure disclosed herein, and one or more excipients wherein the formulation is dispensed in a suitable closed container, wherein the kit optionally further comprises a label that provides information about one or more of (1) the F1C's chemical structure, (2) any recommended dosing regimen, (3) any adverse effects of administering the F1C to a subject that are required to be disclosed and (4) the amount of the F1C that is present in each unit dose or in the entire container.

140. A method to treat a symptom or condition associated with one or more delayed adverse or unwanted effects of radiation exposure or therapy in a subject in need thereof comprising administering to the subject, or delivering to the subject's tissues, an effective amount of a compound of formula 1, wherein the F1C is administered or delivered to the subject's tissues beginning at least 2 weeks after the subject has been exposed to a dose of radiation that will cause or could potentially cause the one or more delayed adverse or unwanted effects of the radiation exposure, or wherein the F1C is administered or delivered to the subject's tissues beginning at least 2 weeks after the subject has been exposed to at least one subdose of a planned course of radiation exposures that will cause or could potentially cause the one or more delayed adverse effects or unwanted effects of the radiation exposure.

141. The method of embodiment 140 wherein the subject has received, or is anticipated to receive, a total radiation dose of at least about 0.5 Gy to about 300 Gy, wherein the subject received the radiation dose in a single dose or in two or more divided doses, e.g., a total radiation dose of at least about Gy 1 to about 12 Gy, or at least about Gy 1 to about 8 Gy.

142. The method of embodiment 140 or 141 wherein the symptom or condition associated with one or more delayed adverse effect of radiation is one or more of encephalopathy, myelopathy, nausea, vomiting, diarrhea, acute inflammation, e.g., of the lung, chronic inflammation, e.g., of the lung, edema, pain, headache, depression, fever, malaise, weakness, hair loss, skin atrophy, skin ulceration, skin lesion, keratosis, telangiectasia, infection, hypoplasia, atrophy, fibrosis, pneumonitis, bone marrow hypoplasia, hemorrhage, leukopenia or thrombocytopenia.

143. The method of embodiment 140, 141 or 142 wherein the symptom or condition associated with one or more delayed adverse or unwanted effect of the radiation exposure or therapy is caused by or associated with radiation damage to one or more of bone marrow cells, bowel epithelium, bone marrow, testicles, ovaries, brain nerves or tissue, peripheral nerves, spinal cord nerves or tissue or skin epithelium.

Variations and modifications of these embodiments, the claims and the remaining portions of this disclosure will be apparent to the skilled artisan after a reading thereof. Such variations and modifications are within the scope and spirit of this invention. All citations herein are incorporated herein by reference in their entirety. All citations herein are incorporated herein by reference with specificity.

EXAMPLES

The following examples further illustrate the invention and they are not intended to limit it in any way. Variations of these examples that are included in the invention may include, e.g., any of the F1Cs described herein or parts or all of any of the methods, formulations, treatment protocols and/or assays described herein.

Example 1

Treatment of cytopenia. Primates treated to induce neutropenia or thrombocytopenia are used to characterize their response to treatment with a F1C. Mitigation of cytopenia, e.g., neutropenia or thrombocytopenia, by the F1C is observed. In an exemplary protocol, Cynomolgus monkeys of about 3.5-8 years of age and weighing about 2.5 to 8 kg are dosed at 35 mg/kg with carboplatin (sterile 10 mg/mL solution in 0.9% sodium chloride) by intravenous infusion over 30 minutes. Beginning at 1 or 2 days after the carboplatin infusion, each animal is dosed once daily or once every other day with the F1C for 1, 2, 3, 4, 5, 6, 7, 8, 9 or 10 days, e.g., once per day for 5 consecutive days beginning 2 days after carboplatin infusion. The F1C is in a suitable sterile solution or suspension formulation in suitable excipients, e.g., a suspension containing 0.1% w/v carboxymethyl-cellulose, 0.9% w/v sodium chloride and 0.05% v/v phenol. The suspension contains micronized F1C. Control animals receive the formulation without any F1C. The animals are dosed with the F1C subcutaneously in the interscapular region of the back or intramuscularly in the thigh at a dosage of about 1-45 mg/kg, e.g., 1.25, 2.5, 7.65 or 42.5 mg/kg of the F1C. Blood samples of about 1-1.5 mL are withdrawn at various times, e.g., on days −5 (pre-carboplatin), −2 (pre-carboplatin), 1 (4 hr post-dosing), 3, 7, 10, 12, 14, 16, 18, 20, 22, 24, 26, 28, 32 and 36 days, for analysis such as neutrophil, platelet, reticulocyte, erythrocyte counts. The degree of reduced time and/or severity of cytopenia such as neutropenia is then observed in F1C treated and control animals. F1C that are used include 3β-hydroxy-17β-aminoandrost-5-ene, 3β-hydroxy-17β-aminoandrost-1,5-ene, 3β-hydroxy-17β-methylaminoandrost-5-ene, 3β,17β-dihydroxyandrost-5-ene, 3β,17β-dihydroxyandrost-1,5-diene, 3β,17β-dihydroxy-16α-fluoroandrost-5-ene, 3β,7β-dihydroxy-17β-aminoandrost-5-ene, 3β,16α-dihydroxy-17β-aminoandrost-5-ene and 2-oxa or 11-oxa analogs of these compounds.

Example 2

Treatment of ionizing radiation exposure. The effect of selected F1Cs on survival of lethally-irradiated female B6D2F1 mice were compared to control animals treated with vehicle alone. The animals were exposed to 10 Gy of total body irradiation at 2.5 Gy/min using a $^{137}$Cs source. Groups of 12 animals were used in a total of 5 groups. For Groups 1, 2, 3, and 5, test article was administered as a 100 µL volume, by subcutaneous injection, for three consecutive days, with the first dose administered 2 to 4 hours following exposure to radiation. For Group 4, test article was administered as a 50 µL volume, by intramuscular injection for three consecutive days. The formulation was a suspension containing 0.1% w/v carboxymethyl-cellulose, 0.9% w/v sodium chloride and 0.05% v/v phenol. The formulations were agitated to uniformly resuspend the F1C before syringing, and injected into animals within a few minutes of drawing into the syringe to prevent settling in the syringe.

The groups of animals were treated as follows. Group 1 received vehicle only by daily subcutaneous injection for 3 consecutive days. Group 2 received 0.6 mg in 100 µL of a suspension of 3β,17β-dihydroxyandrost-5-ene by daily subcutaneous injection for 3 consecutive days. Group 3 received 3.0 mg in 100 µL of a suspension of 3β,17β-dihydroxyandrost-5-ene by daily subcutaneous injection for 3 consecutive days. Group 4 received 0.6 mg in 50 µL of a suspension of 3β,17β-dihydroxyandrost-5-ene by daily intramuscular injection for 3 consecutive days. Group 5 received 0.6 mg in 100 µL of a suspension of 3β-hydroxy-17β-aminoandrost-5-ene by daily subcutaneous injection for 3 consecutive days.

Survival of the animals was monitored for 21 days after irradiation and the following results were obtained. The number of surviving animals is shown for day 6, 7, 12 and 21. The results show that the F1Cs increased the rate of survival of subjects that were exposed to an otherwise lethal dose of ionizing radiation.

|  | Day | | | |
| --- | --- | --- | --- | --- |
| Group | 6 | 7 | 12 | 21 |
| 1 vehicle control | 12 | 11 | 4 | 1 |
| 2 0.6 mg s.c. | 12 | 11 | 10 | 7 |
| 3 3.0 mg s.c. | 12 | 12 | 9 | 7 |
| 4 0.6 mg i.m. | 12 | 12 | 11 | 9 |
| 5 0.6 mg s.c. | 12 | 12 | 12 | 11 |

Example 3

Cystic fibrosis treatment. Treatment with a F1C is conducted on human cystic fibrosis ("CF") patients, e.g., 18 years of age or older, who may have two or more of the following characteristics: (1) sweat chloride≧60 mEq/L, e.g., by quantitative pilocarpine iontophoresis test, (2) homozygosity for the F508 genetic mutation, or heterozygosity for 2 well-characterized mutations, e.g., as described herein, associated with CF, (3) $FEV_1$≧40% predicted at screening, (4) $SaO_2$≧90% at screening, (5) ability to perform pulmonary function tests and (6) clinical stability, with no evidence of acute upper or lower respiratory tract infection or current pulmonary exacerbation. The treatment regimen consists of 1, 2, 3, 4 or 5 consecutive days of once daily dosing of a F1C or placebo equivalent followed by a 40-day observation period. Daily dosages are about 10-150 mg/day, e.g., about 25 mg/day, 50 mg/day, 75 mg/day or 100 mg/day. The F1C is administered as described herein such as by a parenteral route, e.g., intramuscular or subcutaneous delivery, or by transmucosal delivery, e.g., buccal or sublingual. A follow-up visit will occur 6 weeks after the last treatment course to collect final samples for safety and activity. Patients receive, e.g., 3 treatment courses over a 14-week period, 6 treatment courses over a 28-week period or more courses of treatment over a longer period. F1Cs that are used include 3β-hydroxy-16α-bromo-17-oxoandrostane, 3β-hydroxy-16α-bromo-17-oxoandrostane hemihydrate, 3β,16α-dihydroxy-17-oxoandrostane, 3α,16α-dihydroxy-17-oxoandrostane, 3β,16α,17β-trihydroxyandrostane or 3α,16α,17β-trihydroxyandrostane or another F1C disclosed herein. The patients are optionally monitored for the status of their condition or in improvement of one or more CF symptoms after dosing, e.g., reduction in the numbers of neutrophils in bronchiolar or alveolar lavage samples, e.g., about a 30%, 40%, 50% or greater reduction, or levels of one or more CF-related inflammation markers, e.g., reduced levels or activity of IL-6, IL-8, IKK-β kinase or neutrophil elastase, or in the reduced occurrence, severity or progression of infections such as a *Burkholderia* (*Pseudomonas*) cepacia infection.

Example 4

Enhancement of tissue repair and stem cells in damaged tissues. Mice (8-10 week old male BDF1 mice) are held for 2 weeks in individually ventilated cages in an SPF (*H. Pylori*-negative) barrier unit. The mice are divided into groups of about 6 as follows. Group 1 is exposed to 13 Gy of X-radiation. Group 2 is treated with a F1C at about 24 hours before radiation, exposed to 13 Gy of X-radiation and dosed on the same day about 2 hours later with the F1C, followed by 2 consecutive days of once daily dosing with the F1C. Group 3 is treated with the F1C once daily for 3 consecutive days, the first dose being administered about 2 hr following a 13 Gy irradiation. Group 4 receives vehicle without the F1C 24 hr prior to irradiation and then once daily for 3 consecutive days, the first dose being administered 2 hr following irradiation. Group 5 is an unirradiated, untreated control group. All mice are analyzed at 4 days post-irradiation. The small intestine is removed and placed in Carnoy's fixative. Samples are paraffin embedded and processed for histology.

The number of surviving and/or regenerating intestinal crypts in each treatment group, and the control groups, are scored. The mean number of crypts per cross-section in each group is determined. Surviving crypt widths is measured to correct for size-induced scoring anomalies. For each mouse, about 10 cross-sections of intestine is analysed (see, e.g., C. S. Potten et al., *Cell Proliferation* 36:115-129 2003) to obtain the numbers of repopulating intestinal crypts. The capacity of the F1C to enhance repopulation is observed as increased numbers of repopulating crypts in animals treated with a F1C compared to irradiated controls. F1Cs such as one or more of 3β-hydroxy-17β-aminoandroat-5-ene, 3α-hydroxy-17β-aminoandroat-5-ene, 3β-hydroxy-17β-aminoandroat-1,5-diene, 3α-hydroxy-17β-aminoandroat-1,5-diene, 3β,17β-dihydroxyandroat-5-ene, 3β,17β-dihydroxy-16α-haloandroat-5-ene and 3β,17β-dihydroxy-16α-haloandroat-1,5-diene are tested.

Example 5

Human and primate virus treatment protocol. Humans infected with a virus, e.g., HCV, HBV or a retrovirus such as HIV1 or HIV2 or primates infected with a virus such as HCV, HIV1, HIV2, SIV or $SHIV_{229}$ are treated with a F1C formulation. Daily dosages of about 0.05 to about 25 mg/kg are administered daily or on an intermittent basis. The F1C is administered, e.g., orally, by subcutaneous injection, by intramuscular injection or by transmucosal delivery. A typical intermittent dosing protocol for human patients comprises daily dosing of about 0.1-5 mg/kg of the F1C for 1, 2, 3, 4, 5 or 6 days, followed by no dosing for about 1, 2, 3, 4, 5, 6, 7 or 8 weeks, daily dosing again for 1, 2, 3, 4, 5 or 6 days, no dosing for about 1, 2, 3, 4, 5, 6, 7 or 8 weeks and optionally repeating this dosing schedule as desired, e.g., for 3, 4, 5, 10, 15 or more rounds of dosing. A related dosing protocol involves dosing on every $2^{nd}$ or $3^{rd}$ day to deliver 2, 3, 4, 5 or 6 doses of the F1C, no dosing for about 2, 3, 4, 5, 6, 7 or 8 weeks and optionally repeating this dosing schedule as desired, e.g., for 3, 4, 5, 10, 15 or more rounds of dosing. Typical daily F1C doses in human treatment protocols is about 5 mg to about 1000 mg, usually about 10-150 mg. Daily doses can vary depending on the route of F1C administration and on the patient's weight and clinical condition, with oral administration usually requiring higher daily doses than parenteral or transmucosal administration.

In treating a viral infection such as a human HIV1 or HIV2 infection, one can optionally monitor one or more aspects of the patient's response, e.g., periodic assay for viral load or for the level or activity of a given immune cell type or a biomolecule described herein such as $CD4^+$ T cells, $CD123^+$ dendritic cells, IL-6, IL-10 or TNFα. Changes in cell types, viral load or biomolecules can be transient, e.g., detectably changed over a period of about 2-48 hours, or sustained, e.g., detectably changed for about 3-6 days or about 1-8 weeks. Other aspects of the patient's response may also be monitored such as the incidence, severity or rate of progression of symptoms or associated conditions such as coinfection, fatigue, weight loss or side effects of other suitable therapies. In retrovirus-infected patients that are treated with the F1C, the rate or progression of a clinically significant coinfection by *Mycobacteria* or *Pneumocystis* is generally reduced, including for patients with a $CD4^+$ T cell count of less than about 100 cells/mm$^3$ or less than about 75 cells/mm$^3$.

Example 6

Four-day in vivo protocol for inhibition of *Plasmodium berghei*. The assay consists of the inoculation of parasitised erythrocytes on the first day of the experiment ($D_0$), followed by an injection of the F1C, which is also administered on the $2^{nd}$, $3^{rd}$ and $4^{th}$ days of the protocol. On the $5^{th}$ day, blood films are taken and antimalarial activity is assessed either by calculating parasitemia, or by scoring parasite numbers on a predetermined scale (i.e., 1-5). W. Peters *Ann. Trop. Med. Parasitol.* 64:25-40, 1970.

The protocol is summarized as follows. Five female TO mice are used per test group. *P. berghei* HP15 ANKA parasites are collected by cardiac puncture using a heparinised syringe from a donor mouse having a 30+% parasitaemia. The blood is diluted with diluting agent (50% HIFCS+50% sterile PBS) to a final concentration of 1% parasitaemia or $1\times10^7$ infected erythrocytes per 0.2 mL of the infecting suspension. Each mouse is inoculated intravenously, which produced a more uniform infection rate than intraperitoneal administration of 0.2 mL of the infecting suspension. Test compounds are prepared at doses of 100 mg/kg in (16.7% DMSO+83.3% Celacol). The steroid formulations are administered intraperitoneally 2 hours after parasite inoculation. The compounds are administered once a day starting on $D_0$, and continued on the following three days. Blood films are made from tail blood on the day after the last dosing of compound and the blood is fixed with 100% methanol and stained with 10% Giemsa. Parasitaemias are scored on a scale of 0-5, where 5 is equal to the control.

An inoculum of 1% parasitaemia $1\times10^7$ erythrocytes/mL, 0.2 mL per mouse (female strain TO mice), is delivered by intravenous injection. Drug administration commenced 2 hours after inoculation on Day 1 and continued for 3 days. The results are shown below from blood films from all 20 mice on Day 5 when parasitaemias are assessed.

Example 7

Stimulation of phagocytosis. The capacity of F1Cs to influence phagocytosis of *Plasmodium* parasite-infected RBC is examined using adherent human monocytes. The parasitemia level is about 8-10% and human monocytes are obtained from buffy coats from blood as follows. Peripheral blood mononuclear cells are separated from freshly collected platelet-poor buffy coats discarded from blood samples of healthy adult donors of both sexes. Separated cells are washed once with luke-warm PBS supplemented with 10 mM glucose (PBS-G) and resuspended at $5\times10^6$ cells/mL in ice-cold RPMI 1640 medium supplemented with 23 mM $NaHCO_3$ and 25 mM Hepes, pH 7.4 (RMBH). Dynabeads M450 Pan B and Pan T (Dynal) are added to cells in a 4:1 ratio for 20 min at 4° C. B-lymphocytes and T-lymphocytes are removed as specified by the manufacturer. The remaining monocytes are washed 2 times in RMBH, resuspended in AIM V cell culture medium (Gibco) at $1\times10^6$ cell/mL. The monocyte layer is collected, washed with PBS-G at 37° C. and resuspended in AIM V medium at $1\times10^6$ cells/mL. Purified cells are >90% monocytes as assessed by CD14 expression.

Phagocytosis of opsonized parasitized RBC (PE) is determined as follows. Phagocytosis of fresh-serum opsonized PE is initiated by mixing 10 PE/monocyte. Suspensions are briefly centrifuged (150xg for 5 sec at room temperature) to improve contact between PE and monocytes. To avoid attachment of monocytes after centrifugation and during the whole incubation period, cells are kept in suspension at $5\times10^6$ cells/5 mL AIM V medium in 6 cm diameter teflon bottom dishes (Heraeus) in a humidified incubator (95% air, 5% $CO_2$) at 37° C. On average, at least 90% of the monocytes phagocytose PE, as assessed by microscopic inspection. Control cells are kept under similar conditions without phagocytosis. Quantitative assessment of phagocytosis is performed by a previously described bioluminescence method (E. Schwarzer, et al., *Br. J. Haematol.* 1994 88: 740-745).

Erythrocyte treatments and parasite cultures are as follows. Fresh blood (Rh+) is used to isolate erythrocytes (RBC). Washed RBC are infected with schizont/trophozoite parasite stages (Palo Alto strain, mycoplasma-free). Stage specific parasites are isolated by the Percoll-mannitol method. Briefly, normal schizont-stage parasitized RBC (SPE) separated on Percoll-mannitol gradient (parasitemia>95% SPE) are mixed with RBC suspended in growth medium (RPMI 1640 medium containing 25 mmol/L Hepes, 20 mmol/L glucose, 2 mmol/L glutamine, 24 mmol/L $NaHCO_3$, 32 mg/L gentamicin and 10% AB or A human serum, pH 7.30) to start synchronous cultures at selected hematocrit values. The inoculum parasitemia is adjusted to 20% normal SPE for isolation of ring parasitized RBC (RPE) and to 5% normal SPE for isolation of trophozoite-stage parasitized RBC (TPE). At 14-18 hours after inoculum parasites are at ring-stage in the first cycle; at 34-33 hours, parasites are at trophozoite-stage in the first cycle; and at 40-44 hours after inoculum parasites are at schizont-stage in the first cycle. RPE, TPE and SPE are separated on Percoll-mannitol gradients. The parasitemia is usually 8-10% RPE, and >95% TPE. Nonparasitized and parasitized RBC are counted electronically. To assess total parasitemia and relative contribution of RPE, TPE and SPE, slides are prepared from cultures at indicated times, stained with Diff-Quik™ parasite stain and about 400-1000 cells are examined microscopically.

The effect of a formula 1 compound such as F1C in parasitized RBC is examined using various concentrations of the compound, e.g., F1C, e.g., 0.5 µM, 1 µM, 10 µM, 25 µM and 50 µM. Trophozoite-parasitized RBC, schizont-parasitized RBC or ring-parasitized RBC are examined as described.

Example 8

Cyclodextrin formulation. A cyclodextrin formulation containing a F1C is prepared by mixing a sulfobutyl β-cyclodextrin and the F1C in one or more liquids such as ethanol, DMSO, N-methylpyrrolidine, pyridine or water. The sulfobutyl β-cyclodextrin contains one or more butyl sulfonate or —O—$(CH_2)_4$—$SO_3^-Na^+$ moieties, typically about 5, 6 or 7 per cyclodextrin molecule. F1Cs that contain a positive charge are especially helpful in forming complexes with the multiple negative charges of sulfobutyl cyclodextrin. For parenteral formulations, the maximum concentrations could be achieved at about the maximum cyclodextrin concentration that is still syringable, about 50% w:v. The F1C can be added to a solution of sulfobutyl β-cyclodextrin at a molar ratio of about 1:1, e.g., 0.5:1 to about 2:1, and stirred with or without heat for up to about 1 week to form the complex. The solution is optionally filtered or sterilized before filling in vials or injection delivery by any route. The vials can be sterilized by radiation or by sterile filtration. An exemplary preparation is made using 500 grams of sulfobutyl β-cyclodextrin (about 230 mmoles) combined with about 230 mmoles of the F1C. Solutions containing about 20-80 mg/mL of the F1C are typically obtained. For pharmaceutical formulations, the complex is prepared under GMP compliance conditions. The dried complex is prepared by lyophilization and can be reconstituted, e.g., using sterile 0.9% NaCl. The cyclodextrin complex can also be dried for preparation of formulations for oral or transmucosal administration or reconstituted with water for parenteral delivery, e.g., by subcutaneous or intramuscular injection. F1Cs that are used include 3β,17β-dihydroxyandrost-5-ene, 3β,17β-dihydroxy-16α-fluoroandrost-5-ene, 3β,7β,17β-trihydroxyandrost-5-ene, 3β-hydroxy-3α-methyl-17β-aminoandrost-4-ene, 3α-hydroxy-3β-methyl-17β-aminoandrost-4-ene and 3β-hydroxy-17β-aminoandrost-5-ene.

Example 9

Inhibition of inflammation. The capacity of formula 1 compounds to limit or inhibit inflammation or symptoms of inflammation is shown using animal models for inflammatory bowel disease. In an exemplary protocol, groups of 3 male Wistar rats (180±20 grams) fasted for 24 hours before 2,4-dinitrobenzene sulfonic acid (DNBS) or saline challenge are used. Distal colitis is induced by intra-colonic instillation of 0.5 mL of an ethanolic solution of DNBS (30 mg in 0.5 mL of a 30% ethanol in saline solution) after which 2 mL of air is injected through the cannula to ensure that the solution remained in the colon. The volume used is 0.1 mL per injection of 2 and 20 mg/mL of a F1C in a liquid formulation, which is administered by subcutaneous injection once a day for 6 days. The formulation contained 100 mg/mL of the F1C in a non-aqueous suspension, e.g., 2% benzyl alcohol w/v, 0.1% Brij 96 w/v and equal volumes of PEG 300 and propylene glycol. Concentrations of 2 mg/mL and 20 mg/mL are obtained by diluting the 20 mg/mL formulation with vehicle that lacked the F1C.

The first F1C dose is given 30 minutes after DNBS challenge. Sulfasalazine (30 mg/mL in 2% Tween 80 in distilled water) is administered orally (PO) once a day (10 mL/kg/day) for 7 days, the first two doses beginning 24 hours and 2 hours before DNBS challenge. The presence of diarrhea is recorded daily by examining the anal area. Animals are fasted for 24 hours prior to being sacrificed. Animals are sacrificed on day 7 or day 8 and their colons are removed and weighed. Before removal of the colon, signs of adhesion between the colon and other organs are recorded. Also, the presence of ulcerations is noted after weighing of each colon. The "net" change of colon-to-body weight (BW) ratio is normalized relative to saline-challenged baseline group. A 30% decrease in "net" colon-to-body weight ratio is considered significant.

Example 10

Modulation of delayed type hypersensitivity. The capacity of F1Cs to modulate delayed type hypersensitivity (DTH) is determined in mice. Groups of five female BALB/cByJ mice (20-25 grams) are anesthetized and 100 µL of a 3% solution of oxazolone is applied on day 0 to the shaved abdomen and dried. Seven days later, on day 7, the mice are challenged by applying 5 µL of oxazolone topically to each side of the right ear. The F1C (at about 20-100 mg/mL) in vehicle is administered by subcutaneous injection (2 mg/day) one time on day 6, 24 hours before the oxazolone challenge. The vehicle as a non-aqueous suspension of the F1C in, e.g., 2% benzyl alcohol w/v, 0.1% Brij 96 w/v and equal volumes of PEG 300 and propylene glycol.

Dexamethasone in saline (0.2 mg/mL) is administered daily for 9 days (day −1 to 7), first dose 24 hours before sensitization, last dose at challenge by subcutaneous injection (0.01 mg/dose, 50 µL/injection). On Day 8, 24 hours following the oxazolone challenge, both the right and left ear thicknesses are measured using a micrometer caliper and the differences are determined. The differential ear thickness is measured as an indicator of the DTH response to topical oxazolone challenge. The DTH response is expressed as the difference in the thickness (mm) between the right and the left ears for each animal.

The differential ear thickness in animals receiving vehicle alone is 0.225 mm and treatment with dexamethasone (high dose) or cyclophosphamide reduced the DTH response (0.144 mm and 0.092 mm, respectively).

Example 11

Reversal of immunosenescence. Healthy aged (20-month) or immunologically-mature (3-month) BALB/c mice are vaccinated with hepatitis B surface antigen (HbsAg) (2 µg; Recombivax-HB; Merck) and Alum (2.75 µg). The aged mice are vaccinated with the antigen and also received a single subcutaneous injection of either 0.3 mg or 3.0 mg of selected F1Cs or the vehicle (placebo control).

Blood samples are collected 14, 21 and 34 days after treatment and the sera are analyzed by ELISA to determine the concentration of HbsAg-specific IgG (total IgG). In addition, samples obtained on day 21 are analyzed to determine the concentration of HbsAg-specific IgG1 and IgG2a subclasses. The results can be summarized as average values obtained with blood samples collected 21 days after vaccination of groups of 8 mice. Subcutaneous injection is performed after shaving the hair from the thighs of each mouse. The injected volume is 50 µL containing 3.0 mg or 0.3 mg of compound or placebo, and for vaccine preparation. The vehicle control consists of carboxymethyl-cellulose (0.5%) in saline (0.9%). Antibody titers are determined by ELISA.

Treatment of aged, vaccinated animals with the F1Cs, can result in higher anti-HbsAg IgG titers than aged animals receiving the vaccination only. Such results would show that the F1Cs can enhance immune response to antigen challenge in immune senescent animals.

The serum samples are also analyzed for the titers of HbsAg-specific, IgG1 or IgG2a immunoglobulin subclasses. A bias to IgG1 is seen in aged mice and this is considered symptomatic of immune senescence or a suboptimal immune response associated with immune senescence. The IgG1IgG2a ratio is an indicator of immune status. Th2 cells predominantly assist in the generation of humoral immunity, while Th1 cells enhance, e.g., cellular immunity. Humoral immunity (Th2) becomes predominant with age, while the decreasing cellular (Th1) immunity leads to increased susceptibility to, e.g., infectious diseases.

To examine the secondary antibody response, 42 days after the initial exposure to HbsAg, serum samples are taken from the mice and these are tested for anti-HbsAg IgG. At this time-point, vaccine-specific IgG titers are either low or undetectable. Three days later (45 days after first vaccination), the mice are injected again with HbsAg in alum, but this time, none of the mice receive any F1C (secondary vaccination). Serum samples collected 7 days and 14 days after the second exposure to HbsAg vaccine are assayed for anti-HbsAg antibody. In the young mice, a marked increase in specific antibody is seen in response to the second vaccination. In aged mice that had receive no F1C with the first HbsAg injection, levels of anti-HbsAg are measured. The data is analyzed for increases in anti-HbsAg titers following secondary vaccination in aged animals that had been treated with a F1C in conjunction with the first HbsAg exposure.

Example 12

Vaccine adjuvant activity. Selected F1Cs are used to modulate the immune response to an antigen(s) such as malaria antigens encoded by DNA expression vectors. Antigens such as a *Plasmodium*, e.g., *P. yoelii*, *P. falciparum*, *P. vivax* or *P. berghei*, circumsporozoite or merozoite protein are used to immunize a subject. The F1C is administered on the same day or a day or two before antigen challenge. Suitable antigens, expression vectors and their delivery to a subject have been described. See, e.g., S. L. Hoffman et al., *Vaccine* 1994 12:1529-1533, R. Weiss et al., *Infect. Immunity* 2000 68:5914-5919, J. C. Rayner et al., *Proc. Nat'l. Acad. Sci. U.S.A.* 2000 97:9648-9653, S. Scheiblhofer et al., *Eur. J. Immunol.* 2001 31:692-298. The capacity of the compounds to enahnce immune responses to the antigens by, e.g., measuring cytotoxic T lymphocytes or antibody titer after delivery of the formula 1 compound and immunization with an antigen(s). Typically the immune response is measured at about 10 days to about 21 days after a primary immunization. Methods to measure immune responses are essentially as described herein or in appropriate cited references. DNAs that encode an antigen(s) that is associated with, e.g., an infectious agent or a tumor described herein may be used in these assays.

Example 13

Suppression of TNF-α induced adhesion molecule expression. The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-α), is a proinflammatory cytokine and stimulates all three CAMs on endothelial cells. It may be involved in a wide variety of inflammatory responses, often resulting in a pathological outcome. The capacity of a formula 1 compound to mediate a suppression of TNF-α induced CAM expression can be examined. A modified ELISA assay which uses Ecs as a solid phase absorbent is employed to measure the amount of CAM expression on TNF-α treated Ecs when co-stimulated with a member of the FGF family of proteins. To perform the experiment, human umbilical vein endothelial cell (HUVEC) cultures are obtained from pooled cord harvests and maintained in growth medium (EGM-2, Clonetics, San Diego, Calif.) supplemented with 10% FCS and 1% penicillin/streptomycin in a 37° C. humidified incubator containing 5% $CO_2$. HUVECs are seeded in 96-well plates at concentrations of about $1 \times 10^4$ cells/well in EGM medium at 37° C. for 18-24 hrs or until confluent. The monolayers are subsequently washed 3 times with a serum-free solution of RPMI-1640 optionally supplemented with 100 U/mL penicillin and 100 mg/mL streptomycin, and treated with a given cytokine and/or growth factor(s) for 24 h at 37° C. Following incubation, the cells are then evaluated for CAM expression.

HUVECs are grown in a standard 96 well plate to confluence. Growth medium is removed from the cells and replaced with 90 μL of 199 Medium (10% FBS). Samples for testing and positive or negative controls are added to the plate in triplicate (in 10 μL volumes). Plates are incubated at 37° C. for either 5 h (selectin and integrin expression) or 24 h (integrin expression). Plates are aspirated to remove medium and 100 pL of 0.1% paraformaldehyde-PBS (with $Ca^{++}$ and $Mg^{++}$) is added to each well. Plates are held at 4° C. for 30 min. Fixative is then removed from the wells and wells are washed 1x with PBS(+Ca,Mg)+0.5% BSA and drained. Do not allow the wells to dry. 10 pL of diluted primary antibody is added to the test and control wells. Anti-ICAM-1-Biotin, Anti-VCAM-1-Biotin and Anti-E-selectin-Biotin are used at a concentration of 10 pg/ml (1:10 dilution of 0.1 mg/ml stock antibody). Cells are incubated at 37° C. for 30 min. in a humidified environment. Wells are washed ×3 with PBS (with Ca, Mg) and 0.5% BSA. Then add 20 pL of diluted ExtrAvidin-Alkaline Phosphotase (1:5,000 dilution) to each well and incubate at 37° C. for 30 min. Wells are washed ×3 with PBS (with Ca, Mg) and 0.5% BSA. 1 tablet of p-Nitrophenol Phosphate pNPP is dissolved in 5 mL of glycine buffer (pH 10.4). 100 pl of pNPP substrate in glycine buffer is added to each test well. Standard wells in triplicate are prepared from the working dilution of the ExtrAvidin-Alkaline Phosphotase in glycine buffer: 5 pL of each dilution is added to triplicate wells and the resulting AP content in each well is 5.50 ng, 1.74 ng, 0.55 ng, 0.18 ng. 100 pl of pNNP reagent is then be added to each of the standard wells. The plate is incubated at 37° C. for 4 h. A volume of 50 pL of 3M NaOH is added to all wells. The results are quantified on a plate reader at 405 nm. The background subtraction option is used on blank wells filled with glycine buffer only. The template is set up to indicate the concentration of AP-conjugate in each standard well. Results are indicated as amount of bound AP-conjugate in each sample.

Example 14

Effects on the CNS. The effects of the formula 1 compounds on memory, learning, motor function or the status of a neurological condition or neurodegeneration condition are assayed using standard methods. For example, aged, two year old mice are tested in the Morris water maze procedure by training the mice to locate a pedestal in less than 15 seconds in three consecutive trials. Immediately upon completion of training one group of mice is treated with a formula 1 compound (5-30 mg/kg) and a second group is treated with a placebo. The treatment comprises one, two or three intraperitoneal, subcutaneous, intramuscular or intravenous injections of the formula 1 compound and the vehicle placebo. The injections are given once per day. Two weeks after treatment, the time to rescue is timed in the Morris water maze procedure and the control result is compared to the placebo control. The use of Morris water maze and other procedures to measure the effect of various conditions or compounds on learning, memory or neurological conditions have been described, see e.g., R. Gerlai *Trends Neurosci.* 1996, 19:177-181, J. L. W. Lau et al., Proc. Nat'l. Acad. Sci. 2001, 98:4716-4721, U.S. Pat. Nos. 6,348,489, 6,251,942 and 6277886.

Scopolamine induced amnesia is examined essentially as follows. Groups of 13 to 16 C57BL76 mice (about 35 gm) are trained in the Morris water maze procedure to locate a pedestal in less than 15 seconds in three consecutive trials. Immediately upon completion of training the mice in each of three groups are treated with scopolamine (1 mg/kg), scopolamine plus a formula 1 compound at one or more dosages (e.g., about 5-50 mg/kg), and scopolamine plus a placebo. The treatment comprises one, two or three intraperitoneal, subcutaneous, intramuscular or intravenous injections of the formula 1 compound and the vehicle placebo. The injections are given once per day. Six days after treatment the average time (sec) to rescue is timed using the Morris water maze procedure and the results from each group are compared. Results for a F1C such as 3α,17β-dihydroxy-16α-fluoroandrost-5-ene or 3β-hydroxy-17β-aminoandrost-5-ene are optionally compared to the results that are obtained in these protocols using another control compound, e.g., (S)-(−)-N-propargl-1-aminoindan or nefiracetam, or another F1C.

Example 15

Ischemia treatment. The capacity of F1Cs to limit injury associated with ischemia and reperfusion is determined in an animal model essentially as follows. Male Sprague-Dawley rats weighing 130-170 g are randomly assigned to no pre-treatment, vehicle pre-treatment or formula 1 compound pre-treatment using one or more dosages, e.g., about 1-10 mg/kg. Animals are treated with vehicle or F1C the day before and the day of surgery. Anesthesia is induced with intraperitoneal pentobarbital (60-70 mg/kg). The rats are placed on a heating pad, and body temperature is maintained at about 36° C. Detection of the cremaster muscle on its neurovascular pedicle is performed essentially according to conventional techniques, e.g., Anderson, G. L. et al., *Microvascular Res.* 1988 36:56-63, Siemionow, M. et al., *Microcirc. Endoth. Lymphatics* 1991 7:183-197, Siemionow, M. et al., *J. Hand Surgery* 1993 18A:963-971.

Briefly, a skin incision is made from the anterior iliac spine to the tip of the scrotum. The testis with cremaster muscle intact is then dissected away from the scrotum. An opening of 1 cm is made on the ventral surface of the cremaster, and the testis and spermatic cord are removed. Under a microscope, the neurovascular pedicle, consisting of the pubic-epigastric arteries, vein, and genitofemoral nerve, is then completely isolated by dissecting to the origin of the vessels from the external iliac artery and vein. The front wall of the cremaster muscle sac is opened and the island cremaster muscle flap is prepared for intravital videomicroscopy. The rat is secured on a tissue bath, and the cremaster muscle flap is spread over the coverglass in the opening at the bottom of the bath and fixed with 5-0 silk sutures. It is then transilluminated from below, using a fiber optic tungsten lamp. The muscle is kept moist and covered with impermeable plastic film. The tissue bath, designed specifically for temperature control, is filled with 0.9% saline and the temperature maintained at between 35-36° C. The microscope is equipped with a color video camera. The video image of the microcirculation is displayed on a 19" monitor, where the final magnification is 1800×. Measurement of microvascular activity is recorded after isolation of the muscle to establish the pre-ischemia baseline. After proper positioning of clamps to completely shut down blood flow to the muscle flap, the duration of the ischemic period is six hours. Following removal of clamps to induce reperfusion injury, activity in the microvasculature is measured at e.g., 30, 60 and 90 minutes post-reperfusion. In all experimental subjects, ischemia is followed by reflow and then by an initial period of flow of blood through the microcirculation. This burst of circulatory activity is followed by marked reperfusion injury that induces loss of flow.

One or more of the following parameters are used to evaluate the state of the cremaster muscle microvasculatory system prior to ischemia and after reperfusion. The density of perfused capillaries in each of three flap regions is measured by counting the number of flowing capillaries in proximity to the preselected post-capillary venule. Nine visual fields of capillaries are counted at each postcapillary venule site, for a total of 27 fields per cremaster muscle flap.

A leukocyte count in postcapillary venules is taken using video scans of three pre-selected post-capillary venules in proximal, middle and distal flap regions. For each venule, the number of leukocytes rolling through the lumen, the number adhering to the endothelium and the number migrating across the endothelium over a two-minute period are recorded. Results are optionally obtained for rollers, strikers and diapedesis.

Red blood cell velocities in first order and second order arterioles are measured. Red blood cell velocities are recorded in the main arterioles of the cremaster flap using an optical Doppler velocimeter. Results are obtained for velocity of venous and arterial blood.

In an exemplary protocol, six rats are untreated and six rats are pre-treated with vehicle. Under conditions of six hours of ischemia and 90 minutes of reperfusion, the absolute number of rolling, sticking and transmigrated leukocytes is determined within 60 minutes of reperfusion and at 90 minutes. Rats are pre-treated with a formula 1 compound by subcutaneous injection the day before and the day of surgery to measure any protective effect of the therapy. One or more of the three parameters are determined and are compared to normal values. The endothelial-adherent properties compared to baseline values are optionally determined, using numbers of rolling, sticking and transmigrating leukocytes. Red cell velocities in second order arterioles are compared to normal rates of flow at, e.g., 90 minutes post-reperfusion.

Example 16

Pulmonary vasoconstriction. The capacity of F1Cs to limit hypoxia induced pulmonary vasoconstriction is demonstrated using an animal model essentially as follows. Isolated perfused ferret lungs are an established animal model to study secondary pulmonary hypertension. In brief, male ferrets are anesthetized with intraperitoneal pentobarbital sodium and the chest is opened. Stainless steel cannulae are secured in the left atrium and pulmonary artery, and the pulmonary artery and the aorta are ligated. The lungs are perfused with a mixture of autologous blood and Krebs-Henseleit buffer in a circulating manner at a constant rate of about 85 mL/min. The perfusion circuit includes a perfusate reservoir, a roller perfusion pump, filter, and a heat exchanger. The perfusion system is made of, e.g., tygon tubing, which is used for connections and for passage through the perfusion pump. The temperature of the perfusate is kept about 37-38° C. and the pH is maintained at 7.35 to 7.40 by adding sodium bicarbonate to the reservoir as needed. The venous reservoir is placed below the lowermost portion of the lung.

The lungs are ventilated with a hypoxic gas mixture of 5% $CO_2$, 4% $O_2$, and 91% $N_2$ by a tracheotomy with a Harvard animal respirator for 30 minutes. The animals are ventilated with a tidal volume of 30 mL, at a rate of 18 breaths/min. and with 2 cm of $H_2O$ positive end-expiatory pressure. For measurements, pulmonary arterial, left atrial and tracheal pressures are monitored using Gould Statha P231D pressure transducers or an equivalent connected to the inflow circulation and recorded on, e.g., a Grass polygraph. After 30 minutes of ventilation with hypoxic gas mixture, a formula 1 compound in a dose between about 5-25 mg/kg body weight is added to the reservoir, and perfusate is allowed to perfuse the ferret lungs for 1.5 hours. Pulmonary artery pressure is measured until the end of the experiment, i.e., a total of two hours. Pressure that remains at or near basal level indicates the vasodilatory effect of the F1C in pulmonary circulation that is otherwise constricted in response to hypoxia. The effects of the F1Cs can be compared to the effects and duration of nitric oxide, a therapeutic agent that is optionally used in this model as a control.

Example 17

Hematopoiesis modulaton. Enhanced hematopoiesis is observed in mammals with immune injury from, e.g., radiation exposure or from an immunosuppressive chemotherapy. In an example, animals are used to demonstrate the effect of formula 1 compounds on hematopoiesis after immune system injury due to radiation. Hematopoiesis in the murine immune system after radiation is optionally used because of the similar responses of murine and human hematopoiesis to drugs and toxic insults (see, e.g., J. H. Hendry and B. I. Lord, editors, *Radiation toxicology: Bone marrow and leukaemia* 1995 Taylor & Francis Inc., London).

In an exemplary protocol, B6D2F1/J female mice (Jackson Laboratory, Bar Harbor, Me.), 18-24 weeks of age, 22-30 g body weight, are obtained and held in quarantine for two weeks. Up to 10 mice are housed in sanitized 46×24×15 cm polycarbonate boxes with filter covers (MicroIsolator; Lab Products, Inc, Maywood, N.J.) on autoclaved hardwood chip bedding. Mice are given feed and acidified (pH 2.5) water freely. The animal holding room is maintained with conditioned fresh air at approximately 21° C. and 50° (±10%) relative humidity and with a 12-h light/dark full spectrum lighting cycle.

Mice are placed in ventilated Plexiglas containers and exposed bilaterally to gamma-radiation from a $^{60}Co$ source. Exposure time is adjusted so that each animal received a midline tissue-absorbed dose of 1-12 Gy at a nominal dose rate of 0.4 Gy/min at ambient temperature. Using a standardized technique, the midline dose rate is measured by placing a 0.5 cc tissue-equivalent ionization chamber at the center of a 2.5-cm diameter cylindrical acrylic mouse phantom. The tissue-air ratio, defined as the ratio of the dose rate measured in the phantom to the dose rate in free air, for this array is about 0.96. Variation within the exposure field is less than about 4%. Dosimetric measurements are made in accordance with the American Association of Physicists in Medicine protocol for the determination of absorbed dose from high-energy photon and electron beams (*Med. Phys.* 1983 10:741-771). Sham-irradiated mice are treated in the same way as the irradiated animals, except that the animals are not irridiated.

Various formula 1 compounds are formulated with a suitable vehicle (e.g., PEG-400) or sterile 0.9% NaCl (saline) optionally containing other excipients such as a cyclodextrin. The compounds are injected subcutaneously in a volume of about 0.1 mL or they are delivered orally or they are administered by another route. Doses typically range from about 1 mg/kg to about 350 mg/kg, e.g., about 1, 10, 20, 40, 80, 160 or 320 mg/kg.

Blood (0.6-1.0 mL) is obtained from halothane-anesthetized mice by cardiac puncture using a heparinized syringe attached to a 21-gauge needle. Blood is collected in EDTA-containing sample tubes. Mice are euthanized by cervical dislocation after blood collection. White blood cell (WBC), red blood cell (RBC) and platelet (PLT) counts are performed using, e.g., a Hematology System 9000 (Biochem Immunosystems). Wright-stained blood smears from the same samples are made for differential counts of neutrophils and lymphocytes by light microscopy.

Hemopoietic progenitor cells committed to granulocyte-macrophage differentiation (GM-CFC) are assayed by a single-layer modification of a doubleayer semisolid agar technique essentially as described (Patchen et al. *Adv. Space Res.* 1992 12:223-248). For example, femoral marrow is extracted and cell suspensions are prepared by flushing with 3 mL of McCoy's 5A medium containing 10% heat-inactivated fetal bovine serum (HIFBS; Hyclone, Logan, Utah). Each cell suspension represented a pool of marrow from four femurs, i.e., both femurs from each of two mice. The total number of nucleated cells in each suspension is determined with, e.g., a Coulter counter. The agar-medium mixture consisted of equal volumes of 0.66% agar and double-strength supplemented CMRL 1066 medium (Gibco, Grand Island, N.Y.). The medium is supplemented with final concentrations of 10% HIFBS, 5% tryptic soy broth, 5% heat-inactivated horse serum, antibiotics, and L-serine. One milliliter of the agar-medium mixture is added to each 35-mm plastic Petri dish (two dishes per suspension) and mixed with 50 μL of 0.1 ng/μL recombinant mouse GM-CSF (Genzyme, Cambridge, Mass.). Cell suspensions are then mixed into the agar-medium mixture to a final concentration of $0.5 \times 10^5$ cells/mL for uni-irradiated animals, and $1.0 \times 10^5$ or $1.5 \times 10^5$ cells/mL for irradiated animals to ensure sufficient colonies per plate for quantitation. Control experiments are done to confirm linearity of colonies at cell concentrations of $0.5$-$1.5 \times 10^5$ cells/mL. Colonies (>50 cells) are counted after seven days incubation in a 37° C. humidified environment containing 5% $CO_2$. The average of the counts for the two dishes is taken as the value for each pool. About six animals are used per group in each of two experiments.

For histological examination of myeloid hyperplasia in bone marrow after administration of the formula 1 compound, mice are euthanized with halothane, tissues are immersed in formalin, bones are decalcified and routine H&E-stained 6-μm paraffin sections are prepared.

For induced-infection studies, a clinical isolate of *K. pneumoniae*, capsule type 5 (strain AFRRI 7), that is kept frozen at 70° C. in skim milk, is grown overnight at 35° C. on Trypticase Soy Agar (Becton-Dickinson, Sparks, Md.). Five typical colonies are inoculated into 8 mL of brain heart infusion broth (Becton-Dickinson) and incubated overnight at 35° C. Two milliliters of this overnight suspension is inoculated into 95 mL of prewarmed brain heart infusion broth. The culture is incubated at 35° C. with shaking for approximately 2.5 h. The optical density of bacterial growth is monitored with a spectrophotometer at a wavelength of 550 nm. Late log-phase cells are washed and suspended in cold saline to yield $10^9$ viable bacteria per mL. Appropriate dilutions for inoculations are made in cold saline.

To induce a bacterial infection, all mice are injected sc with *K. pneumoniae* four days after sham-irradiation or irradiation when circulating leukocytes are depressed. Mice are inoculated sc rather than iv or ip, to establish infection leading to sepsis, but not rapid septic shock. After sc inoculations of *K. pneumoniae* in the mice, the infection remains largely localized to the injection site. *K. pneumoniae* are not detectable in blood of inoculated mice until a few hours before death.

Different doses of the bacteria are inoculated for each of three radiation dose levels (0, 1 or 3 Gy) to approximate the $LD_{95/30}$ (radiation dose that is lethal for 30-95% of animals), because the effects of radiation on hematopoiesis and susceptibility to infection are dependent on the dose of radiation. The $LD_{95/30}$ for bacteria at each radiation dose is calculated from probit analysis. The actual doses are estimated by dilution plating of inocula onto Trypticase Soy Agar and incubating overnight at 35° C. Since different bacterial doses are expected to be needed for different radiation doses, the $LD_{95/30}$ is estimated for each group and different mortality rates are observed in the vehicle-injected control groups. Bacterial doses for induced-infection experiments are prepared and calculated in the same manner.

Animals are checked frequently, e.g., once or twice daily, six or seven days per week, to monitor survival and to euthanize mice that are in a moribund state. To verify that mortality in the induced-infection experiments is associated with *K. pneumoniae* injection, heart blood from recently deceased animals (or moribund animals euthanized by cervical dislocation) is cultured overnight at 35° C. on Columbia sheep blood agar plates (Becton-Dickinson, Sparks, Md.). Colonies are identified as *K. pneumoniae* by a suitable means, e.g., Biolog analysis.

For histological analysis of bone marrow, coded slides are scored blind using a five-level semiquantitative scale and the results analyzed with a randomization t-test to obtain exact P-values. Thirty-day survival values are compared using the generalized Savage (Mantel-Cox) procedure (BMDP Statistical Software, Inc, Los Angeles, Calif.). To calculate dose reduction factors (DRFs), probit analysis is performed on mortality data.

To characterize the potency of formula 1 compounds to ameliorate radiation-induced defects in hematopoiesis, mice are exposed to bilateral whole-body gamma-radiation and receive a dose of 3 Gy (or are sham-irradiated). One hour after irradiation or sham-irradiation, mice are injected with 320 mg/kg 3β,17β-dihydroxyandrost-5-ene ("AED") or PEG400 vehicle. Between-group differences in blood cell elements, e.g., neutrophils, GM-CFC and platelets are generally determined. Irradiation results in a decrease in neutrophils at about four days after radiation compared to sham-irradiated animals.

Example 18

Antiglucocorticoid effects of formula 1 compounds. A series of tests is run in triplicate using BALB/c mouse spleen cells to demonstrate the effect of the F1Cs and hydrocortisone ("Hycort") on cellular proliferation in the absence of a mitogen. Cultures of spleen cells are prepared and F1Cs are added at, e.g., 0.1, 0.5, 1 and 5 μM. Suitable controls are used. Twenty four hours after setup, about 50 μCi [$^3$H]-thymidine is added to each cell. Four to six hours later, the cells are harvested and counted on a scintillation counter.

Spleen cells are obtained from normal BALB/c mice and prepared as a single cell suspension at a concentration of about $1 \times 10^7$ cells/ml in RPMI 1640 supplemented with 2 mM L-glutamine, $5 \times 10^{-5}$ M 2-mercaptoethanol, 20 μg/ml gentamycin-sulfate, and 1% Nutridona-NS (Boehringer-Mannheim). Individual aliquots of cells are then pulsed for 30 minutes at 37° C. with selected concentrations of formula 1 compounds. After pulsing, the cells are washed several times in balanced salt solution, resuspended in fresh medium, and then dispensed into 24-well culture plates with a stimulatory concentration of anti-CD3 (e.g., Leo et al. Proc. Natl. Acad. Sci. U.S.A., 84:1374 (1987)). After a 24-hour incubation period, culture supernatants are harvested for assessment of proliferation or cytokine production, e.g., IL-2, IL-3 or IL-4 using, e.g., the method of Mossman (J. Immunol. Meth. 65:55 (1983)). 100% control titers of IL-3, IL-2 or IL-4 from normal stimulated splenocytes are obtained, exemplary values may be about 640 units/mL or IL-2 and 160 units/mL for IL-4.

Effects of formula 1 compounds and Hydrocortisone on Proliferation in the Presence of a Mitogen. A series of spleen cell cultures is run using a formula 1 compound and/or hydrocortisone with cell cultures to which concanavalin A is added. Preliminary tests on cultures to which concanavalin A is added at concentrations of 10.0, 5.0, 2.5 and 1.0 ng/mL. All tests on the effects of invention compounds on cultures stimulated with concanavalin A are performed with concanavalin A at, e.g., about 2.5 ng/mL. A mitogen such as ConA generally increases cell proliferation and the glucocorticoid steroid ("GCS") can decrease proliferation. Detectable partial or complete reversal of the inhibitor effects of hydrocortisone indicate an anti-glucorticoid effect by the formula 1 compounds.

Effect of formula 1 compounds on IL-3 production. Exemplary formula 1 compounds are characterized for their effect on the level of the cytokine IL-3 expression by spleen cells in tissue culture and for their capacity to reverse the effects of a GCS in IL-3 expression. The spleen cell cultures are prepared in accordance with the general method above. After 30 hours the level of IL-3 in the supernatants of the cultures was measured using the IL-3 ELISA kit manufactured by EndoGen Inc., Boston, Mass. A GCS such as hydrocortisone will generally suppress the production of IL-3 and the invention compounds are examined for their capacity to modify this effect. The IL-3 expressed by cells in culture may be recovered from the media containing IL-3 by known methods such as single or sequential reverse-phase HPLC steps on a preparative HPLC column. (See Urdal, et al., J. Chromatog. 296:171 (1984) and U.S. Pat. No. 5,128,450).

Example 19

Treatment of neurodegenerative conditions. Experimental allergic encephalomyelitis (EAE), is demyelinating disease of the central nervous system with many pathological and clinical similarities with multiple sclerosis (MS). EAE is thus a recognized animal model for human autoimmune conditions such as MS. F1Cs such as 3β,7β-dihydroxy-17β-aminoandrost-5-ene and 3β-hydroxy-17β-aminoandrost-5-ene are tested for their capacity to delay the onset of EAE or to reduce its symptoms. Female SJL mice (5 animals per group) are immunized with 150 to 200 μg of PLP-139-151 peptide/CFA to induce EAE. Starting 7 days before injection of the peptide, the animals are given daily injections (s.c.) of the compounds (3.0 mg) in 0.1 mL vehicle, or vehicle alone for 33 days. The vehicle consisted of a suspension of the formula 1 compound in saline and carboxymethylcellulose. Delayed onset, reduced peak clinical score (from 5.2±0.6 to 2.8±1.8) and cumulative disease index (>60%) of EAE, and prevention of or significant attenuation of relapses are measured. Reduced numbers of PLP-139-151 specific T cell responses and reduced numbers of TNF-α producing cells in the CNS indicate reduced disease progression or severity. Reduced production of autoimmune Th-1 associated cytokines, is consistent with restoration of a more normal Th-1/Th-2 immune balance and/or with reduction of inflammation in this model.

The efficacy of the formula 1 compounds to treat other autoimmune conditions can be determined by incorporating their use with suitable animal models or assay methods, e.g., collagen-induced arthritis as a model for human autoimmune polyarthritis (e.g., L. K. Myers et al., *Clin. Immunol.* 2002, 102:185-191, A. Matejuk et al., *Endocrinology* 2002, 143: 313-319, S. Thornton et al., *J. Immunol.* 165:1557-1563). The effect of the compounds on markers of inflammation such as TNFα, MIP-1, IL-13, IL-15, IL-17 or IL-18, e.g., reduced expression or activity, is optionally observed in any autoimmune or inflammatory condition.

Example 20

Modulation of transcription. The effect of 16α-bromoepiandrosterone ("BrEA") on transcript levels in cells in vitro was studied using a microarray to allow simultaneous monitoring of the expression of many genes to allow detailed analysis of the molecular pathways involved in biological responses to the compound.

In general, microarray technology works by covalently linking short DNA sequences that are complementary to the transcripts of many different genes on a single slide or array chip. mRNAs from test and control samples are generated and labeled with one or more colored fluorescent dyes or probes. The probes are hybridized with the array, which is then scanned by laser. The color and intensity of the fluorescent signal at each spot denotes relative expression level of each gene. The capacity of other F1Cs described herein, e.g., a F1C in compound group 1, 2, 3, 4 or 5, to modulate gene expression is characterized in a similar manner.

The array used in the experiment described below, contained about 12,000 known genes. The experiment used U937 human promonocytic leukemia cells that differentiate to monocyte/macrophage cells in the presence of phorbol-12-myristate-13-acetate ("PMA"). The U937 cells were PMA treated and then exposed to BrEA for 1 hr, 2 hrs, or 4 hrs, followed by bacterial lipopolysaccharide ("LPS") stimulation for 1 hr, 2 hrs or 4 hrs. The level of transcripts of the genes on the array was measured at the time points using RNA prepared from BrEA-treated and control (no BrEA) cells. U937 cells were plated at $1 \times 10^5$ cells/mL in the presence of 3 ng/mL PMA (Sigma, Catalog # P-8139) for 48 hrs. Cells were then treated with either 10 μM BrEA or DMSO (vehicle) for 1 hr, 2 hr, and 4 hrs. At each time point, cells were harvested and total RNA was extracted using Qiagen Rneasy kit according to manufacturer's specification. Total RNA samples were then analyzed by Mergen Ltd. (San Leandro, Calif.) to perform microarray assay.

For the microarray assay, Dnase-treated total RNA (20 micrograms) was reverse-transcribed using an oligo[(dT)$_{24}$ T7 promoter]$_{65}$ primer (consisting of the nucleotide binding sequence for the T7 RNA polymerase followed by 24 thymidine nucleotides). This was followed by second strand synthesis. The reaction mixture was then treated with Rnase I to digest the remaining RNA. The double-stranded cDNA was phenol-chloroform extracted and used as template for in vitro transcription (T7 MEGAscript, Ambion, Inc.) to generate biotin-labeled cRNA probes. These probes were hybridized overnight at 30° C. with continuous agitation to Mergen's ExpressChip HO5 DNA Microarray System (catalog number HO5-001) containing 12,000 genes. The arrays were then washed, and hybridized probes were detected using Mergen's cyanine-3 fluorescent dye-conjugated protein. Chips were imaged using an Affymetrix 417-418 form Affymetrix/Genetic MicroSystems (www.affymetrix.com) and spot intensity was quantitated. using ImaGene from BioDiscovery Inc. (www.biodiscovery.com).

The results showed that BrEA was capable of substantially up-regulating a number of genes. A number of genes were differentially regulated by BrEA based on two criteria: 1) the expression level of any particular gene in a BrEA-treated sample is at least two-fold higher than that of the control-treated sample; and 2) the expression level of any particular gene in a BrEA-treated sample is significantly higher than background. The up-regulation of many of these genes most apparent at 4 hr after treatment, at which time roughly 700 genes were within the above criteria. Some examples are shown in the following list. The ratios given in the list are from BrEA treated cells compared to control cells not treated with BrEA.

| Ratio* | UniGene ID | UniGene symbol | HO5 gene description |
|---|---|---|---|
| 5.3 | Hs.460 | ATF3 | Activating transcription factor 3 |
| 5.4 | Hs.78546 | ATP2B1 | ATPase, Ca++ transporting, plasma membrane 1 |
| 10.2 | Hs.2128 | DUSP5 | Dual specificity phosphatase 5 |
| 9.7 | Hs.155119 | EHD1 | EH-domain containing 1 |
| 9.6 | Hs.75765 | GRO2 | GRO2 oncogene |
| 124.7 | Hs.89690 | GRO3 | GRO3 oncogene |
| 7.8 | Hs.274402 | HSPA1B | Heat shock 70 kD protein 1B |
| 32.0 | Hs.177781 | MGC5618 | Hypothetical protein MGC5618 |
| 6.6 | Hs.75063 | HIVEP2 | immunodeficiency virus type I enhancer-binding protein 2 |
| 21.5 | Hs.727 | INHBA | Inhibin, beta A (activin A, activin AB alpha polypeptide) |
| 53.0 | Hs.81134 | IL1RN | Interleukin 1 receptor antagonist |

| Ratio* | UniGene ID | UniGene symbol | HO5 gene description |
|---|---|---|---|
| 27.5 | Hs.126256 | IL1B | Interleukin 1, beta |
| 7.6 | Hs.12503 | IL15RA | Interleukin 15 receptor, alpha |
| 131.8 | Hs.98309 | IL23A | Interleukin 23, alpha subunit p19 |
| 16.9 | Hs.50640 | SSI-1 | JAK binding protein |
| 7.7 | Hs.24684 | KIAA1376 | KIAA1376 protein |
| 6.9 | Hs.164719 | KIAA1726 | KIAA1726 protein |
| 7.1 | Hs.151988 | MAP3K5 | Mitogen-activated protein kinase kinase kinase 5 |
| 25.5 | Hs.301183 | MAIL | Molecule possessing ankyrin repeats induced by lipopolysaccharide (MAIL), homolog of mouse |
| 30.0 | Hs.75607 | MACS | Myristoylated alanine-rich protein kinase C substrate (MARCKS, 80K-L) |
| 6.4 | Hs.109281 | NAF1 | Nef-associated factor 1 |
| 11.3 | Hs.81328 | NFKBIA | Nuclear factor of kappa light polypeptide gene enhancer in B-cells inhibitor, alpha |
| 26.1 | Hs.77729 | OLR1 | Oxidised low density lipoprotein receptor 1 |
| 1348.4 | Hs.2050 | PTX3 | Pentaxin-related gene, rapidly induced by IL-1 beta |
| 14.5 | Hs.80205 | PIM2 | Pim-2 oncogene |
| 9.2 | Hs.239138 | PBEF | Pre-B-cell colony-enhancing factor |
| 5.4 | Hs.3407 | PKIG | Protein kinase (cAMP-dependent, catalytic) inhibitor gamma |
| 6.6 | Hs.103755 | RIPK2 | Receptor-interacting serine-threonine kinase 2 |
| 29.2 | Hs.183601 | RGS16 | Regulator of G-protein signalling 16 |
| 5.3 | Hs.115521 | REV3L | REV3 (yeast homolog)-like, catalytic subunit of DNA polymerase zeta |
| 5.9 | Hs.27018 | LOC51285 | Ris |
| 8.4 | Hs.82085 | SERPINE1 | Serine (or cysteine) proteinase inhibitor, clade E (nexin, plasminogen activator inhibitor type 1), member 1 |
| 9.0 | Hs.1087 | STK2 | Serine/threonine kinase 2 |
| 5.9 | Hs.167503 | STAT5A | Signal transducer and activator of transcription 5A |
| 40.4 | Hs.72918 | SCYA1 | Small inducible cytokine A1 (I-309, homologous to mouse Tca-3) |
| 67.3 | Hs.75703 | SCYA4 | Small inducible cytokine A4 (homologous to mouse Mip-1b) |
| 174.0 | Hs.75498 | SCYA20 | Small inducible cytokine subfamily A (Cys-Cys), member 20 |
| 7.0 | Hs.271387 | SCYA8 | Small inducible cytokine subfamily A (Cys-Cys), member 8 (monocyte chemotactic protein 2) |
| 39.7 | Hs.318885 | SOD2 | Superoxide dismutase 2, mitochondrial |
| 17.4 | Hs.112259 | TRG@ | T cell receptor gamma locus |
| 15.0 | Hs.2134 | TRAF1 | TNF receptor-associated factor 1 |
| 10.3 | Hs.17839 | GG2-1 | TNF-induced protein |
| 17.4 | Hs.101382 | TNFAIP2 | Tumor necrosis factor, alpha-induced protein 2 |
| 5.1 | Hs.211600 | TNFAIP3 | Tumor necrosis factor, alpha-induced protein 3 |
| 1733.0 | Hs.29352 | TNFAIP6 | Tumor necrosis factor, alpha-induced protein 6 |

*Ratio of BrEA treated cells compared to control cells not treated with BrEA

As seen from the data shown above, BrEA was capable of inducing an increase in the level of transcription of a number of genes. These increases ranged from about a 2-fold increase to an increase of greater than about 1700-fold. For some genes, levels of mRNA increased from a nearly undetectable level to a very high level. For genes that are modulated by the formula 1 compounds, the level of mRNA, protein or one or more biological activities associated with the gene product can thus include an increase or a decrease of at least about 3-fold, at least about 5-fold, at least about 1 0-fold, at least about 20-fold, at least about 50-fold or at least about 100-fold. This increase or decrease may occur for 1, 2, 3, 4, 5, 6 or more of the affected genes.

Pathways through which BrEA may mediate its effects include one or more of the following. At 1 hr, transcripts of USF1, c-Fos, EGR1, and Cul1 were increased. Cul1 activates NFkB1p50. At 2 hrs, USF1 increases FCAR transcript levels. At 4 hrs, c-Fos/C/EBPβ stimulate transcription of RANTES, NFκB1p50, IL6, ICAM1, TSG (TNFAIP6), and IL1β. NFκB1p50/RelA induces IL-2Rα, IL6, GRO2 and GRO3. At 5 hrs, USF1 increases HO1 transcript levels. Alternatively, at 4 hrs, Jun B is also increased, and c-Fos/JunB & JunB/ATF3 increase c-Jun. c-Fos/cJun increases ATF-3, MMP1, TNFα and TSG-6 (TNFAIP3). Elevated AP1 or EGR1 increases TGFβ. ATF-3/c-Jun & c-Fos increase MMP3. Activity associated with the presence of the NFkBp50/RelA complex increases IL-8. NFkBp50, STAT5A and STAT5B induce IL2Rα (interleukin-2 receptor α). STAT5B Induces CDKN1A. IFNγR2 induces T-bet. Other formula 1 compounds will generally affect one or more of these pathways in a similar manner.

In general, the genes showing the greatest increases in expression belong to the following families: chemokines (GRO2, GRO3, SCYA1, SCYA4, SCYA20, and SCYA8), cytokines and their receptors (IL1RN, IL1B, IL15RA, and IL23A), TNFα-related/induced genes (TRAF1, GG2-1, TNFAIP2, TNFAIP3, and TNFAIP6), and members of several different signal transduction pathways (e.g. $MAP3K_5$, STAT5A, SSI-1, RGS16, and NFκBIA). Changes in the expression level of 1, 2, 3, 4, 5, 6, 7, 8, 9, 10, 11, 12 or more of these genes or other genes described herein are useful as a screening assay or method to analyze other test compounds or other formula 1 compounds. The assay can identify the relative potency of the test compound compared to the activity of BrEA or a formula 1 compound, or the assay can identify a distinct subset of the activities seen with BrEA or another formula 1 compound, for example.

As discussed above, BrEA was found to increase immunity in a non-inflammatory cellular context, e.g., in the absence of LPS here, but BrEA decreased inflammation when the cells were in the presence of a strong inducer of inflammation. Thus, BrEA was capable of mediating both apparently contradictory activities by context-specific regulation of activities. The formula 1 compounds act differently in different tissues, depending on the physiological condition of cells or tissues in a subject or cells or tissues in vitro. In multiple systems, both in animals and in humans, the formula 1 compounds appear to drive immune function toward homeostasis. This was observed in the context of HIV where BrEA stimulated immune response in a condition of immune suppression. But, in the context of autoimmunity, the formula 1 compounds generally limit unwanted autoimmune responses. Depending on the state of the target cell, genes will be regulated in a manner that optimizes desired immune responses while limiting unwanted immune responses. Responses to formula 1 compounds in resting cells (e.g. at vaccination) will be different than responses in activated cells (e.g. chronic inflammation).

Screening assays using a formula 1 compound or another compound would include any method that measures the expression level of one or more of these genes in the presence of a test compound as compared to their expression in the absence of the test compound and/or compared to the expression seen with BrEA or another formula 1 compound. This can be done by microarray essentially as described above, as well as by mini or custom array on a focused list of genes (such as the list above and optionally including 1, 2, 3, 4, 5, 6, 7, 8, 9, 10, 11, 12 or more of the genes disclosed herein), quantitative PCR assays such as eXpres Profiling or real-time PCR (Althea Technologies, San Diego, Calif.), and Northern blot analysis. In some cases, when a target gene product is a secreted protein, such as SCYA1, measuring protein level in the culture media for cells in tissue culture by ELISA could also be used as a screening assay. Also, cells for this type of analysis can be obtained from a subject who has been dosed with a formula 1 compound or another test compound. In this case, the cells could be obtained from blood, e.g., white blood cells, or from bone marrow, lymph tissue, spleen tissue or thymus tissue.

It will be appreciated that the methods and compositions of the instant invention can be incorporated in the form of a variety of embodiments, some of which are disclosed herein. It will be apparent to the artisan that other embodiments exist and do not depart from the scope of the invention. Thus, the described embodiments are illustrative and should not be construed as restrictive.

For any of the uses of formula 1 compounds described herein, e.g., in any of the examples above, the results or biological effects that are obtained using individual formula 1 compounds are optionally compared to the results or biological effects that are obtained using a reference formula 1 compound such as 3β,17β-dihydroxyandrost-5-ene, 3β,7β,17β-trihydroxyandrost-5-ene or BrEA. A reference F1C can serve as a positive control or negative control for modulation of gene transcription or activity. Other known modulators of a gene whose biological activity is associatiated with a symptom or clinical condition of interest could also be used as a reference control with or without a reference F1C control. Such comparisons provide guidance for using the formula 1 compounds in the different methods or clinical conditions. Such comparison information allows, e.g., tailoring of dosages, dosing schedules, routes of administration or drug interactions with other therapeutic treatments in any selected application for the F ICs.

Example 21

The effect of F1Cs on transcript or gene product levels in cells in vitro is studied in vitro using a cell type of interest, e.g., the murine macrophage cell line designated RAW264.7 ("RAW" cells). For the RAW cells, the cells are maintained in a suitable medium, e.g., RPMI 1640 supplemented with 10% FBS, standard Penn/Strep antibiotic solution and 2 mM glutamine. The T1C is dissolved in a suitable solvent, e.g., DMSO or pyrrolidone, to generate a 10 mM stock solution. For DMSO solutions, appropriate dilutions are made to give a F1C final concentration in culture media of about 1 nM to about 10 μM, with a final DMSO content of no more than 0.1% v/v. The cells are induced with LPS at 100 ng/ml (stock solution in water, diluted in serum-free culture media).

In a typical protocol, on day 0 the cells are plated at a density to reach a sub-confluent state of greater than about 75% confluency on the following day. For 6-well plates, about 500,000 to 700,000 cells/well are plated. On the following day, day 1, the cells are treated with the F1C or vehicle, e.g., DMSO, with or without LPS, for selected times, e.g., 0.5, 1, 2, 4, 6, 8, 10, 12, 16, 24, 36, 48 hours. After incubation, cells are harvested with a cell scraper and total RNA is extracted to generate samples for PCR analysis. 1 mL of culture media is optionally saved at −20° C. for future ELISA analysis to determine gene transcript levels. On day 2, cells are harvested after, e.g., 24 hr of F1C in DMSO treatment. LPS induction is started in cells pre-treated with F1C in, e.g., DMSO. Exemplary treatment conditions and time points for cell harvesting are as follows:

| No treatment | 0 hr | | | | 24 hr |
|---|---|---|---|---|---|
| DMSO + LPS | | 1 hr | 4 hr | 8 hr | 24 hr |
| F1C 10 μM + LPS | | 1 hr | 4 hr | 8 hr | 24 hr |
| F1C 1 μM + LPS | | 1 hr | 4 hr | 8 hr | 24 hr |
| F1C 10 nM + LPS | | 1 hr | 4 hr | 8 hr | 24 hr |
| DMSO | 24 hr + LPS | 1 hr | 4 hr | 8 hr | 24 hr |
| F1C 10 μM | 24 hr + LPS | 1 hr | 4 hr | 8 hr | 24 hr |
| F1C 1 μM | 24 hr + LPS | 1 hr | 4 hr | 8 hr | 24 hr |
| F1C 10 nM | 24 hr + LPS | 1 hr | 4 hr | 8 hr | 24 hr |

Exemplary genes of interest that can be analyzed by this or a similar protocol include 1, 2, 3, 4, 5, 6 or more of iNOS (inducible nitric oxide synthase), eNOS (constitutive nitric oxide synthase), COX-2 (cycloxygenase-2, PGE2 synthase), IκBβ, TNFα, IL-1β, IL-1Ra (interleukin 1 receptor antagonist), NFκB1 (p105), NFκB2 (p49/p100), IL-6, MCP-1 (monocyte chemoattractant prtein-1 or CCL2), MIP-2 (macrophage inflammatory protein-2), MMP9 (matrix metalloproteinase 9), gelatinase B, HO-1 (heme oxygenase 1), HIF1α (hypoxia inducible factor 1, alpha subunit), GCLC (gamma glutamylcycleine synthetase catalytic (heavy) subunit or γGCS-hs), GCLM (gamma glutamylcycleine synthetase modifier (light) subunit or γGCS-Is), xCT (cystine/glutamate exchange transporter), NQO1 (NAD(P)H: quinone oxidoreductase 1), TXNRD1 (thioredoxin reduatase 1), EBBP(estrogen responsive B-box protein), CYP1A1 (cytochrome P450), CD36 (SR-B), SR-A (scavenger receptor A or Msr1), ABCA1 (ATP-binding cassette transporter A1), ABCG1 (ATP-binding cassette transporter G1), LDLR (low-density lipoprotein receptor), NR1H3 (nuclear receptor 1H3 or LXRα), NR1C3 (nuclear receptor 1C3 or PPARγ), SCD-1 (stearoyl-CoA desaturase 1) and NR4A1 (nuclear receptor 4A1 or Nur77). F1C that can be characterized in this manner include the F1Cs in the compound groups described above, e.g., one or more of 16α-bromoepiandrosterone, 3β,16α-dihydroxyandrostane-17-one, 3β,16α,17β-trihydroxyandrostane, 3α,16α,17β-trihydroxyandrostane, 3β,17β-dihydroxy-16α-fluoroandrost-5-ene, 3β,17β-dihydroxy-16α-fluoroandrost-1,5-diene, 3β-hydroxy-17β-aminoandrost-5-ene, 3β,7β-dihydroxy-17β-aminoandrost-5-ene, 3β-hydroxy-7-oxo-17β-aminoandrost-5-ene, 3α-hydroxy-17β-aminoandrost-5-ene, 3β-hydroxy-17β-aminoandrost-1,5-ene, 3α-hydroxy-17β-aminoandrost-1,5-diene, 3β-hydroxy-16α-fluoro-17β-aminoandrost-5-ene or 3p3-hydroxy-16α-fluoro-17β-aminoandrost-1,5-diene.

To the extent not already indicated, it will be understood by those of ordinary skill in the art that any of the various specific embodiments, compounds or compositions described herein may be modified to incorporate other appropriate features, e.g., as shown in any other of the specific embodiments disclosed herein or in the cited references.

What is claimed is:

1. A compound having the structure

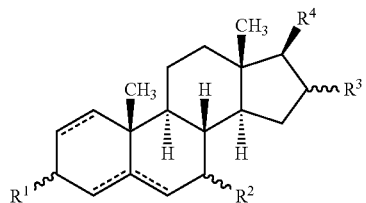

wherein
R$^1$ is —OH or an ester;
R$^2$ is —OH or an ether;
R$^3$ is —OH, =O, a halogen, an ester or =CH$_2$; and
R$^4$ is an optionally substituted amine, an amide, an N-linked amino acid, =NOH or —NHOH.

2. The compound of claim 1 having the structure

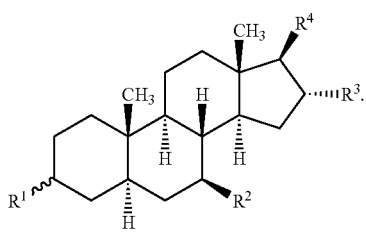

3. The compound of claim 2 wherein
R$^1$ is —OH;
R$^2$ is —OH;
R$^3$ is —OH, =O, —F, —Br, —O—C(O)—CH$_3$ or —O—C(O)—CH$_2$CH$_3$; and
R$^4$ is —NH$_2$, —NH—C(O)CH$_3$, =NOH, —NHCH$_3$, —N(CH$_3$)$_2$, —NH—C$_2$H$_5$ or —NHOH.

4. The compound of claim 3 having the structure

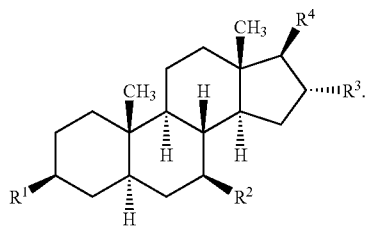

5. The compound of claim 4 wherein the compound is 3β,7β-dihydroxy-16α-fluoro-17β-aminoandrostane.

6. The compound of claim 1 having the structure

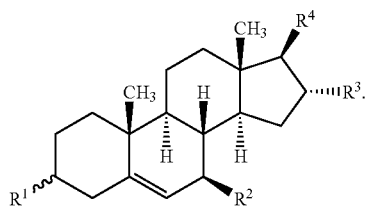

7. The compound of claim 6 wherein
R$^1$ is —OH;
R$^2$ is —OH;
R$^3$ is —OH, =O, —F, —Br, —O—C(O)—CH$_3$ or —O—C(O)—CH$_2$CH$_3$; and
R$^4$ is —NH$_2$, —NH—C(O)CH$_3$, =NOH, —NHCH$_3$, —N(CH$_3$)$_2$, —NH—C$_2$H$_5$ or —NHOH.

8. The compound of claim 7 having the structure

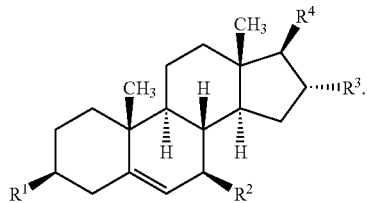

9. The compound of claim 8 wherein the compound is 3β,7β-dihydroxy-16-oxo-17β-aminoandrost-5-ene.

10. A pharmaceutical formulation comprising one or more excipients and a compound having the structure

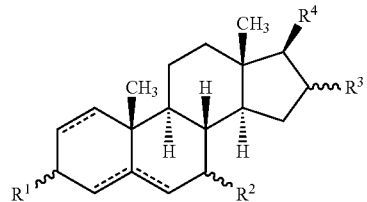

wherein
R$^1$ is —OH or an ester;
R$^2$ is —OH or an ether;
R$^3$ is —OH, =O, a halogen, an ester or =CH$_2$; and
R$^4$ is an optionally substituted amine, an amide, an N-linked amino acid, =NOH or —NHOH.

11. The pharmaceutical formulation of claim 10 wherein the compound has the structure

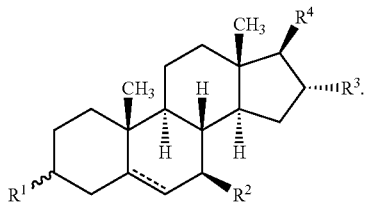

12. The pharmaceutical formulation of claim 11 wherein
R$^1$ is —OH;
R$^2$ is —OH;
R$^3$ is —OH, =O, —F, —Br, —O—C(O)—CH$_3$ or —O—C(O)—CH$_2$CH$_3$; and
R$^4$ is —NH$_2$, —NH—C(O)CH$_3$, =NOH, —NHCH$_3$, —N(CH$_3$)$_2$, —NH—C$_2$H$_5$ or —NHOH.

13. The pharmaceutical formulation of claim 12 wherein the compound is 3β,7β-dihydroxy-16α-fluoro-17β-aminoandrostane or 3β,7β-dihydroxy-16-oxo-17β-aminoandrost-5-ene.

* * * * *